US 7,645,780 B2

(12) United States Patent
John et al.

(10) Patent No.: US 7,645,780 B2
(45) Date of Patent: Jan. 12, 2010

(54) ACETYL 2-HYDROXY-1, 3-DIAMINOALKANES

(75) Inventors: Varghese John, San Francisco, CA (US); Michel Maillard, Redwood Shores, CA (US); James P. Beck, Zionsville, IN (US); Eric T. Baldwin, Carmel, IN (US); Robert Hughes, Eureka, MO (US); Shon R. Pulley, Carmel, IN (US); Ruth T. TenBrink, Labadie, MO (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 282 days.

(21) Appl. No.: 11/447,789

(22) Filed: Jun. 6, 2006

(65) Prior Publication Data
US 2007/0293483 A1  Dec. 20, 2007

Related U.S. Application Data

(63) Continuation of application No. 10/658,959, filed on Sep. 10, 2003, now Pat. No. 7,244,725.

(60) Provisional application No. 60/409,453, filed on Sep. 10, 2002, provisional application No. 60/452,231, filed on Mar. 5, 2003, provisional application No. 60/491,757, filed on Aug. 1, 2003.

(51) Int. Cl.
C07D 213/56 (2006.01)
A61K 31/44 (2006.01)

(52) U.S. Cl. .................. 514/357; 514/378; 514/623; 514/625; 546/336; 546/139; 548/240

(58) Field of Classification Search .................. None
See application file for complete search history.

(56) References Cited

U.S. PATENT DOCUMENTS

| | | | |
|---|---|---|---|
| 5,350,429 A | 9/1994 | Mohr et al. | |
| 5,362,912 A | 11/1994 | Sowin et al. | |
| 5,387,742 A | 2/1995 | Cordell | |
| 5,612,486 A | 3/1997 | McConlogue et al. | |
| 5,628,991 A | 5/1997 | Samain et al. | |
| 5,696,270 A | 12/1997 | Kempf et al. | |
| 5,720,936 A | 2/1998 | Wadsworth et al. | |
| 5,766,846 A | 6/1998 | Schlossmacher et al. | |
| 5,811,633 A | 9/1998 | Wadsworth et al. | |
| 5,850,003 A | 12/1998 | McLonlogue et al. | |
| 5,877,015 A | 3/1999 | Hardy et al. | |
| 5,877,399 A | 3/1999 | Hsiao et al. | |
| 5,892,052 A | 4/1999 | Kempf et al. | |
| 6,024,768 A | 2/2000 | Bittner et al. | |
| 6,150,416 A | 11/2000 | Kick et al. | |
| 6,150,530 A | 11/2000 | Kempf et al. | |

FOREIGN PATENT DOCUMENTS

| | | |
|---|---|---|
| WO | 96/39385 | 12/1996 |
| WO | 00/17369 | 3/2000 |

OTHER PUBLICATIONS

Kempf et al., "Symmetry-Based Inhibitors of HIV Protease. Structure-Activity Stuides of Acylated 2,4-Diamino-1,5-dephenyl-3-hydroxypentane and 2,5-Diamino-1,6-diphenylhexane-3,4-diol," J. Med. Chem., 36, 320-330 (1993).
International Search Report for PCT/US03/28503.
Hall et al., "A simple Method for Converting Nitriles to Amides. Hydrolysis with Potassium Hydroxide in tert-Butyl Alcohol," J. Org. Chem., 41(23):3769-3770 (1976).
Games et al., "Alzheimer-type neuropathology in transgenic mice overexpressing V717F β-Amyloid precursor protein," Letters to Nature, 373(6514):523-527 (1995).
Kang et al., "Synthesis of 1,4-diaminocyclitois from L-Serine Methyl Ester," J. Org. Chem., 61, 5528-5531 (1996).
Benedetti et al., "Versatile and Steroselective Synthesis of Diamino Diol Dipeptide Isosteres, Core Unites of Pseudopeptide HIV Protease Inhibitors," J. Org. Chem., 62, 9348-9353 (1997).
Zuccarello et al., "HIV-1 Protease Inhibitors Based on Acyclic Carbohydrates," J. Org. Chem., 63, 4898-4906 (1998).
Lee et al., "Development of a New Type of Protease Inhibitors, Efficiacious against FIV and HIV Variants," J. Am. Chem. Soc., 121, 1145-1155 (1991).
Albright et al., "Synthesis of 1,4,5,6-Tetrahydropyrazolo[3,4-d]pyrido[3,2-b]azepine," J. Heterocyclic Chm., 37, 41-46 (2000).
Xu, Ping et al., "The Study on HCMV Protease Inhibitors (1) Design and Liquid-phase Combinatorial Building Block Synthesis of Peptidomimetic Inhibitors," Chinese Journal of Medicinal Chemistry, 11(1)32-36 (2001).

*Primary Examiner*—Zinna N Davis
(74) *Attorney, Agent, or Firm*—McDonnell Boehnen Hulbert & Berghoff LLP

(57) ABSTRACT

Disclosed are compounds of the formula:

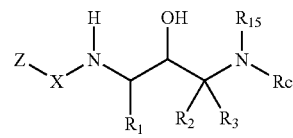

where variables Z, X, $R_{15}$, $R_2$, $R_3$, and $R_c$ are defined herein. Compounds disclosed herein are inhibitors of the beta-secretase enzyme and are therefore useful in the treatment of Alzheimer's disease and other diseases characterized by deposition of A beta peptide in a mammal.

14 Claims, No Drawings

ACETYL 2-HYDROXY-1, 3-DIAMINOALKANES

This application is a continuation application of U.S. Ser. No. 10/658,959 filed Sep. 10, 2003; now U.S. Pat. No. 7,244,725 which claims priority from U.S. Provisional application Nos. 60/409,453 filed Sep. 10, 2002; 60/452,231 filed Mar. 5, 2003; and 60/491,757 filed Aug. 1, 2003.

BACKGROUND OF THE INVENTION

1. Field of the Invention

The invention relates to acetyl 2-hydroxy-1,3-diaminoalkanes and to such compounds that are useful in the treatment of Alzheimer's disease and related diseases. More specifically, it relates to such compounds that are capable of inhibiting beta-secretase, an enzyme that cleaves amyloid precursor protein to produce amyloid beta peptide (A beta), a major component of the amyloid plaques found in the brains of Alzheimer's sufferers.

2. Background of the Invention

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39-42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sinha et al., 1999, *Nature* 402:537-554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325-327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1-19.

BACE1 knockout mice fail to produce A beta, and present a normal phenotype. When crossed with transgenic mice that over express APP, the progeny show reduced amounts of A beta in brain extracts as compared with control animals (Luo et al., 2001 *Nature Neuroscience* 4:231-232). This evidence further supports the proposal that inhibition of beta-secretase activity and reduction of A beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

The invention encompasses the compounds of formula (I) shown below, pharmaceutical compositions containing the compounds and methods employing such compounds or compositions in the treatment of Alzheimer's disease and more specifically compounds that are capable of inhibiting beta-secretase, an enzyme that cleaves amyloid precursor protein to produce A-beta peptide, a major component of the amyloid plaques found in the brains of Alzheimer's sufferers.

In a broad aspect, the invention provides compounds of formula I

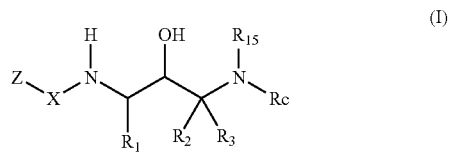

and pharmaceutically acceptable salts thereof, wherein

Z is hydrogen, or

Z is $(C_3\text{-}C_7 \text{ cycloalkyl})_{0\text{-}1}(C_1\text{-}C_6 \text{ alkyl})$-, $(C_3\text{-}C_7 \text{ cycloalkyl})_{0\text{-}1}(C_2\text{-}C_6 \text{ alkenyl})$-, $(C_3\text{-}C_7 \text{ cycloalkyl})_{0\text{-}1}(C_2\text{-}C_6 \text{ alkynyl})$- or $(C_3\text{-}C_7 \text{ cycloalkyl})$-, wherein each of said groups is optionally substituted with 1, 2, or 3 $R_z$ groups, wherein 1 or 2 methylene groups within said $(C_3-C_7$ cycloalkyl$)_{0-1}(C_1-C_6$ alkyl$)$-, $(C_3-C_7$ cycloalkyl$)_{0-1}(C_2-C_6$ alkenyl$)$-, $(C_3-C_7$ cycloalkyl$)_{0-1}(C_2-C_6$ alkynyl$)$- or $(C_3-C_7$ cycloalkyl$)$- groups are optionally replaced with —(C=O)—;

$R_Z$ at each occurrence is independently halogen (in one aspect, F or Cl), —OH, —SH, —CN, —CF$_3$, —OCF$_3$, $C_1-C_6$ alkoxy, $C_3-C_7$ cycloalkyl, $C_3-C_7$ cycloalkoxy or —NR$_{100}$R$_{101}$;

$R_{100}$ and $R_{101}$ at each occurrence are independently H, $C_1-C_6$ alkyl, phenyl, CO($C_1-C_6$ alkyl) or SO$_2$C$_1$-C$_6$ alkyl;

X is —(C=O)— or —(SO$_2$)—;

$R_1$ is $C_1-C_{10}$ alkyl optionally substituted with 1, 2, or 3 groups independently selected from halogen, —OH, =O, —SH, —CN, —CF$_3$, —OCF$_3$, —C$_{3-7}$ cycloalkyl, —C$_1$-C$_4$ alkoxy, amino, mono- or dialkylamino, aryl, heteroaryl, and heterocycloalkyl, wherein each aryl group is optionally substituted with 1, 2 or 3 R$_{50}$ groups; each heteroaryl is optionally substituted with 1 or 2 R$_{50}$ groups; and each heterocycloalkyl group is optionally substituted with 1 or 2 groups that are independently R$_{50}$ or =O;

$R_{50}$ is selected from halogen, OH, SH, CN, —CO—(C$_1$-C$_4$ alkyl), —NR$_7$R$_8$, —S(O)$_{0-2}$—(C$_1$-C$_4$ alkyl), C$_1$-C$_6$ alkyl, C$_2$-C$_6$ alkenyl, C$_2$-C$_6$ alkynyl, C$_1$-C$_6$ alkoxy and C$_3$-C$_8$ cycloalkyl; wherein the alkyl, alkenyl, alkynyl, alkoxy and cycloalkyl groups are optionally substituted with 1 or 2 substituents independently selected from C$_1$-C$_4$ alkyl, halogen, OH, —NR$_5$R$_6$, CN, C$_1$-C$_4$ haloalkoxy, NR$_7$R$_8$, and C$_1$-C$_4$ alkoxy; wherein R$_5$ and R$_6$ are independently H or C$_1$-C$_6$ alkyl; or R$_5$ and R$_6$ and the nitrogen to which they are attached form a 5 or 6 membered heterocycloalkyl ring;

R$_7$ and R$_8$ are independently selected from H; —C$_1$-C$_4$ alkyl optionally substituted with 1, 2, or 3 groups independently selected from —OH, —NH$_2$, and halogen; —C$_3$-C$_6$ cycloalkyl; —(C$_1$-C$_4$ alkyl)-O—(C$_1$-C$_4$ alkyl); —C$_2$-C$_4$ alkenyl; and —C$_2$-C$_4$ alkynyl;

R$_2$ and R$_3$ are independently selected from H; F; —C$_1$-C$_6$ alkyl optionally substituted with —F, —OH, —C≡N, —CF$_3$, C$_1$-C$_3$ alkoxy, or —NR$_5$R$_6$; —(CH$_2$)$_{0-2}$—R$_{17}$; —(CH$_2$)$_{0-2}$—R$_{18}$; —C$_2$-C$_6$ alkenyl or C$_2$-C$_6$ alkynyl, wherein the alkenyl and alkynyl groups are optionally substituted with 1 or 2 groups that are independently —F, —OH, —C≡N, —CF$_3$ or C$_1$-C$_3$ alkoxy; —(CH$_2$)$_{0-2}$—C$_3$-C$_7$ cycloalkyl, which is optionally substituted with 1 or 2 groups that are independently —F, —OH, —C≡N, —CF$_3$, C$_1$-C$_3$ alkoxy and —NR$_5$R$_6$;

R$_{17}$ at each occurrence is an aryl group (preferably selected from phenyl, 1-naphthyl, 2-naphthyl indanyl, indenyl, dihydronaphthyl and tetralinyl) wherein said aryl group is optionally substituted with one or two groups that are independently —C$_1$-C$_3$ alkyl; —C$_1$-C$_4$ alkoxy; CF$_3$; —C$_2$-C$_6$ alkenyl or —C$_2$-C$_6$ alkynyl each of which is optionally substituted with one substituent selected from F, OH, C$_1$-C$_3$ alkoxy; halogen; OH; —C≡N; —C$_3$-C$_7$ cycloalkyl; —CO—(C$_1$-C$_4$ alkyl); or —SO$_2$—(C$_1$-C$_4$ alkyl);

R$_{18}$ is a heteroaryl group (preferably selected from pyridinyl, pyrimidinyl, quinolinyl, indolyl, pryidazinyl, pyrazinyl, isoquinolyl, quinazolinyl, quinoxalinyl, phthalazinyl, imidazolyl, isoxazolyl, oxazolyl, thiazolyl, furanyl, thienyl, pyrrolyl, oxadiazolyl or thiadiazolyl,) wherein said heteroaryl groups are optionally substituted with one or two groups that are independently —C$_1$-C$_6$ alkyl optionally substituted with one substituent selected from OH, C≡N, CF$_3$, C$_1$-C$_3$ alkoxy, and —NR$_5$R$_6$;

R$_{15}$ is selected from hydrogen, C$_1$-C$_6$ alkyl, C$_1$-C$_6$ alkoxy, C$_1$-C$_6$ alkoxy C$_1$-C$_6$ alkyl, hydroxy C$_1$-C$_6$ alkyl, halo C$_1$-C$_6$ alkyl, each of which is unsubstituted or substituted with 1, 2, 3, or 4 groups independently selected from halogen, C$_1$-C$_6$ alkyl, hydroxy, C$_1$-C$_6$ alkoxy, and NH$_2$, and —R$_{26}$-R$_{27}$; wherein R$_{26}$ is selected from a bond, —C(O)—, —SO$_2$—, —CO$_2$—, —C(O)NR$_5$—, and —NR$_5$C(O)—, R$_{27}$ is selected from C$_1$-C$_6$ alkyl, C$_1$-C$_6$ alkoxy, aryl C$_1$-C$_6$ alkyl, heterocycloalkyl, and heteroaryl, wherein each of the above is unsubstituted or substituted with 1, 2, 3, 4, or 5 groups that are independently C$_1$-C$_4$ alkyl, C$_1$-C$_4$ alkoxy, halogen, haloalkyl, hydroxyalkyl, —NR$_5$R$_6$, or —C(O)NR$_5$R$_6$; or R$_2$, R$_3$ and the carbon to which they are attached form a C$_3$-C$_7$ carbocycle, wherein 1, 2, or 3 carbon atoms are optionally replaced by groups that are independently selected from —O—, —S—, —SO$_2$—, —C(O)—, or —NR$_7$—;

R$_c$ is selected from —(CH$_2$)$_{0-3}$—(C$_3$-C$_8$)cycloalkyl wherein the cycloalkyl is optionally substituted with 1, 2, or 3 groups independently selected from —R$_{205}$; and —CO$_2$—(C$_1$-C$_4$ alkyl); —(CR$_{245}$R$_{250}$)$_{0-4}$-aryl; —(CR$_{245}$R$_{250}$)$_{0-4}$-heteroaryl; —(CR$_{245}$R$_{250}$)$_{0-4}$-heterocycloalkyl; —(CR$_{245}$R$_{250}$)$_{0-4}$-aryl-heteroaryl; —(CR$_{245}$R$_{250}$)$_{0-4}$-aryl-heterocycloalkyl; —(CR$_{245}$R$_{250}$)$_{0-4}$-aryl-aryl; —(CR$_{245}$R$_{250}$)$_{0-4}$-heteroaryl-aryl; —(CR$_{245}$R$_{250}$)$_{0-4}$-heteroaryl-heterocycloalkyl; —(CR$_{245}$R$_{250}$)$_{0-4}$-heteroaryl-heteroaryl; —CHR$_{245}$—CHR$_{250}$-aryl; —(CR$_{245}$R$_{250}$)$_{0-4}$-heterocycloalkyl-heteroaryl; —(CR$_{245}$R$_{250}$)$_{0-4}$-heterocycloalkyl-heterocycloalkyl; —(CR$_{245}$R$_{250}$)$_{0-4}$-heterocycloalkyl-aryl; a monocyclic or bicyclic ring of 5, 6, 7 8, 9, or 10 carbons fused to 1 or 2 aryl (preferably phenyl), heteroaryl (preferably pyridyl, imidazolyl, thienyl, thiazolyl, or pyrimidyl), or heterocycloalkyl (preferably piperidinyl or piperazinyl) groups;

wherein 1, 2 or 3 carbons of the monocyclic or bicyclic ring are optionally replaced with —NH—, —N(CO)$_{0-1}$R$_{215}$—, —N(CO)$_{0-1}$R$_{220}$—, —O—, or —S(=O)$_{0-2}$—, and wherein the monocyclic or bicyclic ring is optionally substituted with 1, 2 or 3 groups that are independently —R$_{205}$, —R$_{245}$, —R$_{250}$ or =O;

and —C$_2$-C$_6$ alkenyl optionally substituted with 1, 2, or 3 R$_{205}$ groups;

wherein each aryl or heteroaryl group attached directly or indirectly to the —(CR$_{245}$R$_{250}$)$_{0-4}$ group is optionally substituted with 1, 2, 3 or 4 R$_{200}$ groups;

wherein each heterocycloalkyl attached directly or indirectly to the —(CR$_{245}$R$_{250}$)$_{0-4}$ group is optionally substituted with 1, 2, 3, or 4 R$_{210}$;

R$_{200}$ at each occurrence is independently selected from —C$_1$-C$_6$ alkyl optionally substituted with 1, 2, or 3 R$_{205}$ groups; —OH; —NO$_2$; -halogen; —C≡N; —(CH$_2$)$_{0-4}$—CO—NR$_{220}$R$_{225}$; —(CH$_2$)$_{0-4}$—CO—(C$_1$-C$_8$ alkyl); —(CH$_2$)$_{0-4}$—CO—(C$_2$-C$_8$ alkenyl); —(CH$_2$)$_{0-4}$—CO—(C$_2$-C$_8$ alkynyl); —(CH$_2$)$_{0-4}$—CO—(C$_3$-C$_7$ cycloalkyl); —(CH$_2$)$_{0-4}$—(CO)$_{0-1}$-aryl (preferably phenyl); —(CH$_2$)$_{0-4}$—(CO)$_{0-1}$-heteroaryl (preferably pyridyl, pyrimidyl, furanyl, imidazolyl, thienyl, oxazolyl, thiazolyl, or pyrazinyl); —(CH$_2$)$_{0-4}$—(CO)$_{0-1}$-heterocycloalkyl (preferably imidazolidinyl, piperazinyl, pyrrolidinyl, piperidinyl, or tetrahydropyranyl); —(CH$_2$)$_{0-4}$—CO$_2$R$_{215}$; —(CH$_2$)$_{0-4}$—SO$_2$—NR$_{220}$R$_{225}$; —(CH$_2$)$_{0-4}$—S(O)$_{0-2}$—(C$_1$-C$_8$ alkyl);

—$(CH_2)_{0-1}$—$S(O)_{0-2}$—$(C_3$-$C_7$ cycloalkyl); —$(CH_2)_{0-4}$—$N(H$ or $R_{215})$—$CO_2R_{215}$; —$(CH_2)_{0-4}$—$N(H$ or $R_{215})$—$SO_2$—$R_{220}$; —$(CH_2)_{0-4}$—$N(H$ or $R_{215})$—$CO$—$N(R_{215})_2$; —$(CH_2)_{0-4}$—$N($—$H$ or $R_{215})$—$CO$—$R_{220}$; —$(CH_2)_{0-4}$—$NR_{220}R_{225}$; —$(CH_2)_{0-4}$—$O$—$CO$—$(C_1$-$C_6$ alkyl); —$(CH_2)_{0-4}$—$O$—$(R_{215})$; —$(CH_2)_{0-4}$—$S$—$(R_{215})$; —$(CH_2)_{0-4}$—$O$—$(C_1$-$C_6$ alkyl optionally substituted with 1, 2, 3, or 5 -F); —$C_2$-$C_6$ alkenyl optionally substituted with 1 or 2 $R_{205}$ groups; —$C_2$-$C_6$ alkynyl optionally substituted with 1 or 2 $R_{205}$ groups; adamantly, and —$(CH_2)_{0-4}$—$C_3$-$C_7$ cycloalkyl;

each aryl and heteroaryl group included within $R_{200}$ is optionally substituted with 1, 2, or 3 groups that are independently —$R_{205}$, —$R_{210}$ or —$C_1$-$C_6$ alkyl substituted with 1, 2, or 3 groups that are independently $R_{205}$ or $R_{210}$;

each heterocycloalkyl group included within $R_{200}$ is optionally substituted with 1, 2, or 3 groups that are independently $R_{210}$;

$R_{205}$ at each occurrence is independently selected from —$C_1$-$C_6$ alkyl, —$C_2$-$C_6$ alkenyl, —$C_2$-$C_6$ alkynyl, —$C_1$-$C_6$ haloalkoxy, —$(CH_2)_{0-3}(C_3$-$C_7$ cycloalkyl), -halogen, —$(CH_2)_{0-6}$—OH, —O-phenyl, OH, SH, —$(CH_2)_{0-6}$—C≡N, —$(CH_2)_{0-6}$—C(=O)$NR_{235}R_{240}$, —$CF_3$, —$C_1$-$C_6$ alkoxy, $C_1$-$C_6$ alkoxycarbonyl, and —$NR_{235}R_{240}$;

$R_{210}$ at each occurrence is independently selected from —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; $C_1$-$C_6$ alkanoyl; —$SO_2$—($C_1$-$C_6$ alkyl); —$C_2$-$C_6$ alkynyl optionally substituted with 1, 2, or 3 $R_{205}$ groups; -halogen; —$C_1$-$C_6$ alkoxy; —$C_1$-$C_6$ haloalkoxy; —$NR_{220}R_{225}$; —OH; —C≡N; —$C_3$-$C_7$ cycloalkyl optionally substituted with 1, 2, or 3 $R_{205}$ groups; —CO—($C_1$-$C_4$ alkyl); $SO_2$—$NR_{235}R_{240}$; —CO—$NR_{235}R_{240}$; —$SO_2$—($C_1$-$C_4$ alkyl); and =O;

$R_{215}$ at each occurrence is independently selected from —$C_1$-$C_6$ alkyl, —$(CH_2)_{0-2}$-(aryl), —$C_2$-$C_6$ alkenyl, —$C_2$-$C_6$ alkynyl, —$C_3$-$C_7$ cycloalkyl, —$(CH_2)_{0-2}$-(heteroaryl), and —$(CH_2)_{0-2}$-(heterocycloalkyl); wherein the aryl group included within $R_{215}$ is optionally substituted with 1, 2, or 3 groups that are independently —$R_{205}$ or —$R_{210}$; wherein the heterocyloalkyl and heteroaryl groups included within $R_{215}$ are optionally substituted with 1, 2, or 3 $R_{210}$;

$R_{220}$ and $R_{225}$ at each occurrence are independently H, —$C_1$-$C_6$ alkyl, —CHO, hydroxy $C_1$-$C_6$ alkyl, $C_1$-$C_6$ alkoxycarbonyl, -amino $C_1$-$C_6$ alkyl, —$SO_2$—$C_1$-$C_6$ alkyl, $C_1$-$C_6$ alkanoyl optionally substituted with up to three halogens, —C(O)$NH_2$, —C(O)NH($C_1$-$C_6$ alkyl), —C(O)N($C_1$-$C_6$ alkyl)($C_1$-$C_6$ alkyl), -halo $C_1$-$C_6$ alkyl, —$(CH_2)_{0-2}$—($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, -aryl (preferably phenyl), -heteroaryl, or -heterocycloalkyl; wherein the aryl, heteroaryl and heterocycloalkyl groups included within $R_{220}$ and $R_{225}$ is optionally substituted with 1, 2, or 3 $R_{270}$ groups, $R_{270}$ at each occurrence is independently —$R_{205}$, —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; —$C_2$-$C_6$ alkynyl optionally substituted with 1, 2, or 3 $R_{205}$ groups; —phenyl; -halogen; —$C_1$-$C_6$ alkoxy; —$C_1$-$C_6$ haloalkoxy; —$NR_{235}R_{240}$; —OH; —C≡N; —$C_3$-$C_7$ cycloalkyl optionally substituted with 1, 2, or 3 $R_{205}$ groups; —CO—($C_1$-$C_4$ alkyl); —$SO_2$—$NR_{235}R_{240}$; —CO—$NR_{235}R_{240}$; —$SO_2$—($C_1$-$C_4$ alkyl); and =O;

$R_{235}$ and $R_{240}$ at each occurrence are independently —H, —$C_1$-$C_6$ alkyl, $C_2$-$C_6$ alkanoyl, —$SO_2$—($C_1$-$C_6$ alkyl), or -phenyl;

$R_{245}$ and $R_{250}$ at each occurrence are independently selected from H, —$(CH_2)_{0-4}CO_2C_1$-$C_4$ alkyl, —$(CH_2)_{0-4}C(=O)C_1$-$C_4$ alkyl, —$C_1$-$C_4$ alkyl, —$C_1$-$C_4$ hydroxyalkyl, —$C_1$-$C_4$ alkoxy, —$C_1$-$C_4$ haloalkoxy, —$(CH_2)_{0-4}$—$C_3$-$C_7$ cycloalkyl, —$C_2$-$C_6$ alkenyl, —$C_2$-$C_6$ alkynyl, —$(CH_2)_{0-4}$ aryl, —$(CH_2)_{0-4}$ heteroaryl, and —$(CH_2)_{0-4}$ heterocycloalkyl, or $R_{245}$ and $R_{250}$ are taken together with the carbon to which they are attached to form a monocycle or bicycle of 3, 4, 5, 6, 7 or 8 carbon atoms, where 1, 2, or 3 carbon atoms are optionally replaced by 1, 2, or 3 groups that are independently —O—, —S—, —$SO_2$—, —C(O)—, —$NR_{220}$—, or —$NR_{220}R_{220}$— wherein both $R_{220}$ groups are alkyl; and wherein the ring is optionally substituted with 1, 2, 3, 4, 5, or 6 groups that are independently $C_1$-$C_4$ alkyl, $C_1$-$C_4$ alkoxy, hydroxyl, $NH_2$, $NH(C_1$-$C_6$ alkyl), $N(C_1$-$C_6$ alkyl)($C_1$-$C_6$ alkyl), —NH—C(O)$C_1$-$C_5$ alkyl, —NH—$SO_2$—($C_1$-$C_6$ alkyl), or halogen;

wherein the aryl, heteroaryl or heterocycloalkyl groups included within $R_{245}$ and $R_{250}$ are optionally substituted with 1, 2, or 3 groups that are independenly halogen, $C_{1-6}$ alkyl, CN or OH.

The invention also provides methods for the treatment or prevention of Alzheimer's disease, mild cognitive impairment Down's syndrome, Hereditary Cerebral Hemorrhage with Amyloidosis of the Dutch-Type, cerebral amyloid angiopathy, other degenerative dementias, dementias of mixed vascular and degenerative origin, dementia associated with Parkinson's disease, dementia associated with progressive supranuclear palsy, dementia associated with cortical basal degeneration, diffuse Lewy body type of Alzheimer's disease comprising administration of a therapeutically effective amount of a compound or salt of formula I, to a patient in need thereof.

Preferably, the patient is a human.

More preferably, the disease is Alzheimer's disease.

More preferably, the disease is dementia.

The invention also provides pharmaceutical compositions comprising a compound or salt of formula I and at least one pharmaceutically acceptable carrier, solvent, adjuvant or diluent.

The invention also provides the use of a compound or salt according to formula I for the manufacture of a medicament.

The invention also provides the use of a compound or salt of formula I for the treatment or prevention of Alzheimer's disease, mild cognitive impairment Down's syndrome, Hereditary Cerebral Hemorrhage with Amyloidosis of the Dutch-Type, cerebral amyloid angiopathy, other degenerative dementias, dementias of mixed vascular and degenerative origin, dementia associated with Parkinson's disease, dementia associated with progressive supranuclear palsy, dementia associated with cortical basal degeneration, or diffuse Lewy body type of Alzheimer's disease.

The invention also provides compounds, pharmaceutical compositions, kits, and methods for inhibiting beta-secretase-mediated cleavage of amyloid precursor protein (APP). More particularly, the compounds, compositions, and methods of the invention are effective to inhibit the production of A-beta peptide and to treat or prevent any human or veterinary disease or condition associated with a pathological form of A-beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD, and for treating frontotemporal dementias with parkinsonism (FTDP).

The compounds of the invention possess beta-secretase inhibitory activity. The inhibitory activities of the compounds of the invention is readily demonstrated, for example, using one or more of the assays described herein or known in the art.

Unless the substituents for a particular formula are expressly defined for that formula, they are understood to carry the definitions set forth in connection with the preceding formula to which the particular formula makes reference.

The invention also provides methods of preparing the compounds of the invention and the intermediates used in those methods.

The invention also provides the use of compounds and pharmaceutically acceptable salts of formula I for the manufacture of a medicament for use in: treating a subject who has, or in preventing a subject from developing Alzheimer's disease (AD); preventing or delaying the onset of Alzheimer's disease; treating subjects with mild cognitive impairment (MCI); preventing or delaying the onset of Alzheimer's disease in subjects who would progress from MCI to AD; treating Down's syndrome; treating subjects who have Hereditary Cerebral Hemorrhage with Amyloidosis of the Dutch-Type; treating cerebral amyloid angiopathy and preventing its potential consequences; treating other degenerative dementias; treating dementia associated with Parkinson's disease, progressive supranuclear palsy, or cortical basal degeneration; treating diffuse Lewy body type AD; and treating frontotemporal dementias with parkinsonism (FTDP).

DETAILED DESCRIPTION OF THE INVENTION

As noted above, the invention provides compounds of formula I. In accordance with compounds of formula I and other applicable formulas below, when Z is $(C_3-C_7 \text{ cycloalkyl})_{0-1}(C_1-C_6 \text{ alkyl})$-, $(C_3-C_7 \text{ cycloalkyl})_{0-1}(C_2-C_6 \text{ alkenyl})$-, $(C_3-C_7 \text{ cycloalkyl})_{0-1}(C_2-C_6 \text{ alkynyl})$- or $(C_3-C_7 \text{ cycloalkyl})$-, 1 or 2 methylene groups within said $(C_3-C_7 \text{ cycloalkyl})_{0-1}(C_1-C_6 \text{ alkyl})$-, $(C_3-C_7 \text{ cycloalkyl})_{0-1}(C_2-C_6 \text{ alkenyl})$-, $(C_3-C_7 \text{ cycloalkyl})_{0-1}(C_2-C_6 \text{ alkynyl})$- or $(C_3-C_7 \text{ cycloalkyl})$-groups are optionally replaced with —(C=O)—. This optionally substitution may be alpha to X, e.g., α,β-diketo compounds are contemplated by the invention Further such carbonyl substitution contemplates compounds, for example, in which a methylene group is replaced in the cyclic portion the cycloalkyl group (to form a cyclic ketone moiety) and/or in which a methylene group is replaced in the alkyl, alkenyl or alkynyl portion of such groups.

Preferred compounds of formula I include those wherein Z is $(C_3-C_7 \text{ cycloalkyl})_{0-1}(C_1-C_6 \text{ alkyl})$-, $(C_3-C_7 \text{ cycloalkyl})_{0-1}(C_2-C_6 \text{ alkenyl})$-, $(C_3-C_7 \text{ cycloalkyl})_{0-1}(C_2-C_6 \text{ alkynyl})$- or $(C_3-C_7 \text{ cycloalkyl})$-, wherein each of said groups is optionally substituted with 1, 2, or 3 $R_Z$ groups;

$R_Z$ at each occurrence is independently halogen, —OH, —CN, $C_1$-$C_6$ alkoxy, $C_3$-$C_7$ cycloalkyl, $C_3$-$C_7$ cycloalkoxy, or —$NR_{100}R_{101}$;

$R_{100}$ and $R_{101}$ are independently H, $C_1$-$C_6$ alkyl, phenyl, $CO(C_1$-$C_6$ alkyl) or $SO_2C_1$-$C_6$ alkyl.

In another preferred embodiment, the invention encompasses compounds of formula I wherein Z is as defined above and X is —(C=O)—. In an alternative embodiment, X is —(C=O)—, and Z is H. In another preferred embodiment, X is —(C=O)—, and Z is $C_1$-$C_4$ alkyl, more preferably $C_1$-$C_3$ alkyl, even more preferably methyl.

Preferred compounds of formula I further include those wherein $R_1$ is $C_1$-$C_{10}$ alkyl optionally substituted with 1 or 2 groups independently selected from halogen, —OH, =O, —$CF_3$, —$OCF_3$, —$C_{3-7}$ cycloalkyl, —$C_1$-$C_4$ alkoxy, amino and aryl, wherein the aryl (preferably phenyl) group is optionally substituted with 1 or 2 $R_{50}$ groups;

$R_{50}$ is selected from halogen, OH, —CO—($C_1$-$C_4$ alkyl), —$NR_7R_8$, $C_1$-$C_6$ alkyl, $C_1$-$C_6$ alkoxy and $C_3$-$C_8$ cycloalkyl; wherein the alkyl, alkoxy and cycloalkyl groups are optionally substituted with 1 or 2 substituents independently selected from $C_1$-$C_4$ alkyl, halogen, OH, —$NR_5R_6$, $NR_7R_8$, and $C_1$-$C_4$ alkoxy;

$R_5$ and $R_6$ at are independently H or $C_1$-$C_6$ alkyl; or $R_5$ and $R_6$ and the nitrogen to which they are attached form a 5 or 6 membered heterocycloalkyl ring; and $R_7$ and $R_8$ are independently selected from —H; —$C_1$-$C_4$ alkyl optionally substituted with 1, 2, or 3 groups independently selected from —OH, —$NH_2$, and halogen; —$C_3$-$C_6$ cycloalkyl; and —($C_1$-$C_4$ alkyl)-O—($C_1$-$C_4$ alkyl).

Preferred compounds of formula I also include those wherein $R_1$ is —$CH_2$-phenyl where the phenyl ring is optionally substituted with 1 or 2 groups independently selected from halogen, $C_1$-$C_2$ alkyl, $C_1$-$C_2$ alkoxy and hydroxy. More preferably, $R_1$ is benzyl, 3-fluorobenzyl or 3,5-difluorobenzyl.

Preferred compounds of formula I include those wherein $R_2$ and $R_3$ are independently —H or —$C_1$-$C_6$ alkyl.

Equally preferred compounds of formula I include those wherein $R_{15}$ is H.

In another aspect, the invention provides compounds of the formula II:

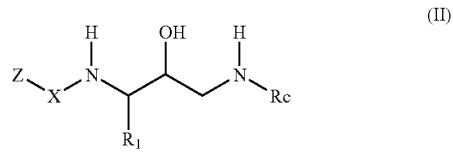

and pharmaceutically acceptable salts thereof, wherein
Z is hydrogen, —$C_1$-$C_6$ alkyl, —$C_2$-$C_6$ alkenyl, —$C_2$-$C_6$ alkynyl or —$C_3$-$C_7$ cycloalkyl, where each of said groups is optionally substituted with 1 or 2 $R_Z$ groups, wherein 1 or 2 methylene groups within said —$C_1$-$C_6$ alkyl, —$C_2$-$C_6$ alkenyl, —$C_2$-$C_6$ alkynyl or —$C_3$-$C_7$ cycloalkyl groups are optionally replaced with —(C=O)—;

$R_Z$ at each occurrence is independently halogen, —OH, —CN, —CF$_3$, $C_1$-$C_6$ alkoxy, $C_3$-$C_7$ cycloalkyl, $C_3$-$C_7$ cycloalkoxy or —NR$_{100}$R$_{101}$;

$R_{100}$ and $R_{101}$ are independently H, $C_1$-$C_6$ alkyl, phenyl, CO(C$_1$-C$_6$ alkyl) or SO$_2$C$_1$-C$_6$ alkyl;

X is —C(=O)—;

$R_1$ is $C_1$-$C_{10}$ alkyl optionally substituted with 1 or 2 groups independently selected from halogen, —OH, =O, —CN, —CF$_3$, —OCF$_3$, —C$_3$-C$_7$ cycloalkyl, —C$_1$-C$_4$ alkoxy, amino, mono-dialkylamino, aryl, heteroaryl or heterocycloalkyl, wherein the aryl group is optionally substituted with 1 or 2 R$_{50}$ groups;

$R_{50}$ is halogen, OH, CN, —CO—(C$_1$-C$_4$ alkyl), —NR$_7$R$_8$, C$_1$-C$_6$ alkyl, C$_2$-C$_6$ alkenyl, C$_2$-C$_6$ alkynyl, C$_1$-C$_6$ alkoxy, and C$_3$-C$_8$ cycloalkyl;

$R_7$ and $R_8$ are selected from H; —C$_1$-C$_4$ alkyl optionally substituted with 1, 2, or 3 groups selected from —OH, —NH$_2$ and halogen; —C$_3$-C$_6$ cycloalkyl; —(C$_1$-C$_4$ alkyl)—O—(C$_1$-C$_4$ alkyl); —C$_2$-C$_4$ alkenyl; and —C$_2$-C$_4$ alkynyl;

$R_c$ is selected from —(CR$_{245}$R$_{250}$)$_{0-4}$-aryl; —(CR$_{245}$R$_{250}$)$_{0-4}$-heteroaryl; —(CR$_{245}$R$_{250}$)$_{0-4}$-heterocycloalkyl; where the aryl and heteroaryl groups attached to the —(CR$_{245}$R$_{250}$)$_{0-4}$— group are optionally substituted with 1, 2, 3 or 4 R$_{200}$ groups; where the heterocycloalkyl group attached to the —(CR$_{245}$R$_{250}$)$_{0-4}$— group is optionally substituted with 1, 2, 3, or 4 R$_{210}$ groups; and $R_{245}$ $R_{250}$, $R_{200}$, and $R_{210}$ are as defined above.

In another aspect, the invention provides compounds wherein $R_c$ is —(CR$_{245}$R$_{250}$)$_{0-4}$-heterocycloalkyl (preferably piperidinyl, piperazinyl, pyrrolidinyl, 2-oxo-tetrahydroquinolinyl, 2-oxo-dihydro-1H-indolyl, or imidazolidinyl); where the heterocycloalkyl group attached to the —(CR$_{245}$R$_{250}$)$_{0-4}$— group is optionally substituted with 1, 2, 3, or 4 R$_{210}$ groups.

In a further preferred embodiment for compounds of formula II, Z is —C$_1$-C$_6$ alkyl;

$R_1$ is $C_1$-$C_{10}$ alkyl optionally substituted with 1 or 2 aryl groups, which are optionally substituted with 1 or 2 R$_{50}$ groups, each $R_{50}$ is independently halogen, OH, CN, —NR$_7$R$_8$ or C$_1$-C$_6$ alkyl, $R_7$ and $R_8$ are independently —H; —C$_1$-C$_4$ alkyl optionally substituted with 1 or 2 groups independently selected from —OH, —NH$_2$, and halogen; or —C$_3$-C$_6$ cycloalkyl; and $R_c$ is —(CR$_{245}$R$_{250}$)$_{0-4}$-aryl or —(CR$_{245}$R$_{250}$)$_{0-4}$-heteroaryl (preferably the heteroaryl is pyridyl, pyrimidyl, quinolinyl, isoquinolinyl, more preferably pyridyl), where the aryl and heteroaryl groups are optionally substituted with 1 or 2 R$_{200}$ groups, where R$_{200}$ is as defined above.

Still more preferred compounds of formula II, include those wherein $R_1$ is $C_1$-$C_{10}$ alkyl substituted with one aryl group, where the aryl (preferably phenyl or naphthyl, still more preferably phenyl) group is optionally substituted with 1 or 2 R$_{50}$ groups;

$R_c$ is —(CR$_{245}$R$_{250}$)$_{1-4}$-aryl or —(CR$_{245}$R$_{250}$)$_{1-4}$-heteroaryl, $R_{245}$ and $R_{250}$ are independently selected from H, —(CH$_2$)$_{0-4}$CO$_2$C$_1$-C$_4$ alkyl, —(CH$_2$)$_{0-4}$CO$_2$H, —C$_1$-C$_4$ alkyl, —(C$_1$-C$_4$ alkyl)OH, or $R_{245}$, $R_{250}$ and the carbon to which they are attached form a monocycle or bicycle of 3, 4, 5, 6, 7 or 8 carbon atoms, where 1 or 2 carbon atoms are optionally replaced by —O—, —S—, —SO$_2$—, or —NR$_{220}$—, where R$_{220}$ is as defined above; and wherein the aryl and heteroaryl groups attached to the —(CR$_{245}$R$_{250}$)$_{1-4}$— groups are optionally substituted with 1 or 2 R$_{200}$ groups.

In another preferred embodiment of compounds of formula II, $R_1$ is $C_1$-$C_{10}$ alkyl substituted with one aryl group (preferably phenyl or naphthyl), which is optionally substituted with 1 or 2 R$_{50}$ groups, R$_{50}$ is independently halogen, OH, or C$_1$-C$_6$ alkyl;

$R_c$ is —(CR$_{245}$R$_{250}$)-aryl or —(CR$_{245}$R$_{250}$)-heteroaryl, wherein the aryl and heteroaryl groups attached to the —(CR$_{245}$R$_{250}$)$_{1-4}$— groups are optionally substituted with 1 or 2 substituents selected from —Cl, —Br, —I, —C$_1$-C$_3$ alkyl, —(C$_1$-C$_3$ alkyl)OH, —CN, —C≡CH, —C≡C—CH$_2$—OH, —CF$_3$, -thienyl optionally substituted with a —C(=O)H group, -phenyl optionally substituted with 1 or 2 C$_1$-C$_3$ alkyl groups, —(C$_1$-C$_3$ alkyl)OH group or —CO(C$_1$-C$_3$ alkyl) group, -isoxazolyl optionally substituted with a C$_1$-C$_4$ alkyl group, or —(C$_1$-C$_2$ alkyl)oxazolyl where the oxazole ring is optionally substituted with —C$_1$-C$_2$ alkyl group;

$R_{245}$ and $R_{250}$ at each occurance are independently —H, —C$_1$-C$_3$ alkyl, —(C$_1$-C$_3$ alkyl)CO$_2$H, —(C$_1$-C$_3$ alkyl)CO$_2$(C$_1$-C$_3$ alkyl), or —(C$_1$-C$_3$ alkyl)OH, or $R_{245}$ and $R_{250}$ are taken together with the carbon to which they are attached to form a monocycle or bicycle of 3, 4, 5, 6, 7 or 8 carbon atoms, where 1 or 2 carbon atoms is optionally replaced by —O—, —S—, —SO$_2$—, or —NR$_{220}$—, and $R_{220}$ is as defined above.

In another aspect, the invention provides compounds of the formula III:

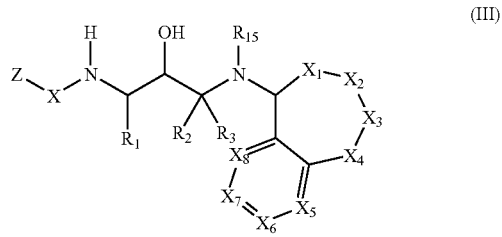

(III)

and pharmaceutically acceptable salts thereof; where

Z, X, $R_1$, $R_2$, $R_3$ and $R_{15}$ are as definded above;

$X_1$ is CH$_2$, CHR$_{200}$, C(R$_{200}$)$_2$, or —(C=O)—;

$X_2$, and $X_3$ are independently CH$_2$, CHR$_{200}$, C(R$_{200}$)$_2$, O, C=O, S, SO$_2$, NH, or NR$_7$;

$X_4$ is a bond, CH$_2$, CHR$_{200}$, C(R$_{200}$)$_2$O, C=O, S, SO$_2$, NH, or NR$_7$;

provided that when $X_1$ is —(C=O)—, $X_2$ is CH$_2$, CHR$_{200}$, C(R$_{200}$)$_2$, O, NH or NR$_7$ and the X$_3$ group attached to X$_2$ is CH$_2$, CHR$_{200}$, C(R$_{200}$)$_2$, or SO$_2$ when X$_2$ is NH or NR$_7$ and X$_4$ is CH$_2$, CHR$_{200}$, or C(R$_{200}$)$_2$ or a bond; or —X$_2$-X$_3$— is —(C=O)O—, —O(C=O)—, —(C=O)NH—, —NH(C=O)—, —(C=O)NR$_7$—, or —NR$_7$(C=O)—, with the proviso that X$_1$ is not —(C=O)— and with the proviso that X$_4$ is CH$_2$, CHR$_{200}$, or C(R$_{200}$)$_2$ or a bond; or —X$_3$-X$_4$— is —(C=O)O—, —O(C=O)—, —(C=O)NH—, —NH(C=O)—, —(C=O)NR$_7$—, or —NR$_7$(C=O)—, with the proviso that X$_2$ is CH$_2$, CHR$_{200}$, or C(R$_{200}$)$_2$; or —$X_2$-$X_3$-$X_4$— is —(C=O)NH—$SO_2$— or —$SO_2$—NH(C=O)—, —(C=O)$NR_7$—$SO_2$— or —$SO_2$—$NR_7$(C=O)—, with the proviso that $X_1$ is not —(C=O)—; and $X_5$, $X_6$, $X_7$ and $X_8$ are CH or $CR_{200}$, where 1 or 2 of $X_5$, $X_6$, $X_7$ and $X_8$ is optionally replaced with N, and where $R_{200}$ and $R_7$ are as defined above.

In a preferred embodiment of compounds of formula III, the invention further provides compounds of the formula IV:

wherein

Z is hydrogen, —$C_1$-$C_6$ alkyl, —$C_2$-$C_6$ alkenyl, —$C_2$-$C_6$ alkynyl or —$C_3$-$C_7$ cycloalkyl, where each is optionally substituted with 1 or 2 $R_z$ groups, and wherein 1 or 2 methylene groups within said —$C_1$-$C_6$ alkyl, —$C_2$-$C_6$ alkenyl, —$C_2$-$C_6$ alkynyl or —$C_3$-$C_7$ cycloalkyl groups are optionally replaced with —(C=O)—;

$R_z$ at each occurrence is independently halogen, —OH, —CN, —$CF_3$, $C_1$-$C_6$ alkoxy, $C_3$-$C_7$ cycloalkyl, $C_3$-$C_7$ cycloalkoxy or —$NR_{100}R_{101}$;

$R_{100}$ and $R_{101}$ are independently H, $C_1$-$C_6$ alkyl, phenyl, CO($C_1$-$C_6$ alkyl) or $SO_2C_1$-$C_6$ alkyl;

X is —C(=O)—;

$R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl optionally substituted with 1 or 2 $R_{50}$ groups, heteroaryl or heterocycloalkyl;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy or $C_3$-$C_8$ cycloalkyl; and $R_7$ and $R_8$ are selected from H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl.

In other preferred compounds of formula IV,

Z is —$C_1$-$C_6$ alkyl;

$R_1$ is $C_1$-$C_{10}$ alkyl optionally substituted with 1 or 2 aryl (preferably phenyl or naphthyl) groups, which are optionally substituted with 1 or 2 $R_{50}$ groups, $R_{50}$ is independently halogen, OH, CN, —$NR_7R_8$ or $C_1$-$C_4$ alkyl, $R_7$ and $R_8$ are independently H; —$C_1$-$C_4$ alkyl optionally substituted with 1 or 2 groups independently selected from —OH, —$NH_2$, and halogen; or —$C_3$-$C_6$ cycloalkyl; and $X_1$, $X_2$ or $X_3$ are $CH_2$ or $CHR_{200}$, where one of $X_2$ or $X_3$ is optionally replaced with O, C=O, $SO_2$, NH, $NR_7$, $X_4$ is a bond; and $X_5$, $X_6$, $X_7$ and $X_8$ are CH or $CR_{200}$, where one of $X_5$, $X_6$, $X_7$ or $X_8$ is optionally replaced with N, and $R_{200}$ is as defined above.

In yet another preferred aspect of the invention for compounds of formula VI, $R_1$ is $C_1$-$C_{10}$ alkyl substituted with one aryl group, where the aryl group is optionally substituted with 1 or 2 $R_{50}$ groups;

$X_1$, $X_2$ and $X_3$ are $CH_2$, $CHR_{200}$, or C($R_{200}$)$_2$, where one of $X_2$ or $X_3$ is optionally replaced with O, NH or $NR_7$, and where $X_4$ is a bond; and $X_5$, $X_6$, $X_7$ and $X_8$ are CH or $CR_{200}$, where one of $X_5$, $X_6$, $X_7$ or $X_8$ is optionally replaced with N, where $R_{50}$, $R_{200}$ and $R_7$ are as defined above.

In a further preferred embodiment of compound of formula IV, $R_1$ is $C_1$-$C_{101}$ alkyl substituted with one aryl group (preferably phenyl or naphthyl, more preferably phenyl), where the aryl group is optionally substituted with 1 or 2 $R_{50}$ groups, $R_{50}$ is independently halogen, OH, or $C_1$-$C_6$ alkyl;

$X_1$, $X_2$ and $X_3$ are $CH_2$ or $CHR_{200}$, where one of $X_2$ or $X_3$ is optionally replaced with O, NH or $NR_7$;

$X_4$ is a bond;

$X_5$, $X_6$, $X_7$ and $X_8$ are CH or $CR_{200}$, where one of $X_5$, $X_6$, $X_7$ and $X_8$ is optionally replaced with N; and $R_{200}$ is —$C_{1-4}$ alkyl, -halogen; —O—$C_{1-3}$ alkyl; -pyrrolyl or —($CH_2$)$_{1-3}$—N($R_7$)$_2$, where $R_7$ is as defined above.

In another aspect, the invention provides compounds of V:

and a pharmaceutically acceptable salt thereof, wherein

Z is hydrogen, —$C_1$-$C_6$ alkyl, —$C_2$-$C_6$ alkenyl, —$C_2$-$C_6$ alkynyl or —$C_3$-$C_7$ cycloalkyl, where each of said groups is optionally substituted with 1 or 2 $R_z$ groups, wherein 1 or 2 methylene groups within said —$C_1$-$C_6$ alkyl, —$C_2$-$C_6$ alkenyl, —$C_2$-$C_6$ alkynyl or —$C_3$-$C_7$ cycloalkyl groups are optionally replaced with —(C=O)—;

$R_z$ at each occurrence is independently halogen, —OH, —CN, —$CF_3$, $C_1$-$C_6$ alkoxy, $C_3$-$C_7$ cycloalkyl, $C_3$-$C_7$ cycloalkoxy or —$NR_{100}R_{101}$;

$R_{100}$ and $R_{101}$ are independently H, $C_1$-$C_6$ alkyl, phenyl, CO($C_1$-$C_6$ alkyl) or $SO_2C_1$-$C_6$ alkyl;

X is —C(=O)—;

$R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl optionally substituted with 1 or 2 $R_{50}$ groups, heteroaryl or heterocycloalkyl;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy and $C_3$-$C_8$ cycloalkyl;

$R_7$ and $R_8$ are selected from H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl;

$X_1$-$X_8$ are independently CH or $CR_{200}$, where 1, 2, 3 or 4 of $X_1$-$X_8$ are optionally replaced with N (more preferably, 1, 2, or 3 are replaced with N);

where $R_{200}$ is as definded above.

In another preferred embodiment for compounds of formula V,

Z is —$C_1$-$C_6$ alkyl;

$R_1$ is $C_1$-$C_{10}$ alkyl optionally substituted with 1 or 2 aryl groups, where each aryl group is optionally substituted with 1 or 2 $R_{50}$ groups, $R_{50}$ is independently halogen, OH, CN, —$NR_7R_8$ or $C_1$-$C_6$ alkyl, $R_7$ and $R_8$ are independently H; —$C_1$-$C_4$ alkyl optionally substituted with 1 or 2 groups independently selected from —OH, —$NH_2$, and halogen; or —$C_3$-$C_6$ cycloalkyl; and $X_1$-$X_8$ are CH or $CR_{200}$, where one or two of $X_1$-$X_8$ is optionally replaced with N, and $R_{50}$ and $R_{200}$ are as defined above.

In another preferred embodiment for compounds of formula V, $R_1$ is $C_1$-$C_{10}$ alkyl substituted with one aryl group, where the aryl group (preferably phenyl) is optionally substituted with 1 or 2 $R_{50}$ groups, $R_{50}$ is independently selected from halogen, OH, or $C_1$-$C_6$ alkyl;

$X_1$-$X_8$ are CH or $CR_{200}$, where one of $X_1$-$X_8$ is optionally replaced with N.

In another preferred embodiment for compounds of formula V, $R_{200}$ is —$C_1$-$C_5$ alkyl, —$C_2$-$C_5$ alkenyl, —$C_3$-$C_6$ cycloalkyl, halogen, —$CF_3$, —O—$C_1$-$C_3$ alkyl, —($C_1$-$C_3$ alkyl)-O—($C_1$-$C_3$ alkyl), pyrrolyl, or —$(CH_2)_{1-3}$—$N(R_7)_2$.

In a further aspect, the invention provides compounds of the formula VI:

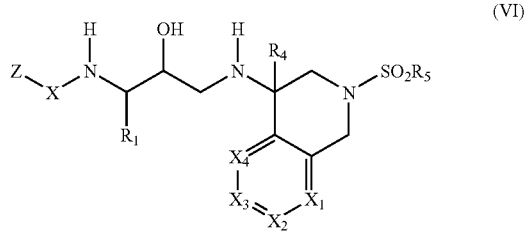

(VI)

and a pharmaceutically acceptable salt thereof, wherein

Z is hydrogen, —$C_1$-$C_6$ alkyl, —$C_2$-$C_6$ alkenyl, —$C_2$-$C_6$ alkynyl or —$C_3$-$C_7$ cycloalkyl, where each of said groups is optionally substituted with 1 or 2 $R_Z$ groups, wherein 1 or 2 methylene groups within said —$C_1$-$C_6$ alkyl, —$C_2$-$C_6$ alkenyl, —$C_2$-$C_6$ alkynyl or —$C_3$-$C_7$ cycloalkyl groups are optionally replaced with —(C=O)—;

$R_Z$ at each occurrence is independently halogen, —OH, —CN, —$CF_3$, $C_1$-$C_6$ alkoxy, $C_3$-$C_7$ cycloalkyl, $C_3$-$C_7$ cycloalkoxy or —$NR_{100}R_{101}$;

$R_{100}$ and $R_{101}$ are independently H, $C_1$-$C_6$ alkyl, phenyl, CO($C_1$-$C_6$ alkyl) or $SO_2C_1$-$C_6$ alkyl;

X is —C(=O)—;

$R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl, heteroaryl and heterocycloalkyl, wherein the aryl, heterocycloalkyl and heteroaryl groups are optionally substituted with 1 or 2 $R_{50}$ groups, wherein the heterocycloalkyl group is optionally further substituted with =O;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy and $C_3$-$C_8$ cycloalkyl;

$R_7$ and $R_8$ are selected from H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl;

$R_4$ is H or —$C_1$-$C_4$ alkyl;

$R_5$ is —$C_1$-$C_4$ alkyl;

$X_1$-$X_4$ are independently CH or $CR_{200}$, where 1 or 2 of $X_1$-$X_4$ are optionally replaced with N; and where $R_{200}$ is as defindted above.

In a preferred embodiment for compounds of formula VI,

Z is —$C_1$-$C_6$ alkyl;

$R_1$ is $C_1$-$C_{10}$ alkyl optionally substituted with 1 or 2 aryl groups, where each aryl group is optionally substituted with 1 or 2 $R_{50}$ groups, each $R_{50}$ is independently halogen, OH, CN, —$NR_7R_8$ or $C_1$-$C_6$ alkyl, $R_7$ and $R_8$ are independently H; —$C_1$-$C_4$ alkyl optionally substituted with 1 or 2 groups independently selected from —OH, —$NH_2$, and halogen; or —$C_3$-$C_6$ cycloalkyl; and $X_1$-$X_4$ are CH or $CR_{200}$, where one or two of $X_1$-$X_4$ is optionally replaced with N, $R_{200}$ is as defined above.

In a further preferred embodiment for compounds of formula VI, $R_1$ is $C_1$-$C_{10}$ alkyl substituted with one aryl group (preferably phenyl), where the aryl group is optionally substituted with 1 or 2 $R_{50}$ groups, $R_{50}$ is independently selected from halogen, OH, or $C_1$-$C_6$ alkyl;

$X_1$-$X_4$ are CH or $CR_{200}$, where one of $X_1$-$X_4$ is optionally replaced with N, and where $R_{50}$ and $R_{200}$ are as defined above.

In yet another preferred embodiment for compounds of formula VI, $R_{200}$ is —$C_3$-$C_5$ alkyl, —$C_1$-$C_5$ alkenyl, —$C_3$-$C_6$ cycloalkyl, halogen, —$CF_3$, —O—$C_1$-$C_3$ alkyl, —($C_1$-$C_3$ alkyl)-O—($C_1$-$C_3$ alkyl), pyrrolyl, or —$(CH_2)_{1-3}$—$N(R_7)_2$.

In another aspect, the invention provides compounds of the formula VII:

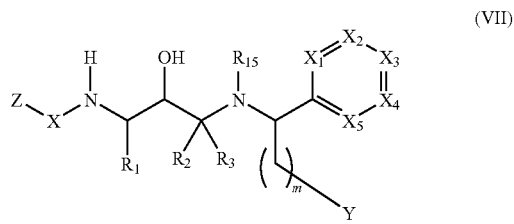

(VII)

and pharmaceutically acceptable salts thereof, wherein

Z, X, $R_1$, $R_2$ and $R_3$ are as defined above;

m is 0 or an integer of 1-6;

Y is H, CN, OH, $C_1$-$C_6$ alkoxy, $CO_2H$, $CO_2R_{215}$, $NH_2$, aryl or heteroaryl; and $X_1$-$X_5$ are independently CH or $CR_{200}$, where 1, or 2 of $X_1$-$X_5$ are optionally replaced with N, and $R_{200}$ is as defindted as above.

In a preferred embodiment of compounds of formula VII, $R_2$, $R_3$ and $R_{15}$ are H;

Z is hydrogen, —$C_1$-$C_6$ alkyl, —$C_2$-$C_6$ alkenyl, —$C_2$-$C_6$ alkynyl or —$C_3$-$C_7$ cycloalkyl, where each of said groups is optionally substituted with 1 or 2 $R_z$ groups, wherein 1 or 2 methylene groups within said —$C_1$-$C_6$ alkyl, —$C_2$-$C_6$ alkenyl, —$C_2$-$C_6$ alkynyl or —$C_3$-$C_7$ cycloalkyl groups are optionally replaced with —(C=O)—;

$R_Z$ at each occurrence is independently halogen, —OH, —CN, —$CF_3$, $C_1$-$C_6$ alkoxy, $C_3$-$C_7$ cycloalkyl, $C_3$-$C_7$ cycloalkoxy or —$NR_{100}R_{101}$;

$R_{100}$ and $R_{101}$ are independently H, $C_1$-$C_6$ alkyl, phenyl, $CO(C_1$-$C_6$ alkyl) or $SO_2C_1$-$C_6$ alkyl;

X is —C(=O)—;

$R_1$ is $C_1$-$C_{10}$ alkyl optionally substituted with 1 or 2 groups independently selected from halogen, —OH, =O, —CN, —$CF_3$, —$OCF_3$, —$C_3$-$C_7$ cycloalkyl, —$C_1$-$C_4$ alkoxy, amino, mono-dialkylamino, aryl, heteroaryl or heterocycloalkyl, wherein the aryl, heterocycloalkyl and heteroaryl groups are optionally substituted with 1 or 2 $R_{50}$ groups, and wherein the heterocycloalkyl group is optionally further substituted with =O;

$R_{50}$ is halogen, OH, CN, —CO—($C_1$-$C_4$ alkyl), —$NR_7R_8$, $C_1$-$C_6$ alkyl, $C_2$-$C_6$ alkenyl, $C_2$-$C_6$ alkynyl, $C_1$-$C_6$ alkoxy or $C_3$-$C_8$ cycloalkyl;

$R_7$ and $R_8$ are independently H; —$C_1$-$C_4$ alkyl optionally substituted with 1, 2, or 3 groups selected from —OH, —$NH_2$ and halogen; —$C_3$-$C_6$ cycloalkyl; —($C_1$-$C_4$ alkyl)-O—($C_1$-$C_4$ alkyl); —$C_2$-$C_4$ alkenyl; or —$C_2$-$C_4$ alkynyl;

Y is as defined above;

$X_1$-$X_5$ are independently CH or $CR_{200}$, where 1 or 2 of $X_1$-$X_5$ are optionally replaced with N; and $R_{200}$ is as definded above.

In yet another preferred embodiment for compounds of formula VII,

Z is —$C_1$-$C_6$ alkyl;

$R_1$ is $C_1$-$C_{10}$ alkyl optionally substituted with 1 or 2 aryl groups, where each aryl group is optionally substituted with 1 or 2 $R_{50}$ groups, $R_{50}$ is independently halogen, OH, CN, —$NR_7R_8$ or $C_1$-$C_6$ alkyl, $R_7$ and $R_8$ are independently —H; —$C_1$-$C_4$ alkyl optionally substituted with 1 or 2 groups independently selected from —OH, —$NH_2$, and halogen; or —$C_3$-$C_6$ cycloalkyl;

$X_1$-$X_5$ are CH or $CR_{200}$, where one or two of $X_1$-$X_5$ is optionally replaced with N.

More preferably for compounds of formula VII, $R_1$ is $C_1$-$C_{10}$ alkyl substituted with one aryl group, where the aryl group is optionally substituted with 1 or 2 $R_{50}$ groups, where $R_{50}$ is independently selected from halogen, OH, or $C_1$-$C_6$ alkyl;

wherein $X_1$-$X_5$ are CH or $CR_{200}$, where one of $X_1$-$X_5$ is optionally replaced with N, where $R_{50}$ and $R_{200}$ are as definded above.

In yet another preferred embodiment for compounds of formula VII, $R_{200}$ is —$C_1$-$C_5$ alkyl, —$C_1$-$C_5$ alkenyl, —$C_3$-$C_6$ cycloalkyl, halogen, —$CF_3$, —O—$C_1$-$C_3$ alkyl, —($C_1$-$C_3$ alkyl)-O—$C_1$-$C_3$ alkyl), pyrrolyl, or —$(CH_2)_{1-3}$—$N(R_7)_2$, where $R_7$ is as defined above.

In another aspect, the invention provides compounds of formula II, i.e., compounds of formula II-a, wherein $R_1$ is $C_1$-$C_{10}$ alkyl optionally substituted with 1 or 2 groups independently selected from halogen, —OH, =O, —$CF_3$, —$OCF_3$, —$C_{3-7}$ cycloalkyl, —$C_1$-$C_4$ alkoxy, amino and aryl, wherein the aryl group is optionally substituted with 1 or 2 $R_{50}$ groups;

wherein $R_{50}$ is selected from halogen, OH, —CO—($C_1$-$C_4$ alkyl), —$NR_7R_8$, $C_1$-$C_6$ alkyl, $C_1$-$C_6$ alkoxy and $C_3$-$C_8$ cycloalkyl; and $R_7$ and $R_8$ are independently —H; —$C_1$-$C_4$ alkyl optionally substituted with 1, 2, or 3 groups independently selected from —OH, —$NH_2$, and halogen; —$C_3$-$C_6$ cycloalkyl; or —($C_1$-$C_4$ alkyl)-O—($C_1$-$C_4$ alkyl).

Preferred compounds of formula II-a, include those of formula II-b, i.e., compounds wherein $R_c$ is $(CR_{245}R_{250})_1$-aryl, where the aryl is optionally substituted with 1, 2, or 3 $R_{200}$ groups; and $R_{245}$ is H and $R_{250}$ is H or $C_1$-$C_6$ alkyl; or $R_{245}$ and $R_{250}$ are independently $C_1$-$C_3$ alkyl (preferably both are methyl); or $CR_{245}R_{250}$ represents a $C_3$-$C_7$ cycloalkyl group.

Preferred compounds of formula II-b, include those of formula II-c, i.e., compounds wherein the $(CR_{245}R_{250})_1$-aryl is $(CR_{245}R_{250})_1$-phenyl where the phenyl is optionally substituted with 1, 2, or 3 $R_{200}$ groups.

Preferred compounds of formula II-c, include those of formula II-d, i.e., compounds wherein the phenyl in $(CR_{245}R_{250})_1$-phenyl is substituted with 1-3 independently selected $R_{200}$ groups, or 1 or 2 independently selected $R_{200}$ groups, and 1 heteroaryl group optionally substituted with 1 $R_{200}$ group or 1 phenyl group optionally substituted with 1 $R_{200}$ group.

Other preferred comounds include those wherein the phenyl is substituted with a heterocycloalkyl group, which is optionally substituted with 1 or 2 $R_{200}$ groups and/or =O.

Preferred compounds of formula II-d, include those of formula II-e, i.e., compounds wherein $R_{245}$ is hydrogen and $R_{250}$ is $C_1$-$C_3$ alkyl.

Preferred compounds of formula II-d, include those of formula II-f, i.e., compounds wherein $R_{245}$ and $R_{250}$ are both hydrogen.

Preferred compounds of formula II-f, include those of formula II-g, i.e., compounds wherein the phenyl in $(CR_{245}R_{250})_1$-phenyl is substituted with 1 $R_{200}$ group, and 1 heteroaryl group optionally substituted with 1 $R_{200}$ group or 1 $R_{200}$ group, and 1 phenyl group optionally substituted with 1 $R_{200}$ group; or 1 $R_{200}$ group, and 1 heterocycloalkyl, which is optionally substituted with one $R_{200}$ or =O.

Preferred compounds of formula II-g, include those of formula II-h, i.e., compounds wherein $R_{200}$ is $C_1$-$C_6$ alkyl, $C_2$-$C_6$ alkenyl, $C_1$-$C_6$ alkoxy, hydroxy($C_1$-$C_6$)alkyl, $C_1$-$C_6$ alkoxy($C_1$-$C_6$)alkyl, heterocycloalkyl, heteroaryl, halogen, hydroxy, cyano, or —$NR_{220}R_{225}$, where $R_{220}$ and $R_{225}$ are independently hydrogen or alkyl.

Preferred compounds of formulas II-g and II-h, include those of formula II-i, i.e., compounds wherein $R_1$ is benzyl where the phenyl portion is optionally substituted with 1 or 2 groups independently selected from halogen, $C_1$-$C_2$ alkyl, $C_1$-$C_2$ alkoxy, —O-allyl, and hydroxy.

Preferred compounds of formula II-i, include those of formula II-j, i.e., compounds wherein Z is hydrogen or $C_1$-$C_3$ alkyl.

Preferred compounds of formula II-i, include those of formula II-k, i.e., compounds wherein the phenyl in $(CR_{245}R_{250})_1$-phenyl is substituted with 1 $R_{200}$ group, and 1 heteroaryl group, wherein the heteroaryl is a 5-6 membered heteroaromatic ring containing 0 or 1-3 nitrogen atoms and 0 or 1 oxygen atoms provided that the ring contains at least one nitrogen or oxygen atom, and where the ring is optionally substituted with one or two groups which are independently $C_1$-$C_6$ alkyl, $C_1$-$C_6$ alkoxy, hydroxy($C_1$-$C_6$)alkyl, hydroxy, halogen, cyano, nitro, trifluoromethyl, amino, mono($C_1$-$C_6$)alkylamino, or di($C_1$-$C_6$)alkylamino.

Other preferred compounds include those of formula II-i, i.e., compounds of formula II-K-1, wherein the phenyl in $(CR_{245}R_{250})_1$-phenyl is substituted with $R_{200}$ group, and 1 heterocycloalkyl group, which is piperazinyl, piperidinyl or pyrrolidinyl and where the ring is optionally substituted with one or two groups which are independently $C_1$-$C_6$ alkyl, $C_1$-$C_6$ alkoxy, hydroxy($C_1$-$C_6$)alkyl, hydroxy, halogen, cyano, nitro, trifluoromethyl, —$SO_2$—($C_1$-$C_4$ alkyl), —$C_1$-$C_6$ alkanoyl, amino, mono($C_1$-$C_6$) alkylamino, or di($C_1$-$C_6$)alkylamino.

Preferred compounds of formula II-k include those of formula II-1, i.e., compounds wherein the heteroaryl is pyridinyl, pyrimidinyl, imidazolyl, pyrazolyl, furanyl, thiazolyl, or oxazolyl, each of which is optionally substituted with one or two groups which are independently $C_1$-$C_6$ alkyl, $C_1$-$C_6$ alkoxy, hydroxy($C_1$-$C_6$) alkyl, hydroxy, halogen, cyano, nitro, trifluoromethyl, amino, mono($C_1$-$C_6$)alkylamino, or di($C_1$-$C_6$)alkylamino.

Preferred compounds of formula II-1 include those of formula II-m, i.e., compounds wherein $R_{200}$ is $C_1$-$C_6$ alkyl, or $C_2$-$C_6$ alkenyl.

Preferred compounds of formula II-d include those of formula II-n, i.e., compounds wherein $CR_{245}R_{250}$ represents a $C_3$-$C_7$ cycloalkyl group.

Preferred compounds of formula II-n include those of formula II-o, i.e., compounds wherein $CR_{245}R_{250}$ represents a $C_5$-$C_7$ cycloalkyl group.

Preferred compounds of formula II-n, include those of formula II-p, i.e., compounds wherein $CR_{245}R_{250}$ represents a $C_3$-$C_6$ cycloalkyl group.

Preferred compounds of formula II-p include those of formula II-q, i.e., compounds wherein $CR_{245}R_{250}$ represents a $C_6$ cycloalkyl.

Preferred compounds of formula II-q include those of formula II-r, i.e., compounds wherein the phenyl in $(CR_{245}R_{250})_1$-phenyl is substituted with 1 $R_{200}$ group; or 1 $R_{200}$ group and one heteroaryl group optionally substituted with one $R_{200}$ group or 1 $R_{200}$ group and one phenyl group optionally substituted with one $R_{200}$ group.

Preferred compounds of formula II-r include those of formula II-s, i.e., compounds wherein the phenyl in $(CR_{245}R_{250})_1$-phenyl is substituted with 1 $R_{200}$ group.

Preferred compounds of formula II-s, include those of formula II-t, i.e., compounds wherein $R_{200}$ is $C_1$-$C_6$ alkyl, $C_2$-$C_6$ alkenyl, $C_1$-$C_6$ alkoxy, hydroxy ($C_1$-$C_6$)alkyl, $C_1$-$C_6$ alkoxy($C_1$-$C_6$)alkyl, halogen, hydroxy, cyano, or —$NR_{220}R_{225}$, where $R_{220}$ and $R_{225}$ are independently hydrogen or alkyl.

Preferred compounds of formula II-t, include those of formula II-u, i.e., compounds wherein $R_1$ is benzyl where the phenyl portion of the benzyl group is optionally substituted with 1 or 2 groups independently selected from halogen, $C_1$-$C_2$ alkyl, $C_1$-$C_2$ alkoxy, —O-allyl, and hydroxy.

Preferred compounds of formula II-u, include those of formula II-v, i.e., compounds wherein Z is H or $C_1$-$C_3$ alkyl.

Preferred compounds of formula II-v, include those of formula II-w, i.e., compounds wherein $R_{200}$ is $C_1$-$C_6$ alkyl or $C_2$-$C_6$ alkenyl.

Preferred compounds of formula II-w, include those of formula II-x, i.e., compounds wherein Z is $C_1$-$C_2$ alkyl and $R_1$ is benzyl, 3-fluorobenzyl or 3,5-difluorobenzyl.

Preferred compounds of formula II-m, include those of formula II-y, i.e., compounds wherein Z is $C_1$-$C_2$ alkyl optionally substituted with one halogen (which is preferably F or Cl) and $R_1$ is benzyl, 3-fluorobenzyl or 3,5-difluorobenzyl.

Preferred compounds of formula II-w, include those of formula II-z, i.e., compounds wherein $R_{200}$ is $C_3$-$C_5$ alkyl.

Preferred compounds of formula II-m, include those of formula II-aa, i.e., compounds wherein $R_{200}$ is $C_3$-$C_5$ alkyl.

In another aspect, the invention provides compounds of formula II-bb, i.e., compounds of formulas II to II-aa, wherein $R_2$ is H, methyl, or hydroxymethyl and $R_3$ is H.

Other preferred compounds of formula II include those of formula II-cc, wherein $R_c$ is a monocyclic or bicyclic ring of 5, 6, 7 8, 9, or 10 carbons fused to 1 aryl (preferably phenyl), heteroaryl (preferably pyridyl, imidazolyl, thienyl, or pyrimidyl), or heterocycloalkyl (preferably piperidinyl or piperazinyl) groups;

wherein 1, 2 or 3 carbons of the monocyclic or bicyclic ring are optionally replaced with —NH—, —N(CO)$_{0-1}$R$_{215}$—, —N(CO)$_{0-1}$R$_{220}$—, —O—, or —S(=O)$_{0-2}$—, and wherein the monocyclic or bicyclic ring is optionally substituted with 1, 2 or 3 groups that are independently —R$_{205}$, —R$_{245}$, —R$_{250}$ or =O. More preferably, R$_c$ is as defined above and R$_1$ is $C_1$-$C_{10}$ alkyl substituted with one aryl group (preferably phenyl), where the aryl group is optionally substituted with 1 or 2 $R_{50}$ groups. More preferably, Z is also —CH$_2$— halogen or —CH$_3$.

Other preferred compounds of formula II include those of formula II-dd, wherein $R_c$ is —CHR$_{245}$—CHR$_{250}$-phenyl; wherein the phenyl is optionally substituted with 1, 2, 3 or 4 $R_{200}$ groups; and $R_{245}$ and $R_{250}$ are taken together with the carbon to which they are attached to form a monocycle or bicycle of 5, 6, 7 or 8 carbon atoms, where 1, or 2 carbon atoms are optionally replaced by 1 or 2 groups that are independently —O—, —S—, —SO$_2$—, —C(O)—, or —NR$_{220}$—, and wherein the ring is optionally substituted with 1, 2, 3, 4, 5, or 6 groups that are independently $C_1$-$C_4$ alkyl, $C_1$-$C_4$ alkoxy, hydroxyl, NH$_2$, NH($C_1$-$C_6$ alkyl), N($C_1$-$C_6$ alkyl)($C_1$-$C_6$ alkyl), —NH—C(O)$C_1$-$C_5$ alkyl, —NH—SO$_2$—($C_1$-$C_6$ alkyl), or halogen; and $R_1$ is $C_1$-$C_{10}$ alkyl substituted with one aryl group (preferably phenyl), where the aryl group is optionally substituted with 1 or 2 $R_{50}$ groups. More preferably, Z is also —CH$_2$— halogen or —CH$_3$.

Preferred compounds of formula II-cc include those of formula II-dd, i.e. compounds of formula II-cc, wherein $R_{245}$ and $R_{250}$ are taken together with the carbons to which they are attached to form a monocycle or bicycle of 5, 6, 7 or 8 carbon atoms, and wherein the ring is optionally substituted with 1, 2, 3, 4, 5, or 6 groups that are independently $C_1$-$C_4$ alkyl, $C_1$-$C_4$ alkoxy, hydroxyl, NH$_2$, NH($C_1$-$C_6$ alkyl), N($C_1$-$C_6$ alkyl)($C_1$-$C_6$ alkyl), —NH—C(O)$C_1$-$C_5$ alkyl, —NH—SO$_2$—($C_1$-$C_6$ alkyl), or halogen.

Preferred compounds of formula II-dd include those of formula II-ee, i.e. compounds of formula II-dd, wherein $R_{245}$ and $R_{250}$ are taken together with the carbons to which they are attached to form a monocycle or bicycle of 5, or 6, carbon atoms, and wherein the ring is optionally substituted with 1, 2, 3, 4, 5, or 6 groups that are independently $C_1$-$C_4$ alkyl, $C_1$-$C_4$ alkoxy, hydroxyl, NH$_2$, NH($C_1$-$C_6$ alkyl), N($C_1$-$C_6$ alkyl) ($C_1$-$C_6$ alkyl), —NH—C(O)$C_1$-$C_5$ alkyl, —NH—SO$_2$—($C_1$-$C_6$ alkyl), or halogen.

Preferred compounds of formula II include those of formula II-ff, i.e. compounds of formula II wherein $R_c$ is —(CR$_{245}$R$_{250}$)-heteroaryl (preferred heteroaryl groups include thienyl, pyridyl, pyrimidyl, quinolinyl, oxazolyl, and thiazolyl), wherein the heteroaryl group attached to the —$(CR_{245}R_{250})_{1-4}$— group is optionally substituted with 1 or 2 substitutents selected from —Cl, —Br, —I, —$C_1$-$C_6$ alkyl, —($C_1$-$C_3$ alkyl)OH, —CN, —C≡CH, —C≡C—$CH_2$—OH, —$CF_3$, or -phenyl optionally substituted with 1 or 2 $C_1$-$C_3$ alkyl groups, —($C_1$-$C_3$ alkyl)OH group or —CO($C_1$-$C_3$ alkyl) group, wherein $R_{245}$ and $R_{250}$ at each occurance are independently —H, —$C_1$-$C_3$ alkyl, —($C_1$-$C_3$ alkyl)$CO_2$H, or —($C_1$-$C_3$ alkyl)OH, (in one aspect $R_{245}$ is H; in another aspect, $R_{245}$ and $R_{250}$ are H; in another aspect, $R_{245}$ and $R_{250}$ are both methyl) or $R_{245}$ and $R_{250}$ are taken together with the carbon to which they are attached to form a monocycle or bicycle of 3, 4, 5, 6, 7 or 8 carbon atoms (preferably 6 carbon atoms), where 1 or 2 carbon atoms is optionally replaced by —O—, —C(O)—, —S—, —$SO_2$—, or —$NR_{220}$—, and $R_{220}$ is as defined above.

In another aspect, the invention provides compounds of the formula VIII:

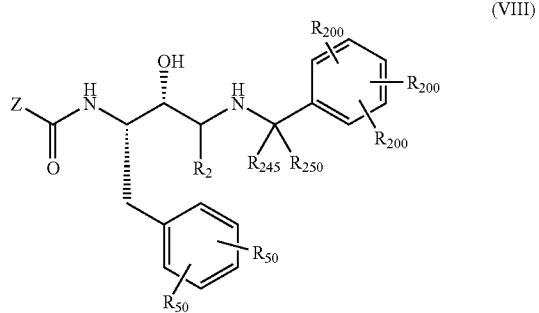

(VIII)

and pharmaceutically acceptable salts thereof, wherein $R_{245}$ and $R_{250}$ are taken together with the carbon to which they are attached to form a monocycle or bicycle of 3, 4, 5, 6, 7, or 8 carbon atoms, where 1, 2, or 3 $CH_2$ groups are optionally replaced by 1, 2, or 3 groups that are independently —O—, —S—, —$SO_2$—, —C(O)—, or —$NR_{220}$—; and wherein the ring is optionally substituted with 1, 2, 3, 4, 5, or 6 groups that are independently $C_1$-$C_4$ alkyl, $C_1$-$C_4$ alkoxy, =O, hydroxyl and halogen;

Z, $R_2$, $R_{50}$, $R_{200}$, and $R_{220}$ are as defined for formula I.

Preferred compounds of formula VIII include compounds of formula VIII-a, i.e., compounds of formula VIII, wherein at least one of the $R_{50}$ groups is a halogen.

Preferred compounds of formula VIII-a, include compounds of formula VIII-b, i.e., compounds wherein Z is —$CH_2$-halogen (preferably the halogen is F or Cl) or $CH_3$.

Preferred compounds of formula VIII-b include compounds of formula VIII-c, i.e., compounds of formula VIII-b, wherein at least one $R_{50}$ group is halogen. More preferably, the other $R_{50}$ group is H, OH or —O-allyl.

In another aspect, both $R_{50}$ groups are halogen and more preferably, F or Cl. Still more preferably, both $R_{50}$ groups are F. Still more preferably, the $R_{50}$ groups are "meta" relative to each other, i.e., 1-3 to each other.

Preferred compounds of formula VIII, VIII-a, VIII-b and VIII-c include compounds of formula VIII-d, wherein $R_{245}$ and $R_{250}$ are taken together with the carbon to which they are attached to form a monocycle of 3, 4, 5, 6, or 7 carbon atoms (preferably 4, 5, or 6 carbon atoms, more preferably, 5 or 6 carbon atoms), wherein the ring is optionally substituted with 1, 2, 3, 4, 5, or 6 groups that are independently $C_1$-$C_4$ alkyl, $C_1$-$C_4$ alkoxy, hydroxyl, =O, and halogen. More preferably, the ring is optionally substituted with 1, 2, or 3 groups. Still more preferably, if the ring is substituted, one of the groups is =O.

Preferred compounds of formula VIII, VIII-a, VIII-b and VIII-c include compounds of formula VIII-e, wherein $R_{245}$ and $R_{250}$ are taken together with the carbon to which they are attached to form a bicycle of 5, 6, 7, or 8 carbon atoms, where 1, carbon atom is optionally replaced by a group selected from —O—, —S—, —$SO_2$—, —C(O)—, and —$NR_{220}$—; and wherein the ring is optionally substituted with 1, 2, 3, 4, 5, or 6 groups that are independently $C_1$-$C_4$ alkyl, $C_1$-$C_4$ alkoxy, hydroxyl and halogen. Preferably the bicycle is bicyclo[3.1.0]hexyl, 6-aza-bicyclo[3.1.0]hexane wherein the nitrogen is optionally substituted with —C(O)$CH_3$ or $CH_3$, octahydro-cyclopenta[c]pyrrolyl, 5-oxo-octahydro-pentalenyl, or 5-hydroxy-octahydro-pentalenyl, each of which is optionally substituted with 1, 2, 3, 4, 5, or 6 groups that are independently $C_1$-$C_4$ alkyl, $C_1$-$C_4$ alkoxy, hydroxyl and halogen.

Preferred compounds of formulas VIII-c, VIII-d and VIII-e include compounds wherein one $R_{200}$ is imidazolyl, thiazolyl, oxazolyl, tetrazolyl, thienyl, furanyl, benzyl, piperidinonyl, or pyridyl, wherein each is optionally substituted with halogen, or $C_1$-$C_4$ alkyl. Also preferred are compounds wherein a second $R_{200}$ is $C_1$-$C_6$ alkyl (preferably $C_2$-$C_6$ alkyl, more preferably tert-butyl, neopentyl or isopropyl.)

Preferred compounds of formula VIII, VIII-a, VIII-b and VIII-c, and include compounds of formula VIII-f, i.e., compounds wherein $R_{245}$ and $R_{250}$ are taken together with the carbon to which they are attached to form a monocycle of 3, 4, 5, 6, or 7 carbon atoms, where at least 1, but up to 3 carbon atoms are replaced by groups that are independently —O—, —S—, —$SO_2$—, —C(O)—, or —$NR_{220}$— (in one aspect, preferably —O—); and wherein the ring is optionally substituted with 1, 2, 3, 4, 5, or 6 groups that are independently $C_1$-$C_4$ alkyl, $C_1$-$C_4$ alkoxy, hydroxyl and halogen. Preferably the monocycle is tetrahydropyranyl, 2-oxo-tetrahydropyrimidinonyl, piperidinyl, 2-oxo(1,3)oxazinonyl, or cyclohexanonyl. Preferably, $R_{220}$ is H, —$C_1$-$C_6$ alkyl, —CHO, hydroxy $C_1$-$C_6$ alkyl, $C_1$-$C_6$ alkoxycarbonyl, -amino $C_1$-$C_6$ alkyl, —$SO_2$—$C_1$-$C_6$ alkyl, $C_1$-$C_6$ alkanoyl optionally substituted with up to three halogens, —C(O)$NH_2$, —C(O)NH($C_1$-$C_6$ alkyl), —C(O)N($C_1$-$C_6$ alkyl) ($C_1$-$C_6$ alkyl), -halo $C_1$-$C_6$ alkyl, or —$(CH_2)_{0-2}$—($C_3$-$C_7$ cycloalkyl). More preferably, $R_{220}$ is H, —$C_1$-$C_6$ alkyl, $C_1$-$C_6$ alkoxycarbonyl, —$SO_2$—$C_1$-$C_6$ alkyl, —C(O)$CF_3$, —C(O)$NH_2$, —C(O)NH($C_1$-$C_6$ alkyl), or —C(O)N($C_1$-$C_6$ alkyl) ($C_1$-$C_6$ alkyl).

Preferred compounds of formulas VIII-d and VIII-e include compounds of formula VIII-g, i.e., compounds wherein at least one $R_{200}$ is $C_1$-$C_6$ alkyl. More preferably, $R_{200}$ is $C_2$-$C_6$ alkyl. Still more preferably it is $C_3$-$C_6$ alkyl.

Preferred compounds of formula VIIIa-VIIIg include compounds of formula VIII-h, i.e., compounds wherein $R_c$ is of the formula:

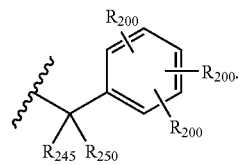

More preferably, $R_c$ is of the formula:

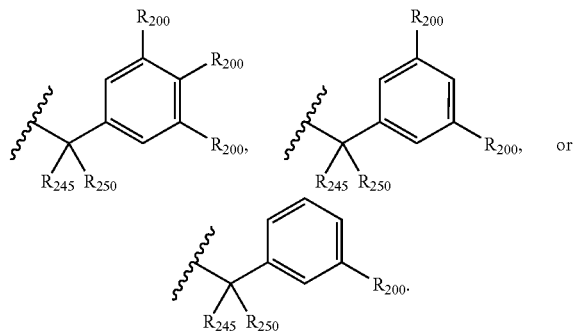

In another aspect, the invention provides compounds of formulas VIII-VIII-h, wherein $R_2$ is H.

In another aspect, the invention provides compounds of formulas VIII-VIII-h, wherein $R_2$ is $C_1$-$C_4$ alkyl or hydroxy $C_1$-$C_4$ alkyl.

In another aspect, the invention provides compounds of formula IX:

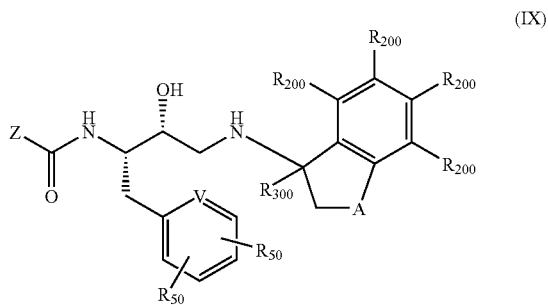

wherein

A is —$CH_2$-$CR_{100}R_{101}$—, —$CH_2$—S—, —$CH_2$—S(O)—, —$CH_2$—S(O)$_2$—, —$CH_2$—$NR_{100}$—, —$CH_2$—C(O)—, —$CH_2$—O—, —O—$CR_{100}R_{101}$—, —$SO_2$—$NR_{100}$, or —C(O)—O—;

$R_{100}$ and $R_{101}$ are independently H, $C_1$-$C_6$ alkyl, phenyl, CO($C_1$-$C_6$ alkyl) or $SO_2C_1$-$C_6$ alkyl;

V is CH, $CR_{50}$, or N;

$R_{300}$ is H or $C_1$-$C_4$ alkyl (preferably the alkyl is methyl); and

Z, $R_{50}$ and $R_{200}$ are as defined for formula I.

Preferred compounds of formula IX include compounds of formula IX-a, i.e., compounds of formula IX, wherein at least one of the $R_{50}$ groups is a halogen. In another aspect, the other $R_{50}$ group is H, OH, or —O-allyl. Preferred compounds of formula IX-a, include compounds of formula IX-b, i.e., compounds wherein Z is —$CH_2$-halogen (where the halogen is preferably F or Cl) or $CH_3$. Preferred compounds of formula IX-b include compounds of formula IX-c, i.e., compounds of formula IX-b, wherein both $R_{50}$ groups are halogen and more preferably, F or Cl. Still more preferably, both $R_{50}$ groups are F. In other preferred compounds, at least one $R_{50}$ is OH or —O-benzyl. More preferably, a second $R_{50}$ is present and it is a halogen (preferably F or Cl.)

Preferred compounds of formula IX, IX-a, IX-b, and IX-c, include those of formula IX-d, i.e., compounds wherein at least one $R_{200}$ is $C_1$-$C_6$ alkyl. In one aspect, $R_{200}$ is $C_3$-$C_6$ alkyl, preferably neopentyl, tert-butyl or isopropyl. In another aspect, $R_{200}$ is $C_1$-$C_4$ alkyl.

Preferred compounds of formula IX-d include those wherein A is —$CH_2$—O— or —$CH_2$—$CH_2$—. Also preferred are compounds wherein A is —C(O)—O—, Also preferred are compounds wherein A is —$CH_2$—$NR_{100}$—. Also preferred are compounds wherein A is —$CH_2$—S—, —$CH_2$—S(O)—, or —$CH_2$—S(O)$_2$—.

Preferred compounds of formula IX include compounds wherein one $R_{200}$ is $C_1$-$C_6$ alkyl, preferably $C_2$-$C_6$ alkyl, more preferably $C_3$-$C_5$ alkyl.

Also preferred are compounds wherein a second $R_{200}$ is present and it is imidazolyl, thiazolyl, oxazolyl, tetrazolyl, thienyl, furanyl, benzyl, or pyridyl, wherein each cyclic group is optionally substituted with —$R_{205}$, halogen, and/or $C_1$-$C_4$ alkyl. In another aspect, they are substituted with halogen, and/or $C_1$-$C_4$ alkyl. Also preferred are compounds wherein a second $R_{200}$ is $C_1$-$C_6$ alkyl. Also preferred are compounds wherein $R_{100}$ and $R_{101}$ are independently H or $C_1$-$C_6$ alkyl.

In another aspect, preferred compounds of formula IX-d include those wherein $R_{300}$ is methyl. In another aspect, when $R_{300}$ is methyl, A is —$CH_2$—O— or —$CH_2$—$CH_2$—.

In one aspect, the invention provides compounds of the formula A-I:

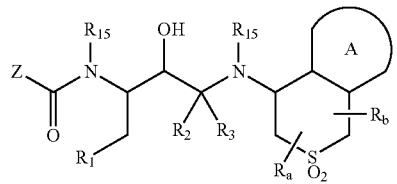

and a pharmaceutically acceptable salt thereof, wherein the A ring is a heteroaryl group, selected from pyridinyl, pyrimidinyl, imidazolyl, oxazolyl, thiazolyl, furanyl, thienyl, pyrrolyl, wherein said heteroaryl groups are optionally substituted with one, two, three, or four $R_C$ and/or $R_d$ groups, wherein $R_c$ and $R_d$ at each occurrence are independently $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; or OH; $NO_2$; halogen; $CO_2H$; C≡N; —$(CH_2)_{0-4}$—CO—$NR_{21}R_{22}$ wherein $R_{21}$ and $R_{22}$ are the same or different and are selected from H; —$C_1$-$C_6$ alkyl optionally substituted with one substituent selected from OH and —$NH_2$; —$C_1$-$C_6$ alkyl optionally substituted with one to three groups that are independently —F, —Cl, —Br, or —I; —$C_3$-$C_7$ cycloalkyl; —($C_1$-$C_2$ alkyl)-($C_3$-$C_7$ cycloalkyl); —($C_1$-$C_6$ alkyl)-O—($C_1$-$C_3$ alkyl); —$C_2$-$C_6$ alkenyl; —$C_2$-$C_6$ alkynyl; —$C_1$-$C_6$ alkyl chain with one double bond and one triple bond; $R_{17}$; and $R_{18}$; or —$(CH_2)_{0-4}$—CO—($C_1$-$C_{12}$ alkyl); —$(CH_2)_{0-4}$—CO—($C_2$-$C_{12}$ alkenyl); —$(CH_2)_{0-4}$—CO—($C_2$-$C_{12}$ alkynyl); —$(CH_2)_{0-4}$—CO—($C_3$-$C_7$ cycloalkyl); —$(CH_2)_{0-4}$—CO—$R_{17}$; —$(CH_2)_{0-4}$—CO—$R_{18}$; —$(CH_2)_{0-4}$—CO—$R_{19}$; or —$(CH_2)_{0-4}$—CO—$R_{11}$ wherein $R_{17}$ at each occurrence is an aryl group selected from phenyl, 1-naphthyl, 2-naphthyl and indanyl, indenyl, dihydronaphthyl, or tetralinyl, wherein said aryl groups are optionally substituted with one, two, three, or four groups that are independently $C_1$-$C_6$ alkyl optionally substituted with one, two or three substituents selected from $C_1$-$C_3$ alkyl, F, Cl, Br, I, OH, SH, and —$NR_5R_6$, C≡N, $CF_3$, and $C_1$-$C_3$ alkoxy; or $C_2$-$C_6$ alkenyl or $C_2$-$C_6$ alkynyl each of which is optionally substituted with one, two or three substituents selected from F, Cl, OH, SH, C≡N, $CF_3$, $C_1$-$C_3$ alkoxy, and —$NR_5R_6$; or halogen; —$C_1$-$C_6$ alkoxy optionally substituted with one, two, or three F; —$NR_{21}R_{22}$; OH; C≡N; $C_3$-$C_7$ cycloalkyl, optionally substituted with one, two or three substituents selected from F, Cl, OH, SH, C≡N, $CF_3$, $C_1$-$C_3$ alkoxy, and —$NR_5R_6$; or —CO—($C_1$-$C_4$ alkyl); —$SO_2$—$NR_5R_6$; —CO—$NR_5R_6$; or —$SO_2$—($C_1$-$C_4$ alkyl);

$R_{18}$ at each occurrence is a heteroaryl group selected from pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, wherein said heteroaryl group is optionally substituted with one, two, three, or four groups that are independently $C_1$-$C_6$ alkyl optionally substituted with one, two or three substituents selected from $C_1$-$C_3$ alkyl, F, Cl, Br, I, OH, SH, C≡N, $CF_3$, $C_1$-$C_3$ alkoxy, and —$NR_5R_6$; or $C_2$-$C_6$ alkenyl or $C_2$-$C_6$ alkynyl each of which is optionally substituted with one, two or three substituents selected from —F, —Cl, —OH, —SH, —C≡N, —$CF_3$, $C_1$-$C_3$ alkoxy, and —$NR_5R_6$; or halogen; —$C_1$-$C_6$ alkoxy optionally substituted with one, two, or three —F; —$NR_{21}R_{22}$; —OH; —C≡N; $C_3$-$C_7$ cycloalkyl optionally substituted with one, two or three substituents independently selected from F, Cl, OH, SH, C≡N, $CF_3$, $C_1$-$C_3$ alkoxy, and —$NR_5R_6$;

—CO—($C_1$-$C_4$ alkyl); —$SO_2$—$NR_5R_6$; —CO—$NR_5R_6$; or —$SO_2$—($C_1$-$C_4$ alkyl);

$R_{19}$ at each occurrence is independently morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, or homothiomorpholinyl S-oxide; wherein said $R_{19}$ group is optionally substituted with one, two, three, or four groups that are independently $C_1$-$C_6$ alkyl optionally substituted with one, two or three substituents selected from $C_1$-$C_3$ alkyl, F, Cl, Br, I, OH, SH, C≡N, $CF_3$, $C_1$-$C_3$ alkoxy, and —$NR_5R_6$;

$C_2$-$C_6$ alkenyl or $C_2$-$C_6$ alkynyl, wherein each is optionally substituted with one, two or three substituents selected from F, Cl, OH, SH, C≡N, $CF_3$, $C_1$-$C_3$ alkoxy, and —$NR_5R_6$;

halogen; $C_1$-$C_6$ alkoxy; $C_1$-$C_6$ alkoxy optionally substituted with one, two, or three F; OH; C≡N; —$NR_{21}R_{22}$; $C_3$-$C_7$ cycloalkyl optionally substituted with one, two, or three substituents independently selected from F, Cl, OH, SH, C≡N, $CF_3$, $C_1$-$C_3$ alkoxy, and —$NR_5R_6$; —CO—($C_1$-$C_4$ alkyl); —$SO_2$—$NR_5R_6$; —CO—$NR_5R_6$; —$SO_2$—($C_1$-$C_4$ alkyl); or =O;

$R_{11}$ is selected from morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four groups that are independently $C_1$-$C_6$ alkyl, $C_1$-$C_6$ alkoxy, and halogen;

or $R_c$ and $R_d$ at each occurrence are independently —(CH$_2$)$_{0-4}$—$CO_2R_{20}$; —(CH$_2$)$_{0-4}$—$SO_2$—$NR_{21}R_{22}$; —(CH$_2$)$_{0-4}$—SO—($C_1$-$C_8$ alkyl); —(CH$_2$)$_{0-4}$—$SO_2$—($C_1$-$C_{12}$ alkyl), —(CH$_2$)$_{0-4}$—$SO_2$—($C_3$-$C_7$ cycloalkyl); —(CH$_2$)$_{0-4}$—N(H or $R_{20}$)—CO—O—$R_{20}$; —(CH$_2$)$_{0-4}$—N(H or $R_{20}$)—CO—N($R_{20}$)$_2$; —(CH$_2$)$_{0-4}$—N—CS—N($R_{20}$)$_2$; —(CH$_2$)$_{0-4}$—N(—H or $R_{20}$)—CO—$R_{21}$; —(CH$_2$)$_{0-4}$—$NR_{21}R_{22}$; —(CH$_2$)$_{0-4}$—$R_{11}$; —(CH$_2$)$_{0-4}$—O—CO—($C_1$-$C_6$ alkyl); —(CH$_2$)$_{0-4}$—O—P(O)—(O$R_5$)$_2$; —(CH$_2$)$_{0-4}$—O—CO—N($R_{20}$)$_2$; —(CH$_2$)$_{0-4}$—O—CS—N($R_{20}$)$_2$; —(CH$_2$)$_{0-4}$—O—($R_{20}$)$_2$; —(CH$_2$)$_{0-4}$—O—($R_{20}$)—$CO_2H$; —(CH$_2$)$_{0-4}$—S—($R_{20}$); —(CH$_2$)$_{0-4}$—O—($C_1$-$C_6$ alkyl optionally substituted with one, two, three, four, or five halogens); $C_3$-$C_7$ cycloalkyl; —(CH$_2$)$_{0-4}$—N(—H or $R_{20}$)—$SO_2$—$R_{21}$; or —(CH$_2$)$_{0-4}$—$C_3$-$C_7$ cycloalkyl;

wherein $R_{20}$ is selected from $C_1$-$C_6$ alkyl, —(CH$_2$)$_{0-2}$—($R_{17}$), $C_2$-$C_6$ alkenyl, $C_2$-$C_6$ alkynyl, $C_3$-$C_7$ cycloalkyl, and —(CH$_2$)$_{0-2}$—($R_{18}$);

or $R_c$ and $R_d$ at each occurrence are independently $C_2$-$C_6$ alkenyl or $C_2$-$C_6$ alkynyl, each of which is optionally substituted with $C_1$-$C_3$ alkyl, F, Cl, Br, I, OH, SH, C≡N, $CF_3$, $C_1$-$C_3$ alkoxy, or —$NR_5R_6$; or the A ring is an aromatic hydrocarbon selected from phenyl, naphthyl, tetralinyl, indanyl, dihydronaphthyl or 6,7,8,9-tetrahydro-5H-benzo[a]cycloheptenyl, wherein each aromatic hydrocarbon is optionally substituted with one, two, three, or four $R_c$ and/or $R_d$ groups which at each occurrence can be the same or different and are:
$C_1$-$C_6$ alkyl, optionally substituted with one, two or three substituents selected from $C_1$-$C_3$ alkyl, halogen, OH, SH, C≡N, $CF_3$, $C_1$-$C_3$ alkoxy, and —$NR_5R_6$;
or
—OH; —$NO_2$; halogen; —$CO_2H$; —C≡N; —$(CH_2)_{0-4}$—CO—$NR_{21}R_{22}$; —$(CH_2)_{0-4}$—CO—($C_1$-$C_{12}$ alkyl), —$(CH_2)_{0-4}$—CO—($C_2$-$C_{12}$ alkenyl), —$(CH_2)_{0-4}$—CO—($C_2$-$C_{12}$ alkynyl), —$(CH_2)_{0-4}$—CO—($C_3$-$C_7$ cycloalkyl), —$(CH_2)_{0-4}$—CO—$R_{17}$; —$(CH_2)_{0-4}$—CO—$R_{18}$; —$(CH_2)_{0-4}$—CO—$R_{19}$; —$(CH_2)_{0-4}$—CO—$R_{11}$; —$(CH_2)_{0-4}$—$CO_2R_{20}$; —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl), —$(CH_2)_{0-4}$—$SO_2$—($C_3$-$C_7$ cycloalkyl); —$(CH_2)_{0-4}$—N(H or $R_{20}$)—$CO_2R_{20}$; —$(CH_2)_{0-4}$—N(H or $R_{20}$)—CO—N($R_{20}$)$_2$; —$(CH_2)_{0-4}$—N—CS—N($R_{20}$)$_2$; —$(CH_2)_{0-4}$—N(—H or $R_{20}$)—CO—$R_{21}$; —$(CH_2)_{0-4}$—$NR_{21}R_{22}$; —$(CH_2)_{0-4}$—$R_{11}$; —$(CH_2)_{0-4}$—O—CO—($C_1$-$C_6$ alkyl); —$(CH_2)_{0-4}$—O—P(O)—(O$R_5$)$_2$; —$(CH_2)_{0-4}$—O—CO—N($R_{20}$)$_2$; —$(CH_2)_{0-4}$—O—CS—N($R_{20}$)$_2$; —$(CH_2)_{0-4}$—O—($R_{20}$)$_2$; —$(CH_2)_{0-4}$—O—($R_{20}$)—$CO_2R_{20}$; —$(CH_2)_{0-4}$—S—($R_{20}$); —$(CH_2)_{0-4}$—O—($C_1$-$C_6$ alkyl optionally substituted with one, two, three, four, or five —F); $C_3$-$C_7$ cycloalkyl; —$(CH_2)_{0-4}$—N(—H or $R_{20}$)—$SO_2$—$R_{21}$; —$(CH_2)_{0-4}$—$C_3$-$C_7$ cycloalkyl;
or
$C_2$-$C_6$ alkenyl or $C_2$-$C_6$ alkynyl each of which is optionally substituted with $C_1$-$C_3$ alkyl, F, Cl, Br, I, OH, SH, C≡N, $CF_3$, $C_1$-$C_3$ alkoxy, or —$NR_5R_6$;
$R_a$ and $R_b$ are independently selected from $C_1$-$C_3$ alkyl, F, OH, SH, C≡N, $CF_3$, $C_1$-$C_6$ alkoxy, =O, and —$NR_5R_6$; or
$R_a$ and $R_b$ and the carbon to which they are attached form a $C_3$-$C_7$ spirocycle which is optionally substituted with 1 or 2 groups that are independently $C_1$-$C_4$ alkyl, $C_1$-$C_4$ alkoxy, halogen, $CF_3$, or CN;
$R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino and —OC(=O)-mono- or dialkylamino; or
$R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino; or
$R_1$ is aryl, heteroaryl, heterocyclyl, aryl $C_1$-$C_6$ alkyl, heteroaryl $C_1$-$C_6$ alkyl, or heterocycloalkyl $C_1$-$C_6$ alkyl, wherein
each aryl group at each occurrence is optionally substituted with 1, 2, 3, 4, or 5 $R_{50}$ groups;
each heteroaryl at each occurrence is optionally substituted with 1, 2, 3, 4, or 5 $R_{50}$ groups;
each heterocycloalkyl group at each occurrence is optionally substituted with 1, 2, 3, 4, or 5 groups that are independently $R_{50}$ or =O;
$R_1$ is G-L-A-E-W-, wherein
W is a bond, absent, —S—, —S(O)—, —$SO_2$—, —O—, —NH— or —N($C_1$-$C_4$ alkyl);
E is a bond, absent, or $C_1$-$C_3$ alkylene;
A is absent, alkyl, aryl or cycloalkyl where each aryl or cycloalkyl is optionally substituted with one, two or three $R_{100}$ groups; heteroaryl optionally substituted with 1 or 2 $R_{100}$ groups; or heterocycloalkyl optionally substituted with 1 or 2 $R_{200}$ groups, wherein
$R_{100}$ at each occurrence is independently selected from $NO_2$, C≡N, $C_1$-$C_6$ alkyl, $C_2$-$C_6$ alkenyl, $C_2$-$C_6$ alkynyl, —N(R)CO(R')R, —$CO_2$—$R_{25}$, —NH—$CO_2$—$R_{25}$, —O—($C_2$-$C_6$ alkyl)—$CO_2H$, —NRR', —SR, $CH_2OH$, —C(O)—($C_1$-$C_6$)alkyl, —C(O)NRR', —$SO_2NRR'$, $CO_2H$, $CF_3$, halogen, $C_1$-$C_3$ alkoxy, —$OCF_3$, —$NH_2$, OH, CN, halogen, and —(C$H_2$)$_{0-2}$—O—(CH$_2$)$_{0-2}$—OH;
wherein
$R_{25}$ is selected from $C_1$-$C_6$ alkyl, —$(CH_2)_{0-2}$-cycloalkyl, —$(CH_2)_{0-2}$-aryl, where the aryl is optionally substituted with halogen, hydroxy, $C_1$-$C_6$ alkyl, $C_1$-$C_6$ alkyl, amino, mono($C_1$-$C_6$)alkylamino, or di($C_1$-$C_6$)alkylamino, and hydrogen, and
R and R' at each occurrence are independently hydrogen, $C_1$-$C_6$ alkyl, —$(CH_2)_{0-2}$-aryl, or —$(CH_2)_{0-2}$-cycloalkyl, where each aryl or cycloalkyl is optionally substituted with halogen, hydroxy, $C_1$-$C_6$ alkyl, $C_1$-$C_6$ alkyl, amino, mono($C_1$-$C_6$)alkylamino, or di($C_1$-$C_6$)alkylamino;
$R_{200}$ at each occurrence is independently selected from =O, $C_1$-$C_3$ alkyl, $CF_3$, F, Cl, Br, I, $C_1$-$C_3$ alkoxy, $OCF_3$, $NH_2$, OH, and C≡N;
provided that L is a bond or absent when G is absent,
or
L is —C(O)—, —S(O)—, —$SO_2$—, —O—, —C($R_{110}$)($R_{112}$)O—, —OC($R_{110}$)($R_{112}$)—, —N($R_{110}$)—, —CON($R_{110}$)—, —N($R_{110}$)CO—, —C($R_{110}$)(R')—, —C(OH)$R_{110}$, —$SO_2NR_{110}$, —N($R_{110}$)$SO_2$—, —N($R_{110}$)CON($R_{112}$)—, N($R_{110}$)CSN($R_{112}$)—, —$OCO_2$—, —$NCO_2$—, or —OCON($R_{110}$)—, wherein
$R_{110}$ and $R_{112}$ are independently hydrogen, $C_1$-$C_4$ alkyl, $C_1$-$C_4$ hydroxyalkyl, $C_1$-$C_4$ alkoxy $C_1$-$C_4$ alkyl or $C_1$-$C_4$ fluoroalkyl;
and
G is absent or $C_1$-$C_{10}$ alkyl optionally substituted with 1, 2, or 3 groups independently selected from —$CO_2H$, —$CO_2$($C_1$-$C_4$ alkyl), $C_1$-$C_6$ alkoxy, —OH, —NRR', —$C_1$-$C_6$ haloalkyl, —($C_1$-$C_{10}$ alkyl)-O—($C_1$-$C_3$ alkyl), —$C_2$-$C_{10}$ alkenyl, —$C_2$-$C_{10}$ alkynyl, —$C_4$-$C_{10}$ alkyl chain with one double bond and one triple bond, aryl optionally substituted with 1, 2, or 3 $R_{100}$, heteroaryl optionally substituted with 1, 2, or 3 $R_{100}$, and $C_1$-$C_6$ alkyl;
or
G is —$(CH_2)_{0-3}$—($C_3$-$C_7$)cycloalkyl where the cycloalkyl is optionally substituted with one, two or three substituents independently selected from —$CO_2H$, —$CO_2$—($C_1$-$C_4$ alkyl), $C_1$-$C_6$ alkoxy, OH, —$NH_2$, —$C_1$-$C_6$ haloalkyl, —($C_1$-$C_{10}$ alkyl)—O—($C_1$-$C_3$ alkyl), —$C_2$-$C_{10}$ alkenyl with 1 or 2 double bonds, $C_2$-$C_{10}$ alkynyl with 1 or 2 triple bonds, —$C_4$-$C_{10}$ alkyl chain with one double bond and one triple bond, aryl optionally substituted with $R_{100}$, heteroaryl optionally substituted with $R_{100}$, mono($C_1$-$C_6$ alkyl)amino, di($C_1$-$C_6$ alkyl)amino, and $C_1$-$C_6$ alkyl,
or
G is —$(CH_2)_{0-4}$-aryl, —$(CH_2)_{0-4}$-heteroaryl, or —$(CH_2)_{0-4}$-heterocycle, wherein the aryl, heteroaryl —$(CH_2)_{0-4}$-heterocycle, groups are optionally substituted with 1, 2, or 3 $R_{100}$, wherein the heterocycle group is optionally substituted with 1 or 2 $R_{200}$ groups; or
G is —C($R_{10}$)($R_{12}$)—CO—NH—$R_{14}$ wherein
$R_{10}$ and $R_{12}$ are the same or different and are selected from H, —$C_1$-$C_6$ alkyl, —($C_1$-$C_4$ alkyl)-aryl, where the aryl is optionally substituted with 1, 2, or 3 $R_{100}$ groups; —($C_1$-$C_4$ alkyl)-heteroaryl where the heteroaryl is optionally substituted with 1, 2, or 3 $R_{100}$ groups; —($C_1$-$C_4$ alkyl)- heterocycle, where the heterocycle is optionally substituted with 1 or 2 $R_{200}$ groups; heteroaryl optionally substituted with 1, 2, or 3 $R_{100}$ groups; heterocycle optionally substituted with 1 or 2 $R_{200}$ groups; —(CH$_2$)$_{1-4}$—OH, —(CH$_2$)$_{1-4}$—Y—(CH$_2$)$_{1-4}$-aryl where the aryl is optionally substituted with 1, 2, or 3 $R_{100}$ groups; —(CH$_2$)$_{1-4}$—Y—(CH$_2$)$_{1-4}$-heteroaryl where the heteroaryl is optionally substituted with 1, 2, or 3 $R_{100}$ groups; -aryl optionally substituted with 1, 2, or 3 $R_{100}$ groups, —heteroaryl optionally substituted with 1, 2, or 3 $R_{100}$ groups, and -heterocycle optionally substituted with 1, 2, or 3 $R_{200}$ groups, wherein Y is —O—, —S—, —NH—, or —NH(C$_1$-C$_6$ alkyl); and $R_{14}$ is H, —C$_1$-C$_6$ alkyl, -aryl optionally substituted with 1, 2, or 3 $R_{100}$ groups, -heteroaryl optionally substituted with 1, 2, or 3 $R_{100}$ groups, -heterocycle optionally substituted with 1 or 2 $R_{200}$ groups, —(C$_1$-C$_4$ alkyl)-aryl, where the aryl is optionally substituted with 1, 2, or 3 $R_{100}$ groups; —(C$_1$-C$_4$ alkyl)-heteroaryl where the heteroaryl is optionally substituted with 1, 2, or 3 $R_{100}$ groups; —(C$_1$-C$_4$ alkyl)-heterocycle, where the heterocycle is optionally substituted with 1 or 2 $R_{200}$ groups, or —(CH$_2$)$_{0-2}$—O—(CH$_2$)$_{1-2}$—OH;

$R_2$ and $R_3$ are independently selected from —H, C$_1$-C$_6$ alkyl, optionally substituted with one, two or three substituents selected from C$_1$-C$_3$ alkyl, —F, —Cl, —Br, —I, —OH, —SH, —C≡N, —CF$_3$, C$_1$-C$_3$ alkoxy, and —NR$_5$R$_6$; —(CH$_2$)$_{0-4}$—R$_{17}$; —(CH$_2$)$_{0-4}$—R$_{18}$; C$_2$-C$_6$ alkenyl or C$_2$-C$_6$ alkynyl, wherein each is optionally substituted with one, two or three substituents selected from —F, —Cl, —OH, —SH, —C≡N, —CF$_3$, C$_1$-C$_3$ alkoxy, and —NR$_5$R$_6$; —(CH$_2$)$_{0-4}$—C$_3$-C$_7$ cycloalkyl, optionally substituted with one, two or three substituents selected from —F, —Cl, —OH, —SH, —C≡N, —CF$_3$, C$_1$-C$_3$ alkoxy, and —NR$_5$R$_6$; wherein $R_5$ and $R_6$ at each occurrence are independently H or C$_1$-C$_6$ alkyl; or $R_5$ and $R_6$ and the nitrogen to which they are attached, at each occurrence form a 5 or 6 membered heterocycloalkyl ring; or $R_2$, $R_3$ and the carbon to which they are attached form a carbocycle of three thru seven carbon atoms, wherein one carbon atom is optionally replaced by a group selected from —O—, —S—, —SO$_2$—, or —NR$_7$—;

$R_{15}$ at each occurrence is independently selected from hydrogen, C$_1$-C$_6$ alkyl, C$_1$-C$_6$ alkoxy, C$_1$-C$_6$ alkoxy C$_1$-C$_6$ alkyl, hydroxy C$_1$-C$_6$ alkyl, halo C$_1$-C$_6$ alkyl, C$_1$-C$_6$ alkanoyl, each of which is unsubstituted or substituted with 1, 2, 3, or 4 groups independently selected from halogen, alkyl, hydroxy, alkoxy, NH$_2$, and —R$_{26}$-R$_{27}$; and —R$_{26}$-R$_{27}$; wherein $R_{26}$ is selected from a bond, —C(O)—, —SO$_2$—, —CO$_2$—, —C(O)NR$_5$—, and —NR$_5$C(O)—, $R_{27}$ is selected from C$_1$-C$_6$ alkyl, C$_1$-C$_6$ alkoxy, aryl C$_1$-C$_6$ alkyl, heterocycloalkyl, and heteroaryl, wherein each of the above is unsubstituted or substituted with 1, 2, 3, 4, or 5 groups that are independently C$_1$-C$_4$ alkyl, C$_1$-C$_4$ alkoxy, halogen, haloalkyl, hydroxyalkyl, —NR$_5$R$_6$, —C(O)NR$_5$R$_6$;

Z is selected from H; C$_1$-C$_6$ alkoxy; C$_1$-C$_6$ alkyl optionally substituted with 1, 2, or 3 groups that are independently OH, halogen, C$_1$-C$_4$ alkoxy, CF$_3$, OCF$_3$, NO$_2$, CN, and NR$_5$R$_6$; aryl; heteroaryl; arylalkyl; and heteroarylalkyl; and wherein each aryl, heteroaryl, arylalkyl, and heteroarylalkyl group is optionally substituted with 1 or 2 groups that are independently C$_1$-C$_4$ alkyl, halogen, haloalkyl, and C$_1$-C$_4$ alkoxy.

Preferred compounds of formula A-I include those wherein $R_2$ and $R_3$ are independently selected from H; C$_1$-C$_6$ alkyl optionally substituted with 1, 2, or 3 substituents that are independently selected from C$_1$-C$_4$ alkyl, halogen, —CF$_3$, and C$_1$-C$_4$ alkoxy; and C$_2$-C$_6$ alkenyl or C$_2$-C$_6$ alkynyl wherein each is optionally substituted with one, two or three substituents selected from —F, —Cl, —OH, —SH, —C≡N, —CF$_3$, C$_1$-C$_3$ alkoxy, and —NR$_5$R$_6$; or $R_2$, $R_3$ and the carbon to which they are attached form a carbocycle of three thru seven carbon atoms, wherein one carbon atom is optionally replaced by a group selected from —O—, —S—, —SO$_2$—, or —NR$_7$—; wherein $R_7$ is selected from H, —C$_1$-C$_8$ alkyl optionally substituted with 1, 2, or 3 groups independently selected from —OH, —NH$_2$, phenyl and halogen; C$_3$-C$_8$ cycloalkyl; —(C$_1$-C$_2$ alkyl)-(C$_3$-C$_8$ cycloalkyl); —(C$_1$-C$_6$ alkyl)-O—(C$_1$-C$_4$ alkyl); C$_2$-C$_6$ alkenyl; C$_2$-C$_6$ alkynyl; phenyl; naphthyl; heteroaryl; heterocycloalkyl.

Equally preferred compounds of formula A-I include those wherein $R_{15}$ at each occurrence is independently selected from hydrogen, C$_1$-C$_4$ alkyl, C$_1$-C$_4$ alkoxy, C$_1$-C$_4$ alkanoyl, each of which is unsubstituted or substituted with 1, 2, 3, or 4 groups independently selected from halogen, alkyl, hydroxy, C$_1$-C$_4$ alkoxy, and NH$_2$; and —R$_{26}$-R$_{27}$; wherein $R_{26}$ is selected from a bond, —C(O)—, —SO$_2$—, —CO$_2$—, —C(O)NR$_5$—, and —NR$_5$C(O)—; and $R_{27}$ is selected from C$_1$-C$_6$ alkyl, C$_1$-C$_6$ alkoxy, and benzyl, wherein each of the above is unsubstituted or substituted with 1, 2, 3, 4, or 5 groups that are independently C$_1$-C$_4$ alkyl, C$_1$-C$_4$ alkoxy, halogen, halo C$_1$-C$_4$ alkyl, hydroxyalkyl, —C(O)NR$_5$R$_6$, or —NR$_5$R$_6$.

Other equally preferred compounds of formula A-I include those wherein $R_1$ is C$_1$-C$_{10}$ alkyl optionally substituted with 1, 2, or 3 groups independently selected from halogen, —OH, =O, —SH, —CN, —CF$_3$, —C$_1$-C$_4$ alkoxy, amino, mono- or dialkylamino, —N(R)C(O)R', —OC(=O)-amino and —OC(=O)-mono- or dialkylamino; or $R_1$ is C$_2$-C$_6$ alkenyl or C$_2$-C$_6$ alkynyl, each of which is optionally substituted with 1, 2, or 3 groups independently selected from halogen, OH, SH, C≡N, CF$_3$, OCF$_3$, C$_1$-C$_4$ alkoxy, amino, and mono- or dialkylamino; or $R_1$ is aryl, heteroaryl, heterocyclyl, aryl C$_1$-C$_6$ alkyl, heteroaryl C$_1$-C$_6$ alkyl, or heterocycloalkyl C$_1$-C$_6$ alkyl; wherein each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O; and $R_{50}$ at each occurrence is independently selected from halogen, OH, SH, CN, —CO—(C$_1$-C$_4$ alkyl), —CO$_2$—(C$_1$-C$_4$ alkyl), —SO$_2$—NR$_5$R$_6$, —NR$_7$R$_8$, —CO—NR$_5$R$_6$, —CO—NR$_7$R$_8$, —SO$_2$—(C$_1$-C$_4$ alkyl), C$_1$-C$_6$ alkyl, C$_2$-C$_6$ alkenyl, C$_2$-C$_6$ alkynyl, C$_1$-C$_6$ alkoxy, or C$_3$-C$_8$ cycloalkyl;

wherein the alkyl, alkenyl, alkynyl, alkoxy, or cycloalkyl groups are optionally substituted with 1, 2, or 3 substituents independently selected from C$_1$-C$_4$ alkyl, halogen, OH, SH, —NR$_5$R$_6$, CN, C$_1$-C$_4$ haloalkyl, C$_1$-C$_4$ haloalkoxy, phenyl, NR$_7$R$_8$, and C$_1$-C$_4$ alkoxy.

Still other equally preferred compounds of formula A-I include those of formula A-I-1, i.e., compounds of formula A-I wherein R$_c$ and R$_d$ are independently selected from C$_1$-C$_6$ alkyl optionally substituted with one, two or three substituents selected from C$_1$-C$_3$ alkyl, halogen, OH, SH, C≡N, CF$_3$, C$_1$-C$_3$ alkoxy, and —NR$_5$R$_6$; hydroxy; nitro; halogen; —CO$_2$H; cyano; and —(CH$_2$)$_{0-4}$—CO—NR$_{21}$R$_{22}$; wherein R$_{21}$ and R$_{22}$ independently represent hydrogen, C$_1$-C$_6$ alkyl, hydroxyl(C$_1$-C$_6$)alkyl, amino (C$_1$-C$_6$)alkyl, haloalkyl, C$_3$-C$_7$ cycloalkyl, —(C$_1$-C$_2$ alkyl)-(C$_3$-C$_7$ cycloalkyl), —(C$_1$-C$_6$ alkyl)-O—(C$_1$-C$_3$ alkyl), —C$_2$-C$_6$ alkenyl, —C$_2$-C$_6$ alkynyl, —C$_1$-C$_6$ alkyl chain with one double bond and one triple bond, phenyl, naphthyl, heteroaryl; or R$_c$ and R$_d$ are independently selected from —(CH$_2$)$_{0-4}$—CO—(C$_1$-C$_{12}$ alkyl); —(CH$_2$)$_{0-4}$—CO—(C$_2$-C$_{12}$ alkenyl); CH$_2$)$_{0-4}$—CO—(C$_2$-C$_{12}$)alkynyl; —(CH$_2$)$_{0-4}$—CO—(C$_3$-C$_7$ cycloalkyl); —(CH$_2$)$_{0-4}$—CO-phenyl; —(CH$_2$)$_{0-4}$—CO-naphthyl; —(CH$_2$)$_{0-4}$—CO-heteroaryl; —(CH$_2$)$_{0-4}$—CO-heterocycloalkyl; —(CH$_2$)$_{0-4}$—CO$_2$R$_{20}$; wherein R$_{20}$ is selected from C$_1$-C$_6$ alkyl, —(CH$_2$)$_{0-2}$-(phenyl), —(CH$_2$)$_{0-2}$-(naphthyl), C$_2$-C$_6$ alkenyl, C$_2$-C$_6$ alkynyl, C$_3$-C$_7$ cycloalkyl, and —(CH$_2$)$_{0-2}$-(heteroaryl), or R$_c$ and R$_d$ are independently selected from —(CH$_2$)$_{0-4}$—SO$_2$—NR$_{21}$R$_{22}$; —(CH$_2$)$_{0-4}$—SO—(C$_1$-C$_8$ alkyl); —(CH$_2$)$_{0-4}$—SO$_2$—(C$_1$-C$_{12}$ alkyl); —(CH$_2$)$_{0-4}$—SO$_2$—(C$_3$-C$_7$ cycloalkyl); —(CH$_2$)$_{0-4}$—N(H or R$_{20}$)—CO$_2$R$_{20}$; —(CH$_2$)$_{0-4}$—N(H or R$_{20}$)—CO—N(R$_{20}$)$_2$; —(CH$_2$)$_{0-4}$—N—CS—N(R$_{20}$)$_2$; —(CH$_2$)$_{0-4}$—N(—H or R$_{20}$)—CO—R$_{21}$; —(CH$_2$)$_{0-4}$—NR$_{21}$R$_{22}$; —(CH$_2$)$_{0-4}$-heterocycloalkyl; —(CH$_2$)$_{0-4}$—O—CO—(C$_1$-C$_6$ alkyl); —(CH$_2$)$_{0-4}$—O—P(O)—(OR$_5$)$_2$; —(CH$_2$)$_{0-4}$—O—CO—N(R$_{20}$)$_2$; —(CH$_2$)$_{0-4}$—O—CS—N(R$_{20}$)$_2$; —(CH$_2$)$_{0-4}$—O—(R$_{20}$); —(CH$_2$)$_{0-4}$—O—(R$_{20}$)—CO$_2$H; —(CH$_2$)$_{0-4}$—S—(R$_{20}$); —(CH$_2$)$_{0-4}$—O-halo(C$_1$-C$_6$)alkyl; —(CH$_2$)$_{0-4}$—O—(C$_1$-C$_6$)alkyl; C$_3$-C$_8$ cycloalkyl; and —(CH$_2$)$_{0-4}$—N(—H or R$_{20}$)—SO$_2$—R$_{21}$; or R$_c$ and R$_d$ are independently C$_2$-C$_6$ alkenyl or C$_2$-C$_6$ alkynyl, each of which is optionally substituted with C$_1$-C$_4$ alkyl, halogen, hydroxy, SH, cyano, CF$_3$, C$_1$-C$_4$ alkoxy, or NR$_5$R$_6$; wherein each aryl group at each occurrence is optionally substituted with 1, 2, 3, 4, or 5 R$_{50}$ groups;

each heteroaryl at each occurrence is optionally substituted with 1, 2, 3, 4, or 5 R$_{50}$ groups;

each heterocycloalkyl group at each occurrence is optionally substituted with 1, 2, 3, 4, or 5 groups that are independently R$_{50}$ or =O;

R$_{50}$ at each occurrence is independently selected from halogen, OH, SH, CN, —CO—(C$_1$-C$_4$ alkyl), —CO$_2$—(C$_1$-C$_4$ alkyl), —SO$_2$—NR$_5$R$_6$, —NR$_7$R$_8$, —CO—NR$_5$R$_6$, —CO—NR$_7$R$_8$, —SO$_2$—(C$_1$-C$_4$ alkyl), C$_1$-C$_6$ alkyl, C$_2$-C$_6$ alkenyl, C$_2$-C$_6$ alkynyl, C$_1$-C$_6$ alkoxy, or C$_3$-C$_8$ cycloalkyl;

wherein the alkyl, alkenyl, alkynyl, alkoxy, or cycloalkyl groups are optionally substituted with 1, 2, or 3 substituents independently selected from C$_1$-C$_4$ alkyl, halogen, OH, SH, —NR$_5$R$_6$, CN, C$_1$-C$_6$ haloalkyl, C$_1$-C$_6$ haloalkoxy, phenyl, NR$_7$R$_8$, and C$_1$-C$_6$ alkoxy.

Preferred compounds of formula A-I-1 include those of formula A-II:

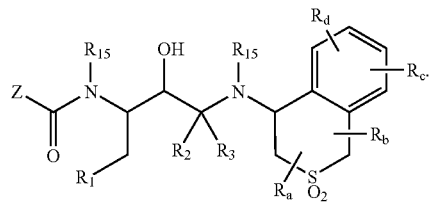

Preferred compound of formula A-II include those wherein

R$_2$ and R$_3$ are independently selected from H; C$_1$-C$_6$ alkyl optionally substituted with 1, 2, or 3 substituents that are independently selected from C$_1$-C$_4$ alkyl, halogen, —CF$_3$, and C$_1$-C$_4$ alkoxy; C$_2$-C$_6$ alkenyl or C$_2$-C$_6$ alkynyl, wherein each is optionally substituted with one, two or three substituents selected from —F, —Cl, —OH, —SH, —C≡N, —CF$_3$, C$_1$-C$_3$ alkoxy, and —NR$_5$R$_6$;

R$_5$ and R$_6$ at each occurrence are independently H or C$_1$-C$_6$ alkyl; or

R$_5$ and R$_6$ and the nitrogen to which they are attached, at each occurrence form a 5 or 6 membered heterocycloalkyl ring;

or

R$_2$, R$_3$ and the carbon to which they are attached form a carbocycle of three thru six carbon atoms, wherein one carbon atom is optionally replaced by a group selected from —O—, —S—, —SO$_2$—, or —NR$_7$—; wherein R$_7$ is selected from H; —C$_1$-C$_4$ alkyl optionally substituted with 1, 2, or 3 groups independently selected from —OH, —NH$_2$, and halogen; —C$_3$-C$_6$ cycloalkyl; —(C$_1$-C$_4$ alkyl)-O—(C$_1$-C$_4$ alkyl); —C$_2$-C$_4$ alkenyl; and —C$_2$-C$_4$ alkynyl.

Even more preferred compounds of formula A-II include those wherein

R$_{15}$ at each occurrence is independently selected from hydrogen, C$_1$-C$_4$ alkyl, C$_1$-C$_6$ alkanoyl, benzyl optionally substituted with OCH$_3$, —C(O)-tertiary butyl, and —CO$_2$-benzyl.

Still even more preferred compounds of formula A-II include those wherein

R$_1$ is C$_1$-C$_{10}$ alkyl optionally substituted with 1, 2, or 3 groups independently selected from halogen, —OH, =O, —SH, —CN, —CF$_3$, —C$_1$-C$_4$ alkoxy, amino, mono- or dialkylamino, —N(R)C(O)R', —OC(=O)-amino OC(=O)-mono- and dialkylamino; or R$_1$ is C$_2$-C$_6$ alkenyl or C$_2$-C$_6$ alkynyl, each of which is optionally substituted with 1, 2, or 3 groups independently selected from halogen, OH, SH, C≡N, CF$_3$, OCF$_3$, C$_1$-C$_4$ alkoxy, amino, and mono- or dialkylamino; or R$_1$ is aryl, heteroaryl, heterocyclyl, aryl C$_1$-C$_6$ alkyl, heteroaryl C$_1$-C$_6$ alkyl, or heterocycloalkyl C$_1$-C$_6$ alkyl;

each aryl group at each occurrence is optionally substituted with 1, 2, 3, 4, or 5 R$_{50}$ groups;

each heteroaryl at each occurrence is optionally substituted with 1, 2, 3, 4, or 5 R$_{50}$ groups;

each heterocycloalkyl group at each occurrence is optionally substituted with 1, 2, 3, 4, or 5 groups that are independently R$_{50}$ or =O;

R$_{50}$ at each occurrence is independently selected from halogen, OH, SH, CN, —CO—(C$_1$-C$_4$ alkyl), —CO$_2$—(C$_1$-C$_4$ alkyl), —SO$_2$—NR$_5$R$_6$, —NR$_7$R$_8$, —CO—NR$_5$R$_6$, —CO—NR$_7$R$_8$, —SO$_2$—(C$_1$-C$_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Still more preferred compounds of formula A-II include those of formula A-II-1, i.e., compound of formula A-II wherein $R_{50}$ at each occurrence is independently selected from halogen, OH, SH, —$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Preferred compounds of formula A-II-1 include those of formula A-III:

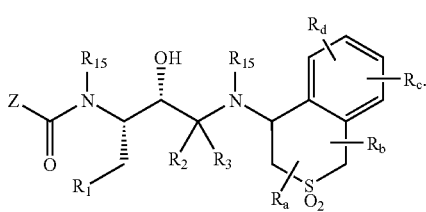

More preferred compounds of formula A-III include those of formula A-III-1, i.e., compounds of formula A-III wherein $R_1$ is phenyl, phenyl $C_1$-$C_6$ alkyl, naphthyl, or naphthyl $C_1$-$C_6$ alkyl, wherein the phenyl or naphthyl group is optionally substituted with 1, 2, 3, 4, or 5 $R_{50}$ groups.

Still more preferred compound of formula A-III-1 include those of formula A-III-2, i.e., compound of formula A-III-1 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is H, —$C_1$-$C_8$ alkyl optionally substituted with 1, 2, or 3 groups independently selected from —OH, —$NH_2$, and halogen; —$C_2$-$C_4$ alkenyl; or —$C_2$-$C_4$ alkynyl.

Preferred compounds of formula A-III-2 include those of formula A-III-3, i.e., compounds of formula A-III-2 wherein $R_2$, $R_3$ and the carbon to which they are attached form a carbocycle of three thru six carbon atoms.

Equally preferred compound of formula A-III-2 include those of formula A-III-4, i.e., compounds of formula A-III-2 compounds wherein $R_2$, $R_3$ and the carbon to which they are attached form a heterocycloalkyl group containing 2 to 5 carbon atoms and one group selected from —O—, —S—, —$SO_2$—, and —$NR_7$—; wherein $R_7$ is H, —$C_1$-$C_8$ alkyl optionally substituted with 1, 2, or 3 groups independently selected from —OH, —$NH_2$, and halogen; —$C_2$-$C_4$ alkenyl; or —$C_2$-$C_4$ alkynyl.

Other equally preferred compounds of formula A-III-1 include those compounds of formula A-III-5, i.e., compounds of formula A-III-1 wherein $R_2$ and $R_3$ are independently selected from H; $C_1$-$C_6$ alkyl optionally substituted with 1, 2, or 3 substituents that are independently selected from $C_1$-$C_4$ alkyl, halogen, —$CF_3$, and $C_1$-$C_4$ alkoxy; $C_2$-$C_6$ alkenyl; and $C_2$-$C_6$ alkynyl.

More preferred compound of formulas A-III-3, A-III-4, and A-III-5 include those of formula A-III-6, i.e., compound of formulas A-III-3, A-III-4, and A-III-5 wherein $R_a$ and $R_b$ are independently selected from $C_1$-$C_6$ alkyl, $C_1$-$C_6$ alkoxy, halogen, CN, OH, hydroxyalkyl, $C_1$-$C_6$ haloalkyl, $C_1$-$C_6$ haloalkoxy, and —$C_1$-$C_6$ alkyl-$NR_5R_6$; or $R_a$ and $R_b$ are attached to the same carbon and form a $C_3$-$C_7$ spirocycle; and $R_{15}$ at each occurrence is independently H or $C_1$-$C_4$ alkyl.

Preferred compound of formula A-III-6 include those of formula A-III-6a, i.e., compounds of formula A-III-6 wherein $R_c$ and $R_d$ are independently selected from $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; hydroxy; halogen; $C_2$-$C_6$ alkenyl or $C_2$-$C_6$ alkynyl, wherein the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$.

Other preferred compound of formula A-III-6 include those wherein $R_c$ and $R_d$ are —$(CH_2)_{0-4}$—CO—$NR_{21}R_{22}$, —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl); —$(CH_2)_{0-4}$—$SO_2$—($C_3$-$C_7$ cycloalkyl); —$(CH_2)_{0-4}$—N(H or $R_{20}$)—CO—O—$R_{20}$; —$(CH_2)_{0-4}$—N(H or $R_{20}$)—CO—N($R_{20}$)$_2$; —$(CH_2)_{0-4}$—N—CS—N($R_{20}$)$_2$; —$(CH_2)_{0-4}$—N(—H or $R_{20}$)—CO—$R_{21}$; or —$(CH_2)_{0-4}$—$NR_{21}R_{22}$; wherein $R_{21}$ and $R_{22}$ independently represent hydrogen, $C_1$-$C_6$ alkyl, hydroxyl ($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, phenyl, naphthyl, or heteroaryl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Still other preferred compound of formula A-III-6 include those wherein $R_c$ and $R_d$ are —$(CH_2)_{0-4}$—CO—($C_1$-$C_{12}$ alkyl); —$(CH_2)_{0-4}$—CO—($C_2$-$C_{12}$ alkenyl); $(CH_2)_{0-4}$—CO—($C_2$-$C_{12}$) alkynyl; —$(CH_2)_{0-4}$—CO—($C_3$-$C_7$ cycloalkyl); —$(CH_2)_{0-4}$—CO-phenyl; —$(CH_2)_{0-4}$—CO-naphthyl; —$(CH_2)_{0-4}$—CO-heteroaryl; —$(CH_2)_{0-4}$—CO-heterocyloalkyl; —$(CH_2)_{0-4}$—$CO_2R_{20}$; where $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, and —$(CH_2)_{0-2}$-(heteroaryl);

each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Yet still other preferred compounds of formula A-III-6 include those wherein $R_c$ and $R_d$ are —$(CH_2)_{0-4}$—O—CO—($C_1$-$C_6$ alkyl); —$(CH_2)_{0-4}$—O—P(O)—$(OR_5)_2$; —$(CH_2)_{0-4}$—O—CO—N$(R_{20})_2$; —$(CH_2)_{0-4}$—O—CS—N$(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo ($C_1$-$C_6$)alkyl; —(C $H_2)_{0-4}$—O—($C_1$-$C_6$)alkyl; $C_3$-$C_8$ cycloalkyl; or —($CH_2)_{0-4}$—N(—H or $R_{20}$)—$SO_2$-$R_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —$CO_2$—($C_1$-$C_4$ alkyl), —$SO_2$—$NR_5R_6$, —$NR_7R_8$, —CO—$NR_5R_6$, —CO—$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Other preferred compounds of formula A-III include those of formula A-III-7, i.e., compound of formula A-III wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino and —OC(=O)-mono- or dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino.

More preferred compounds of formula A-III-7 include those compounds of formula A-III-8, i.e., compounds of formula A-III-7 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is selected from H or —$C_1$-$C_4$ alkyl optionally substituted with 1 group selected from —OH, —$NH_2$, and halogen.

Preferred compounds of formula A-III-8 include those compounds of formula A-III-9, i.e., compounds of formula A-III-8 wherein $R_2$, $R_3$ and the carbon to which they are attached form a carbocycle of three thru six carbon atoms.

Other preferred compounds of formula A-III-8 include those compounds of formula A-III-10, i.e., compounds of formula A-III-8 wherein $R_2$, $R_3$, and the carbon to which they are attached form a heterocycloalkyl group containing 2 to 5 carbon atoms and one group selected from —O—, —S—, —$SO_2$—, and —$NR_7$—; wherein $R_7$ is selected from H or —$C_1$-$C_4$ alkyl optionally substituted with 1 group selected from —OH, —$NH_2$, and halogen.

Still other preferred compounds of formula A-III-8 include those compounds of formula A-III-11, i.e., compounds of formula A-III-8 wherein $R_2$ and $R_3$ are independently selected from H; $C_1$-$C_6$ alkyl optionally substituted with 1, or 2 substituents that are independently selected from $C_1$-$C_4$ alkyl, halogen, —$CF_3$, and $C_1$-$C_4$ alkoxy; $C_2$-$C_6$ alkenyl; and $C_2$-$C_6$ alkynyl.

More preferred compound of formulas A-III-9, A-III-10, and A-III-11 include those of formula A-III-12, i.e., compound of formulas A-III-9, A-III-10, and A-III-11 wherein $R_a$ and $R_b$ are independently selected from $C_1$-$C_3$ alkyl, F, OH, C≡N, $CF_3$, $C_1$-$C_6$ alkoxy, and —$NR_5R_6$; and $R_{15}$ at each occurrence is independently H or $C_1$-$C_4$ alkyl.

Preferred compounds of formula A-III-12 include those compounds wherein $R_c$ and $R_d$ are independently selected from $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; hydroxy; halogen;

$C_2$-$C_6$ alkenyl and $C_2$-$C_6$ alkynyl; wherein the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$.

Other preferred compounds of formula A-III-12 include those compounds wherein $R_c$ and $R_d$ are —$(CH_2)_{0-4}$—CO—$NR_{21}R_{22}$, —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_1$-$C_{12}$ alkyl); —$(CH_2)_{0-4}$—$SO_2$—($C_3$-$C_7$ cycloalkyl); —$(CH_2)_{0-4}$—N(H or $R_{20}$)—CO—O—$R_{20}$; —$(CH_2)_{0-4}$—N(—H or $R_{20}$)—CO—N$(R_{20})_2$; —$(CH_2)_{0-4}$—N—CS—N$(R_{20})_2$; —$(CH_2)_{0-4}$—N(—H or $R_{20}$)—CO—$R_{21}$; or —$(CH_2)_{0-4}$—$NR_{21}R_{22}$; wherein $R_{21}$ and $R_{22}$ independently represent hydrogen, $C_1$-$C_6$ alkyl, hydroxyl ($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, phenyl, naphthyl, or heteroaryl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Still other preferred compounds of formula A-III-12 include those compounds wherein $R_c$ and $R_d$ are —$(CH_2)_{0-4}$—CO—($C_1$-$C_{12}$ alkyl); —$(CH_2)_{0-4}$—CO—($C_2$-$C_{12}$ alkenyl); $(CH_2)_{0-4}$—CO—($C_2$-$C_{12}$) alkynyl; —$(CH_2)_{0-4}$—CO—($C_3$-$C_7$ cycloalkyl); —$(CH_2)_{0-4}$—CO-phenyl; —$(CH_2)_{0-4}$—CO-naphthyl; —$(CH_2)_{0-4}$—CO-heteroaryl; —$(CH_2)_{0-4}$—CO-heterocycloalkyl;

—$(CH_2)_{0-4}$—$CO_2R_{20}$; where $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, —$(CH_2)_{0-2}$-(heterocycloalkyl) and —$(CH_2)_{0-2}$-(heteroaryl);

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Yet still other preferred compounds of formula A-III-12 include those compounds wherein $R_c$ and $R_d$ are —$(CH_2)_{0-4}$—O—CO—($C_1$-$C_6$ alkyl); —$(CH_2)_{0-4}$—O—P(O)—$(OR_5)_2$; —$(CH_2)_{0-4}$—O—CO—N$(R_{20})_2$; —$(CH_2)_{0-4}$—O—CS—N$(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo($C_1$-$C_6$)alkyl; —$(CH_2)_{0-4}$—O—($C_1$-$C_6$)alkyl; $C_3$-$C_8$ cycloalkyl; or —($CH_2)_{0-4}$—N(—H or $R_{20}$)—$SO_2$-$R_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —$CO_2$—($C_1$-$C_4$ alkyl), —$SO_2$—$NR_5R_6$, —$NR_7R_8$, —CO—$NR_5R_6$, —CO—$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Preferred compounds of formula A-III-6a include those of formula A-IV

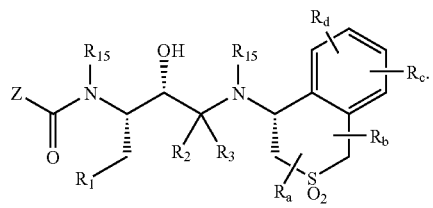

Preferred compounds of formula A-IV include those wherein $R_2$ and $R_3$ are independently H or $C_1$-$C_4$ alkyl.

Other preferred compounds of formula A-IV include those of formula A-IV-1, i.e., compounds of formula A-IV wherein $R_a$ and $R_b$ are independently H or $C_1$-$C_3$ alkyl; and $R_1$ is phenyl, optionally substituted with 1, 2, or 3 $R_{50}$ groups; and $R_{15}$ at each occurrence is independently H or $C_1$-$C_4$ alkyl.

Preferred compounds of formula A-IV-1 include those of formula A-IV-2, i.e., compounds of formula A-IV-1 wherein $R_1$ is a dihalophenyl; and $R_2$ and $R_3$ are independently H or $C_1$-$C_4$ alkyl.

Preferred compounds of formula A-IV-2 include compounds of formula A-V

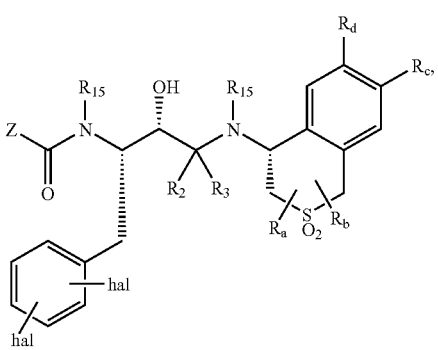

wherein hal at each occurrence is independently selected from F, Cl, Br, and I.

More preferred compounds of formula A-V include those compounds wherein $R_c$ is a $C_1$-$C_4$ alkyl group.

Other preferred compounds of formula A-IV-2 include compounds of formula A-VI

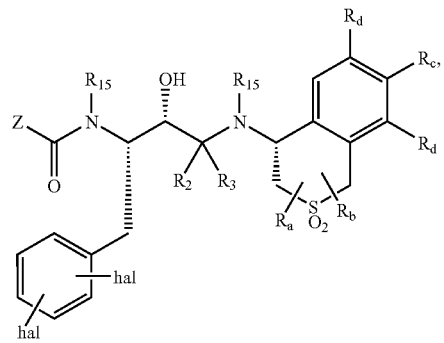

wherein hal at each occurrence is independently selected from F, Cl, Br, and I.

Preferred compounds of formula A-VI include those compounds wherein $R_c$ is a $C_1$-$C_4$ alkyl group.

Other preferred compounds of formula A-IV-2 include compounds of formula A-VII

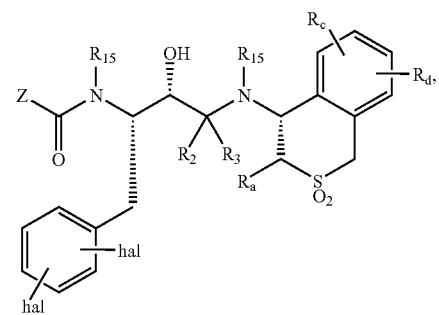

wherein $R_b$ is H.

Still other preferred compounds of formula A-IV-2 include compounds of formula A-VIII

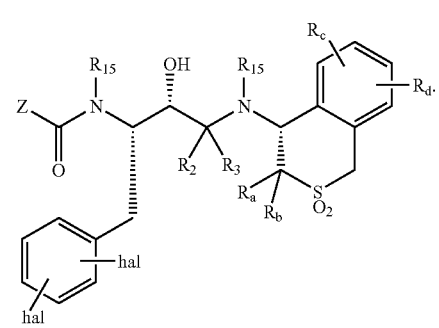

Other preferred compounds of formula A-I-1 include those compounds of formula A-IX, i.e., compounds of formula A-I-1 wherein

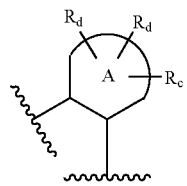

is a 5 or 6 membered heteroaryl group.

Preferred compounds of formula A-IX include compounds of formula A-IX-1, i.e., compounds of formula A-IX wherein $R_2$ and $R_3$ are independently selected from H; $C_1$-$C_6$ alkyl optionally substituted with 1, 2, or 3 substituents that are independently selected from $C_1$-$C_4$ alkyl, halogen, —$CF_3$, and $C_1$-$C_4$ alkoxy; $C_2$-$C_6$ alkenyl or $C_2$-$C_6$ alkynyl wherein each is optionally substituted with one, two, or three substituents selected from —F, —Cl, —OH, —SH, —C≡N, —$CF_3$, $C_1$-$C_3$ alkoxy, and —$NR_5R_6$; or $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is selected from H; —$C_1$-$C_4$ alkyl optionally substituted with 1, 2, or 3 groups independently selected from —OH, —$NH_2$, and halogen; —$C_3$-$C_8$ cycloalkyl; —($C_1$-$C_4$ alkyl)-O—($C_1$-$C_4$ alkyl); —$C_2$-$C_4$ alkenyl; and —$C_2$-$C_4$ alkynyl.

Preferred compounds of formula A-IX-1 include those of formula A-IX-2, i.e., compounds of formula A-IX-1, wherein $R_{15}$ at each occurrence is independently selected from hydrogen, $C_1$-$C_4$ alkyl, $C_1$-$C_6$ alkanoyl, benzyl optionally substituted with $OCH_3$, —C(O)-tertiary butyl, and —$CO_2$-benzyl.

Preferred compounds of formula A-IX-2 include those of formula A-IX-3, i.e., compounds of formula A-IX-2, wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino OC(=O)-mono- and dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino; or $R_1$ is aryl, heteroaryl, heterocyclyl, aryl $C_1$-$C_6$ alkyl, heteroaryl $C_1$-$C_6$ alkyl, or heterocycloalkyl $C_1$-$C_6$ alkyl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —$CO_2$—($C_1$-$C_4$ alkyl), —$SO_2$—$NR_5R_6$, —$NR_7R_8$, —CO—$NR_5R_6$, —CO—$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Preferred compounds of formula A-IX-3 include those of formula A-IX-4, i.e., compounds of formula A-IX-3, wherein $R_{50}$ at each occurrence is independently selected from halogen, OH, SH, —$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_4$ haloalkyl, $C_1$-$C_4$ haloalkoxy, phenyl, $NR_7R_8$, and $C_1$-$C_4$ alkoxy.

Preferred compounds of formula A-IX-4 include those of formula A-IX-5, i.e., compounds of formula A-X-4, of the formula

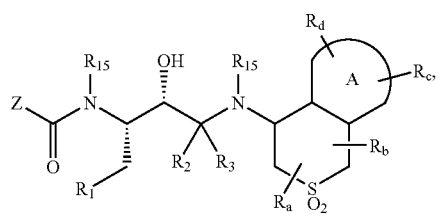

wherein

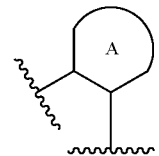

is selected from pyridinyl, pyrimidinyl, imidazolyl, oxazolyl, thiazolyl, furanyl, thienyl, pyrazole, isoxazole, and pyrrolyl.

Preferred compounds of formula A-IX-5 include compounds of formula A-IX-6, i.e., compounds of formula A-IX-5 wherein wherein, $R_1$ is phenyl $C_1$-$C_6$ alkyl or naphthyl $C_1$-$C_6$ alkyl, wherein the phenyl or naphthyl group is optionally substituted with 1, 2, 3, 4, or 5 $R_{50}$ groups.

Preferred compounds of formula A-IX-6 include compounds of formula A-IX-7, i.e., compounds of formula A-IX-6 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is H, —$C_1$-$C_8$ alkyl optionally substituted with 1, 2, or 3 groups independently selected from —OH, —$NH_2$, and halogen; —$C_2$-$C_4$ alkenyl; or —$C_2$-$C_4$ alkynyl.

Preferred compounds of formula A-IX-7 include compounds of formula A-IX-8, i.e., compounds of formula A-IX-7 wherein $R_2$, $R_3$ and the carbon to which they are attached form a carbocycle of three thru six carbon atoms.

Other preferred compounds of formula A-IX-7 include compounds of formula A-IX-9, i.e., compounds of formula A-IX-7 wherein $R_2$, $R_3$ and the carbon to which they are attached form a heterocycloalkyl group containing 2 to 5 carbon atoms and one group selected from —O—, —S—, —$SO_2$—, and —$NR_7$—; wherein $R_7$ is H, —$C_1$-$C_6$ alkyl optionally substituted with 1, 2, or 3 groups independently selected from —OH, —$NH_2$, and halogen; —$C_2$-$C_4$ alkenyl; or —$C_2$-$C_4$ alkynyl.

Other preferred compounds of formula A-IX-6 include compounds of formula A-IX-10, i.e., compounds of formula A-IX-6 wherein $R_2$ and $R_3$ are independently selected from H; $C_1$-$C_4$ alkyl optionally substituted with 1 substituent that is selected from halogen, —$CF_3$, and $C_1$-$C_4$ alkoxy; $C_2$-$C_4$ alkenyl; $C_2$-$C_4$ alkynyl; and —$CO_2$—($C_1$-$C_4$ alkyl); wherein $R_5$ and $R_6$ are at each occurrence are independently H or $C_1$-$C_6$ alkyl; or $R_5$ and $R_6$ and the nitrogen to which they are attached, at each occurrence form a 5 or 6 membered heterocycloalkyl ring.

Preferred compounds of formulas A-IX-8, A-IX-9, or A-IX-10 include those of formula A-IX-11, i.e., compounds of formulas A-IX-8, A-IX-9, or A-IX-10 wherein $R_a$ and $R_b$ are independently selected from $C_1$-$C_6$ alkyl, $C_1$-$C_6$ alkoxy, halogen, CN, OH, hydroxyalkyl, $C_1$-$C_6$ haloalkyl, $C_1$-$C_6$ haloalkoxy, and —$C_1$-$C_6$ alkyl-$NR_5R_6$; or $R_a$ and $R_b$ are attached to the same carbon and form a $C_3$-$C_7$ spirocycle; and $R_{15}$ at each occurrence is independently H or $C_1$-$C_4$ alkyl.

Preferred compounds of formula A-IX-11 include those wherein $R_c$ and $R_d$ are independently selected from $C_1$-$C_6$ alkyl optionally substituted with one, two or three substituents selected from $C_1$-$C_3$ alkyl, halogen, OH, SH, C≡N, $CF_3$, $C_1$-$C_3$ alkoxy, and —$NR_5R_6$; hydroxy; halogen; $C_2$-$C_6$ alkenyl or $C_2$-$C_6$ alkynyl, wherein the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$.

Other preferred compounds of formula A-IX-11 include those wherein $R_c$ and $R_d$ are —$(CH_2)_{0-4}$—CO—$NR_{21}R_{22}$, —$(CH_2)_{0-4}$—$SO_2$—$NR_{21}R_{22}$; —$(CH_2)_{0-4}$—SO—($C_1$-$C_8$ alkyl); —$(CH_2)_{0-4}$—$SO_2$—($C_0$-$C_{12}$ alkyl); —$(CH_2)_{0-4}$—$SO_2$—($C_3$-$C_7$ cycloalkyl); —$(CH_2)_{0-4}$—N(H or $R_{20}$)—CO—O—$R_{20}$; —$(CH_2)_{0-4}$—N(H or $R_{20}$)—CO—N($R_{20}$)$_2$; —$(CH_2)_{0-4}$—N—CS—N($R_{20}$)$_2$; —$(CH_2)_{0-4}$—N(—H or $R_{20}$)—CO—$R_{21}$; or —$(CH_2)_{0-4}$—$NR_{21}R_{22}$; wherein $R_{21}$ and $R_{22}$ independently represent hydrogen, $C_1$-$C_6$ alkyl, hydroxyl ($C_1$-$C_6$)alkyl, amino($C_1$-$C_6$)alkyl, haloalkyl, $C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, phenyl, naphthyl, or heteroaryl;

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Still other preferred compounds of formula A-IX-11 include those wherein $R_c$ and $R_d$ are —$(CH_2)_{0-4}$—CO—($C_1$-$C_{12}$ alkyl); —$(CH_2)_{0-4}$—CO—($C_2$-$C_{12}$ alkenyl); $CH_2)_{0-4}$—CO—($C_2$-$Cl_2$) alkynyl; —$(CH_2)_{0-4}$—CO—($C_3$-$C_7$ cycloalkyl); —$(CH_2)_{0-4}$—CO-phenyl; —$(CH_2)_{0-4}$—CO-naphthyl; —$(CH_2)_{0-4}$—CO-heteroaryl; —$(CH_2)_{0-4}$—CO-heterocycloalkyl; —$(CH_2)_{0-4}$—$CO_2R_{20}$; where $R_{20}$ is selected from $C_1$-$C_6$ alkyl, —$(CH_2)_{0-2}$-(phenyl), —$(CH_2)_{0-2}$-(naphthyl), $C_2$-$C_6$ alkenyl, $C_2$-$C_6$ alkynyl, $C_3$-$C_7$ cycloalkyl, —$(CH_2)_{0-2}$-(heterocycloalkyl) and —$(CH_2)_{0-2}$-(heteroaryl);

each aryl group at each occurrence is optionally substituted with 1, 2, 3, 4, or 5 $R_{50}$ groups;

each heteroaryl at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O.

Yet still other preferred compounds of formula A-IX-11 include those wherein $R_c$ and $R_d$ are —$(CH_2)_{0-4}$—O—CO—($C_1$-$C_6$ alkyl); —$(CH_2)_{0-4}$—O—P(O)—$(OR_5)_2$; —$(CH_2)_{0-4}$—O—CO—N$(R_{20})_2$; —$(CH_2)_{0-4}$—O—CS—N$(R_{20})_2$; —$(CH_2)_{0-4}$—O—$(R_{20})$; —$(CH_2)_{0-4}$—O—$(R_{20})$—$CO_2H$; —$(CH_2)_{0-4}$—S—$(R_{20})$; —$(CH_2)_{0-4}$—O-halo ($C_1$-$C_6$)alkyl; —$(CH_2)_{0-4}$—O—($C_1$-$C_6$)alkyl; $C_3$-$C_8$ cycloalkyl; or —$(CH_2)_{0-4}$—N(—H or $R_{20}$)—$SO_2$—$R_{21}$; wherein each aryl group and each heteroaryl group at each occurrence is optionally substituted with 1, 2, 3, 4, or 5 $R_{50}$ groups;

each heterocycloalkyl group at each occurrence is optionally substituted with 1, 2, 3, 4, or 5 groups that are independently $R_{50}$ or =O;

$R_{50}$ at each occurrence is independently selected from halogen, OH, SH, CN, —CO—($C_1$-$C_4$ alkyl), —$CO_2$—($C_1$-$C_4$ alkyl), —$SO_2$—$NR_5R_6$, —$NR_7R_8$, —CO—$NR_5R_6$, —CO—$NR_7R_8$, —$SO_2$—($C_1$-$C_4$ alkyl), $C_1$-$C_6$ alkyl, $C_2$-$C_6$ alkenyl, $C_2$-$C_6$ alkynyl, $C_1$-$C_6$ alkoxy, or $C_3$-$C_8$ cycloalkyl;

wherein the alkyl, alkenyl, alkynyl, alkoxy, or cycloalkyl groups are optionally substituted with 1, 2, or 3 substituents independently selected from $C_1$-$C_4$ alkyl, halogen, OH, SH, —$NR_5R_6$, CN, $C_1$-$C_6$ haloalkyl, $C_1$-$C_6$ haloalkoxy, phenyl, $NR_7R_8$, and $C_1$-$C_6$ alkoxy.

Other preferred compounds of formula A-IX-5 include those of formula A-IX-12, i.e., compounds of formula A-IX-5, wherein $R_1$ is $C_1$-$C_{10}$ alkyl optionally substituted with 1, 2, or 3 groups independently selected from halogen, —OH, =O, —SH, —CN, —$CF_3$, —$C_1$-$C_4$ alkoxy, amino, mono- or dialkylamino, —N(R)C(O)R', —OC(=O)-amino and —OC(=O)-mono- or dialkylamino; or $R_1$ is $C_2$-$C_6$ alkenyl or $C_2$-$C_6$ alkynyl, each of which is optionally substituted with 1, 2, or 3 groups independently selected from halogen, OH, SH, C≡N, $CF_3$, $OCF_3$, $C_1$-$C_4$ alkoxy, amino, and mono- or dialkylamino.

Preferred compounds of formula A-IX-12, include those of formula A-IX-13, i.e., compounds of formula A-IX-12 wherein $R_2$, $R_3$ and the carbon to which they are attached form a carbocycle of three thru six carbon atoms, wherein one carbon atom is optionally replaced by a group selected from —O—, —S—, —$SO_2$—, or —$NR_7$—; wherein $R_7$ is selected from H or —$C_1$-$C_4$ alkyl optionally substituted with 1 group selected from —OH, —$NH_2$, and halogen.

Preferred compounds of formula A-IX-13, include those of formula A-IX-14, i.e., compounds of formula A-IX-13 wherein $R_2$, $R_3$ and the carbon to which they are attached form a carbocycle of three thru six carbon atoms.

Other preferred compounds of formula A-IX-13, include those of formula A-IX-15, i.e., compounds of formula A-IX-13 wherein $R_2$, $R_3$ and the carbon to which they are attached form a heterocycloalkyl group containing 2 to 5 carbon atoms and one group selected from —O—, —S—, —SO$_2$—, and —NR$_7$—; wherein $R_7$ is selected from H and —C$_1$-C$_4$ alkyl optionally substituted with 1 group selected from —OH, —NH$_2$, and halogen.

Other preferred compounds of formula A-IX-13, include those of formula A-IX-16, i.e., compounds of formula A-IX-13 wherein $R_2$ and $R_3$ are independently selected from H; C$_1$-C$_4$ alkyl optionally substituted with 1 substituent that is selected from halogen, —CF$_3$, and C$_1$-C$_4$ alkoxy; C$_2$-C$_4$ alkenyl; and C$_2$-C$_4$ alkynyl; wherein $R_5$ and $R_6$ are at each occurrence are independently —H or C$_1$-C$_6$ alkyl; or $R_5$ and $R_6$ and the nitrogen to which they are attached, at each occurrence form a 5 or 6 membered heterocycloalkyl ring.

Preferred compounds of formulas A-IX-14, A-IX-15, A-IX-16 include compounds of formula A-IX-17, i.e., compounds of formulas A-IX-14, A-IX-15, A-IX-16 wherein $R_a$ and $R_b$ are independently selected from C$_1$-C$_3$ alkyl, F, OH, SH, C≡N, CF$_3$, C$_1$-C$_6$ alkoxy, and —NR$_5$R$_6$; and $R_{15}$ at each occurrence is independently H or C$_1$-C$_4$ alkyl.

Preferred compounds of formula A-IX-17, include those compounds wherein $R_c$ and $R_d$ are independently selected from C$_1$-C$_6$ alkyl optionally substituted with one, two or three substituents selected from C$_1$-C$_3$ alkyl, halogen, OH, SH, C≡N, CF$_3$, C$_1$-C$_3$ alkoxy, and —NR$_5$R$_6$; hydroxy; halogen; C$_2$-C$_6$ alkenyl or C$_2$-C$_6$ alkynyl, wherein the alkenyl or alkynyl group is optionally substituted with C$_1$-C$_4$ alkyl, halogen, hydroxy, SH, cyano, CF$_3$, C$_1$-C$_4$ alkoxy, or NR$_5$R$_6$.

Other preferred compounds of formula A-IX-17, include those compounds wherein $R_c$ and $R_d$ are —(CH$_2$)$_{0-4}$—CO—NR$_{21}$R$_{22}$, —(CH$_2$)$_{0-4}$—SO$_2$—NR$_{21}$R$_{22}$; —(CH$_2$)$_{0-4}$—SO—(C$_1$-C$_8$ alkyl); —(CH$_2$)$_{0-4}$—SO$_2$—(C$_1$-C$_{12}$ alkyl); —(CH$_2$)$_{0-4}$—SO$_2$—(C$_3$-C$_7$ cycloalkyl); —(CH$_2$)$_{0-4}$—N(H or R$_{20}$)—CO$_2$R$_{20}$; —(CH$_2$)$_{0-4}$—N(H or R$_{20}$)—CO—N(R$_{20}$)$_2$; —(CH$_2$)$_{0-4}$—N—CS—N(R$_{20}$)$_2$; —(CH$_2$)$_{0-4}$—N(—H or R$_{20}$)—CO—R$_{21}$; or —(CH$_2$)$_{0-4}$—NR$_{21}$R$_{22}$; wherein $R_{21}$ and $R_{22}$ independently represent hydrogen, C$_1$-C$_6$ alkyl, hydroxyl (C$_1$-C$_6$)alkyl, amino(C$_1$-C$_6$)alkyl, haloalkyl, C$_3$-C$_7$ cycloalkyl, —(C$_1$-C$_2$ alkyl)-(C$_3$-C$_7$ cycloalkyl), —(C$_1$-C$_6$ alkyl)-O—(C$_1$-C$_3$ alkyl), —C$_2$-C$_6$ alkenyl, —C$_2$-C$_6$ alkynyl, phenyl, naphthyl, or heteroaryl;

each aryl group and each heteroaryl group at each occurrence is optionally substituted with 1, 2, 3, 4, or 5 R$_{50}$ groups;

each heterocycloalkyl group at each occurrence is optionally substituted with 1, 2, 3, 4, or 5 groups that are independently R$_{50}$ or =O.

Still other preferred compounds of formula A-IX-17, include those compounds wherein $R_c$ and $R_d$ are —(CH$_2$)$_{0-4}$—CO—(C$_1$-C$_{12}$ alkyl); —(CH$_2$)$_{0-4}$—CO—(C$_2$-C$_{12}$ alkenyl); (CH$_2$)$_{0-4}$—CO—(C$_2$-C$_{12}$) alkynyl; —(CH$_2$)$_{0-4}$—CO—(C$_3$-C$_7$ cycloalkyl); —(CH$_2$)$_{0-4}$—CO-phenyl; —(CH$_2$)$_{0-4}$—CO-naphthyl; —(CH$_2$)$_{0-4}$—CO-heteroaryl; —(CH$_2$)$_{0-4}$—CO-heterocycloalkyl; —(CH$_2$)$_{0-4}$—CO$_2$R$_{20}$; where $R_{20}$ is selected from C$_1$-C$_6$ alkyl, —(CH$_2$)$_{0-2}$-(phenyl), —(CH$_2$)$_{0-2}$-(naphthyl), C$_2$-C$_6$ alkenyl, C$_2$-C$_6$ alkynyl, C$_3$-C$_7$ cycloalkyl, —(CH$_2$)$_{0-2}$-(heterocycloalkyl) and —(CH$_2$)$_{0-2}$-(heteroaryl);

each aryl group at each occurrence is optionally substituted with 1, 2, 3, 4, or 5 R$_{50}$ groups;

each heteroaryl at each occurrence is optionally substituted with 1, 2, 3, 4, or 5 R$_{50}$ groups;

each heterocycloalkyl group at each occurrence is optionally substituted with 1, 2, 3, 4, or 5 groups that are independently R$_{50}$ or =O.

Yet still other preferred compounds of formula A-IX-17, include those compounds wherein $R_c$ and $R_d$ are —(CH$_2$)$_{0-4}$—O—CO—(C$_1$-C$_6$ alkyl); —(CH$_2$)$_{0-4}$—P(O)—(OR$_5$)$_2$; —(CH$_2$)$_{0-4}$—O—CO—N(R$_{20}$)$_2$; —(CH$_2$)$_{0-4}$—O—CS—N(R$_{20}$)$_2$; —(CH$_2$)$_{0-4}$—O—(R$_{20}$); —(CH$_2$)$_{0-4}$—O—(R$_{20}$)—CO$_2$H; —(CH$_2$)$_{0-4}$—S—(R$_{20}$); —(CH$_2$)$_{0-4}$—O-halo(C$_1$-C$_6$)alkyl; —(CH$_2$)$_{0-4}$—O—(C$_1$-C$_6$)alkyl; C$_3$-C$_8$ cycloalkyl; or —(CH$_2$)$_{0-4}$—N(—H or R$_{20}$)—SO$_2$—R$_{21}$; wherein each aryl group and each heteroaryl group at each occurrence is optionally substituted with 1, 2, 3, 4, or 5 R$_{50}$ groups;

each heterocycloalkyl group at each occurrence is optionally substituted with 1, 2, 3, 4, or 5 groups that are independently R$_{50}$ or =O;

$R_{50}$ at each occurrence is independently selected from halogen, OH, SH, CN, —CO—(C$_1$-C$_4$ alkyl), —CO$_2$—(C$_1$-C$_4$ alkyl), —SO$_2$—NR$_5$R$_6$, —NR$_7$R$_8$, —CO—NR$_5$R$_6$, —CO—NR$_7$R$_8$, —SO$_2$—(C$_1$-C$_4$ alkyl), C$_1$-C$_6$ alkyl, C$_2$-C$_6$ alkenyl, C$_2$-C$_6$ alkynyl, C$_1$-C$_6$ alkoxy, or C$_3$-C$_8$ cycloalkyl;

wherein the alkyl, alkenyl, alkynyl, alkoxy, or cycloalkyl groups are optionally substituted with 1, 2, or 3 substituents independently selected from C$_1$-C$_4$ alkyl, halogen, OH, SH, —NR$_5$R$_6$, CN, C$_1$-C$_6$ haloalkyl, C$_1$-C$_6$ haloalkoxy, phenyl, NR$_7$R$_8$, and C$_1$-C$_6$ alkoxy.

Other preferred compounds of formula A-IX-4 include those of formula A-X

Preferred compounds of formula A-X include compounds of formula A-X-1, i.e., compounds of formula A-X wherein $R_1$ is phenyl C$_1$-C$_6$ alkyl or naphthyl C$_1$-C$_6$ alkyl, wherein the phenyl or naphthyl group is optionally substituted with 1, 2, 3, 4, or 5 R$_{50}$ groups; and $R_2$ and $R_3$ are independently H or C$_1$-C$_4$ alkyl.

Preferred compounds of formula A-X-1 include compounds of formula A-X-2, i.e., compounds of formula A-X-1 wherein $R_a$ and $R_b$ are independently H or C$_1$-C$_4$ alkyl; or $R_a$ and $R_b$ are attached to the same carbon and form a C$_3$-C$_6$ carbocycle;

$R_1$ is phenyl, optionally substituted with 1, 2, or 3 R$_{50}$ groups; and $R_{15}$ at each occurrence is independently H or C$_1$-C$_4$ alkyl.

Preferred compounds of formula A-X-2 include compounds of formula A-X-3, i.e., compounds of formula A-X-2 wherein $R_1$ is a dihalophenyl.

Preferred compounds of formulas A-IX-5, A-X and A-X-3 include compounds of formula A-X-4, i.e., compounds of formulas A-IX-5, A-X and A-X-3 having the following structure,

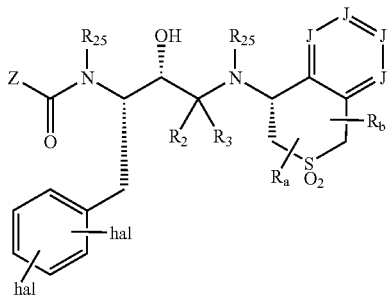

wherein
wherein J at each occurrence is independently selected from N or $CR_c$, wherein
$R_c$ at each occurrence is independently selected from $C_1$-$C_6$ alkyl, optionally substituted with 1, 2, or 3 substituents independently selected from $C_1$-$C_3$ alkyl, halogen, OH, SH, C≡N, $CF_3$, $C_1$-$C_6$ alkoxy, $C_3$-$C_8$ cycloalkyl, and $NR_5R_6$; hydroxy; halogen; $C_2$-$C_6$ alkenyl or $C_2$-$C_6$ alkynyl, wherein
the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$;

provided that at least two Js are $CR_c$.

Other preferred compounds of formulas A-IX-5, A-X and A-X-3 include compounds of formula A-X-5, i.e., compounds of formulas A-IX-5, A-X and A-X-3 having the following structure,

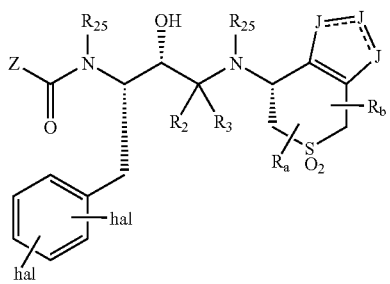

wherein
represents a single or double bond, provided that only one of the dashed bonds is a double bond;
J is selected from N, S, O, and $CR_c$, wherein
$R_c$ at each occurrence is independently selected from $C_1$-$C_6$ alkyl, optionally substituted with 1, 2, or 3 substituents independently selected from $C_1$-$C_3$ alkyl, halogen, OH, SH, C≡N, $CF_3$, $C_1$-$C_6$ alkoxy, $C_3$-$C_8$ cycloalkyl, and $NR_5R_6$; hydroxy; halogen; $C_2$-$C_6$ alkenyl or $C_2$-$C_6$ alkynyl, wherein
the alkenyl or alkynyl group is optionally substituted with $C_1$-$C_4$ alkyl, halogen, hydroxy, SH, cyano, $CF_3$, $C_1$-$C_4$ alkoxy, or $NR_5R_6$;

provided that at least one J is $CR_c$.

Other preferred compounds include those compounds according to any one of embodiments A-I to A-X-5, wherein Z is $C_1$-$C_6$ alkyl, optionally substituted with 1 or 2 groups that are independently OH, halogen, $C_1$-$C_4$ alkoxy, $CF_3$, $OCF_3$, $NO_2$, CN, and $NR_5R_6$. More preferably, Z is $C_1$-$C_4$ alkyl. Another preferred embodiment, Z is phenyl, benzyl, imidazolyl, or —$C_1$-$C_4$-imidazolyl.

Still other preferred compounds include those compounds according to any one of embodiments A-I to A-X-5, wherein $R_5$ and $R_6$ at each occurrence are independently H or $C_1$-$C_4$ alkyl. Preferably, Z is $C_1$-$C_4$ alkyl.

In another aspect, the invention provides a method of preparing compounds of formula (I)

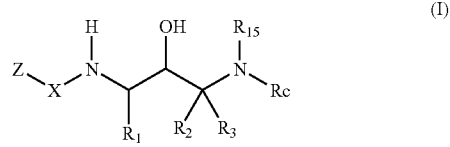

and a pharmaceutically acceptable salt thereof, wherein Z, X, $R_1$, $R_2$, $R_3$, $R_{15}$ and $R_c$ are as defined above.

In another aspect, the invention provides the intermediates that are useful in the preparation of the compounds of interest.

The invention also provides methods for treating a patient who has, or in preventing a patient from getting, a disease or condition selected from Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound of formula (I) and a pharmaceutically acceptable salts thereof.

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease.

In an embodiment, this method of treatment can prevent a disease from developing.

In an embodiment, this method of treatment can employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The invention also includes pharmaceutical compositions which include a compound of formula (I) and pharmaceutically acceptable salts thereof.

The invention also includes the use of a compound of formula (I) or pharmaceutically acceptable salts thereof for the manufacture of a medicament for use in treating a patient who has, or in preventing a patient from getting, a disease or condition selected from Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a compound of formula (I) can be employed where the disease is Alzheimer's disease.

In an embodiment, this use of a compound of formula (I) can help prevent or delay the onset of Alzheimer's disease.

In an embodiment, this use of a compound of formula (I) can be employed where the disease is mild cognitive impairment.

In an embodiment, this use of a compound of formula (I) can be employed where the disease is Down's syndrome.

In an embodiment, this use of a compound of formula (I) can be employed where the disease is Hereditary Cerebral Hemorrhage with Amyloidosis of the Dutch-Type.

In an embodiment, this use of a compound of formula (I) can be employed where the disease is cerebral amyloid angiopathy.

In an embodiment, this use of a compound of formula (I) can be employed where the disease is degenerative dementias.

In an embodiment, this use of a compound of formula (I) can be employed where the disease is diffuse Lewy body type of Alzheimer's disease.

In an embodiment, this use of a compound employs a pharmaceutically acceptable salt selected from salts of the following acids hydrochloric, hydrobromic, hydroiodic, nitric, sulfuric, phosphoric, citric, methanesulfonic, $CH_3$—$(CH_2)_n$—COOH where n is 0 thru 4, HOOC—$(CH_2)_n$—COOH where n is as defined above, HOOC—CH=CH—COOH, and phenyl-COOH.

The invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain. These methods each include administration of a therapeutically effective amount of a compound of formula (I) and pharmaceutically acceptable salts thereof.

The invention also includes a method for inhibiting beta-secretase activity, including exposing said beta-secretase to an effective inhibitory amount of a compound of formula (I), and pharmaceutically acceptable salt thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of a compound of formula (I), and a pharmaceutically acceptable salt thereof.

In an embodiment, this method employs a cleavage site: between Met652 and Asp653, numbered for the APP-751 isotype; between Met 671 and Asp 672, numbered for the APP-770 isotype; between Leu596 and Asp597 of the APP-695 Swedish Mutation; between Leu652 and Asp653 of the APP-751 Swedish Mutation; or between Leu671 and Asp672 of the APP-770 Swedish Mutation.

In an embodiment, this method exposes said reaction mixture in vitro.

In an embodiment, this method exposes said reaction mixture in a cell.

In an embodiment, this method exposes said reaction mixture in an animal cell.

In an embodiment, this method exposes said reaction mixture in a human cell.

The invention also includes a method for inhibiting production of amyloid beta peptide (A beta) in a cell, including administering to said cell an effective inhibitory amount of a compound of formula (I), and a pharmaceutically acceptable salt thereof.

In an embodiment, this method includes administering to an animal.

In an embodiment, this method includes administering to a human.

The invention also includes a method for inhibiting the production of beta-amyloid plaque in an animal, including administering to said animal an effective inhibitory amount of a compound of formula (I), and a pharmaceutically acceptable salt thereof.

In an embodiment, this method includes administering to a human.

The invention also includes a method for treating or preventing a disease characterized by beta-amyloid deposits in the brain including administering to a patient an effective therapeutic amount of a compound of formula (I), and a pharmaceutically acceptable salt thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The invention also includes a composition including beta-secretase complexed with a compound of formula (I), and a pharmaceutically acceptable salt thereof.

The invention also includes a method for producing a beta-secretase complex including exposing beta-secretase to a compound of formula (I), and a pharmaceutically acceptable salt thereof, in a reaction mixture under conditions suitable for the production of said complex.

In an embodiment, this method employs exposing in vitro.

In an embodiment, this method employs a reaction mixture that is a cell.

The invention also includes a component kit including component parts capable of being assembled, in which at least one component part includes a compound of formula I enclosed in a container.

In an embodiment, this component kit includes lyophilized compound, and at least one further component part includes a diluent.

The invention also includes a container kit including a plurality of containers, each container including one or more unit dose of a compound of formula (I):, and a pharmaceutically acceptable salt thereof.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The invention also includes an agent kit including a compound of formula (I), and a pharmaceutically acceptable salt thereof; and one or more therapeutic agent selected from an antioxidant, an anti-inflammatory, a gamma secretase inhibitor, a neurotrophic agent, an acetyl cholinesterase inhibitor, a statin, an A beta peptide, and an anti-A beta antibody.

The invention also includes a composition including a compound of formula (I), and a pharmaceutically acceptable salt thereof; and an inert diluent or edible carrier.

In an embodiment, this composition includes a carrier that is an oil.

The invention also includes a composition including: a compound of formula (I), and a pharmaceutically acceptable salt thereof; and a binder, excipient, disintegrating agent, lubricant, or gildant.

The invention also includes a composition including a compound of formula (I), and a pharmaceutically acceptable salt thereof; disposed in a cream, ointment, or patch.

The invention provides compounds of formula (I), and the other formulas contained herein, that are useful in treating and preventing Alzheimer's disease. The compounds of the invention can be prepared by one skilled in the art based only on knowledge of the compound's chemical structure. The chemistry for the preparation of the compounds of this invention is known to those skilled in the art. In fact, there is more than one process to prepare the compounds of the invention. Specific examples of methods of preparation can be found in the art. For examples, see *J. Org. Chem.* 1998, 63, 4898-4906; *J. Org. Chem.* 1997, 62, 9348-9353; *J. Org. Chem.* 1996, 61, 5528-5531; *J. Med. Chem.* 1993, 36, 320-330; *J. Am. Chem. Soc.* 1999, 121, 1145-1155; and references cited therein. See also U.S. Pat. Nos. 6,150,530, 5,892,052, 5,696,270, and 5,362,912, which are incorporated herein by reference, and references cited therein.

An example of one of many various processes that can be used to prepare the compounds of the invention is set forth in Scheme I.

Scheme I

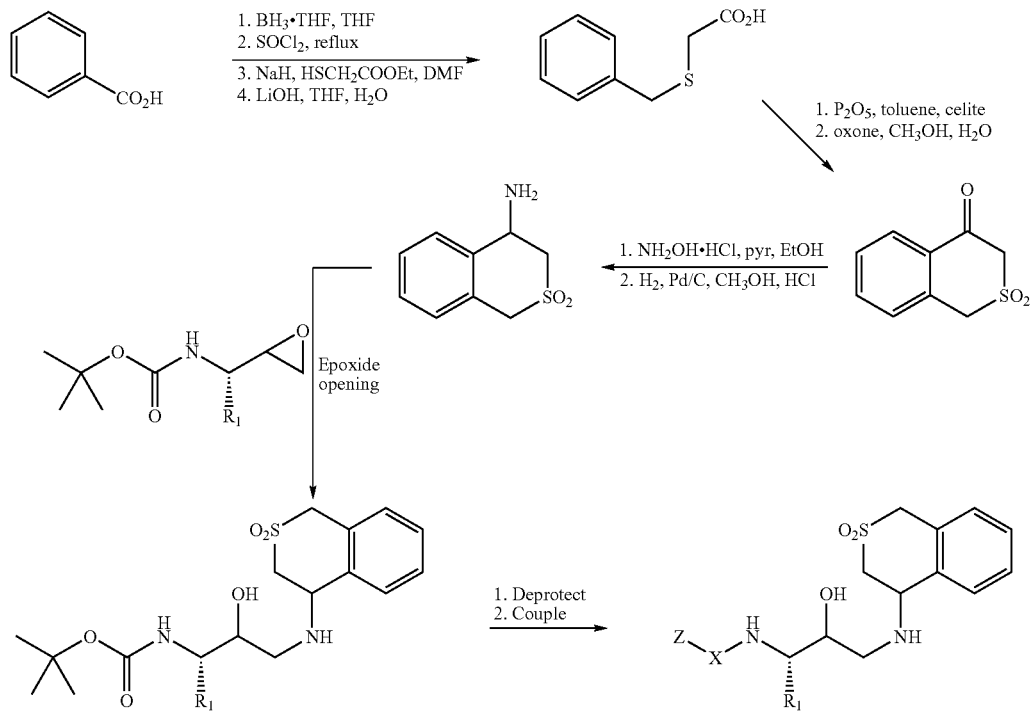

where $R_1$, X, and Z are as defined above or below.

Scheme I illustrates the preparation of compounds wherein $R_c$ is an isothiochroman 2,2-dioxide using an optionally substituted benzoic acid as the starting material. One of skill in the art will recognize that optionally substituted benzyl halides or benzyl alcohols may also be used as starting materials.

In Scheme I, the benzoic acid is reduced to a benzyl alcohol, which is then converted into a benzyl halide. Alternatively, the benzyl alcohol may be modified to include a leaving group such as, for example, a tosylate, brosylate, nosylate, triflate or mesylate. The benzyl compound is then reacted with a sulfide to generate the thioether. The carboxylic ester is then hydrolyzed to form a carboxylic acid, which is then subjected to annulation reaction conditions to form the desired bicyclic ring system. The annulation can be carried out using a Lewis acid, polyphosphoric acid, or $P_2O_5$. Other suitable reagents that effect cyclization are known in the art.

The resulting bicyclic sulfide is oxidized to form the sulfone. The keto group is converted into an amine directly via reductive amination or indirectly through the generation of an oxime, which is then reduced to form the amine. Transition metal catalysts and hydrogen or other reducing agents, such as $NaBH_4$, $LiAlH_4$ or $NaCNBH_3$, may be used to effect the reduction.

The resulting amine is used to open the epoxide to form the resulting coupled product. The coupled product is then deprotected to form a free amine, which is acylated or sulfonylated to generate the desired final product. In Scheme I, the use of a Boc protecting group is illustrated, but one of skill in the art will appreciate that other protecting groups, such as CBz, benzyl or others can also be used.

Scheme II

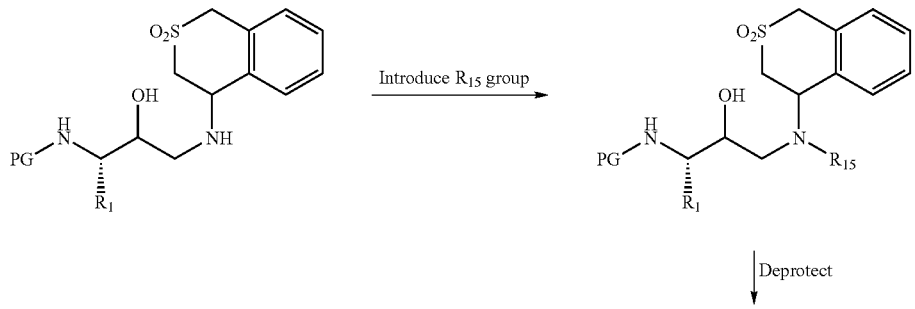

-continued

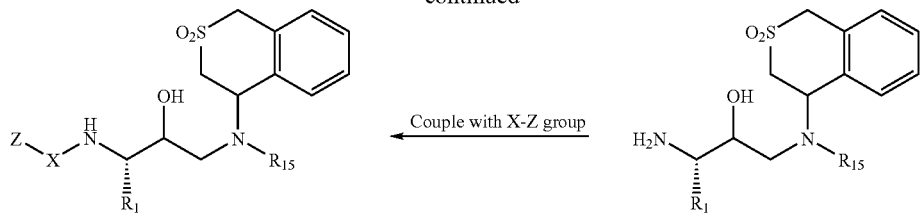

Scheme II illustrates the introduction of a non-hydrogen $R_{15}$ group on the 3-position nitrogen atom in the 1,3-diaminopropane portion of the molecule. The free nitrogen is reacted with an electrophile, an aldehyde or ketone and a reducing agent, an acid chloride, an acid anhydride or an acid with a coupling agent, such as DCC (dicyclohexyl carbodiimide), DIC (1,3 diisopropyl carbodiimide), EDCI (1-ethyl-3-(3'-dimethylaminopropyl)carbodiimide hydrochloride), BBC (1-benzotriazol-1-yloxy-bis(pyrrolidino)uronium hexafluorophosphate), BDMP (5-(1H-benzotriazol-1-yloxy)-3,4-dihydro-1-methyl 2H-pyrrolium hexachloroantimonate), BOMI (benzotriazol-1-yloxy-N,N-dimethylmethaniminium hexachloroantimonate), HATU (O-(7-azabenzotriazol-1-yl)-1,1,3,3-tetramethyluronium hexafluorophosphate), HAPyU=O-(7-azabenzotriazol-1-yl)-1,1,3,3-bis(tetramethylene)uronium hexafluorophosphate, HBTU which is O-(benzotriazol-1-yl)-1,1,3,3-tetramethyluronium hexafluorophosphate, TAPipU which is O-(7-azabenzotriazol-1-yl)-1,1,3,3-bis(pentamethylene)uronium etrafluoroborate, AOP (O-(7-azabenzotriazol-1-yl)-tris(dimethylamino)phosphonium hexafluorophosphate), BDP (benzotriazol-1-yl diethyl phosphate), BOP (1-benzotriazolyoxy-tris(dimethylamino)phosphonium hexafluorophosphate), PyAOP (7-azobenzotriazolyoxytris(pyrrolidino)phosphonium hexafluorophosphate), PyBOP (1-benzotriazolyoxytris(pyrrolidino)phosphonium hexafluorophosphate), TDBTU (2-(3,4-dihydro-4-oxo-1,2,3-benzotriazin-3-yl)-1,1,3,3-tetramethyluronium tetrafluoroborate), TNTU (2-(5-norbornene-2,3-dicarboximido)-1,1,3,3-tetramethyluronium tetrafluoroborate), TPTU (2-(2-oxo-1(2H)-pyridyl-1,1,3,3-tetramethyluronium tetrafluoroborate), TSTU (2-succinimido-1,1,3,3-tetramethyluronium tetrafluoroborate), BEMT (2-bromo-3-ethyl-4-methyl thiazolium tetrafluoroborate), BOP-Cl (bis(2-oxo-3-oxazolidinyl)phosphinic chloride), BroP (bromotris(dimethylamino)phosphonium hexafluorophosphate), BTFFH (bis(tetramethylenefluoroformamidinium) hexafluorophosphate), ClP (2-chloro-1,3-dimethylimidazolidinium hexafluorophosphate), DEPBT (3-(diethoxyphosphoryloxy)-1,2,3-benzotriazin-4(3H)-one), Dpp-Cl (diphenylphosphinic chloride), EEDQ (2-ethoxy-1-ethoxycarbonyl-1,2-dihydroquinoline), FDPP (pentafluorophenyl diphenylphosphinate), HOTT (S-(1-oxido-2-pyridinyl)-1,1,3,3-tetramethylthiouronium hexafluorophosphate), PyBroP (bromotris(pyrrolydino)phophonium hexafluorophosphate), PyCloP (chlorotris(pyrrolydino)phophonium hexafluorophosphate), TFFH (tetramethylfluoroformamidinium hexafluorophosphate), and TOTT (S-(1-oxido-2-pyridinyl)-1,1,3,3-tetramethylthiouronium tetrafluoroborate) to generate the monosubstituted product, which can then be deprotected and coupled to the "X-Z" group. Conversely, the monosubstituted product can be deprotected, and the free nitrogen reacted with an electrophile, an aldehyde or ketone and a reducing agent, an acid chloride, an acid anhydride or an acid with a coupling agent, such as those previously exemplified to generate the disubstituted product, which is then coupled to the "X-Z" group.

Scheme III

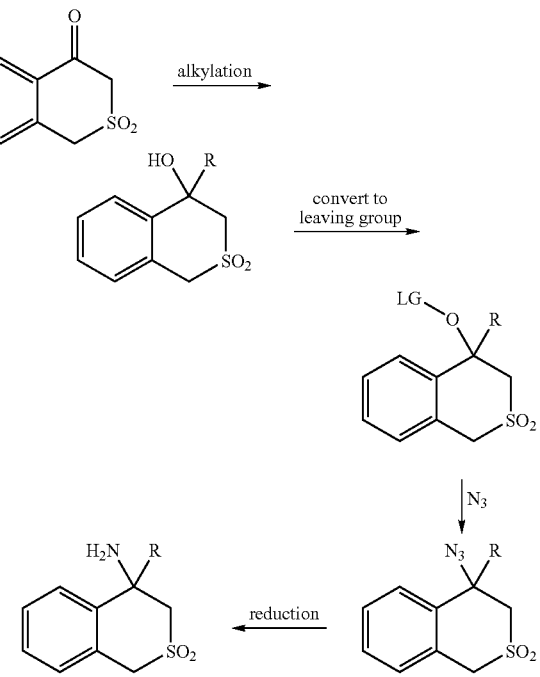

Scheme III illustrates the introduction of a tertiary amine (R is not hydrogen) or a secondary amine (R is hydrogen) onto the isothiochroman 2,2-dioxide scaffold. First, the sulfoketone is alkylated using, for example, a Grignard reagent or other alkylating agent, to generate the tertiary alcohol, which is then converted into a leaving group. One of skill in the art will appreciate that many possible leaving groups may be used. Particular examples include, but are not limited to triflate, mesylate, paratoluene sulfonate, nosylate, and brosylate. The leaving group is then displaced using an azide, such as DPPA or $NaN_3$. Substituted azides may be used in place of the unsubstituted azide. Alternatively, the desired compounds can be generated from the alcohol directly without first converting the alcohol into a leaving group. Such transformations can be readily accomplished using conventional $SN_1$ conditions according to procedures available in the literature.

The resulting azide is then reduced to generate the desired amine. Many reducing agents that will effect the desired transformation are known. Examples include $H_2$ and Pd, $H_2$ and Pt, $NaBH_4$, and $NaCNBH_3$. Stronger reducing agents, such as $LiAlH_4$ and DIBAL may be used, but the sulfone may also be reduced. If the sulfone is reduced, it may be reoxidized using methods known in the art, such as MCPBA.

Scheme IV

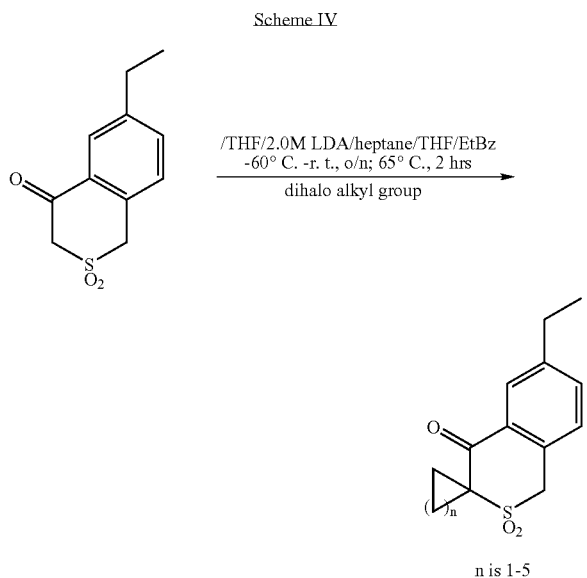

n is 1-5

As shown in scheme IV, spirocycles may be generated by alkylating a compound in the presence of a strong base. Examples of strong bases include, LDA, KHMDS, and tertiary-butyl lithium. One of skill in the art will appreciate that many other bases are strong enough to deprotonate the starting material and effect the desired transformation.

The alkylating agent dictates the size the of the spirocycle that is formed. Dibromo ethane, diiodoethane, or bromo iodoethane will generate a spirocyclopropyl compound, wherein n is 1. However, longer alkyl chains generate larger spirocycloalkyl compounds. For example, a 1,5-dihalopentane generates a spirocyclohexyl compound, wherein n is 4. Although dihalo compounds are illustrated, one of skill in the art will appreciate that other leaving groups, such as, for example, mesylate, tosylate, triflate, brosylate, and nosylate may be used. The leaving groups may, but need not, be identical.

Scheme V illustrates the preparation of fluorene derivatives using optionally substituted salicylic esters as starting materials. Non-commercially available substituted salicylic esters may be obtained by a variety of methods well known to those skilled in the art of organic synthesis. Such methods include, but are not limited to, halogenations [Rozen and Lerman (J. Org. Chem. 1993, 239-240)], Suzuki couplings [Miyaura and Suzuki (Chem. Rev. 1995, 2457-2483)], Sonagashiri couplings [Sonagashira (Metal-Catalyzed Cross-Coupling Reactions, 1998, Wiley-VCH publishers)], Negishi couplings [Zhu, et al. (J. Org. Chem. 1991, 1445-1453)], Stille cross-couplings [Littke et al. (Angew. Chem. Int. Ed. 1999, 2411-2413)], Heck couplings [Whitcombe et al. (Tetrahedron 2001, 7449-7476)], aminations [Wolfe et al. (J. Org. Chem. 2000, 1144-1157)], oxygenations [Fu and Littke (Angew. Chem. Int. Ed. 2002, 4177-4211)] and carbonylations [Cai et al. (J Chem Soc, Perkin Trans 1 1997, 2273-2274)]. One of skill in the art will recognize that optionally substituted ortho halo benzoates may also be used as starting materials.

Phenols of the general formula (1) are readily converted into triflates employing a triflating source and a base in an inert solvent. Triflating sources include, but are not limited to, trifluoromethanesulfonic anhydride, trifluoromethanesulfonyl chloride and N-phenyltrifluoromethanesulfonimide. Bases include, but are not limited to, trialkyl amines (preferably diisopropylethylamine or triethylamine), aromatic amines (preferably pyridine, 4-dimethylaminopyridine or 2,6-lutidine) or alkali metal hydrides (preferably sodium hydride). Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene) or haloalkanes (preferably dichloromethane). Preferred reaction temperatures range from 0° C. to room temperature. The progress of

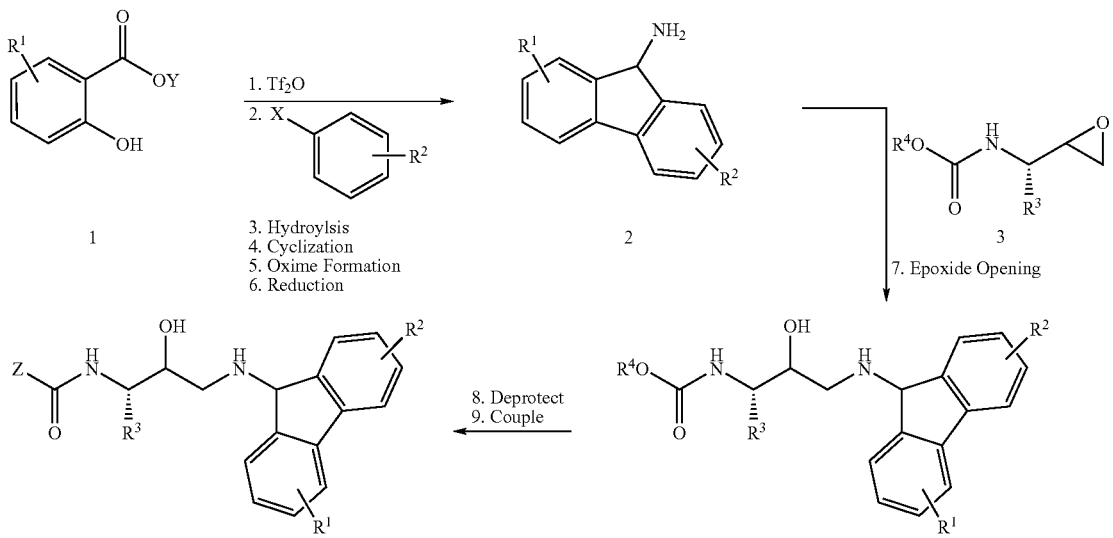

Scheme V: Preparation of Fluorene Derivatives this conversion is monitored by standard chromatographic and spectroscopic methods known to one skilled in the art of organic synthesis.

Triflates may be treated with an aryl boronic acid or aryl boronic acid ester where X is equivalent to $B(OH)_2$ or $B(OR^a)(OR^b)$ (where $R^a$ and $R^b$ are lower alkyl, ie. $C_1$-$C_6$, or taken together $R^a$ and $R^b$ are lower alkylene, ie. $C_2$-$C_{12}$) in the presence of a metal catalyst with or without a base in an inert solvent to give birayls. Metal catalysts include, but are not limited to, salts or phosphine complexes of Cu, Pd or Ni (eg. $Cu(OAc)_2$, $Pd(PPh_3)_4$, $NiCl_2(PPh_3)_2$). Bases include, but are not limited to, alkaline earth metal carbonates, alkaline earth metal bicarbonates, alkaline earth metal hydroxides, alkali metal hydrides (preferably sodium hydride), alkali metal alkoxides (preferably sodium ethoxide or sodium methoxide), trialkyl amines (preferably diisopropylethylamine or triethylamine) or aromatic amines (preferably pyridine). Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane), alkyl alcohols (preferably methyl alcohol or ethyl alcohol), or water. Preferred reaction temperatures range from room temperature to the boiling point of the solvent employed. Non-commercially available boronic acids or boronic esters may be obtained from the corresponding optionally substituted aryl halide as described by Gao, et al. (Tetrahedron 1994, 50, 979 -988). The progress of the coupling reaction is monitored by standard chromatographic and spectroscopic methods known to one skilled in the art of organic synthesis.

Alternately, triflates may be treated with organozinc reagents as taught by Zhu, et al. (J. Org. Chem. 1991, 1445-1453).

One skilled in the art of organic synthesis will appreciate that the nature of the coupling partners described above could be reversed and the coupling reaction conducted in substantially the same manner as described above.

The biaryl ester is hydrolyzed to form a carboxylic acid. The hydrolysis reaction may be run under a wide variety of conditions familiar to one skilled in the art of organic synthesis. The hydrolysis reaction is run in the presence of a base such as, but not limited to, lithium hydroxide and sodium hydroxide. Typical solvents include, but are not limited to, tetrahydrofuran, diethyl ether, dichloromethane, alkyl alcohols (including methyl alcohol and ethyl alcohol) and water. The reactions may be successfully run at temperatures ranging from room temperature to the boiling point of the solvent employed. The progress of the hydrolysis reaction is monitored by standard chromatographic and spectroscopic methods known to one skilled in the art of organic synthesis.

The carboxylic acid may be subjected to a cyclization reaction, under a wide variety of conditions known to one skilled in the art of organic synthesis, to form the desired tricycle. The cyclization reaction is carried out in the presence of an acidic reagent. Either Bronsted acids including, but not limited to, sulfuric acid, hydrochloric acid, methanesulfonic acid and polyphosphoric acid, or Lewis acids including, but not limited to, aluminum trichloride, titanium tetrachloride and tin tetrachloride are useful for effecting this transformation. The reaction may be performed neat or with the addition of a co-solvent. Typical co-solvents include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane) or alkyl alcohols (preferably methyl alcohol or ethyl alcohol). The reactions may be successfully run at temperatures ranging from room temperature to the boiling point of the solvent employed. The progress of the hydrolysis reaction is monitored by standard chromatographic and spectroscopic methods known to one skilled in the art of organic synthesis.

Alternately, the carboxylic acid may be cyclized through the intermediacy of the corresponding activated acid as taught by Alder, et al (Justus Liebigs Ann. Chem. 1950; 230-238) Stiles and Libbey (J. Org. Chem 1957, 1243-1245) and Ladd, et al. (J. Med. Chem. 1986 1904-1912).

The ketone may be converted to the corresponding oxime. The condensation reaction is carried out in the presence of a hydroxylamine (of the general formula $RONH_2$; where R=H, $C_1$-$C_4$) with or without a base in an inert solvent. Bases include, but are not limited to, alkaline earth metal carbonates, alkaline earth metal bicarbonates, alkaline earth metal hydroxides, alkali metal hydrides (preferably sodium hydride), alkali metal alkoxides (preferably sodium ethoxide or sodium methoxide), trialkyl amines (preferably diisopropylethylamine or triethylamine) or aromatic amines (preferably pyridine). Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane), alkyl alcohols (preferably methyl alcohol or ethyl alcohol), or water. Preferred reaction temperatures range from room temperature to the boiling point of the solvent employed. The progress of the condensation reaction is monitored by standard chromatographic and spectroscopic methods known to one skilled in the art of organic synthesis.

Reduction of the corresponding oxime to the desired amine proceeds in the presence of a reducing agent in an inert solvent. Suitable reducing agents include, but are not limited to, transition metals with or without hydrogen and hydride donating agents. Transition metals that may or may not be used catalytically with or without the addition of hydrogen include, but are not limited to, Pd, Pt and Zn. Hydride donating agents, include but are not limited to $BH_3$, $NaBH_4$, $LiBH_4$, $NaCNBH_3$ and $LiAlH_4$. Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane), alkyl alcohols (preferably methyl alcohol or ethyl alcohol), or water. Preferred reaction temperatures range from 0° C. to the boiling point of the solvent employed. The progress of the condensation reaction is monitored by standard chromatographic and spectroscopic methods known to one skilled in the art of organic synthesis.

One skilled in the art will appreciate, alternatively to the indirect procedure described above, that the ketone may be directly converted to the corresponding amine directly via a reductive amination as taught by Dei et al. (Bioorg. Med. Chem. 2001, 2673-2682).

The resulting amines of general formula (2) may be treated with a protected epoxide of general formula (3), including, but not limited to, Boc protected epoxides, with or without catalysis in an inert solvent. Catalysts include, but are not limited to, salts or complexes of Yb, Sn, Ti, B and Cu. Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane), alkyl alcohols (preferably isopropyl alcohol or tert-butyl alcohol). Preferred reaction temperatures range from room temperature to the boiling point of the solvent employed. The progress of the coupling reaction is monitored by standard chromatographic and spectroscopic methods known to one skilled in the art of organic synthesis.

The resulting coupled products of general formula (4) may be deprotected to yield the amine by treatment with acidic additives in inert solvents. Acidic additives include, but are not limited to, TFA, HCl, HBr, AcOH and trichloroacetic acid. Inert solvents may include, but are not limited to, acetonitrile, dialkyl ethers (preferably diether ether), cyclic ethers (preferably tetrahydrofuran or 1,4-dioxane), haloalkanes (preferably dichloromethane), alkyl alcohols (preferably isopropyl alcohol or tert-butyl alcohol). Prefered reaction temperatures range from 0° C. to room temperature. The progress of the deprotection reaction is monitored by standard chromatographic and spectroscopic methods known to one skilled in the art of organic synthesis.

The resulting amine may be treated with an acid to give the final product of general formula (5). The transformation may be effected utilizing an acid (or equivalent source) and a coupling reagent with or without a base and in an inert solvent. Coupling agents include, but are not limited to, DCC, EDC, HBTU, HATU, CDI, and PyBOP. Bases include, but are not limited to, alkaline earth metal carbonates, alkaline earth metal bicarbonates, alkaline earth metal hydroxides, alkali metal alkoxides (preferably sodium ethoxide or sodium methoxide), trialkyl amines (preferably diisopropylethylamine or triethylamine) or aromatic amines (preferably pyridine). Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane), alkyl alcohols (preferably methyl alcohol or ethyl alcohol), or water. Preferred reaction temperatures range from 0° C. to room temperature. The progress of the condensation reaction is monitored by standard chromatographic and spectroscopic methods known to one skilled in the art of organic synthesis.

Alternately, the resulting amine may be treated with an activated acylating agent to give the final product of general formula (5). The transformation may be effected utilizing an active acylating agent and with or without a base and in an inert solvent. Active acylating agents include, but are not limited to, acyl halides, acyl imidazoles, acyl anhydrides (symmetrical and unsymmetrical) and acyl oximes. Bases include, but are not limited to, alkaline earth metal carbonates, alkaline earth metal bicarbonates, alkaline earth metal hydroxides, alkali metal hydrides (preferably sodium hydride), alkali metal alkoxides (preferably sodium ethoxide or sodium methoxide), trialkyl amines (preferably diisopropylethylamine or triethylamine) or aromatic amines (preferably pyridine). Inert solvents may include, but are not limited to, acetonitrile, dialkyl ethers (preferably diether ether), cyclic ethers (preferably tetrahydrofuran or 1,4-dioxane), N,N-dialkylacetamides (preferably dimethylacetamide), N,N-dialkylforamides (preferably dimethylformamide), dialkylsulfoxides (preferably dimethylsulfoxide), aromatic hydrocarbons (preferably benzene or toluene), haloalkanes (preferably dichloromethane), alkyl alcohols (preferably methyl alcohol or ethyl alcohol), or water. Preferred reaction temperatures range from 0° C. to room temperature. The progress of the condensation reaction is monitored by standard chromatographic and spectroscopic methods known to one skilled in the art of organic synthesis.

Scheme VI

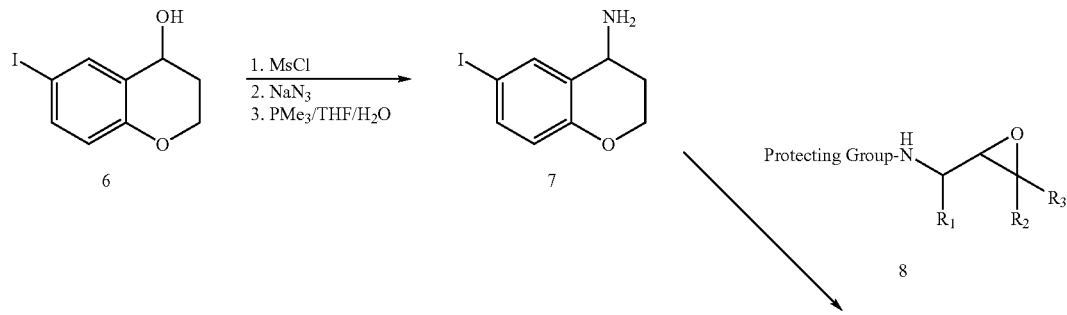

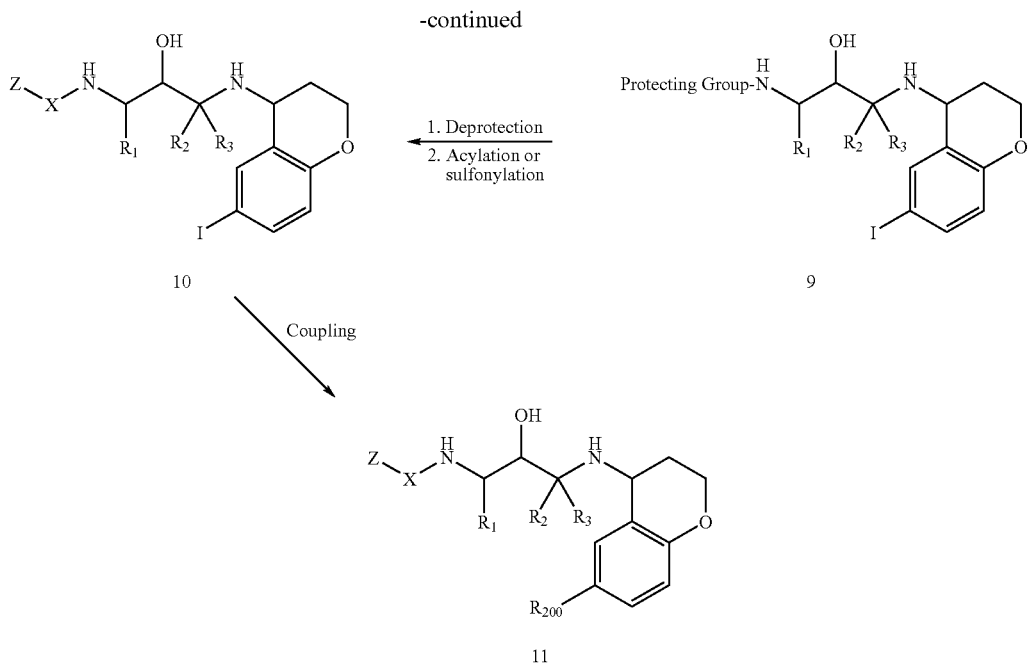

Scheme VI

As described above and below, one aspect of the invention provides for compounds of formula (11) as shown above. These compounds may be made by methods known to those skilled in the art from starting compounds that are also known to those skilled in the art. The process chemistry is further well known to those skilled in the art. A suitable process for the preparation of compounds of formula (11) is set forth in Scheme VI above.

Scheme VI illustrates the preparation of the desired compounds using the readily obtainable 6-iodo-chroman-4-ol (6) as a starting material (see *Synthesis*, 1997, 23-25). One skilled in the art will recognize that there are several methods for the conversion of the alcohol functionality to the desired amino compounds of formula (7). In Scheme VI the alcohol (6) is first activated with methane sulfonyl chloride and the resulting mesylate displaced with sodium azide $NaN_3$. Alternative methods for the conversion of an alcohol to an azide are well known to one skilled in the art. The resulting azide is subsequently reduced using trimthylphosphine in a mixture of THF and water. One skilled in the art will recognize that there are several methods for the reduction of an azide to the corresponding amine. For examples, see Larock, R. C. in *Comprehensive Organic Transformations*, Wiley-VCH Publishers, 1999. This reduction of the azide produces a mixture of enantiomers of the amine (7). This enantiomeric mixture can be separated by means known to those skilled in the art such as low temperature recrystallization of a chiral salt or by chiral preparative HPLC, most preferably by HPLC, employing commercially available chiral columns.

The resulting amine (7) is used to open the epoxide (8) to afford the protected (6-iodo-3,4-dihydro-2H-chromen-4-yl) amino propyl carbamate (9). Suitable reaction conditions for opening the epoxide (8) include running the reaction in a wide range of common and inert solvents. $C_1$-$C_6$ alcohol solvents are preferred and isopropyl alcohol most preferred. The reactions can be run at temperatures ranging from 20-25° C. up to the reflux temperature of the alcohol employed. The preferred temperature range for conducting the reaction is between 50° C. and the refluxing temperature of the alcohol employed.

The protected iodo-chromen (9) is deprotected to the corresponding amine by means known to those skilled in the art for removal of amine protecting groups. Suitable means for removal of the amine protecting group depend on the nature of the protecting group. Those skilled in the art, knowing the nature of a specific protecting group, know which reagent is preferable for its removal. For example, it is preferred to remove the preferred protecting group, BOC, by dissolving the protected iodo-chroman in a trifluoroacetic acid/dichloromethane (1/1) mixture. When complete the solvents are removed under reduced pressure to give the corresponding amine (as the corresponding salt, i.e. trifluoroacetic acid salt) which is used without further purification. However, if desired, the amine can be purified further by means well known to those skilled in the art, such as for example recrystallization. Further, if the non-salt form is desired that also can be obtained by means known to those skilled in the art, such as for example, preparing the free base amine via treatment of the salt with mild basic conditions. Additional BOC deprotection conditions and deprotection conditions for other protecting groups can be found in T. W. Green and P. G. M. Wuts in *Protecting Groups in Organic Chemistry*, 3$^{rd}$ edition, John Wiley and Sons, 1999.

The amine is then reacted with an appropriately substituted amide forming agent Z-(CO)—Y to produce coupled amides (10) by nitrogen acylation means known to those skilled in the art. Nitrogen acylation conditions for the reaction of amine with an amide forming agent Z-(CO)—Y are known to those skilled in the art and can be found in R. C. Larock in *Comprehensive Organic Transformations*, VCH Publishers, 1989, p. 981, 979, and 972. Y comprises —OH (carboxylic acid) or halide (acyl halide), preferably chlorine, imidazole (acyl imidazole), or a suitable group to produce a mixed anhydride.

The acylated iodo-chromen (10) is coupled with an appropriately functionalzed organometallic $R_{200}M$ to afford compounds of formula (11) using conditions known to those skilled in the art. One skilled in the art will recognize that there are several methods for coupling various alkyl and aryl groups to an aromatic iodide. For examples, see L. S. Hegedus *Transition Metals in the Synthesis of Complex Organic Molecules*, University Science, 1999.

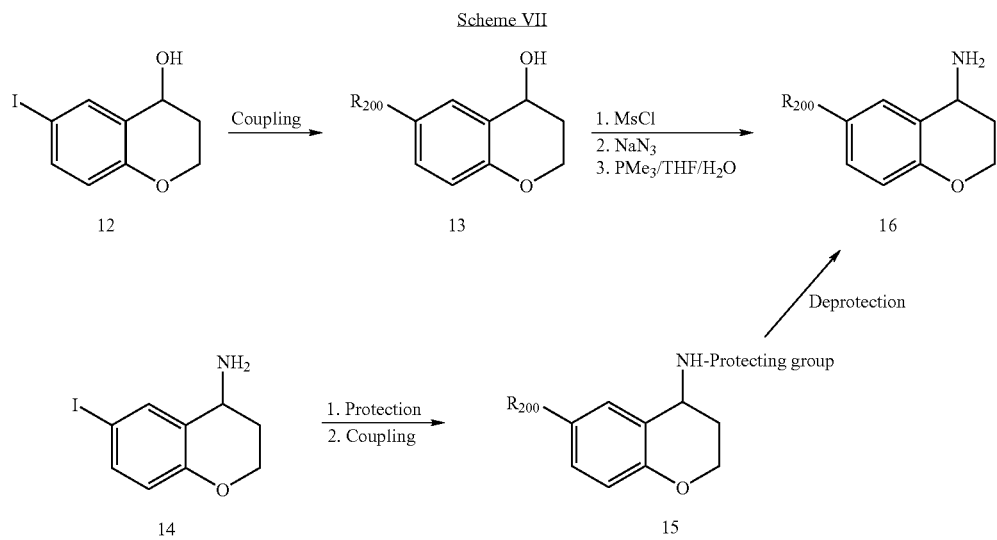

Scheme VII sets forth alternative routes to 4-aminochromanes, which are useful for preparing compounds of formula (11). Amines of formula (16) can be prepared by coupling the appropriately functionalized organometallic to 6-iodo-chroman-4-ol (12) or to the appropriately protected iodo-amino chroman of the formula (14). Further elaboration of the coupled products using methods known to one of skill in the art, ultimately yields the desired amines of formula (16). The chemistry from this point forward follows the generalizations described in Scheme VIII for converting compound 9 to 10.

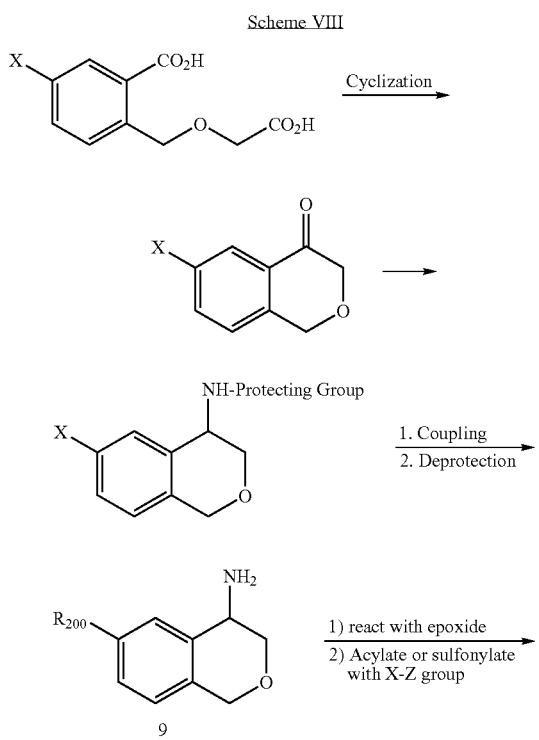

Scheme VIII illustrates another general preparation of amines of formula (9) that upon following the generalizations outlined in Schemes VI and VII will result in compounds of the formula (10). From this point forward, the chemistry is essentially the same as described for Schemes VI and VII.

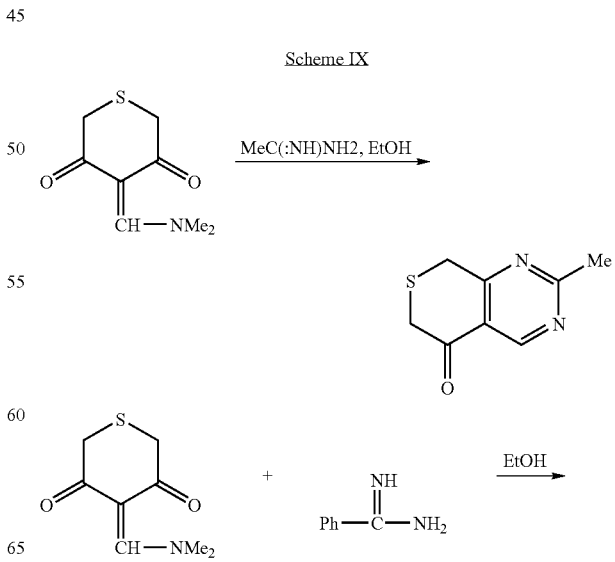

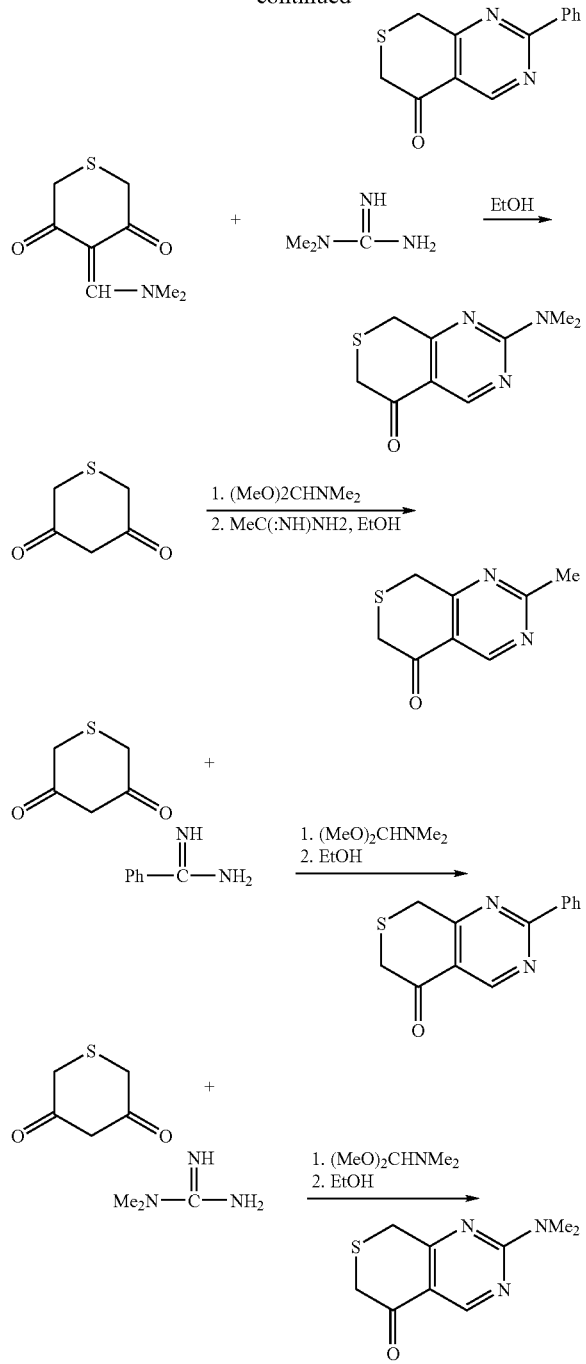

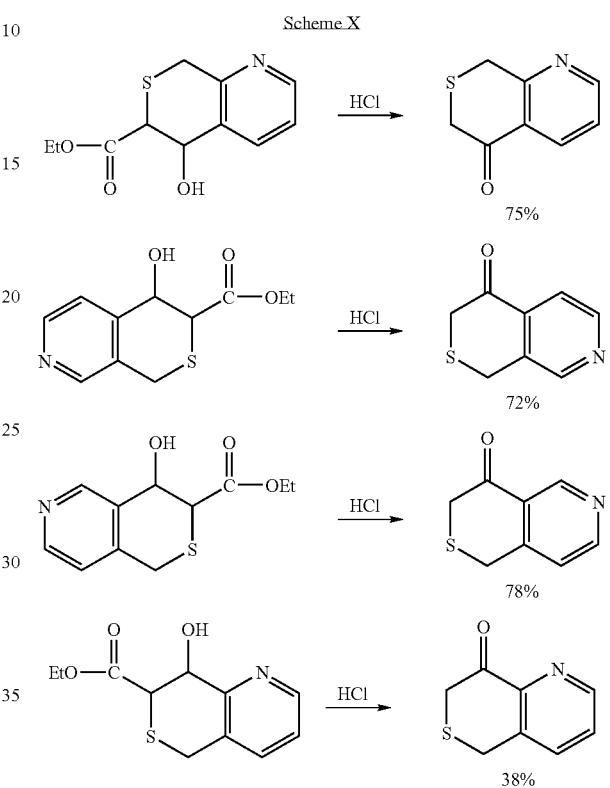

It is also understood that the pyrimidyl ring can be further substituted by means known in the art. For example, the pyridyl ring can be alkylated, halogenated, acylated, and/or nitrated. See Organic Transformations by Richard C. LaRock. All references are herein incorporated by reference in their entirety, for all purposes.

Scheme X illustrates the synthesis of various 1H-thiopyranopyridinones. Suitable reaction conditions are described in, for example, J. Chem. Soc., Perkin Trans. 1, (7), 1501-5; 1984

One of ordinary skill will appreciate that treating the sulfide with an oxidizing agent, such as parachlorobenzoic acid (MCPBA) or oxone, generates the sulfoxide or the sulfone. The oxidation of the sulfide can be done sequentially, i.e., generating and isolating the sulfoxide and then oxidizing it to the sulfone, or the sulfone can be generated directly from the sulfide. Further manipulations of the ketone are described in the application.

It is also understood that the pyridyl ring can be further substituted by means known in the art. For example, by way of illustration, the pyridyl ring can be alkylated, halogenated, acylated, and/or nitrated. See Organic Transformations by Richard C. LaRock.

Scheme IX illustrates the synthesis of various 5H-thiopyranopyrimidinones from a variety of starting materials. Suitable reaction conditions are described in, for example, J. Heterocycl. Chem., 21(5), 1437-40; 1984.

One of ordinary skill will appreciate that treating the sulfide with an oxidizing agent, such as parachlorobenzoic acid (MCPBA) or oxone, generates the sulfoxide or the sulfone. The oxidation of the sulfide can be done sequentially, i.e., generating and isolating the sulfoxide and then oxidizing it to the sulfone, or the sulfone can be generated directly from the sulfide. Further manipulations of the ketone are described in the application.

Scheme XI

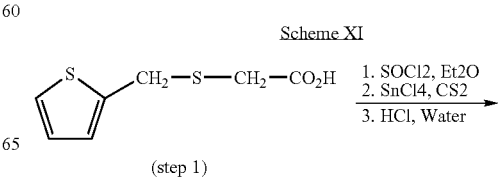

(step 1)

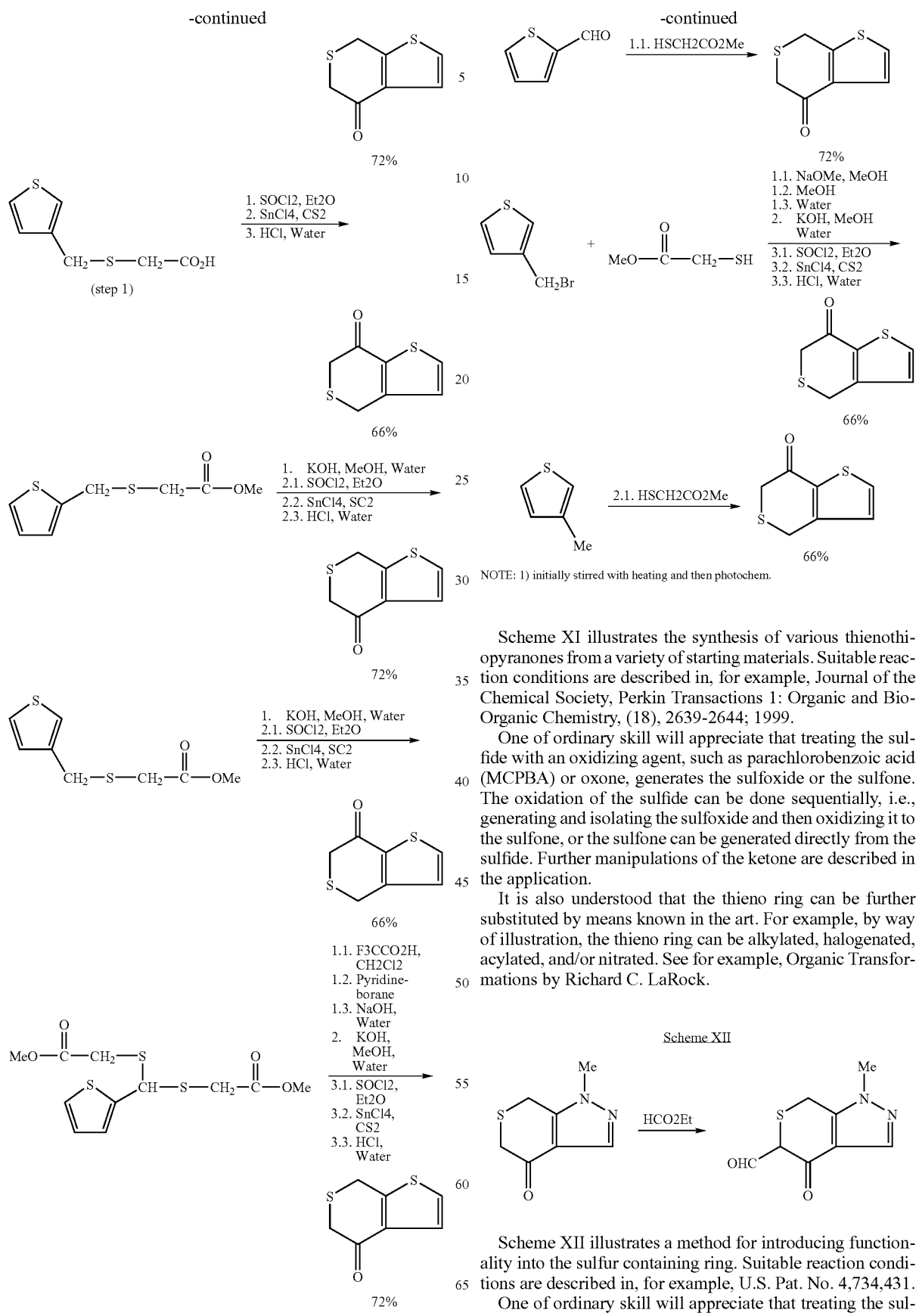

NOTE: 1) initially stirred with heating and then photochem.

Scheme XI illustrates the synthesis of various thienothiopyranones from a variety of starting materials. Suitable reaction conditions are described in, for example, Journal of the Chemical Society, Perkin Transactions 1: Organic and Bio-Organic Chemistry, (18), 2639-2644; 1999.

One of ordinary skill will appreciate that treating the sulfide with an oxidizing agent, such as parachlorobenzoic acid (MCPBA) or oxone, generates the sulfoxide or the sulfone. The oxidation of the sulfide can be done sequentially, i.e., generating and isolating the sulfoxide and then oxidizing it to the sulfone, or the sulfone can be generated directly from the sulfide. Further manipulations of the ketone are described in the application.

It is also understood that the thieno ring can be further substituted by means known in the art. For example, by way of illustration, the thieno ring can be alkylated, halogenated, acylated, and/or nitrated. See for example, Organic Transformations by Richard C. LaRock.

Scheme XII

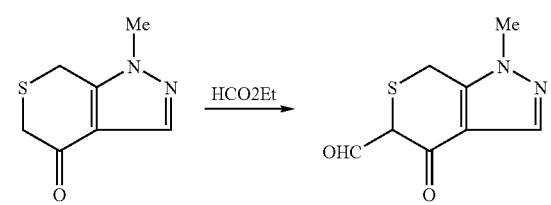

Scheme XII illustrates a method for introducing functionality into the sulfur containing ring. Suitable reaction conditions are described in, for example, U.S. Pat. No. 4,734,431.

One of ordinary skill will appreciate that treating the sulfide with an oxidizing agent, such as parachlorobenzoic acid (MCPBA) or oxone, generates the sulfoxide or the sulfone. The oxidation of the sulfide can be done sequentially, i.e., generating and isolating the sulfoxide and then oxidizing it to the sulfone, or the sulfone can be generated directly from the sulfide. Further manipulations of the ketone are described in the application.

It is also understood that the pyrazole ring can be further substituted by means known in the art. For example, by way of illustration, the pyrazole ring can be alkylated, halogenated, and/or acylated. See for example, Organic Transformations by Richard C. LaRock.

Scheme XIII

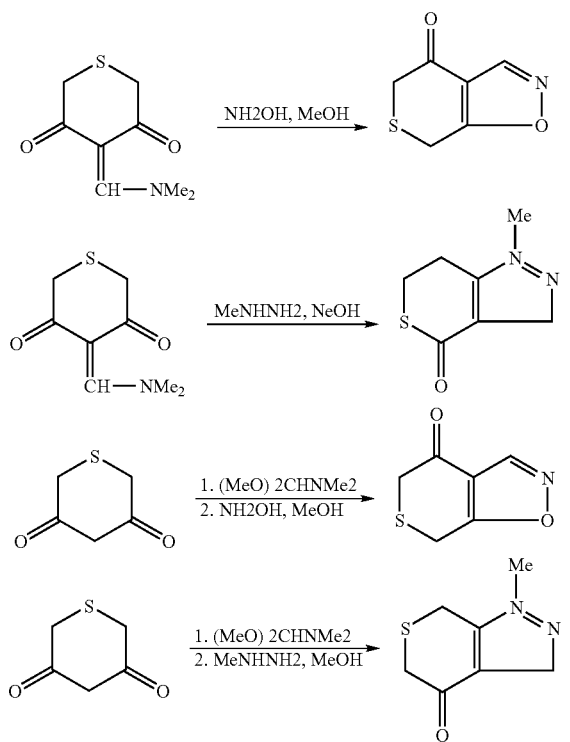

Scheme XIII illustrates the preparation of isoxazole and pyrazole containing bicyclic ring systems. Suitable reaction conditions are described in, for example, J. Heterocycl. Chem., 21(5), 1437-40; 1984. One of skill in the art will recognize that various reagents can be used to introduce functionality into the above ring systems. For example, substituted hydrazines are commercially available and can be used to prepare substituted pyrazoles. Furthermore, standard reactions such as alkylations and halogenations are known in the art.

One of ordinary skill will appreciate that treating the sulfide with an oxidizing agent, such as parachlorobenzoic acid (MCPBA) or oxone, generates the sulfoxide or the sulfone. The oxidation of the sulfide can be done sequentially, i.e., generating and isolating the sulfoxide and then oxidizing it to the sulfone, or the sulfone can be generated directly from the sulfide. Further manipulations of the ketone are described in the application.

It is also understood that the pyrazole or isoxazole ring can be further substituted by means known in the art. For example, by way of illustration, the pyrazole and isoxazole rings can be alkylated, halogenated, and/or acylated. See for example, Organic Transformations by Richard C. LaRock.

Scheme XIV

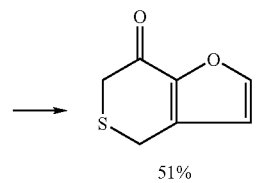

Scheme XIV illustrates the formation of a furan containing bicyclic ring system. Suitable reaction conditions are described in, for example, J. Heterocycl. Chem., 13(2), 365-7; 1976

One of ordinary skill will appreciate that treating the sulfide with an oxidizing agent, such as parachlorobenzoic acid (MCPBA) or oxone, generates the sulfoxide or the sulfone. The oxidation of the sulfide can be done sequentially, i.e., generating and isolating the sulfoxide and then oxidizing it to the sulfone, or the sulfone can be generated directly from the sulfide. Further manipulations of the ketone are described in the application.

It is also understood that the furyl ring can be further substituted by means known in the art. For example, by way of illustration, the furyl ring can be alkylated, halogenated, and/or acylated. See for example, Organic Transformations by Richard C. LaRock.

Scheme XV

The compounds of the invention that comprise tetrahydroquinoline moieties can be made by methods known in the art. The following general scheme can also be useful for tetrahydroquiniline compound synthesis.

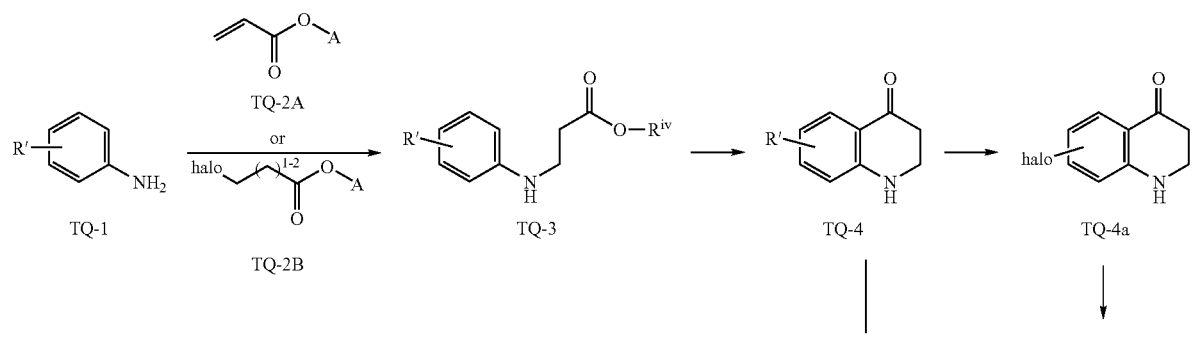

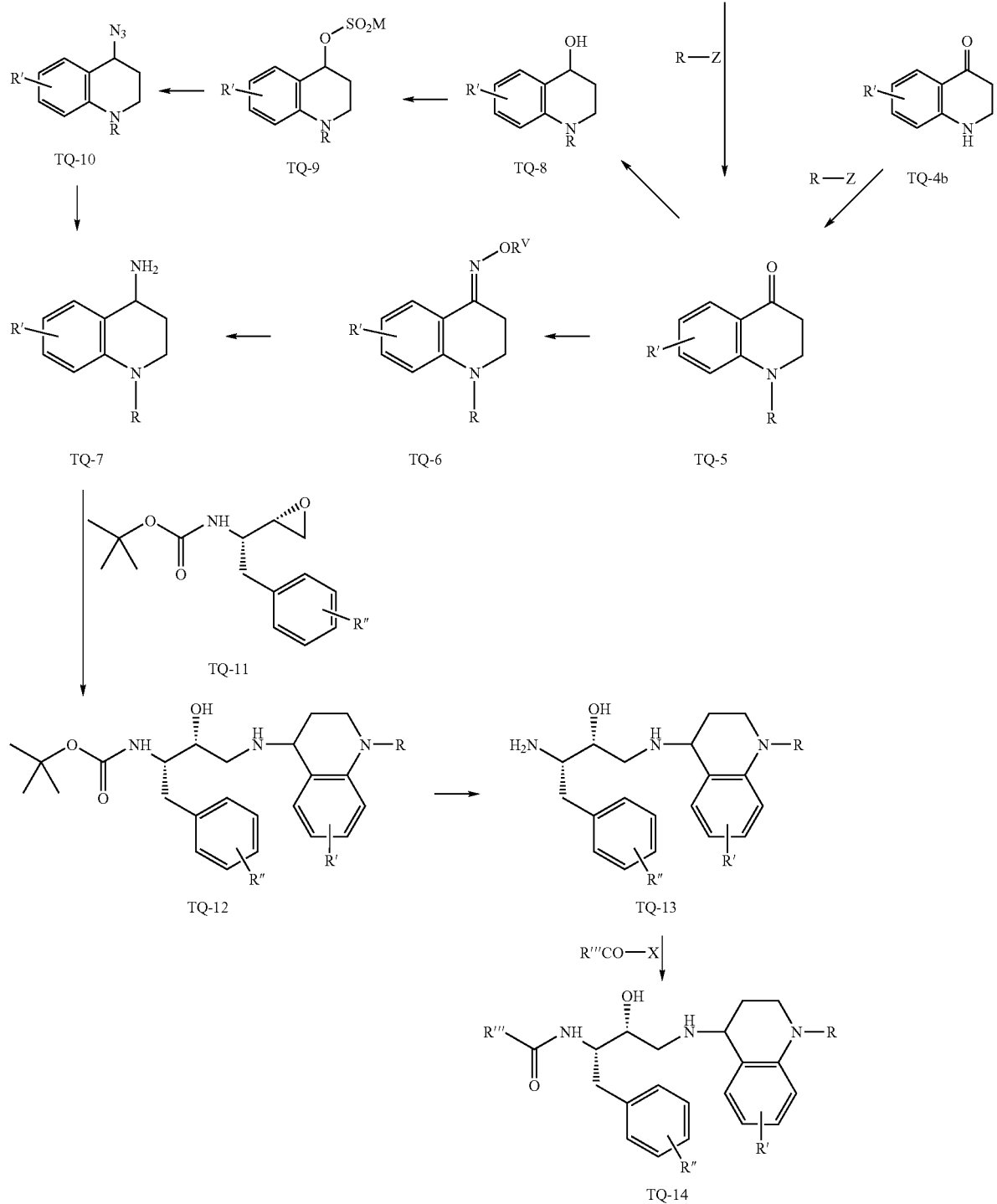

Description of General Synthetic Scheme

Aniline TQ-1 is alkylated with a halide TQ-2B or acrylate TQ-2A to give TQ-3. TQ-3 is then treated with a strong acid or with a Lewis acid at temperatures ranging from 0° C. to 140° C., preferably with phosphorus pentoxide and methanesulfonic acid at 130° C., to give ketone TQ-4. The nitrogen of TQ-4 is then either protected with a protecting group, many of which are listed in Protective Groups in Organic Synthesis, Greene and Wuts, 3$^{rd}$ edition, 1999, Wiley-Interscience, or is substituted with an alkyl group, an acyl group, or a sulfonyl group, using methods well known to those versed in the art, using R-Z, to give protected ketone TQ-5. An alternative preparation of TQ-5 starts with TQ-4 where R' is hydrogen. Halogenation with halogenating reagents such as N-bromosuccinimide, N-iodosuccinimide, dibromatin, and the like gives TQ-4a where R' is preferably bromine or iodine. Treatment of TQ-4a under cross coupling conditions such as those described by Negishi (Tet. Lett. 1983, 3823), Huo (Org. Lett.

2003, 423) and reviewed by Knochel (Tetrahedron 1998, 8275) provides TQ-4b where R' is alkyl. Further treatment of TQ-4b with R-Z as described above gives TQ-5.

Protected ketone TQ-5 is then converted to amine TQ-7 by several methods, the choice of which may depend on the nature of the R group. In the first method, TQ-5 is treated with a hydroxyl amine in the presence of a base and a catalytic amount of acid in solvents such as methanol, ethanol, butanol, and the like, at temperatures ranging from room temperature to the reflux temperature of the solvent, to give oxime TQ-6. TQ-6 is then reduced to amine TQ-7 using a suitable catalyst, preferably palladium, in solvents such as methanol, ethanol, or ethyl acetate, under a blanket of hydrogen at pressures ranging from atmospheric to 100 pounds per square inch. Alternatively, protected ketone TQ-5 is reduced to alcohol TQ-8 using reducing agents known to those well versed in the art, preferably and depending on the nature of group R using sodium borohydride in methanol or ethanol at temperatures ranging from 0 to 100° C. Alcohol TQ-8 is then converted to sulfonate ester TQ-9 with reagents such as methanesulfonyl chloride or toluenesulfonyl chloride using methods known to those well-versed in the art. Displacement of the sulfonate ester with azide using, for example, sodium azide in solvents such as dichloromethane and DMF at temperatures ranging from room temperature to 120° C., gives azide TQ-10. Azide TQ-10 is then reduced to amine T-7 using, for example, trimethylphosphine in solvents such as THF and the like at temperatures between 0° C. to the reflux temperature of the solvent. Other methods of reduction of the azide group are known; the choice of reducing agent will depend on the nature of the R and R' groups and will be known to those well versed in the art and can be found in references such as Smith and March, March's Advanced Organic Chemistry: Reactions, Mechanisms, and Structure, 5$^{th}$ ed., 2001, Wiley-Interscience. Amine TQ-7 is then stirred in the presence of epoxide TQ-11 in preferably, but not limited to, alcoholic solvents such as ethanol, isopropropyl, tert-butyl, or n-butyl alcohol, at temperatures ranging from 50° C. to the reflux temperature of the solvent, to give Boc-amine TQ-12. Boc-amine TQ-12 is then treated with strong acid such as trifluoroacetic acid in non-reactive solvents such as dichloromethane or with dry HCl in solvents such as dialkyl ethers or alcoholic solvents at temperatures ranging from room temperature to 80° C. to give, after washing with base, triamine TQ-13. Triamine TQ-13 is acylated by means well-known to those versed in the art, for example condensation with a carboxylic acid using coupling agents such as EDC, DCC, HATU, or HBTU and the like. Preferred methods are acylation with acyl imidazole or acetylation with N,N-diacetylmethoxyamine to give TQ-14.

Experimental Procedures

EXAMPLE 1

Preparation of 7-Bromo-1-tetralone

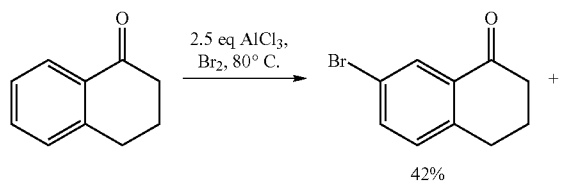

42%

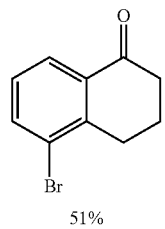

51%

7-bromo-1-tetralone was prepared according to the procedure described in Cornelius, L. A. M.; Combs, D. W. *Synthetic Communications* 1994, 24, 2777-2788. The above isomers were separated using silica gel flash chromatography (Biotage Flash 75, elution solvent 20/1 hexanes:MTBE) to yield 5-bromo-1-tetralone (11.59 g, 51%) and 7-bromo-1-tetralone (9.45 g, 42%).

Tetralin-1-ol compounds may be prepared as shown in Example 2 below. Mores specifically, (R)-7-ethyltetralin-1-ol was prepared in three steps starting from 7-ethyl-1-tetralone. The first step involves an asymmetric reduction of the ketone using borane and Corey's oxazaboralidine chiral auxilliary. This reduction produced a 97:3 mixture of (presumably) R/S enantiomers. A Mitsunobu-like $S_n2$ conversion to the azide and LiAlH$_4$ reduction to the amine produced material 98:2 S/R.

EXAMPLE 2

Preparation of (R)-7-Ethyltetralin-1-ol

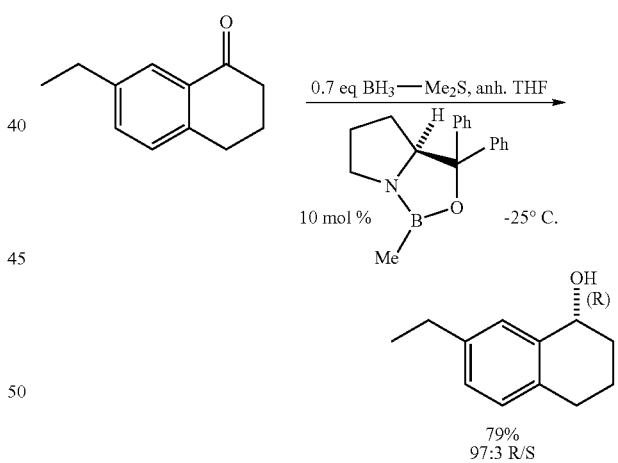

79%
97:3 R/S

See generally: Jones, T. K.; Mohan, J. J.; Xavier, L. C.; Blacklock, T. J.; Mathre, D. J.; Sohar, P.; Turner-Jones, E. T.; Reamer, R. A.; Roberts, F. E.; Grabowski, E. J. J. *J. Org. Chem.* 1991, 56, 763-769. More particularly, 7-ethyl-1-tetralone (2.29 g, 13.1 mmol) was placed in a 100 mL round bottomed flask and dissolved in anhydrous THF (40 mL). Activated 4 Å molecular sieves were added and the mixture was aged for 2 h before transferring via cannula to a 250 ml three-necked round bottom flask fitted with a dropping funnel, thermometer, and a nitrogen inlet. The solution was cooled to −25° C. and 1M (S)-tetrahydro-1-methyl-3,3-diphenyl-1H,3H-pyrollo[1,2-c][1,3,2]oxazaborole in toluene (1.3 mL, 1.3 mmol) was added. The source of the oxazoborole was Aldrich, cat. no. 45,770-1, "(S)-2-methyl-CBS-oxazaborolidine". Use of the S-auxilliary will produce R-alcohols. In accordance with the forging references, the use of 5 mol % oxazaborolidine catalyst should give comparable results.

The dropping funnel was charged with a solution of borane-methylsulfide (0.70 g, 0.87 mL, 9.3 mmol) in anhydrous THF (15 mL, dried over 4A sieves). The borane solution was added dropwise over 20 min keeping the reaction temperature less than −20° C. The mixture was stirred for 1 h at −15 to −20° C. whereupon TLC analysis indicated consumption of the ketone. The reaction was quenched by careful addition of methanol (15 mL) at −20° C. and allowed to warm to ambient temperature and stir for 16 h. The volatiles were removed in vacuo and the residue was purified by silica gel chromatography (Biotage Flash 65, elution solvent 6/1 hexanes:ethyl acetate) to yield (R)-7-ethyltetralin-1-ol (1.82 g, 79%). Analytical chiral HPLC indicated a 96.6/3.4 mixture of enantiomers (Chirocel OD-H column, isocratic elution 2:98 IPA/hexane, 0.9 mL/min, RT 15.2 min (minor enantiomer), 17.5 min (major enantiomer).

EXAMPLE 3

Preparation of (S)-7-Ethyl-1,2,3,4-tetrahydro-1-napthylamine hydrochloride

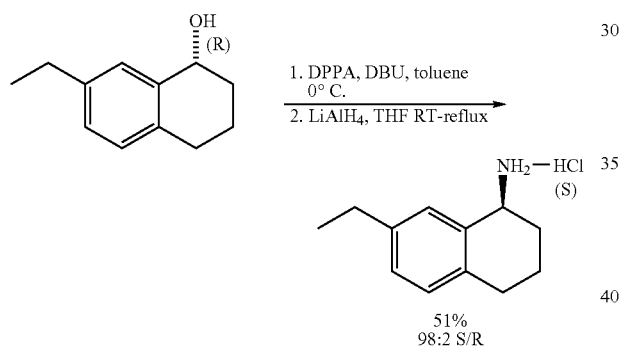

51%
98:2 S/R

See generally: Rover, S.; Adam, G.; Cesura, A. M.; Galley, G.; Jenck, F.; Monsma Jr., F. J.; Wichmann, J.; Dautzenberg, F. M. *J. Med. Chem.* 2000, 43, 1329-1338. The authors therein report a somewhat diminished yield due to partial formation of a dihydronapthalene via elimination of the hydroxyl moiety.

More specifically, a solution of (R)-7-ethyltetralin-1-ol (1.77 g, 10.1 mmol) in toluene (25 mL) was cooled in an ice bath and treated with diphenylphosphorylazide (DPPA, 3.3 g, 2.7 mL, 12 mmol). A solution of 1,8-diazabicyclo[5.4.0]undec-7-ene (DBU, 1.8 g, 1.8 mL, 12 mmol) in toluene (8 mL) was added over 20 min and the mixture was allowed to stir at 0° C. for 2 h and ambient temp for 16 h. The mixture was filtered through a pad of silica gel (eluted 6:1 hexanes/ethyl acetate) to remove precipitates and the volatiles were removed in vacuo to give an oily residue of the crude S-azide. This material was used directly in the next step without further characterization.

The azide was dissolved in dry THF (20 mL) and added dropwise at RT to a slurry of lithium aluminum hydride (0.459 g, 12 mmol) in dry THF (20 mL). The mixture was stirred at RT for 1 h and then heated to reflux for 1 h. The reaction was cooled to RT and quenched by successive addition of water (0.45 mL), 15% aq NaOH (0.45 mL) and water (1.4 mL). The resulting mixture was stirred for 1 h and then filtered through a pad of Celite (eluted diethyl ether). The volatiles were removed in vacuo and the residue taken up into ethyl acetate (40 mL) and treated with 4N HCl in dioxane (3 mL). The resulting precipitate was filtered (wash ethyl acetate), collected and vacuum dried to give (S)-7-ethyl-1,2,3,4-tetrahydro-1-napthylamine hydrochloride as a white solid (1.09 g, 51%). Analytical chiral HPLC indicated a 96:4 mixture of enantiomers (Daicel Crownpak (−) column, isocratic elution 10% methanol in water (0.1% TFA), 0.8 mL/min, RT 56.2 min (minor enantiomer), 78.2 min (major enantiomer).

Scheme VIII below depicts formation of a tetralinol, prepared in three steps starting from 7-bromo-1-tetralone. The first step involves an asymmetric reduction of the ketone using borane and Corey's oxazaboralidine chiral auxilliary. This reduction produced a 98:2 mixture of (presumably) R/S enantiomers. A Mitsunobu-like $S_N 2$ conversion to the azide and LiAlH$_4$ reduction to the amine produced material 96:4 S/R.

EXAMPLE 4

Preparation of (R)-7-Bromotetralin-1-ol

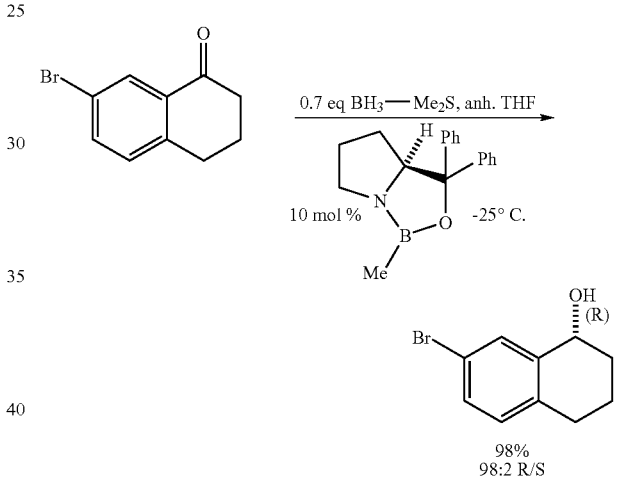

98%
98:2 R/S

The reduction is performed using the general procedure described in example 2. Analytical chiral HPLC of the product indicated a 98:2 mixture of enantiomers (Chirocel OD-H column, isocratic elution 2:98 IPA/hexane, 0.9 mL/min, RT 18.4 min (minor enantiomer), 19.5 min (major enantiomer). Proton NMR was consistent with that previously reported for the racemate: Saito, M.; Kayama, Y.; Watanabe, T.; Fukushima, H.; Hara, T. *J. Med. Chem.* 1980, 23, 1364-1372.

EXAMPLE 5

Preparation of (S)-7-Bromo-1,2,3,4-tetrahydro-1-napthylamine hydrochloride

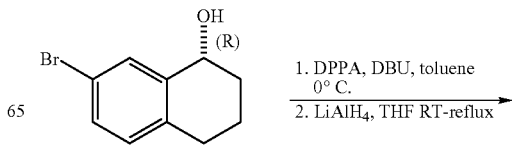

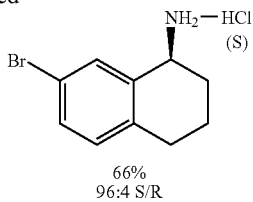

66%
96:4 S/R

The above compound is prepared essentially according to the procedure described in Example 3. The final compound is obtained as a white solid. Analytical chiral HPLC indicated a 96:4 mixture of enantiomers (Daicel Crownpak (−) column, isocratic elution 10% methanol in water (0.1% TFA), 0.8 mL/min, RT 39.4 min (minor enantiomer), 57.6 min (major enantiomer).

EXAMPLE 6

Preparation of Precursor Substituted Amines

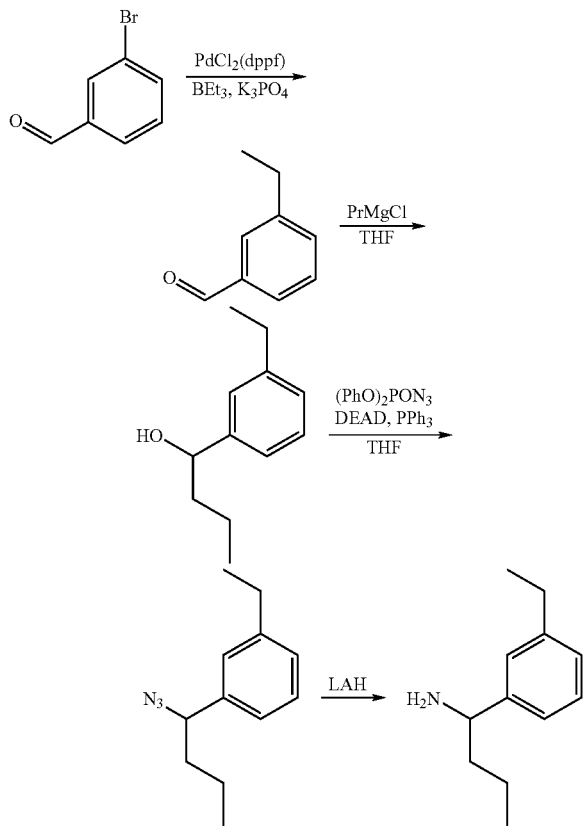

Precursore amines can generally be prepared as shown above. Specific examples are described below.

EXAMPLE 7

Preparation of 3-Ethylbenzaldehyde from 3-bromobenzaldehyde

3-Bromobenzaldehyde (Aldrich, 1.17 mL, 10.0 mmol) was dissolved in THF (20 mL) at rt. To it was added $PdCl_2$(dppf).$CH_2Cl_2$ complex (Aldrich, 82 mg, 0.10 mmol), 2 M potassium phosphate (aq, 10 mL, 20 mmol), and triethylborane (Aldrich, 1.0 M solution in hexanes, 10 mL, 10 mmol). This was heated to reflux for 4 h, whereupon the mixture was allowed to cool to rt. The reaction mixture was partitioned between EtOAc and water. The organic layer was separated, dried ($MgSO_4$), and concentrated under reduced pressure. The residue was purified by flash chromatography (20% EtOAc/hexanes elution) to give a clear, colorless oil which was used without further purification: mass spec (CI) 135.1.

EXAMPLE 8

Preparation of 3-Ethyl-α-propylbenzyl alcohol from 3-ethylbenzaldehyde

To a solution of 3-ethylbenzaldehyde (641 mg, 4.78 mmol) in THF (15 mL) cooled to 0° C. was added a solution of propylmagnesium chloride (Aldrich, 2.0 M in diethyl ether, 7.0 mL, 14.0 mmol) dropwise with stirring. Upon completion of addition, the reaction mixture was allowed to warm to rt for 2 h. Reaction was then quenched by addition of water (1 mL), then concentrated under reduced pressure. The residue was purified by flash chromatography ($R_f$=0.71 in 30% EtOAc/hexanes) to give a colorless oil as product (804 mg, 94%): mass spec (CI) 161.1 (M−OH).

EXAMPLE 9

Preparation of 3-Ethyl-α-propylbenzyl azide from 3-ethyl-α-propylbenzyl alcohol

3-Ethyl-α-propylbenzyl alcohol (803 mg, 4.51 mmol) was dissolved in THF (10 mL), and cooled to 0° C. Triphenylphosphine (Aldrich, 1.416 g, 5.40 mmol), diethyl azodicarboxylate (Aldrich, 0.85 mL, 5.40 mmol), and diphenyl phosphoryl azide (1.16 mL, 5.38 mmol) was added in succession by syringe. This was stirred at 0° C. for 1¾ h, then at rt for 2 h, whereupon the reaction mixture was concentrated under reduced pressure. The residue was purified by flash chromatography (EtOAc/hexanes elution) to give a clear, colorless oil as product: $^1$H NMR (300 MHz) δ 7.35-7.25 (m, 1H), 7.20-7.05 (m, 2H), 4.39 (t, J=7.2 Hz, 1H), 2.67 (q, J=7.6 Hz, 2H), 1.95-1.60 (m, 2H), 1.52-1.25 (m, 2H), 1.25 (t, J=7.6 Hz, 3H), 0.93 (t, J=7.3 Hz, 3H).

EXAMPLE 10

Preparation of 3-Ethyl-α-propylbenzyl amine from 3-ethyl-α-propylbenzyl azide

3-Ethyl-α-propylbenzyl azide (724 mg, 3.57 mmol) in dry THF (10 mL) was added to a suspension of lithium aluminum hydride (280 mg, 7.38 mmol) in THF (10 mL) at 0° C. This was stirred at 0° C. for 30 min, then at rt for 1 h, whereupon the reaction was quenched using water (0.2 mL), 15% aq. NaOH (0.2 mL), and water (0.6 mL) in succession. This was stirred at rt for 1 h. The reaction mixture was then filtered through diatomaceous earth ($CH_2Cl_2$ elution), and the filtrate concentrated under reduced pressure. This material was used in subsequent reactions without further purification: $^1$H NMR (300 MHz) δ 7.35-7.20 (m, 1H), 7.20-7.04 (m, 2H), 3.87 (t, J=6.9 Hz, 1H), 2.65 (q, J=7.6 Hz, 2H), 1.72-1.57 (m, 2H), 1.50-1.20 (m, 2H), 1.24 (t, J=7.6 Hz, 3H), 0.91 (t, J=7.3 Hz, 3H); mass spec (CI) 161.1 (M−$NH_2$).

EXAMPLE 11

Preparation of 1-(3-Ethyl-phenyl)-cyclohexanol from 1-bromo-3-ethylbenzene

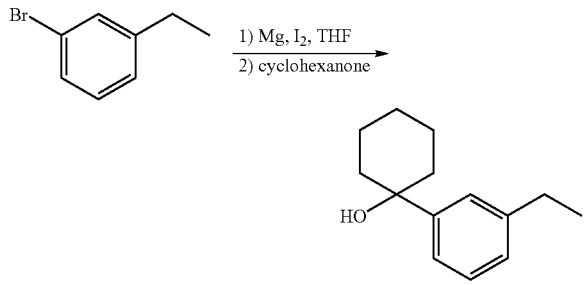

Magnesium turnings (1.35 g, 55.53 mmol) were activated via vigorous stirring overnight under $N_2$ (g) inlet. A few crystals of iodine were added to the flask, which was then flamed-dried under vacuum. Anhydrous THF (3 mL) was added to the reaction flask followed by 1-bromo-3-ethylbenzene (Avocado, 2.0 mL, 14.59 mmol). The reaction was initiated after briefly heating with a heat gun. To this was added the remainder of 1-bromo-3-ethylbenzene (1.7 mL, 12.43 mmol) in a THF solution (15 mL). The reaction mixture was refluxed for 2 h. A cyclohexanone (2.2 mL, 21.22 mmol) in THF (8 mL) solution was added once the flask was cooled to 0° C. After 3.5 h the reaction mixture was quenched with $H_2O$ over an ice bath and partitioned between $Et_2O$ and $H_2O$. The organic layer was removed and acidified with 1N HCl. The organic layer was separated, dried ($Na_2SO_4$), and concentrated under reduced pressure. The residue was purified by flash chromatography (100% $CHCl_3$) to give the desired alcohol (4.152 g, 96%): mass spec (CI) 187.1 (M-16).

EXAMPLE 12

Preparation of 1-(1-Azido-cyclohexyl)-3-ethyl-benzene from 1-(3-Ethyl-phenyl)-cyclohexanol 1-(3-Ethyl-phenyl)-cyclohexanol (4.02 g, 19.68 mmol) in anhydrous chloroform (45 mL) was cooled to 0° C. under $N_2$ (g) inlet. Sodium azide (3.97 g, 61.07 mmol) was added followed by dropwise addition of trifluoroacetic acid (7.8 mL, 101.25 mmol). The reaction mixture was refluxed for 2 h and allowed to stir at rt o/n. This was then partitioned between $H_2O$ and $Et_2O$. The aqueous layer was removed and the mixture was washed with $H_2O$ followed by 1.0N $NH_4OH$. The organic layer was separated, dried ($Na_2SO_4$), and concentrated under reduced pressure. The crude product was used without further purification (3.30 g, 73%): mass spec (CI) 187.1 (M-42).

EXAMPLE 13

Preparation of 1-(3-Ethyl-phenyl)-cyclohexylamine from 1-(1-azido-cyclohexyl)-3-ethyl-benzene

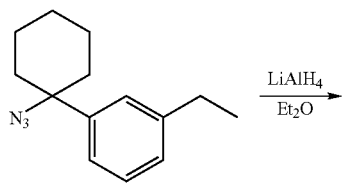

-continued

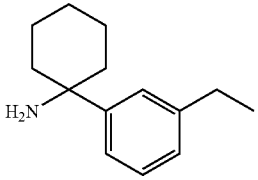

The above compound is prepared essentially according to the procedure described in Example 10. The final compound is used without further purification: mass spec (CI) 187.1 (M-16).

EXAMPLE 14

Preparation of N-{(1S,2R)-1-(3,5-difluorobenzyl)-3-[(2-ethyl-7-fluoro-9H-fluoren-9-yl)amino]-2-hydroxypropyl}acetamide Step 1: To 3.0 g (16.6 mmol) of methyl 5-ethyl-2-hydroxybenzoate in 100 mL of $CH_2Cl_2$ at 0° C. was added 5.8 mL (41.5 mmol, 2.5 eq.) of $Et_3N$. To this stirred solution was added dropwise 3.6 mL (21.6 mmol, 1.3 eq.) of $Tf_2O$. Following complete addition 0.2 g (cat.) of 4-dimethylamino pyridine was added and the reaction mixture was allowed to warm to room temperature. After 4 h stirring at this temperature the reaction was judged complete, and quenched by the addition of a saturated aqueous solution of $NaHCO_3$ (100 mL). The resulting layers were separated and the aqueous layer extracted twice with $CH_2Cl_2$ (100 mL). The combined organic layers were dried over $MgSO_4$, filtered and concentrated under reduced pressure. The resulting residue was purified by column chromatography to yield the desired methyl 5-ethyl-2-{[(trifluoromethyl)sulfonyl]oxy}benzoate. $^1H$ NMR (400 MHz, $CDCl_3$): δ=7.94 (d, J=2.3 Hz, 1H), 7.47 (dd, J=2.3, 8.4 Hz, 1H), 7.24 (d, J=8.4 Hz, 1H), 4.00 (s, 3H), 2.76 (q, J=7.6 Hz, 2H), 1.28 (t, J=7.6 Hz, 3H).

Step 2: To 1.5 g (4.8 mmol) of product from Step 1 in 12.5 mL of toluene at room temperature was added 0.28 g (0.24 mmol, 0.05 eq.) of $Pd(PPh_3)_4$. After stirring for 5 min, 1.1 g (5.7 mmol, 1.2 eq.) of 4-fluorophenylboronic acid in 5.5 mL of EtOH followed by 11.5 mL of 2 M aqueous $Na_2CO_3$ were added. After heating at 90° C. for 12 h the reaction was judged complete, cooled and diluted with $Et_2O$ (100 mL) and water (50 mL). The resulting layers were separated and the aqueous layer extracted twice with $Et_2O$ (100 mL). The combined organic layers are dried over $MgSO_4$, filtered and concentrated under reduced pressure. The resulting residue was purified by column chromatography to yield the desired methyl 4-ethyl-4'-fluoro-1,1'-biphenyl-2-carboxylate. $C_{16}H_{15}O_2F+H^+$ requires 258 found 258.

Step 3: To 1.1 g (4.3 mmol) of the product from Step 2 in 50 mL of 2:2:1 THF:water:MeOH was added 0.9 g (21 mmol) of LiOH. The mixture was heated to 55° C. for 5 h at which point the reaction was judged complete. Upon cooling the volatiles were removed under reduced pressure and the residue portioned between 10% aqueous HCl (50 mL) and EtOAc (200 mL). The resulting layers were separated and the aqueous layer extracted twice with EtOAc (100 mL). The combined organic layers were dried over $Na_2SO_4$, filtered and concentrated. The resulting residue, 4-ethyl-4'-fluoro-1,1'-biphenyl-2-carboxylic acid, was pure enough to use directly in the next step. $C_{15}H_{13}F_1O_2+H^+$ requires 244, found 244.

Step 4: To 0.25 g (1 mmol) of product from Step 3 was added 1 mL of $H_2SO_4$ and the resulting mixture was heated to 110° C. for 20 min after which time the reaction was judged complete. Upon cooling, the mixture was poured onto ice water (100 mL) and extracted twice with $Et_2O$ (200 mL). The combined organic extracts were washed twice with a saturated aqueous solution of $NaHCO_3$ (100 mL), dried over $MgSO_4$, and concentrated under reduced pressure. The resulting residue, 2-ethyl-7-fluoro-9H-fluoren-9-one, was pure enough to use directly in the next step. $C_{15}H_{11}F_1O_1+H^+$ requires 226, found 226.

Step 5: To 0.8 g (3.6 mmol) of the product from Step 4 was added 10 mL of EtOH and 3.2 mL of pyridine. To this stirred solution was added 1.0 g (14.6 mmol, 4 eq.) of $NH_2OH.HCl$ and the mixture heated to 65° C. for 6 h after which time the reaction was judged complete. Upon cooling, the volatiles were removed under reduced pressure and the residue portioned between 10% aqueous HCl (50 mL) and EtOAc (250 mL). The resulting layers were separated and the organic layers washed twice more with 10% aqueous HCl (50 mL). The organic layer was dried over $MgSO_4$, filtered and concentrated under reduced pressure. The resulting residue, (9Z)-2-ethyl-7-fluoro-9H-fluoren-9-one oxime, was pure enough to use directly in the next step. $C_{15}H_{12}F_1O_1N_1+H^+$ requires 242, found 242.

Step 6: To 0.8 g (3.3 mmol) of the product from Step 5 was added 3 mL of AcOH, 0.1 mL of water and 0.7 g (9.9 mmol, 3 eq.) of Zn. The resulting mixture was vigorously stirred for 20 min after which time the reaction was judged complete. After filtration to remove the solids the volatiles were removed under reduced pressure. The resulting residue was portioned between EtOAc (200 mL) and 10% aqueous KOH (100 mL). The resulting layers were separated and the organic layer washed once more with 10 % aqueous KOH (50 mL). The organic layer was dried over $Na_2SO_4$, filtered and concentrated under reduced pressure. The resulting residue 2-ethyl-7-fluoro-9H-fluoren-9-amine was pure enough to use directly in the next step. $C_{15}H_{14}F_1N_1+H^+$ requires 227, found 211 ($-NH_3$)

Step 7: To 0.45 g (2.0 mmol) of the product of Step 6 was added 6 mL of isopropyl alcohol and 0.55 g (1.8 mmol, 0.9 eq.) of Example 134. The mixture was heated at 65° C. for 12 h after which time the reaction was judged complete. Upon cooling, the volatiles were removed under reduced pressure. The resulting residue was purified by column chromatography to yield the desired tert-butyl (1S,2R)-1-(3,5-difluorobenzyl)-3-[(2-ethyl-7-fluoro-9H-fluoren-9-yl)amino]-2-hydroxypropylcarbamate. $C_{30}H_{33}F_3N_2O_3+H^+$ requires 527, found 527.

Steps 8&9: To 0.1 g (0.19 mmol) of product from Step 7 was added 3 mL of $CH_2Cl_2$ and 0.5 mL (excess) of TFA. The resulting mixture was stirred for 1 h at room temperature after which time the reaction was judged complete. The reaction mixture was diluted with toluene (2 mL) and the volatiles were removed under reduced pressure. After drying under high vacuum for 1 h, the residue was dissolved in 5 mL of $CH_2Cl_2$ and 0.061 mL (0.4 mmol, 2.2 eq.) of $Et_3N$ followed by 0.02 g (0.2 mmol, 1.05 eq.) of acetyl-imidazole were added. After stirring for 12 h at room temperature the reaction was judged complete and poured in a saturated aqueous solution of $NaHCO_3$ (10 mL). The resulting layers were separated and the aqueous layer extracted once with EtOAc (50 mL). The combined organic layers were dried over $Na_2SO_4$, filtered and concentrated under reduced pressure. The resulting residue was purified by column chromatography to yield the desired N-{(1S,2R)-1-(3,5-difluorobenzyl)-3-[(2-ethyl-7-fluoro-9H-fluoren-9-yl)amino]-2-hydroxypropyl}acetamide. $C_{27}H_{27}F_3N_2O_2+H^+$ requires 469, found 469.

EXAMPLE 15

Preparation of N-((1S,2R)-1-(3,5-difluorobenzyl)-3-{[(4S)-6-ethyl-3,4-dihydro-2H-chromen-4-yl]amino}-2-hydroxypropyl)acetamide

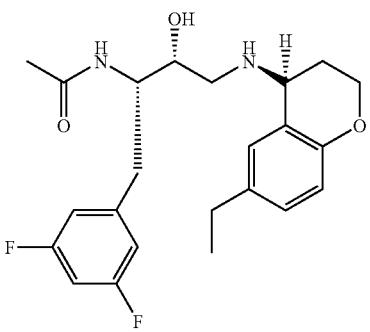

Step 1 Preparation of 6-Iodo-chroman-4-ylamine

To a $CH_2Cl_2$ (80 ml) solution of 6-iodo-4-chromanol (10.0 g, 36 mmol) and diisopropylethyl amine (19 ml, 108 mmol), at 0° C., was added the MsCl (4.2 ml, 54 mmol). After stirring for 1.5 h the solvent was removed in vacuo and the resulting residue dissolved in 150 ml of DMF followed by the addition of Na $N_3$ (3.5 g, 54 mmol). The reaction was heated to 70° C. for 6.5 h then cooled to rt. followed by the addition of 900 ml 0f 1 N HCl and extraction with $Et_2O$ (4×200 ml). The combined $Et_2O$ layers were dried over $MgSO_4$ and concentrated in vacuo to yield 9.5 g of the azide as yellow oil. MS (ESI+) for $C_9H_8IN_3O$ m/z 300.97 $(M+H)^+$. The crude azide (5.0 g, 16.6 mmol) was dissolved in THF (50 ml) and treated with $PPh_3$ (5.2 g, 20.0 mmol). The mixture stirred at rt. for 30 min. followed by the addition of 4 ml of $H_2O$. The mixture was then heated to 60° C. overnight. After cooling the mixture was concentrated in vacuo and the resulting residue treated with 1 N HCl. The aqueous layer was washed with $CH_2Cl_2$ and then adjusted to pH=12 with NaOH pellets. The basic aqueous layer was extracted with $CH_2Cl_2$ and the combined organic layers dried over $Na_2SO_4$ and treated with activated carbon. The mixture was filtered through Celite® and concentrated in vacuo to yield 6-Iodo-chroman-4-ylamine 3.6 g (79%) as clear oil that solidifies upon standing. MS (ESI+) for $C_9H_{10}INO$ m/z 275.98 $(M+H)^+$.

Step 2 Preparation of tert-butyl (1S,2R)-1-(3,5-difluorobenzyl)-2-hydroxy-3-[(6-iodo-3,4-dihydro-2H-chromen-4-yl)amino]propylcarbamate

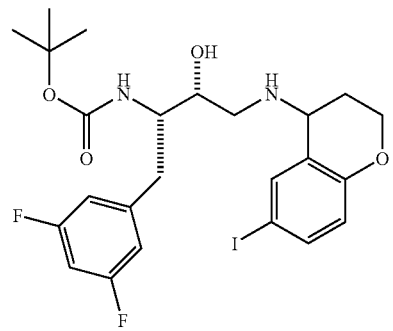

An isopropyl alcohol (25 ml) solution of Example 134 (2.2 g, 7.2 mmol) and 6-Iodo-chroman-4-ylamine (3.0 g, 10.9 mmol) was stirred at 75° C. for 0 h. The IPA was removed in vacuo and the resulting residue dissolved in EtOAc (200 ml). The organic layer was washed with 1 N HCl (4×50 ml), followed by NaHCO$_3$ (2×50 ml), and brine (1×50 ml). The organic layer was dried over Na$_2$SO$_4$ and concentrated in vacuo to yield 3.5 g (85%) of the title compound as a mixture of diastereomers as an off white solid. MS (ESI+) for C$_{24}$H$_{29}$F$_2$IN$_2$O$_4$ m/z 574.8 (M+H)$^+$.

Step 3 Preparation of N-{(1S,2R)-1-(3,5-difluorobenzyl)-2-hydroxy-3-[(6-iodo-3,4-dihydro-2H-chromen-4-yl)amino]propyl}acetamide Tert-butyl (1S,2R)-1-(3,5-difluorobenzyl)-2-hydroxy-3-[(6-iodo-3,4-dihydro-2H-chromen-4-yl)amino]propylcarbamate (3.0 g, 5.2 mmol) was dissolved in 30 mL of 25% TFA/CH$_2$Cl$_2$ and stirred at room temperature for 30 min. The mixture was diluted with CH$_2$Cl$_2$ 50 mL and washed with NaHCO$_3$ (2×30 mL). The organic layer was washed with brine (1×50 mL) and dried over Na$_2$SO$_4$. The solvent was removed in vacuo and the resulting residue dissolved in 52 mL of CH$_2$Cl$_2$. The mixture was chilled to 0° C. followed by the addition of Et$_3$N (1. mL, 11.9 mmol) and acetyl imidazole (0.68 g, 6.2 mmol). The mixture was warm spontaneously over night. The CH$_2$Cl$_2$ was removed in vacuo and the residue dissolved in EtOAc (100 mL) and washed with 1N HCl (2×30 mL), NaHCO$_3$ (1×30 mL), brine, dried over Na$_2$SO$_4$, and conc. in vacuo to yield 2.5 g (92%) of the title compound as a light yellow solid. MS (ESI+) for C$_{21}$H$_{23}$F$_2$IN$_2$O$_3$ m/z 517.0 (M+H)$^+$.

Step 4 Preparation N-((1S,2R)-1-(3,5-difluorobenzyl)-3-{[(4S)-6-ethyl-3,4-dihydro-2H-chromen-4-yl]amino}-2-hydroxypropyl)acetamide

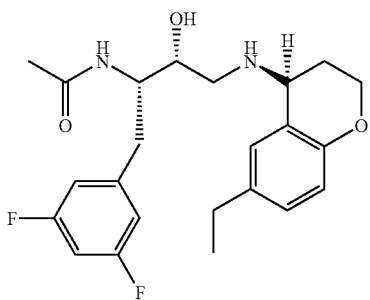

N-{(1S,2R)-1-(3,5-difluorobenzyl)-2-hydroxy-3-[(6-iodo-3,4-dihydro-2H-chromen-4-yl)amino]propyl}acetamide (1.0 g, 1.9 mmol) and Pd(dppf)Cl$_2$ (0.078 g, 0.1 mmol) was dissolved in 20 mL of degassed THF. To the mixture was added 10 mL of 2.0 M K$_3$PO$_4$ followed by the addition of Et$_3$B (3.8 mL, 3.8 mmol, 1.0 M in THF) via syringe. The reaction mixture was heated to 65° C. under a nitrogen atmosphere. After 2.5 h the reaction was determined to be complete and diluted with EtOAc (100 mL) and washed with brine (3×30 mL). The organic layer was dried over Na$_2$SO$_4$ and conc. in vacuo to yield brown solid. The diastereomers of the title compound were separated by preparative chiral HPLC (Chiralpak AD, 20% IPA/80% heptane, 0.1% DEA). MS (ESI+) for C$_{23}$H$_{26}$F$_2$N$_2$O$_3$ m/z 419 (M+H)$^+$.

The following compounds are prepared essentially according to the procedures described in the schemes and preparations set forth above:

| Example | | MS |
|---|---|---|
| Example 15 A | N—{(1S,2R)-1-(3,5-difluorobenzyl)-2-hydroxy-3-[(6-isopropyl-3,4-dihydro-2H-chromen-4-yl)amino]propyl}acetamide | MS (ESI+) for C$_{24}$H$_{30}$F$_2$N$_2$O$_3$ m/z 432.9 (M + H)$^+$ |
| Example 15 B | N—((1S,2R)-1-(3,5-difluorobenzyl)-2-hydroxy-3-{[(4S)-6-isobutyl-3,4-dihydro-2H-chromen-4-yl]amino}propyl)acetamide | MS (ESI+) for C$_{25}$H$_{32}$F$_2$N$_2$O$_3$ m/z 447.4 (M + H)$^+$ |
| Example 15 C | N—{(1S,2R)-1-(3,5-difluorobenzyl)-2-hydroxy-3-[(6-neopentyl-3,4-dihydro-2H-chromen-4-yl)amino]propyl}acetamide | MS (ESI+) for C$_{26}$H$_{34}$F$_2$N$_2$O$_3$ m/z 461.3 (M + H)$^+$ |
| Example 15 D | N—[(1S,2R)-3-{[(4S)-6-cyano-3,4-dihydro-2H-chromen-4-yl]amino}-1-(3,5-difluorobenzyl)-2-hydroxypropyl]acetamide | MS (ESI+) for C$_{22}$H$_{23}$F$_2$N$_3$O$_3$ m/z 416.4 (M + H)$^+$ |
| Example 15 E | N—((1S,2R)-1-(3,5-difluorobenzyl)-2-hydroxy-3-{[(4S)-6-(1H-pyrrol-3-yl)-3,4-dihydro-2H-chromen-4-yl]amino}propyl)acetamide | MS (ESI+) for C$_{25}$H$_{27}$F$_2$N$_3$O$_3$ m/z 456.2 (M + H)$^+$ |
| Example 15 F | N—[(1S,2R)-1-(3,5-difluorobenzyl)-3-(3,4-dihydro-2H-chromen-4-ylamino)-2-hydroxypropyl]acetamide | MS (ESI+) for C$_{21}$H$_{24}$F$_2$N$_2$O$_3$ m/z 391.3 (M + H)$^+$. |

EXAMPLE 16

Preparation of Representative Chroman Intermediates

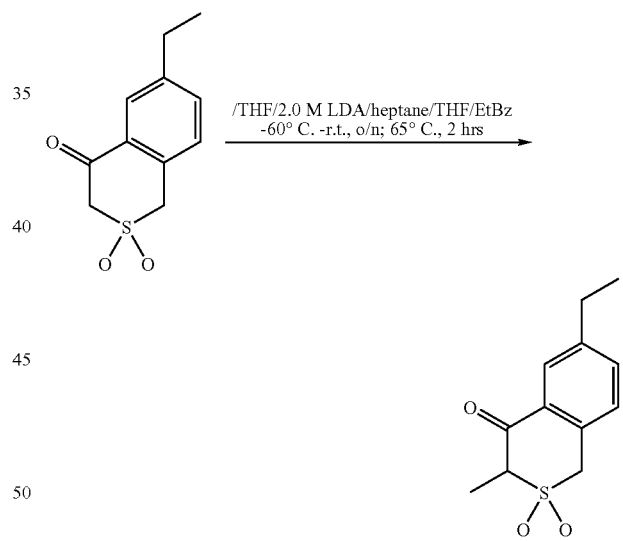

To 0.9 g (4 mmole) of sulfone ketone in 40 ml of THF is added 2.5 ml (5 mmole, 1.25 eq.) of 2 M of Lithium diisopropylamine(LDA) in heptane/THF/ethylbenzene at −60° C. The mixture is stirred for about 15 minutes, and then 1.24 ml (20 mmole, 5 eq.) of methyl iodide is added. The reaction mixture is stirred for 1 hour at −60° C., and then the cold bath is removed. After stirring overnight, the reaction mixture is partitioned between EtOAc and water, washed with 0.5N HCl, aqueous sodium bicarbonate solution, and brine, dried over anhydrous sodium sulfate, filtered and concentrated. The concentrate was purified by column chromatography to afford 0.68 g of the desired product as an oil, which solidified upon standing. TLC (30% EtOAc/Hexane, Rf=0.39). Mass spec. m/e=239.1.

The following compounds were prepared essentially according to the procedures described above:

| Example | | MS |
|---|---|---|
| Example 16 A | N-[1-(3,5-Difluoro-benzyl)-3-(6-ethyl-2,2-dioxo-2λ⁶-isothiochroman-4-ylamino)-2-hydroxy-propyl]-propionamide | (MS 481.1) |
| Example 16 B | N-[1-(3,5-Difluoro-benzyl)-3-(6-ethyl-2,2-dioxo-2λ⁶-isothiochroman-4-ylamino)-2-hydroxy-propyl]-2-(1H-imidazol-4-yl)-acetamide | (MS 533.1) |
| Example 16 C | N-[1-(3,5-Difluoro-benzyl)-3-(6-ethyl-2,2-dioxo-2λ⁶-isothiochroman-4-ylamino)-2-hydroxy-propyl]-2-methyl-2-methylamino-propionamide | (MS 524.1) |
| Example 16 D | {[1-(3,5-Difluoro-benzyl)-3-(6-ethyl-2,2-dioxo-2λ⁶-isothiochroman-4-ylamino)-2-hydroxy-propylcarbamoyl]-methyl}-methyl-carbamic acid tert-butyl ester | (MS 596.1) |
| Example 16 E | N-[1-(3,5-Difluoro-benzyl)-3-(6-ethyl-2,2-dioxo-2λ⁶-isothiochroman-4-ylamino)-2-hydroxy-propyl]-2-phenyl-acetamide | (MS 543.1) |
| Example 16 F | N-[1-(3,5-Difluoro-benzyl)-3-(6-ethyl-2,2-dioxo-2λ⁶-isothiochroman-4-ylamino)-2-hydroxy-propyl]-3-hydroxy-butyramide | (MS 511.1) |
| Example 16 G | N-[1-(3,5-Difluoro-benzyl)-3-(6-ethyl-2,2-dioxo-2λ⁶-isothiochroman-4-ylamino)-2-hydroxy-propyl]-3-hydroxy-propionamide | (MS 497.1) |
| Example 16 H | N-[1-(3,5-Difluoro-benzyl)-3-(6-ethyl-2,2-dioxo-2λ⁶-isothiochroman-4-ylamino)-2-hydroxy-propyl]-3-hydroxy-2,2-dimethyl-propionamide | (MS 525.1) |
| Example 16 I | N-[1-(3,5-Difluoro-benzyl)-3-(6-ethyl-2,2-dioxo-2λ⁶-isothiochroman-4-ylamino)-2-hydroxy-propyl]-3-methyl-butyramide | (MS 509.1) |
| Example 16 J | 2-Amino-N-[1-(3,5-difluoro-benzyl)-3-(6-ethyl-2,2-dioxo-2λ⁶-isothiochroman-4-ylamino)-2-hydroxy-propyl]-acetamide | (MS 482.1) |
| Example 16 K | N-[1-(3,5-Difluoro-benzyl)-3-(6-ethyl-2,2-dioxo-2λ⁶-isothiochroman-4-ylamino)-2-hydroxy-propyl]-2-methylamino-acetamide | (MS 496.1) |

EXAMPLE 17

N-[(1S,2R)-1-(3,5-difluorobenzyl)-3-(3,4-dihydro-2H-chromen-4-ylamino)-2-hydroxypropyl]acetamide

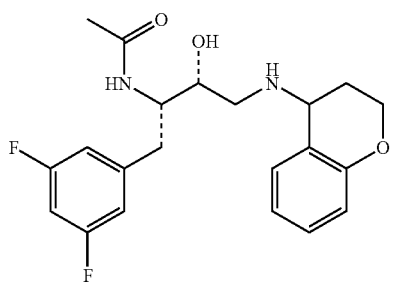

Step One: Chroman-4-ol

To a MeOH (250 ml) solution of 4-chromanone (16.6 g, 11 mmol), at 0° C., was added NaBH₄ (5.5 g, 145 mmol) in 1 g portions over a 30 min. period. After complete addition the mixture was stirred for 1 h with spontaneous warming. The reaction was quenched with the slow addition of aq. NH₄Cl (100 ml). The MeOH was removed in vacuo and the residue extracted with Et₂O (2×100 ml). The organic layers were dried over MgSO₄ and treated with activated carbon. After filtration the Et₂O was removed in vacuo to yield 15.8 g of chroman-4-ol as a clear oil. HRMS (ESI+) calcd for C₉H₁₀O₂ m/z 150.0681 (M+H)⁺. Found 150.0679.

Step Two: 3,4-dihydro-2H-chromen-4-ylamine

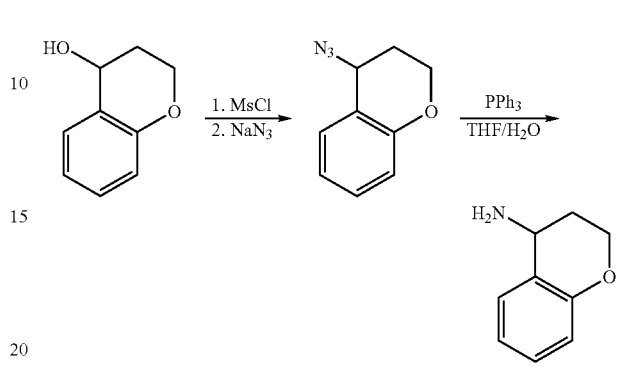

To a CH₂Cl₂ (80 ml) solution of chroman-4-ol (3.1 g, 20.6 mmol) and DIEA (8 ml, 42 mmol), at 0° C., was added the MsCl (2.1 ml, 27 mmol) via syringe. After complete addition the cold bath was removed and stirring continued at room temperature. After 15 h the CH₂Cl₂ was removed in vacuo and the residue dissolved in 80 ml of DMF followed by the addition of NaN₃ (1.8 g, 27 mmol). The mixture was heated to 75° C. (oil bath) for 5 h then cooled to room temperature. The mixture was diluted with Et₂O (400 ml) and washed with 1 N HCl (2×100 ml); NaHCO₃ (2×100 ml) and brine (100 ml). The organic layer was dried over Na₂SO₄ and concentrated in vacuo to yield the azide as a yellow oil. ¹H NMR (400 MHz, CDCl₃) δ 7.27-7.21 (m, 2H), 6.97-6.87 (m, 2H), 4.61 (appt, J=3.84 Hz, 1H), 4.31-4.19 (m, 2H), 2.18 (m, 1H), 2.03 (m, 1H). MS (ESI−) for C₉H₁₀N₃O m/z 173.0 (M−H)⁻. The crude azide was dissolved in 60 ml of THF followed by the addition of PPh₃ (6.5 g, 25 mmol) and the mixture stirred at room temperature for 30 min. The mixture was treated with 8 ml of H₂O and heated to 60° C. (oil bath) overnight. The mixture was concentrated in vacuo and the resulting residue treated with 1 N HCl. The aqueous mixture was extracted with CH₂Cl₂ then the pH was adjusted to 12 with NaOH and re-extracted with CH₂Cl₂. The second CH₂Cl₂ layers were combined; dried over Na₂SO₄ and concentrated in vacuo to yield 3,4-dihydro-2H-chromen-4-ylamine as a slightly yellow oil. HRMS (ESI+) calcd for C₉H₁₁NO m/z 150.0919 (M+H)⁺. Found 150.0920.

Step Three: tert-butyl (1S,2R)-1-(3,5-difluorobenzyl)-3-(3,4-dihydro-2H-chromen-4-ylamino)-2-hydroxypropylcarbamate

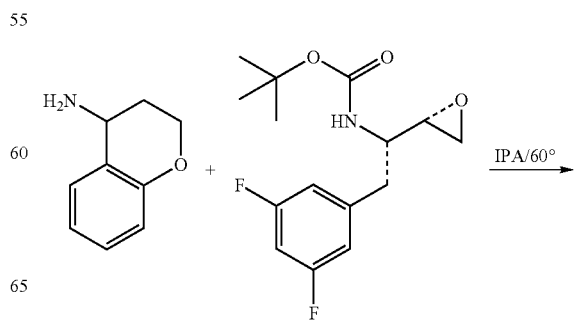

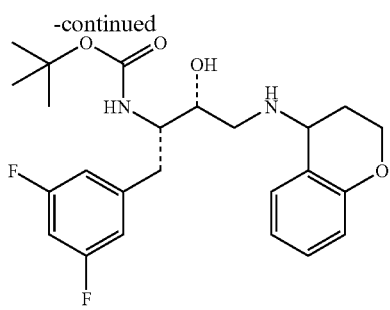

An IPA (15 ml) solution of Example 134 (0.54 g, 1.8 mmol) and 3,4-dihydro-2H-chromen-4-ylamine (0.40 g, 2.6 mmol) was heated at 60° C. (oil bath) with stirring overnight. The IPA was removed in vacuo and the residue dissolved in EtOAc and washed with 1 N HCl. The organic layer was dried over $MgSO_4$ and concentrated in vacuo to yield 0.75 g of the desired product as a mixture of epimers. HRMS (ESI+) calcd for $C_{24}H_{30}N_2O_4F_2$ m/z 449.2252 (M+H)$^+$. Found 449.2258.

Step Four: N-[(1S,2R)-1-(3,5-difluorobenzyl)-3-(3,4-dihydro-2H-chromen-4-ylamino)-2-hydroxypropyl]acetamide The above compound, which is obtained as a clear glass, is prepared essentially according to the procedure described in Example 15, step 3. Preparative reverse phase HPLC yields two fractions:

$^1$H NMR (400 MHz, CDCl$_3$) δ 7.29 (m, 1H), 7.20 (m, 1H), 6.92 (m, 1H), 6.85 (dd, J=6.85, 0.93 Hz, 1H), 6.79–6.67 (m, 3H), 5.69 (d, J=8.91 Hz, 1H), 4.35–4.23 (m, 2H), 4.15 (m, 1H), 3.87 (m, 1H), 3.58 (m, 1H), 3.03 (m, 1H), 2.91–2.75 (m, 3H), 2.15–2.08 (m, 1H), 2.04–1.99 (m, 1H), 1.94 (s, 3H). MS (ESI+) for $C_{21}H_{24}F_2N_2O_3$ m/z 391.3 (M+H)$^+$.

$^1$H NMR (400 MHz, CDCl$_3$) δ 7.31 (m, 1H), 7.21 (m, 1H), 6.93 (m, 1H), 6.86 (dd, J=8.29, 1.04 Hz, 1H), 6.79–6.67 (m, 3H), 5.69 (d, J=8.91 Hz, 1H), 4.36–4.24 (m, 2H), 4.17 (m, 1H), 3.87 (appt, J=4.04 Hz, 1H), 3.54 (m, 1H), 3.03 (dd, J=14.31, 4.56 Hz, 1H), 2.95 (m, 1H), 2.88–2.79 (m, 2H), 2.16–2.00 (m, 2H), 1.92 (s, 3H). MS (ESI+) for $C_{21}H_{24}F_2N_2O_3$ m/z 391.3 (M+H)$^+$.

EXAMPLE 18

N-((1S,2R)-1-(3,5-difluorobenzyl)-3-{[(4S)-6-ethyl-3,4-dihydro-2H-chromen-4-yl]amino}-2-hydroxypropyl)acetamide

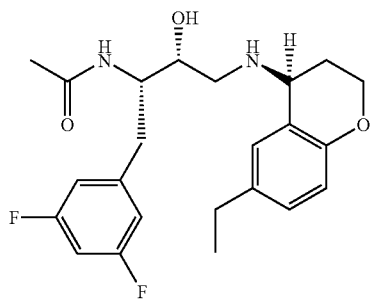

Step One: 6-iodochroman-4-ol To a solution of chroman-4-ol (19.6 g, 131 mmol) in $CH_2Cl_2$ (500 mL), at rt., was added HgO (29.7 g, 137 mmol) and $I_2$ (34.8 g, 137 mmol) under $N_2$. After stirring for 48 h. the mixture was filtered through a plug of silica gel and the plug washed plug with 30% EtOAc/Hexanes. The filtrate was washed with 15% $Na_2S_2O_3$ and the organic layer was dried over $Na_2CO_3$; filtered and concentrated in vacuo, yielding 6-iodochroman-4-ol as an off-white solid (32.44 g, 90% crude yield). Recrystallization was performed by dissolving product in hot dichloromethane (250 mL) and slowly adding petroleum ether (250 mL). Overall yield 25.9 g, 72% yield. Anal. Calcd for $C_9H_9IO_2$; C, 39.16,H, 3.29; found C, 39.26, H, 3.27.

Step Two: 6-Iodo-chroman-4-ylamine

The above compound is prepared essentially according to the procedure described in Example 17, step 2. The above compound is obtained as a clear oil that solidifies upon standing. HRMS (ESI+) calcd for $C_9H_{10}INO$ m/z 275.9887 (M+H)$^+$. Found 275.9893.

Step Three: tert-butyl (1S,2R)-1-(3,5-difluorobenzyl)-2-hydroxy-3-[(6-iodo-3,4-dihydro-2H-chromen-4-yl)amino]propylcarbamate The above compound is prepared essentially according to the procedure described in Example 15, step 2; it is obtained as a mixture of diastereomers, which is used without purification. MS (ESI+) for $C_{24}H_{29}F_2IN_2O_4$ m/z 574.8 (M+H)$^+$.

Step Four: N-{(1S,2R)-1-(3,5-difluorobenzyl)-2-hydroxy-3-[(6-iodo-3,4-dihydro-2H-chromen-4-yl)amino]propyl}acetamide The title compound is obtained from the propylcarbamate, essentially according to the methods described herein, as a light yellow solid. MS (ESI+) for $C_{21}H_{23}F_2IN_2O_3$ m/z 517.0 (M+H)$^+$. Chiral preparative HPLC (20% IPA/Heptane, 0.1% DEA) yields the two diastereomers.

N-((1S,2R)-1(3,5-difluorobenzyl)-2-hydroxy-3-{[(4S)-6-iodo-3,4-dihydro-2H-chromen-4-yl]amino}propyl)acetamide $^1$H NMR (400 MHz, DMSO-d$_6$) δ 7.73 (d, J=9.12 Hz, 1H), 7.62 (d, J=2.07 Hz, 1H), 7.40 (dd, J=8.50, 2.28 Hz, 1H), 7.01 (m, 1H), 6.89 (m, 2H), 6.58 (d, J=8.50 Hz, 1H), 4.97 (d, J=6.01 Hz, 1H), 4.23 (m, 1H), 4.14 (m, 1H), 3.93 (m, 1H), 3.68 (m, 1H), 3.47 (m, 1H), 3.01 (dd, J=13.89, 3.32 Hz, 1H), 2.61 (m, 2H), 1.90 (m, 2H), 1.71 (s, 3H).

N-((1S,2R)-1-(3,5-difluorobenzyl)-2-hydroxy-3-{[(4R)-6-iodo-3,4-dihydro-2H-chromen-4-yl]amino}propyl)acetamide $^1$H NMR (400 MHz, DMSO-d$_6$) δ 7.75 (d, J=9.33 Hz, 1H), 7.64 (d, J=2.07 Hz, 1H), 7.41 (dd, J=8.60, 2.18 Hz, 1H), 7.02 (m, 1H), 6.92 (m, 2H), 6.59 (d, J=8.50 Hz, 1H), 4.96 (d, J=5.80 Hz, 1H), 4.22 (m, 1H), 4.15 (m, 1H), 3.95 (m, 1H), 3.68 (m, 1H), 3.45 (m, 1H), 2.98 (dd, J=13.99, 2.80 Hz, 1H), 2.73 (m, 1H), 2.63–2.57 (m, 1H), 1.87 (m, 2H), 1.70 (s, 3H).

Step Five: N-((1S,2R)-1-(3,5-difluorobenzyl)-3-{[6-ethyl-3,4-dihydro-2H-chromen-4-yl]amino}-2-hydroxypropyl)acetamide N-{(1S,2R)-1-(3,5-difluorobenzyl)-2-hydroxy-3-[(6-iodo-3,4-dihydro-2H-chromen-4-yl)amino]propyl}acetamide (1.0 g, 1.9 mmol) and Pd(dppf)Cl$_2$ (0.078 g, 0.1 mmol) was dissolved in 20 mL of degassed THF. To the mixture was added 10 mL of 2.0 M $K_3PO_4$ followed by the addition of Et$_3$B (3.8 mL, 3.8 mmol, 1.0 M in THF) via syringe. The reaction mixture was heated to 65° C. under a nitrogen atmosphere. After 2.5 h the reaction was determined to be complete and diluted with EtOAc (100 mL) and washed with brine (3×30 mL). The organic layer was dried over Na$_2$SO$_4$ and conc. in vacuo to yield brown solid. The diastereomers of N-((1S,2R)-1-(3,5-difluorobenzyl)-3-{[(4S)-6-ethyl-3,4-dihydro-2H-chromen-4-yl]amino}-2-hydroxypropyl)acetamide were separated by preparative chiral HPLC (Chiralpak AD, 20% IPA/80% heptane, 0.1% DEA). MS (ESI+) for C$_{23}$H$_{26}$F$_2$N$_2$O$_3$ m/z 419 (M+H)$^+$.

To a MTBE (20 ml), CH$_2$Cl$_2$ (5 ml), MeOH (0.5 ml) solution of N-((1S,2R)-1-(3,5-difluorobenzyl)-3-{[(4S)-6-ethyl-3,4-dihydro-2H-chromen-4-yl]amino}-2-hydroxypropyl)acetamide (0.2 g, 0.5 mmol) was added 1N HCl in Et$_2$O (0.38 ml) and the mixture stirred at room temperature. The final white solid was isolated by removing the solvent and trituration with Et$_2$O. HRMS (ESI+) calcd for C$_{23}$H$_{28}$F$_2$N$_2$O$_3$ m/z 419.2146 (M+H)$^+$. Found 419.2166.

EXAMPLE 19

N-((1S,2R)-1-(3,5-difluorobenzyl)-2-hydroxy-3-{[(4S)-6-isobutyl-3,4-dihydro-2H-chromen-4-yl]amino}propyl)acetamide

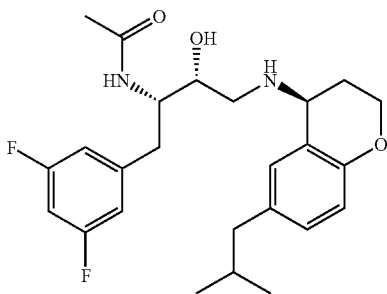

Step One: (4R)-6-iodochroman-4-ol

The above compound is prepared essentially according to the procedure described in Example 18, step1. Chiral HPLC separation is performed at this stage. HRMS (EI) calcd for C$_9$H$_9$IO$_2$ 275.9649, found 275.9646. (4S)-6-iodochroman-4-ol [α]$^{20}_D$=+13 (20 mg, MeOH) (4R)-6-iodochroman-4-ol [α]$^{20}_D$=−13 (20 mg, MeOH).

Step Two: (4S)-6-iodochroman-4-amine

To a solution of (4R)-6-iodochroman-4-ol (6.85 g, 24.81 mmol) and toluene (100 mL) under nitrogen at 0° C. was added diphenylphosphoryl azide (6.42 mL, 29.76 mmol). To this mixture was added a chilled solution of DBU (4.45 mL, 29.76 mmol) as a toluene solution (25 mL) via syringe. Reaction mixture was allowed to warm to ambient temperature overnight. Azide solution was filtered through silica gel using 6:1 hexanes:EtOAc as eluant. Filtrate was concentrated in vacuo, then dissolved in anh. THF (100 mL) to which was added 1.0M Me$_3$P in THF (29.76 mL, 29.76 mmol). After 1 h, deionized H$_2$O (5 mL) was added and reaction mixture was stirred overnight under nitrogen. Concentrated in vacuo, dissolved in EtOAc, washed with 10% NaHCO$_3$, brine, then the organic layers were dried over Na$_2$SO$_4$, filtered, and concentrated in vacuo to give (4S)-6-iodochroman-4-amine as a white solid. $^1$H NMR (400 MHz, CDCl$_3$) δ 1.70 (s, 2H), 1.86 (m, 1H), 2.13 (m, 1H), 4.03 (t, J=5 Hz, 1H), 4.23 (m, 2H), 6.60 (d, J=9 Hz, 1H), 7.42 (d, J=9 Hz, 1H), 7.64 (s, 1H). MS (ESI+) for C$_9$H$_{10}$INO m/z 258.8 (M+H)$^+$.

Step Three: tert-butyl (1S,2R)-1-(3,5-difluorobenzyl)-2-hydroxy-3-{[(4S)-6-iodo-3,4-dihydro-2H-chromen-4-yl]amino}propylcarbamate The above compound was prepared essentially according to the method of Example 17, step 3. The crude product was purified via column chromatography using 3% MeOH/DCM as eluant. The desired compound was obtained as a colorless solid (6.89 g, 79%). HRMS (ESI); calcd for C$_{24}$H$_{29}$N$_2$O$_4$IF$_2$+ H1 575.1220, found 575.1194; Specific Rotation (25 C D)=30 (c=1.04) MeOH.

Step Four: N-((1S,2R)-1-(3,5-difluorobenzyl)-2-hydroxy-3-{[(4S)-6-iodo-3,4-dihydro-2H-chromen-4-yl]amino}propyl)acetamide The title compound is prepared using procedures described herein, and isolated as a yellow solid. $^1$H NMR (400 MHz, CDCl$_3$) δ 1.93 (s, 3H), 1.97 (m, 1H), 2.08 (m, 1H), 2.80 (m, 3H), 3.09 (dd, J=4, 14 Hz, 1H), 3.55 (m, 1H), 3.84 (m, 1H), 4.13 (m, 1H), 4.24 (m, 1H), 4.31 (m, 1H), 5.61 (m, 1H), 6.62 (d, J=9 Hz, 1H), 6.70 (m, 1H), 6.77 (d, J=6 Hz, 2H), 7.44 (dd, J=2, 9 Hz, 1H), 7.62 (s, 1H).

Step Five: N-((1S,2R)-1-(3,5-difluorobenzyl)-2-hydroxy-3-{[(4S)-6-isobutyl-3,4-dihydro-2H-chromen-4-yl]amino}propyl)acetamide To a solution of the product from step 4, (0.300 g, 0.58 mmol) and anh. THF (2.3 mL) was added Pd(dppf)Cl$_2$ (0.024 g, 0.03 mmol) under nitrogen with stirring. To this solution was added isobutylzinc bromide (9.2 mL of a 0.5M THF solution, 4.6 mmol) and reaction mixture was stirred overnight. Quenched with methanol, then added Dowex 50WX2-400 resin (used an excess, 4.6 meq/g). Filtered through a frit, washed resin with methanol. The alkylated material was released from the resin using 7N NH$_3$/MeOH. The filtrate was concentrated in vacuo and then purified via preparative HPLC to yield a colorless solid fully characterized as the HCl salt.

To a MeOH (10 ml) solution of N-((1S,2R)-1-(3,5-difluorobenzyl)-2-hydroxy-3-{[(4S)-6-isobutyl-3,4-dihydro-2H-chromen-4-yl]amino}propyl)acetamide (2.0 g, 4.5 mmol), at 0° C., was added 3 equiv. of HCl as a solution in MeOH. Results in 1.97 g of N-((1S,2R)-1-(3,5-difluorobenzyl)-2-hydroxy-3-{[(4S)-6-isobutyl-3,4-dihydro-2H-chromen-4-yl]amino}propyl)acetamide hydrochloride as a white powder after trituration with CH$_2$Cl$_2$. HRMS (ESI+) calcd for C$_{25}$H$_{32}$F$_2$N$_2$O$_3$ m/z 447.2459 (M+H)$^+$. Found 447.2440. Anal calcd for C$_{25}$H$_{32}$F$_2$N$_2$O$_3$.HCl; C, 62.17; H, 6.89; N, 5.80; found C, 62.68; H, 7.05; N, 5.75.

EXAMPLES 20-50

General Procedure for Negishi Coupling to 6-Substituted Chromans

To a solution of the product of Example 19, step 4 (0.300 g, 0.58 mmol) and anh. THF (2.3 mL) was added Pd(dppf)Cl$_2$ (0.024 g, 0.03 mmol) under nitrogen with stirring. To this solution was added the zinc bromide reagent (9.2 mL of a 0.5M THF solution, 4.6 mmol) and reaction mixture was stirred overnight. Quenched with methanol, then added Dowex 50WX2-400 resin (used an excess, 4.6 meq/g). Filtered through a frit, washed resin with methanol to remove impurities. Product was released from resin using 7N NH$_3$/MeOH. Filtrate was concentrated in vacuo and then purified via preparative HPLC. Final product was a colorless solid.

| | | |
|---|---|---|
| Example 20 | N—[(1S,2R)-3-{[(4S)-6-(2-cyanophenyl)-3,4-dihydro-2H-chromen-4-yl]amino}-1-(3,5-difluorobenzyl)-2-hydroxypropyl]acetamide | MS (ESI+) for C$_{28}$H$_{27}$F$_2$N$_3$O$_3$ m/z 492.2205 (M + H)$^+$. |
| Example 21 | N—[(1S,2R)-3-{[(4S)-6-(4-cyanophenyl)-3,4-dihydro-2H-chromen-4-yl]amino}-1-(3,5-difluorobenzyl)-2-hydroxypropyl]acetamide | MS (ESI+) for C$_{28}$H$_{27}$F$_2$N$_3$O$_3$ m/z 492.3219 (M + H)$^+$. |
| Example 22 | N—[(1S,2R)-3-{[(4S)-6-sec-butyl-3,4-dihydro-2H-chromen-4-yl]amino}-1-(3,5-difluorobenzyl)-2-hydroxypropyl]acetamide | MS (ESI+) for C$_{25}$H$_{32}$F$_2$N$_2$O$_3$ m/z 447.316 (M + H)$^+$. |
| Example 23 | N—[(1S,2R)-3-{[(4S)-6-cyclopentyl-3,4-dihydro-2H-chromen-4-yl]amino}-1-(3,5-difluorobenzyl)-2-hydroxypropyl]acetamide | MS (ESI+) for C$_{26}$H$_{32}$F$_2$N$_2$O$_3$ m/z 459.3178 (M + H)$^+$. |
| Example 24 | N—((1S,2R)-1-(3,5-difluorobenzyl)-3-{[(4S)-6-(1,1-dimethylpropyl)-3,4-dihydro-2H-chromen-4-yl]amino}-2-hydroxypropyl)acetamide | MS (ESI+) for C$_{26}$H$_{34}$F$_2$N$_2$O$_3$ m/z 461.2516 (M + H)$^+$. |
| Example 25 | N—[(1S,2R)-3-{[(4S)-6-cyclohexyl-3,4-dihydro-2H-chromen-4-yl]amino}-1-(3,5-difluorobenzyl)-2-hydroxypropyl]acetamide | MS (ESI+) for C$_{27}$H$_{34}$F$_2$N$_2$O$_3$ m/z 473.3156 (M + H)$^+$. |
| Example 26 | N—((1S,2R)-1-(3,5-difluorobenzyl)-2-hydroxy-3-{[(4S)-6-(3-methylbutyl)-3,4-dihydro-2H-chromen-4-yl]amino}propyl)acetamide | MS (ESI+) for C$_{26}$H$_{34}$F$_2$N$_2$O$_3$ m/z 461.3249 (M + H)$^+$. |
| Example 27 | N—[(1S,2R)-3-{[(4S)-6-(2-cyanobenzyl)-3,4-dihydro-2H-chromen-4-yl]amino}-1-(3,5-difluorobenzyl)-2-hydroxypropyl]acetamide | MS (ESI+) for C$_{29}$H$_{29}$F$_2$N$_3$O$_3$ m/z 506.2569 (M + H)$^+$. |
| Example 28 | N—[(1S,2R)-3-{[(4S)-6-(4-cyanobenzyl)-3,4-dihydro-2H-chromen-4-yl]amino}-1-(3,5-difluorobenzyl)-2-hydroxypropyl]acetamide | MS (ESI+) for C$_{29}$H$_{29}$F$_2$N$_3$O$_3$ m/z 506.2145 (M + H)$^+$. |
| Example 29 | N—[(1S,2R)-3-({(4S)-6-[(1S,4R)-bicyclo[2.2.1]hept-2-yl]-3,4-dihydro-2H-chromen-4-yl}amino)-1-(3,5-difluorobenzyl)-2-hydroxypropyl]acetamide | MS (ESI+) for C$_{28}$H$_{34}$F$_2$N$_2$O$_3$ m/z 485.3293 (M + H)$^+$. |
| Example 30 | N—((1S,2R)-1-(3,5-difluorobenzyl)-2-hydroxy-3-{[(4S)-6-(1-methylbutyl)-3,4-dihydro-2H-chromen-4-yl]amino}propyl)acetamide | MS (ESI+) for C$_{26}$H$_{34}$F$_2$N$_2$O$_3$ m/z 461.3311 (M + H)$^+$. |
| Example 31 | N—((1S,2R)-1-(3,5-difluorobenzyl)-2-hydroxy-3-{[(4S)-6-(1-methylpentyl)-3,4-dihydro-2H-chromen-4-yl]amino}propyl)acetamide | MS (ESI+) for C$_{27}$H$_{36}$F$_2$N$_2$O$_3$ m/z 475.3686 (M + H)$^+$. |
| Example 32 | N—((1S,2R)-1-(3,5-difluorobenzyl)-3-{[(4S)-6-(1-ethylpropyl)-3,4-dihydro-2H-chromen-4-yl]amino}-2-hydroxypropyl)acetamide | MS (ESI+) for C$_{26}$H$_{34}$F$_2$N$_2$O$_3$ m/z 461.3334 (M + H)$^+$. |
| Example 33 | N—((1S,2R)-1-(3,5-difluorobenzyl)-3-{[(4S)-6-(1-ethylbutyl)-3,4-dihydro-2H-chromen-4-yl]amino}-2-hydroxypropyl)acetamide | MS (ESI+) for C$_{27}$H$_{36}$F$_2$N$_2$O$_3$ m/z 475.3723 (M + H)$^+$. |
| Example 34 | N—((1S,2R)-1-(3,5-difluorobenzyl)-2-hydroxy-3-{[(4S)-6-(1-propylbutyl)-3,4-dihydro-2H-chromen-4-yl]amino}propyl)acetamide | MS (ESI+) for C$_{28}$H$_{38}$F$_2$N$_2$O$_3$ m/z 489.2886 (M + H)$^+$. |
| Example 35 | N—((1S,2R)-1-(3,5-difluorobenzyl)-3-{[(4S)-6-(2-ethylbutyl)-3,4-dihydro-2H-chromen-4-yl]amino}-2-hydroxypropyl)acetamide | MS (ESI+) for C$_{27}$H$_{36}$F$_2$N$_2$O$_3$ m/z 475.334 (M + H)$^+$. |
| Example 36 | N—[(1S,2R)-3-{[(4S)-6-(cyclohexylmethyl)-3,4-dihydro-2H-chromen-4-yl]amino}-1-(3,5-difluorobenzyl)-2-hydroxypropyl]acetamide | MS (ESI+) for C$_{28}$H$_{36}$F$_2$N$_2$O$_3$ m/z 487.4099 (M + H)$^+$. |
| Example 37 | N—[(1S,2R)-3-{[(4S)-6-(5-cyano-5-methylhexyl)-3,4-dihydro-2H-chromen-4-yl]amino}-1-(3,5-difluorobenzyl)-2-hydroxypropyl]acetamide | MS (ESI+) for C$_{29}$H$_{37}$F$_2$N$_3$O$_3$ m/z 514.1028 (M + H)$^+$. |
| Example 38 | N—((1S,2R)-1-(3,5-difluorobenzyl)-2-hydroxy-3-{[(4S)-6-(4-methoxyphenyl)-3,4-dihydro-2H-chromen-4-yl]amino}propyl)acetamide | MS (ESI+) for C$_{28}$H$_{30}$F$_2$N$_2$O$_4$ m/z 497.2083 (M + H)$^+$. |
| Example 39 | N—((1S,2R)-1-(3,5-difluorobenzyl)-2-hydroxy-3-{[(4S)-6-(6-methylpyridin-2-yl)-3,4-dihydro-2H-chromen-4-yl]amino}propyl)acetamide | MS (ESI+) for C$_{27}$H$_{29}$F$_2$N$_3$O$_3$ m/z 482.3209 (M + H)$^+$. |
| Example 40 | N—((1S,2R)-1-(3,5-difluorobenzyl)-2-hydroxy-3-{[(4S)-6-(5-methylpyridin-2-yl)-3,4-dihydro-2H-chromen-4-yl]amino}propyl)acetamide | MS (ESI+) for C$_{27}$H$_{29}$F$_2$N$_3$O$_3$ m/z 482.2673 (M + H)$^+$. |
| Example 41 | N—((1S,2R)-1-(3,5-difluorobenzyl)-2-hydroxy-3-{[(4S)-6-(4-methylpyridin-2-yl)-3,4-dihydro-2H-chromen-4-yl]amino}propyl)acetamide | MS (ESI+) for C$_{27}$H$_{29}$F$_2$N$_3$O$_3$ m/z 482.3107 (M + H)$^+$. |
| Example 42 | N—[(1S,2R)-3-{[(4S)-6-(4-cyanobutyl)-3,4-dihydro-2H-chromen-4-yl]amino}-1-(3,5-difluorobenzyl)-2-hydroxypropyl]acetamide | MS (ESI+) for C$_{26}$H$_{31}$F$_2$N$_3$O$_3$ m/z 472.2164 (M + H)$^+$. |
| Example 43 | N—[(1S,2R)-3-{[(4S)-6-(6-cyanohexyl)-3,4-dihydro-2H-chromen-4-yl]amino}-1-(3,5-difluorobenzyl)-2-hydroxypropyl]acetamide | MS (ESI+) for C$_{28}$H$_{35}$F$_2$N$_3$O$_3$ m/z 500.2705 (M + H)$^+$. |
| Example 44 | N—[(1S,2R)-3-{[(4S)-6-(3-cyanophenyl)-3,4-dihydro-2H-chromen-4-yl]amino}-1-(3,5-difluorobenzyl)-2-hydroxypropyl]acetamide | MS (ESI+) for C$_{28}$H$_{27}$F$_2$N$_3$O$_3$ m/z 492.1755 (M + H)$^+$. |
| Example 45 | (2S)-3-((4S)-4-{[(2R,3S)-3-(acetylamino)-4-(3,5-difluorophenyl)-2-hydroxybutyl]amino}-3,4-dihydro-2H-chromen-6-yl)-2-Methylpropanoate | MS (ESI+) for C$_{26}$H$_{32}$F$_2$N$_2$O$_5$ m/z 491.3261 (M + H)$^+$. |
| Example 46 | N—((1S,2R)-1-(3,5-difluorobenzyl)-3-{[(4S)-6-(4-fluorophenyl)-3,4-dihydro-2H-chromen-4-yl]amino}-2-hydroxypropyl)acetamide | MS (ESI+) for C$_{27}$H$_{27}$F$_3$N$_2$O$_3$ m/z 485.3275 (M + H)$^+$. |
| Example 47 | methyl (2R)-3-((4S)-4-{[(2R,3S)-3-(acetylamino)-4-(3,5-difluorophenyl)-2-hydroxybutyl]amino}-3,4-dihydro-2H-chromen-6-yl)-2-Methylpropanoate | MS (ESI+) for C$_{26}$H$_{32}$F$_2$N$_2$O$_5$ m/z 491.2724 (M + H)$^+$. |
| Example 48 | N—[(1S,2R)-1-(3,5-difluorobenzyl)-3-({(4S)-6-[2-(1,3-dioxolan-2-yl)ethyl]-3,4-dihydro-2H-chromen-4-yl}amino)-2-hydroxypropyl]acetamide | MS (ESI+) for C$_{26}$H$_{32}$F$_2$N$_2$O$_5$ m/z 491.2323 (M + H)$^+$. |
| Example 49 | N—((1S,2R)-1-(3,5-difluorobenzyl)-2-hydroxy-3-{[(4S)-6-(6-methoxypyridin-2-yl)-3,4-dihydro-2H-chromen-4-yl]amino}propyl)acetamide | MS (ESI+) for C$_{27}$H$_{29}$F$_2$N$_3$O$_4$ m/z 498.3047 (M + H)$^+$. |
| Example 50 | N—[(1S,2R)-3-{[(4S)-6-cyano-3,4-dihydro-2H-chromen-4-yl]amino}-1-(3,5-difluorobenzyl)-2-hydroxypropyl]acetamide | MS (ESI+) for C$_{22}$H$_{23}$F$_2$N$_3$O$_3$ m/z 416.4 (M + H)$^+$. |

EXAMPLE 51

N-((1S,2R)-1-(3,5-difluorobenzyl)-2-hydroxy-3-{[(4S)-6-(1H-pyrrol-3-yl)-3,4-dihydro-2H-chromen-4-yl]amino}propyl)acetamide

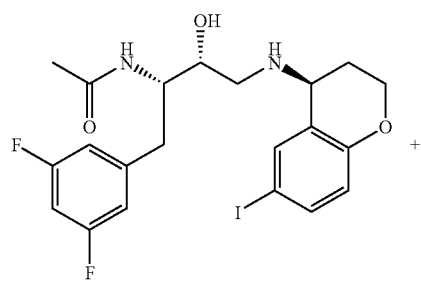

+

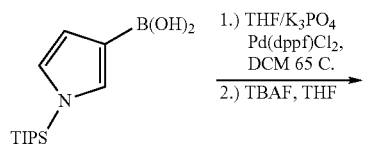

1.) THF/K$_3$PO$_4$
Pd(dppf)Cl$_2$,
DCM 65 C.
2.) TBAF, THF

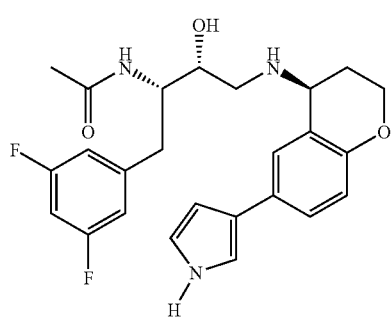

To a solution of N-((1S,2R)-1-(3,5-difluorobenzyl)-2-hydroxy-3-{[(4S)-6-iodo-3,4-dihydro-2H-chromen-4-yl]amino}propyl)acetamide (0.300 g, 0.58 mmol) and anhydrous THF (5 mL) was added Pd(dppf)Cl$_2$ (0.030 g, 0.03 mmol) and K$_3$PO$_4$ (2.9 mL, 5.80 mmol). To this mixture was added boronic acid (0.310 g, 1.16 mmol) (J. Org. Chem. 1992, 57, 1653) and the reaction mixture was heated to 65° C. overnight under nitrogen with stirring. Reaction was quenched with deionized water and then extracted with ethyl acetate. Organic layers were washed with brine, then dried with MgSO$_4$, filtered, and concentrated in vacuo. The TIPS-protected compound (0.100 g, 0.16 mmol) was dissolved in THF (3 mL) and then 0.1M solution of TBAF in THF (0.32 mL, 0.32 mmol) was added. Reaction mixture was stirred for 2 h, then concentrated in vacuo. Dissolved in ethyl acetate, filtered through silica gel plug, then concentrated in vacuo to give the desired product as an amber oil (130 mg), which is purified by reverse phase prep-HPLC. HRMS (ESI); calcd for C25H27N3O3F2+H1 456.2099, found 456.2092.

EXAMPLE 52

N-((1S,2R)-1-(3,5-difluorobenzyl)-2-hydroxy-3-{[(4S)-6-neopentyl-3,4-dihydro-2H-chromen-4-yl]amino}propyl)acetamide

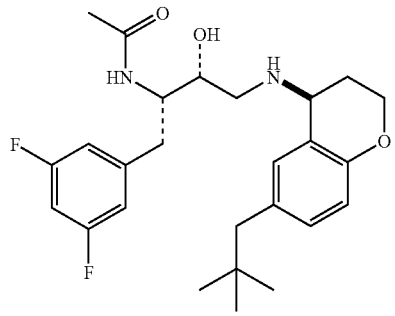

Step One: 6-neopentylchroman-4-ol

To a solution of 6-iodochroman-4-ol (1.0 g, 3.6 mmol) in 18 ml of THF, at 0° C., was added the Pd(dppf)Cl$_2$.CH$_2$Cl$_2$ (0.15 g, 0.18 mmol), followed by neopentylmagnesium bromide (10.8 ml, 10.8 mmol, 1.0 M in Et$_2$O). The cold bath was maintained for 10 min., then removed and stirring continued overnight. The mixture was quenched with NH$_4$Cl (30 ml) and extracted with EtOAc (3×50 ml). The combined organic layers were dried over MgSO$_4$ and concentrated in vacuo to yield a brown oil. The crude oil was absorbed onto silica gel followed by flash chromatography (biotage 40S) 10% EtOAc/heptanes to yield 0.36 g (46%) of 6-neopentylchroman-4-ol as a white solid. R$_f$=0.11. HRMS (ESI+) calcd for C$_{14}$H$_{20}$O$_2$ m/z 220.1463 (M+H)$^+$; found 220.1460.

Step Two: 6-neopentyl-3,4-dihydro-2H-chromen-4-ylamine

The above compound was prepared essentially according to the procedure of Example 19, Step 2. First, the azide was prepared. $^1$H NMR (400 MHz, CDCl$_3$) δ 6.94 (dd, J=8.40, 2.18 Hz, 1H), 6.89 (d, J=2.07 Hz, 1H), 6.71 (d, J=8.29 Hz, 1H), 4.50 (appt, J=3.73 Hz, 1H), 4.15 (m, 2H), 2.36 (s, 2H), 2.08 (m, 1H), 1.93 (m, 1H), 0.83 (s, 9H). Second, the azide was reduced to afford the amine as a slightly colored oil (1.6 g). The amine was taken to the next step without further purification. HRMS (ESI+) calcd for C$_{14}$H$_{21}$NO m/z 219.1623 (M+H)$^+$. Found 219.1628.

Step Three: tert-butyl (1S,2R)-1-(3,5-difluorobenzyl)-2-hydroxy-3-[(6-neopentyl-3,4-dihydro-2H-chromen-4-yl)amino]propylcarbamate The above compound is prepared essentially according to the procedure of Example 17, step 3; it is obtained as an off white solid. Flash chromatography (3% MeOH/CHC$_3$, 1 ml of NH$_4$OH per liter) yields the desired product as a mixture of epimers. HRMS (ESI+) calcd for C$_{29}$H$_{40}$N$_2$O$_4$F$_2$ m/z 519.3034 (M+H)$^+$. Found 519.3040.

Step Four: N-((1S,2R)-1-(3,5-difluorobenzyl)-2-hydroxy-3-{[(4S)-6-neopentyl-3,4-dihydro-2H-chromen-4-yl]amino}propyl)acetamide

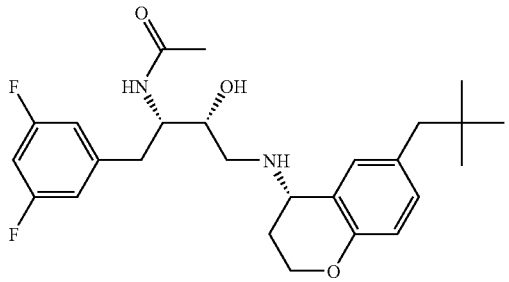

The above compound was prepared essentially according the method of Example 15, step 3, which resulted in a mixture of epimers. The epimers were then separated using chiral preparative HPLC (10% IPA/heptanes, 0.1% DEA) AD column:

N-((1S,2R)-1-(3,5-difluorobenzyl)-2-hydroxy-3-{[(4S)-6-neopentyl-3,4-dihydro-2H-chromen-4-yl]amino}propyl)acetamide.

$^1$H NMR (400 MHz, CDCl$_3$) δ 7.01 (d, J=1.87 Hz, 1H), 6.96 (dd, J=8.29, 2.07 Hz, 1H), 6.79-6.67 (m, 4H), 5.69 (d, J=8.50 Hz, 1H), 4.32-4.15 (m, 3H), 3.85 (bs, 1H), 3.60 (bs, 1H), 3.02 (m, 1H), 2.88 (m, 2H), 2.76 (dd, J=12.13, 6.74 Hz, 1H), 2.46 (s, 2H), 2.15-2.08 (m, 1H), 2.04-1.98 (m, 1H), 1.94 (s, 3H), 0.91 (s, 9H). HRMS (ESI+) calcd for C$_{26}$H$_{34}$F$_2$N$_2$O$_3$ m/z 461.2615 (M+H)$^+$. Found 461.2621.

N-((1S,2R)-1-(3,5-difluorobenzyl)-2-hydroxy-3-{[(4R)-6-neopentyl-3,4-dihydro-2H-chromen-4-yl]amino}propyl)acetamide.

$^1$H NMR (400 MHz, CDCl$_3$) δ 7.04 (d, J=2.07 Hz, 1H), 6.96 (dd, J=8.29, 1.87 Hz, 1H), 6.77-6.67 (m, 4H), 5.69 (d, J=8.91 Hz, 1H), 4.31-4.16 (m, 3H), 3.86 (bs, 1H), 3.57 (bs, 1H), 3.00 (m, 2H), 2.82 (m, 2H), 2.44 (s, 2H), 2.18-2.00 (m, 3H), 1.90 (s, 3H), 0.91 (s, 9H). HRMS (ESI+) calcd for C$_{26}$H$_{34}$F$_2$N$_2$O$_3$ m/z 461.2615 (M+H)$^+$. Found 461.2630. Anal. Calcd for C$_{26}$H$_{34}$F$_2$N$_2$O$_3$; C, 67.81; H, 7.44; N, 6.08. Found C, 67.65; H, 7.51; N, 6.05.

EXAMPLE 52 A

Chiral Synthesis of Amine

Step One: (4R)-6-neopentylchroman-4-ol

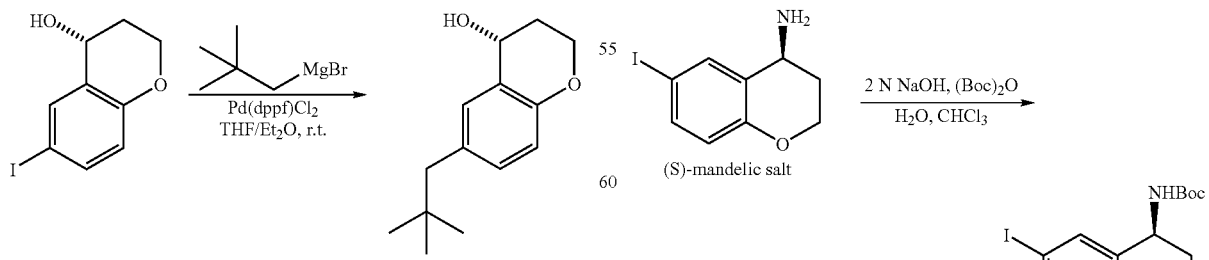

(4R)-6-iodochroman-4-ol is converted into (4R)-6-neopentylchroman-4-ol essentially according to the procedure of Example 52, step 1. The produce is obtained as a white solid. Anal. Calcd for C$_{14}$H$_{20}$O$_2$; C, 76.33; H, 9.15. Found C, 76.31; H, 9.06. [α]$_D$=22.3, c=1.14 (CH$_2$Cl$_2$).

Step Two:
(4S)-6-neopentyl-3,4-dihydro-2H-chromen-4-ylamine

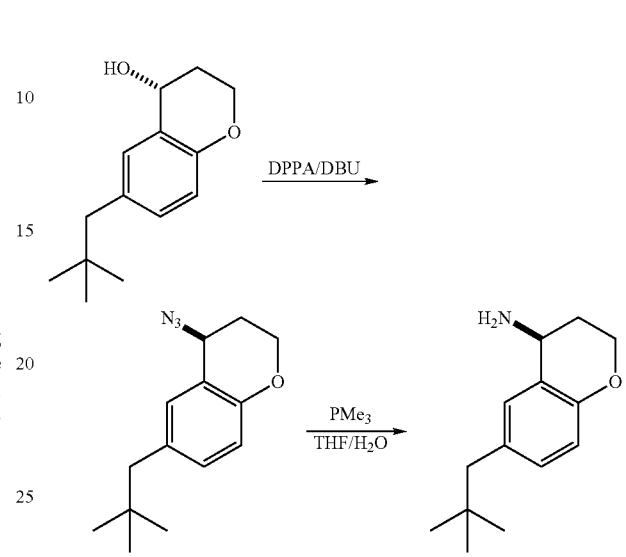

(4R)-6-neopentylchroman-4-ol is converted into (4S)-6-neopentyl-3,4-dihydro-2H-chromen-4-ylamine essentially according to the procedure of Example 19, step 2.

EXAMPLE 52 B

Alternative Chiral Synthesis of Amine

Step B-1

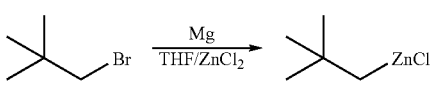

Neopentyl zinc was prepared according to the procedure described in *Tetrahedron Lett.* 1983, 24, 3823-3824.

Step B-2 tert-butyl (4S)-6-iodo-3,4-dihydro-2H-chromen-4-ylcarbamate

To a suspension of amine (S)-mandelic salt (4.55 g, 10.6 mmol) in water (50 mL) was added sodium hydroxide (21 mL, 2 N, 42 mmol) followed by di-tert-butyl dicarbonate (2.58 g, 11.7 mmole) and chloroform (50 mL). The reaction mixture was stirred at room temperature for 2 h and then diluted with methylene chloride (100 mL) and water (50 mL). The organic layer was separated washed with saturated sodium chloride, dried (sodium sulfate), filtered, and concentrated under reduced pressure. The residue was triturated with 1:1 hexanes/ethyl ether. The resulting white solid was collected by filtration and washed with hexanes to provided tert-butyl (4S)-6-iodo-3,4-dihydro-2H-chromen-4-ylcarbamate (3.30 g, 83%): $^1$H NMR (300 MHz, CDCl$_3$) δ 7.55 (d, J=1.8 Hz, 1H), 7.42 (dd, J=8.6,2.2 Hz, 1H), 6.58 (d, J=8.6 Hz, 1H), 4.78 (m, 2H), 4.28-4.20 (m, 1H), 4.18-4.10 (m, 1H), 2.19-2.10 (m, 1H), 2.06-1.96 (m, 1H), 1.49 (s, 9H).

Step B-3 Coupling of neopentyl zinc reagent to tert-butyl (4S)-6-iodo-3,4-dihydro-2H-chromen-4-ylcarbamate

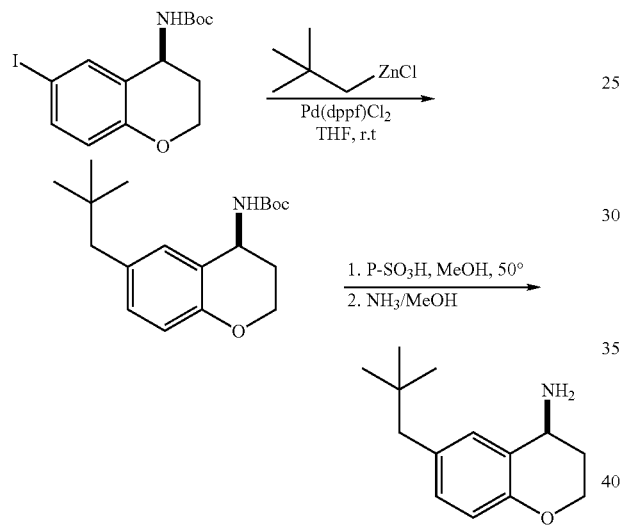

To a suspension of the 0.3 M neopentyl zinc reagent in THF (60 ml, 15 mmol) was added the tert-butyl (4S)-6-iodo-3,4-dihydro-2H-chromen-4-ylcarbamate (1.8 g, 5.0 mmol) and Pd(dppf)Cl$_2$ (0.2 g, 0.25 mmol) as solids in one portion. The mixture was stirred at r.t. under nitrogen for 48 hours (progress monitored by LC/MS and HPLC). The mixture was quenched with aqueous NH$_4$Cl (20 ml) and extracted with EtOAc (3×50 ml). The organic layer was dried over Na$_2$SO$_4$ and concentrated in vacuo. The crude residue was dissolved in MeOH(25 ml) and treated with DOWEX® 50WX2-400 ion exchange resin. The mixture was heated to 50° C. for six hours and then the resing was collected by filtration. The resin was washed successively with MeOH and CH$_2$Cl$_2$ these washings were discarded. The resin was then treated with 7 N NH$_3$/MeOH to elute the free amine from the resin. The elutions were concentrated in vacuo to yield a light brown oil (0.63 g, 57%) of (4S)-6-neopentyl-3,4-dihydro-2H-chromen-4-ylamine. This material was consistent with previous preparations and was used as obtained for the subsequent opening of the di-fluoroPhe epoxide. S)-6-neopentyl-3,4-dihydro-2H-chromen-4-ylamine was previously characterized as the mono.HCl salt. $^1$H NMR (300 MHz, DMSO-d$_6$) δ); 7.25 (s, 1H), 7.02 (m, 1H,), 6.76 (m, 1H), 4.47 (bs, 1H), 4.21 (m, 2H), 2.38 (s, 2H), 2.24 (m, 1H), 2.10 (m, 1H), 0.87 (s, 9H). HRMS (ESI+) calculated for C$_{14}$H$_{21}$N$_1$O$_1$ 220.1701; found m/z 220.1698 (M+H)$^+$. Anal. Calcd for C$_{14}$H$_{21}$NO.HCl: C, 65.74; H, 8.67; N, 5.48. Found: C, 65.62; H, 8.53; N, 5.42. [α]$^{23}_D$=15.6, c=1.17 in CH$_3$OH.

EXAMPLE 52-C

Coupling of Chiral Amine with Epoxide

Preparation of tert-butyl (1S,2R)-1-(3,5-difluorobenzyl)-2-hydroxy-3-{[(4S)-6-neopentyl-3,4-dihydro-2H-chromen-4-yl]amino}propylcarbamate

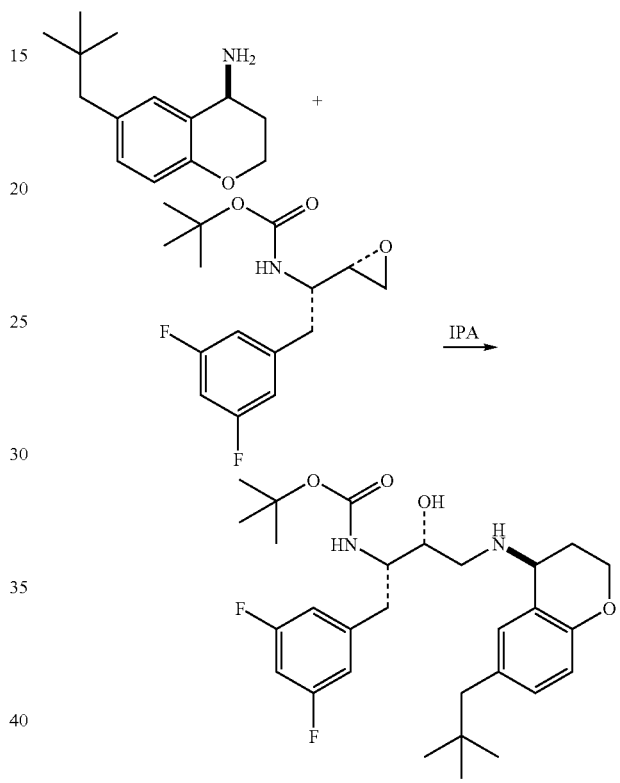

The above compound was prepared essentially according to the method of Example 15, step 2; it was obtained as a white foam. R$_f$=0.25 (in 3% MeOH in CHCl$_3$ with 1 ml of NH$_4$OH per liter). HRMS (ESI+) calcd for C$_{29}$H$_{40}$N$_2$O$_4$F$_2$ m/z 519.3034 (M+H)$^+$. Found 519.3057.

EXAMPLE 52-D

Alternative Preparation of tert-butyl (1S,2R)-1-(3,5-difluorobenzyl)-2-hydroxy-3-{[(4S)-6-neopentyl-3,4-dihydro-2H-chromen-4-yl]amino}propylcarbamate

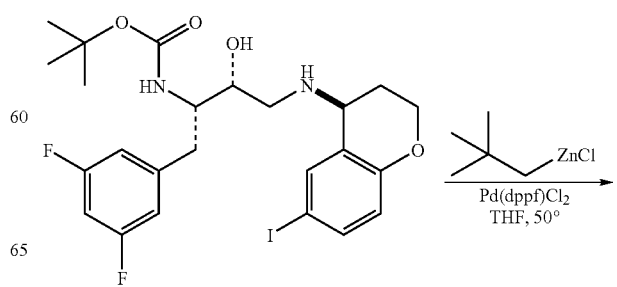

-continued

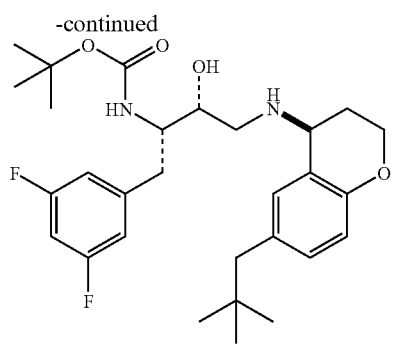

To neopentyl zinc chloride (prepared as previously described) (51 ml, 11 mmol, 0.2 M in THF) under a nitrogen atmosphere at r.t. was added tert-butyl (1S,2R)-1-(3,5-difluorobenzyl)-2-hydroxy-3-{[(4S)-6-iodo-3,4-dihydro-2H-chromen-4-yl]amino}propylcarbamate (1.3 g, 2.2 mmol) and Pd(dppf)Cl$_2$ (0.09 g, 0.1 mmol) as solids. The reaction mixture was stirred at r.t. for 12 h and then heated to 50° C. for 8 h. The reaction was cooled to r.t. then quenched with 20 ml of aqueous NH$_4$Cl and extracted with EtOAc (3×100 ml). The combined organic layers were dried over Na$_2$SO$_4$ and concentrated in vacuo to yield a brown oil. The residue was dissolved in CH$_2$Cl$_2$ and absorbed onto 6 g of silica gel. Flash chromatography (3-5% MeOH/CHCl$_3$ with 20 drops of NH$_4$OH/L, Biotage 40M) yields the desired product, which is identical to the material prepared by the previously described methods.

EXAMPLE 52-E

Alternative Preparation of N-((1S,2R)-1-(3,5-difluorobenzyl)-2-hydroxy-3-{[(4S)-6-neopentyl-3,4-dihydro-2H-chromen-4-yl]amino}propyl)acetamide The above compound is prepared essentially according to the method of Example 15, step 3. First, the Boc group is removed to afford the crude amine as a yellow oil. $^1$H NMR (400 MHz, CDCl$_3$) δ 7.00 (d, J=2.07 Hz, 1H), 6.95 (dd, J=8.29, 2.28 Hz, 1H), 6.78-6.68 (m, 4H), 4.26 (m, 2H), 3.82 (appt, J=4.15 Hz, 1H), 3.57 (ddd, J=8.60, 5.29, 3.52 Hz, 1H), 3.13 (ddd, J=9.89, 5.55, 3.73 Hz, 1H), 3.07 (dd, J=11.82, 3.52 Hz, 1H), 2.96 (dd, J=13.58, 3.42 Hz, 1H), 2.83 (dd, J=11.71, 8.60 Hz, 1H), 2.53 (dd, J=13.58, 9.85 Hz, 1H), 2.44 (s, 2H), 2.14-1.99 (m, 2H), 0.91 (s, 9H).

Second, the crude amine was acylated. The crude acylated material was purified by flash chromatography (3.5% MeOH/CHC$_3$ with 1 ml of NH$_4$OH per liter), Biotage 40L, affording the desired product as a white powder. This material was spectroscopically identical to the N-((1S,2R)-1-(3,5-difluorobenzyl)-2-hydroxy-3-{[(4S)-6-neopentyl-3,4-dihydro-2H-chromen-4-yl]amino}propyl)acetamide prepared by previous methods.

EXAMPLE 52-F

Alternative Preparation of N-((1S,2R)-1-(3,5-difluorobenzyl)-2-hydroxy-3-{[(4S)-6-neopentyl-3,4-dihydro-2H-chromen-4-yl]amino}propyl acetamide

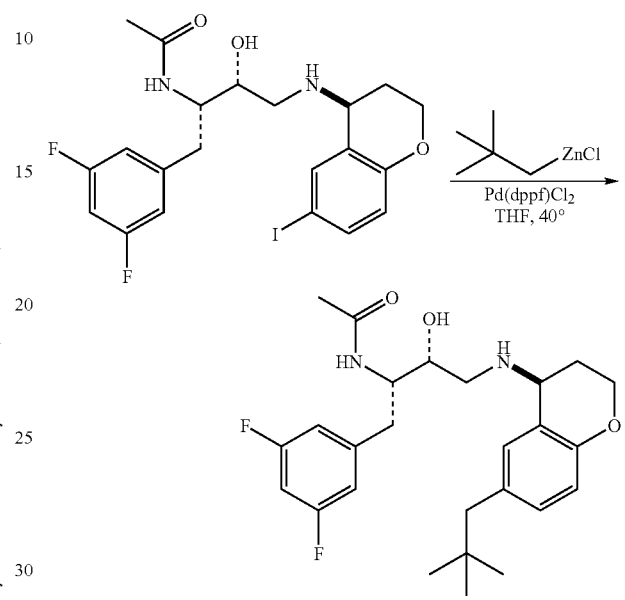

The above compound is prepared essentially according to the procedure of Example 19, step 5. The resulting residue was dissolved in CH$_2$Cl$_2$ and absorbed onto 6 g of silica gel. Flash chromatography (3-5% MeOH/CHCl$_3$ with 20 drops of NH$_4$OH/L, Biotage 40M) yields two fractions. Fraction one yielded 650 mg of the desired product that was 93% pure by analytical HPLC. The second fraction (430 mg) was a 60:40 mixture of the desired product and the dehalogenated compound. The first fraction was re-subjected to preparative reverse phase HPLC (1% TFA in water/0.6% TFA in CH$_3$CN) to yield 500 mg (38%) of a white powder after neutralization. This material was spectroscopically identical to the N-((1S,2R)-1-(3,5-difluorobenzyl)-2-hydroxy-3-{[(4S)-6-neopentyl-3,4-dihydro-2H-chromen-4-yl]amino}propyl)acetamide prepared by previous methods.

EXAMPLE 52-G

Preparation of the HCl Salt of N-((1S,2R)-1-(3,5-difluorobenzyl)-2-hydroxy-3-{[(4S)-6-neopentyl-3,4-dihydro-2H-chromen-4-yl]amino}propyl)acetamide The free base (from Ex. 52-F, 0.5 g, 1.08 mmol) was dissolved in MeOH (10 ml) and treated with HCl/Et$_2$O (2.5 ml, 1.0 M). The solution was stirred at r.t. for 10 min. then the solvent removed in vacuo to yield a clear glass. The glass was tritrated with Et$_2$O to yield 536 mg of a white solid that was dried in vacuo at 40° C. for 48 h. Anal Calcd for C$_{26}$H$_{34}$F$_2$N$_2$O$_3$.HCl.0.5H$_2$O, C, 61.71; H, 7.17; N, 5.54. Found C, 61.69; H, 7.31; N, 5.64. HRMS (ESI+) calcd for C$_{26}$H$_{34}$N$_2$O$_3$F$_2$ m/z 461.2615 (M+H)$^+$. Found 461.2627.

EXAMPLE 53

N-((1S,2R)-1-(3-fluorobenzyl)-2-hydroxy-3-{[(4S)-6-neopentyl-3,4-dihydro-2H-chromen-4-yl]amino}propyl)acetamide

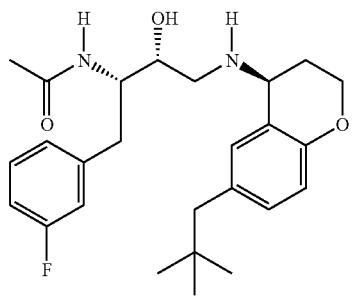

Step One: tert-butyl (1S,2R)-1-(3-fluorobenzyl)-2-hydroxy-3-{[(4S)-6-neopentyl-3,4-dihydro-2H-chromen-4-yl]amino}propylcarbamate

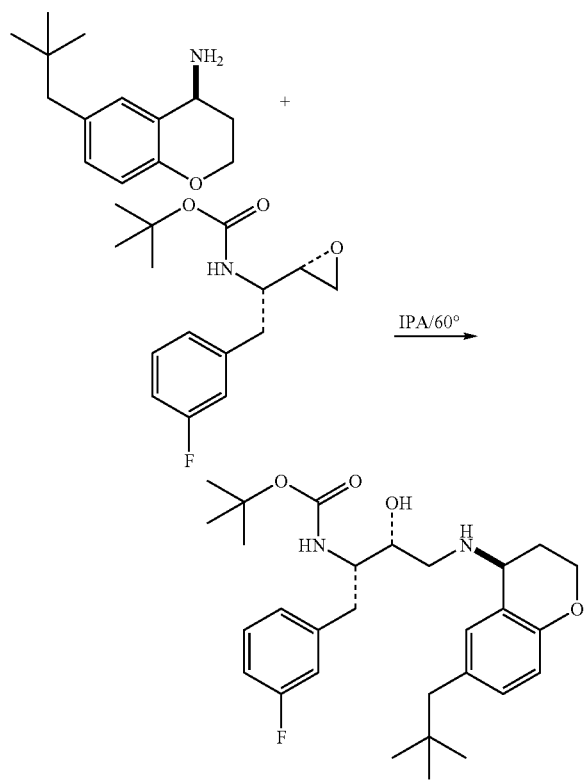

The above product was prepared essentially according to the method of Example 17, step 3. The crude product was then purified by flash chromatography (3% MeOH/CHCl$_3$). HRMS (ESI+) calcd for $C_{29}H_{41}N_2O_4F$ m/z 501.3128 (M+H)$^+$. Found 501.3150.

Step two: N-((1S,2R)-1-(3-fluorobenzyl)-2-hydroxy-3-{[(4S)-6-neopentyl-3,4-dihydro-2H-chromen-4-yl]amino}propyl)acetamide The above compound was prepared essentially according to the method of Example 15, step 3. The crude product was dissolved in MeOH and purified by reverse phase preparatory HPLC. HRMS (ESI+) calcd for $C_{26}H_{35}N_2O_3F$ m/z 443.2710 (M+H)$^+$. Found 443.2710.

EXAMPLE 54

N-((1S,2R)-1-benzyl-2-hydroxy-3-{[(4S)-6-neopentyl-3,4-dihydro-2H-chromen-4-yl]amino}propyl)acetamide

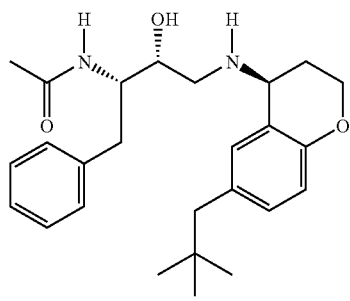

Step One: tert-butyl (1S,2R)-1-benzyl-2-hydroxy-3-{[(4S)-6-neopentyl-3,4-dihydro-2H-chromen-4-yl]amino}propylcarbamate

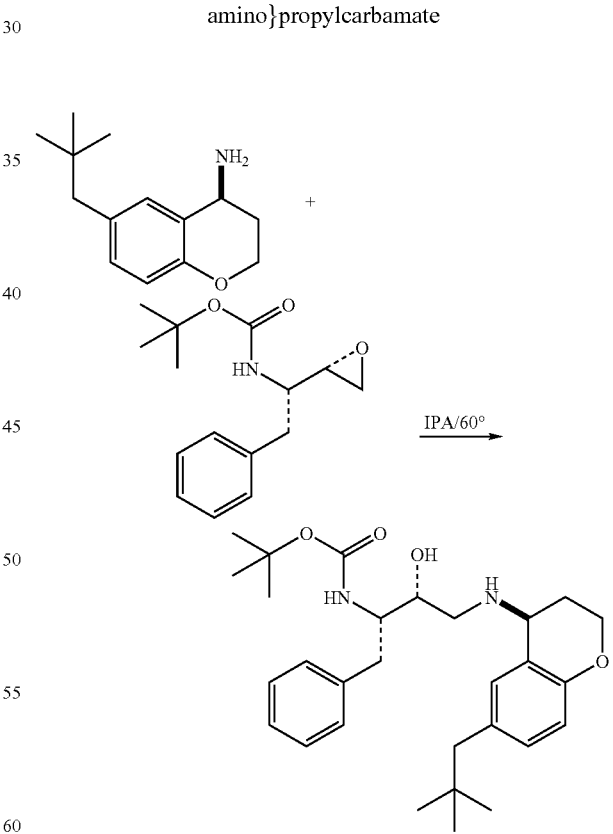

The above compound was prepared essentially according to the method of Example 17, step 3. The resulting crude product was purified by preparative HPLC (1% TFA in water/0.6% TFA in CH$_3$CN). HRMS (ESI+) calcd for $C_{29}H_{42}N_2O_4$ m/z 483.3222 (M+H)$^+$. Found 483.3219.

Step Two: N-((1S,2R)-1-benzyl-2-hydroxy-3-{[(4S)-6-neopentyl-3,4-dihydro-2H-chromen-4-yl]amino}propyl)acetamide

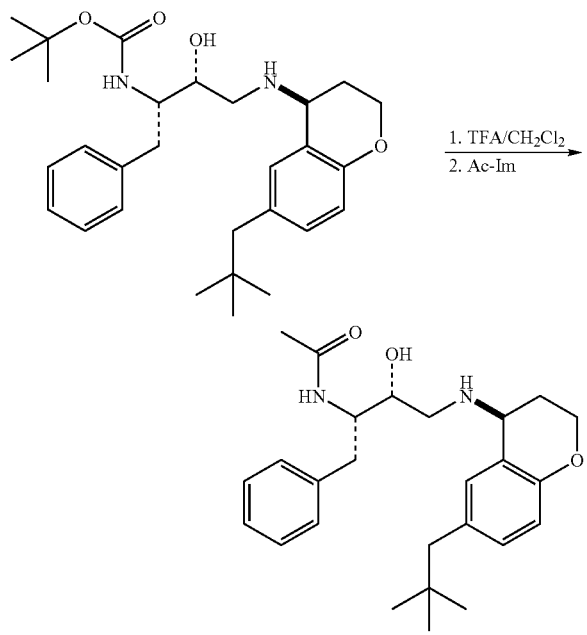

The above compound is prepared essentially according to the method of Example 17, step 3. The resulting crude product was dissolved in MeOH (5 mL) and purified by reverse phase preparatory HPLC which gave a white powder. HRMS (ESI+) calcd for $C_{26}H_{36}N_2O_3$ m/z 425.2804 (M+H)$^+$. Found 425.2801.

EXAMPLE 55

N-((1S,2R)-1-(3,5-difluorobenzyl)-2-hydroxy-3-{[(4S)-6-isopropyl-3,4-dihydro-2H-chromen-4-yl]amino}propyl)acetamide

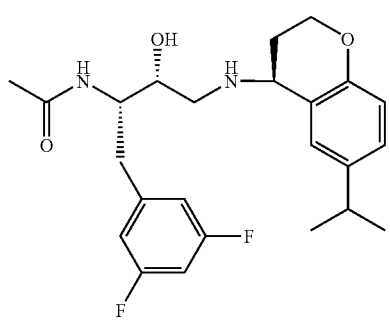

Step One:
6-isopropyl-2,3-dihydro-4H-chromen-4-one

A $CH_2Cl_2$ (350 ml) solution of 1-isopropyl-4-methoxy benzene (25 g, 166 mmol) and 3-chloro-propionly chloride (21 ml, 216 mmol), at r.t., was treated with $AlCl_3$ (33 g, 249 mmol) in 1-2 g portions over a 1 h period. Stirring was maintain at r.t. for 24 h at which time the mixture was poured onto crushed ice followed by the addition of 30 ml of conc. HCl. The mixture was diluted with 300 ml of $CH_2Cl_2$ and carefully washed (avoid emulsion) with 2 N NaOH. The organic layer was dried over $MgSO_4$ and concentrated in vacuo a pale yellow oil. Flash chromatography (10% EtOAc/Heptanes) yields 6-isopropyl-2,3-dihydro-4H-chromen-4-one (7.5 g, 24%). $R_f$=0.3. HRMS (ESI+) calcd for $C_{12}H_{14}O_2$ m/z 191.1072 (M+H)$^+$. Found 191.1071.

Step Two: 6-isopropylchroman-4-ol

The above compound was prepared essentially according to the method of Example 17, step 1; it was obtained as a white solid. HRMS (ESI+) calcd for $C_{12}H_{16}O_2$ m/z 192.1150 (M+H)$^+$. Found 192.1152.

Step Three:
6-isopropyl-3,4-dihydro-2H-chromen-4-ylamine

The above compound was prepared essentially according to the method of Example 17, step 2. First the azide was prepared as a yellow oil (7.53 g, 86% crude yield. HRMS calcd for $C_{12}H_{15}N_3O$+H1 217.1215, found 217.1218. Second, the azide was reduced with 1.0M $Me_3P$ in THF (42.00 mL, 41.59 mmol). The resulting amine was obtained as a yellow oil (3.5 g, 53% crude. yield). HRMS calcd for $C_{12}H_{17}NO$+H1 192.1388, found 192.1384. The crude racemic amine was purified and resolved using chiral preparative HPLC (5% EtOH/heptanes, 0.1% DEA) using a Chiralpak AD column. Obtained 1.5 g of (+)-(4R)-6-isopropyl-chroman-4-ylamine retention time 15.5 min. $[\alpha]_D$=4.2 (c=2.0 in MeOH) and 1.5 g of (−)-(4S)-6-isopropyl-chroman-4-ylamin retention time 18.3 min. $[\alpha]_D$=−3.9 (c=2.0 in MeOH). $^1$H NMR as the HCl salt (300 MHz, $CD_3OD$) δ 1.25 (d, J=6 Hz, 6H), 2.15 (m, 1H), 2.38 (m, 1H), 2.89 (m, 1H), 4.27 (m, 2H), 4.55 (t, J=6 Hz, 1H), 6.83 (d, J=9 Hz, 1H), 7.19 (dd, J=3, 9 Hz, 1H), 7.25 (d, J=3 Hz, 1H).

Step Four: tert-Butyl (1S,2R)-1-(3,5-difluorobenzyl)-2-hydroxy-3-{[(4S)-6-isopropyl-3,4-dihydro-2H-chromen-4-yl]amino}propylcarbamate The above compound was prepared essentially according to the method of Example 17, step 3. The crude material was used in the next reaction without purification. $^1$H NMR (crude-DMSO-$d_6$) δ 7.75 (d, J=9 Hz, 1H), 7.14 (br s, 1H), 7.02 (m, 2H), 6.9 (m, 1H), 6.68 (d, J=9 Hz, 1H), 5.3 (br s, 2H), 4.22 (m, 1H), 4.12 (m, 1H), 3.9 (m, 1H), 3.68 (m, 1H), 3.50 (m, 1H), 3.02 (dd, J=11, 3 Hz, 1H), 2.78 (sept, J=7 Hz, 1H), 2.67 (s, 1H), 2.57 (dd, J=4, 10 Hz, 1H), 1.59 (s, 9H), 1.14 (d, J=7 Hz, 6H). LRMS (m/z) M+H: 490.3.

Step Five: N-((1S,2R)-1-(3,5-difluorobenzyl)-2-hydroxy-3-{[(4S)-6-isopropyl-3,4-dihydro-2H-chromen-4-yl]amino}propyl)acetamide The product from step 4 was converted into the above compound essentially according to the method of Example 15, step 3. First, the free amine was obtained as a glassy solid/foam. $^1$H NMR (crude-$CDCl_3$) δ 7.75 (d, J=9 Hz, 1H), 7.14 (br s, 1H), 7.02 (m, 2H), 6.9 (m, 1H), 6.68 (d, J=9 Hz, 1H), 4.4 (br s, 2H), 4.12 (m, 1H), 3.9 (m, 1H), 3.68 (m, 1H), 3.50 (m, 1H), 3.32 (m, 1H), 3.02 (dd, J=11, 3 Hz, 1H), 2.78 (sept, J=7 Hz, 1H), 2.67 (s, 1H), 2.57 (dd, J=4, 10 Hz, 1H), 1.11 (d, J=7 Hz, 6H). LRMS (m/z) M+H:390.2

Second, the amine was acylated to afford the acetamide as an oil, which was purified by prep-HPLC. HRMS (ESI+) calcd for $C_{24}H_{30}F_2N_2O_3$ m/z 433.2303 (M+H)+. Found 433.2307.

The same procedure using (+)-(4R)-6-isopropyl-chroman-4-ylamine results in the epimer N-((1S,2R)-1-(3,5-difluorobenzyl)-2-hydroxy-3-{[(4R)-6-isopropyl-3,4-dihydro-2H-chromen-4-yl]amino}propyl)acetamide. $^1$H NMR (DMSO-$d_6$) δ 7.76 (d, J=9 Hz, 1H), 7.01 (m, 2H), 7.14 (d, J=2 Hz, 1H), 6.99 (dd, J=8.5, 2 Hz, 1H), 6.91 (m, 1H), 6.65 (d, J=8.5 Hz, 1H), 4.96 (d, J=6 Hz, 1H), 4.2 (dt, J=10, 3.4 Hz, 1H), 4.1 (m, 1H), 3.99 (m, 1H), 3.64 (br s, 1H), 3.47 (m, 1H), 3.0 (dd, J=14, 3 Hz, 1H), 2.78 (sept, J=8 Hz, 1H), 2.75 (m, 1H), 2.6 (m, 2H), 1.86 (m, 3H), 1.7 (s, 3H), 1.16 (d, J=7 Hz, 6H). HRMS (ESI+) calcd for $C_{24}H_{30}F_2N_2O_3$ m/z 433.2303 (M+H)$^+$. Found 433.2301.

EXAMPLE 56

N-((1S,2R)-1-(3,5-difluorobenzyl)-2-hydroxy-3-{[(4S)-6-iodo-3,4-dihydro-2H-chromen-4-yl]amino}propyl)-2-hydroxy-2-methylpropanamide

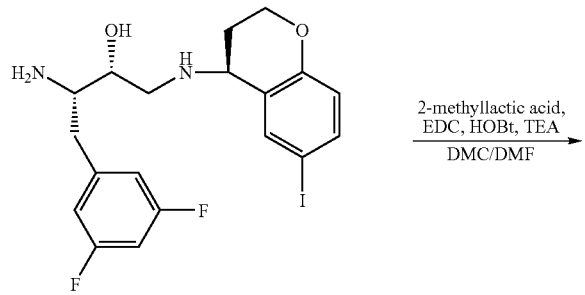

(2R,3S)-3-amino-4-(3,5-difluorophenyl)-1-{[(4S)-6-iodo-3,4-dihydro-2H-chromen-4-yl]amino}butan-2-ol (1 equiv) was combined with 2-methylacetic acid, (1.25 equiv), EDC (1.5 equiv) and HOBt (1.5 equiv) in DMF/DCM (1:1, 10 mL). The reaction mixture was treated with Et$_3$N and stirred at ambient temperature for 6h. HPLC determined that the amine had been consumed by this time, and the reaction mixture was poured onto EtOAc and washed with 1M HCl, then the organics were dried over MgSO$_4$ and concentrated to give an oil which was purified by reverse phase preparative HPLC. HRMS (ESI+) calcd for $C_{23}H_{27}F_2IN_2O_4$ m/z 561.1063 (M+H)$^+$. Found 561.1047.

EXAMPLE 57

N-((1S,2R)-1-(3,5-difluorobenzyl)-2-hydroxy-3-{[(4S)-6-iodo-3,4-dihydro-2H-chromen-4-yl]amino}propyl)-1-hydroxycyclopropanecarboxamide

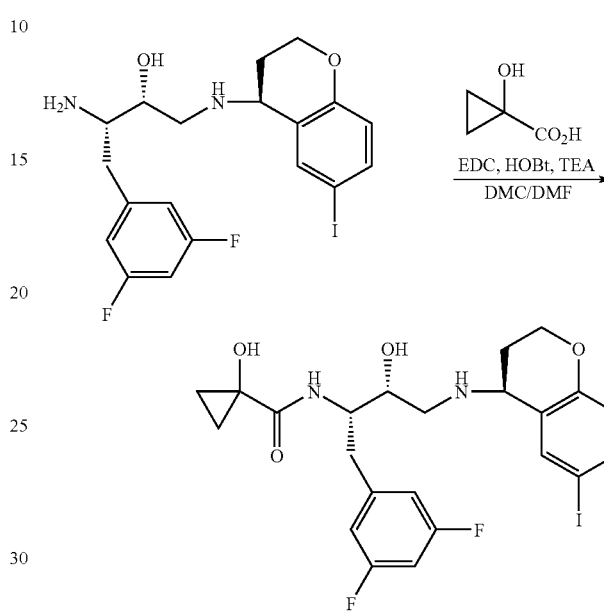

The above compound is prepared using the basic methodology described in Example 56. HRMS (ESI+) calcd for $C_{23}H_{25}F_2IN_2O_4$ m/z 559.0907 (M+H)$^+$. Found 559.0903.

EXAMPLE 58

N-((1S,2R)-1-(3,5-difluorobenzyl)-2-hydroxy-3-{[(4S)-6-iodo-3,4-dihydro-2H-chromen-4-yl]amino}propyl)methanesulfonamide

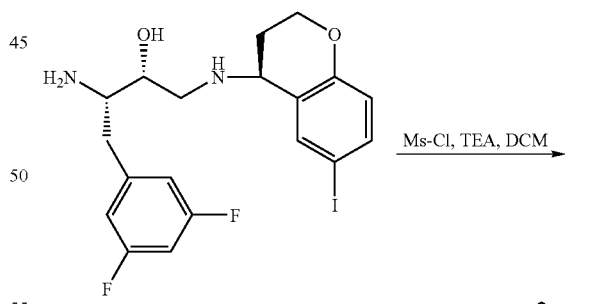

(2R,3S)-3-amino-4-(3,5-difluorophenyl)-1-{[(4S)-6-iodo-3,4-dihydro-2H-chromen-4-yl]amino}butan-2-ol (1 equiv) was dissolved in DCM with TEA (2 equiv) then cooled to 0° C. and treated with MsCl (1.25 equiv)while stirring. The reaction mixture was removed from the cold bath, brought to ambient temperature, then quenched with MeOH and concentrated. The residue was dissolved in EtOAc and washed with 1M HCl (2×10 mL). The organics were dried and concentrated and chromatographed over silica gel. $^1$H NMR (CD$_3$OD) δ 7.74 (d, J=2.0 Hz, 1H), 7.53 (dd, J=2.0, 8.7 Hz, 1H), 6.88 (m, 2H), 6.77 (m, 1H), 6.67 (d, J=8.7 Hz, 1H), 4.23-4.39 (m, 2H), 4.25 (br m, 1H), 4.12 (m, 1H), 3.87 (td, J=3.1, 7.8 Hz, 1H), 3.29 (dd, J=3.5, 13.9 Hz, 1H), 3.11 (s, 3H), 3.05 (dd, J=3.2, 12.7 Hz, 1H), 2.98 (dd, J=7.9, 12.6 Hz, 1H), 2.74 (dd, J=11.0, 13.9 Hz, 1H), 2.14 (br m, 2H). MS (ESI+) calcd for C$_{20}$H$_{23}$F$_2$IN$_2$O$_4$S m/z 553.38 (M+H)$^+$. Found 553.4.

EXAMPLE 59

(1S,2R)-1-(3,5-difluorobenzyl)-2-hydroxy-3-{[(4S)-6-neopentyl-3,4-dihydro-2H-chromen-4-yl]amino}propylformamide

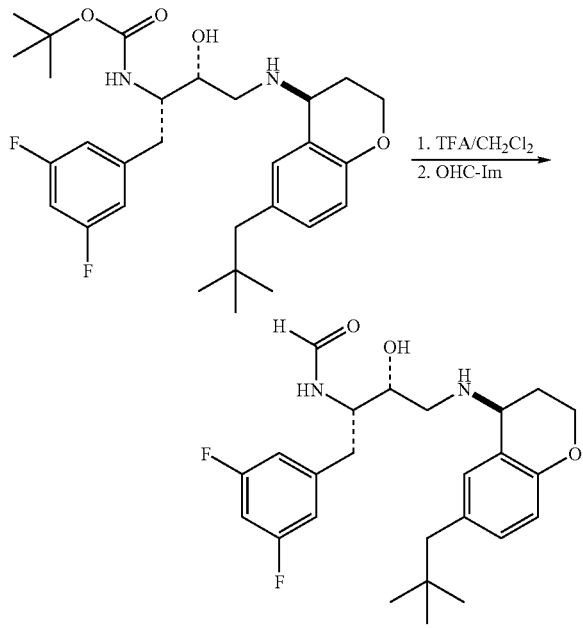

The Boc protected amine (1 equiv) was dissolved in 10:1 DCM:TFA (to 0.1M) for 3 h at ambient temperature. The reaction mixture was concentrated and the residue partitioned between EtOAc and 1M NaOH. The aqueous layer was removed and the organics washed with brine (50 mL) then dried over MgSO$_4$ and concentrated to a glassy solid/foam. LRMS (m/z) M+H:418.5. This was dissolved in CH$_2$Cl$_2$ (to 0.1M), cooled to 0° C. and treated with formyl imidizole (1.25 equiv). The reaction was removed from the cold bath, then stirred for 2 h at ambient temp. When done by HPLC, the reaction mixture was concentrated and dissolved in MeOH (1.5 mL) and purified by reversed phase preparative HPLC (2 in. column) to give a film which scraped down to a white powder. $^1$H NMR (DMSO-d$_6$) δ 8.46 (br s, 1H), 7.75 (d, J=9 Hz, 1H), 7.14 (br s, 1H), 7.02 (m, 2H), 6.91 (m, 1H), 6.69 (d, J=9 Hz, 1H), 5.0 (br s, 2H), 4.21 (m, 1H), 4.09 (m, 1H), 3.94 (m, 1H), 3.72 (m, 1H), 3.43 (m, 1H), 3.08 (dd, J=11, 3 Hz, 1H), 2.77 (s, 2H), 2.57 (dd, J=4, 10 Hz, 1H), 1.69 (s, 3H), 1.04 (s, 9H). MS (ESI+) for C$_{25}$H$_{32}$F$_2$N$_2$O$_3$ m/z 446.54 (M+H)$^+$. Found 446.3.

EXAMPLE 60

N-{(1S,2R)-1-(3,5-difluorobenzyl)-2-hydroxy-3-[(4-methyl-6-neopentyl-3,4-dihydro-2H-chromen-4-yl)amino]propyl}acetamide

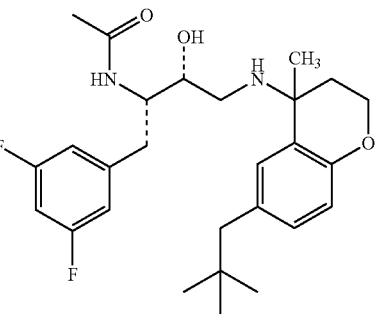

Step One: 6-iodo-2,3-dihydro-4H-chromen-4-one

To a CH$_2$Cl$_2$ (300 ml) suspension of 6-iodo-4-chromanol (15 g, 54.3 mmol) and 30 g of silica gel, at r.t., was added PCC (15.2 g, 70.6 mmol) as a solid. The mixture was stirred at r.t. for 3 h at which time TLC (20% EtOAc/hexanes) indicated complete reaction. The reaction mixture was filtered through a silica gel plug and the filtrate concentrated in vacuo to yield 14.9 g (95%) of 6-iodo-2,3-dihydro-4H-chromen-4-one as a white solid consistent with the literature report (*Synthesis* 1997, 23-25). HRMS (ESI+) calcd for C$_9$H$_7$IO$_2$ m/z 273.9492; found 273.9500.

Step Two: 6-iodo-4-methylchroman-4-ol

CeCl$_3$ (4.9 g, 19.8 mmol) was dried in vacuo at 140° C. for 3 h and then slurried with dry THF (100 ml) for 1 h. The white suspension was chilled to −78° C. followed by the addition of MeLi.LiBr (14.2 ml, 21.4 mmol) over 15 minutes. The mixture was stirred for 30 min followed by the addition of a THF (20 ml) solution of 6-iodo-2,3-dihydro-4H-chromen-4-one dropwise via syringe. After 30 min TLC (15% EtOAc/hexanes) indicated complete reaction. The mixture was treated with NH$_4$Cl (aq.) 30 ml and diluted with water 150 ml. The mixture was extracted with EtOAc and the organic layer dried over Na$_2$SO$_4$. The Na2SO4 was removed by filtration and the filtrate concentrated in vacuo to yield 6-iodo-4-methylchroman-4-ol as an off white solid 4.7 g (95%). HRMS (ESI+) calcd for C$_{10}$H$_{11}$IO$_2$ m/z 289.9806 (M+H)$^+$. Found 289.9803.

Step Three: 6-iodo-4-methylchroman-4-amine

To a mixture of 6-iodo-4-methylchroman-4-ol (1.0 g, 3.4 mmol) and NaN$_3$ (0.7 g, 10.3 mmol) in CHCl$_3$ (15 ml), at 0° C., was added TFA (1.3 ml, 17.2 mmol) as a solution in 10 ml of CHCl$_3$ dropwise via addition funnel. The addition was carried out over 2 h and stirring continued for an additional 2 h at 0° C. The mixture was warmed to r.t. and stirred overnight. The mixture was diluted with 30 ml of water and extracted with CH$_2$Cl$_2$. The organic layer was dried over Na₂SO₄ and concentrated in vacuo to yield 4-azido-6-iodo-4-methylchroman as a yellow oil. ¹H NMR (400 MHz, CDCl₃) δ 7.65 (d, J=2.07 Hz, 1H), 7.50 (dd, J=8.71, 2.07 Hz, 1H), 6.66 (d, J=8.71 Hz, 1H), 4.27 (m, 2H), 2.06 (m, 2H), 1.68 (s, 3H). MS (ESI+) for C₁₀H₁₀IN₃O m/z 273.0 (M+H)⁺ loss of azide. The crude azide was dissolved in THF (15 ml) followed by the addition of trimethylphosphine (4 ml, 1.0 M in THF) at r.t. After 15 min. 3 ml of water was added and stirring continued at r.t. for 2 h until complete as indicated by LC/MS. The solvent was removed in vacuo and the residue diluted with water (75 ml) and extracted with CH₂Cl₂ (3×50 ml). The organic layer was dried over Na₂SO₄ and concentrated in vacuo to yield 6-iodo-4-methylchroman-4-amine (0.900 g, 91%) as a yellow oil. This material was used in the next step without purification. ¹H NMR (400 MHz, CDCl₃) δ 7.77 (d, J=2.07 Hz, 1H), 7.40 (dd, J=8.60, 2.18 Hz, 1H), 6.59 (d, J=8.50 Hz, 1H), 4.25 (m, 2H), 2.01 (m, 2H), 1.53 (s, 3H). MS (ESI+) for C₁₀H₁₂INO m/z 273.2 (M+H)⁺ loss of NH₃.

Step Four: tert-butyl (1S,2R)-1-(3,5-difluorobenzyl)-2-hydroxy-3-[(6-iodo-4-methyl-3,4-dihydro-2H-chromen-4-yl)amino]propylcarbamate The above compound was prepared essentially according to the method of example 17, step 3. The resulting crude material was dissolved in CH₂Cl₂, absorbed onto 7.8 g of silica gel, and purified by flash chromatography using 50% EtOAc/Heptanes (Biotage 40 M column) as the eluent. Three fractions were obtained. The final fraction was recovered amine. Obtained 0.500 g of each of the following diastereomers overall yield from epoxide 83%.

Diastereomer A: ¹H NMR (400 MHz, CDCl₃) δ 7.67 (bs, 1H), 7.42 (dd, J=8.50, 2.07 Hz, 1H), 6.71 (m, 3H), 6.59 (d, J=8.50 Hz, 1H), 4.52 (d, J=9.12 Hz, 1H), 4.35 (m, 1H), 4.21 (m, 1H), 3.82 (m, 1H), 3.42 (m, 1H), 3.06 (m, 1H), 2.81 (dd, J=14.3, 8.7 Hz, 1H), 2.62 (m, 2H), 2.26 (m, 1H), 1.84 (m, 1H), 1.40 (m, 2H), 1.35 (m, 12H). HRMS (ESI+) for C₂₅H₃₁N₂O₄F₂I+1H calcd for 589.1376 m/z found 589.1397 (M+H)⁺.

Diastereomer B: ¹H NMR (400 MHz, CDCl₃) δ 7.65 (d, J=2.07 Hz, 1H), 7.44 (d, J=8.50 Hz, 1H), 6.71 (m, 3H), 6.67 (d, J=8.71 Hz, 1H), 4.54 (bs, 1H), 4.34 (m, 1H), 4.16 (m, 1H), 3.77 (m, 1H), 3.48 (m, 1H), 3.10 (m, 1H), 2.75 (m, 1H), 2.75 (m, 1H), 2.62 (m, 2H), 2.24 (m, 1H), 1.93 (m, 1H), 1.60 (m, 2H), 1.42 (s, 9H), 1.39 (s, 3H). HRMS (ESI+) for C₂₅H₃₁N₂O₄F₂I+1H calcd for m/z 589.1376; found 589.1375 (M+H)⁺.

Step Five: N-{(1S,2R)-1-(3,5-difluorobenzyl)-2-hydroxy-3-[(6-iodo-4-methyl-3,4-dihydro-2H-chromen-4-yl)amino]propyl}acetamide To a CH₂Cl₂ (5 ml) solution of tert-butyl (1S,2R)-1-(3,5-difluorobenzyl)-2-hydroxy-3-[(6-iodo-4-methyl-3,4-dihydro-2H-chromen-4-yl)amino]propylcarbamate (Diastereomer B). (0.47 g, 0.79 mmol), at r.t., was added 25 ml of 20% TFA/CH₂Cl₂. The mixture was stirred at r.t for 30 min. The solvent was removed in vacuo and the residue dissolved in CH₂Cl₂ (75 ml) and washed with aqueous NaHCO₃ and brine. The organic layer was dried over Na₂SO₄ and concentrated in vacuo to yield a white foam. The residue was dissolved in CH₂Cl₂ (5 ml) and chilled to 0° C. followed by the addition of Et₃N (0.24 ml, 1.7 mmol) and acetyl imidazole (0.10 g, 0.90 mmol). The mixture was then warmed to r.t. and stirred overnight. The reaction mixture was diluted with CH₂Cl₂ (25 ml) and washed with water and brine. The organic layer was dried over Na₂SO₄ and concentrated in vacuo to yield a white foam (0.35 g, 84%) after flash chromatograph 5% MeOH/CHCl₃ (Biotage 40 S). R$_f$=0.29. HRMS (ESI+) calcd for C₂₂H₂₅N₂O₃IF₂+1H calcd m/z 531.0958; found 531.0958 (M+H)⁺.

Same procedure diastereomer A yields 0.28 g (70%) of the epimer. ¹H NMR (400 MHz, DMSO-d₆) δ 7.75 (d, J=2.28 Hz, 1H), 7.36 (dd, J=8.71, 2.28 Hz, 1H), 6.79 (m, 3H), 6.57 (d, J=8.50 Hz, 1H), 4.31 (m, 1H), 4.17 (m, 1H), 4.08 (m, 1H), 3.51 (m, 1H), 3.11 (dd, J=14.1, 3.73 Hz, 1H), 2.62 (dd, J=14.1, 10.4 Hz, 1H), 2.52 (m, 1H), 2.45 (dd, J=11.9, 3.63 Hz, 1H), 2.25 (m, 1H), 1.79 (s, 3H), 1.74 (m, 1H), 1.47 (s, 3H). Anal. Calcd for C₂₂H₂₅F₂IN₂O₃; C, 49.82; H, 4.75; N, 5.28. Found C, 49.87; H, 4.94; N, 5.05.

Step Six: N-{(1S,2R)-1-(3,5-difluorobenzyl)-2-hydroxy-3-[(4-methyl-6-neopentyl-3,4-dihydro-2H-chromen-4-yl)amino]propyl}acetamide

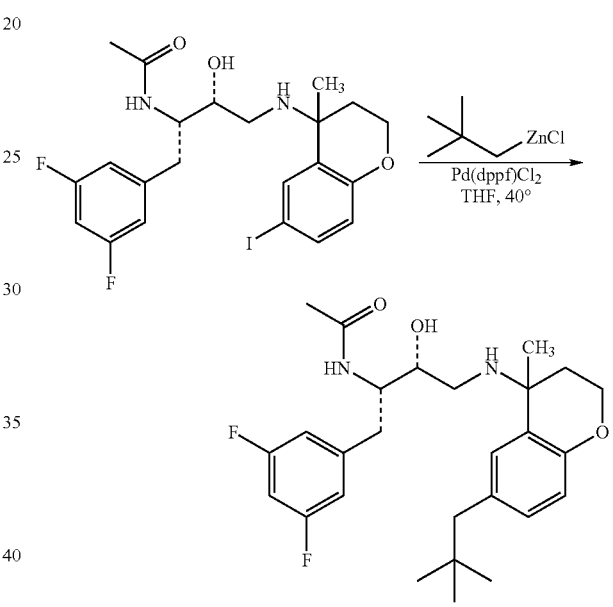

To a 20 ml serum capped vial containing N-{(1S,2R)-1-(3,5-difluorobenzyl)-2-hydroxy-3-[(6-iodo-4-methyl-3,4-dihydro-2H-chromen-4-yl)amino]propyl}acetamide (0.20 g, 0.37 mmol) and Pd(dppf)Cl₂ (0.015 g, 0.018 mmol) under nitrogen was added 3.7 ml of a 0.5 M neopentyl zinc chloride (1.85 mmol) prepared as previously described. The mixture was shaken on an orbital shaker for 12 h at which time LC/MS indicated only a trace of the desired compound. An additional 5 eq. of the zinc reagent and another 5 mol % of catalyst was added and the reaction mixture was warmed to 40° C. After 6 h LC/MS indicated complete consumption of SM. The reaction mixture was quenched with NH₄Cl and extracted with EtOAc. The organic layer was dried over Na₂SO₄ and concentrated in vacuo to yield a light brown solid (150 mg) after flash chromatography (4% MeOH/CHCl₃ Biotage 40S). This material was subjected to a final reverse phase preparative column (1% TFA in H₂O/0.6% TFA in CH₃CN) to yield 50 mg of a light yellow solid. This material was dissolved in 4 ml of CH₂Cl₂ and treated with 0.5 g of 3-mercaptopropyl functionalized silica gel and stirred at r.t. for 30 min. The mixture was filtered through Celite® to remove the resin and the filtrate concentrated in vacuo to yield a white powder (44 mg, 20%). ¹H NMR (400 MHz, DMSO-d₆) δ 7.08 (d, J=2.07 Hz, 1H), 6.87 (dd, J=8.29, 2.07 Hz, 1H), 6.78 (m, 3H), 6066 (d, J=8.29 Hz, 1H), 4.27 (m, 1H), 4.12 (m, 1H), 4.04 (m, 1H), 3.54 (m, 1H), 3.06 (dd, J=13.99, 3.63 Hz, 1H), 2.56 (m, 2H), 2.45 (bs, 2H), 2.37 (dd, J=11.82, 7.67 Hz, 1H), 2.25 (m, 1H), 1.81 (s, 3H), 1.78 (m, 1H); 1.49 (s, 3H), 0.91 (s, 9H). MS (ESI+) for $C_{27}H_{36}N_2O_3F_2$ m/z 475.2772 (M+H)$^+$; found, 475.2774.

Same procedure yields 0.049 g (28%) of the epimer $^1$H NMR (400 MHz, DMSO-d$_6$) δ 7.17 (d, J=2.07 Hz, 1H), 6.87 (dd, J=8.29, 2.07 Hz, 1H), 6.77 (m, 3H), 6.66 (d, J=8.29 Hz, 1H), 4.27 (m, 1H), 4.11 (m, 2H), 3.53 (m, 1H), 3.06 (dd, J=14.10, 3.52 Hz, 1H), 2.53 (m, 3H), 2.43 (s, 2H), 2.27 (m, 1H), 1.78 (m, 4H), 1.49 (s, 3H), 0.90 (s, 9H). MS (ESI+) calcd for $C_{27}H_{36}N_2O_3F_2$ m/z 475.2772 (M+H)$^+$; found, 475.2788.

EXAMPLE 60 A

An Alternative Synthesis of 4-methyl-6-neopentylchroman-4-ol

Step 1: 6-neopentylchroman-4-ol

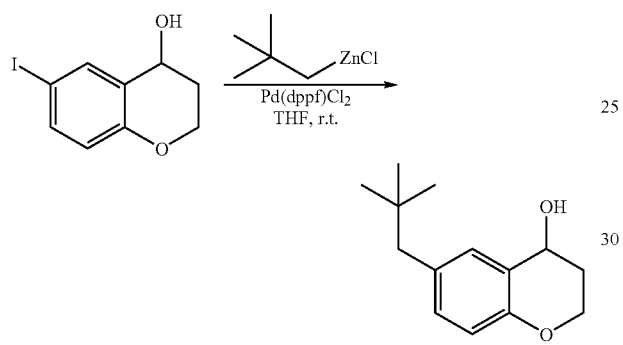

To a flame dried round bottom flask containing 6-iodochroman-4-ol (3.0 g, 10.8 mmol) and Pd(dppf)Cl$_2$ (0.44 g, 0.54 mmol) was added 6 ml of anhydrous THF and the mixture chilled to 0° C. The mixture was treated with neopentyl zinc chloride (prepared as previously described) (50 ml, 30 mmol, 0.6 M in THF) and stirred under nitrogen at r.t. for 19 h. followed by 5 h at 50° C. (oil bath). The reaction was cooled to r.t. and quenched with NH$_4$Cl and extracted with EtOAc. The organic layer was dried over Na$_2$SO$_4$ and concentrated in vacuo to 1.9 g (79%) of a white solid after flash chromatography (10% EtOAc/heptanes, Biotage 40M) R$_f$=0.11. HRMS (ESI+) calcd for $C_{14}H_{20}O_2$ m/z 220.1463 (M+H)$^+$; found 220.1460.

Step 2: 6-neopentyl-2,3-dihydro-4H-chromen-4-one

The alcohol was oxidized to the ketone essentially according to the method of Example 60, step 1; the ketone was obtained as a clear oil. This material was carried forward without further purification. HRMS (ESI+) calcd for $C_{14}H_{18}O_2$ m/z 219.1385 (M+H)$^+$; found 219.1393.

Step 3: 4-methyl-6-neopentylchroman-4-ol

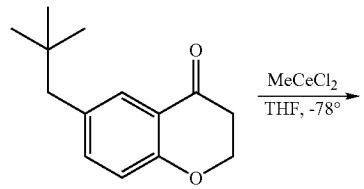

-continued

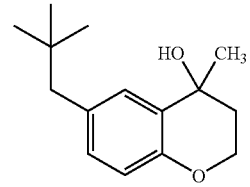

The above compound was prepared essentially according to the method of Example 60, step 2; the product was obtained as a clear oil, which was used without further purification. $^1$H NMR (300 MHz, CDCl$_3$) δ 7.23 (d, J=2.07 Hz, 1H), 6.95 (dd, J=8.29, 2.26 Hz, 1H), 6.73 (d, J=8.29 Hz, 1H), 4.25 (m, 2H), 2.44 (s, 2H), 2.09 (m, 2H), 1.64 (s, 3H), 0.91 (s, 9H). MS (ESI+) calcd for $C_{15}H_{22}O_2$ m/z 234.2 (M+H)$^+$; found 217.3 loss of water.

EXAMPLE 61

N-((1S,2R)-1-(3,5-difluorobenzyl)-2-hydroxy-3-{[(4S)-6-isopropoxy-3,4-dihydro-2H-chromen-4-yl]amino}propyl)acetamide

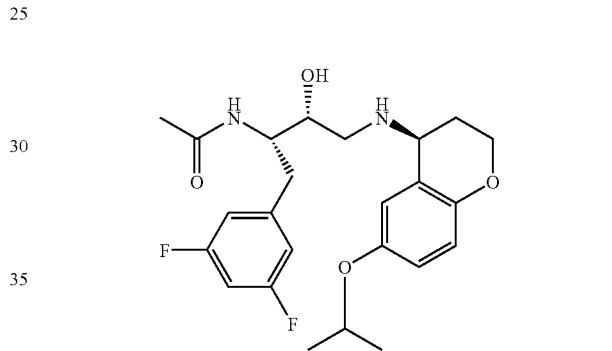

Step One: tert-butyl (4S)-6-(4,4,5,5-tetramethyl-1,3,2-dioxaborolan-2-yl)-3,4-dihydro-2H-chromen-4-ylcarbamate

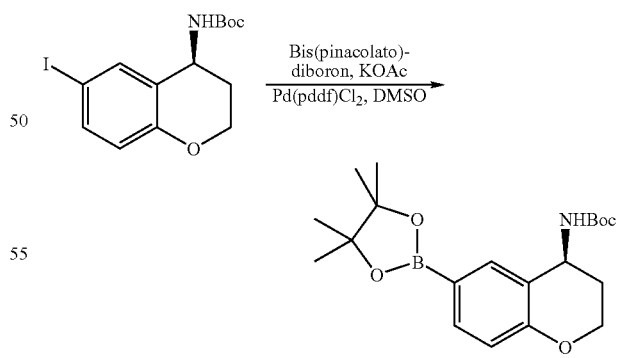

To a mixture of tert-butyl (4S)-6-iodo-3,4-dihydro-2H-chromen-4-ylcarbamate (3.30 g, 8.8 mmol) and bis(pinacolato)diboron (2.51 g, 9.7 mmol) in methyl sulfoxide (30 mL) was added potassium acetate (2.60 g, 26.4 mmol) followed by [1,1'-bis(diphenylphosphino)ferrocene]dichloropalladium (II) complex with dichloromethane (1:1) (410 mg, 0.5 mmol). The reaction mixture was heated under argon at 80° C. for 2 h and then cooled to room temperature. The reaction mixture was diluted with ethyl ether (100 mL) and washed with water and saturated sodium chloride, dried (sodium sulfate), filtered, and concentrated under reduced pressure. Purification by flash column chromatography (silica gel, 10-20% ethyl acetate/hexanes) provided the desired product (3.25 g, 98%): $^1$H NMR (300 MHz, CDCl$_3$) δ 7.72 (s, 1H), 7.62 (dd, J=8.2, 1.5 Hz, 1H), 6.80 (d, J=8.2 Hz, 1H), 4.79 (m, 2H), 4.31-4.24 (m, 1H), 4.21-4.15 (m, 1H), 2.14-2.11 (m, 2H), 1.48 (s, 9H), 1.34 (s, 6H), 1.33 (s, 6H).

Step Two: tert-butyl (4S)-6-hydroxy-3,4-dihydro-2H-chromen-4-ylcarbamate

To a solution of tert-butyl (4S)-6-(4,4,5,5-tetramethyl-1,3,2-dioxaborolan-2-yl)-3,4-dihydro-2H-chromen-4-ylcarbamate (1.09 g, 2.90 mmol) in tetrahydrofuran (10 mL) was added sodium hydroxide (6 mL, 1 N, 6 mmol) followed by hydrogen peroxide (10 mL, 30%). The reaction mixture was stirred at room temperature for 2 h and then quenched with sodium hydrogen sulfite (5 g in 10 mL of water). The mixture was adjusted to pH 4 with 2 N sodium hydroxide and then extracted with ethyl acetate (3×50 mL). The combined extracts were washed with saturated sodium chloride, dried (sodium sulfate), filtered, and concentrated under reduced pressure. Flash chromatography (silica gel, 10-25% ethyl acetate/hexanes) provided (650 mg, 85%) of the desired product. $^1$H NMR (300 MHz, CDCl$_3$) δ 7.89 (s, 1H), 6.75 (d, J=2.7 Hz, 1H), 6.72-6.63 (m, 1H), 5.03 (d, J=7.5 Hz, 1H), 4.77-4.75 (m, 1H), 4.16-4.08 (m, 2H), 2.30 (s, 1H), 2.16-2.13 (m, 1H), 2.05-1.99 (m, 1H), 1.47 (s, 9H).

Step Three: tert-butyl (4S)-6-isopropoxy-3,4-dihydro-2H-chromen-4-ylcarbamate

To a solution of the alcohol, from step two, (325 mg, 1.22 mmol) in acetone (10 mL) was added cesium carbonate (800 mg, 2.45 mmol) followed by 2-bromopropane (360 mg, 2.93 mmol). The reaction mixture was stirred at 60° C. for 24 h. The solvent was removed under reduced pressure. The residue was diluted with ethyl acetate (100 mL) and water (50 mL). The organic layer was separated and washed with saturated sodium chloride, dried (sodium sulfate), filtered, and concentrated under reduced pressure to provide tert-butyl (4S)-6-isopropoxy-3,4-dihydro-2H-chromen-4-ylcarbamate (340 mg, 90%): $^1$H NMR (300 MHz, CDCl$_3$) δ 6.80 (d, J=2.1 Hz, 1H), 6.77-6.62 (m, 2H), 4.81 (m, 2H), 4.45-4.35 (m, 1H), 4.23-4.16 (m, 1H), 4.14-4.06 (m, 1H), 2.22-2.14 (m, 1H), 2.05-1.95 (m, 1H), 1.48 (s, 9H), 1.29 (d, J=6.2 Hz, 6H). This material was used in the next step without further purification.

Step Four: (4S)-6-isopropoxychroman-4-amine.

To a solution of tert-butyl (4S)-6-isopropoxy-3,4-dihydro-2H-chromen-4-ylcarbamate (340 mg, 1.11 mmol) in methanol (2 mL) was added hydrochloric acid (2 mL, 4 N in 1,4-dioxane, 8 mmol). The reaction mixture was stirred at room temperature for 2 h. The solvent was removed under reduced pressure. The residue was diluted with methylene chloride (50 mL) and water (50 mL). The organic layer was separated and the aqueous layer was extracted with methylene chloride (2×50 mL). The combined extracts were washed with saturated sodium chloride, dried (sodium sulfate), filtered, and concentrated under reduced pressure to provide (4S)-6-isopropoxychroman-4-amine (240 mg, 99% crude yield): $^1$H NMR (300 MHz, CDCl$_3$) δ 6.96 (d, J=2.7 Hz, 1H), 6.90-6.86 (m, 1H), 6.80 (d, J=9.0 Hz, 1H), 4.55-4.46 (m, 2H), 4.24-4.17 (m, 2H), 2.40-2.31 (m, 1H), 2.18-2.08 (m, 1H), 1.28 (d, J=6.0 Hz, 6H). This material was used in the next step without further purification.

Step Five: tert-butyl (1S,2R)-1-(3,5-difluorobenzyl)-2-hydroxy-3-{[(4S)-6-isopropoxy-3,4-dihydro-2H-chromen-4-yl]amino}propylcarbamate

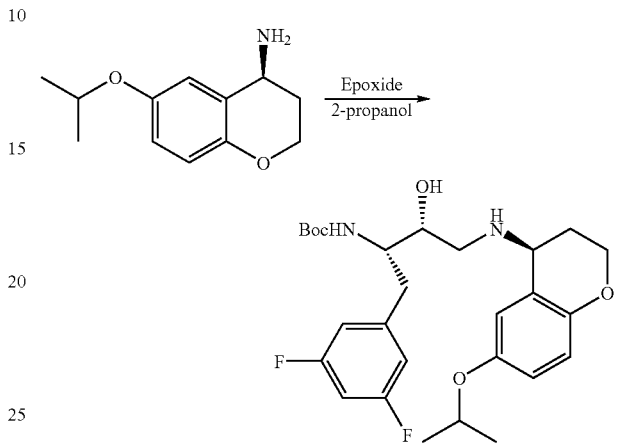

The above compound was prepared essentially according to the method of Example 17, step 3. Flash chromatography of the crude product (silica gel, 20-50% ethyl acetate/hexanes) afforded 95 mg of amine and the desired product (330 mg, 93%): $^1$H NMR (300 MHz, CDCl$_3$) δ 6.84 (s, 1H), 6.79-6.73 (m, 4H), 6.70-6.63 (m, 1H), 4.52 (d, J=9.4 Hz, 1H), 4.45-4.37 (m, 1H), 4.25-4.13 (m, 2H), 3.77-3.69 (m, 2H), 3.45-3.39 (m, 1H), 3.09-3.03 (m, 1H), 2.83-2.75 (m, 3H), 2.05-2.01 (m, 1H), 1.95-1.87 (m, 1H), 1.37 (s, 9H), 1.30 (d, J=6.1 Hz, 6H).

Step Six: (2R,3S)-3-amino-4-(3,5-difluorophenyl)-1-{[(4S)-6-isopropoxy-3,4-dihydro-2H-chromen-4-yl]amino}butan-2-ol hydrochloride To a solution of the product from step 6 (330 mg, 0.65 mmol) in 1,4-dioxane (2 mL) was added hydrochloric acid (2 mL, 4 N in 1,4-dioxane, 8 mmol). The reaction mixture was stirred at room temperature for 4 h. The solvent was removed under reduced pressure. The residue was triturated with ethyl ether. The resulting white solid was collected by filtration and washed with ethyl ether to provide (2R,3S)-3-amino-4-(3,5-difluorophenyl)-1-{[(4S)-6-isopropoxy-3,4-dihydro-2H-chromen-4-yl]amino}butan-2-ol hydrochloride (302 mg, 97%): ESI MS m/z 407 $[C_{22}H_{28}F_2N_2O_3+H]^+$. This material was used in the next step without further purification.

Step Seven: N-((1S,2R)-1-(3,5-difluorobenzyl)-2-hydroxy-3-{[(4S)-6-isopropoxy-3,4-dihydro-2H-chromen-4-yl]amino}propyl)acetamide To a solution of the product from step 7 (302 mg, 0.63 mmol) in methylene chloride (5 mL) was added triethylamine (322 mg, 3.15 mmol) followed by 1-acetylimidazole (71 mg, 0.63 mmol). The reaction mixture was stirred at room temperature overnight. The mixture was washed successively with 1N hydrochloric acid, water, saturated sodium bicarbonate and saturated sodium chloride, and dried (sodium sulfate), filtered, and concentrated under reduced pressure. Purification by flash column chromatography (silica gel, 0-5% methanol/methylene chloride provided the desired product (190 mg, 67%) as a white solid: ESI MS m/z 449 $[C_{24}H_{30}F_2N_2O_4+H]^+$; HPLC (Method A) 98.7% (AUC), $t_R$=8.69 min. Anal. Calcd for $C_{24}H_{30}F_2N_2O_4$: C, 64.27; H, 6.74; N, 6.24. Found: C, 64.11; H, 6.65; N, 6.17.

EXAMPLE 62

N-((1S,2R)-1-(3,5-difluorobenzyl)-2-hydroxy-3-{[(4S)-6-hydroxy-3,4-dihydro-2H-chromen-4-yl]amino}propyl)acetamide

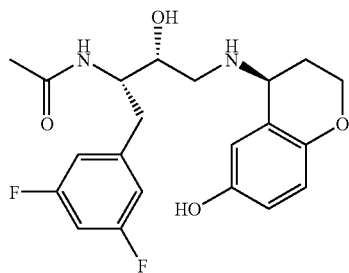

Step One: tert-butyl (1S,2R)-1-(3,5-difluorobenzyl)-2-hydroxy-3-{[(4S)-6-hydroxy-3,4-dihydro-2H-chromen-4-yl]amino}propylcarbamate A mixture of (4S)-4-aminochroman-6-ol (165 mg, 1.0 mmol) and Example 134 (300 mg, 1.0 mmol) in 2-propanol (5 mL) was stirred at 60° C. for 16 h. The solvent was removed under reduced pressure. Flash chromatography (silica gel, 0-5% methanol/methylene chloride) recovered 54 mg of starting amine and provided the desired product (200 mg, 64%): $^1$H NMR (300 MHz, CDCl$_3$) δ 7.26-6.63 (m, 6H), 4.55 (d, J=9.0 Hz, 1H), 4.21-4.14 (m, 2H), 3.73-3.71 (m, 2H), 3.47-3.44 (m, 1H), 3.10-3.02 (m, 1H), 2.84-2.75 (m, 3H), 2.10-2.02 (m, 1H), 1.94-1.90 (m, 1H), 1.37 (s, 9H).

Step Two: (4S)-4-{[(2R,3S)-3-amino-4-(3,5-difluorophenyl)-2-hydroxybutyl]amino}chroman-6-ol hydrochloride The above compound was prepared essentially according to the method of Example 61, step 7. ESI MS m/z 365 $[C_{19}H_{22}F_2N_2O_3+H]^+$. This material was used in the next step without further purification.

Step Three: N-((1S,2R)-1-(3,5-difluorobenzyl)-2-hydroxy-3-{[(4S)-6-hydroxy-3,4-dihydro-2H-chromen-4-yl]amino}propyl)acetamide

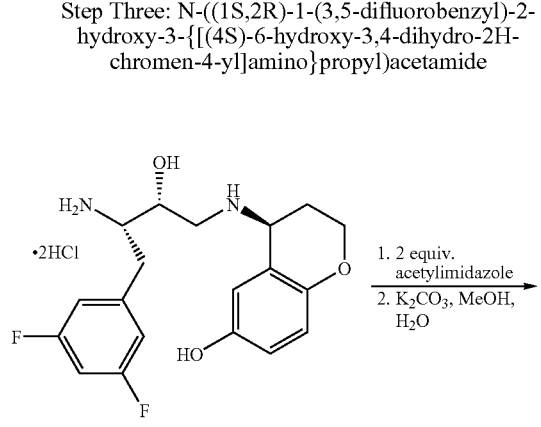

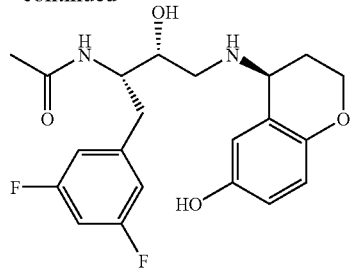

To a solution of the product from step 2 (200 mg, 0.43 mmol) in methylene chloride (5 mL) was added triethylamine (217 mg, 2.15 mmol) followed by 1-acetylimidazole (95 mg, 0.86 mmol). The reaction mixture was stirred at room temperature for 16 h. The solvent was removed under reduced pressure. The residue was dissolved in methanol (6 mL) and water (3 mL) and treated with potassium carbonate (300 mg, 2.17 mmol). The reaction mixture was stirred at room temperature for 2 h. The solvent was removed under reduced pressure. The residue was acidified with 1N hydrochloric acid and extracted with ethyl acetate (3×50 mL). The combined extracts were washed with saturated sodium chloride, and dried (sodium sulfate), filtered, and concentrated under reduced pressure. Purification by flash column chromatography (silica gel, 0-5% methanol/methylene chloride provided the desired product (85 mg, 49%) as a white foam. ESI MS m/z 407 $[C_{21}H_{24}F_2N_2O_4+H]^+$; HPLC (Method B) 98.0% (AUC), $t_R$=7.01 min. Anal. Calcd for $C_{21}H_{24}F_2N_2O_4 \cdot 0.25H_2O$: C, 61.38; H, 6.01; N, 6.82. Found: C, 61.60; H, 5.68; N, 6.59.

Scheme for Preparing isochromen-4-yl Compounds

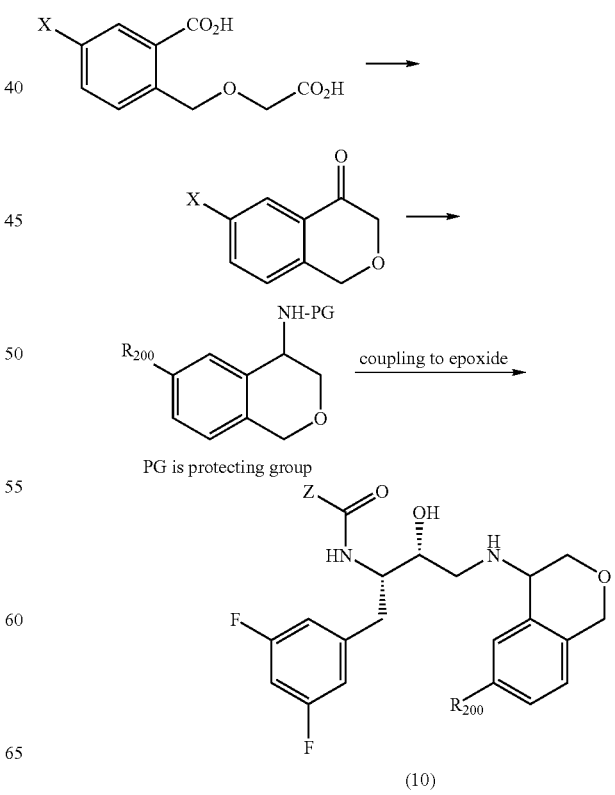

(10)

EXAMPLE 63

N-[(1S,2R)-1-(3,5-difluorobenzyl)-3-(3,4-dihydro-1H-isochromen-4-ylamino)-2-hydroxypropyl]acetamide

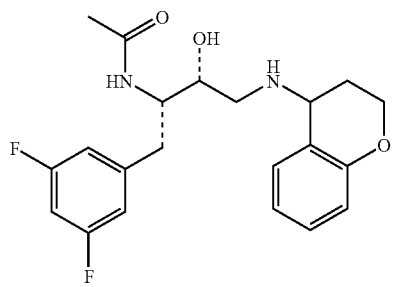

Step One: 2-[(carboxymethoxy)methyl]benzoic acid

A mixture of (2-cyano-benzyloxy)-acetic acid ethyl ester (*J. Org. Chem.* 1985, 50, 2128) (30 g, 136 mmol) and KOH (38 g, 680 mmol) in 1:1 EtOH/$H_2O$ (270 ml) was heated to 90° C. (oil bath) for 15 h. After cooling to room temperature the mixture was treated with conc. HCl until the pH=1 and extracted with $CH_2Cl_2$. The combined organic layers were dried concentrated in vacuo to yield an orange oil. The oil was dissolved in aq. $Na_2CO_3$, treated with activated carbon, filtered and the pH adjusted to 1 with conc. HCl. The resulting solid was collected by filtration and dried to yield 8.2 g of 2-[(carboxymethoxy)methyl]benzoic acid as a tan solid. $^1$H NMR (400 MHz, DMSO-$d_6$) δ 12.9 (bs, 1H), 7.87 (dd, J=7.77, 1.14 Hz, 1H), 7.66 (m, 1H), 7.59 (m, 1H), 7.39 (m, 1H), 4.90 (s, 2H), 4.15 (m, 2H).

Step Two: 1H-isochromen-4(3H)-one

A mixture of the product of step one (8.2 g, 39.0 mmol), KOAc (16.5 g, 167.8 mmol) and $Ac_2O$ (117 ml) was heated to reflux for 2 h. The mixture was cooled to room temperature then poured onto ice. The mixture was extracted with $Et_2O$ (3×100 ml) and the combined organic layers dried over Mg $SO_4$ and concentrated in vacuo. The resulting residue was dissolved in 40 ml of EtOH followed by the addition of 15 ml of 2 N NaOH. Stirring was continued at room temperature for 2h then the EtOH was removed in vacuo. The resulting aqueous layer was extracted with $Et_2O$ (3×75 ml) and the combined organic layers dried over $MgSO_4$, concentrated in vacuo to yield 2.7 g of 1H-isochromen-4(3H)-one as a slight yellow oil after flash chromatography (10% EtOAc/Hexanes) $R_f$=0.25. $^1$H NMR (400 MHz, CDCl$_3$) δ 8.05 (d, J=7.88 Hz, 1H), 7.59 (m, 1H), 7.43 (appt, J=7.36 Hz, 1H), 7.24 (d, J=7.67 Hz, 1H), 4.91 (s, 2H), 4.39 (s, 2H). Anal calcd for $C_9H_8O_2$; C, 72.96; H, 5.44; found C, 72.50; H, 5.29. MS (ESI+) for $C_9H_8O_2$ m/z 148.8 (M+H)$^+$.

Alternative Preparation of 1H-isochromen-4(3H)-one

Step 1A

1-[(allyloxy)methyl]-2-iodobenzene

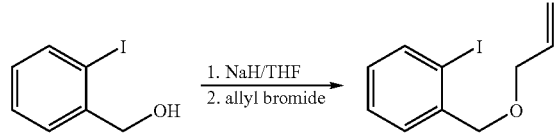

To a THF (200 ml) solution of 2-iodo-benzyl alcohol (25 g, 107 mmol), at r.t., was added the NaH (5.12 g, 128 mmol) in small portions. After complete addition of the NaH the allyl bromide (11.1 ml, 128 mmol) was added via syringe. The mixture was stirred overnight at room temperature. The resulting white heterogeneous mixture was quenched with $H_2O$ (100 ml) and diluted with 300 ml of $Et_2O$ followed by washing with $H_2O$ (2×100 ml) and brine (1×100 ml). The organic layer was dried over $MgSO_4$ and concentrated in vacuo to yield 31 g of 1-[(allyloxy)methyl]-2-iodobenzene as a faint yellow oil. HRMS (ESI+) calcd for $C_{10}H_{11}IO$ m/z 273.9857 (M+H)$^+$. Found 273.9855.

Step 2A 1H-isochromen-4(3H)-one

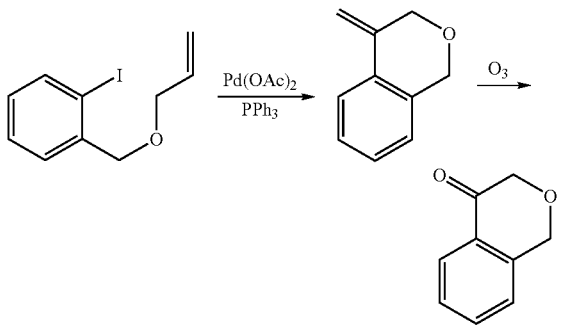

1-[(allyloxy)methyl]-2-iodobenzene (23 g, 83.9 mmol) was dissolved in 100 ml of $CH_3CN$ and 58 ml of $Et_3N$. The solution was vacuum degassed (3 cycles) followed by the addition of Pd(OAc)$_2$ (0.9 g, 4.2 mmol) and PPh$_3$ (2.2 g, 8.4 mmol). The mixture was heated to 80° C. until HPLC indicated complete reaction. The mixture was cooled to room temperature and diluted with $Et_2O$ (200 ml). The mixture was washed with 1N HCl (2×50 ml); NaHCO$_3$ (2×50 ml); brine (1×50 ml); dried over $Na_2SO_4$ and concentrated in vacuo to yield 4-methylene-3,4-dihydro-1H-isochromene (*Heterocycles* 1994, 39, 497) as an oil. HRMS (ESI+) calcd for $C_{10}H_{10}O$ m/z 146.0732 (M+H)$^+$. Found 146.0728. The crude oil was dissolved in 1:1 $CH_3OH/CH_2Cl_2$ (500 ml) and 5 ml of pyridine added. The mixture was chilled to −78° C. and ozone was bubbled through the mixture for 1 h, at which time TLC indicated complete reaction. The mixture was purged with $N_2$ at −78° C. and treated with Me$_2$S, then allowed to warm to room temperature and stir for 3 h. The reaction was then diluted with CH$_2$Cl$_2$ and washed with H$_2$O and brine. The organic layer was dried over Na$_2$SO$_4$ and concentrated in vacuo to yield 5.1 g of 1H-isochromen-4(3H)-one as a slight yellow oil after flash chromatography (10% EtOAc/Hexanes) R$_f$=0.25. $^1$H NMR (400 MHz, CDCl$_3$) δ 8.05 (d, J=7.88 Hz, 1H), 7.59 (m, 1H), 7.43 (appt, J=7.36 Hz, 1H), 7.24 (d, J=7.67 Hz, 1H), 4.91 (s, 2H), 4.39 (s, 2H. Anal calcd for C$_9$H$_8$O$_2$; C, 72.96; H, 5.44; found C, 72.50; H, 5.29. MS (ESI+) for C$_9$H$_8$O$_2$ m/z 148.8 (M+H)$^+$.

Step Three: 3,4-dihydro-1H-isochromen-4-ol

The alcohol was prepared from the ketone essentially according to the method of Example 17, step 1; it was obtained as a white solid. $^1$H NMR (400 MHz, CDCl$_3$) δ 7.48 (m, 1H), 7.31 (m, 2H), 7.04 (m, 1H), 4.84 (d, J=15 Hz, 1H), 4.72 (d, J=15 Hz, 1H), 4.58 (appt, J=2.38 Hz, 1H), 4.14 (dd, J=12.02, 2.70 Hz, 1H), 3.91 (dd, J=12.02, 2.70 Hz, 1H), 2.24 (bs, 1H). Anal calcd for C$_9$H$_{10}$O$_2$; C, 71.98; H, 6.71; found C, 71.80; H, 6.94.

Step Four: 3,4-dihydro-1H-isochromen-4-amine

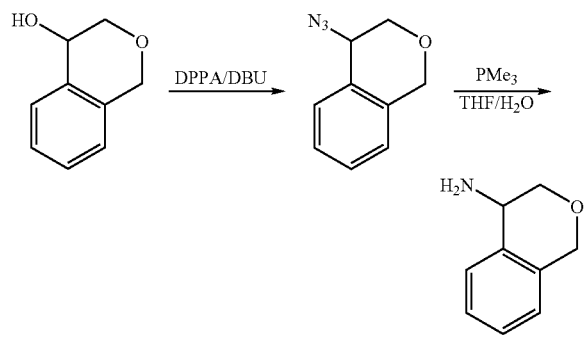

The above compound was prepared from the alcohol, essentially according to the method of Example 19, step 2. First, the alcohol is converted to the azide, which is obtained as a yellow oil. $^1$H NMR (300 MHz, CDCl$_3$) δ 7.41-7.09 (m, 4H), 4.90 (d, J=15.26 Hz, 1H), 4.75 (d, J=15.26 Hz, 1H), 4.23 (m, 2H), 3.98 (dd, J=12.43, 3.39 Hz, 1H). The crude azide was then reduced using PMe$_3$, affording the amine. $^1$H NMR (300 MHz, CDCl$_3$) δ 7.42 (m, 1H), 7.30-7.22 (m, 2H), 7.01 (m, 1H), 4.85 (d, J=15 Hz, 1H), 4.75 (d, J=15 Hz, 1H), 4.00-3.86 (m, 3H), 1.80 (bs, 2H). $^{13}$C NMR (100 MHz, CDCl$_3$) δ 138.4, 134.6, 128.6, 127.5, 127.4, 124.5, 72.75, 68.61, 48.23.MS (ESI+) for C$_9$H$_{11}$NO m/z 133.2 (M+H)$^+$ (loss of NH$_2$).

Step Five: tert-butyl (1S,2R)-1-(3,5-difluorobenzyl)-3-(3,4-dihydro-1H-isochromen-4-ylamino)-2-hydroxypropylcarbamate

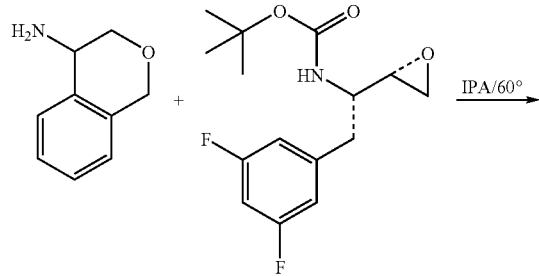

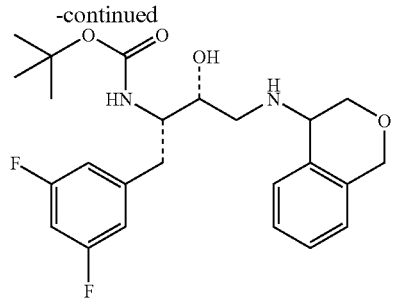

The coupled product was prepared essentially according to the method of Example 17, step 3; the resulting mixture of epimers was obtained as an off white solid and was used in the next step without further purification. HRMS (ESI+) calcd for C24H$_{30}$F$_2$N$_2$O$_4$ m/z 449.2252 (M+H)$^+$. Found 449.2244.

Step Six: N-[(1S,2R)-1-(3,5-difluorobenzyl)-3-(3,4-dihydro-1H-isochromen-4-ylamino)-2-hydroxypropyl]acetamide The above compound was prepared essentially according to the method of Example 15, step 3; the acetamide was obtained as a white foam. Small scale reverse phase HPLC of the mixture of epimers results in partial separation.

$^1$H NMR (400 MHz, CDCl$_3$) δ 7.35 (m, 1H), 7.28 (m, 2H), 7.04 (m, 1H), 6.77 (m, 2H), 6.68 (m, 1H), 5.90 (d, J=8.50 Hz, 1H), 4.83 (d, J=15.13 Hz, 1H), 4.73 (d, J=15.13 Hz, 1H), 4.18 (m, 2H), 3.85 (dd, J=11.82, 2.90 Hz, 1H), 3.70 (m, 1H), 3.62 (m, 1H), 3.00-2.84 (m, 3H), 2.71 (dd, J=12.34, 7.15 Hz, 1H), 1.93 (s, 3H). MS (ESI+) for C$_{21}$H$_{24}$F$_2$N$_2$O$_3$ m/z 391.5 (M+H)$^+$.

$^1$H NMR (400 MHz, CDCl$_3$) δ 7.40 (m, 1H), 7.29 (m, 2H), 7.05 (m, 1H), 6.77 (m, 2H), 6.68 (m, 1H), 5.88 (d, J=8.91 Hz, 1H), 4.87 (d, J=15.13 Hz, 1H), 4.74 (d, J=15.13 Hz, 1H), 4.26-4.16 (m, 2H), 3.84 (m, 2H), 3.75 (bs, 1H), 3.57 (m, 2H), 3.04-2.85 (m, 3H), 2.76 (dd, J=12.34, 6.53 Hz, 1H), 1.90 (s, 3H). MS (ESI+) for C$_{21}$H$_{24}$F$_2$N$_2$O$_3$ m/z 391.5 (M+H)$^+$.

EXAMPLE 64

N-{(1S,2R)-1-(3,5-difluorobenzyl)-2-hydroxy-3-[(6-isopropoxy-1,1-dimethyl-3,4-dihydro-1H-isochromen-4-yl)amino]propyl}acetamide

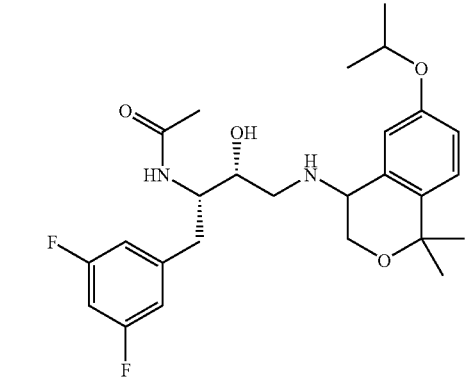

Step One: 6-isopropoxy-1,1-dimethyl-3,4-dihydro-1H-isochromene

The ether was prepared from the alcohol essentially according to the method of Example 61, step 3; the ether was obtained as a pale yellow oil: $^1$H NMR (300 MHz, CDCl$_3$) δ 7.00 (d, J=8.5 Hz, 1H), 6.71 (dd, J=8.5, 2.6 Hz, 1H), 6.59 (d, J=2.5 Hz, 1H), 4.54-4.46 (m, 1H), 3.92 (t, J=5.5 Hz, 2H), 2.77 (t, J=5.5 Hz, 2H), 1.49 (s, 6H), 1.32 (d, J=6.0 Hz, 6H).

Step Two: 4-bromo-6-isopropoxy-1,1-dimethyl-3,4-dihydro-1H-isochromene

A solution of the product from step 1 (0.22 g, 1.0 mmol), N-bromosuccinimide (0.19 g, 1.05 mmol), and AIBN (catalytic) in carbon tetrachloride (3 mL) was degassed with nitrogen for 10 min, and then stirred at 65° C. for 2.5 h. The reaction mixture was cooled in an ice-water bath, diluted with methylene chloride (150 mL) and washed with water (2×50 mL), saturated sodium chloride (50 mL), dried (sodium sulfate), filtered, and concentrated. The crude product was purified by flash chromatography (silica, 10:1 hexanes/ethyl acetate) to afford the bromide (1.02 g, 53%) as a pale-yellow oil: $^1$H NMR (300 MHz, CDCl$_3$) δ 6.98 (d, J=8.5 Hz, 1H), 6.86 (d, J=2.5 Hz, 1H), 6.80 (dd, J=8.5, 2.6 Hz, 1H), 5.18 (m, 1H), 4.54-4.48 (m, 1H), 4.19 (dd, J=12.8, 3.0 Hz, 1H), 4.11 (dd, J=12.8, 3.0 Hz, 1H), 1.59 (s, 3H), 1.47 (s, 3H), 1.33 (d, J=6.0 Hz, 6H).

Step Three: tert-butyl (1S,2R)-1-(3,5-difluorobenzyl)-2-hydroxy-3-[(6-isopropoxy-1,1-dimethyl-3,4-dihydro-1H-isochromen-4-yl)amino]propyl carbamate

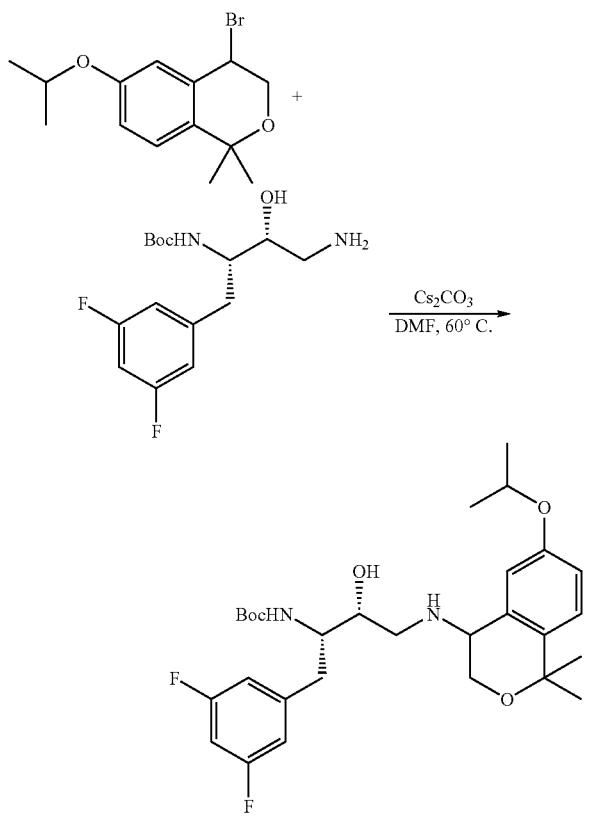

A solution of 4-bromo-6-isopropoxy-1,1-dimethyl-3,4-dihydro-1H-isochromene (0.61 g, 2.04 mmol), cesium carbonate (1.33 g, 4.08 mmol), and tert-butyl (1S,2R)-3-amino-1-(3,5-difluorobenzyl)-2-hydroxypropylcarbamate (0.64 g, 2.04 mmol) in N,N-dimethylformamide (10 mL) was stirred at 60° C., under nitrogen, for 24 h. The reaction mixture was diluted with ethyl acetate (100 mL) and washed with 5% lithium chloride (3×40 mL), water (2×30 mL), saturated sodium chloride (30 mL), dried (sodium sulfate), and concentrated under reduced pressure. The crude product was purified by flash chromatography (silica, 95:5 methylene chloride/methanol) to afford the desired product (0.51 g, 47%) as a pale-yellow foam: ESI MS m/z 535 [C$_{29}$H$_{40}$F$_2$N$_2$O$_5$+H]$^+$.

Step Four: (2R,3S)-3-amino-4-(3,5-difluorophenyl)-1-[(6-isopropoxy-1,1-dimethyl-3,4-dihydro-1H-isochromen-4-yl)amino]butan-2-ol hydrochloride The free amine was prepared from the Boc-amine essentially according to the method of Example 61, step 7; the amine was obtained as a yellow solid: ESI MS m/z 435 [C$_{24}$H$_{32}$F$_2$N$_2$O$_3$+H]$^+$.

Step Five: N-{(1S,2R)-1-(3,5-difluorobenzyl)-2-hydroxy-3-[(6-isopropoxy-1,1-dimethyl-3,4-dihydro-1H-isochromen-4-yl)amino]propyl}acetamide

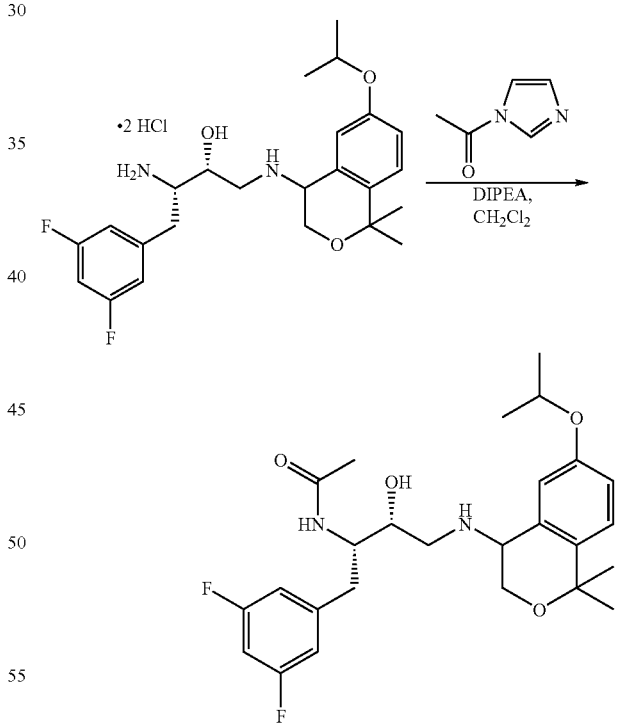

The acetamide was prepared from the free amine essentially according to the method of Example 61, step 7. The crude product was purified by flash chromatography (silica, 95:5 methylene chloride/methanol) to afford the acetamide as a white foam: $^1$H NMR (300 MHz, CDCl$_3$) δ 7.01 (d, J=8.4 Hz, 1H), 6.82-6.74 (m, 4H), 6.69-6.63 (m, 1H), 5.81-5.78 (m, 1H), 4.56-4.52 (m, 1H), 4.21-4.17 (m, 1H), 3.94 (d, J=2.1 Hz, 2H), 3.50-3.48 (m, 2H), 3.00-2.85 (m, 3H), 2.71-2.64 (m, 1H), 1.88 (s, 3H), 1.52 (s, 3H), 1.45 (s, 3H), 1.33 (d, J=6.0 Hz, 6H); ESI MS m/z 477 $[C_{26}H_{34}F_2N_2O_4+H]^+$; HPLC (Method A) >99% mixture of diastereomers (AUC), $t_R$=6.12 and 6.77 min.

EXAMPLE 65

N-{(1S,2R)-1-(3,5-difluorobenzyl)-2-hydroxy-3-[(6-neopentyl-3,4-dihydro-1H-isochromen-4-yl)amino]propyl}acetamide

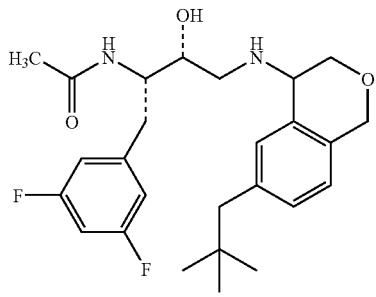

Step One:
5-Bromo-2-carboxymethoxymethyl-benzoic acid

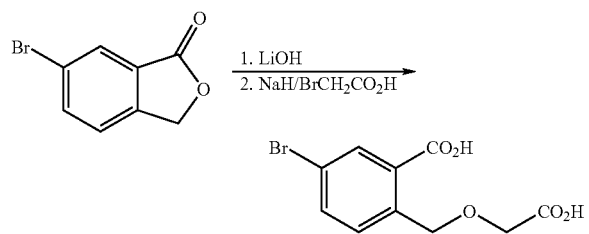

Lithium hydroxide monohydrate (11.80 g, 281.6 mmol) was added at room temperature over several minutes to a solution of 5-bromophthalide (20.0 g, 93.88 mmol) in a 2:1:1 solution of tetrahydrofuran/methanol/water (570 mL) and the reaction mixture stirred at room temperature overnight. The reaction mixture was concentrated under reduced pressure and azeotropically dried with benzene to give 5-Bromo-2-hydroxymethyl-benzoic acid as a white solid. The material was used without further purification: $^1$H NMR (300 MHz, CDCl$_3$+CD$_3$OD) δ 7.89 (d, J=8.3 Hz, 1H), 7.67 (d, J=1.9 Hz, 1H), 7.50 (dd, J=8.3, 1.9 Hz, 1H), 3.99 (s, 2H); ESI MS (negative mode) m/z 229 $[C_8H_7BrO_3-H]^-$. Sodium hyride (15.0 g, 375 mmol, 60% dispersion in mineral oil) was added in small portions over the course of 0.5 h at room temperature to a solution of 5-Bromo-2-hydroxymethyl-benzoic acid in tetrahydrofuran (235 mL) containing bromoacetic acid (14.35 g, 103.2 mmol) and sodium iodide (1.41 g, 9.4 mmol). The reaction mixture was heated at reflux overnight. The reaction mixture was cooled to room temperature and poured into water and then extracted with diethyl ether. The aqueous phase was acidified with 10% hydrochloric acid to pH 3-4 and extracted several times with ethyl acetate. The combined ethyl acetate phases were washed with water and saturated sodium chloride, dried (sodium sulfate), filtered, and concentrated to yield -Bromo-2-carboxymethoxymethyl-benzoic acid as a white solid. The material was used without further purification: $^1$H NMR (300 MHz, CD$_3$OD) δ 7.93-7.86 (m, 2H), 7.55-7.50 (m, 1H), 4.98 (s, 2H), 4.23 (s, 2H); ESI MS (negative mode) m/z 287 $[C_{10}H_9BrO_5-H]^-$.

Step Two: 6-Bromo-isochroman-4-one

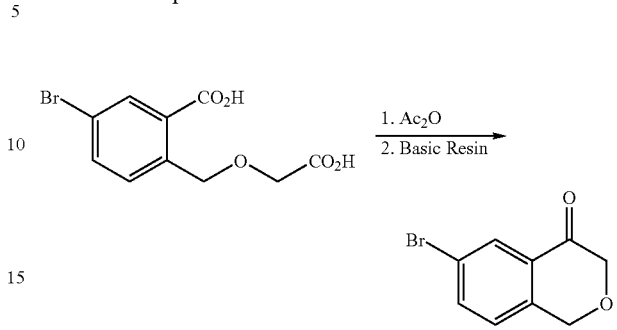

A solution of Bromo-2-carboxymethoxymethyl-benzoic acid in acetic anhydride (350 mL) containing potassium acetate (170 g) was heated at reflux for 2 h. The reaction mixture was cooled to room temperature and concentrated under reduced pressure and the residue partitioned between ethyl acetate and water. The phases were separated and the aqueous phase extracted with ethyl acetate. The combined ethyl acetate phase was then washed with saturated sodium chloride, dried (sodium sulfate), filtered, and concentrated to yield a red semi-solid. Purification by flash column chromatography over silica (85:15 hexanes/ethyl acetate) gave the enol acetate (7.59 g, 29% for three steps) as a golden syrup: $^1$H NMR (300 MHz, CDCl$_3$) δ 7.37 (dd, J=8.2, 1.9 Hz, 1H), 7.19 (d, J=1.9 Hz, 1H), 6.82 (d, J=8.2 Hz, 1H), 5.04 (s, 2H), 2.29 (s, 3H). Unactivated Dowex 500A OH anion exchange resin (1 g) added in one portion to a solution of the acetate enol acetate (5.95 g, 22.11 mmol) in methanol (50 mL) and the reaction mixture stirred at room temperature overnight. The reaction mixture was gravity filtered and the resin washed with fresh methanol. The combined filtrate was then concentrated under reduced pressure to yield 6-Bromo-isochroman-4-one (4.32 g, 86%) as a yellow oil, which solidified on standing: $^1$H NMR (300 MHz, CDCl$_3$) δ 7.90 (d, J=8.3 Hz, 1H), 7.56 (dd, J=8.3, 1.7 Hz, 1H), 7.41 (d, J=1.7 Hz, 1H), 4.86 (s, 2H), 4.36 (s, 2H).

Step Three: 6-Bromo-isochroman-4-ol

A solution of sodium borohydride (300 mg, 7.93 mmol) dissolved in a minimum amount of ice cold water was added dropwise at 0° C. to a solution of 6-Bromo-isochroman-4-one (1.49 g, 6.56 mmol) in absolute ethanol (27.0 mL). The reaction mixture was stirred at room temperature for 2 h. The reaction mixture was partitioned between ethyl acetate and saturated sodium bicarbonate solution. The phases were separated and the organic phase washed with water and saturated sodium chloride, dried (sodium sulfate), filtered, and concentrated under reduced pressure to yield 6-Bromo-isochroman-4-ol (1.44 g, 95%) as a white solid: $^1$H NMR (300 MHz, CDCl$_3$) δ 7.40 (dd, J=8.3, 1.8 Hz, 1H), 7.30 (d, J=8.3 Hz, 1H), 7.15 (d, J=1.8 Hz, 1H), 4.63 (ABq, J=15.3 Hz, 2H), 4.49 (d, J=8.6 Hz, 1H), 4.07 (dd, J=12.0, 2.8 Hz, 1H), 3.83 (dd, J=12.0, 2.8 Hz, 1H), 2.60 (d, J=9.2 Hz, 1H).

Step Four: (6-Bromo-isochroman-4-yl)-carbamic acid tert-butyl ester

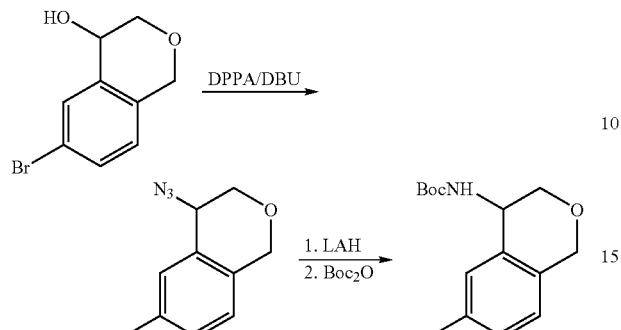

Diphenyphosphoryl azide (2.11 mL, 9.8 mmol) was added at 0° C. to a solution of 6-Bromo-isochroman-4-ol (1.87 g, 8.16 mmol) in toluene (17 mL). To this was added dropwise over 0.5 h a mixture of 1,8-diazabicyclo[5.4.0]undec-7-ene (1.46 ml, 9.8 mmol) in toluene (5.0 ml). The reaction mixture was then stirred at room temperature overnight. The reaction mixture was then passed through a plug of silica and the plug rinsed with 6:1 hexanes/ethyl acetate. The combined filtrates were concentrated under reduced pressure to provide the azide as a yellow oil: $^1$H NMR (300 MHz, CDCl$_3$) δ 7.46-7.33 (m, 3H), 4.76 (ABq, J=15.5 Hz, 2H), 4.22-4.16 (m, 3H), 3.93 (dd, J=11.7, 2.6 Hz, 1H). A solution of lithium aluminum hydride (391 mg, 9.79 mmol) in a minimum amount of tetrahydrofuran (2.0 mL) was added dropwise at 0° C. to a solution of the azide in tetrahydrofuran (30 mL) and the reaction mixture was heated at reflux for 1 h. The reaction mixture was cooled to room temperature and quenched with water (0.5 mL), 15% sodium hydroxide (1.2 ml), water (0.5 mL) and the reaction mixture stirred at room temperature for 1 h. The resulting mixture was then passed through a plug of silica and the plug rinsed with ether. The combined filtrates were concentrated under reduced pressure to afford a oil which was dissolved in a minimum amount of ethyl acetate to which was added hydrogen chloride (3.0 ml, 4 N in 1,4-dioxane, 12 mmol) and the reaction mixture stirred at room temperature overnight. The reaction mixture was vacuum filtered to afford the desired amine salt (1.54 g, 72% for two steps) as a white solid: $^1$H NMR (300 MHz, CDCl$_3$) δ 7.54-7.44 (m, 2H), 7.37 (s, 1H), 4.80 (ABq, J=15.5 Hz, 2H), 4.42 (d, J=12.8 Hz, 1H), 4.34 (s, 1H), 3.87 (dd, J=12.8, 2.2 Hz, 1H), 3.66 (s, 3H); ESI MS m/z 228 [C$_9$H$_{10}$BrNO+H]$^+$.

Di-tert-butyl dicarbonate (1.40 g, 6.40 mmol) was added in portions to a solution of amine (1.54 g, 5.82 mmol) in acetonitrile (25 mL) containing N,N-diisopropylethylamine (4.0 mL, 23.28 mmol) and the reaction mixture stirred at room temperature overnight. The reaction mixture was concentrated under reduced pressure and partitioned between ethyl acetate and water. The organic phase was dried (sodium sulfate), filtered, and concentrated under reduced pressure to afford a yellow syrup. Purification by flash column chromatography over silica (80:20 hexanes/ethyl acetate) yielded the desired product (1.05 g, 55%) as a white solid: $^1$H NMR (300 MHz, CDCl$_3$) δ 7.41-7.23 (m, 2H), 7.15 (s, 1H), 5.10-5.07 (m, 1H), 4.69 (ABq, J=15.5 Hz, 2H), 4.04-4.00 (m, 1H), 3.89-3.81 (m, 1H), 1.45 (s, 9H).

Step Five: 6-(2,2-Dimethyl-propyl)-isochroman-4-ylamine hydrochloride

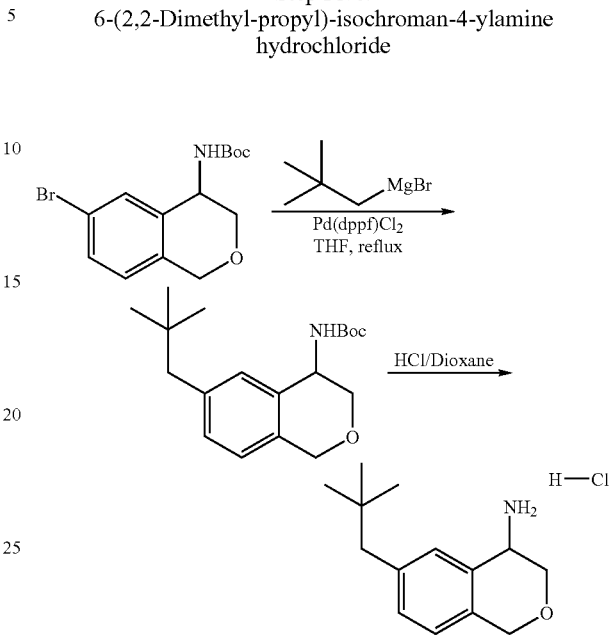

Neo-pentylmagnesium bromide (10 mL, 9.1 mmol, 1.0 M in ether) was added dropwise to a solution of zinc chloride (18.2 mL, 0.5 M in tetrahydrofuran, 9.1 mmol) over 0.5 h and the reaction mixture stirred at RT for an additional 0.5 h. [1,1'-Bis(diphenylphosphino)ferrocene]dichloropalladium (II) complex with dichloromethane (1:1) (250 mg, 0.30 mmol) was added to the reaction mixture followed by (6-Bromo-isochroman-4-yl)-carbamic acid tert-butyl ester (1.00 g, 3.04 mmol) and the reaction mixture heated at reflux for 1 h. The reaction mixture was cooled and then concentrated under reduced pressure. The residue was re-dissolved in ethyl acetate and washed with water, sodium chloride, dried (sodium sulfate), filtered, and concentrated under reduced pressure. Purification by flash column chromatography over silica (83:17 hexanes/ethyl acetate) yielded the desired protected amine (303 mg, 31%) as a white solid: $^1$H NMR (300 MHz, CDCl$_3$) δ 7.30-7.23 (m, 1H), 7.00 (d, J=6.3 Hz, 1H), 6.74 (s, 1H), 5.09-5.06 (m, 1H), 4.79-4.65 (m, 3H), 4.13-3.85 (m, 2H), 2.45 (s, 2H), 1.46 (s, 9H), 0.89 (s, 9H); ESI MS m/z 320 [C$_{19}$H$_{29}$NO$_3$+H]$^+$. A solution of protected amine (303 mg, 0.95 mmol) in hydrogen chloride (20 mL, 4 N in 1,4-dioxane, 80 mmol) was stirred at room temperature overnight. The reaction mixture was concentrated under reduced pressure to give 6-(2,2-Dimethyl-propyl)-isochroman-4-ylamine hydrochloride (210 mg, quantitative) as a white solid: $^1$H NMR (300 MHz, CDCl$_3$) δ 7.28 (d, J=7.6 Hz, 1H), 7.01 (d, J=7.6, 1.2 Hz, 1H), 6.73 (d, J=1.2 Hz, 1H), 4.75 (ABq, J=15.0 Hz, 2H), 3.96-3.80 (m, 3H), 2.44 (s, 2H), 1.73 (m, 2H), 0.89 (s, 9H); ESI MS m/z 220 [C$_{14}$H$_{21}$NO+H]$^+$.

Step Six: tert-butyl (1S,2R)-1-(3,5-difluorobenzyl)-2-hydroxy-3-[(6-neopentyl-3,4-dihydro-1H-isochromen-4-yl)amino]propylcarbamate The above compound was prepared essentially according to the method of Example 17, step 3. The resulting crude material was purified by flash column chromatography over Step Seven: N-{(1S,2R)-1-(3,5-difluorobenzyl)-2-hydroxy-3-[(6-neopentyl-3,4-dihydro-1H-isochromen-4-yl)amino]propyl}acetamide

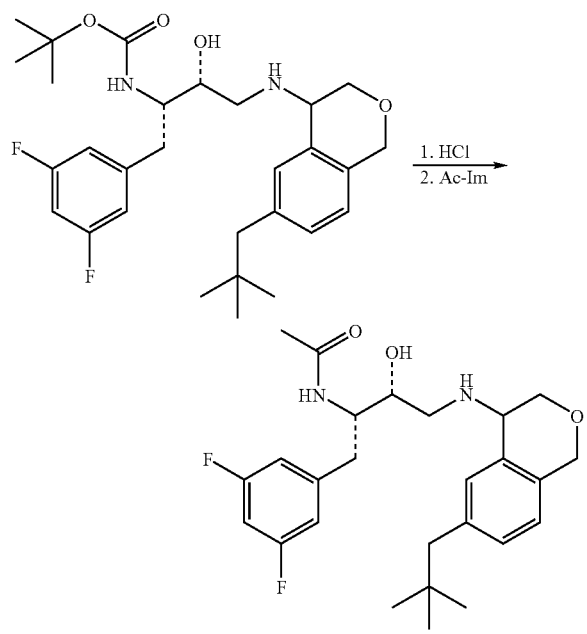

The acetamide was prepared from the Boc-protected amine essentially according to the method of Example 61, steps 7 and 8. First, the Boc-protected amine was deprotected to afford the free amine as a white solid. Second, the free amine was acylated to form the acetamide, as a mixture of epimers. $^1$H NMR (300 MHz, CDCl$_3$) δ 7.24-7.16 (m, 2H), 7.01-6.98 (m, 1H), 6.76-6.66 (m, 4H), 5.83 (ABq, J=15.0 Hz, 2H), 4.10-4.05 (m, 2H), 3.83-3.79 (m, 1H), 3.55-3.51 (m, 2H), 2.93-2.72 (m, 3H), 2.69-2.65 (m, 1H), 2.45 (s, 2H), 1.89 (m, 4H), 0.89 (s, 9H); ESI MS m/z 461 [C$_{26}$H$_{34}$F$_2$N$_2$O$_3$+H]$^+$; HPLC (1-99, 220) 68.1% Major Epimer (AUC), t$_R$=10.89 min and 31.8% Minor Epimer (AUC), t$_R$=11.19 min.

EXAMPLE 66

N-((1S,2R)-1-(3,5-difluorobenzyl)-2-hydroxy-3-{[(1S)-2-(hydroxymethyl)-7-neopentyl-1,2,3,4-tetrahydronaphthalen-1-yl]amino}propyl)acetamide

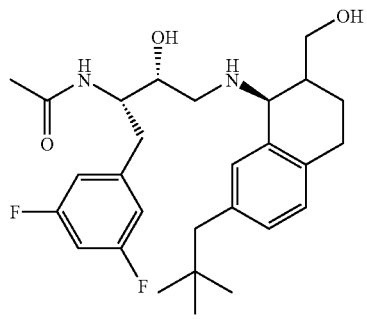

Step One: 7-(2,2-Dimethyl-propyl)-1-hydroxy-3,4-dihydro-naphthalene-2-carboxylic acid methyl ester

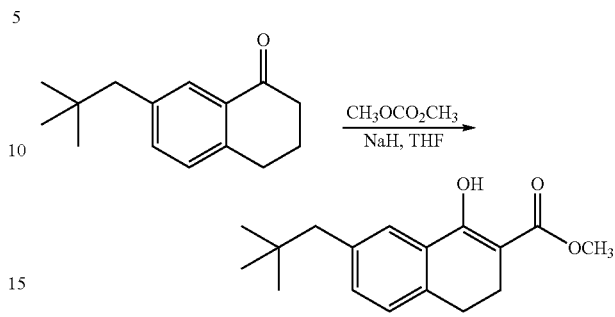

To a solution of tetralone (2.16 g, 10 mmol) in tetrahydrofuran (50 mL) was added sodium hydride (60%, 1.49 g, 37.1 mmol) followed by dimethyl carbonate (2.73 g, 30 mmol). The reaction mixture was heated at ref lux for 3 h and then allowed to cool to room temperature and quenched with acetic acid (3.6 mL). The solvent was removed under reduced pressure and the residue was diluted with ethyl ether (100 mL) and water (50 mL). The organic layer was separated and the aqueous layer was extracted with ethyl ether (2×50 mL). The combined extracts were washed with saturated sodium chloride, dried (sodium sulfate), filtered, and concentrated under reduced pressure. Flash column chromatography (silica gel, 10-20% ethyl acetate/hexanes) provided the desired product (2.50 g, 91%): $^1$H NMR (300 MHz, CDCl$_3$) δ 12.48 (s, 1H), 7.60 (s, 1H), 7.17-7.08 (m, 2H), 3.85 (s, 3H), 2.84-2.79 (m, 2H), 2.62-2.57 (m, 2H), 2.54 (s, 2H), 0.94 (s, 9H).

Step Two: 2-(tert-Butyl-dimethyl-silanyloxymethyl)-7-(2,2-dimethyl-propyl)-3,4-dihydro-2H-naphthalen-1-one To an ice-cooled solution of 7-(2,2-Dimethyl-propyl)-1-hydroxy-3,4-dihydro-naphthalene-2-carboxylic acid methyl ester (2.49 g, 9.07 mmol) in tetrahydrofuran (20 mL) was added lithium aluminum hydride (1 M in tetrahydrofuran, 9 mL, 9 mmol). The reaction mixture was stirred at 0° C. for 2 h and then quenched with saturated ammonium chloride and ethyl acetate. The resulting emulsion was filtered through diatomaceous earth. The organic layer was separated and the aqueous layer was extracted with ethyl acetate. The combined extracts were washed with saturated sodium chloride, dried (sodium sulfate), filtered, and concentrated under reduced pressure. Flash column chromatography (silica gel, 10-20% ethyl acetate/hexanes) provided hydroxymethyl tetralone (1.55 g, 70%): $^1$H NMR (300 MHz, CDCl$_3$) δ 7.78 (d, J=1.4 Hz, 1H), 7.27 (dd, J=7.8, 1.4 Hz, 1H), 7.16 (d, J=7.8 Hz, 1H), 4.00-3.90 (m, 1H), 3.85-3.75 (m, 1H), 3.20-3.10 (m, 1H), 3.08-2.90 (m, 2H), 2.75-2.60 (m, 1H), 2.52 (s, 2H), 2.15-2.05 (m, 1H), 2.00-1.85 (m, 1H), 0.90 (s, 9H).

To a solution of hydroxymethyl tetralone (1.50 g, 6.09 mmol) in N,N-dimethyl formamide (6 mL) was added imidazole (500 mg, 7.25 mmol) followed by tert-butyldimethylsilyl chloride (1.03 g, 6.64 mmol). The reaction mixture was stirred at room temperature for 2 h and then diluted with 1:1 hexanes/ethyl acetate (100 mL). The mixture was washed successively with 1N hydrochloric acid, water, saturated sodium bicarbonate and saturated sodium chloride, and dried (sodium sulfate), filtered, and concentrated under reduced pressure to provide 2-(tert-Butyl-dimethyl-silanyloxymethyl)-7-(2,2-dimethyl-propyl)-3,4-dihydro-2H-naphthalen-1-one (2.20 g, 99% crude yield): $^1$H NMR (300 MHz, CDCl$_3$) δ 7.76 (d, J=1.8 Hz, 1H), 7.23 (dd, J=7.8, 1.8 Hz, 1H), 7.14 (d, J=7.8 Hz, 1H), 4.16-4.08 (m, 2H), 3.90-3.84 (m, 1H), 3.01-2.95 (m, 2H), 2.68-2.60 (m, 1H), 2.51 (s, 2H), 2.42-2.33 (m, 1H), 2.03-1.95 (m, 1H), 0.89 (s, 9H), 0.87 (s, 9H), 0.07 (s, 3H), 0.06 (s, 3H). This material was used in the next step without further purification.

Step Three: 2-(tert-Butyl-dimethyl-silanyloxymethyl)-7-(2,2-dimethyl-propyl)-1,2,3,4-tetrahydro-naphthalen-1-ol

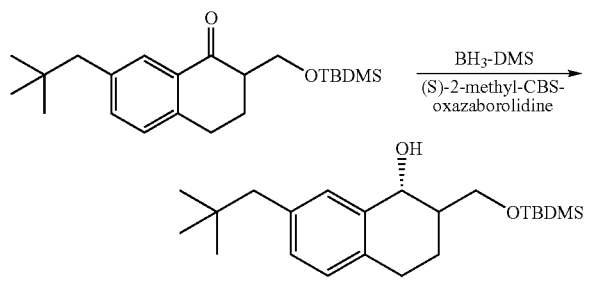

To a −30° C. cooled solution of 2-(tert-Butyl-dimethyl-silanyloxymethyl)-7-(2,2-dimethyl-propyl)-3,4-dihydro-2H-naphthalen-1-one (2.20 g, 6.09 mmol) in tetrahydrofuran (20 mL) was added (S)-2-methyl-Cbs-oxazaborolidine (1 M in toluene, 0.61 mL, 0.61 mmol) and a solution of borane-methyl sulfide complex (2 M in tetrahydrofuran, 2.15 mL, 4.3 mmol) in tetrahydrofuran (5 mL). The reaction mixture was heated at −20 to −5° C. for 5 h. The reaction mixture was quenched with methanol (8.3 mL) at −5° C. and then allowed to warm to room temperature and stirred overnight. The solvent was removed under reduced pressure. Flash column chromatography (silica gel, 0-5% ethyl acetate/hexanes) recovered 790 mg of ketone and provided chiral 2-(tert-Butyl-dimethyl-silanyloxymethyl)-7-(2,2-dimethyl-propyl)-1,2,3,4-tetrahydro-naphthalen-1-ol (980 mg, 70%): $^1$H NMR (300 MHz, CDCl$_3$) δ 7.14 (s, 1H), 7.03-6.96 (m, 2H), 4.84 (d, J=2.5 Hz, 1H), 3.92-3.82 (m, 2H), 3.04 (d, J=3.7 Hz, 1H), 2.92-2.67 (m, 2H), 2.46 (s, 2H), 2.04-1.86 (m, 2H), 1.75-1.63 (m, 1H), 0.91 (s, 9H), 0.90 (s, 9H), 0.10 (s, 3H), 0.09 (s, 3H).

Step Four: [1-Amino-7-(2,2-dimethyl-propyl)-1,2,3,4-tetrahydro-naphthalen-2-yl]-methanol The alcohol was converted into an amine essentially according to the method of Example 65, step 4. However, the resulting amine was not protected, as in Example 65, step 4. First the alcohol was converted to the azide, which was purified by flash column chromatography (silica gel, 0-5% ethyl acetate/hexanes). $^1$H NMR (300 MHz, CDCl$_3$) δ 7.15 (s, 1H), 7.03-6.97 (m, 2H), 4.42 (d, J=2.5 Hz, 1H), 3.75 (dd, J=10.1, 5.1 Hz, 1H), 3.67 (dd, J=10.1, 4.8 Hz, 1H), 2.81-2.67 (m, 2H), 2.48 (s, 2H), 2.07-1.98 (m, 2H), 1.80-1.67 (m, 1H), 0.91 (s, 9H), 0.89 (s, 9H), 0.08 (s, 3H), 0.07 (s, 3H).

Second, the azide was reduced to the amine. $^1$H NMR (300 MHz, CDCl$_3$) δ 7.06 (s, 1H), 7.01-6.92 (m, 2H), 3.83-3.70 (m, 3H), 2.92-2.72 (m, 3H), 2.47 (s, 2H), 1.85-1.69 (m, 2H), 1.48-1.33 (m, 1H), 0.90 (s, 9H).

Step Five: tert-butyl (1S,2R)-1-(3,5-difluorobenzyl)-2-hydroxy-3-{[(1S)-2-(hydroxymethyl)-7-neopentyl-1,2,3,4-tetrahydronaphthalen-1-yl]amino}propylcarbamate

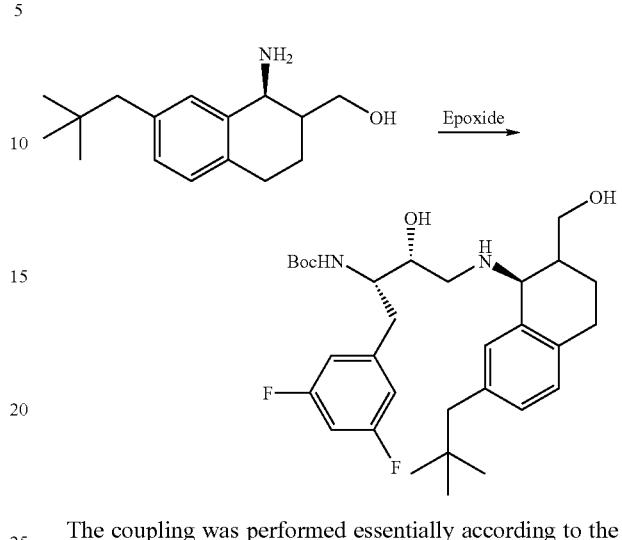

The coupling was performed essentially according to the method of Example 17, step 3. The resulting crude product was purified by flash chromatography (silica gel, 1-10% methanol/methylene chloride). : $^1$H NMR (300 MHz, CDCl$_3$) δ 7.01-6.91 (m, 3H), 6.76-6.60 (m, 5H), 4.62 (d, J=8.9 Hz, 1H), 4.34-4.30 (m, 1H), 4.07-3.89 (m, 2H), 3.83-3.61 (m, 4H), 3.53-3.47 (m, 2H), 2.95-2.86 (m, 2H), 2.80-2.63 (m, 3H), 2.59-2.57 (m, 2H), 2.45 (s, 2H), 2.15-2.05 (m, 1H), 1.81-1.77 (m, 1H), 1.36 (s, 9H), 0.89 (s, 9H).

Step Six: N-((1S,2R)-1-(3,5-difluorobenzyl)-2-hydroxy-3-{[(1S)-2-(hydroxymethyl)-7-neopentyl-1,2,3,4-tetrahydronaphthalen-1-yl]amino}propyl)acetamide

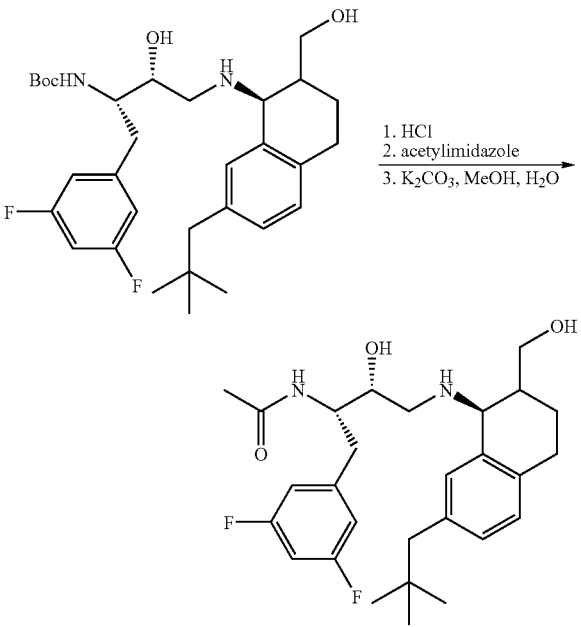

The above compound was prepared essentially according to the method of Example 15, step 3. First the Boc-protected amine was deprotected. ESI MS m/z 447 [C$_{26}$H$_{36}$F$_2$N$_2$O$_2$+H]$^+$.

Second, the amine was acetylated. Then the residue was dissolved in methanol (6 mL) and water (3 mL) and treated with potassium carbonate (300 mg, 2.17 mmol). The reaction mixture was stirred at room temperature for 2 h. The solvent was removed under reduced pressure. The residue was acidified with 1N hydrochloric acid and extracted with ethyl acetate (3×50 mL). The combined extracts were washed with saturated sodium chloride, and dried (sodium sulfate), filtered, and concentrated under reduced pressure. Purification by flash column chromatography (silica gel, 0-5% methanol/methylene chloride provided the desired product (80 mg, 44%) as a white foam: IR (ATR) 3265, 3072, 2948, 2864, 1626, 1595, 1550, 1459, 1364, 1315, 1115, 1071, 984, 842 cm$^{-1}$; $^1$H NMR (300 MHz, CD$_3$OD) δ 7.15 (s, 1H), 7.07-7.00 (m, 2H), 6.83-6.72 (m, 3H), 4.18 (d, J=5.9 Hz, 1H), 4.06-3.99 (m, 1H), 3.74-3.64 (m, 2H), 3.57 (t, J=8.4 Hz, 1H), 3.34 (s, 2H), 3.13-3.07 (m, 1H), 2.94-2.59 (m, 5H), 2.49 (s, 2H), 2.30-2.20 (m, 1H), 2.04-1.98 (m, 1H), 1.81 (s, 3H), 1.64-1.57 (m, 1H), 0.91 (s, 9H); ESI MS m/z 489 [C$_{28}$H$_{38}$F$_2$N$_2$O$_3$+H]$^+$; HPLC (Method C) 98.2% (AUC), t$_R$=9.41 min. Anal. Calcd for C$_{21}$H$_{24}$F$_2$N$_2$O$_4$·H$_2$O: C, 66.38; H, 7.96; N, 5.53. Found: C, 66.18; H, 7.80; N, 5.45.

EXAMPLE 67

5-[(((1S,2R)-1-(3,5-difluorobenzyl)-3-{[(1S)-7-ethyl-1,2,3,4-tetrahydronaphthalen-1-yl]amino}-2-hydroxypropyl)amino]-5-oxopentanoic acid To a solution of 3-amino-4-(3,5-difluoro-phenyl)-1-(7-ethyl-1,2,3,4-tetrahydro-naphthalen-1-ylamino)-butan-2-ol (0.240 g, 0.64 mmol), triethylamine (0.268 mL, 1.92 mmol), and chloroform (3 mL) was added glutaric anhydride (0.073 g, 0.64 mmol) and reaction was stirred overnight at 60° C. Reaction was washed with 1N HCl, 10% NaHCO$_3$, brine, dried over MgSO$_4$, filtered, concentrated in vacuo to give 5-[(((1S,2R)-1-(3,5-difluorobenzyl)-3-{[(1S)-7-ethyl-1,2,3,4-tetrahydronaphthalen-1-yl]amino}-2-hydroxypropyl)amino]-5-oxopentanoic acid (100 mg). Purified via prep-HPLC. $^1$H NMR (400 MHz, CD$_3$OD) δ 1.26 (t, J=8 Hz, 3H), 1.73 (m, 2H), 1.89 (m, 1H), 2.01 (m, 1H), 2.17 (m, 6H), 2.68 (d, J=8 Hz, 2H), 2.93 (d, J=6 Hz, 1H), 3.02 (m, 1H), 3.30 (m, 2H), 3.88 (m, 1H), 4.09 (m, 1H), 4.57 (m, 1H), 6.79 (m, 1H), 6.88 (m, 3H), 6.93 (d, J=6 Hz, 1H), 7.20 (m, 2H), 7.31 (s, 1H); OAMS: ES+ 488.9 ES− 486.9

EXAMPLE 68

4-[(((1S,2R)-1-(3,5-difluorobenzyl)-3-{[(1S)-7-ethyl-1,2,3,4-tetrahydronaphthalen-1-yl]amino}-2-hydroxypropyl)amino]-4-oxobutanoic acid The above compound was prepared essentially according to the method of Example 67. The crude product was purified via prep-HPLC. $^1$H NMR (400 MHz, CD$_3$OD) δ 1.27 (t, J=8 Hz, 3H), 1.88 (m, 1H), 2.04 (m, 1H), 2.25 (m, 3H), 2.48 (m, 2H), 2.70 (m, 4H), 2.81 (m, 1H), 2.93 (m, 1H), 3.12 (dd, J=8, 13 Hz, 1H), 3.32 (m, 2H), 3.87 (m, 1H), 4.04 (m, 1H), 4.51 (s, 1H), 6.80 (m, 1H), 6.86 (d, J=6 Hz, 2H), 7.18 (dd, J=8, 19 Hz, 2H), 7.32 (s, 1H); OAMS: ES+ 474.9, ES− 472.9.

EXAMPLE 69

Preparation of 1-(3-isopropylphenyl)cyclohexanamine hydrochloride 3.

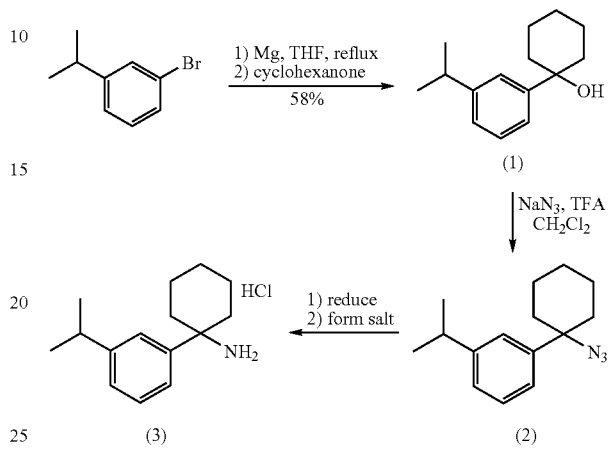

Step 1. Preparation of 1-(3-isopropylphenyl)cyclohexanol 1.

To 1.2 g (50 mmol) of magnesium turnings in 15 mL of dry THF is added a small crystal of iodine followed by 40 μL of dibromoethane. This mixture is placed in a water bath at 50° C. and 3-isopropylbromobenzene (5.0 g, 25 mmol) in 15 mL of dry tetrahydrofuran (THF) is added dropwise over 20 min, while the bath temperature is raised to 70° C. The mixture is stirred and refluxed for 40 additional min. The solution is cooled in an ice-water bath and cyclohexanone (2.0 mL, 19 mmol) in 10 mL of dry THF is added dropwise over 15 min. The ice bath is removed and the mixture is allowed to warm to ambient temperature over 1 h. The solution is decanted into aqueous saturated NH$_4$Cl, and combined with an ether wash of the residual magnesium turnings. The organic phase is washed twice more with aqueous NH$_4$Cl, dried over anhydrous Na$_2$SO$_4$, filtered and concentrated. Chromatography on silica gel, eluting with 10% ethyl acetate in heptane, affords 2.7 g (12 mmol, 60%) of compound 1 as an oil: $^1$H NMR (CDCl$_3$) δ 7.39 (m, 1H), 7.3 (m, 2H), 7.12 (m, 1H), 2.92 (m, 1H), 1.84-1.54 (m, 10H), 1.26 (d, J=7 Hz, 6 H).

Step 2. Preparation of 1-(3-isopropylphenyl)cyclohexylazide (2)

To 3.20 g (14.7 mmol) of compound 1 in 60 mL of CH$_2$Cl$_2$ under nitrogen is added 2.10 g (32.3 mmol) of sodium azide. The stirred suspension is cooled to −5° C. and a solution of trifluoroacetic acid (9.0 mL, 120 mmol) in 35 mL of dichloromethane is added dropwise over 1 h. The resulting suspension is stirred at 0° C. for an additional hour. To the cold, vigorously stirred mixture is added, dropwise, 10 mL of water, followed by dropwise addition of a mixture of 10 mL of water and 10 mL of concentrated ammonium hydroxide. After 30 min the mixture is poured into a separatory funnel containing 350 mL of a 1:1 mixture of heptane and ethyl acetate, and 100 mL of water. The organic phase is washed with an additional portion of water, followed successively by 1 N KH$_2$PO$_4$, water, and brine. It is then dried over anhydrous Na$_2$SO$_4$, filtered and concentrated to afford 3.6 g (14.7 mmol, 100%) of 2 as a pale yellow oil: $^1$H NMR (CDCl$_3$) δ 7.3 (m, 2H), 7.25 (m, 1H), 7.16 (m, 1H), 2.92 (m, 1H), 2.01 (m, 2H), 1.83 (m, 2H), 1.73-1.64 (m, 5H), 1.3 (m, 1H), 1.26 (d, J=7 Hz, 6H).

Step 3. Preparation of 1-(3-isopropylphenyl)cyclohexanamine hydrochloride 3

To 1-(3-isopropylphenyl)cyclohexylazide 2 (2.7 g, 11 mmol) in 200 mL of ethanol is added 20 mL of glacial acetic acid and 0.54 g of 10% palladium on carbon. The mixture is evacuated and placed under 16 psi of hydrogen, with shaking, for 2.5 h. The reaction mixture is filtered, the catalyst is washed with ethanol, and the solvents are removed in vacuo. Residual acetic acid is removed by chasing the residue with toluene. The acetate salt is dissolved in ethyl acetate and 1 N NaOH is added. The organic phase is washed with more 1 N NaOH and then with water, dried over Na$_2$SO$_4$, filtered and concentrated. The residue is dissolved in ether and ethereal HCl (concentrated HCl in ether which has been stored over MgSO$_4$) is added to afford a white solid. This is filtered, washed with ether, collected as a solution in dichloromethane, and concentrated to afford 2.1 g (8.3 mmol, 75%) of hydrochloride 3 as a white solid: $^1$H NMR (CDCl$_3$) δ 8.42 (br s, 3H), 7.43 (m, 2H), 7.25 (m, 1H), 7.15 (m, 1H), 2.92 (hept, J=7 Hz, 1H), 2.26 (m, 2H), 2.00 (m, 2H), 1.69 (m, 2H), 1.45-1.3 (m, 4H), 1.24 (d, J=7 Hz, 6H); IR (diffuse reflectance) 2944, 2864, 2766, 2707, 2490, 2447, 2411, 2368, 2052, 1599, 1522, 1455, 1357, 796, 704 cm −1. MS (EI)m/z (rel intensity) 217 (M+,26), 200 (13), 175 (18), 174 (99), 157 (15), 146 (23), 132 (56), 131 (11), 130 (16), 129 (18). HRMS (ESI) calcd for C$_{15}$H$_{23}$N+H$_1$ 218.190.9, found 218.1910. Anal. Calcd for C$_{15}$H$_{23}$N.HCl: C, 70.98; H, 9.53; N, 5.52; Cl, 13.97. Found: C, 70.98; H, 9.38; N, 5.49.

EXAMPLE 70

Preparation of N-((1S,2R)-1-(3,5-difluorobenzyl)-2-hydroxy-3-{[1-(3-isopropylphenyl)cyclohexyl]amino}propyl)acetamide hydrochloride 7

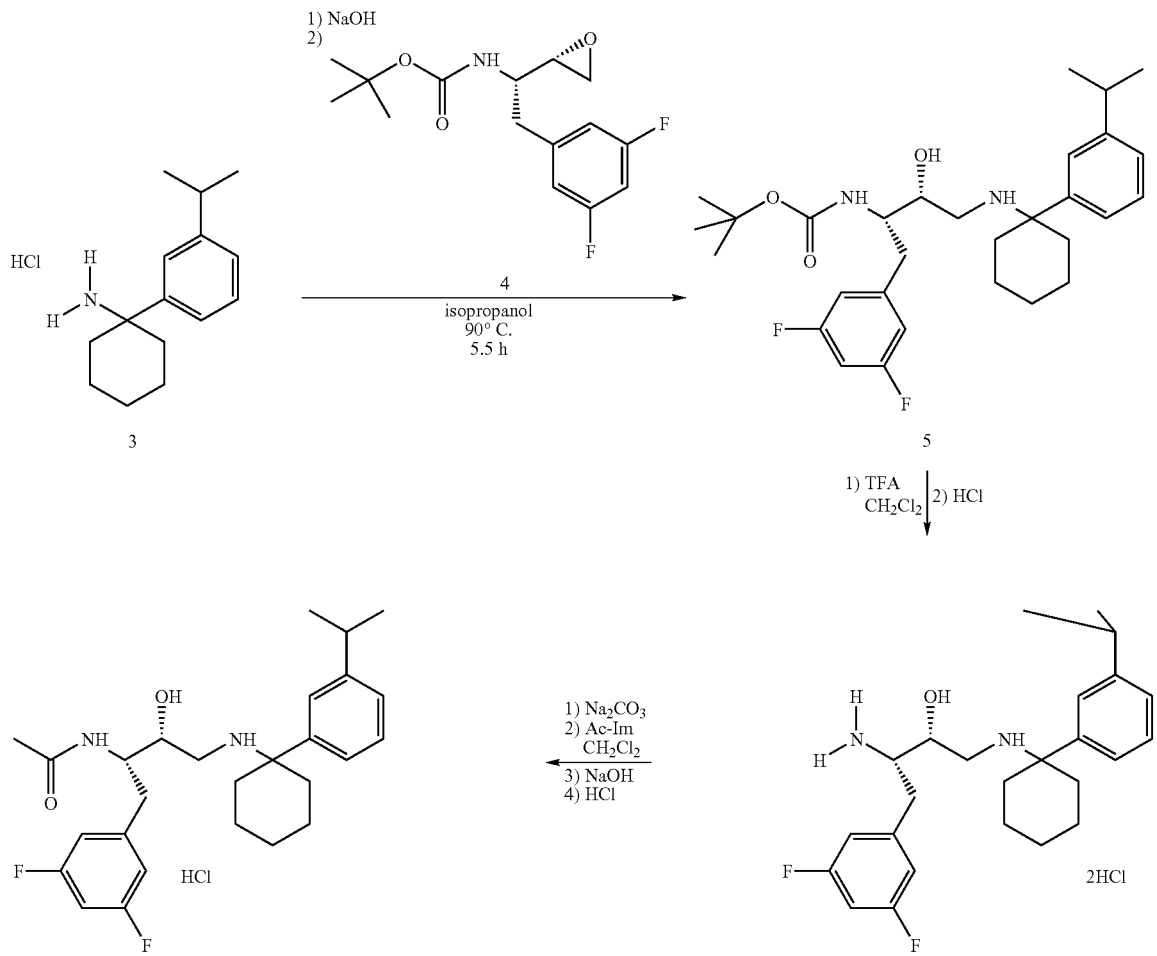

Step 1. Preparation of tert-butyl (1S,2R)-1-(3,5-difluorobenzyl)-2-hydroxy-3-{[1-(3-isopropylphenyl)cyclohexyl]amino}propylcarbamate (5)

Compound 3 (2.1 g, 8.3 mmol) is shaken with aqueous 1 N NaOH and ethyl acetate. The layers are separated and the organic phase is washed sequentially with aqueous NaOH and then with 1N NaHCO$_3$. The organic layer is then dried over Na$_2$SO$_4$, filtered, and concentrated to afford a quantitative yield (1.8 g) of the free amine as an oil. Example 134 (4, 1.5 g, 5.0 mmol) is combined with the free amine in 35 mL of isopropyl alcohol, and the mixture is heated at reflux for 5.5 h, under nitrogen. The mixture is cooled and concentrated in vacuo. The resulting residue is dissolved in 250 mL of ethyl ether, which is washed four times with 30 mL portions of aqueous 10% HCl to remove much of the excess amine 3. The ether phase is then washed twice with 1N NaHCO$_3$, once with brine, dried over Na$_2$SO$_4$, filtered, and concentrated. The concentrate is chromatographed over silica gel, eluting with 4% to 6% methanol (containing 2% NH$_4$OH) in CH$_2$Cl$_2$ to afford 1.98 g (3.8 mmol, 77%) of 5 as a viscous oil: $^1$H NMR (CDCl$_3$) δ 7.28-7.21 (m, 3H), 7.09 (m, 1H), 6.69 (m, 2H), 6.62 (m, 1H), 4.68 (d, J=10 Hz, 1H), 3.74 (m, 1H), 3.47 (m, 1H), 2.93-2.86 (m, 2H), 2.67 (dd, J=8, 14 Hz, 1H), 2.32 (m, 2H), 1.88 (m, 4H), 1.63-1.52 (m, 5H), 1.36 (s+m, 10H), 1.24 (d, J=7 Hz, 6H); MS (CI) m/z 517.4 (MH+).

Step 2. Preparation of (2R,3S)-3-amino-4-(3,5-difluorophenyl)-1-{[1-(3-isopropylphenyl)cyclohexyl]amino}butan-2-ol dihydrochloride 6

To 1.98 g (3.8 mmol) of compound 5 in 15 mL of CH$_2$Cl$_2$ is added 6.5 mL of trifluoroacetic acid. The mixture is stirred under a nitrogen atmosphere for 1 h and then concentrated. The resulting residue is taken up in ethyl acetate and washed twice with 10% Na$_2$CO$_3$ and once with 1 N NaHCO$_3$. The organic layer is dried over anhydrous Na$_2$SO$_4$, filtered, and concentrated to afford 1.6 g (quant.) of a pale yellow oil (free base of 6), which is generally carried on in the next step without characterization. The yellow oil may be dissolved in ether and treated with ethereal HCl to precipitate (dihydrochloride 6 as a white solid after trituration with ether: $^1$H NMR (CDCl$_3$+CD$_3$OD drop) δ 7.55 (s, 1H), 7.45-7.15 (m, 3H), 6.85 (m, 2H), 6.75 (m, 1H), 4.4 (d, J=9.5 Hz, 1H), 3.82 (m, 1H), 2.97 (m, 2H), 2.81 (dd, J=8, 14 Hz, 1H), 2.65 (m, 2H), 2.5 (obscured by water) 2.26 (m, 1H), 2.13 (m, 2H), 1.79 (m, 2H), 1.59 (m, 1H), 1.45-1.25 (m, 3H), 1.28 (d, J=7 Hz, 6H); MS (CI) m/z 417.3 (MH+).

Step 3. Preparation of N-((1S,2R)-1-(3,5-difluorobenzyl)-2-hydroxy-3-{[1-(3-isopropylphenyl)cyclohexyl]amino}propyl)acetamide hydrochloride 7

The free base of compound 6 (1.6 g, 3.8 mmol) is dissolved in 20 mL of CH$_2$Cl$_2$ under nitrogen, and 0.87 g (7.9 mmol) of acetyl imidazole is added with stirring. After 15 min., 30 mL of methanol is added, followed by 15 mL of 1 N NaOH to saponify the ester that is formed along with the amide. The CH$_2$Cl$_2$ is removed in vacuo, and the mixture is neutralized with 1N KH$_2$PO$_4$. The product is extracted into ethyl acetate and the organic phase is washed with water, with 1 N NaHCO$_3$, and with brine. The solution is dried over Na$_2$SO$_4$, filtered and concentrated to an oil, which is chromatographed over silica gel, eluting with 5%-7% methanol (containing 1% of NH$_4$OH) in CH$_2$Cl$_2$. Product-containing fractions are pooled, concentrated, dissolved in a small volume of ethanol, and acidified with 0.6 N HCl in dry ether. Concentration from this solvent mixture affords a gel-like material. This can be dissolved in ethanol and ethyl acetate, and concentrated to 1.65 g (3.3 mmol, 87%) an off-white solid. This solid is triturated with ethyl acetate to remove a pale yellow mother liquor, leaving hydrochloride 7 as a white solid: $^1$H NMR (CDCl$_3$+CD$_3$OD drop) δ 7.44 (s, 1H), 7.37 (m, 2H), 7.29 (m, 1H), 6.70 (m, 2H), 6.62 (m, 1H), 3.94 (m, 1H), 3.87 (m, 1H), 3.0-2.94 (m, 2H), 2.64 (m, 4H), 2.36 (m, 1H), 2.09 (m, 2H), 1.84 (s, 3H), 1.79 (m, 2H), 1.59 (m, 1H), 1.5-1.3 (m, 3 H), 1.27 (d, J=7 Hz, 6H); IR (diffuse reflectance) 3343, 3254, 2958, 2937, 2866, 2497, 2442, 2377, 1660, 1628, 1598, 1553, 1460, 1116, cm$^{-1}$. MS (EI) m/z (rel intensity) 458 (M+, 7), 415 (20), 230 (35), 202 (18), 201 (99), 200 (26), 159 (35), 157 (32), 133 (41), 129 (28), 117 (17). HRMS (ESI) calcd for C$_{27}$H$_{36}$N$_2$O$_2$F$_2$+H$_1$ 459.2823, found 459.2837. Anal. Calcd for C$_{27}$H$_{36}$F$_2$N$_2$O$_2$.HCl: C, 65.51; H, 7.53; N, 5.66; Cl, 7.16; F, 7.68. Found: C, 65.19; H, 7.70; N, 5.67. Found; Cl, 7.08.

EXAMPLE 71

Preparation of N-((1S,2R)-1-(3-(hexyloxy)-5-fluorobenzyl)-2-hydroxy-3-{[1-(3-isopropylphenyl)cyclohexyl]amino}propyl)acetamide hydrochloride 12

Scheme 3

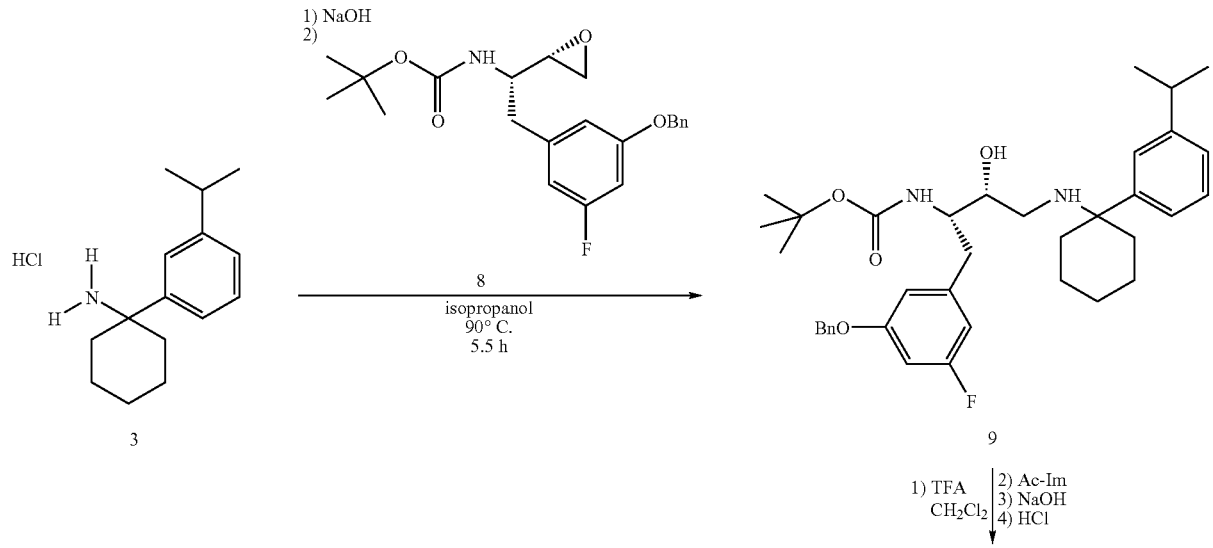

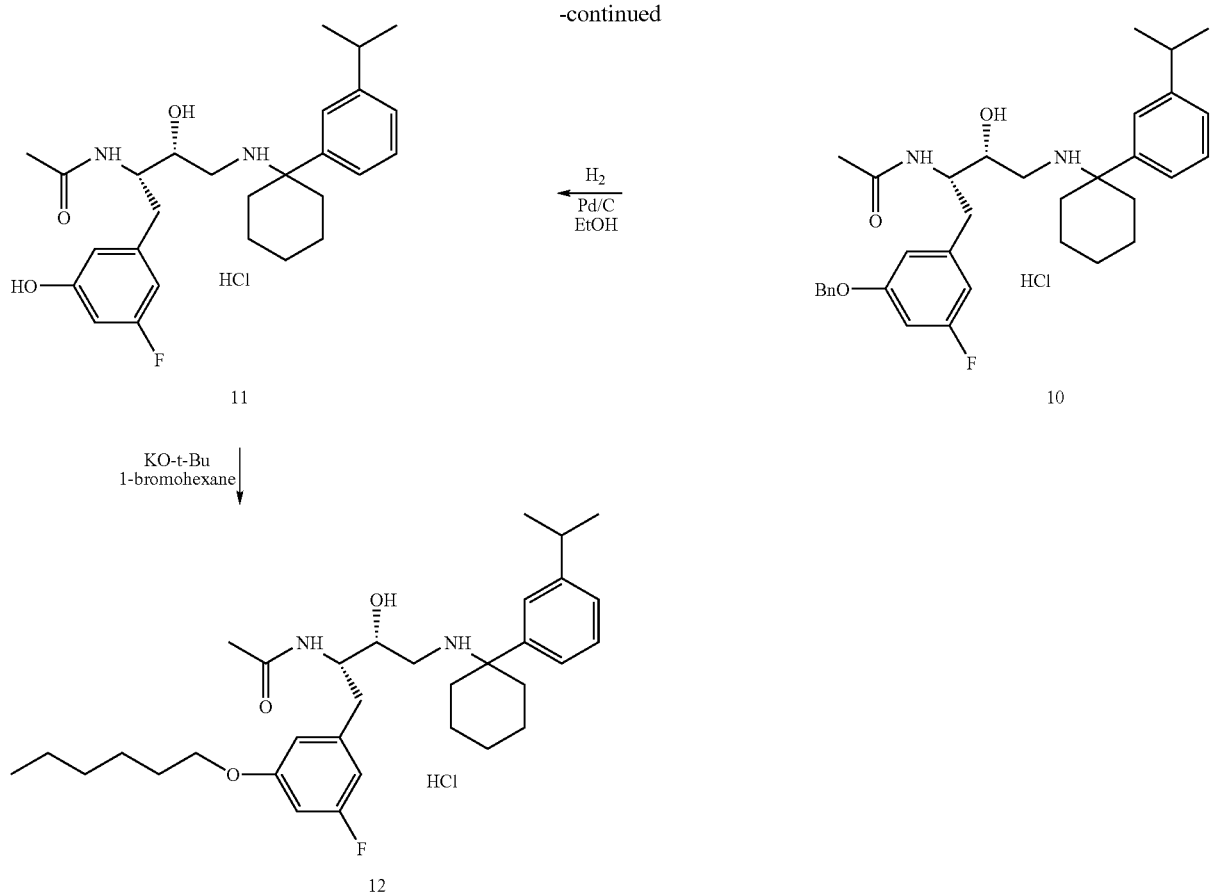

Step 1. Preparation of tert-butyl (1S,2R)-1-(3-(benzyloxy)-5-fluorobenzyl)-2-hydroxy-3-{[1-(3-isopropylphenyl)cyclohexyl]amino}propylcarbanate (9)

Following essentially the procedure described in Step 1 of EXAMPLE 70, the free base of compound 3 (3.9 mmol) is reacted with compound 8 (0.80 g, 2 mmol) in 20 mL of isopropyl alcohol at reflux overnight. After workup and chromatography over silica gel, eluting with 4% methanol (containing 2% NH$_4$OH) in CH$_2$Cl$_2$, compound 9 is obtained as a colorless syrup (0.92 g, 1.5 mmol, 74%): MS (CI) m/z 605.5 (MH+).

Step 2. Preparation of N-((1S,2R)-1-(3-(benzyloxy)-5-fluorobenzyl)-2-hydroxy-3-{[1-(3-isopropylphenyl)cyclohexyl]amino}propyl)acetamide hydrochloride (10)

Following essentially the procedures of Steps 2 and 3 of EXAMPLE 70, compound 9 (0.92 g, 1.5 mmol) is converted to hydrochloride 10, which is a white solid: $^1$H NMR (CDCl$_3$+CD$_3$OD drop) δ 7.46-7.25. (m, 9H), 6.26 (s, 1H), 6.53-6.47 (m, 2H), 5.00 (s, 2H), 4.01 (m, 1H), 3.88 (m, 1H), 2.98-2.89 (m, 2H), 2.68-2.62 (m, 4H), 2.3 (m, 1H, obscured by water), 2.14 (m, 2H), 1.88 (s, 3H), 1.78 (m, 2H), 1.58 (m, 1H), 1.5-1.3 (m, 3H), 1.26 (d, J=7 Hz, 6H); MS (CI) m/z 547.5 (MH+).

Step 3. Preparation of N-((1S,2R)-1-(3-hydroxy-5-fluorobenzyl)-2-hydroxy-3-{[1-(3-isopropylphenyl)cyclohexyl]amino}propyl)acetamide hydrochloride 11

To a solution of compound 10 (0.70 g, 1.2 mmol) in 70 mL of ethanol in a Parr bottle is added 0.33 g of 10% palladium on carbon. The mixture is placed under 20 psi of hydrogen and shaken for 21 h. The mixture is filtered and the catalyst is washed with ethanol. Concentration in vacuo affords a colorless oil, which is treated with ethereal HCl to give a quantitative yield of hydrochloride 11 as a white solid: $^1$H NMR (CDCl$_3$+CD$_3$OD drop) δ 7.44 (s, 1H), 7.37 (m, 2H), 7.28 (m, 1H), 6.59 (s, 1H), 6.40 (m, 1H), 6.31 (m, 1H), 4.0 (m, 1H), 3.79 (m, 1H), 2.95 (m, 2H), 2.63 (m, 4H), 2.44 (m, 1H), 2.05 (m, 2H), 1.90 (s, 3H), 1.79 (m, 2H), 1.59 (m, 1H), 1.5-1.3 (m, 3H), 1.26 (d, J=7 Hz, 6H); MS (CI) m/z 457.4 (MH+).

Step 4. Preparation of N-((1S,2R)-1-(3-(hexyloxy)-5-fluorobenzyl)-2-hydroxy-3-{[1-(3-isopropylphenyl)cyclohexyl]amino}propyl)acetamide hydrochloride 12

To 0.40 mmol of hydrochloride 11 in 3 mL of acetone is added 0.29 mL (2.1 mmol) of 1-bromohexane. The mixture is heated to reflux, and 0.6 mL of a 1 M solution of potassium t-butoxide in THF (0.6 mmol) is added. After 1.2 h the mixture is cooled and aqueous 1 N KH$_2$PO$_4$ and ethyl acetate are added. The organic phase is washed twice with 1 N NaHCO$_3$ and once with brine, dried over Na₂SO₄, and concentrated. Chromatography over silica gel, eluting with 7%-9& methanol (containing 1% of NH₄OH) in CH₂Cl₂, affords a colorless oil. Treatment with ethereal HCl produces 147 mg (0.25 mmol, 64%) of hydrochloride 12 as a white solid: $^1$H NMR (CDCl₃+CD₃OD drop) δ 7.45 (s, 1H), 7.37 (m, 2H), 7.27 (m, 1H), 6.50 (s, 1H), 6.43 (m, 2H), 3.98 (m, 1H), 3.88 (m+t, J=6.5 Hz, 3H), 2.93 (m, 2H), 2.63 (m, 4H), 2.38 (m, 1H), 2.09 (m, 2H), 1.89 (s, 3H), 1.75 (m, 4H), 1.59 (m, 1H), 1.43-1.32 (m, 10H), 1.27 (d, J=7 Hz, 6H), 0.90 (t, J=7 Hz, 3H); MS (CI) m/z 541.5 (MH+).

EXAMPLE 72

Preparation of tert-butyl (1S)-2-[4-(benzyloxy)-3 fluorophenyl]-1-[(2S)-oxiran-2-yl]ethylcarbamate 17 treated with 15 decolorizing charcoal. Filtration and evaporation affords 1-benzyloxy-2-fluoro-4-bromobenzene 13 (13.7 g, 49 mmol, 83%) as a colorless oil which crystallizes to a white solid: $^1$H NMR (CDCl₃) δ 7.43-7.33 (m, 5H), 7.24 (dd, J=2.3, 10 Hz, 1H), 7.14 (dt, J=2, 8.7 Hz, 1H), 6.86 (t, J=8.7 Hz, 1H), 5.12 (s, 2H).

Step 2. Preparation of tert-butyl (1S)-2-(4-(benzyloxy)-3-fluorophenyl)-1-[(4S)-2,2-dimethyl-1,3-dioxolan-4-yl]ethylcarbamate (15)

A solution of 1-benzyloxy-2-fluoro-4-bromobenzene 13 (7.0 g, 25 mmol) in 20 mL of dry THF is added dropwise over 20 min to 1.22 g (50 mmol) of magnesium turnings in 10 mL of refluxing THF under nitrogen and the mixture is refluxed

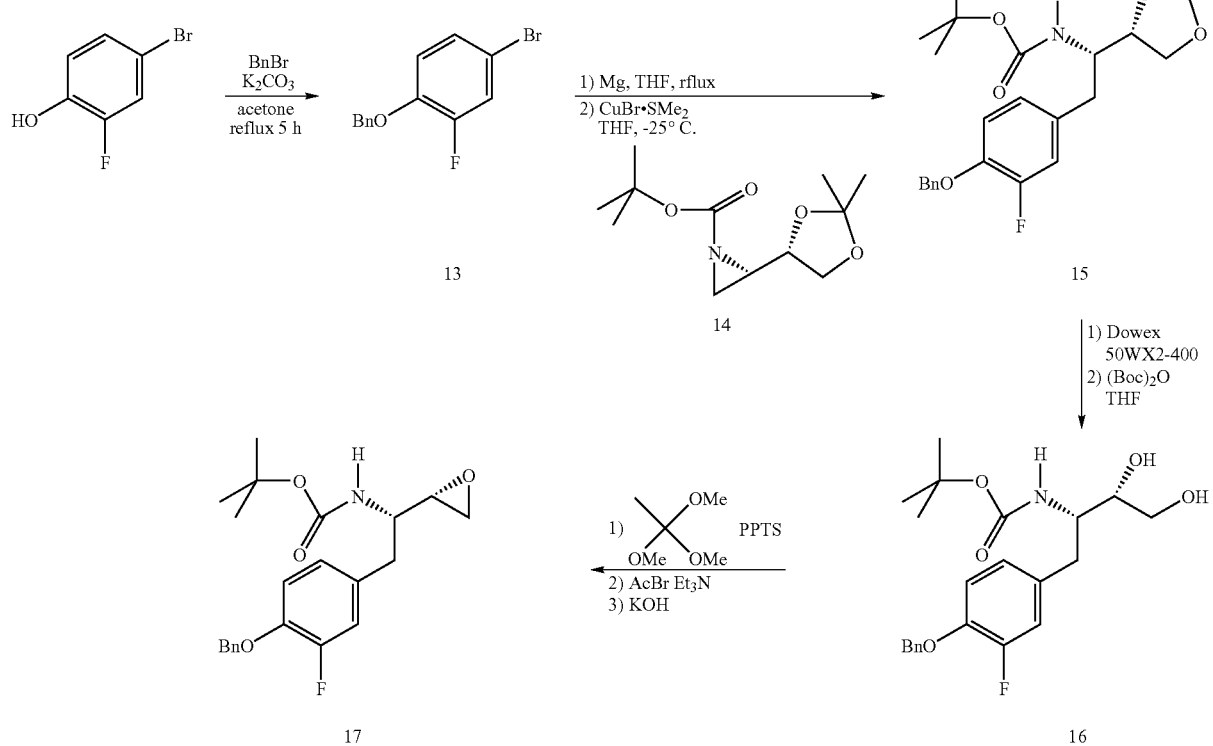

Scheme 4

Step 1. Preparation of 1-Benzyloxy-2-fluoro-4-bromobenzene 13.

To a stirred suspension of pulverized K₂CO₃ (49 g, 350 mmol) in 250 mL of acetone is added 6.5 mL (11.3 g, 59 mmol) of 2-fluoro-4-bromophenol and 7 mL (10 g, 59 mmol) of benzyl bromide. The mixture is refluxed under nitrogen 5 h. It is cooled and filtered, washing the residual K₂CO₃ with acetone. Removal of the solvent leaves 17 g of an off-white solid. This is triturated twice with hexanes, redissolved in 250 mL of CH₂Cl₂, and washed successively with 10% Na₂CO₃, water, and brine. The organic phase is dried over Na₂SO₄ and for an additional 25 min to form the Grignard reagent. The Grignard solution is cooled and added by cannula to a suspension of CuBr-dimethylsulfide complex (0.52 g, 2.5 mmol) in 15 mL of dry THF at −25° C. The brown suspension is stirred at −25° C. for 20 min, and then a solution of tert-butyl (2R)-2-[(4S)-2,2-dimethyl-1,3-dioxolan-4-yl]aziridine-1-carboxylate 14 (3.4 g, 14 mmol) in 15 mL of THF is added dropwise over 5 min. The mixture is allowed to gradually warm to ambient temperature over 3 h. Saturated aqueous NH₄Cl and ethyl ether are added, and the organic phase is washed with two more portions of saturated NH₄Cl and once with brine. The solution is dried over Na₂SO₄ and treated with decolorizing carbon. Filtration and concentration gives a yellow solid, which is triturated twice with ether/heptane to afford 5.4 g (12 mmol, 86%) of compound 15 as a cream-colored solid: MS (CI) m/z 468.3 (MNa+), 446.3 (MH+).

Step 3. Preparation of tert-butyl (1S,2S)-1-[4-(benzyloxy)-3-fluorobenzyl]-2,3-dihydroxypropylcarbamate 16

To a solution of crude (combined solid and mother liquor) compound 15 (maximum 14 mmol) in 90 mL of methanol is added 12 g of Dowex 50WX2-400 which has been extensively washed with water, methanol, and $CH_2Cl_2$, and air-dried. The mixture is warmed to 50° C. and stirred for 2 h. It is filtered, washing first with methanol and a 1:1 mixture of methanol and $CH_2Cl_2$. The receiver is then changed and the product is eluted from the resin with 1:1 methanol:$CH_2Cl_2$ containing 10% of $NH_4OH$. The filtrate is concentrated to afford 2.7 g of a white solid. This solid is dissolved in 60 mL of dry THF under nitrogen, cooled to 0° C., and 2.0 g (9.2 mmol) of di-tert-butyldicarbonate is added. The ice bath is removed and the mixture is stirred at ambient temperature for 18 h. It is concentrated and chromatographed over silica gel, eluting with 49:49:2 to 58:38:4 ethyl acetate:heptane:methanol, affording 3.0 g (7.4 mmol, 53%, two steps) of compound 16 as a white solid: $^1$H NMR (CDCl$_3$) δ 7.45-7.30 (m, 5H), 7.01-6.88 (m, 3H), 5.12 (s, 2H), 4.52 (d, J=9 Hz, 1H), 3.78 (m, 1H), 3.62 (m, 2H), 3.32 (m, 2H), 3.02 (dd, J=4, 14 Hz, 1H), 2.82 (m, 2H), 1.39 (s, 9H); MS (CI) m/z 428.2 (MNa+), 406.3 (MH+).

Step 4. Preparation of tert-butyl (1S)-2-[4-(benzyloxy)-3 fluorophenyl]-1-[(2S)-oxiran-2-yl]ethylcarbamate (17)

Trimethyl orthoacetate (0.94 mL, 7.4 mmol) is added to a suspension of compound 16 (2.9 g, 7.2 mmol) in 30 mL of $CH_2Cl_2$ stirred under nitrogen. Pyridinium p-toluenesulfonate (18 mg, 0.07 mmol) is added and the resulting pale yellow solution is stirred for 30 min and then concentrated to a white solid. This solid is dissolved in 30 mL of $CH_2Cl_2$, triethylamine (0.10 mL, 0.72 mmol) is added, and the mixture, under nitrogen, is cooled in an ice bath. Freshly distilled acetyl bromide (0.55 mL, 7.4 mmol) is added dropwise over 3-4 min with stirring. After 1 h, the ice bath is removed and aqueous 1 N NaHCO$_3$ and CH$_2$Cl$_2$ are added. The aqueous phase is extracted with additional CH$_2$Cl$_2$ and the combined organic phases are dried over MgSO$_4$ and concentrated to a white solid. This solid is suspended in 25 mL of methanol and 6 mL of THF, and cooled in an ice bath, under nitrogen. Pulverized KOH (0.60 g, 11 mmol) in 6 mL of methanol is added all at once. After 15 min the ice bath is removed and the mixture is allowed to come to ambient temperature over 70 min. The mixture is concentrated and taken up in ethyl acetate and aqueous 1N KH$_2$PO$_4$. The organic phase is washed with 1N NaHCO$_3$ and then brine, dried over Na$_2$SO$_4$, and concentrated. Chromatography over silica gel, eluting with 20% ethyl acetate and 5% to 10% CH$_2$Cl$_2$ in heptane affords 2.0 g (5.2 mmol, 72%) of compound 17 as a white solid: $^1$H NMR (CDCl$_3$) δ 7.45-7.30 (m, 5H), 6.99-6.86 (m, 3H), 5.12 (s, 2H), 4.43 (br, 1H), 3.63 (br, 1H), 2.90 (m, 2H), 2.79 (m, 2H), 2.74 (m, 1H), 1.39 (s, 9H); MS (CI) m/z 410.3 (MNa+), 388.3 (MH+).

EXAMPLE 73

Preparation of N-((1S,2R)-1-(3-fluoro-4-hydroxybenzyl)-2-hydroxy-3-{[1-(3-isopropylphenyl)cyclohexyl]amino}propyl)acetamide hydrochloride 20

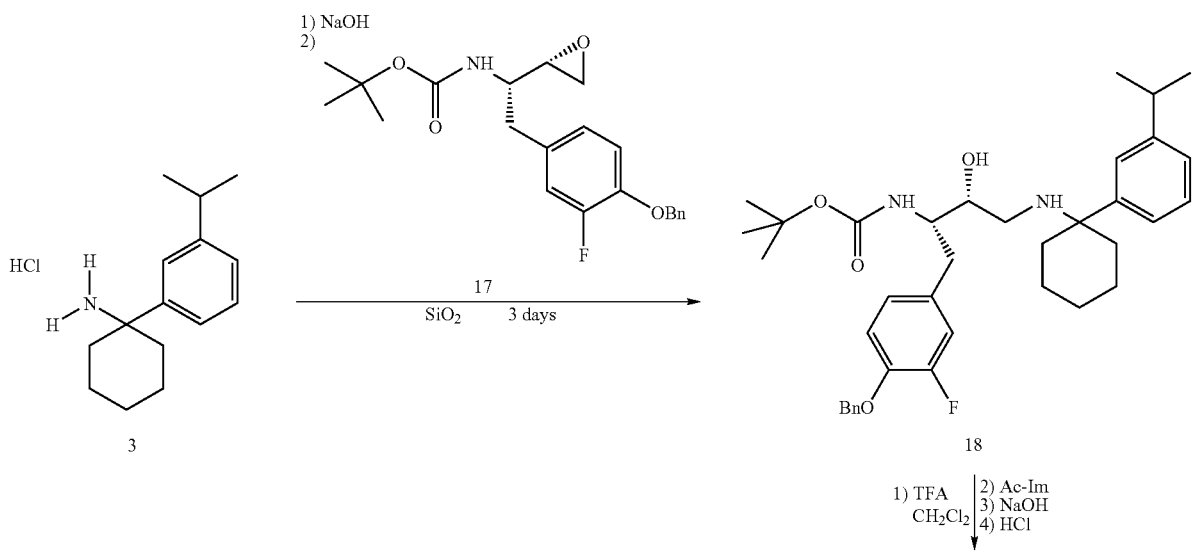

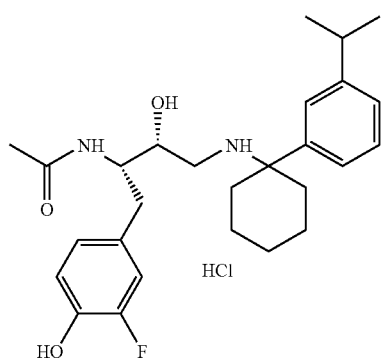

20

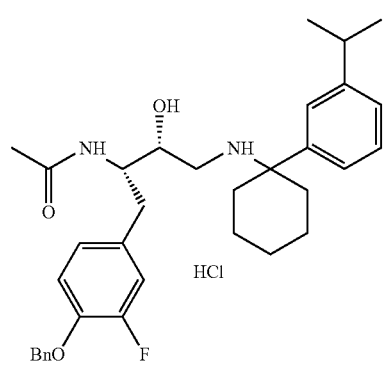

19

Step 1. Preparation of tert-butyl (1S,2R)-1-(3-fluoro-4-(benyloxy)benzyl)-2-hydroxy-3-{[1-(3-isopropylphenyl)cyclohexyl]amino}propylcarbamate (18)

The free base (270 mg, 1.24 mmol) of 1-(3-isopropylphenyl)cyclohexanamine hydrochloride 3 is obtained as a colorless oil by neutralization of the salt with 1N NaOH, extraction into ethyl acetate, drying over $Na_2SO_4$, and concentration. This is dissolved in 10 mL of $CH_2Cl_2$, and to it is added compound 17 (280 mg, 0.73 mmol) and 1.25 g of silica gel. The solvent is removed in vacuo and the reactants on silica are allowed to stand at ambient temperature for three days. The product mixture is eluted from the silica with 10% methanol in $CH_2Cl_2$, concentrated, and chromatographed on silica gel, eluting with 4% methanol (containing 2% $NH_4OH$) in $CH_2Cl_2$, to afford compound 18 (238 mg, 0.39 mmol, 54%) as a colorless oil: $^1H$ NMR ($CDCl_3$) δ 7.43-7.26 (m, 8H), 7.12 (m, 1H), 6.94-6.84 (m, 3H), 5.09 (s, 2H), 4.64 (d, J=9 Hz, 1H), 3.80 (br, 1H), 3.31 (br, 1H), 2.92-2.83 (m, 2H), 2.7 (m, 1H), 2.37 (m, 2H), 2.0-1.95 (m, 4H), 1.67-1.50 (m, 5H), 1.35 (s+m, 10H), 1.25 (d, J=7 Hz, 6H).

Step 2. Preparation of N-((1S,2R)-1-(3-fluoro-4-(benzyloxy)benzyl)-2-hydroxy-3-{[1-(3-isopropylphenyl)cyclohexyl]amino}propyl)acetamide hydrochloride (19)

Following essentially the procedures of Steps 2 and 3 of EXAMPLE 70, compound 18, (0.238 g, 0.39 mmol) as prepared in step 1, above, is deprotected with trifluoroacetic acid and reacted with an excess of acetyl imidazole. This is followed by alkaline hydrolysis to afford, after workup and chromatography over silica gel, eluting with 7%-10% methanol (containing 1% $NH_4OH$) in $CH_2Cl_2$, and conversion to the HCl salt, 0.19 g (0.32 mmol, 75%) hydrochloride 19 as a white solid: MS (CI) m/z 547.5 (MH+).

Step 3. Preparation of N-((1S,2R)-1-(3-fluoro-4-hydroxybenzyl)-2-hydroxy-3-{[1-(3-isopropylphenyl)cyclohexyl]amino}propyl)acetamide hydrochloride 20

Following essentially the procedure of EXAMPLE 71, Step 3, the product from step 2, compound 19, (0.19 g, 0.32 mmol) is deprotected under 20 psi of $H_2$ in the presence of 54 mg of 10% palladium on carbon in 3.5 h, affording, after filtration, concentration and treatment with ethereal HCl, 20 (0.16 g, 0.32 mmol, quant.) as a cream-white solid: $^1H$ NMR ($CDCl_3+CD_3OD$ drop) δ 7.43-7.27 (m, 4H), 6.86-6.77 (m, 3H), 3.95 (br, 1H), 3.8 (br, 1H), 2.93 (m, 2H), 2.6 (m, 4H), 2.4 (m, 1H), 2.06 (m, 2H), 1.85 (s, 3H), 1.8 (m, 2H), 1.59 (m, 1H), 1.5-1.3 (m, 3H), 1.27 (d, J=7 Hz, 6H); IR (diffuse reflectance) 3251, 3113, 3087, 3061, 3053, 3028, 2956, 2941, 2865, 2810, 1645, 1596, 1520, 1446, 1294 cm −1. MS (CI) m/z (rel intensity) 457 (MH+,99), 459 (5), 458 (25), 457 (99), 439 (3), 257 (7), 218 (5), 202 (3), 201 (9), 96 (4), 77 (3). HRMS (ESI) calcd for $C_{27}H_{37}N_2O_3F+H_1$ 457.2866, found 457.2855. Anal. Calcd for $C_{27}H_{37}FN_2O_3 \cdot HCl \cdot 1.5 H_2O$: C, 62.35; H, 7.95; N, 5.39; Found: C, 62.63; H, 7.76; N, 5.47.

EXAMPLE 74

Preparation of 8-(3-isopropylphenyl)-1,4-dioxa-spiro[4.5]decane-8-amine acetate 23

Scheme 6

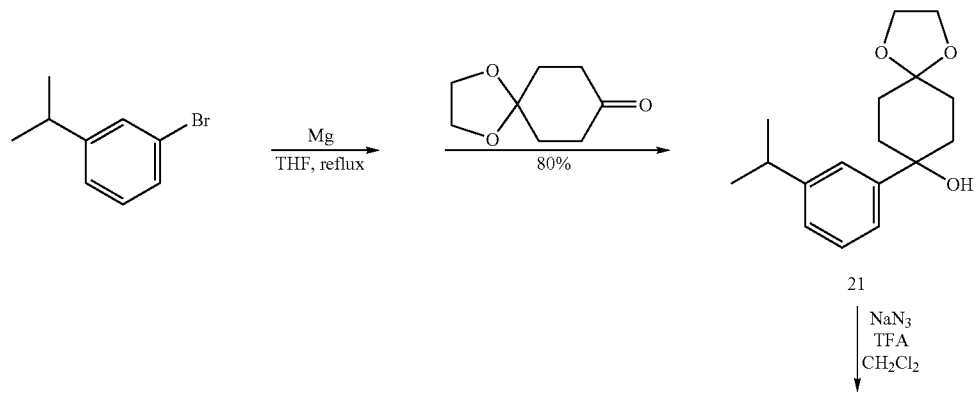

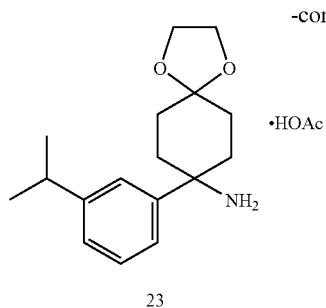
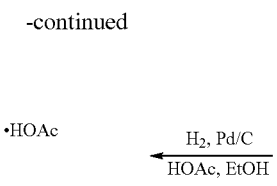
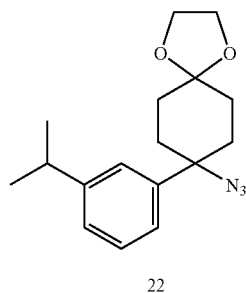

Step 1. Preparation of 8-(3-isopropylphenyl)-1,4-dioxa-spiro[4.5]decane-8-alcohol (21)

Following essentially the procedure described in EXAMPLE 72, Step 2, the Grignard reagent formed from 3-bromoisopropylbenzene (25 mmol) is reacted with 1,4-cyclohexanedione, monoethylene ketal (3.9 g, 25 mmol) to afford, after chromatography over silica gel, eluting with 20% to 30% ethyl acetate in heptane, alcohol 21 (5.6 g, 20 mmol, 80%) as a colorless oil which crystallizes to a white solid on cooling: $^1$H NMR (CDCl$_3$) δ 7.39 (s, 1H), 7.33 (m, 1H), 7.28 (t, J=7.5 Hz, 1H), 7.13 (d, J=7.5 Hz, 1H), 4.0 (m, 4H), 2.91 (hept, J=7 Hz, 1H), 2.15 (m, 4H), 1.82 (br d, J=11.5 Hz, 2H), 1.70 (br d, J=11.5 Hz, 2H), 1.25 (d, J=7 Hz, 6H); MS (CI) m/z 259.2 (M−OH).

Step 2. Preparation of 8-(3-isopropylphenyl)-1,4-dioxa-spiro[4.5]decane-8-azide (22)

Following essentially the procedure described in EXAMPLE 69, Step 2, alcohol 21 (5.5 g, 20 mmol) is converted to the azide 22. The resulting crude material is purified by silica gel chromatography, eluting with 3% acetone in heptane. Concentration of the product-containing fractions affords 2.2 g (7.3 mmol, 36%) of compound 22 as a colorless oil: $^1$H NMR (CDCl$_3$) δ 7.33-7.26 (m, 3H), 7.17 (m, 1H), 3.98 (m, 4H), 2.92 (hept, J=7 Hz, 1H), 2.2-2.12 (m, 2H), 2.07-1.95 (m, 4H), 1.72 (m, 2H), 1.26 (d, J=7 Hz, 6H).

Step 3. Preparation of 8-(3-isopropylphenyl)-1,4-dioxa-spiro[4.5]decane-8-amine acetate 23

Following essentially the procedure described in EXAMPLE 69, Step 3, 2.2 g (7.3 mmol) of compound 22 in 200 mL of ethanol is reduced under 16 psi of hydrogen in the presence of 0.7 g of 10% palladium on carbon for 4.5 h. Filtration and removal of solvents with a toluene azeotrope affords a white solid which is triturated with pentane to yield 2.14 g (6.4 mmol, 87%) of compound 23 as a white solid: $^1$H NMR (CDCl$_3$) δ 7.37-7.33 (m, 2H), 7.30-7.26 (m, 1H), 7.13 (d, J=7.5 Hz, 1H), 5.91 (br, 3H), 3.96 (m, 4H), 2.90 (hept., J=7 Hz, 1H), 2.32 (m, 2H), 2.03 (s, 3H), 2.0-1.85 (m, 4H), 1.63 (m, 2H), 1.25 (d, J=7 Hz, 6H); MS (CI) m/z 259.2 (M−NH$_2$).

EXAMPLE 75

Preparation of N-((1S,2R)-1-(3,5-difluorobenzyl)-2-hydroxy-3-{[1-(3-isopropylphenyl)cyclohexan-4-one]amino}propyl) acetamide 26

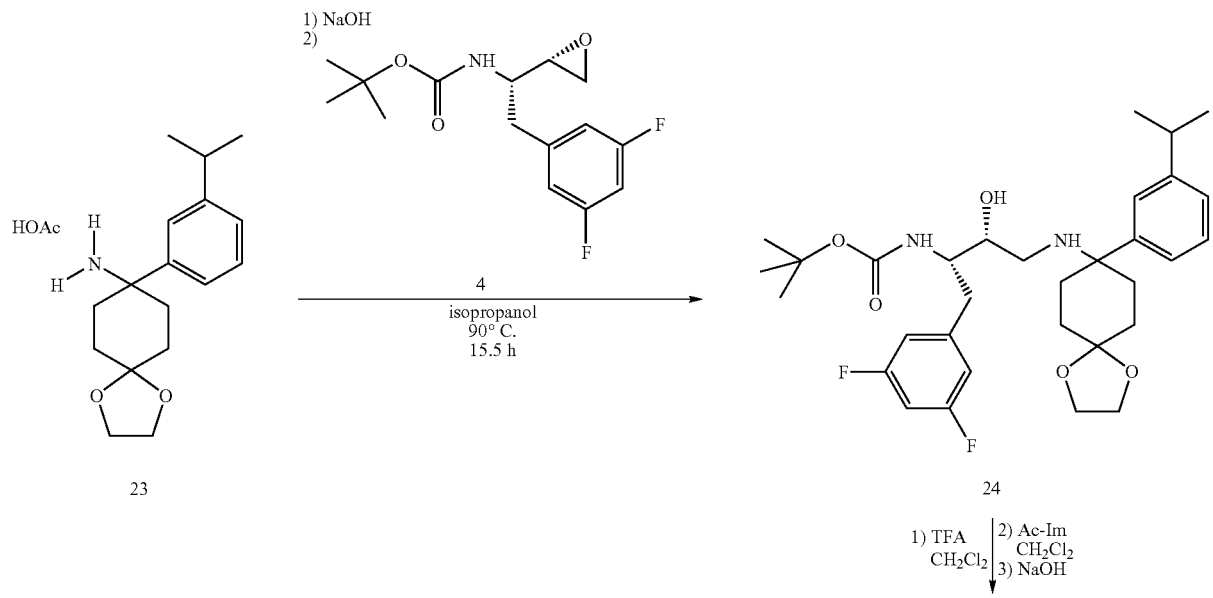

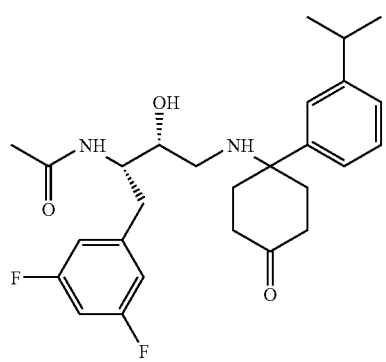

26

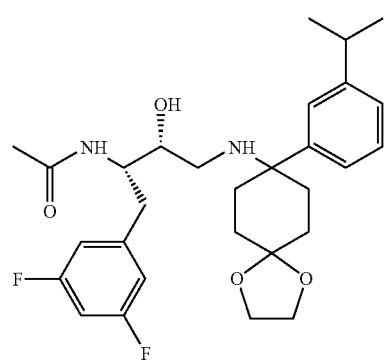

25

Step 1. Preparation of tert-butyl (1S,2R)-1-(3,5-difluorobenzyl)-2-hydroxy-3-{8-(3-isopropylphenyl)-1,4-dioxa-spiro[4.5]decane-8-amino}propyl carbamate (24)

Following essentially the procedure of EXAMPLE 70, compound 23 (3.2 mmol) is neutralized and reacted with Example 134 (4, 0.6 g, 2.0 mmol) in refluxing isopropanol (15 mL) for 15.5 h. The reaction mixture is concentrated and chromatographed over silica gel, eluting with 4% methanol (containing 2% of $NH_4OH$) in $CH_2Cl_2$ to separate the crude product from excess 8-(3-isopropylphenyl)-1,4-dioxa-spiro [4.5]decane-8-amine. The crude product is then re-chromatographed over silica gel, eluting with 10% to 20% acetone in $CH_2Cl_2$ to afford 0.600 g (1.04 mmol, 52%) of compound 24 as a colorless oil: $^1$H NMR ($CDCl_3$) δ 7.27-7.20 (m, 3H), 7.09 (d, J=7 Hz, 1H), 6.69 (m, 2H), 6.63 (m, 1H), 4.64 (d, J=9 Hz, 1H), 3.95 (m, 4H), 3.72 (m, 1H), 3.28 (m, 1H), 2.88 (m, 2H), 2.69 (dd, J=8.5, 14 Hz, 1H), 2.32 (m, 2H), 2.15 (m, 2H), 1.99-1.86 (m, 4H), 1.63 (m, 2H), 1.35 (s, 9H), 1.24 (d, J=7 Hz, 6H); MS (CI) m/z 575.4 (MH+)

Step 2. Preparation of N-((1S,2R)-1-(3,5-difluorobenzyl)-2-hydroxy-3-{8-(3-isopropylphenyl)-1,4-dioxa-spiro[4.5]decane-8-amino}propyl) acetamide (25)

Following essentially the procedures described in EXAMPLE 70, Steps 2 and 3, compound 24 (0.600 g, 1.04 mmol) is deprotected, acetylated, and saponified to afford, after chromatography on silica gel, eluting with 32.5% acetone and 2.5% methanol in $CH_2Cl_2$, acetamide 25 (335 mg, 0.65 mmol, 62%) as a white solid: $^1$H NMR ($CDCl_3$) δ 7.31-7.26 (m, 3H), 7.15 (m, 1H), 6.69-6.61 (m, 3H), 5.9 (br, 1H), 4.13 (m, 1H), 3.95 (m, 4H), 3.48 (m, 1H), 2.92-2.83 (m, 2H), 2.73 (dd, J=8.5, 14 Hz, 1H), 2.45-2.25 (m, 4H), 2.10 (m, 2H), 1.88 (s+m, 5H), 1.62 (m, 2H), 1.25 (d, J=7 Hz, 6H); MS (CI) m/z 517.4 (MH+).

Step 3. Preparation of N-((1S,2R)-1-(3,5-difluorobenzyl)-2-hydroxy-3-{[1-(3-isopropylphenyl)cyclohexan-4-one]amino}propyl)acetamide 26

To acetamide 25 (255 mg, 0.49 mmol) in 5 mL of ethanol and 5 mL of water is added 6 mL of trifluoroacetic acid, and the mixture is refluxed for 2 h under nitrogen. It is concentrated and taken up in aqueous 10% $Na_2CO_3$ and ethyl acetate. The organic phase is washed twice more with 10% $Na_2CO_3$ and then with brine. It is dried over $Na_2SO_4$, and concentrated to a colorless oil. Evaporation in vacuo from ethyl ether affords compound 26 (140 mg, 0.30 mmol, 60%) as a white solid: $^1$H NMR ($CDCl_3$) δ 7.35-7.18 (m, 4H), 6.71-6.64 (m, 3H), 5.65 (br, 1H), 4.12 (m, 1H), 3.43 (m, 1H), 2.95-2.90 (m, 2H), 2.75 (dd, J=8.5, 14 Hz, 1H), 2.64 (m, 2H), 2.4-2.25 (m, 8H), 1.87 (s, 3H), 1.25 (d, J=7 Hz, 6H); MS (CI) m/z 473.4 (MH+). The LC-MS spectrum in methanol solvent shows a small signal at 505.4 (MH+$CH_3OH$) due to hemiketal formation. IR (diffuse reflectance) 3311, 2958, 1710, 1646, 1628, 1595, 1550, 1544, 1460, 1372, 1315, 1116, 983, 846, 707 $cm^{-1}$. MS (EI)m/z(rel intensity) 472 (M+, 6), 472 (6), 417 (5), 416 (33), 415 (99), 398 (8), 397 (30), 327 (11), 244 (9), 215 (13), 214 (6). HRMS (ESI) calcd for $C_{27}H_{34}N_2O_3F_2+H_1$ 473.2615, found 473.2627. Anal. Calcd for $C_{27}H_{34}F_2N_2O_3+0.5$ $H_2O$: C, 67.34; H, 7.33; N, 5.82; Found (av): C, 67.89; H, 7.32; N, 5.86.

EXAMPLE 76

Preparation of N-[(1S,2R)-3-{[1-(3-bromophenyl)-1-methylethyl]amino}-1-(3,5-difluorobenzyl)-2-hydroxypropyl]acetamide 32

Scheme 8

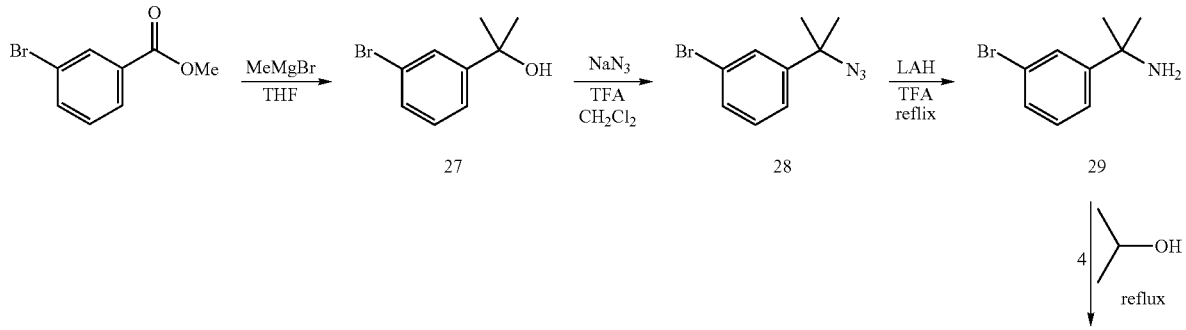

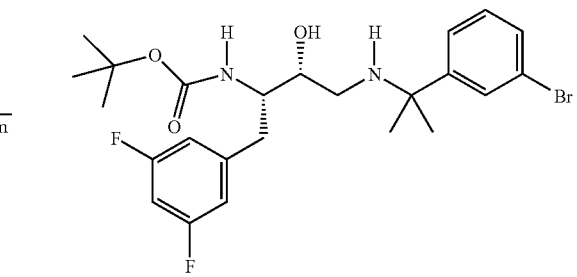

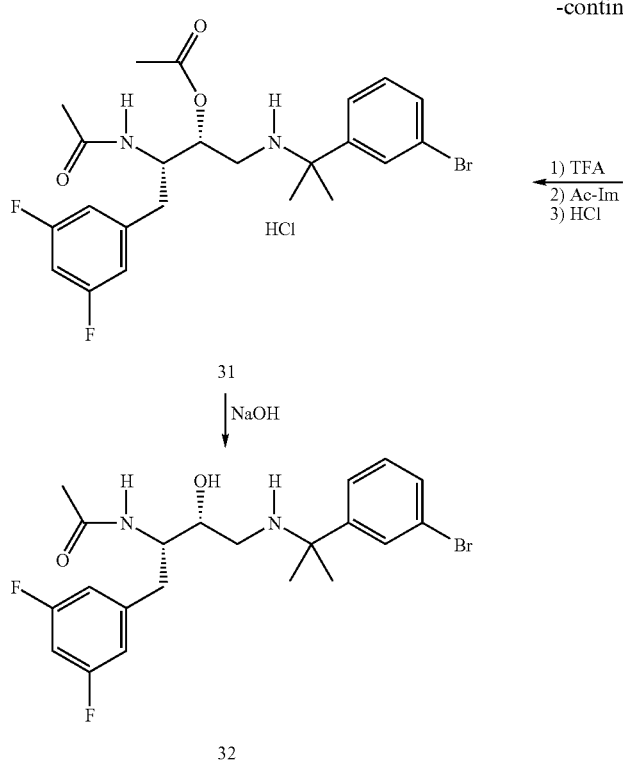

Step 1. Preparation of 2-(3-bromophenyl)-2-propanol 27

To 75 mmol of methylmagnesium bromide in 25 mL of ether stirring at 6° C. is added, dropwise over 10 min, a solution of methyl-3-bromobenzoate (4.3 g, 20 mmol) in 25 mL of dry THF. The mixture is then allowed to warm to ambient temperature and stirred for 3.5 h, then cooled to 0° C. and quenched by dropwise addition of aqueous 10% HCl. The acidified mixture is extracted twice with ethyl acetate, and the combined organic phases are washed with 1 N NaHCO$_3$ and with brine. The solution is dried over Na$_2$SO$_4$, concentrated, and chromatographed over silica gel, eluting with 15% ethyl acetate in heptane, to afford 4.00 g (18.6 mmol, 93%) of 2-(3-bromophenyl)-2-propanol 27 as a pale yellow oil: $^1$H NMR (CDCl$_3$) δ 7.65 (t, J=2 Hz, 1H), 7.39 (m, 2H), 7.20 (t, J=8 Hz, 1H), 1.78 (br s, 1H), 1.57 (s, 6H).

Step 2. Preparation of 2-(3-bromophenyl)-2-propylazide (28)

The above compound was prepared by essentially according to the method of Example 12. The crude product was purified by chromatography over silica gel, eluting with heptane, and thereby affording compound 28 as a colorless oil: $^1$H NMR (CDCl$_3$) δ 7.58 (t, J=2 Hz, 1H), 7.74-7.36 (m, 2H), 7.24 (t, J=8 Hz, 1H), 1.62 (s, 6H).

Step 3. Preparation of 2-(3-bromophenyl)-2-propylamine 29

The above compound was prepared essentially according to the method of Example 10. The crude product was purified by chromatography over silica gel, eluting with 6% methanol (containing 1% NH$_4$OH) in CH$_2$Cl$_2$ to afford compound 29 (7 mmol, 50%) as a pale amber oil: $^1$H NMR (CDCl$_3$) δ 7.67 (t, J=2 Hz, 1H), 7.43 (m, 1H), 7.35 (m, 1H), 7.20 (t, J=8 Hz, 1H), 1.68 (br s, 2H), 1.48 (s, 6H).

Step 4. Preparation of 2-(3-bromophenyl)-2-propylamine hydrochloride

To 2-(3-bromophenyl)-2-propylamine 29 in ether is added ethereal HCl. Solvent removal affords a tan solid, which is dissolved in a small volume of ethanol and diluted with ethyl acetate. The tan crystals which form are filtered to afford 2-(3-bromophenyl)-2-propylamine hydrochloride: $^1$H NMR (CDCl$_3$+CD$_3$OD drop) δ 7.65 (n m, 1H), 7.51 (app t, 2H), 7.32 (m, 1H), 1.77 (s, 6H); MS (CI) m/z 214.0 (MH+)

Step 5. Preparation of tert-butyl (1S,2R)-3-{[1-(3-bromophenyl)-1-methylethyl]amino}-1-(3,5-difluorobenzyl)-2-hydroxypropylcarbamate 30

The above compound was prepared essentially according to the method of example 17, step 3. Purification of the crude material over silica gel, eluting with 4% to 6% of methanol (containing 1% of NH$_4$OH) in CH$_2$Cl$_2$ affords 365 mg (0.71 mmol, 69%) of compound 30 as a colorless oil: $^1$H NMR (CDCl$_3$) δ 7.52 (m, 1H), 7.35 (m, 2H), 7.19 (t, J=8 Hz, 1H), 6.73 (m, 2H), 6.64 (m, 1H), 4.54 (d, J=9 Hz, 1H), 3.73 (m, 1H), 3.29 (m, 1H), 2.99 (dd, J=4, 14 Hz, 1H), 2.73 (dd, J=8.5, 14 Hz, 1H), 2.46-2.35 (m, 2H), 1.45 (s, 6H), 1.37 (s, 9H); MS (CI) m/z 514.2 (MH+).

Step 6. Preparation of (1R,2S)-2-(acetylamino)-1-({[1-(3-bromophenyl)-1-methylethyl]amino}methyl)-3-(3,5-difluorophenyl)propyl acetate hydrochloride 31

To 365 mg (0.71 mmol) of tert-butyl (1S,2R)-3-{[1-(3-bromophenyl)-1-methylethyl]amino}-1(3,5-difluorobenzyl)-2-hydroxypropylcarbamate 30 in 2 mL of $CH_2Cl_2$ is added 1 mL of trifluoroacetic acid, and the mixture is stirred for 30 min. It is concentrated in vacuo, diluted with ethyl acetate, and washed with 10% $Na_2CO_3$ and then brine. The solution is dried over $Na_2SO_4$, filtered and concentrated to a colorless oil. This is dissolved in 3 mL of $CH_2Cl_2$ and 172 mg (1.56 mmol) of acetyl imidazole is added. After 2.5 h the mixture is concentrated and taken up in ethyl acetate and 1 N $KH_2PO_4$. The organic phase is washed with 1N $KH_2PO_4$, with brine, dried over $Na_2SO_4$, concentrated, and chromatographed over silica gel. Elution with 4% methanol (containing 1% of $NH_4OH$) in $CH_2Cl_2$ affords a sticky solid. This is dissolved in ether and treated with ethereal HCl. Concentration afford 260 mg (0.49 mmol, 68%) of compound 31 as a white solid: $^1$H NMR ($CDCl_3+CD_3OD$ drop) δ 7.79 (n m, 1H), 7.59 (m, 2H), 7.36 (t, J=8 Hz, 1H), 6.69-6.62 (m, 3H), 5.15 (m, 1H), 4.17 (m, 1H), 3.07 (d, J=12.5 Hz, 1H), 2.87-2.75 (m, 2H), 2.61 (dd, J=7, 13.5 Hz, 1H), 2.21 (s, 3H), 1.95 (s, 3H), 1.92 (s, 3H), 1.84 (s, 3H); IR (diffuse reflectance) 2985, 2958, 2940, 2755, 2738, 2730, 1749, 1645, 1628, 1596, 1569, 1463, 1372, 1227, 1118 cm$^{-1}$. MS (CI)m/z(rel intensity) 497 (MH+, 86), 500 (15), 499 (99), 497 (86), 419 (28), 283 (18), 231 (22), 136 (17), 77 (46), 60 (13), 58 (18). HRMS (ESI) calcd for $C_{23}H_{27}N_2O_3F_2Br+H_1$ 497.1252, found 497.1248. Anal. Calcd for $C_{23}H_{27}BrF_2N_2O_3+HCl+0.5H_2O$: C, 50.89; H, 5.38; N, 5.16; Found: C, 50.95; H, 5.37; N, 5.05.

Step 7. Preparation of N-[(1S,2R)-3-{[1-(3-bromophenyl)-1-methylethyl]amino}-1-(3,5-difluorobenzyl)-2-hydroxypropyl]acetamide 32

To a solution of 107 mg (0.21 mmol) of hydrochloride 31 in 10 mL of methanol is added 1 mL of 1N NaOH. The mixture is stirred for 45 min at ambient temperature, then quenched with 1N $KH_2PO_4$ and diluted with ethyl acetate. The organic phase is washed with brine, dried over $Na_2SO_4$, filtered and concentrated to a glassy solid. This is dissolved in methanol and treated with ethereal HCl to afford 70 mg (0.14 mmol, 68%) of compound 32 as a white solid: $^1$H NMR ($CDCl_3+CD_3OD$ drop) δ 7.69 (s, 1H), 7.56 (m, 2H), 7.35 (t, J=8 Hz, 1H), 6.71 (m, 2H), 6.63 (m, 1H), 3.98 (m, 2H), 2.98 (m, 1H), 2.8 (m, 1H), 2.68 (m, 1H), 2.39 (m, 1H), 1.92 (s, 3H), 1.83 (s, 6H); IR (diffuse reflectance) 3311, 3283, 3257, 3249, 3058, 3007, 2757, 1655, 1646, 1628, 1596, 1551, 1459, 1116, 697 cm$^{-1}$. MS (CI)m/z(rel intensity) 457 (15), 455 (MH+,97), 458 (17), 457 (99), 456 (15), 455 (97), 377 (5), 259 (9), 216 (6), 214 (6), 96 (27), 69 (5). HRMS (ESI) calcd for $C_{21}H_{25}N_2O_2F_2Br+H_1$ 455.1146, found 455.1145. Anal. Calcd for $C_{21}H_{25}BrF_2N_2O_2.HCl+H_2O$: C, 49.47; H, 5.54; N, 5.49; Found: C, 49.45; H, 5.50; N, 5.54.

EXAMPLE 77

Preparation of N-((1S,2R)-1-(3,5-difluorobenzyl)-3-{[1-(3-ethylphenyl)-1-methylethyl]amino}-2-hydroxypropyl)acetamide hydrochloride 39

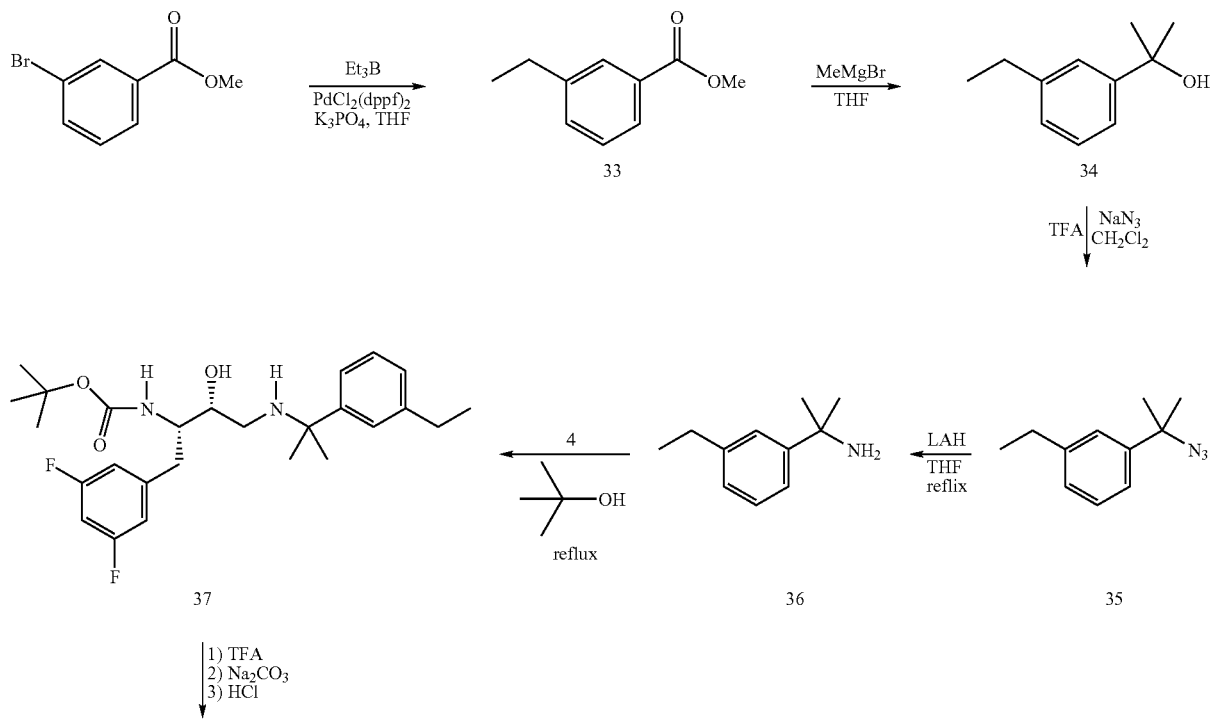

Scheme 9

-continued

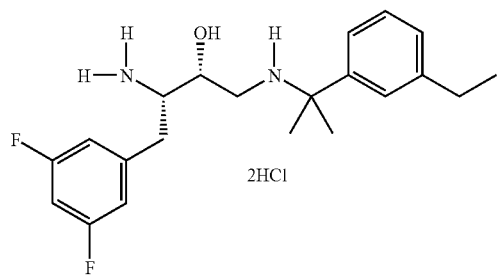

38

1) Ac-Im
2) NaOH
3) HCl
→

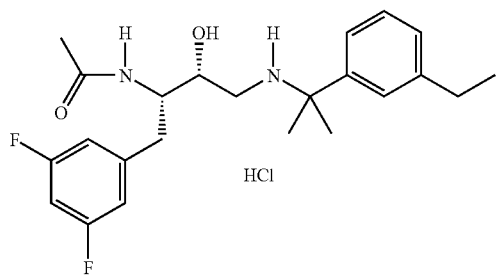

39

Step 1. Preparation of methyl-3-ethylbenzoate 33

Compound 33 was prepared essentially according to the method of Example 7. The crude product was purified by chromatography over silica gel eluting with 2% to 3% of ethyl acetate in hexanes, to afford 6.1 g (37 mmol, 93%) of methyl-3-ethylbenzoate 33 as a colorless oil: $^1$H NMR (CDCl$_3$) δ 7.89-7.84 (m, 2H), 7.40-7.33 (m, 2H), 3.91 (s, 3H), 2.70 (q, J=7.6 Hz, 2H), 1.26 (t, J=7.6 Hz, 3H).

Step 2. Preparation of 2-(3-ethylphenyl)-2-propanol 34

Following essentially the procedure of Example 76, Step 1, methyl-3-ethylbenzoate 33 (6.0 g, 37 mmol) is converted to 2-(3-ethylphenyl)-2-propanol 34 (6 g, quantitative) which is obtained as a pale yellow oil, sufficiently pure without chromatography: $^1$H NMR (CDCl$_3$) δ 7.34 (m, 1H), 7.28 (m, 2H), 7.09 (m, 1H), 2.66 (q, J=7.6 Hz, 2H), 1.75 (s, 1H), 1.59 (s, 6H), 1.25 (t, J=7.6 Hz, 3H).

Step 3. Preparation of 2-(3-ethylphenyl)-2-propylazide 35

Following essentially the procedure of EXAMPLE 69, Step 2, but only stirred at ambient temperature for 1 h, alcohol 34 (6.0 g, 37 mmol) is converted to azide 35 (6.6 g, 35 mmol, 94%) which is obtained as a pale yellow oil, and is sufficiently pure without chromatography: $^1$H NMR (CDCl$_3$) δ 7.25 (m, 3H), 7.12 (m, 1H), 2.67 (q, J=7.6 Hz, 2H), 1.64 (s, 6H), 1.25 (t, J=7.6 Hz, 3H).

Step 4. Preparation of 2-(3-ethylphenyl)-2-propylamine 36

Following essentially the procedure described in EXAMPLE 76, Step 3, azide 35 (6.6 g, 35 mmol) is converted to amine 36 (3.2 g, 20 mmol, 56%) which is obtained as a pale yellow oil after chromatography: $^1$H NMR (CDCl$_3$) δ 7.35-7.24 (m, 3H), 7.07 (d, J=7.4 Hz, 1H), 2.66 (q, J=7.6 Hz, 2H), 1.55 (s, 2H), 1.49 (s, 6H), 1.25 (t, J=7.6 Hz, 3H).

Step 5. Preparation of 2-(3-ethylphenyl)-2-propylamine hydrochloride

To amine 36 in ether is added ethereal HCl. Removal of the mother liquor affords, 2-(3-ethylphenyl)-2-propylamine hydrochloride as a white solid: 1H NMR (CDCl3) δ 8.93 (s, 3H), 7.44 (s, 1H), 7.36 (m, 1H), 7.26 (t, J=7.6 Hz, 1H), 7.13 (d, J=7.6 Hz, 1H), 2.63 (q, J=7.6 Hz, 2H), 1.81 (s, 6H), 1.22 (t, J=7.6 Hz, 3H); MS (CI) m/z 147.0 (MH−NH$_2$)

Step 6. Preparation of tert-butyl (1S,2R)-3-{[1-(3-ethylphenyl)-1-methylethyl]amino}-1-(3,5-difluorobenzyl)-2-hydroxypropylcarbamate 37

Following essentially the procedure described in EXAMPLE 76, Step 5, except that t-butanol is used in place of isopropanol, 2-amine 36 (3.0 g, 18.4 mmol) is reacted with Example 134 (4, 3.0 g, 10 mmol) to afford, after chromatography, protected amine 37 (3.8 g, 8.2 mmol, 82%) as a colorless oil: $^1$H NMR (CDCl$_3$) δ 7.27 (m, 3H), 7.09 (m, 1H), 6.74 (m, 2H), 6.65 (m, 1H), 4.69 (d, J=9.4 Hz, 1H), 3.76 (m, 1H), 3.32 (m, 1H), 2.97 (dd, J=4, 14 Hz, 1H), 2.72 (m, 1H), 2.67 (q, J=7.6 Hz, 2H), 2.45 (m, 2H), 1.49 (s, 6H), 1.40 (s, 9H), 1.26 (t, J=7.6 Hz, 3H).

Step 7. Preparation of (2R,3S)-3-amino-4-(3,5-difluorophenyl)-1-{[1-(3-ethylphenyl)-1-methylethyl]amino}butan-2-ol hydrochloride 38

Following essentially the procedure described in EXAMPLE 76, Step 6, protected amine 37 (3.5 g, 7.6 mmol) is deprotected with TFA to afford a quantitative yield of a slightly yellow oil: $^1$H NMR (CDCl$_3$) δ 7.25 (m, 3H), 7.08 (m, 1H), 6.72-6.6 (m, 3H), 3.39 (m, 1H), 3.02 (m, 1H), 2.82 (dd, J=3.8, 13.6 Hz, 1H), 2.67 (q, J=7.6 Hz, 2H), 2.59 (dd, J=3.6, 11.8 Hz, 1H), 2.45-2.37 (m, 2H), 1,48 (s, 6H), 1.24 (t, J=7.6 Hz, 3H). Treatment with ethereal HCl affords hydrochloride 38 (86%) as a white solid: MS (CI) m/z 363.3 (MH+).

Step 8. Preparation of N-((1S,2R)-1-(3,5-difluorobenzyl)-3-{[1-(3-ethylphenyl)-1-methylethyl]amino}-2-hydroxypropyl)acetamide hydrochloride 39

Following essentially the procedure described for EXAMPLE 76, Step 6, hydrochloride 38 (1.1 mmol) is converted to acetamide 39, which, following chromatography on silica gel, eluting with 8% to 10% methanol (containing 1% NH$_4$OH) in CH$_2$Cl$_2$, is obtained as a colorless oil: $^1$H NMR (CDCl$_3$) δ 7.28-7.20 (m, 3H), 7.07 (d, J=7 Hz, 1H), 6.69-6.61 (m, 3H), 6.28 (d, J=9 Hz, 1H), 4.11 (m, 1H), 3.40 (m, 1H), 2.83 (dd, J=5.2, 14.3 Hz, 1H), 2.73 (dd, J=8.4, 14.2 Hz, 1H), 2.65 (q, J=7.6 Hz, 2H), 2.44 (dd, J=4, 12 Hz, 1H), 2.34 (dd, J=5.3, 12 Hz, 1H), 1.89 (s, 3H), 1.47 (s, 3H), 1.46 (s, 3H), 1.24 (t, J=7.6 Hz, 3H). Treatment with ethereal HCl and concentration affords the hydrochloride 39 (0.22 g, 0.49 mmol, 45%), which is obtained as a white solid: $^1$H NMR (CDCl$_3$+ CD$_3$OD drop) δ 7.37 (m, 3H), 7.24 (m, 1H), 6.71 (m, 2H), 6.62 (m, 1H), 3.98 (m, 2H), 3.0 (dd, J=4, 14.7 Hz, 1H), 2.78-2.65 (m+q, J=7.6 Hz, 4H), 2.46 (m, 1H), 1.91 (s, 3H), 1.84 (s, 3H), 1.83 (s, 3H), 1.26 (t, J=7.6 Hz, 3H); IR (diffuse reflectance) 3250, 3229, 3053, 2967, 2933, 2876, 2786, 2764, 1645, 1628, 1595, 1550, 1459, 1377, 1116 cm$^{-1}$. MS (CI)m/z(rel intensity) 405 (MH+,99), 407 (6), 406 (41), 405 (99), 387 (7), 259 (23), 176 (8), 164 (18), 148 (7), 147 (19), 77 (15). HRMS (ESI) calcd for $C_{23}H_{30}N_2O_2F_2+H_1$ 405.2353, found 405.2369. Anal. Calcd for $C_{23}H_{30}F_2N_2O_2 \cdot HCl+0.5\ H_2O$: C, 61.39; H, 7.17; N, 6.23; Found: C, 61.27; H, 7.07; N, 6.20.

EXAMPLE 78

Preparation of (1S,2R)-1-(3,5-difluorobenzyl)-2-hydroxy-3-{[1-(3-isopropylphenyl)cyclohexyl]amino}propylformamide hydrochloride 41

Scheme 10

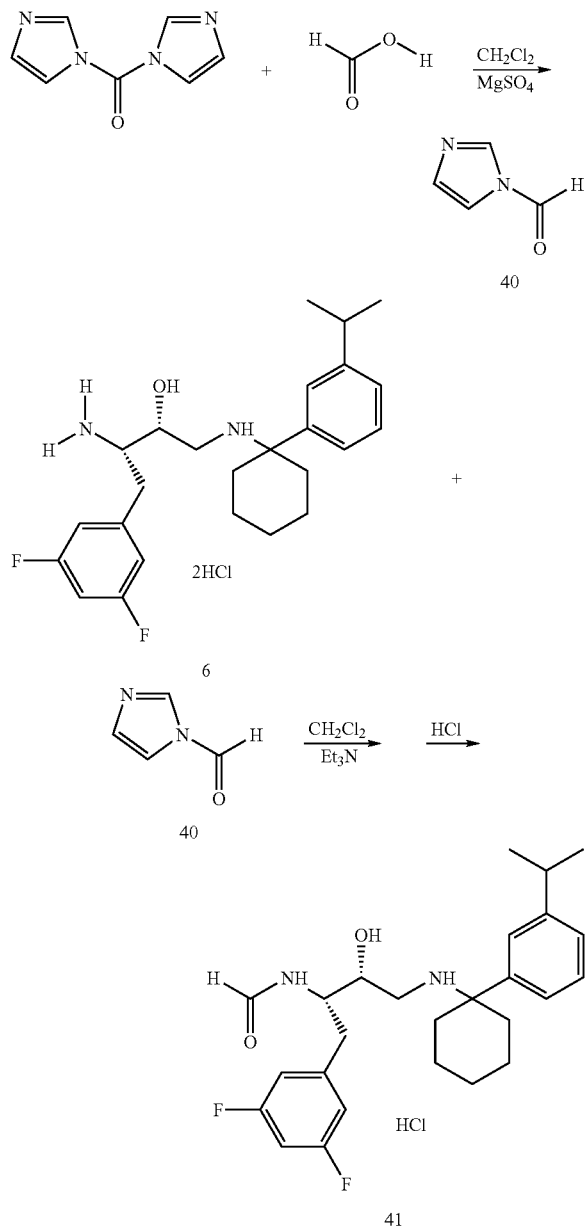

Step 1. Preparation of formyl imidazole 40

To a solution of formic acid (0.76 mL, 20 mmol, 96%) in $CH_2Cl_2$ stirring under nitrogen is added, portionwise over 10 min, 3.6 g (22 mmol) of carbonyldiimidazole, and the mixture is allowed to stir overnight. Anhydrous $MgSO_4$ is added, and after several hours the mixture is filtered and concentrated in vacuo (note: formyl imidazole is volatile and this operation should be carefully monitored for maximum recovery) to afford 0.7 g of iridescent crystals. The NMR spectrum showed the presence of formyl imidazole 40: $^1$H NMR ($CDCl_3$) δ 9.15 (s, 1H), 8.14 (s, 1H), 7.53 (s, 1H), 7.20 (s, 1H). The crystals also contain imidazole (δ 7.71 (s, 1H), 7.13 (s, 2H)) and the relative peak intensity and relative molecular weights are used to determine the weight % of formyl imidazole in the product.

Step 2. Preparation of (1S,2R)-1-(3,5-difluorobenzyl)-2-hydroxy-3-{[1-(3-isopropylphenyl)cyclohexyl]amino}propylformamide hydrochloride 41

To a solution of amine 6 (209 mg, 0.43 mmol) in 4 mL of $CH_2Cl_2$ under nitrogen is added 125 μL (0.9 mmol) of triethylamine. To this mixture is added 75 mg of the solid from Step 1, which is determined by NMR to contain 63% by weight of formyl imidazole (47 mg, 0.49 mmol) and the solution is stirred for 20 min. Methanol (5 mL is added, followed by 2 mL of 1 N NaOH. The mixture is concentrated in vacuo and diluted with 1 N $KH_2PO_4$ and ethyl acetate. The organic phase is washed with 1 N $NaHCO_3$ and brine, and dried over $Na_2SO_4$. Concentration and chromatography over silica gel, eluting with 5% to 7.5% of methanol (containing 1% of $NH_4OH$) in $CH_2Cl_2$ affords a colorless oil. Ether and ethereal HCl are added, and the gel-like precipitate is concentrated in vacuo from ethanol and then ethyl acetate to afford 176 mg (0.37 mmol, 85%) of hydrochloride 41 as a white solid: $^1$H NMR ($CDCl_3+CD_3OD$ drop) δ 7.86 (s, 1H), 7.39-7.28 (m, 4H), 6.67 (m, 2H), 6.60 (m, 1H), 3.96 (m, 1H), 3.79 (m, 1H), 3.08 (dd, 1H), 2.93 (m, 1H), 2.7-2.5 (m, 4H), 2.37 (dd, 1H), 2.05 (m, 2H), 1.78 (m, 2H), 1.6 (m, 1H), 1.45-1.3 (m, 3H), 1.25 (dd, J=1, 7 Hz, 6H); MS (CI) m/z 445.3 (MH+).

EXAMPLE 79

Preparation of N-((1S,2R)-1-(3,5-difluorobenzyl)-2-hydroxy-3-{[1-(3-isopropylphenyl)cyclohexyl]amino}propyl)-2-fluoroacetamide hydrochloride 43

Scheme 11

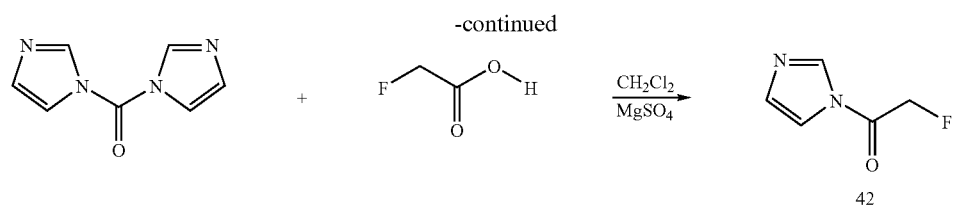

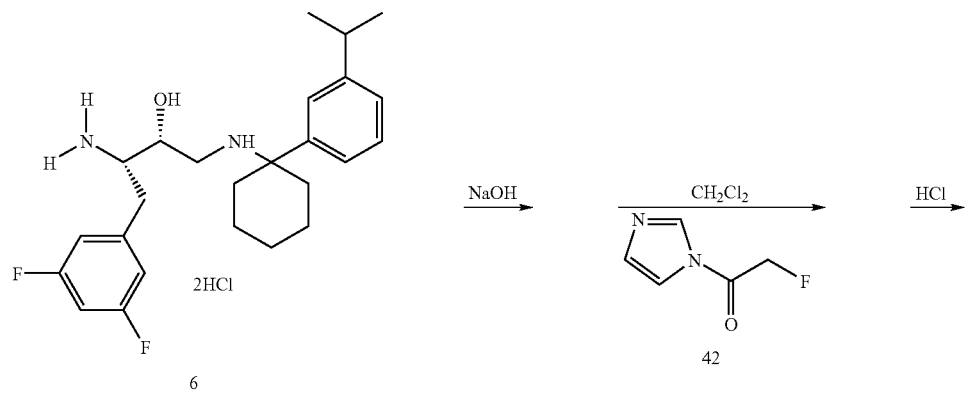

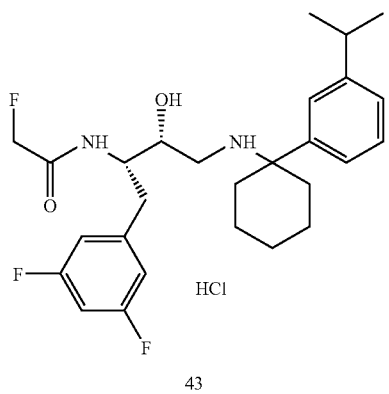

Step 1. Preparation of fluoroacetyl imidazole 42

To a slurry of 1.2 g (12 mmol) of sodium fluoroacetate in 25 mL of $CH_2Cl_2$ is added, with swirling of the flask, 1 mL (12 mmol) of concentrated HCl (note: this operation must be carried out in an efficient hood; fluoroacetic acid is highly toxic!). About 1 teaspoonful of anhydrous $MgSO_4$ is added to the flask, and the contents are filtered, rinsing the filter paper with 15 mL of $CH_2Cl_2$. The combined filtrate and wash are placed under nitrogen, and 1.3 g (8 mmol) of carbonyldiimidazole is added portionwise to the stirring mixture over 20 min. NMR analysis of an aliquot removed 40 min later indicates nearly complete reaction. After 1 h a teaspoonful of $MgSO_4$ is added, and the mixture is allowed to stir overnight. It is filtered and concentrated to remove most of the $CH_2Cl_2$, leaving 1.6 g of a pale yellow oil. The NMR spectrum indicates the presence of $CH_2Cl_2$, fluoroacetic acid, imidazole, and fluoroacetyl imidazole 42: $^1H$ NMR ($CDCl_3$) δ 8.26 (s, 1H), 7.53 (s, 1H), 7.15 (s, 1H), 5.40 (d, J=47 Hz, 2H). Integration reveals the oil to be 28% by weight fluoroacetyl imidazole 42 (0.45 g, 3.5 mmol, 44%). The oil is diluted with $CH_2Cl_2$ to make a solution that is 0.2 M in 42.

Step 2. Preparation of N-((1S,2R)-1-(3,5-difluorobenzyl)-2-hydroxy-3-{[1-(3-isopropylphenyl)cyclohexyl]amino}propyl)-2-fluoroacetamide hydrochloride 43

To amine 6 (0.64 mmol) is added 1 N NaOH and ethyl acetate. The organic phase is washed with more 1N NaOH, brine, and then dried over $Na_2SO_4$ and concentrated to 265 mg of a colorless oil. This free base is dissolved in 3 mL of $CH_2Cl_2$ under nitrogen and 3.2 mL ( 0.64 mmol) of a 0.2 M solution of fluoroacetyl imidazole 42 in $CH_2Cl_2$ is added. The mixture is stirred for 5 min, and then aqueous 1N $KH_2PO_4$ and ethyl acetate are added. The organic phase is washed with 1N $KH_2PO_4$, 1N $NaHCO_3$, and brine, dried over $Na_2SO_4$, and concentrated. Chromatography over silica gel, eluting with 5% methanol (containing 2% of $NH_4OH$) in $CH_2Cl_2$ affords a colorless oil. Ether and ethereal HCl are added, and the solvents are removed in vacuo to yield 256 mg (0.50 mmol, 78%) of hydrochloride 43 as a white solid: $^1H$ NMR ($CDCl_3$) δ 9.85 (m, 1H), 8.0 (m, 1H), 7.51 (s, 1H), 7.37 (m, 2H), 7.27 (m, 1H), 6.80 (d, J=7 Hz, 1H), 6.68 (m, 2H), 6.63 (m, 1H), 4.63 (d, J=47 Hz, 2H), 4.16 (m, 1H), 4.10 (m, 1H), 2.98-2.93

(m, 2H), 2.77-2.64 (m, 4H), 2.35-2.2 (m, 3H), 1.80 (m, 2H), 1.59 (m, 1H), 1.44-1.25 (m, 3H), 1.28 (d, J=7 Hz, 6H); MS (CI) m/z 477.4 (MH+).

EXAMPLE 80

Preparation of N-((1S,2R)-1-(3,5-difluorobenzyl)-3-{[1-(3-ethylphenyl)-1-methylethyl]amino}-2-hydroxypropyl)-2,2-difluoroacetamide hydrochloride 44

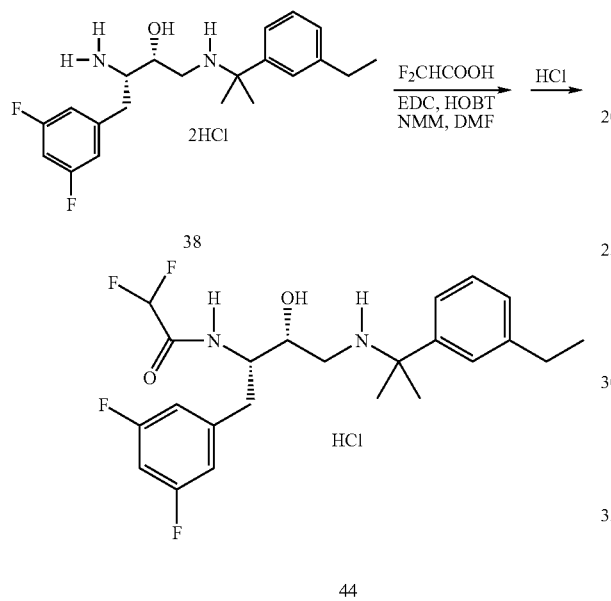

Following the general procedure of Example 56, compound 38 is converted into hydrochloride 44, which is obtained as a white solid: $^1$H NMR (CDCl$_3$) δ 9.9 (m, 1H), 8.1 (m, 1H), 7.35 (m, 4H), 7.23 (d, J=7 Hz, 1H), 6.66-6.58 (m, 3H), 5.95 (t, J=54 Hz, 1H), 4.6 (v br, 1H), 4.37 (m, 1H), 4.10 (m, 1H), 2.89 (dd, J=5, 14 Hz, 1H), 2.80-2.66 (m+q, J=7.6 Hz, 4H), 2.34 (m, 1H), 1.87 (s, 6H), 1.26 (t, J=7.6 Hz, 3H); MS (CI) m/z 441.3 (MH+).

EXAMPLE 81

Preparation of N-((1S,2R)-1-(3,5-difluorobenzyl)-2-hydroxy-3-{[1-(3-isopropylphenyl)cyclohexyl]amino}propyl)ethanethioamide hydrochloride 46

Scheme 13

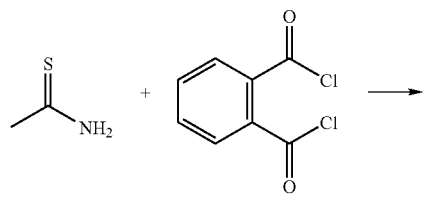

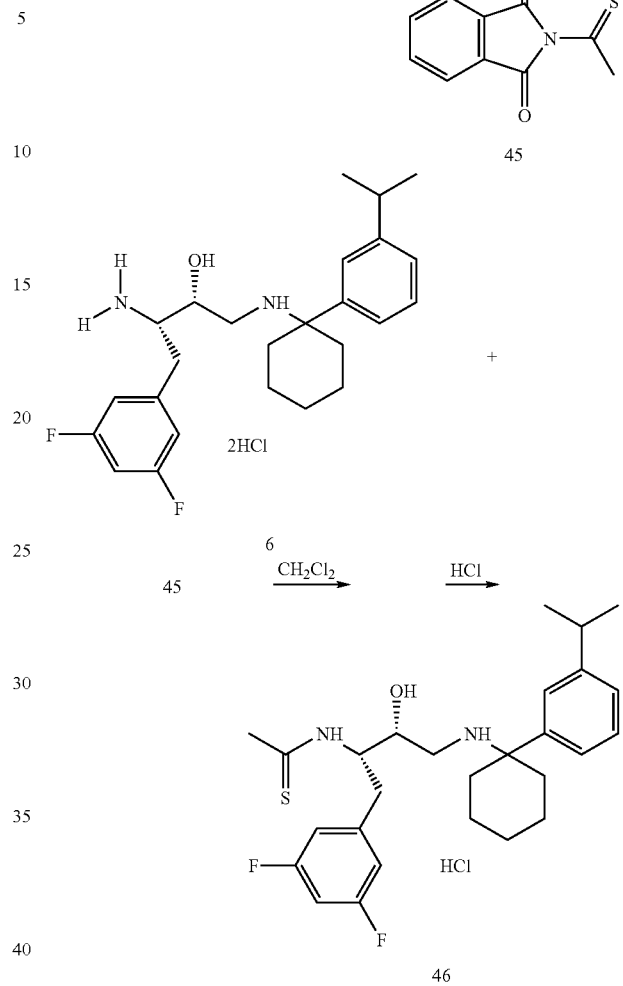

Step 1. Preparation of thioacetyl-N-phthalimide 45

Thioacetamide (1.9 g, 25 mmol) is suspended in 40 mL of CH$_2$Cl$_2$ and cooled in an ice bath under nitrogen. Phthaloyldichloride (3.6 mL, 25 mmol) is added slowly over 10 min via syringe while the mixture is stirred. The mixture becomes a clear orange solution transiently, eventually depositing a precipitate. After stirring for 40 h, the mixture is concentrated in vacuo (in the hood!). The oily coral solid is triturated with hexanes. Within minutes the hexanes mother liquor drops a precipitate, which is filtered off to afford 0.2 g of a light coral solid: $^1$H NMR (CDCl$_3$) δ 7.99 (m, 2H), 7.86 (m, 2H), 3.08 (s, 3H). The residual solids remaining after trituration with hexanes are further triturated with ether and then with CH$_2$Cl$_2$. The combined mother liquors are concentrated to about 3 g of a red oily solid, which is chromatographed over silica gel, eluting with 10% to 20% ethyl acetate in heptane. The red fractions contained a product (concentrated to a coral solid, 0.77 g) with the same TLC retention (R$_f$=0.32, 20% ethyl acetate in heptane) as the coral solid which had precipitated from hexanes. The total recovery is 0.97 g, 4.7 mmol, 19%.

Step 2. Preparation of N-((1S,2R)-1-(3,5-difluorobenzyl)-2-hydroxy-3-{[1-(3-isopropylphenyl)cyclohexyl]amino}propyl)ethanethioamide hydrochloride 46

To 164 mg (0.39 mmol) of the free base of compound 6 in 3 mL of approximately 0° C. $CH_2Cl_2$ under nitrogen, is added solid thioacetyl-N-phthalimide 45 (80 mg, 0.39 mmol). The mixture is stirred for 20 min, and then 3 mL of methanol and 3 mL of 1N NaOH are added. The mixture is taken up in ethyl acetate and washed twice with 1N NaOH, once with water, and once with brine. It is dried over $Na_2SO_4$, concentrated, and chromatographed over silica gel, eluting with 4% methanol (containing 2% $NH_4OH$) in $CH_2Cl_2$. Product-containing fractions are concentrated to a colorless oil, which is dissolved in ether and treated with ethereal HCl. Concentration affords 97 mg (0.19 mmol, 49%) of hydrochloride 46 as a white solid: $^1H$ NMR ($CDCl_3+CD_3OD$ drop) δ 7.42-7.37 (m, 2H), 7.29 (m, 2H), 6.73 (m, 2H), 6.62 (m, 2H), 4.67 (m, 1H), 4.10 (m, 1H), 3.11 (dd, J=5, 14 Hz, 1H), 2.96 (hept, J=7 Hz, 1H), 2.83 (m, 1H), 2.65-2.4 (m, 4H, obscured by solvent), 2.38 (s, 3H), 2.07 (m, 2H), 1.78 (m, 2H), 1.59 (m, 1H), 1.44-1.35 (m, 3H), 1.28 (d, J=7 Hz, 6H); MS (CI) m/z 475.3 (MH+).

EXAMPLE 82

Preparation of N-((1S,2R)-1-(3,5-difluorobenzyl)-3-{[1-(3-ethylphenyl)-1-methylethyl]amino}-2-hydroxypropyl)ethanethioamide hydrochloride 47

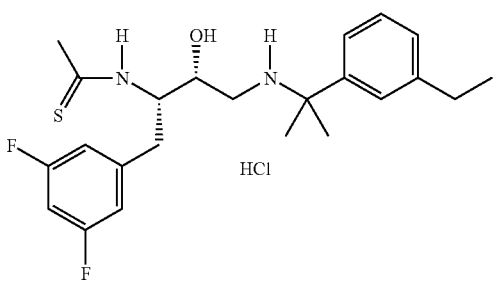

47

Following essentially the procedure described for EXAMPLE 81, compound 38 (220 mg, 0.5 mmol) is converted to the title compound 47, which is obtained as a white solid (79 mg, 0.17 mmol, 34%): MS (CI) m/z 421.3 (MH+).

EXAMPLE 83

Preparation of N-((1S,2R)-1-(3,5-difluorobenzyl)-3-{[(1S)-7-ethyl-1,2,3,4-tetrahydronaphthalen-1-yl]amino}-2-hydroxypropyl)ethanethioamide hydrochloride 48

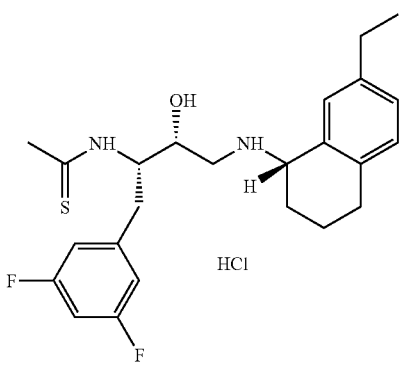

48

Following essentially the procedure described in EXAMPLE 81, (2R,3S)-3-amino-4-(3,5-difluorophenyl)-1-{[(1S)-7-ethyl-1,2,3,4-tetrahydronaphthalen-1-yl]amino}butan-2-ol dihydrochloride (0.71 mmol) is converted to the title compound 48 (158 mg, 0.34 mmol, 47%), which is obtained as a white solid: $^1H$ NMR ($CDCl_3$) δ 9.5 (br s, 1H), 9.1 (d, 1H), 7.95 (br, 1H), 7.39 (s, 1H), 7.15-7.07 (m, 2H), 6.73 (m, 2H), 6.60 (m, 1H), 4.77 (m, 1H), 4.47 (m, 1H), 4.34 (m, 1H), 3.0 (d, J=7 Hz, 2H), 2.97 (m, 1H), 2.73 (m, 3H), 2.61 (q, J=7.5 Hz, 2H), 2.53 (s, 3H), 2.15 (m, 1H), 2.02 (m, 1H), 1.87 (m, 1H), 1.79 (m, 1H), 1.23 (t, J=7.5 Hz, 3H); IR (diffuse reflectance) 3194, 3029, 2964, 2932, 2872, 1627, 1597, 1459, 1439, 1420, 1384, 1153, 1119, 982, 847 $cm^{-1}$. MS (CI)m/z (rel intensity) 433 (MH+,24), 221 (36), 184 (51), 176 (27), 174 (49), 172 (99), 159 (49), 156 (27), 77 (31), 60 (27), 58 (52). HRMS (ESI) calcd for $C_{24}H_{30}N_2OSF_2+H_1$ 433.2125, found 433.2114. Anal. Calcd for $C_{24}H_{30}F_2N_2OS \cdot HCl+H_2O$: C, 59.19; H, 6.83; N, 5.75; Cl, 7.28; S, 6.58; Found: C, 59.84; H, 6.70; N, 5.88; Cl, 6.91; S, 6.40.

EXAMPLE 84

Preparation of N-((1S,2R)-1-(3,5-difluorobenzyl)-3-{[(1S)-7-ethyl-1,2,3,4-tetrahydronaphthalen-1-yl]amino}-2-hydroxypropyl)-2,2-difluoroacetamide hydrochloride 49

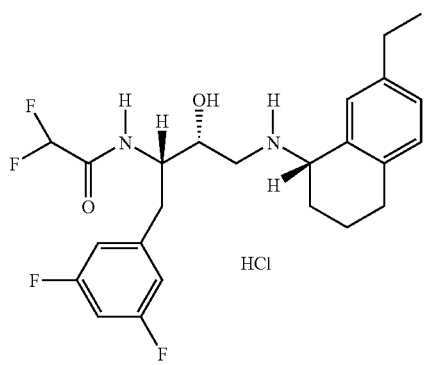

49

Using methods analogus to those previously described, (2R,3S)-3-amino-4-(3,5-difluorophenyl)-1-{[(1S)-7-ethyl-1,2,3,4-tetrahydronaphthalen-1-yl]amino}butan-2-ol dihydrochloride (0.33 mmol) is converted to compound 49 (88 mg, 0.18 mmol, 54%), which is obtained as a white solid: $^1H$ NMR ($CDCl_3$) δ 7.36 (s, 1H), 7.12 (m, 2H), 6.71 (m, 2H), 6.64 (m, 1H), 5.81 (t, J=54 Hz, 1H), 4.46 (m, 1H), 4.18 (m, 1H), 4.07 (m, 1H), 3.12 (m, 2H), 2.77 (m, 4H), 2.63 (q, J=7.5 Hz, 2H), 2.2 (m, 1H), 2.05 (m, 1H), 1.96 (m, 1H), 1.86 (m, 1H), 1.23 (t, J=7.5 Hz, 3H); MS (CI-) m/z 453.5 (MH+).

EXAMPLE 85

Preparation of N-((1S,2R)-1-(3,5-difluorobenzyl)-3-{[(1S)-7-ethyl-1,2,3,4-tetrahydronaphthalen-1-yl]amino}-2-hydroxypropyl)-2-fluoroacetamide hydrochloride 50

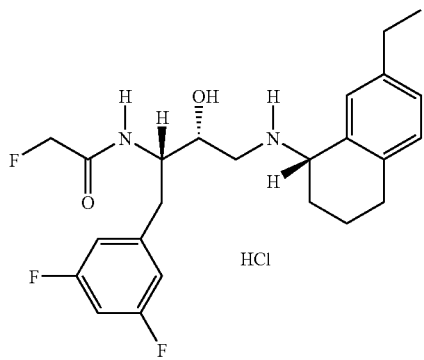

Using methods analogus to those previously described, (2R,3S)-3-amino-4-(3,5-difluorophenyl)-1-{[(1S)-7-ethyl-1,2,3,4-tetrahydronaphthalen-1-yl]amino}butan-2-ol dihydrochloride (0.0.71 mmol) is converted to compound 50 (248 mg, 0.53 mmol, 74%), which is obtained as a white solid: $^1$H NMR (CDCl$_3$) δ 9.85 (br, 1H), 8.41 (br, 1H), 7.45 (s, 1H), 7.09 (m, 2H), 6.97 (d, J=8.6 Hz, 1H), 6.68 (m, 2H), 6.62 (m, 1H), 4.70 (dq, J~50, 11 Hz, 2H), 4.48 (m, 1H), 4.29 (m, 1H), 4.16 (m, 1H), 3.1-3.0 (m, 2H), 2.83-2.69 (m, 4H), 2.59 (q, J=7.5 Hz, 2H), 2.21 (m, 1H), 2.02 (m, 2H), 1.78 (m, 1H), 1.21 (t, J=7.5 Hz, 3H); MS (CI) m/z 435.3 (MH+).

EXAMPLE 86

Preparation of (1S,2R)-1-(3,5-difluorobenzyl)-3-{[(1S)-7-ethyl-1,2,3,4-tetrahydronaphthalen-1-yl]amino}-2-hydroxypropylformamide 51

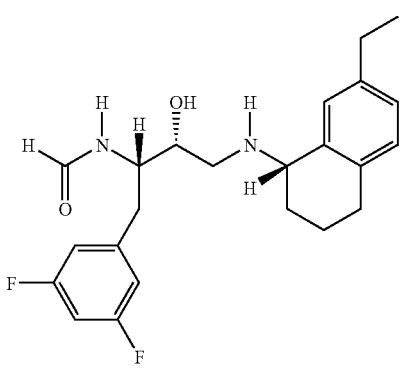

Using methods analogus to those previously described, but without making the HCl salt, (2R,3S)-3-amino-4-(3,5-difluorophenyl)-1-{[(1S)-7-ethyl-1,2,3,4-tetrahydronaphthalen-1-yl]amino}butan-2-ol dihydrochloride (0.0.31 mmol) is converted to compound 51 (70 mg, 0.17 mmol, 56%), which is obtained as a white solid. $^1$H NMR (CDCl$_3$) δ 8.11 (s, 1H), 7.16 (s, 1H), 7.03 (s, 2H), 6.76 (m, 2H), 6.67 (m, 1H), 5.83 (d, J=9 Hz, 1H), 4.25 (m, 1H), 3.74 (m, 1H), 3.53 (m, 1H), 3.03 (dd, J=4.8, 14.4 Hz, 1H), 2.90-2.69 (m, 5H), 2.61 (q, J=7.6 Hz, 2H), 1.85 (m, 3H), 1.76 (m, 1H), 1.23 (t, J=7.6 Hz, 3H); MS (CI) m/z 403.3 (MH+). A trace NMR doublet ( J=11.8 Hz) appears at δ 7.73, tentatively attributed to an intramolecularly cyclized form of the product in the deuterochloroform solution.

EXAMPLE 87

Preparation of N-((1S,2R)-1-(3,5-difluorobenzyl)-3-{[1-(3-ethylphenyl)-1-methylethyl]amino}-2-hydroxypropyl)-2-fluoroacetamide hydrochloride 52

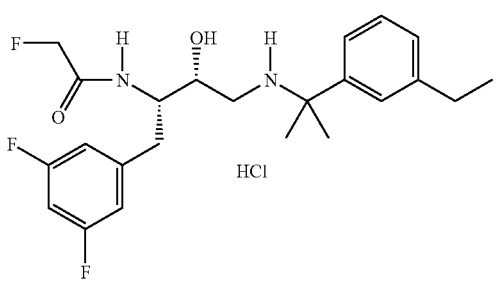

Using methods analogus to those previously described, compound 38 (150 mg, 0.34 mmol) is converted to compound 52 (80 mg, 50%), which is obtained as a white solid: $^1$H NMR (CDCl$_3$) δ 9.95 (br, 1H), 8.37 (br m, 1H), 7.39-7.34 (m, 3H), 7.23 (d, J=7 Hz, 1H), 6.94 (d, J=8 Hz, 1H), 6.67 (m, 2H), 6.60 (m, 1H), 4.68 (dq, J=47, 14 Hz, 2H), 4.27 (m, 1H), 4.16 (m, 1H), 2.97 (dd, 1H), 2.80 (m, 2H), 2.70 (q, J=7.6 Hz, 2H), 2.38 (m, 1H), 1.88 (s, 3H), 1.87 (s, 3H), 1.27 (t, J=7.6 Hz, 3H); MS (CI) m/z 423.3 (MH+).

EXAMPLE 88

Preparation of (1S,2R)-1-(3,5-difluorobenzyl)-3-{[1-(3-ethylphenyl)-1-methylethyl]amino}-2-hydroxypropylformamide hydrochloride 53

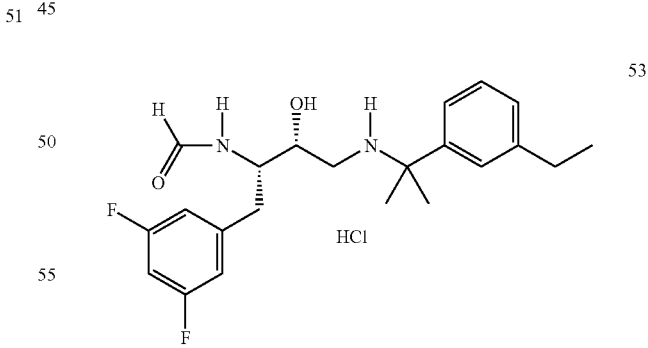

Using methods analogus to those previously described, compound 38 (0.60 mmol) is converted to compound 53 (130 mg, 50%), which is obtained as a white solid: $^1$H NMR (CDCl$_3$+CD$_3$OD drop) δ 7.95 (s, 1H), 7.39-7.31 (m, 3H), 7.24 (d, J=7 Hz, 1H), 6.71 (m, 2H), 6.62 (m, 1H), 4.05 (m, 1H), 3.95 (m, 1H), 3.07 (dd, 1H), 2.80 (m, 1H), 2.70 (q, J=7.6 Hz, 2H), 2.6 (m, obscured, 1H), 2.47 (m, 1H), 1.83 (s, 3H), 1.82 (s, 3H), 1.26 (t, J=7.6 Hz, 3H); MS (CI) m/z 391.3

(MH+). The NMR spectrum of the free base in pure deuterochloroform shows a small doublet (J=11.6 Hz) at δ 7.58 which is tentatively attributed to an intramolecularly cyclized form of the product.

EXAMPLE 89

Preparation of N-((1S,2R)-2-hydroxy-1-(4-hydroxybenzyl)-3-{[1-(3-isopropylphenyl)cyclohexyl]amino}propyl)acetamide hydrochloride 54

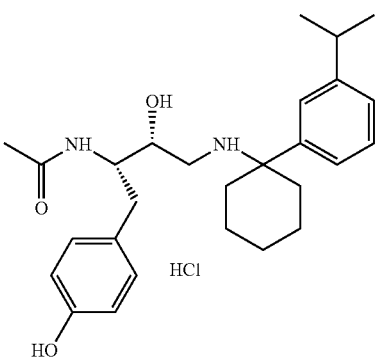

Using methods analogus to those previously described, tert-butyl (1S)-2-(4-hydroxyphenyl)-1-[(2S)-oxiran-2-yl]ethylcarbamate (0.78 mmol) is converted to compound 54 (70 mg, 0.15 mmol, 19%, 3 steps), which is obtained as a white solid: $^1$H NMR (CDCl$_3$+CD$_3$OD drop) δ 7.49 (s, 1H), 7.39 (d, J=4.6 Hz, 2H), 7.28 (m, 1H), 6.91 (d, J=8 Hz, 2H), 6.69 (d, J=8 Hz, 2H), 3.97 (m, 1H), 3.90 (m, 1H), 2.96 (hept, J=7 Hz, 1H), 2.83 (dd, 1H), 2.62 (m, 4H), 2.45 (m, 1H), 2.13 (m, 2H), 1.89 (s, 3H), 1.78 (m, 2H), 1.58 (m, 1H), 1.45-1.3 (m, 3H), 1.27 (d, J=7 Hz, 6H); MS (CI) m/z 439.3 (MH+).

EXAMPLE 90

Preparation of N-((1S,2R)-1-[3-(allyloxy)-5-fluorobenzyl]-2-hydroxy-3-{[1-(3-isopropylphenyl)cyclohexyl]amino}propyl)acetamide hydrochloride 55

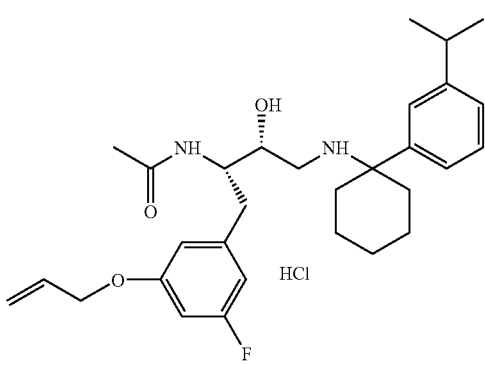

Using methods analogus to those previously described, tert-butyl (1S)-2-[3-(allyloxy)-5-fluorophenyl]-1-[(2S)-oxiran-2-yl]ethylcarbamate (0.61 mmol) is converted to compound 55 (0.31 mmol, 51%, 3 steps), which is obtained as a white solid: $^1$H NMR (CDCl$_3$+CD$_3$OD drop) δ 7.42-7.27 (m, 4H), 6.54 (m, 1H), 6.48 (m, 1H), 6.45 (m, 1H), 6.05-5.98 (m, 1H), 5.39 (m, 1H), 5.28 (m, 1H), 4.48 (m, 2H), 3.95 (m, 1H), 3.77 (m, 1H), 2.96 (m, 2H), 2.60 (m, 4H), 2.4 (m, obscured, 1H), 2.1 (m, 2H), 1.81 (s+m, 5H), 1.6 (m, 1H), 1.45-1.3 (m, 3H), 1.27 (d, J=7 Hz, 6H); MS (CI) m/z 497.4 (MH+).

EXAMPLE 91

Preparation of N-[(1S,2R)-2-hydroxy-3-{[1-(3-isopropylphenyl)cyclohexyl]amino}-1-(thien-2-ylmethyl)propyl]acetamide hydrochloride 56

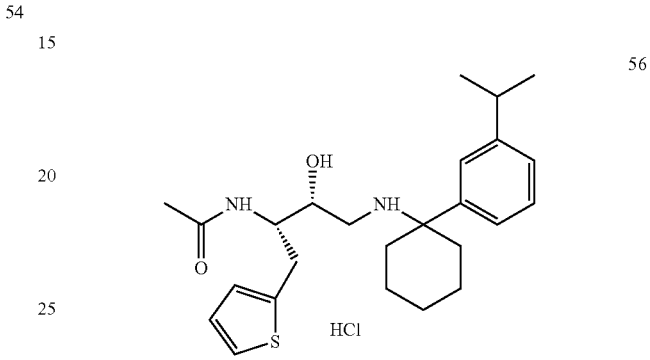

Using methods analogus to those previously described, tert-butyl (1S)-1-[(2S)-oxiran-2-yl]-2-thien-2-ylethylcarbamate (0.92 mmol) is converted to compound 56 (0.51 mmol, 55%, 3 steps), which is obtained as a white solid: $^1$H NMR (CDCl$_3$) δ 9.8 (br, 1H), 8.03 (br, 1H), 7.47 (s, 1H), 7.37 (m, 2H), 7.26 (m, 1H), 7.21 (m, 1H), 7.0 (br, 1H), 6.95 (m, 1H), 6.90 (d, J=5 Hz, 1H), 4.15 (m, 1H), 3.96 (m, 1H), 3.9 (v br, 1H), 2.96 (hept, J=7 Hz, 1H), 2.86 (m, 2H), 2.7-2.55 (m, 3H), 2.24 (m, 3H), 2.00 (s, 3H), 1.8-1.7 (m, 2H), 1.59 (m, 1H), 1.45-1.3 (m, 3H), 1.28 (dd, J=1.7, 7 Hz, 6H); MS (CI) m/z 429.3 (MH+).

EXAMPLE 92

Preparation of N-((1S,2R)-2-hydroxy-1-(3-hydroxybenzyl)-3-{[1-(3-isopropylphenyl)cyclohexyl]amino}propyl)acetamide hydrochloride 57

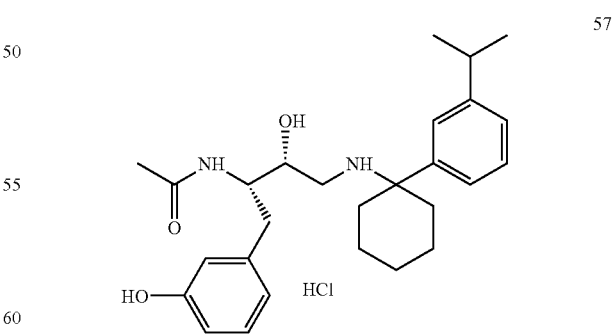

Using methods analogus to those previously described, tert-butyl (1S)-2-[3-(benzyloxy)phenyl]-1-[(2S)-oxiran-2-yl]ethylcarbamate (1.0 mmol) is converted to compound 57 (0.28 mmol, 28%, 4 steps), obtained as a colorless glass-like solid which can be pulverized into a beige powder: $^1$H NMR (CDCl₃+CD₃OD drop) δ 7.43 (s, 1H), 7.37 (m, 2H), 7.28 (m, 1H), 7.08 (t, J=7.7 Hz, 1H), 6.78 (s, 1H), 6.69 (d, J=8 Hz, 1H), 6.57 (d, J=7.5 Hz, 1H), 4.03 (m, 1H), 3.75 (m, 1H), 2.97 (m, 2H), 2.65 (m, 4H), 2.43 (m, 1H), 2.12-2 (m, 2H), 1.85 (s, 3H), 1.78 (m, 2H), 1.59 (m, 1H), 1.45-1.3 (m, 3H), 1.27 (d, J=7 Hz, 6H); MS (CI) m/z 439.3 (MH+).

EXAMPLE 93

Preparation of N-((1S,2R)-1-(3-fluorobenzyl)-2-hydroxy-3-{[1-(3-isopropylphenyl)cyclohexyl]amino}propyl)acetamide hydrochloride 58

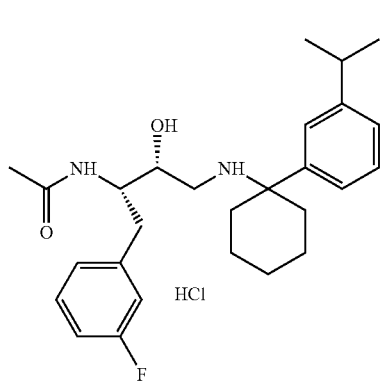

58

Using methods analogus to those previously described, tert-butyl (1S)-2-(3-fluorophenyl)-1-[(2S)-oxiran-2-yl]ethylcarbamate (0.82 mmol) is converted to compound 58 (0.37 mmol, 45%, 3 steps), which is obtained as a white solid:

¹H NMR (CDCl₃+CD₃OD drop) δ 7.45 (s, 1H), 7.4-7.35 (m, 2H), 7.28 (m, 1H), 7.20 (m, 1H), 6.93 (m, 1H), 6.88 (m, 2H), 4.00 (m, 1H), 3.87 (m, 1H), 2.96 (m, 2H), 2.7-2.6 (m, 4H), 2.39 (m, 1H), 2.11 (m, 2H), 1.88 (s, 3H), 1.79 (m, 2H), 1.59 (m, 1H), 1.45-1.3 (m, 3H), 1.27 (d, J=7 Hz, 6H); MS (CI) m/z 441.5 (MH+).

EXAMPLE 94

Preparation of N-((1S,2R)-1-(3-(heptyloxy)-5-fluorobenzyl)-2-hydroxy-3-{[1-(3-isopropylphenyl)cyclohexyl]amino}propyl)acetamide hydrochloride 59

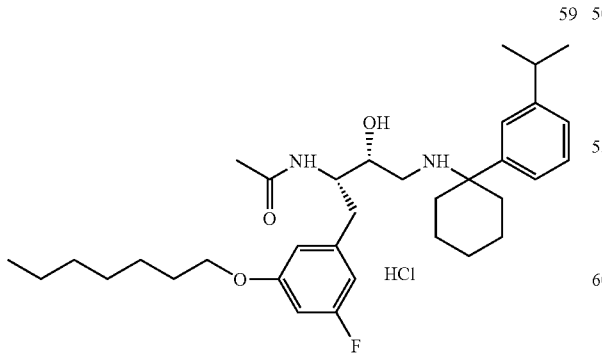

59

Using methods analogus to those previously described, hydrochloride 11 (0.4 mmol) is reacted with 1-bromoheptane to afford the title compound 59 (0.14 mmol, 34%) as a glass, which can be pulverized to an off-white solid: ¹H NMR (CDCl₃+CD₃OD drop) δ 7.49 (s, 1H), 7.37 (m, 2H), 7.27 (m, 1H), 6.51 (s, 1H), 6.45 (s, 1H), 6.43 (s, 1H), 4.05 (m, 1H), 3.98 (m, 1H), 3.88 (t, J=6.5 Hz, 2H), 2.96 (hept, J=7 Hz, 1H), 2.84 (m, 1H), 2.6 (3H obscured by solvent), 2.36 (m, 1H), 2.16 (m, 2H), 2.01 (s, 3H), 1.85-1.75 (m, 4H), 1.58 (m, 1H), 1.5-1.26 (m, 18H), 0.89 (t, J=6.6 Hz, 3H); MS (CI) m/z 555.5 (MH+).

EXAMPLE 95

Preparation of N-((1S,2R)-1-(3-(2-(2-methoxyethoxy)ethoxy)-5-fluorobenzyl)-2-hydroxy-3-{[1-(3-isopropylphenyl)cyclohexyl]amino}propyl)acetamide hydrochloride 60

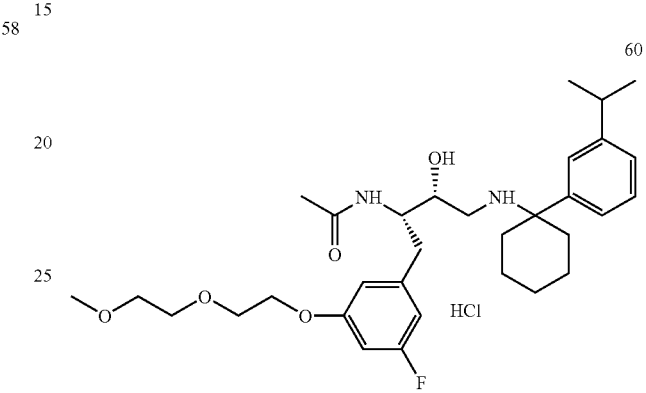

60

Using methods analogus to those previously described, compound 11 (0.4 mmol) is reacted with 1-bromo-2-(2-methoxyethoxy)ethane to afford the title compound 60 ( 0.21 mmol, 52%) as a hygroscopic white solid: ¹H NMR (CDCl₃) δ 9.4 (br, 1H), 8.5 (br, 1H), 8.32 (br, 1H), 7.54 (s, 1H), 7.38 (m, 2H), 7.26 (m, 1H), 6.56 (s, 1H), 6.47 (m, 2H), 4.34 (v br, water H), 4.1 (m, 4H), 3.83 (m, 2H), 3.70 (m, 2H), 3.58 (m, 2H), 3.38 (s, 3H), 2.96 (hept, J=7 Hz, 1H), 2.8-2.6 (m, 5H), 2.4-2.2 (m, 3H), 2.15 (s, 3H), 1.80 (m, 2H), 1.6 (m, 1H), 1.5-1.3 (m, 3H), 1.27 (d, J=7 Hz, 6H); MS (CI) m/z 559.5 (MH+).

EXAMPLE 96

Preparation of N-((1S,2R)-1-[3-(allyloxy)-5-fluorobenzyl]-3-{[(4R)-6-ethyl-2,2-dioxido-3,4-dihydro-1H-isothiochromen-4-yl]amino}-2-hydroxypropyl)acetamide 61

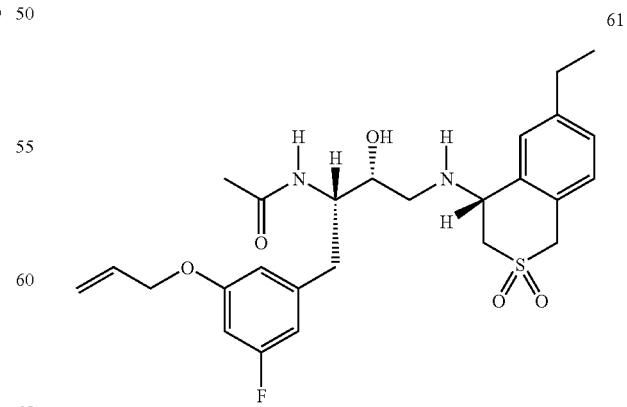

61

Using methods analogus to those previously described, tert-butyl (1S)-2-[3-(allyloxy)-5-fluorophenyl]-1-[(2S)-oxiran-2-yl]ethylcarbamate (0.37 mmol) and (4R)-6-ethyl-3,4-dihydro-1H-isothiochromen-4-amine 2,2-dioxide (0.78 mmol) are reacted together, and the product is further converted, Using methods analogus to those previously described, (except that the HCl salt is not formed) to the title compound 61 (0.16 mmol, 43%), which is obtained as a white solid: $^1$H NMR (CDCl$_3$) δ 7.22-7.19 (m, 2H), 7.13 (m, 1H), 6.57 (m, 1H), 6.51 (m, 2H), 6.06-5.99 (m, 1H), 5.75 (br, 1H), 5.41 (d, J=17 Hz, 1H), 5.30 (d, J=12 Hz, 1H), 4.67 (d, J=15 Hz, 1H), 4.50 (m, 2H), 4.26 (m, 1H), 4.17 (d, J=15 Hz, 1H), 4.1 (m, 1H), 3.66 (m, 2H), 3.48 (m, 1H), 3.36 (dd, 1H), 2.90 (m, 2H), 2.78 (m, 2H), 2.67 (q, J=7.6 Hz, 2H), 1.91 (s, 3H), 1.25 (t, J=7.6 Hz, 3H); MS (CI) m/z 505.4 (MH+).

EXAMPLE 97

Preparation of N-((1S,2R)-1-(cyclohexylmethyl)-3-{[(4R)-6-ethyl-2,2-dioxido-3,4-dihydro-1H-isothiochromen-4-yl]amino}-2-hydroxypropyl) acetamide 62

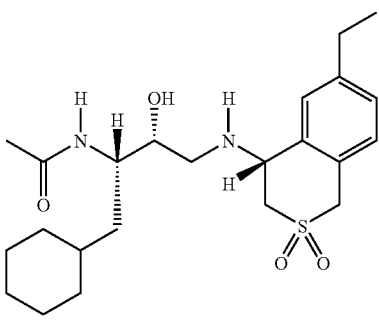

62

Using methods analogus to those previously described, tert-butyl (1S)-2-cyclohexyl-1-[(2S)-oxiran-2-yl]ethylcarbamate (0.91 mmol) and (4R)-6-ethyl-3,4-dihydro-1H-isothiochromen-4-amine 2,2-dioxide (1.15 mmol) are coupled. The resulting product is recovered by chromatography over silica gel, eluting with 3% methanol (containing 1% NH$_4$OH) in CH$_2$Cl$_2$. This material is then converted to compound 62, which is obtained as a white solid: MS (CI) m/z 437.3 (MH+).

EXAMPLE 98

Preparation of (1S,2R)-1-(cyclohexylmethyl)-3-{[(4R)-6-ethyl-2,2-dioxido-3,4-dihydro-1H-isothiochromen-4-yl]amino}-2-hydroxypropyl formamide 63

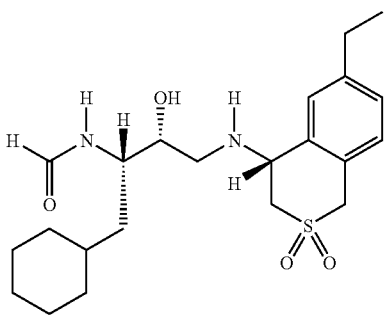

63

Using methods analogus to those previously described, tert-butyl (1S)-2-cyclohexyl-1-[(2S)-oxiran-2-yl]ethylcarbamate (0.91 mmol) and (4R)-6-ethyl-3,4-dihydro-1H-isothiochromen-4-amine 2,2-dioxide (1.15 mmol) are coupled. The resulting product (0.63 mmol, 69%) is purified by chromatography over silica gel, eluting with 3% methanol (containing 1% NH$_4$OH) in CH$_2$Cl$_2$. The purified coupled material is then converted to the title compound 63 (which is obtained as a white solid), using methods analogous to those disclosed herein.: MS (CI) m/z 423.3 (MH+).

EXAMPLE 99

Preparation of N-[(1S, 2R)-1-(3,5-Difluorobenzyl)-3-((1S)-7-ethyl-1,2,3,4-tetrahydro-naphthalen-1-ylamino)-2-hydroxy-propyl]-methanesulfonamide (64)

64

A 30 mg sample of the starting amine in 1 mL of dichloromethane was treated with 33 uL of triethylamine. A solution of 6 uL of methanesulfonyl chloride in 0.5 mL of dichloromethane was added and the solution was stirred overnight. The solvent was evaporated and the product was isolated by reverse-phase HPLC. Mass spectroscopy gave m/z=453.2.

Compounds 65-78 are synthesized in an analogous manner, substituting methansefulfonyl chloride with various reagents.

| Structure (Compound No.) | Name | Mass Spec. |
|---|---|---|
| (65) | N-[(1S, 2R)-1-(3,5-Difluorobenzyl)-3-((1S)-7-ethyl-1,2,3,4-tetrahydro-naphthalen-1-ylamino)-2-hydroxypropyl]-2-hydroxy-acetamide | 432.8 |
| (66) | N-[(1S, 2R)-1-(3,5-Difluorobenzyl)-3-((1S)-7-ethyl-1,2,3,4-tetrahydro-naphthalen-1-ylamino)-2-hydroxy-propyl]-2-methoxy-acetamide | 446.9 |
| (67) | N-[(1S, 2R)-1-(3,5-Difluorobenzyl)-3-((1S)-7-ethyl-1,2,3,4-tetrahydro-naphthalen-1-ylamino)-2-hydroxy-propyl]-propionamide | 430.9 |
| (68) | 2-(2-Butoxy-ethoxy)-N-[(1S, 2R)-1-(3,5-difluorobenzyl)-3-((1S)-7-ethyl-1,2,3,4-tetrahydro-naphthalen-1-ylamino)-2-hydroxy-propyl]-acetamide | 532.9 |

| Structure (Compound No.) | Name | Mass Spec. |
|---|---|---|
| 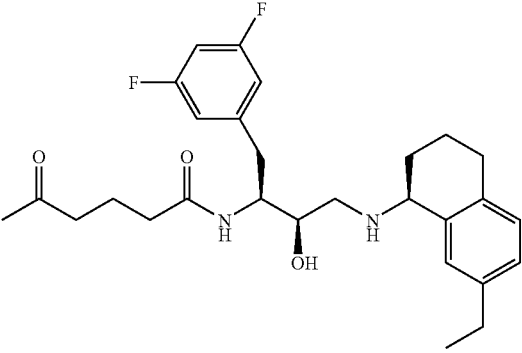<br>(69) | 5-Oxo-hexanoic acid [(1S, 2R)-1-(3,5-difluorobenzyl)-3-((1S)-7-ethyl-1,2,3,4-tetrahydro-naphthalen-1-ylamino)-2-hydroxy-propyl]-amide | 486.9 |
| 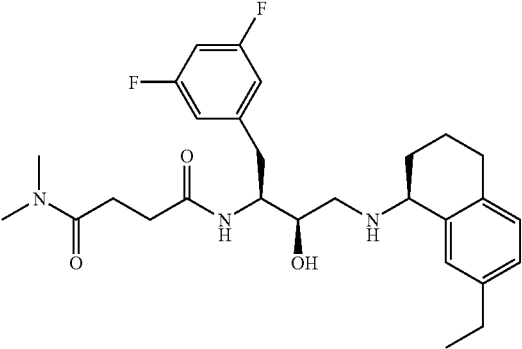<br>(70) | N-[(1S, 2R)-1-(3,5-Difluorobenzyl)-3-((1S)-7-ethyl-1,2,3,4-tetrahydro-naphthalen-1-ylamino)-2-hydroxy-propyl]-N',N'-dimethyl-succinamide | 501.9 |
| 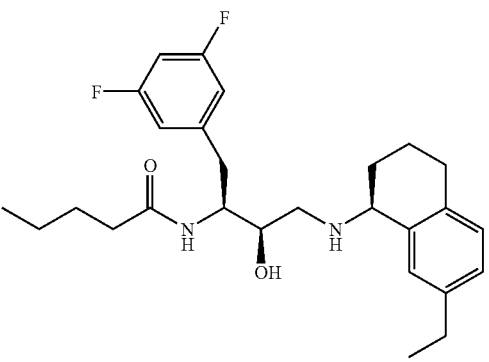<br>(71) | Pentanoic acid [(1S, 2R)-1-(3,5-difluoro-benzyl)-3-((1S)-7-ethyl-1,2,3,4-tetrahydro-naphthalen-1-ylamino)-2-hydroxy-propyl]-amide | 458.9 |
| 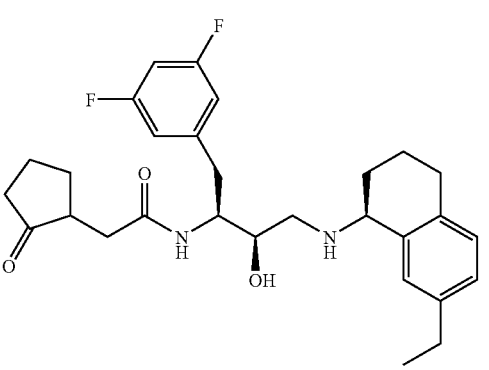<br>(72) | N-[(1S, 2R)-1-(3,5-Difluorobenzyl)-3-((1S)-7-ethyl-1,2,3,4-tetrahydro-naphthalen-1-ylamino)-2-hydroxy-propyl]-2-(2-oxo-cyclopentyl)-acetamide | 498.9 |

| Structure (Compound No.) | Name | Mass Spec. |
|---|---|---|
| 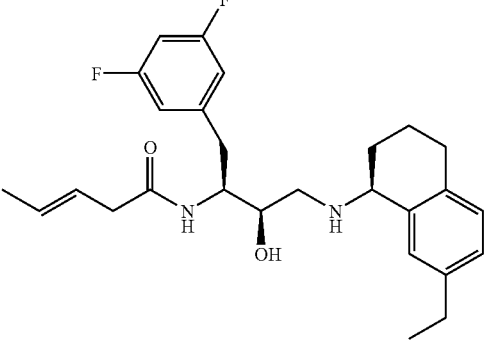<br>(73) | Pent-3-enoic acid [(1s, 2R)-1-(3,5-difluoro-benzyl)-3-((1S)-7-ethyl-1,2,3,4-tetrahydro-naphthalen-1-ylamino)-2-hydroxy-propyl]-amide | 456.9 |
| 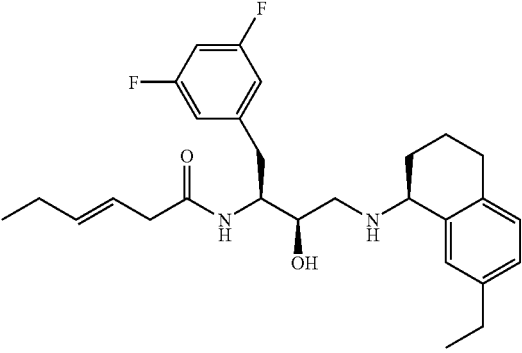<br>(74) | Hex-3-enoic acid [(1S, 2R)-1-(3,5-difluoro-benzyl)-3-((1S)-7-ethyl-1,2,3,4-tetrahydro-naphthalen-1-ylamino)-2-hydroxy-propyl]-amide | 470.9 |
| 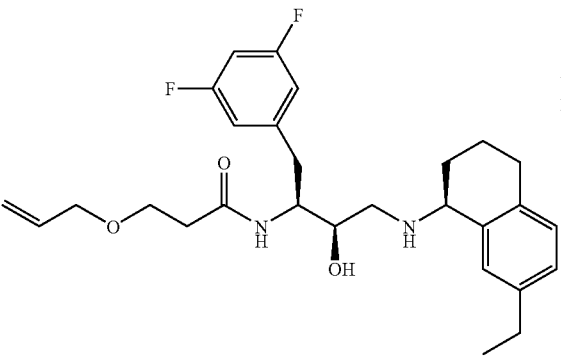<br>(75) | 3-Allyloxy-N-[(1S, 2R)-1-(3,5-difluoro-benzyl)-3-((1S)-7-ethyl-1,2,3,4-tetrahydro-naphthalen-1-ylamino)-2-hydroxy-propyl]-propionamide | 486.9 |
| 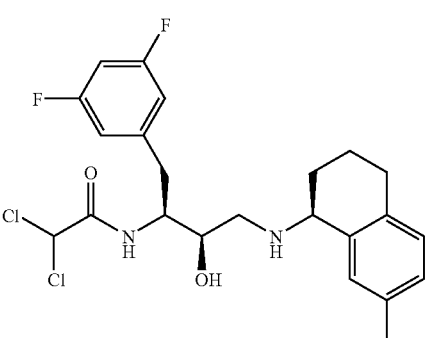<br>(76) | 2,2-Dichloro-N-[(1S, 2R)-1-(3,5-difluoro-benzyl)-3-((1S)-7-ethyl-1,2,3,4-tetrahydro-naphthalen-1-ylamino)-2-hydroxy-propyl]-acetamide | 485.7 |

-continued

| Structure (Compound No.) | Name | Mass Spec. |
|---|---|---|
| (77) | 2-Chloro-N-[(1S, 2R)-1-(3,5-difluoro-benzyl)-3-((1S)-7-ethyl-1,2,3,4-tetrahydro-naphthalen-1-ylamino)-2-hydroxy-propyl]-acetamide | 451.7 |
| (78) | 2-Bromo-N-[(1S, 2R)-1-(3,5-difluoro-benzyl)-3-((1S)-7-ethyl-1,2,3,4-tetrahydro-naphthalen-1-ylamino)-2-hydroxy-propyl]-acetamide | 495.7 |

EXAMPLE 100

A. Preparation of 1-tert-Butyl-3-iodo-benzene from 3-(tert-Butyl)aniline 3-(tert-Butyl)aniline (Oakwood, 6.0 g, 40.21 mmol) was slowly added to a cold solution of 12 N HCl (24.5 mL) while stirring over an ice/acetone bath in a three-neck round bottom flask equipped with a thermometer. A 2.9M solution of sodium nitrite (16 mL) was added via addition funnel to the reaction flask at a rate so as maintain the temperature below 2° C. The solution was stirred for 30 min. prior to being added to a reaction flask containing a 4.2M solution of potassium iodide (100 mL). The reaction mixture was allowed to stir overnight while warming to RT. The mixture was then extracted with a hexane/ether solution (1:1) followed by washing with H$_2$O (2×), 0.2N citric acid (2×) and sat. NaCl. The organic phase was separated, dried (Na$_2$SO$_4$) and concentrated under reduced pressure. The residue was purified by flash chromatography (100% Hexane) to give the desired iodo intermediate (8.33 g, 80%): $^1$H NMR (CDCl$_3$, 300 MHz) δ 1.34 (s, 9H), 7.07 (t, J=8.0 Hz, 1H), 7.39 (d, J=8.0 Hz, 1H), 7.55 (d, J=8.0 Hz, 1H), 7.77 (t, J=2.0 Hz, 1H).

B. Preparation of 1-(3-tert-Butyl-phenyl)-cyclohexanol from 1-tert-Butyl-3-iodo-benzene 1-tert-Butyl-3-iodo-benzene (8.19 g, 31.49 mmol) in anh. THF (35 mL) was cooled to −78° C. A solution of 1.7M tert-butyl lithium was added and the reaction mixture was allowed to stir while under N$_2$ (g) inlet for 2 h. A solution of cyclohexanone in anh. THF (5 mL) was added and the reaction mixture was stirred for 1 h. before transferring to a 0° C. bath for 1 h. and warming to RT for 1 h. The reaction was quenched with H$_2$O and extracted with ether. The organic layer was separated, dried (NaSO$_4$) and concentrated under reduce pressure. The residue was purified by flash chromatography (100% CHCl₃) to give the desired alcohol (4.73 g, 65%): mass spec (CI) 215.2 (M−OH).

C. Preparation of 1-(1-Azido-cyclohexyl)3-tert-butyl-benzene from 1-(3-tert-Butyl-phenyl)-cyclohexanol The above compound was prepared essentially according to the procedure of Example 12. The crude reaction product was purified by flash chromatography (100% hexane) to give the desired azide. mass spec (CI) 215.2 (M−N₃).

D. Preparation of 1-(3-tert-Butyl-phenyl)-cyclohexylamine from 1-(1-Azido-cyclohexyl)3-tert-butyl-benzene

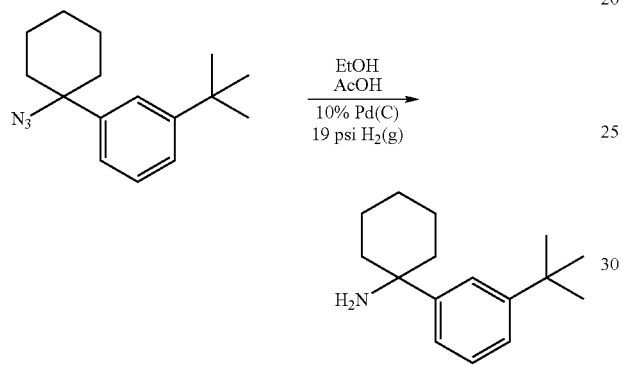

To a solution of 1-(1-Azido-cyclohexyl)-3-tert-butylbenzene dissolved in ethanol (5 mL) was added acetic acid (0.5 mL) and 10% palladium on carbon (0.10 g, 0.94 mmol). The reaction mixture was placed on the hydrogenator at 19 psi for 3.5 h and then filtered through Celite and rinsed with ethanol. The filtrate was collected and concentrated under reduce pressure. This was then partitioned between EtOAc and 1N NaOH. The aqueous layer was removed and the mixture was washed with H₂O. The organic layer was separated, dried (Na₂SO₄), and concentrated under reduced pressure. The crude product was used without further purification: mass spec (CI) 215.2 (M−NH₂).

E. Preparation of (1S,2R)-N-[3-[1-(3-tert-Butyl-phenyl)cyclohexylamino]-1-(3,5-Difluorobenzyl)-2-hydroxy-propyl]acetamide (79)

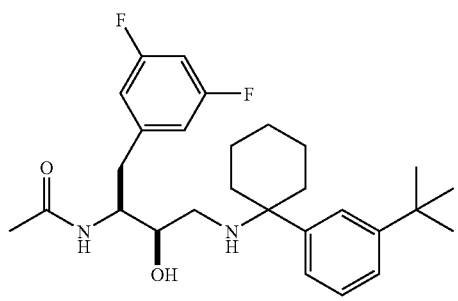

The product from step D is transformed into the above product using methods that are analogous to others described in the application. Mass spec: (CI) 473.2 (M+H).

F. Preparation of 1-(3-Ethynylphenyl)cyclohexylamine from 1-(3-Bromo-phenyl)-cyclohexylamine

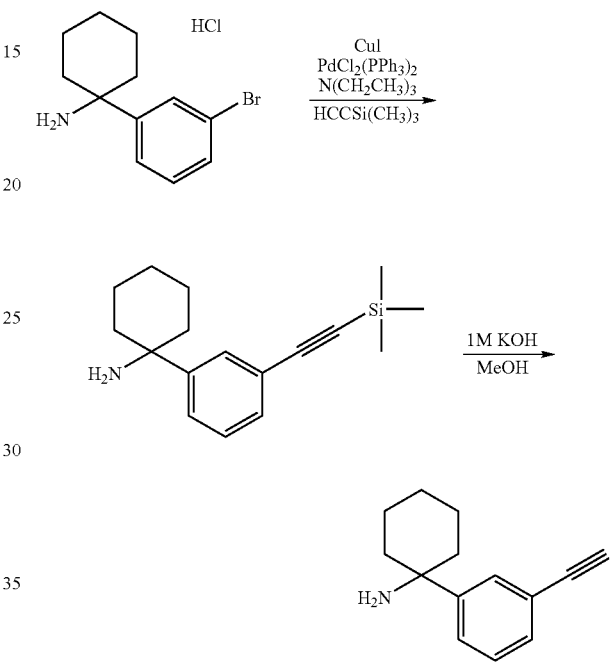

1-(3-Bromo-phenyl)-cyclohexylamine (Pharmacia, 1.04 g, 4.09 mmol) was free based and then dissolved in triethylamine (20 mL, 143 mol) prior to the addition of dicholorbis (triphenylphosphine)palladium(II) (0.119 g, 0.170 mmol) and copper iodide (0.040 g, 0.211 mmole). The reaction mixture was heated to reflux at which point trimethylsilylacetylene (0.85 mL, 6.01 mmole) was added via syringe. After refluxing for 3 h, the reaction mixture was cooled to RT before partitioning between EtOAc and sat. NaHCO₃ (aq). The aqueous phase was collected and extract with EtOAc (3×). The organic phases were then collect and washed with sat. NaCl (aq), separated, dried (Na₂SO₄) and concentrated under reduced pressure. The crude product was used without further purification.

The trimethylsilyl intermediate was dissolved in methanol (5 mL) and 1 N KOH (6 mL) and stirred at RT for 5.5 h. The reaction mixture was then partitioned between EtOAc and sat. NaHCO₃ (aq). The organic layer was separated, dried (Na₂SO₄), and concentrated under reduced pressure. The residue was purified by flash chromatography (5% MeOH, 94.5% CHCl₂, 0.5% NH₄OH) to give the desired amine (0.35 g, 31%): mass spec (CI) 183.1 (M−16).

G. Preparation of (1S, 2R)-N-{1-(3,5-Difluorobenzyl)-3-[1-(3-(ethynylphenyl)cyclohexylamino]-2-hydroxy-propyl}acetamide (80)

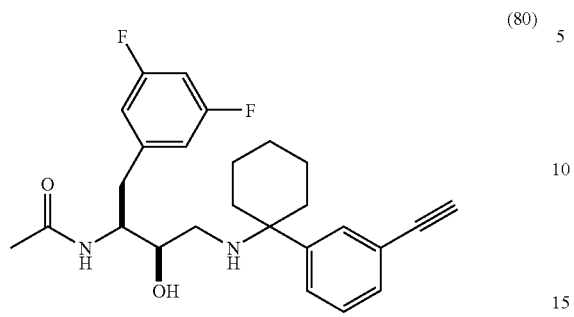

(80)

The product from step F is transformed into the above product using methods that are analogous to others described in the application. Mass spectrometic analysis: (CI) 441.2 (M+H).

H. Preparation of (1S,2R)-N-(1-(3,5-Difluorobenzyl)-3-{1-[3-(2,2-dimethylpropyl)phenyl]cyclohexylamino}-2-hydroxypropyl)acetamide (81)

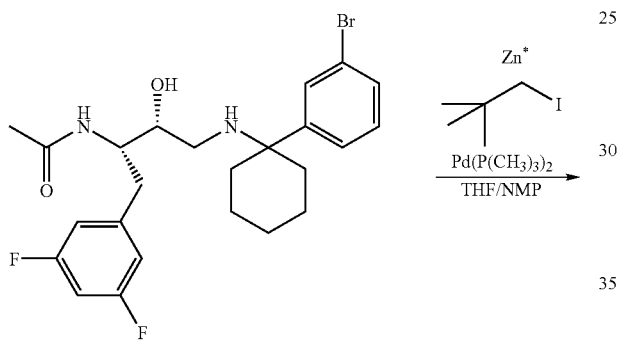

(81)

The desired product is prepared using methods that are analogous to others described in the application. Mass spec: (CI) 487.2 (M+H), 509 (M+Na).

EXAMPLE 101

A. Synthesis of the following inhibitors was performed using essentially the same coupling conditions described above in Example 56, except with the variation of carboxylic acid starting materials as described below.

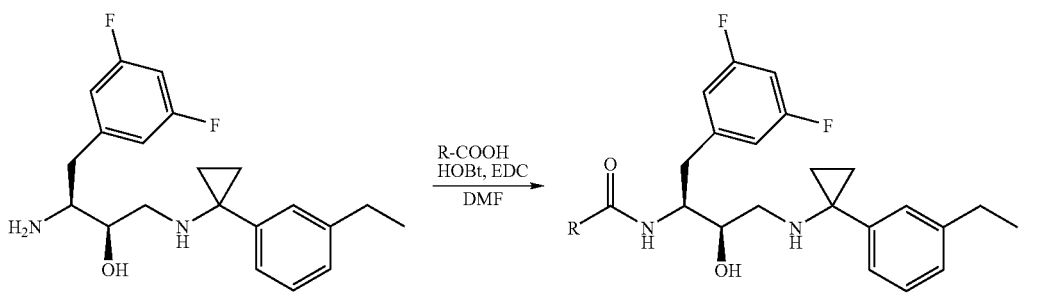

| R = | MH+ | | Compound No. |
|---|---|---|---|
| 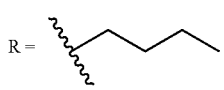 | 445.2 | (1S, 2R) Pentanoic acid {1-(3,5-difluoro-benzyl)-3-[1-(3-ethyl-phenyl)-cyclopropylamino]-2-hydroxy-propyl}-amide | (82) |
| 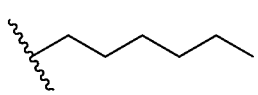 | 473.3 | (1S, 2R) Heptanoic acid {1-(3,5-difluoro-benzyl)-3-[1-(3-ethyl-phenyl)-cyclopropylamino]-2-hydroxy-propyl}-amide | (83) |

-continued

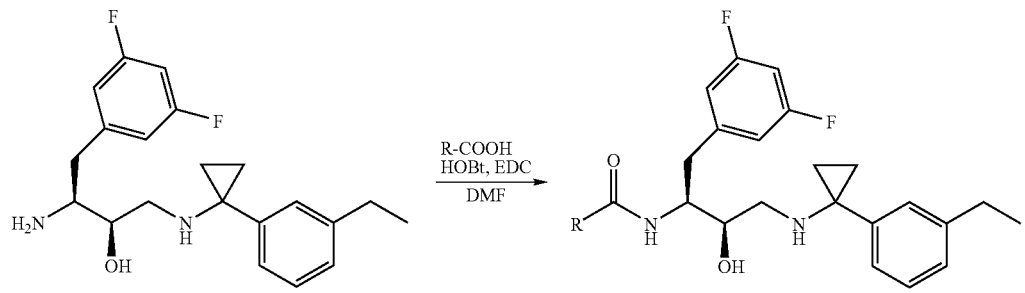

| | MH+ | | Compound No. |
|---|---|---|---|
| ![R1] | 485.3 | (1S, 2R) 2-Cyclohexyl-N-{1-(3,5-difluoro-benzyl)-3-[1-(3-ethyl-phenyl)-cyclopropylamino]-2-hydroxy-propyl}-acetamide | (84) |
| ![R2] | 519.2 | (1S, 2R) 2-(2-Butoxy-ethoxy)-N-{1-(3,5-difluoro-benzyl)-3-[1-(3-ethyl-phenyl)-cyclopropylamino]-2-hydroxy-propyl}-acetamide | (85) |
| ![R3] | 473.2 | (1S, 2R) 5-Oxo-hexanoic acid {1-(3,5-difluoro-benzyl)-3-[1-(3-ethyl-phenyl)-cyclopropylamino]-2-hydroxy-propyl}-amide | (86) |
| ![R4] | 488.2 | (1S, 2R) N-{1-(3,5-Difluoro-benzyl)-3-[1-(3-ethyl-phenyl)-cyclopropylamino]-2-hydroxy-propyl}-N',N'-dimethyl-succinamide | (87) |

B. Preparation of disubstituted benzylamine derivatives was generally performed as follows:
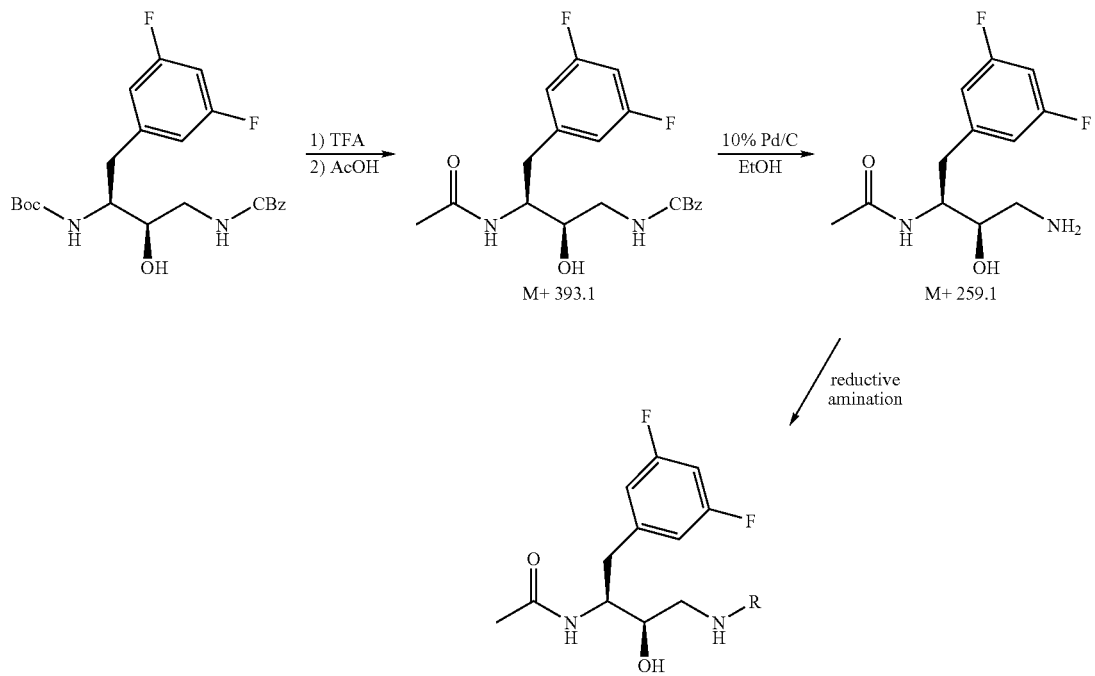
| | M+ | | Compound No. |
|---|---|---|---|
| R = [2-hydroxy-5-tert-butylphenyl-methyl] | 421.2 | (1S, 2R) N-[3-(5-tert-Butyl-2-hydroxy-benzylamino)-1-(3,5-difluoro-benzyl)-2-hydroxy-propyl]-acetamide | (88) |
| [3,5-dibromophenyl-methyl] | 506.9 | (1S, 2R) N-[3-(2,5-Dibromo-benzylamino)-1-(3,5-difluoro-benzyl)-2-hydroxy-propyl]-acetamide | (89) |

EXAMPLE 101A

Preparation of [(1S,2R) N-[3-[3-Bromo-5-(2,2-dimethyl-propyl)-benzylamino]-1-(3,5-difluoro-benzyl)-2-hydroxy-propyl]-acetamide] (90)

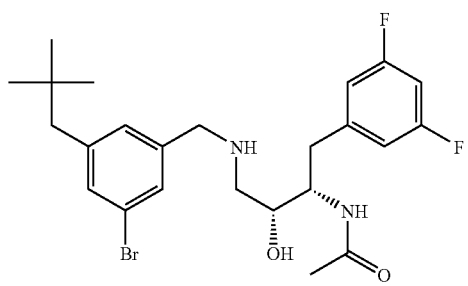

To dibromobenzylamine (1S,2R) N-[3-(2,5-Dibromo-benzylamino)-1-(3,5-difluoro-benzyl)-2-hydroxy-propyl]-acetamide (0.504 g, 1.0 mM, 1 eq) was added 0.5 M THF solution of neopentylzinc iodide (20 mL, 10 eq) and 0.082 g, (0.1 mM, 0.1 eq) of [1,1'-bis(diphenylphosphino)ferrocene]dichloropalladium(II), complex with dichloromethane (Pd(dppf)Cl$_2$ CH$_2$Cl$_2$). A reaction mixture was stirred overnight at room temperature. The reaction was quenched with a saturated aqueous solution of NH$_4$Cl (20 mL) and extracted with ethyl acetate (3×30 mL). Combined organic layers were washed with brine, dried and concentrated.

Compound (90) was purified by HPLC, yielding 0.055 g (11%). $^1$H NMR (300 MHz, DMSO-d$_6$) δ 8.60-9.00 (m, 1H), 7.88 (d, J=8.7 Hz, 1H), 7.61 (s, 1H), 7.39 (s, 1H), 7.08 (s, 1H), 7.05 (t, J=7.5 Hz, 1H), 6.93 (d, J=6.9 Hz, 2H), 4.16 (bs, 2H), 3.85 (m, 1H), 3.70 (m, 1H), 3.02 (m, 2H), 2.81 (m, 1H), 2.57 (m, 1H), 2.47 (s, 2H), 1.69 (s, 3H), 0.87 (s, 9H); $^{13}$C NMR (300 MHz, DMSO-d$_6$) δ 170.0, 164.4, 164.2, 161.1, 160.9, 144.2, 142.9, 134.2, 133.9, 131.8, 131.0, 121.6, 112.9, 112.6, 102.2, 69.3, 53.5, 50.1, 49.1, 35.4, 32.1, 29.6, 23.0; MH+ (CI): 497.2.

EXAMPLE 101B

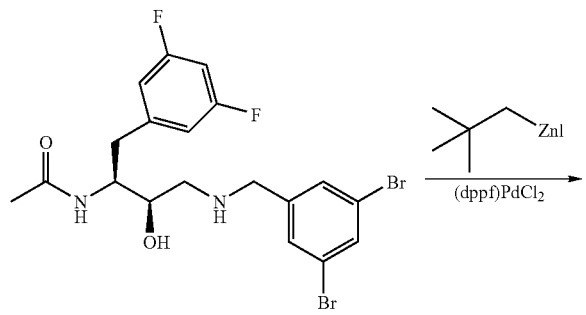

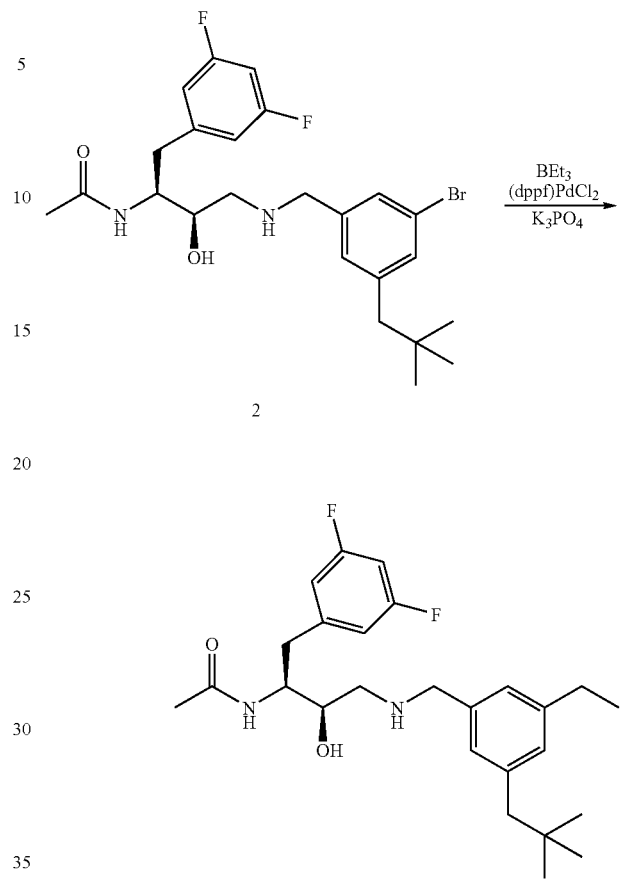

Compound 3 [(1S,2R) N-{1-(3,5-Difluorobenzyl)-3-[3-(2,2-dimethylpropyl)-5-ethyl-benzylamino]-2-hydroxypropyl}-acetamide] was prepared by reacting Example 101A (compound 2) with BEt$_3$, a palladium catalyst and potassium phosphate. MH+(CI): 447.2.

EXAMPLE 101C

Preparation of [(1S,2R) N-{1-(3,5-Difluorobenzyl)-2-hydroxy-3-[1-(3-prop-1-ynyl-phenyl)-cyclopropylamino]-propyl}-acetamide] 5

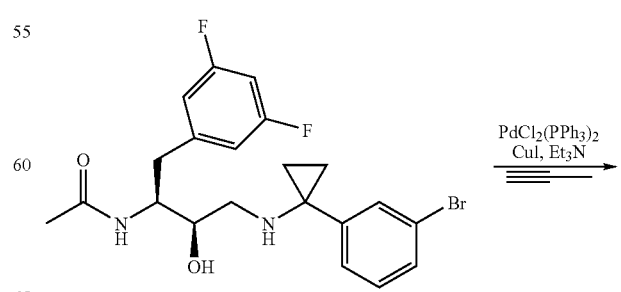

-continued

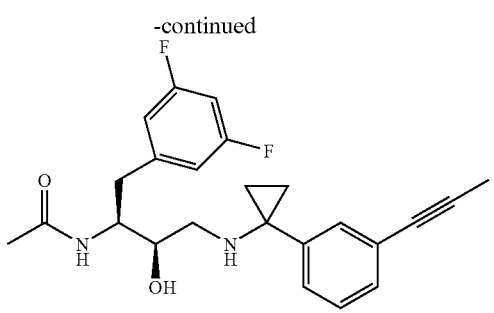

To a solution of (1S,2R) N-[3-[1-(3-Bromo-phenyl)-cyclopropylamino]-1-(3,5-difluoro-benzyl)-2-hydroxy-propyl]-acetamide 4 (0.227 g, 0.5 mM) in Et₃N (2 mL) and DMF (0.5 mL) was added PdCl$_2$(PPh$_3$)$_2$. A reaction mixture was cooled down to −30° C. and propene gas was bubbled through for 1 minute. A reaction tube was sealed and the mixture was stirred for 2 min. before CuI (0.001 g) was added. After stirring for additional 10 min. in a sealed tube at RT color of the reaction mixture changed from yellow to dark brown. The reaction was heated at 50° C. for 48 hrs, cooled down to rt, filtered and stripped solvent. Purified by HPLC; yield 0.030 g (15%); MH+(CI): 413.2.

EXAMPLE 102

A. Preparation of N-(1S,2R)-[1-(3,5-Difluoro-benzyl)-2-hydroxy-3-[(1S)-(7-isobutyl-1,2,3,4-tetrahydronaphthalen-1-ylamino)]-propyl]-acetamide

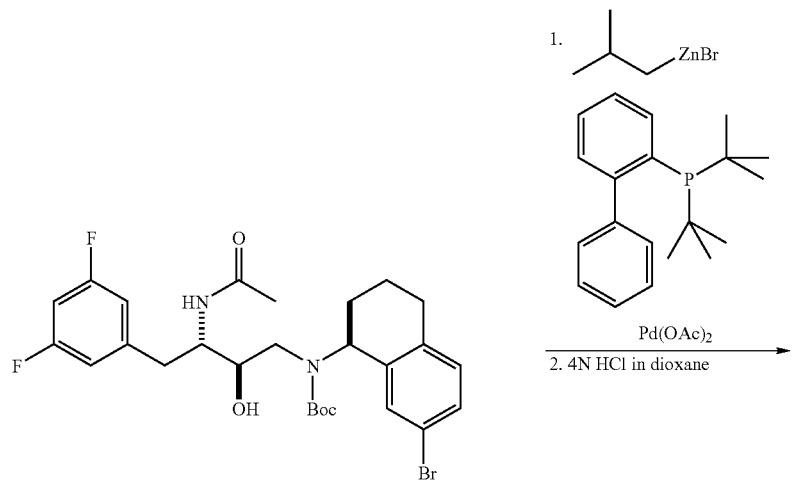

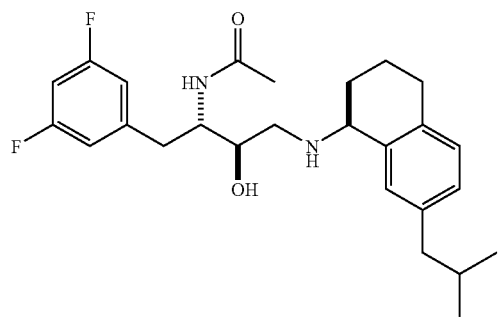

Palladium(II) acetate (0.2 equiv, 0.07 mmol, 15.8 mg) and 2-(di-t-butylphosphino)biphenyl (0.1 equiv, 0.035 mmol, 10.5 mg) were dissolved in THF (2 mL) and deoxygenated with a subsurface $N_2$ (g) purge for 5 minutes. The bromide (1 equiv, 0.352 mmol, 200 mg) was then added to this solution as a solid, followed by isobutyl zinc bromide (0.5 M solution in THF, 3 equiv, 1.1 mmol, 2.1 mL). The reaction was stirred overnight at ambient temperature under a $N_2$ (g) atmosphere. After 12 hours, the reaction was partitioned between EtOAc and $H_2O$, and extracted 3× into EtOAc. The combined organic extracts were washed with brine and dried over $Na_2SO_4$, filtered and concentrated. Column chromatography on $SiO_2$ with 30→50% EtOAc in hexanes gave the pure desired Boc protected product. (148 mg, 77% yield) $M+Na^+$ (CI)=567.2

Removal of the Boc group was achieved by dissolving the above compound in 4N HCl in dioxane (1 mL) and stirring at ambient temperature for 1 hour under a $N_2$ (g) atmosphere. The resulting white cloudy mixture was concentrated to give the final product. (100 mg, 85% yield) $^1$HNMR ($CD_3OD$): δ 7.3 (s, 1H), 7.15 (s, 2H), 6.9 (m, 2H), 6.8 (m, 1H), 4.6 (t, 1H), 4.05 (m, 1H), 3.9 (m, 1H), 3.2 (m, 2H), 3.0 (m, 1H, 2.8 (m, 2H), 2.7 (m, 2H), 2.5 (d, 2H), 2.2 (m, 2H), 2.0 (m, 1H), 1.85 (s, 3H), 1.85, m, 1H), 0.9 (m, 6H). $M+H^+$ (CI)=445.2

B. Preparation of N-(1S,2R)-{1-(3,5-Difluoro-benzyl)-3-[(1S)-7-(2,2-dimethylpropyl)-1,2,3,4-tetrahydro-naphthalen-1-ylamino]-2-hydroxypropyl}-acetamide

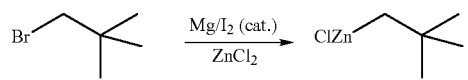

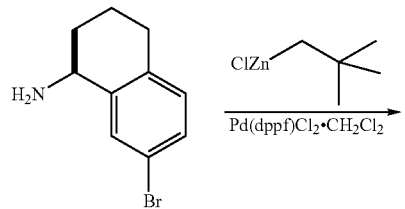

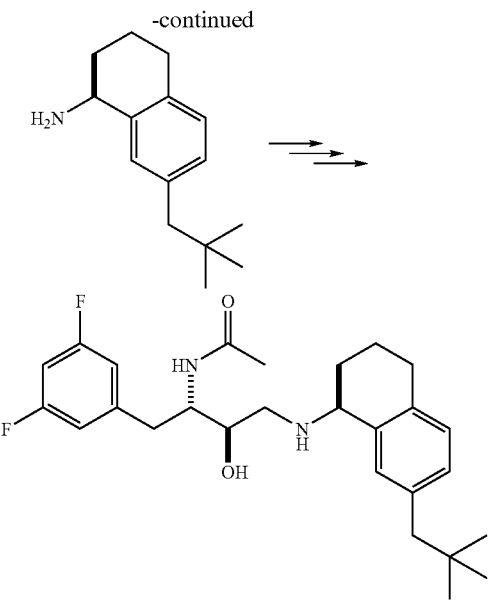

The neopentyl zinc was prepared according to the procedure in Tetrahedron Letters, 1983, volume 24, page 3823-3824.

To the bromotetralin amine (1 equiv, 8 mmol, 1.71 g) was added the crude neopentylzinc chloride suspension (3 equiv, 24 mmol, 48 mL), followed by $Pd(dppf)Cl_2CH_2Cl_2$ (0.05 equiv, 0.4 mmol, 330 mg). The reaction was stirred at ambient temperature under $N_2$ (g) overnight. The suspension quickly turned yellow, and eventually turned purplish overnight. After 12 h, the reaction was quenched with $NH_4Cl$ (aq) and extracted 3× with EtOAc. The combined organic extracts were washed with brine and dried over $Na_2SO_4$, filtered and concentrated. Column chromatography on $SiO_2$ with 2→10% MeOH in $CH_2Cl_2$ gave the desired neopentyl tetralin amine. (1.5 g, 86% yield) $^1$HNMR ($CDCl_3$): δ 7.15 (s, 1H), 6.95 (m, 2H), 3.95 (m, 1H), 2.8 (m, 2H), 2.4 (s, 2H), 2.0 (m, 2H), 1.7 (m, 2H), 1.6 (broad s, 2H), 1.0 (s, 9H); $M-NH_2^+$ (CI)=201.2.

The final compound was synthesized via epoxide opening, protecting group deprotection, and acetylation as previously described: $M+H^+$ (CI)=459.2.

C. Preparation of N-(1S,2R)-{1-(3,5-Difluorobenzyl)-2-hydroxy-3-[1-(3-isopropenyl-phenyl)-cyclopropylamino]-propyl}-acetamide

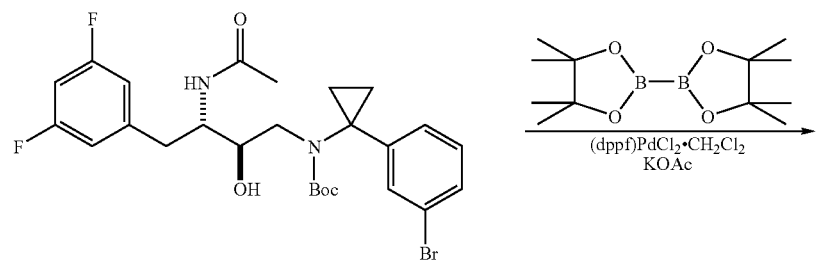

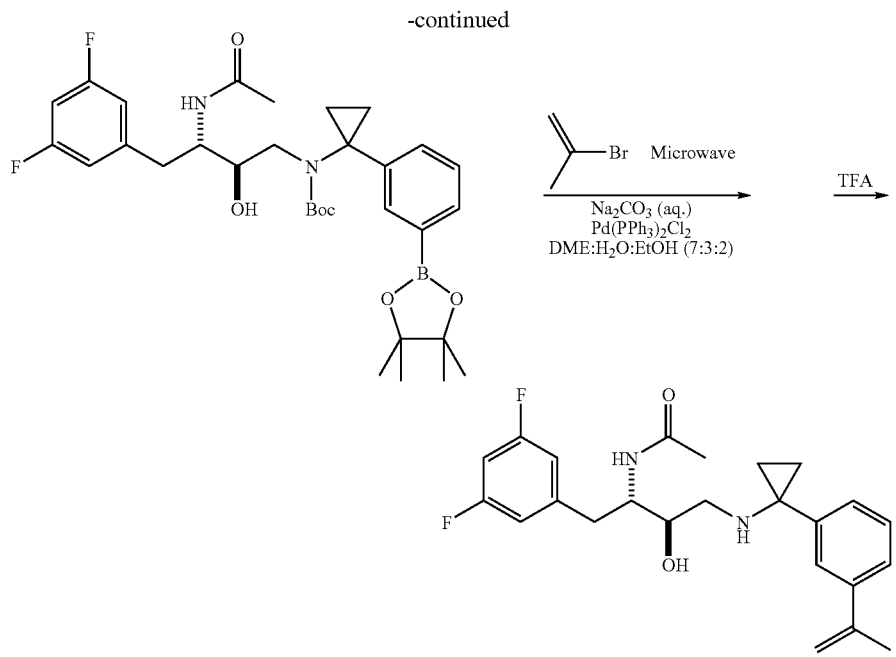

Potassium acetate (5 equiv, 8.8 mmol, 0.864 g), (dppf)PdCl₂.CH₂Cl₂ (0.04 equiv, 0.0704 mmol, 57.5 mg), and diboron reagent (1.15 equiv, 2.03 mmol, 0.515 g), followed by the bromide (1 equiv, 1 g, 1.76 mmol) and DMF (7 mL) were added to a flask. The mixture was deoxygenated via a subsurface N₂ (g) purge, and stirred at 80° C. under N₂ (g) overnight. As soon as heating began, the reaction turned brown. After 18 h, the reaction was partitioned between EtOAc and H₂O, and extracted 3× with EtOAc. The combined organic extracts were washed with brine, dried over Na₂SO₄, and filtered before removal of solvent under vacuum. A quick SiO₂ column with 20→50% EtOAc in hexanes gave the pure boronic ester. (0.75 g, 69% yield) ¹HNMR (CD₃OD): δ 7.6 (t, 1H), 7.25 (m, 1H), 7.1 (m, 1H), 7.8 (dd, 2H), 6.6 (m, 1H), 4.05 (m, 1H), 3.8 (m, 1H), 3.5 (m, 2H), 2.9 (m, 2H), 1.8 (s, 3H), 1.4 (s, 9H), 1.2 (m, 12H), 1.2 (m, 4H). M+Na⁺ (CI)=623.2

The boron ester (1 equiv, 0.167 mmol, 100 mg) followed by Pd(PPh₃)₂Cl₂ (0.1 equiv, 0.017 mmol, 11.7 mg), 2-bromopropene (1.2 equiv, 0.2 mmol, 24.2 mg, 17.8 µL), 2M Na₂CO₃ (aq) (1.5 equiv, 0.25 mmol, 0.125 mL), and finally 7:3:2 DME:H₂O:EtOH (0.7 mL) were placed in a reaction vial equipped with a stir bar. The vial was sealed and the reaction was prestirred for 15 s before being microwaved at 160° C. for 7 minutes at Normal Absportion Level and with Fixed Hold Time on. (A Personal Chemistry Microwave Reactor was used.) The reaction was partitioned between EtOAc and H₂O, and extracted 3× with EtOAc. The combined organic extracts were washed with brine, dried over Na₂SO₄, and filtered before removal of solvent under vacuum. Purification via SiO₂ column run with 10→35% EtOAc in hexanes gave the pure Boc protected styrene compound. (45.9 mg, 53% yield) M+Na⁺ (CI)=537.2

Boc group removal was achieved by treating the above protected compound with 1:4 TFA:CH₂Cl₂ at 0° C. The reaction was stirred for 2 h at 0° C., and then concentrated to give the desired product. HPLC purification gave the pure desired product (7 mg, 36% yield): M+H⁺ (CI)=415.2

D. Preparation of N-(1S, 2R)-{1-(3,5-Difluorobenzyl)-2-hydroxy-3-[1-(3-isopropylphenyl)-cyclopropylamino]-propyl}-acetamide

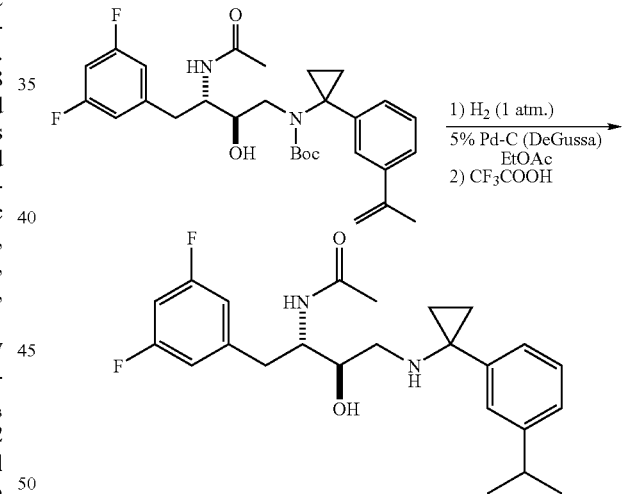

The Boc amine (1 equiv, 0.1 mmol, 55.4 mg) was dissolved in EtOAc before the addition of 5% Pd—C DeGussa catalyst (an unmeasured amount). The air was evacuated from the flask before a balloon of N₂ (g) was applied. The mixture was stirred for 4 h at ambient temperature, at which point HPLC-MS determined the reaction was complete. Filtration through diatomaceous earth followed by removal of solvent by vacuum resulted in the clean crude reduced material. (56.7 mg, quantitative) M+H⁺ (CI)=517.3.

Removal of the Boc group was achieved by dissolving the above compound in 50:50 TFA:CH₂Cl₂ and stirring at ambient temperature for 1 hour under a N₂ (g) atmosphere. The resulting solution was concentrated to give the final product. (41.6 mg, quantitative): ¹H NMR (CD₃OD) δ 7.4 (s, 1H), 7.25 (m, 3H), 6.7 (m, 2H), 6.6 (m, 1H), 4.0 (m, 1H), 3.9 (m, 1H), 2.9 (m, 4H), 2.7 (m, 1H), 1.8 (s, 3H), 1.2 (d, 6H), 1.2 (m, 4H). M+H⁺ (CI)=417.2

EXAMPLE 103
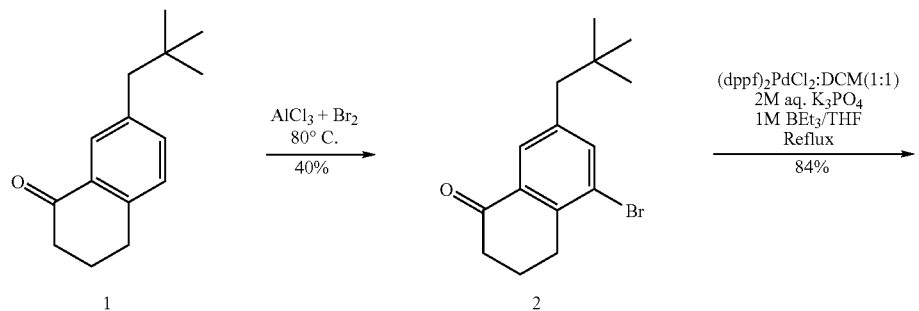
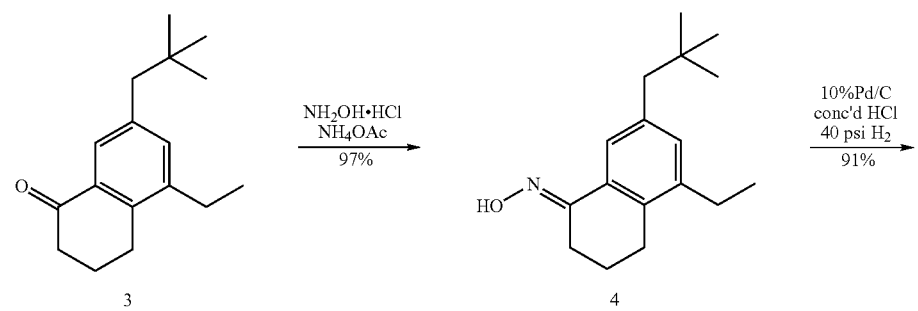
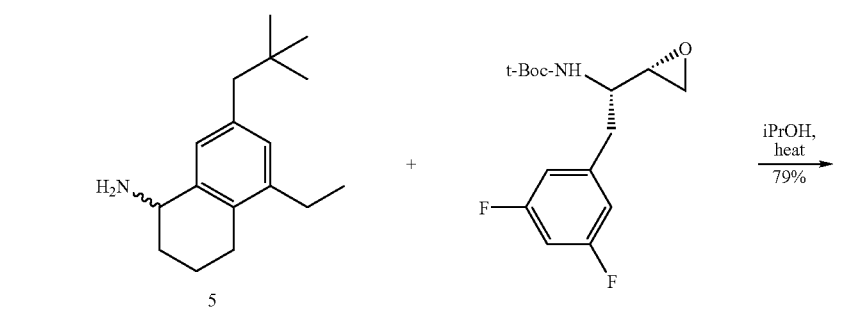
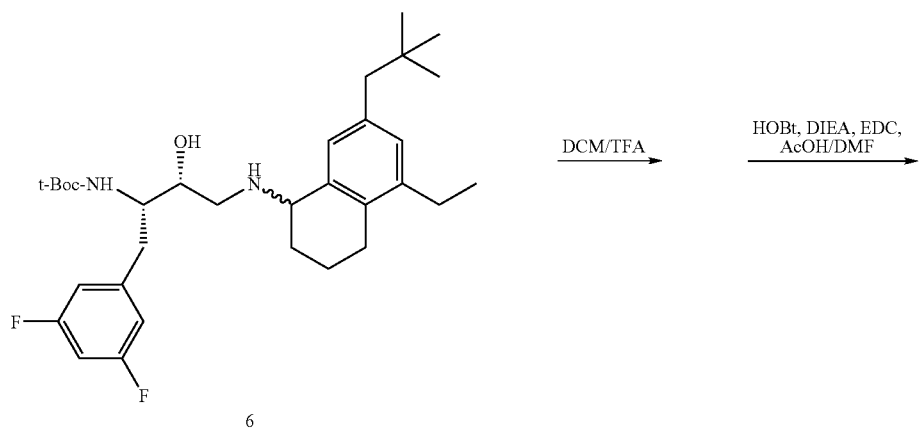

-continued

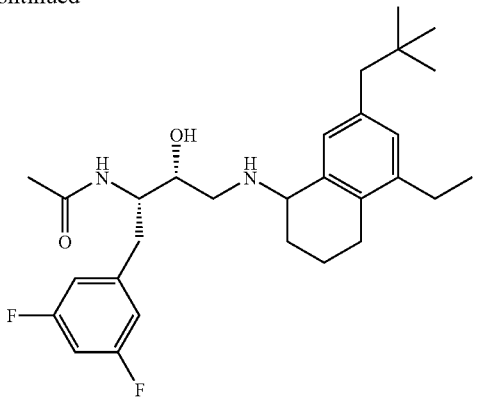

Step 1

The conversion of compound 1 to compound 2 was performed essentially according to the method of Example 1. The resulting crude product was purified by flash column chromatography to afforded compound 2 as a solid: TLC (10% EtOAc/Hexane) $R_f$=0.48; MH+ (CI) 295.0 ($^{79}$Br).

Step 2

Palladium-mediated transfer of the ethyl group onto the aryl bromide was described previously to give compound 3: Yield: 84%; MH+ (CI) 245.2.

Step 3

Formation of the oxime was performed as previously described to give compound 4. Yield: 97%; MH+ (CI) 260.2.

Step 4

Reduction of the oxime to the amine was achieved as previously described to give compound 5: yield: 91%; MH+ (CI) 229.2.

Step 5

Epoxide opening was performed as previously described: yield: 79%; MH+ (CI) 545.3.

Step 6

Boc deprotection and acetylation was performed as previously described. The resultant diastereomeric mixture was purified by reverse-phase HPLC to give both isomers of:

N-(1S,2R)-{1-(3,5-Difluorobenzyl)-3-[7-(2,2-dimethylpropyl)-5-ethyl-1,2,3,4-tetrahydronaphthalen-1-ylamino]-2-hydroxypropyl}acetamide.

Isomer 1: MH+ (CI) 487.3.
Isomer 2: MH+ (CI) 487.3.

EXAMPLE 104

Synthesis of 3,5-Disubstituted Benzylamine Derivatives

A. 3,5-di-tert-butylbenzonitrile from 3,5-di-tert-butylbromobenzene

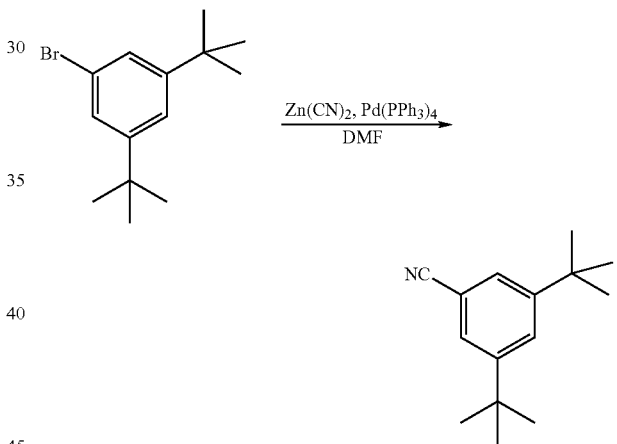

The nitrile is introduced essentially according to the procedure detailed in Dudley, D. A. et al. *J. Med. Chem.* 2000, 43, 4063-4070. The crude product was purified by flash chromatography ($R_f$=0.68 in 10% EtOAc/hexanes) to give the desired product as a white solid: $^1$H NMR (300 MHz, CDCl$_3$) δ 7.64 (s, 1H), 7.48 (d, J=1.8 Hz, 2H), 1.33 (s, 18H); mass spec (CI): 175.1.

B. 3,5-di-tert-butylbenzylamine

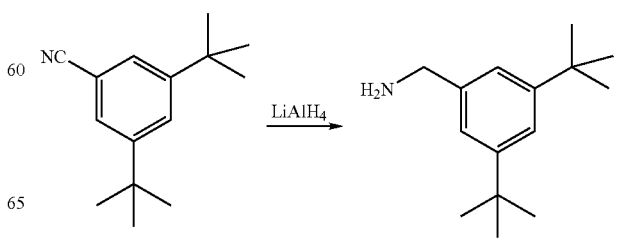

To 3,5-di-tert-butylbenzonitrile (863 mg, 4.02 mmol) in dry THF (10 mL) at 0° C. was added lithium aluminum hydride (304 mg, 8.0 mmol) in one portion. The reaction mixture was allowed to warm to rt for 2 h, whereupon the reaction was quenched (0.2 mL water, followed by 0.2 mL 15% potassium hydroxide solution and 0.6 mL water). The reaction mixture was stirred at rt for 1 h, then filtered through diatomaceous earth ($CH_2Cl_2$ elution). The filtrate was then concentrated and used in the next reaction without further purification: $^1$H NMR (300 MHz, $CDCl_3$) δ 7.33 (s, 1H), 7.16 (d, J=1.8 Hz, 2H), 3.86 (s, 2H), 1.33 (s, 18H); mass spec (CI): 203.2 (M−$NH_2$).

The free amine was further elaborated, using methods analogous to those disclosed herein, to form the final product.

C. N-[(1S,2R)-3-(3,5-Di-tert-butyl-benzylamino)-1-(3,5-difluorobenzyl)-2-hydroxypropyl]acetamide

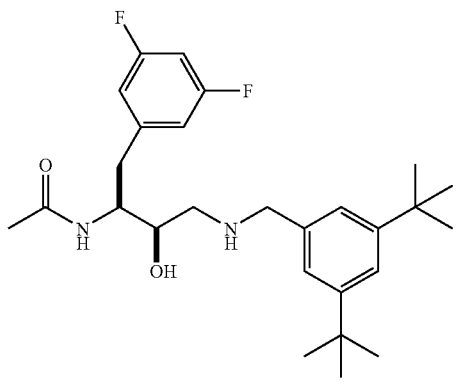

The above compound was prepared using methods analogous to those previously described. $^1$H NMR (300 MHz, $CDCl_3$) δ 7.36 (s, 1H), 7.16 (d, J=1.4 Hz, 2H), 6.90 (d, J=8.8 Hz, 1H), 6.70 (d, J=6.2 Hz, 2H), 6.61 (tt, J=9.0, 2.0 Hz, 1H), 4.22-4.10 (m, 1H), 4.03 (br s, 1H>, 3.80 (d, J=12.9 Hz, 1H), 3.74 (d, J=12.9 Hz, 1H), 3.72-3.60 (m, 1H), 2.90-2.65 (m, 4H), 1.85 (s, 3H), 1.32 (s, 18H); $^{13}$C NMR (75 MHz, $CDCl_3$) δ 170.5, 162.8 (dd, J=248.2, 13.0 Hz, 2C), 151.0, 142.1 (t, J=9.1 Hz, 1C), 137.3, 122.6, 121.5, 111.9 (dd, J=16.9, 7.5 Hz, 2C), 101.8 (t, J=25.3 Hz, 1C), 70.1, 54.2, 53.6, 50.7, 36.1, 34.7, 31.4, 23.2; MH+ (CI): 461.3.

D. N-[(1S,2R)-3-(3,5-Dibromobenzylamino)-1-(3,5-difluorobenzyl)-2-hydroxypropyl]acetamide

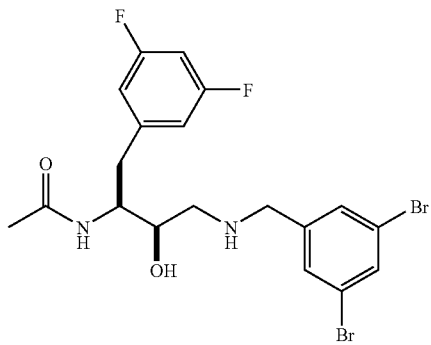

The titled compound was prepared using methods analogous to those previously described. The required dibromo benzylamine is prepared by treating the commercially available aldehyde with a nitrogen source and a reducing agent. $^1$H NMR (300 MHz, $CDCl_3$) δ 7.56 (t, J=1.5 Hz, 1H), 7.40 (d, J=1.5 Hz, 2H), 6.74 (d, J=6.2, 1.8 Hz, 2H), 6.68 (tt, J=9.0, 2.2 Hz, 1H), 5.63 (d, J=8.9 Hz, 1H), 4.20-4.05 (m, 1H), 3.78 (d, J=13.9 Hz, 1H), 3.71 (d, J=13.9 Hz, 1H), 3.51 (q, J=5.3 Hz, 1H), 2.99 (dd, J=14.3, 4.7 Hz, 1H), 2.82 (dd, J=14.3, 8.7 Hz, 1H), 2.67 (d, J=3.0 Hz, 2H), 1.93 (s, 3H); $^{13}$C NMR (75 MHz, $CDCl_3$) δ 170.4, 163.0 (dd, J=248.2, 13.0 Hz, 2C), 143.9, 141.7 (t, J=9.1 Hz, 1C), 132.8, 129.8, 123.0, 112.0 (dd, J=16.9, 7.5 Hz, 2C), 102.2 (t, J=25.3 Hz, 1C), 70.7, 52.9, 52.8, 50.5, 36.1, 23.3; MH+ (CI): 505.0 ($^{79}$Br×2).

EXAMPLE 105

Synthesis of Pyridine Derivatives

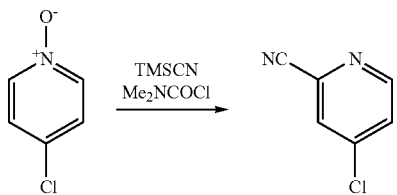

The nitrile was introduced essentially according to the method of Ornstein, P. L. et al. *J. Med. Chem.* 1991, 34, 90-97. The crude product was filtered through silica ($CH_2Cl_2$ elution) to give the product as a white crystalline solid: $^1$H NMR (300 MHz, $CDCl_3$) δ 8.64 (d, J=5.3 Hz, 1H), 7.72 (d, J=1.7 Hz, 1H), 7.56 (dd, J=5.3, 1.7 Hz, 1H); MH+ (CI): 139.0 ($^{35}$Cl).

A. 2-Cyano-4-isopropylpyridine

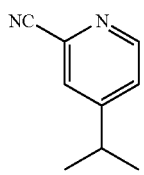

2-Cyano-4-isopropylpyridine was synthesized according to the method of Ornstein, P. L. et al. *J. Med. Chem.* 1991, 34, 90-97: MH+ (CI): 147.1.

B. 2-Cyano-4-tert-butylpyridine

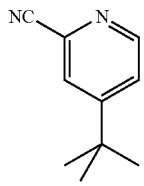

2-Cyano-4-tert-butylpyridine was synthesized according to the method of Ornstein, P. L. et al. *J. Med. Chem.* 1991, 34, 90-97: $^1$H NMR (300 MHz, CDCl$_3$) δ 8.60 (d, J=5.3 Hz, 1H), 7.68 (d, J=1.5 Hz, 1H), 7.49 (dd, J=5.3, 1.9 Hz, 1H), 1.33 (s, 9H); MH+ (CI): 161.1.

C. 2-Cyano-6-neopentylpyridine

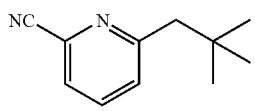

2-Cyano-6-neopentylpyridine was synthesized from 2-neopentylpyridine according to the method of Ornstein, P. L. et al. *J. Med. Chem.* 1991, 34, 90-97: R$_f$=0.62 in 20% EtOAc/hexanes; MH+ (CI): 175.1.

D. 2-Neopentylpyridine from 2-bromopyridine

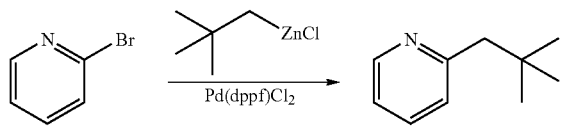

A solution of neopentylzinc chloride was prepared according to the method of Negishi, E.-I. et al. *Tetrahedron Lett.* 1983, 24, 3823-3824.

2-Bromopyridine (Aldrich, 0.48 mL, 5.0 mmol) and [1,1'-bis(diphenylphosphino)ferrocene]dichloropalladium(II), complex with dichloromethane (1:1) (Aldrich, 200 mg, 0.25 mmol) were added to the neopentylzinc chloride suspension. The resulting suspension was stirred at rt for 21 h, whereupon saturated ammonium chloride solution (25 mL) was added. The mixture was extracted with ethyl acetate (3×). The combined organic extracts were dried (Na$_2$SO$_4$), filtered and concentrated under reduced pressure. The residue was dissolved in methylene chloride, and washed with 1 N HCl. The aqueous layer was separated, basified with 10 N NaOH (aq), and extracted with CH$_2$Cl$_2$. The organic layer was dried (Na$_2$SO$_4$), filtered and concentrated under reduced pressure to give 2-neopentylpyridine as an oil: R$_f$=0.33 in 5% MeOH/CH$_2$Cl$_2$.

E. 2-cyano-4-neopentylpyridine

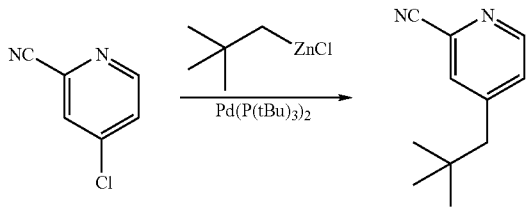

This transformation was performed according to the method of Dai, C. and Fu, G. *J. Am. Chem. Soc.* 2001, 123, 2719-2724. The crude residue was purified by filtration through a small plug of silica (20% ether/hexanes elution) to give the 2-cyano-4-neopentylpyridine: R$_f$=0.25 in 20% Et$_2$O/hexanes; MH+ (CI): 175.1.

F. 4-cyano-2-neopentylpyridine

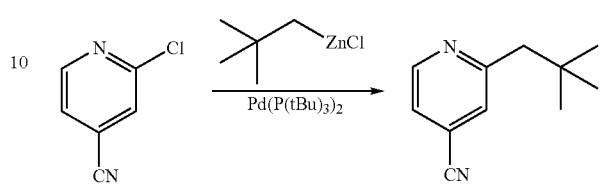

The method for the synthesis of 2-cyano-4-neopentylpyridine was used to convert 2-chloro-4-cyanopyridine (Oakwood) into 4-cyano-2-neopentylpyridine: R$_f$=0.47 in 10% EtOAc/hexanes; $^1$H NMR (300 MHz, CDCl$_3$) δ 8.73 (dd, J=4.9, 0.7 Hz, 1H), 7.55-7.40 (m, 2H), 2.75 (s, 2H), 0.96 (s, 9H); MH+ (CI): 175.1.

G. 2-Cycloalkylamino-4-neopentylpyridine

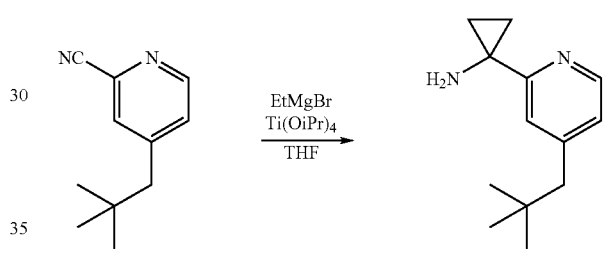

To a solution of 2-cyano-4-neopentylpyridine (380 mg, 2.2 mmol) in dry THF (6 mL) at rt was added titanium(IV) isopropoxide (0.7 mL, 2.4 mmol) and ethylmagnesium bromide (1.0 M in THF, 4.3 mL, 4.3 mmol) in succession with vigorous stirring. After 30 min, 1 mL water was added. The quenched reaction mixture was stirred at rt for 30 min, then filtered through diatomaceous earth (10% iPrOH/CHCl$_3$ elution). The filtrate was concentrated under reduced pressure. The crude residue was purified by flash chromatography (R$_f$=0.26 in 10% MeOH/CH$_2$Cl$_2$) to give 166 mg of the desired product as an oil:
MH+ (CI): 205.1.

H. N-((1S,2R)-1-(3,5-Difluorobenzyl)-3-{[4-(2,2-dimethylpropyl)pyridin-2-ylmethyl]amino}-2-hydroxypropyl)acetamide

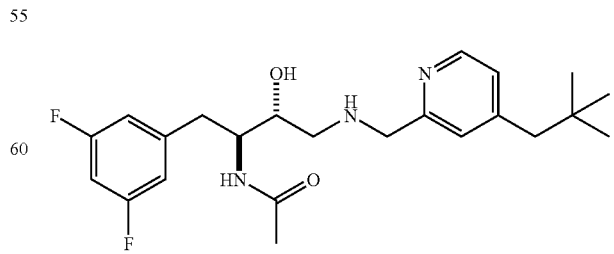

The above compound was prepared from 2-cyano-4-neopentylpyridine by methods analogous to those disclosed herein. $^1$H NMR (300 MHz, CDCl$_3$) δ 8.39 (d, J=5.0 Hz, 1H), 7.03-6.92 (m, 2H), 6.72 (app d, J=6.3 Hz, 2H), 6.63 (tt, J=9.0, 2.2 Hz, 1H), 6.44 (d, J=9.0 Hz, 1H), 4.25-4.10 (m, 1H), 3.93 (s, 2H), 3.72-3.62 (m, 1H), 2.94 (dd, J=14.3, 4.7 Hz, 1H), 2.88-2.70 (m, 3H), 2.48 (s, 2H), 1.87 (s, 3H), 0.91 (s, 9H); $^{13}$C NMR (75 MHz, CDCl$_3$) δ 170.3, 162.8 (dd, J=248.2, 13.0 Hz, 2C), 157.7, 149.8, 148.3, 142.3 (t, J=9.1 Hz, 1C), 124.62, 124.56, 112.0 (dd, J=16.9, 7.4 Hz, 2C), 101.8 (t, J=25.1 Hz, 1C), 71.0, 54.1, 52.9, 51.5, 49.5, 35.7, 31.7, 29.3, 23.1; MH+ (CI): 420.2.

I. N-((1S,2R)-1-(3,5-Difluorobenzyl)-3-{1-[4-(2,2-dimethylpropyl)pyridin-2-yl]cyclopropylamino}-2-hydroxypropyl)acetamide

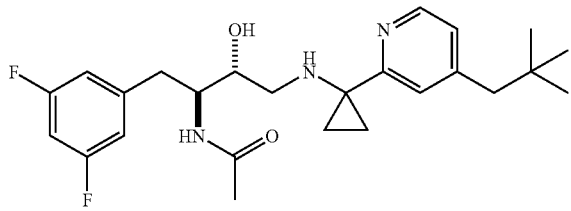

The above compound was prepared by coupling 2-Cycloalkylamino-4-neopentylpyridine and example 134 by methods analogous to those disclosed herein. The coupled product was then further elaborated using to afford the above compound. $^1$H NMR (300 MHz, CDCl$_3$) δ 8.35 (d, J=5.1 Hz, 1H), 6.89 (dd, J=5.1, 1.0 Hz, 1H), 6.80 (s, 1H), 6.73 (dd, J=6.2, 2.0 Hz, 2H), 6.64 (tt, J=9.0, 2.0 Hz, 1H), 5.93 (d, J=9.2 Hz, 1H), 4.22-4.07 (m, 1H), 3.72 (s, 2H), 3.50 (dt, J=6.6, 3.3 Hz, 1H), 2.96 (dd, J=14.3, 4.6 Hz, 1H), 2.90-2.70 (m, 3H), 2.46 (s, 2H), 1.88 (s, 3H), 1.16 (d, J=2.4 Hz, 4H), 0.90 (s, 9H); $^{13}$C NMR (75 MHz, CDCl$_3$) δ 170.0, 163.3 (dd, J=248.2, 13.0 Hz, 2C), 162.2, 149.4, 147.5, 142.1 (t, J=9.1 Hz, 1C), 123.2, 120.9, 112.0 (dd, J=16.9, 7.4 Hz, 2C), 101.9 (t, J=25.1 Hz, 1C), 71.1, 63.6, 53.4, 52.6, 49.7, 49.4, 42.7, 35.8, 31.7, 29.3, 23.2, 19.0, 18.5; MH+ (CI): 446.2.

J. N-((1S,2R)-1-(3,5-Difluorobenzyl)-3-{[2-(2,2-dimethylpropyl)pyridin-4-ylmethyl]-amino}-2-hydroxypropyl)acetamide

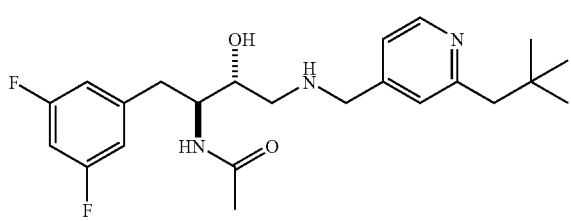

The above compound was prepared essentially according to the previously described methods. $^1$H NMR (300 MHz, CDCl$_3$) δ 8.44 (d, J=5.0 Hz, 1H), 7.07 (d, J=5.0 Hz, 1H), 7.06 (s, 1H), 6.72 (d, J=6.3 Hz, 2H), 6.64 (tt, J=9.0, 2.2 Hz, 1H), 6.56 (d, J=8.7 Hz, 1H), 4.25-4.10 (m, 1H), 3.82 (d, J=14.4 Hz, 1H), 3.76 (d, J=14.4 Hz, 1H), 3.62 (q, J=5.0 Hz, 1H), 3.42 (br s, 2H), 2.93 (dd, J=14.2, 4.9 Hz, 1H), 2.78 (dd, J=14.2, 8.9 Hz, 1H), 2.73 (d, J=4.8 Hz, 2H), 2.66 (s, 2H), 1.88 (s, 3H), 0.94 (s, 9H); $^{13}$C NMR (75 MHz, CDCl$_3$) δ 170.4, 162.7 (dd, J=248.2, 13.0 Hz, 2C), 160.2, 148.7, 148.0, 142.0 (t, J=9.1 Hz, 1C), 123.9, 120.3, 111.8 (dd, J=16.9, 7.5 Hz, 2C), 101.9 (t, J=25.3 Hz, 1C), 70.5, 53.4, 52.6, 51.7, 50.8, 36.0, 31.9, 29.5, 23.1; MH+ (CI): 420.2.

K. N-{(1S,2R)-1-(3,5-Difluorobenzyl)-2-hydroxy-3-[(4-isopropylpyridin-2-ylmethyl)-amino]propyl}acetamide

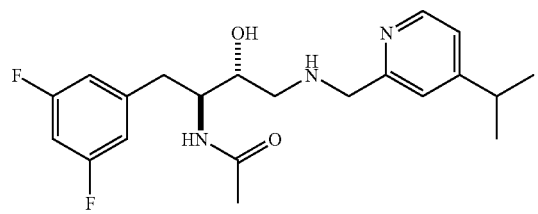

The above compound was prepared essentially according to the previously described methods. $^1$H NMR (300 MHz, CDCl$_3$) δ 8.37 (d, J=4.7 Hz, 1H), 7.10 (s, 1H), 7.06 (d, J=5.2 Hz, 1H), 6.94 (d, J=9.0 Hz, 1H), 6.72 (d, J=6.3 Hz, 2H), 6.61 (tt, J=9.0, 2.2 Hz, 1H), 4.77 (br s, 2H), 4.25-4.10 (m, 1H), 3.93 (s, 2H), 3.80-3.70 (m, 1H), 3.05-2.70 (m, 5H), 1.86 (s, 3H), 1.23 (d, J=7.0 Hz, 6H); $^{13}$C NMR (75 MHz, CDCl$_3$) δ 170.4, 162.7 (dd, J=248.2, 13.0 Hz, 2C), 158.8, 157.4, 148.9, 142.4 (t, J=9.1 Hz, 1C), 120.9, 112.0 (dd, J=16.9, 7.5 Hz, 2C), 101.7 (t, J=25.3 Hz, 1C), 70.8, 54.0, 53.2, 51.6, 35.7, 33.5, 22.9; MH+ (CI): 392.2.

L. N-{(1S,2R)-1-(3,5-Difluorobenzyl)-2-hydroxy-3-[1-(4-isopropylpyridin-2-yl)-cyclopropylamino]propyl}acetamide

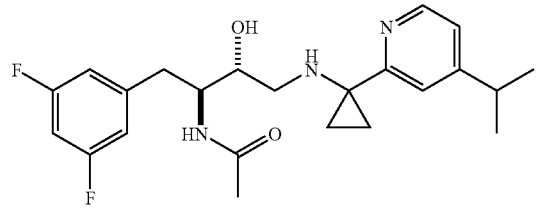

The above compound was prepared essentially according to the previously described methods. MH+ (CI): 418.2.

M. N-[(1S,2R)-3-[(4-tert-Butylpyridin-2-ylmethyl)amino]-1-(3,5-difluorobenzyl)-2-hydroxypropyl]acetamide

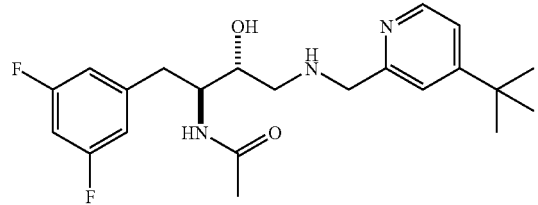

The above compound was prepared essentially according to the previously described methods. $^1$H NMR (300 MHz, CDCl$_3$) δ 8.40 (d, J=5.3 Hz, 1H), 7.22 (s, 1H), 7.19 (dd, J=5.3, 1.7 Hz, 1H), 6.73 (d, J=6.3 Hz, 2H), 6.65 (tt, J=9.0, 2.2 Hz, 1H), 4.26 (br s, 2H), 4.25-4.10 (m, 1H), 3.94 (s, 2H), 3.77-3.67 (m, 1H), 3.05-2.70 (m, 4H), 1.88 (s, 3H), 1.30 (s, 9H); $^{13}$C NMR (75 MHz, CDCl$_3$) δ 170.3, 162.8 (dd, J=248.2, 13.0 Hz, 2C), 161.2, 157.9, 148.8, 142.4 (t, J=9.1 Hz, 1C), 119.6, 119.5, 112.1 (dd, J=16.9, 7.5 Hz, 2C), 101.8 (t, J=25.3 Hz, 1C), 70.9, 54.3, 53.1, 51.7, 35.8, 34.7, 30.4, 28.7, 23.1; MH+ (CI): 406.2.

N. N-[(1S,2R)-3-[1-(4-tert-Butylpyridin-2-yl)cyclopropylamino]-1-(3,5-difluorobenzyl)-2-hydroxypropyl]acetamide

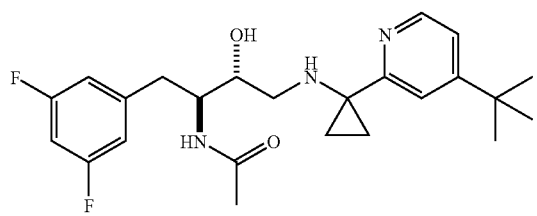

The above compound was prepared essentially according to the previously described methods. $^1$H NMR (300 MHz, CDCl$_3$) δ 8.38 (d, J=5.2 Hz, 1H), 7.15-7.05 (m, 2H), 6.73 (d, J=6.3 Hz, 2H), 6.64 (tt, J=9.0, 2.2 Hz, 1H), 5.88 (d, J=9.1 Hz, 1H), 4.22-4.08 (m, 1H), 3.75 (br s, 2H), 3.50 (td, J=6.5, 3.5 Hz, 1H), 2.99 (dd, J=14.2, 4.5 Hz, 1H), 2.90-2.70 (m, 3H), 1.89 (s, 3H), 1.30 (s, 9H), 1.25-1.10 (m, 4H); $^{13}$C NMR (75 MHz, CDCl$_3$) δ 170.0, 162.9 (dd, J=248.2, 13.0 Hz, 2C), 162.5, 160.8, 148.2, 142.1 (t, J=9.1 Hz, 1C), 118.2, 115.6, 112.0 (dd, J=16.9, 7.5 Hz, 2C), 101.9 (t, J=25.3 Hz, 1C), 70.9, 52.6, 49.4, 43.1, 35.9, 34.8, 30.5, 23.2, 18.8, 18.7; MH+ (CI): 432.2.

O. N-((1S,2R)-1-(3,5-Difluorobenzyl)-3-{[6-(2,2-dimethylpropyl)pyridin-2-ylmethyl]-amino}-2-hydroxypropyl)acetamide

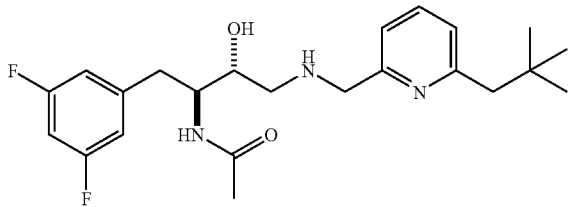

The above compound was prepared essentially according to the previously described methods. $^1$H NMR (300 MHz, CDCl$_3$) δ 7.56 (t, J=7.6 Hz, 1H), 7.06 (d, J=7.6 Hz, 1H), 7.02 (d, J=7.6 Hz, 1H), 6.74 (dd, J=6.3, 2.0 Hz, 2H), 6.64 (tt, J=9.0, 2.2 Hz, 1H), 6.11 (d, J=9.0 Hz, 1H), 4.25-4.10 (m, 1H), 3.92 (d, J=1.2 Hz, 2H), 3.70-3.55 (m, 1H), 3.25 (br s, 1H), 2.93 (dd, J=14.2, 4.9 Hz, 1H), 2.88-2.70 (m, 3H), 2.68 (s, 2H), 1.88 (s, 3H), 0.95 (s, 9H); $^{13}$C NMR (75 MHz, CDCl$_3$) δ170.0, 162.8 (dd, J=248.2, 13.0 Hz, 2C), 159.8, 157.6, 142.2 (t, J=9.1 Hz, 1C), 136.3, 123.3, 119.6, 112.0 (dd, J=16.9, 7.5 Hz, 2C), 101.9 (t, J=25.3 Hz, 1C), 70.8, 54.2, 52.8, 51.6, 51.5, 35.7, 32.0, 29.5, 23.2; MH+ (CI): 420.2.

EXAMPLE 106

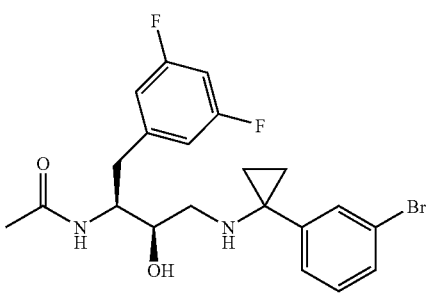

Step 1. Epoxide opening with 1-(3-bromophenyl)cyclopropyl amine

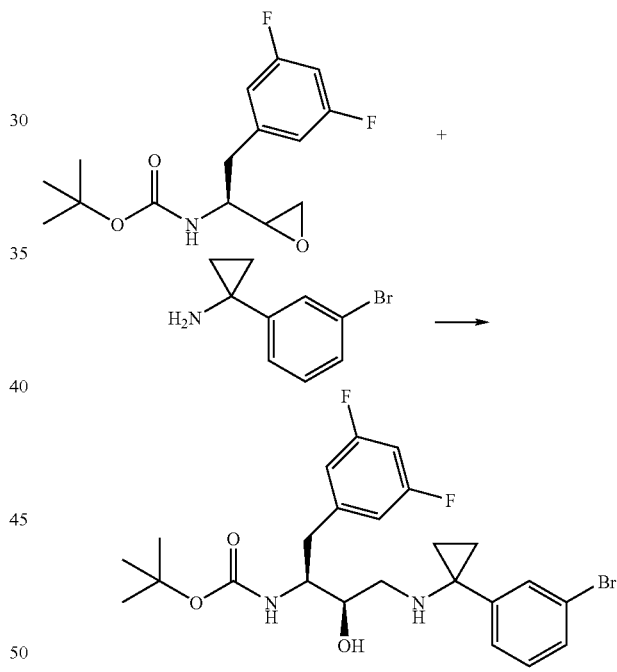

N-BOC-1-(3-bromophenyl)aminocyclopropane (15.60 g, 50.2 mmol) was treated with 4N HCl in dioxane (50 mL) and stirred for 2 h. The volatiles were evaporated in vacuo and the residue taken up into 1N NaOH (250 mL). The mixture was extracted with diethyl ether (2×200 mL). The combined ether extracts were washed with brine (50 mL), dried (sodium sulfate), then filtered and evaporated in vacuo to provide the amine free base.

The amine free base was dissolved in 2-propanol (250 mL) and the epoxide (15.0 g, 50.2 mmol) was added. The mixture was heated to reflux for 22 h and allowed to stand at ambient temperature for 3 d. Analysis by HPLC indicated that the desired product predominated, and that some starting cyclopropylamine remained unreacted. The starting epoxide was consumed. The volatiles were removed in vacuo and the residue was purified by silica gel flash chromatography (eluted 2:1 hexane/ethyl acetate) to provide the final product (13.68 g, 53%).

LC-MS: [M+H]=511, 513, Rt=2.31 min, Phenomenex Luna C18 (30cm×4.6 mm), 20-70% CH$_3$CN/water/0.1% trifluoroacetic acid in 2.33 min, flow rate 1.5 mL/min.

Step 2. Preparation of S,R 1-(3,5-Difluorobenzyl)-3-[1-(3-Bromophenyl)Cyclopropylamino)]-2-Hydroxypropyl Amine

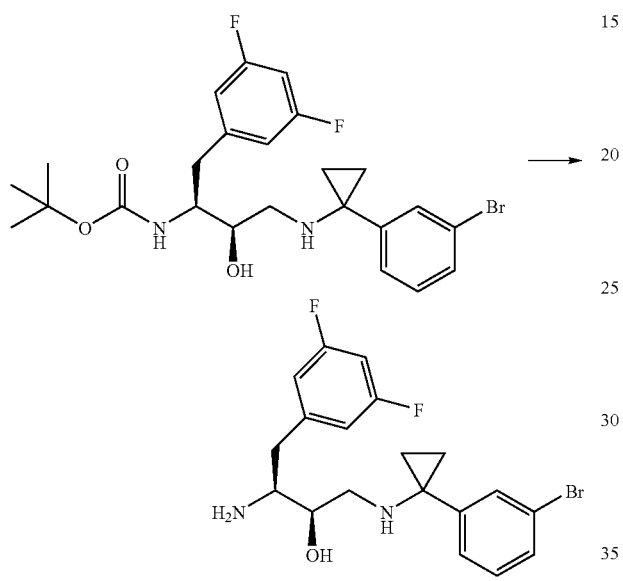

The Boc-protected amine (13.5 g, 26.7 mmol) was treated with 4N HCl in dioxane (30 mL). Methanol (15 mL) was added and the mixture became homogeneous before depositing a precipitate. The mixture was stirred for 3 h before the volatiles were removed in vacuo. The residue was taken up in 1N NaOH (150 mL) and the mixture was extracted with diethyl ether (3×100 mL). The combined ether extracts were washed with brine (50 mL), dried (magnesium sulfate), filtered and evaporated in vacuo to give the desired amine (6.5 g), which was used directly in the next step.

Step 3. Preparation of N-[3-[1-(3-Bromo-phenyl)-cyclopropylamino]-1-(3,5-difluoro-benzyl)-2-hydroxy-propyl]-acetamide

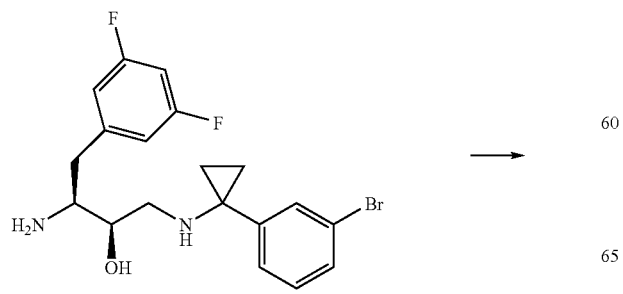

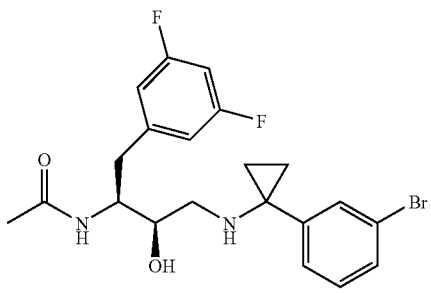

The above product was prepared essentially according to the procedure of Example 56, using acetic acid as the acid. The desired product was obtained as a white solid (11.75 g, 97%). LC-MS analysis indicated a purity of 94%. LC-MS: [M+H]=453, 455, Rt=1.86 min, Phenomenex Luna C18 (30 cm×4.6 mm), 20-70% CH$_3$CN/water/0.1% trifluoroacetic acid in 2.33 min, flow rate 1.5 mL/min.

EXAMPLE 107

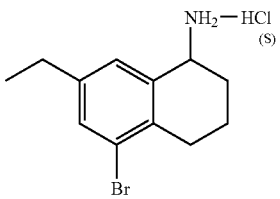

A. Preparation of 5-Bromo-7-ethyl-1-tetralone

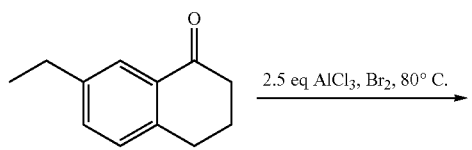

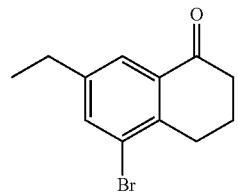

The bromination was performed essentially according to the procedure of Cornelius, L. A. M. Combs, D. W., *Synthetic Communications* 1994, 24, 2777-2788). The product was separated using silica gel flash chromatography (Biotage Flash 75, 10:1 hexanes:MTBE) to yield the purified product (7.4 g, 75%).

207

LC-MS analysis indicated the presence of a dibromoproduct co-eluting with desired product. This material was taken on to the next step and separated.

B. (R)-7-Ethyl-5-bromotetralin-1-ol

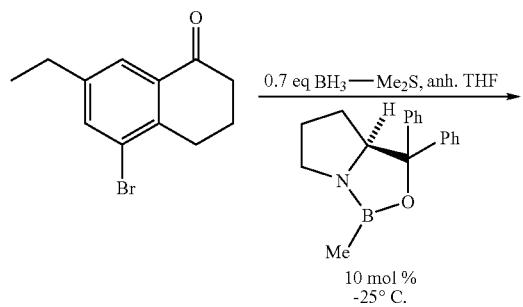

The above product was prepared essentially according to the method of Example 2. The resulting product was purified by silica gel chromatography (Biotage Flash 65, 10/1 hexanes/ethyl acetate) to yield (R)-7-ethyl-5-bromotetralin-1-ol (4.0 g, 53%).

C. (S)-7-Ethyl-5-bromo-1,2,3,4-tetrahydro-1-napthylamine hydrochloride.

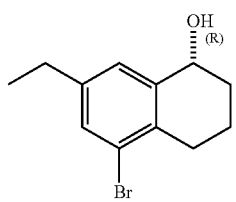

The above compound was prepared essentially according to the method of Example 3. First the azide was prepared. Second, the azide was reduced with lithium aluminum hydride to afford the product as a white solid. LC-MS: [M−NH2]=237, 239, Rt=6.34 min, Phenomenex Luna C18 (30 cm×4.6 mm), 5-20% CH$_3$CN/water/0.1% trifluoroacetic acid in 3.33 min, flow rate 1.5 mL/min.

208

EXAMPLE 108

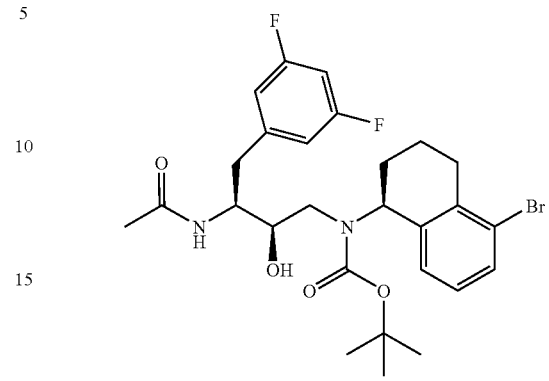

Step 1. Epoxide opening with (S)-7-bromo-1-aminotetralin

The above compound was prepared essentially according to the method of Example 17, step 3. The coupled product was crystallized from isopropyl alcohol. LC-MS analysis indicated about 99% purity. LC-MS: [M+H]=527, Rt=2.34 min, Phenomenex Luna C18 (30 cm×4.6 mm), 20-70% CH$_3$CN/water/0.1% trifluoroacetic acid in 2.33 min, flow rate 1.5 mL/min.

Step 2. Deprotection of Boc Group

The above compound was prepared essentially using the method of example 106, step 2. The resulting material was used directly in the next step.

Step 3. Acylation of N-terminal amine

The above compound was prepared essentially using the method of example 106, step 3. LC-MS analysis indicated a purity of 99%. LC-MS: [M+H]=467, 469, Rt=1.94 min, Phenomenex Luna C18 (30 cm×4.6 mm), 20-70% CH$_3$CN/water/0.1% trifluoroacetic acid in 2.33 min, flow rate 1.5 mL/min.

Step 4. Adding Boc Group

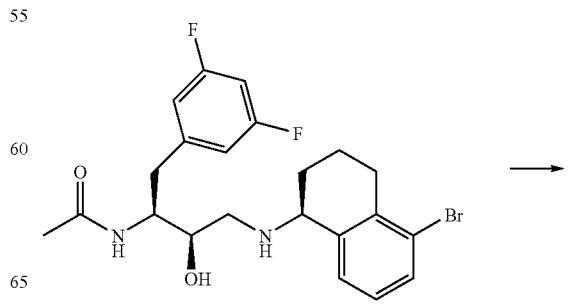

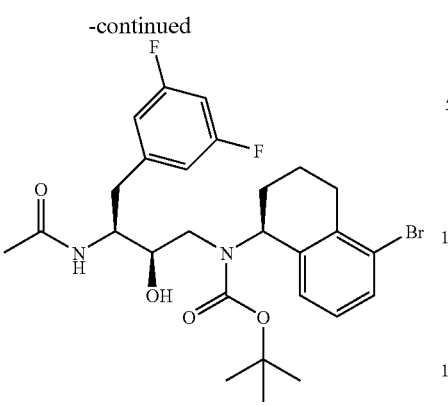

The starting compound (7.80 g, 16.7 mmol) was dissolved in dichloromethane (150 mL). Di-tert-butyldicarbonate (3.82 g, 17.5 mmol) was added and the mixture was stirred for 3 days. The mixture was then concentrated in vacuo and the residue passed through a pad of silica gel (eluted 1L 2:1 hexanes/ethyl acetate, 0.5L 5% MeOH/dichloromethane) to give the desired product (8.52 g, 90%).

LC-MS analysis indicated a purity of 99%. LC-MS: [M+Na]=589, 591, Rt=5.12 min, Phenomenex Luna C18 (30 cm×4.6 mm), 20-70% $CH_3CN$/water/0.1% trifluoroacetic acid in 2.33 min, flow rate 1.5 mL/min.

EXAMPLE 109

N-{(1S,2R)-1-(3,5-difluorobenzyl)-3-[(6-ethyl-1,2,3,4-tetrahydroquinolin-4-yl)amino]-2-hydroxypropyl}acetamide

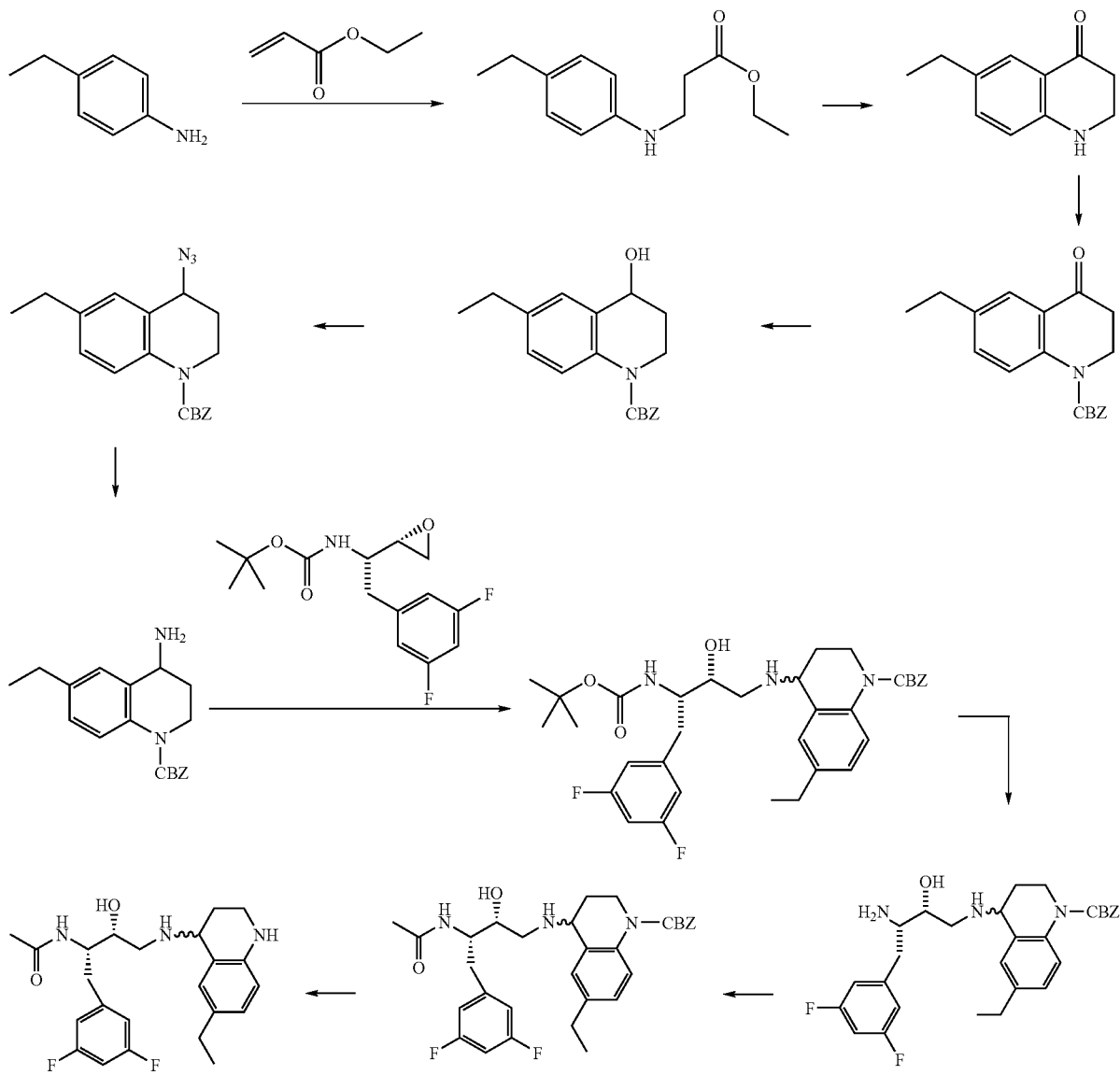

A.1. Ethyl N-(4-Ethylphenyl)-beta-alaninate

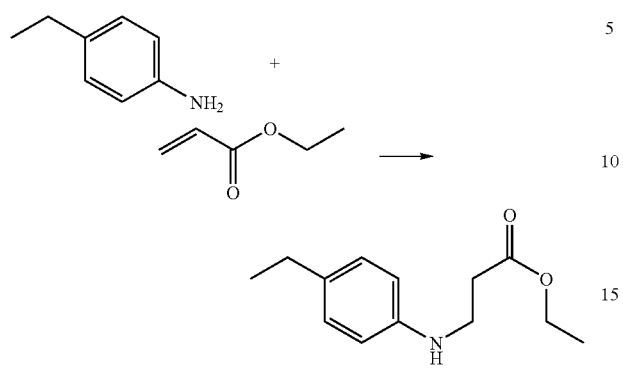

To a solution of 4-ethyl aniline (10.0 g) in acetic acid (25 mL) was added ethyl acrylate (10.8 g). The mixture was heated to 80° C. for 2 hours. Additional ethyl acrylate (1.0 mL) was added, and the mixture was again heated to 80° C. for 1 hour. The mixture was allowed to cool to room temperature and stir for two days. Sodium hydroxide (8N) was added until the pH equaled 9. The mixture was partitioned between dichloromethane and water and the combined organics were washed once with 1N sodium hydroxide, once with brine, dried with sodium sulfate, filtered, and concentrated. The mixture was chromatographed using a 20% ethyl acetate in heptane solvent solution. A mixture of the mono and di ester product (19.5 g) were obtained (1:1 mixture). MS (ESI+) for $C_{13}H_{19}NO_2$ m/z 221.99 (M+H)$^+$.

A.2. 6-Ethyl-2,3-dihydroquinolin-4(1H)-one

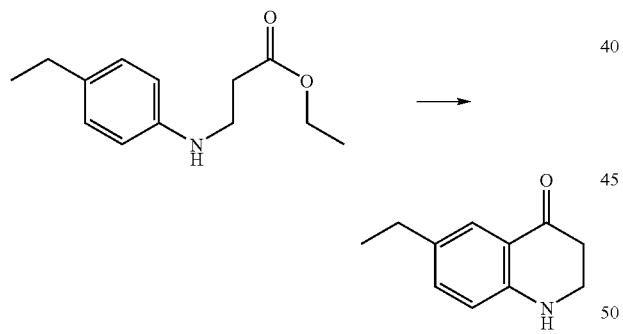

A solution of phosphorus pentoxide (19.53 g) in methane sulfonic acid (200 mL) was heated to 130° C. The mixture was stirred at 130° C. for one hour until all the phosphorus pentoxide had dissolved. The mixture was allowed to cool for 15 minutes and ethyl N-(4-ethylphenyl)-beta-alaninate (19.53 g of mono and di-ester mixture) was added. The mixture was heated to 130° C. for one hour and allowed to slowly cool overnight. The mixture was then cooled in an ice bath and 10N sodium hydroxide was added until the pH reached 9.5. Ethyl acetate was added to the mixture to help dissolve solids. The remaining gummy dark solids were dissolved in methanol and added to the ethyl acetate-aq. sodium hydroxide mixture. Semi-crystalline solids precipitated and were removed by filtration through Celite. The filtrate was washed with water, followed by 1N sodium hydroxide and brine, dried with magnesium sulfate, filtered, and concentrated. Silica gel chromatography using 0.25% ammonium hydroxide in dichloromethane gave mixed fractions. The mixed fractions were combined and re-chromatographed using 30% ethyl acetate in heptane. The resulting material was further upgraded by formation of the hydrochloride salt using 2N HCl in ether. The salt was collected by filtration and washed with heptane and dried in an oven under vacuum at 50° C. overnight. The salt was then partitioned between dichloromethane and 1N sodium hydroxide. The organic layer was extracted twice with dichloromethane, washed with 1N sodium hydroxide, dried with sodium sulfate, filtered, and concentrated to give 3.83 g of the title compound. MS (ESI+) for $C_{11}H_{13}NO$ m/z 175.96 (M+H)$^+$.

A.3. Benzyl 6-ethyl-4-oxo-3,4-dihydroquinoline-1(2H)-carboxylate

To a solution of 6-ethyl-2,3-dihydroquinolin-4(1H)-one (1.25 g) in THF (15 mL) was added sodium bicarbonate (0.84 g). Water (5 mL) followed by benzyl chloroformate (1.58 g) were added to the mixture, and it was stirred at room temperature overnight. The reaction was not complete as determined by TLC, so an additional 0.60 g of $NaHCO_3$ were added to the mixture and it was stirred at room temperature for two additional hours. The mixture was then concentrated under reduced pressure and the residue was partitioned between water and ethyl acetate and the organic layer was washed with brine, dried with magnesium sulfate, filtered, and concentrated. Chromotography on silicia gel using 25% ethyl acetate in heptane solvent solution gave 1.84 g of the title compound. MS (ESI+) for $C_{19}H_{19}NO_3$ m/z 310.03 (M+H)$^+$.

A.4. Benzyl 6-ethyl-4-hydroxy-3,4-dihydroquinoline-1(2H)-carboxylate

The above compound was prepared essentially according to the procedure of Example 17, step 1. The crude product was purified by chromatography on silica gel using a 2% MeOH in dichloromethane solvent solution with 0.5% ammonium hydroxide. $^1$HNMR (CDCl$_3$) δ 1.22 (t, J=8 Hz, 3H), 1.89 (s, 1H), 2.04 (m, 2H), 2.61 (q, J=8 Hz, 2H), 3.66 (m, 1H), 4.11 (m, 1H), 4.74 (t, J=4 Hz, 1H), 5.25 (dd, J=12, 20 Hz, 2H), 7.09 (dd, J=2, 9 Hz, 1H), 7.21 (d, J=2 Hz, 1H), 7.35 (m, 5H), 7.6 (d, J=8 Hz, 1H).

A.5. Benzyl 4-amino-6-ethyl-3,4-dihydroquinoline-1(2H)-carboxylate

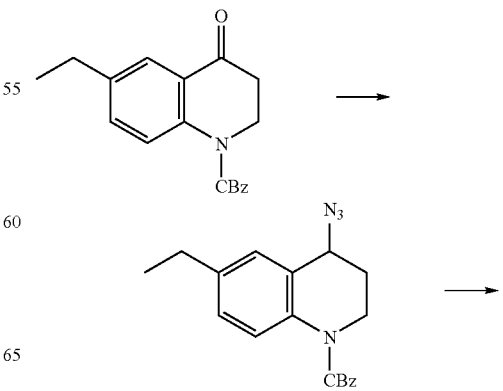

-continued

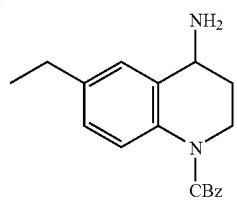

The above compound was prepared essentially according to the method of Example 17, step 2. First, the alcohol was converted to the azide. $^1$H NMR (CDCl$_3$) δ 1.23 (t, J=8 Hz, 3H), 2.09 (m, 2H), 2.62 (q, J=8 Hz, 2H), 3.67 (m, 1H), 4.12 (m, 1H), 4.58 (t, J=4 Hz, 1H), 5.24 (m, 2H), 7.09 (d, J=2 Hz, 1H), 7.13 (dd, J=2, 9 Hz, 1H), 7.35 (m, 5H), 7.82 (d, J=8 Hz, 1H).

Second the azide was reduced using PMe$_3$. MS (ESI+) for C$_{19}$H$_{22}$N$_2$O$_2$ m/z 311.05 (M+H)$^+$.

A.6. Benzyl 4-{[(2R,3S)-3-[(tert-butoxycarbonyl)amino]-4-(3,5-difluorophenyl)-2-hydroxybutyl]amino}-3,4-dihydroquinoline-1(2H)-carboxylate

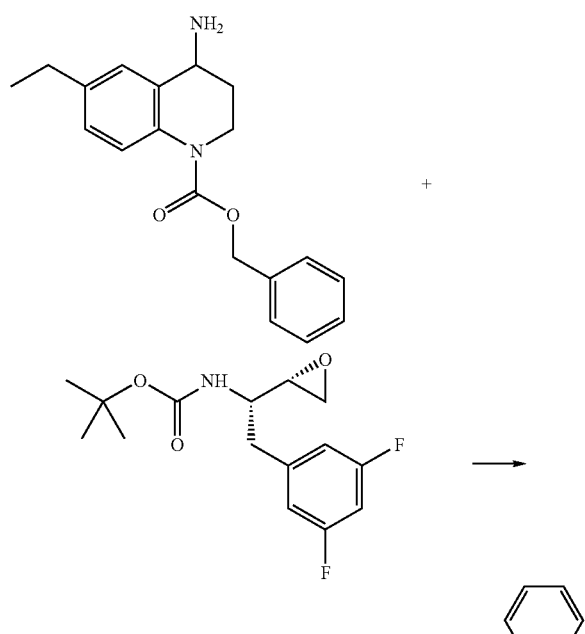

The above compound was prepared essentially according to the method of Example 17, step 3. The crude product was purified by silcica gel chromatography using 2% MeOH in dichloromethane with 0.25% NH$_4$OH as the solvent system. MS (ESI+) for C$_{34}$H$_{41}$F$_2$N$_3$O$_5$ m/z 610.51 (M+H)$^+$.

A.7. Benzyl 4-{[(2R,3S)-3-amino-4-(3,5-difluorophenyl)-2-hydroxybutyl]amino}-6-ethyl-3,4-dihydroquinoline-1(2H)-carboxylate To a solution of the produce from step A.6 (0.76 g) in MeOH (10 mL) was added 2N HCl in Et$_2$O (1.6 mL). The mixture was stirred at room temperature for two hours and an additional 1.0 mL of 2N HCl in Et$_2$O were added. The mixture was stirred for four more hours. The reaction was still not complete, so an additional 3.0 mL of HCl in Et$_2$O were added. The mixture was stirred for two hours and then stripped of solvent under reduced pressure. The residue was dissolved in ethyl acetate washed two times with 1N NaOH, dried with magnesium sulfate, filtered, and concentrated. A silica gel column was run for purification using 4% MeOH in dichloromethane with 0.25% NH$_4$OH as the solvent solution and gave 0.44 g of the title compound. MS (ESI+) for C$_{29}$H$_{33}$F$_2$N$_3$O$_3$ m/z 510.36 (M+H)$^+$.

A.8. Benzyl 4-{[(2R,3S)-3-(acetylamino)-4-(3,5-difluorophenyl)-2-hydroxybutyl]amino}-6-ethyl-3,4-dihydroquinoline-1(2H)-carboxylate To a solution of the product from step A.7 (0.43 g) in dichloromethane (15 mL) was added N,N-diacetyl-O-methylhydroxylamine (0.11 g). The mixture was stirred overnight at room temperature. An additional 0.10 g of N,N-diacetyl-O-methylhydroxylamine were then added and the mixture was stirred for 6 hours. Another 0.10 g of N,N-diacetyl-O-methylhydroxylamine were added and the mixture was stirred overnight and then partitioned between dichloromethane and 1N HCl and brine. The organic layer was dried with magnesium sulfate, filtered, and concentrated. A silica gel column was run for purification using 4% MeOH in dichloromethane with 0.25% NH$_4$OH as the solvent solution and gave 0.35 g of the title compound. MS (ESI+) for C$_{31}$H$_{34}$F$_2$N$_3$O$_4$ m/z 552.32 (M+H)$^+$.

A.9. N-{(1S,2R)-1-(3,5-difluorobenzyl)-3-[(6-ethyl-1,2,3,4-tetrahydroquinolin-4-yl)amino]-2-hydroxypropyl}acetamide

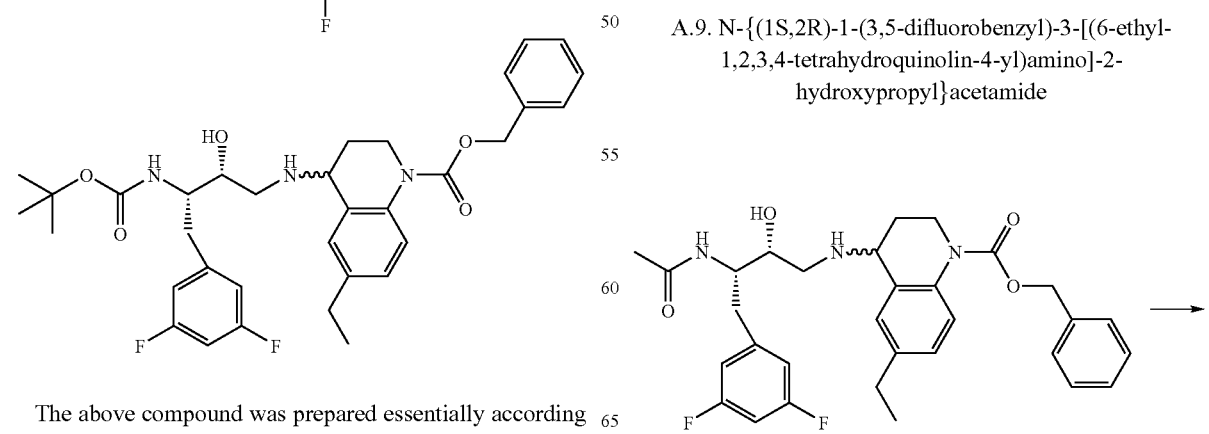

-continued

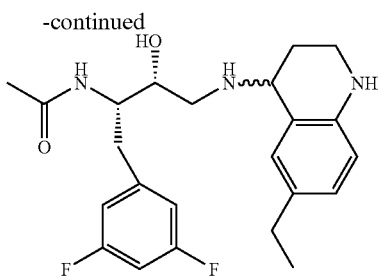

Nitrogen was bubbled through a solution of the product from step A.8 (0.35 g), EtOH (25 mL), and acetic acid (0.75 mL). 10% palladium on carbon (0.29 g) was added to the mixture and it was shaken on a hydrogenation apparatus under 52 psi of hydrogen for 1.25 h. The catalyst was filtered off using Celite and the filtrate was concentrated under reduced pressure. The residue was partitioned between ethyl acetate, aq. sodium hydroxide (pH 10), and brine, and then dried with magnesium sulfate, filtered, and concentrated. A silica gel column was run using 6% MeOH in dichloromethane with 0.25% $NH_4OH$ as the solvent solution and gave 0.04 g of the title compound. MS (ESI+) for $C_{23}H_{29}F_2N_3O_2$ m/z 418.31 (M+H)$^+$.

A.10. N-{(1S,2R)-1-(3,5-difluorobenzyl)-3-[(6-ethyl-1-methyl-1,2,3,4-tetrahydroquinolin-4-yl)amino]-2-hydroxypropyl}acetamide

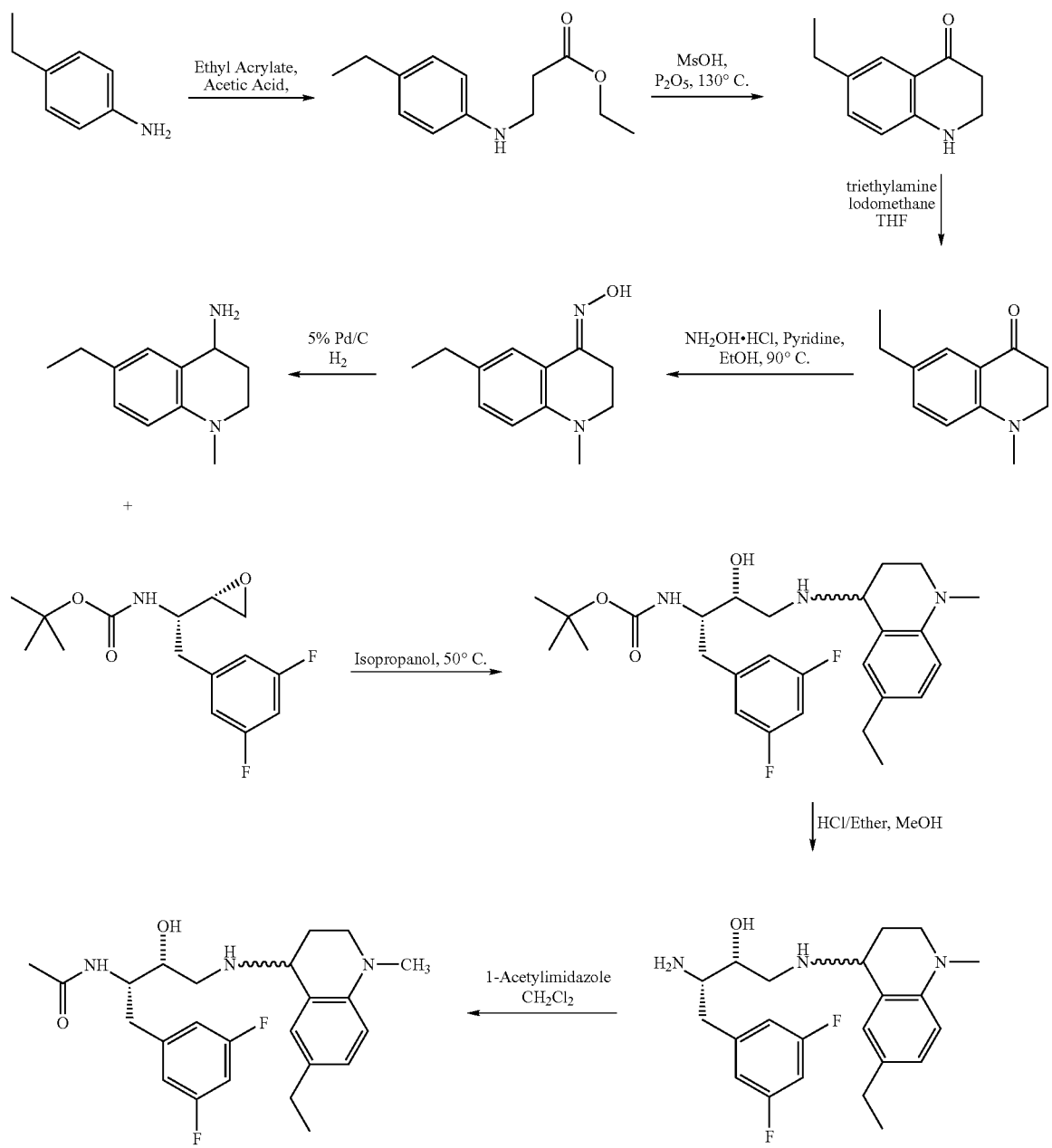

A.11. Ethyl N-(4-ethylphenyl)-beta-alaninate

To a solution of 4-ethyl aniline (10.00 g) in acetic acid (20 mL) was added ethyl acrylate (8.26). The mixture was heated to 70° for 3.5 hours. The mixture was allowed to cool to room temperature. The mixture was partitioned between dichloromethane and water, and was extracted three times. The combined organics were washed once with brine, dried with sodium sulfate, filtered, and concentrated. The mixture was taken on to the next step. MS (ESI+) for $C_{13}H_{19}NO_2$ m/z 223.1 (M+H)+.

A.12. 6-ethyl-2,3-dihydroquinolin-4(1H)-one

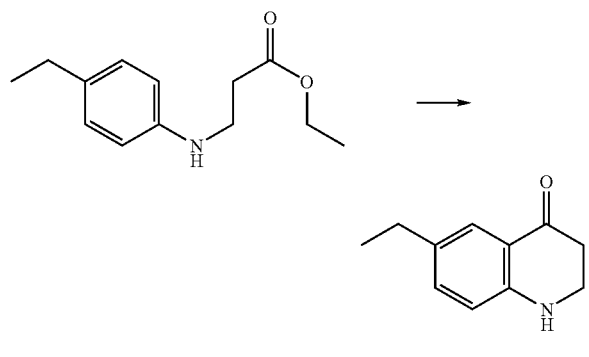

A solution of phosphorus pentoxide (11.14 g) in methane sulfonic acid (114 mL) was heated to 130°. The mixture was stirred at 130° for one hour until all the phosphorus pentoxide had dissolved. The mixture was allowed to cool for 15 minutes, and ethyl N-(4-ethylphenyl)-beta-alaninate (11.14 g of mono and di-ester mixture) was added. The mixture was heated to 130° for 1.5 hours, and the mixture was allowed to cool to room temperature. The mixture was cooled in an ice bath, and 50% sodium hydroxide was added until the pH reached 8. The gummy dark solids were dissolved in MeOH, and added to the mixture. Solids began to crash out, so they were filtered off with celite. The liquids were combined, and were partitioned between dichloromethane and water, and the organics were extracted three times with dichloromethane. The combined organics were washed with brine, dried with sodium sulfate, filtered, and concentrated. The product was chromatographed using a 30% ethyl acetate in heptane solvent solution. 4.10 g of the title product were recovered. (28% yield through first two steps) MS (ESI+) for $C_{11}H_{13}NO$ m/z 176.00 (M+H)+.

A.13. 6-ethyl-1-methyl-2,3-dihydroquinolin-4(1H)-one

To a solution of 6-ethyl-2,3-dihydroquinolin-4(1H)-one (1.00 g) in THF (25 mL) was added triethylamine (0.64 g) followed by iodomethane (0.89 g). The mixture was refluxed at 70° C. overnight. The solvent was stripped under reduced pressure, and the residue was partitioned between aqueous sodium bicarbonate and dichloromethane. The organics were extracted three times, washed with brine, dried with sodium sulfate, filtered, and concentrated. Chromatography was used to purify the title compound using a 40% ethyl acetate in heptane solvent solution. 0.32 g of the title product were recovered. (30% yield). MS (ESI+) for $C_{12}H_{15}NO$ m/z 190.10 (M+H)+.

A.14. (4E)-6-ethyl-1-methyl-2,3-dihydroquinolin-4(1H)-one oxime

To a solution of 6-ethyl-1-methyl-2,3-dihydroquinolin-4 (1H)-one (0.32 g) in ethanol (25 mL) were added pyridine (0.53 g) and hydroxylamine hydrochloride (0.59 g). The mixture was heated to 90° C. for two hours with a reflux condenser attached. The mixture was cooled to room temperature, and the solvent was stripped under reduced pressure. The residue was portioned between water and dichloromethane and the organics were extracted three times. The combined organics were washed once with brine, dried with sodium sulfate, filtered, and concentrated. 0.34 g of the title product were recovered. (98% yield). MS (ESI+) for $C_{12}H_{16}N_2O$ m/z 205.02 (M+H)+.

A.15. 6-ethyl-1-methyl-1,2,3,4-tetrahydroquinolin-4-amine

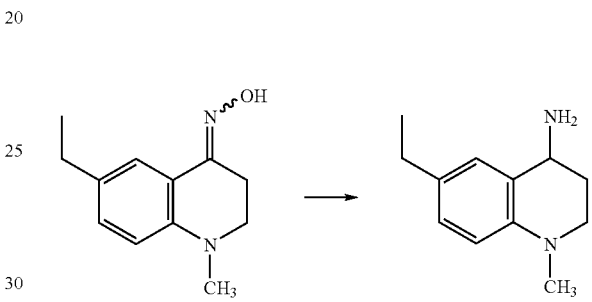

(4E,Z)-6-ethyl-1-methyl-2,3-dihydroquinolin-4(1H)-one oxime (0.34 g), ethanol (20 mL), and acetic acid (0.27 g) were combined in a hydrogenation flask and degassed with nitrogen. 5% Palladium on carbon was carefully added to the mixture (0.04 g) and the mixture was degassed for several more minutes. The mixture was set up on the hydrogenation apparatus, and was put under 50 psi of hydrogen. The mixture was shaken for five and ½ hours, and was taken off the machine, but was not complete by TLC. The mixture was again degassed, and an additional 0.10 g of 5% palladium on carbon were added to the mixture. The mixture was put back on the hydrogenation apparatus, and was shaken overnight. The palladium on carbon was filtered off using celite, and the liquids were concentrated under reduced pressure. The residue was partitioned between aqueous sodium bicarbonate and dichloromethane, and the organics were extracted three times. The combined organics were dried with sodium sulfate, filtered, and concentrated. 0.26 g of the title compound were recovered. (82% yield).

A.16. tert-butyl (1S,2R)-1-(3,5-difluorobenzyl)-3-[(6-ethyl-1-methyl-1,2,3,4-tetrahydroquinolin-4-yl)amino]-2-hydroxypropylcarbamate

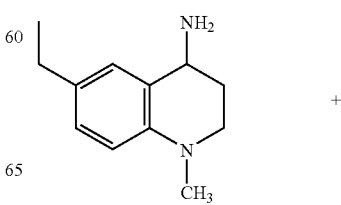

+

-continued

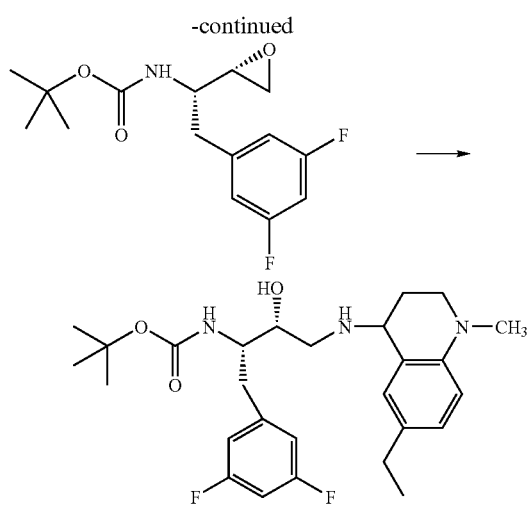

The above compound was prepared essentially according to the method of Example 15, step 2. MS (ESI+) for $C_{27}H_{37}F_2N_3O_3$ m/z 490.59 (M+H)$^+$.

A.17. (2R,3S)-3-amino-4-(3,5-difluorophenyl)-1-[(6-ethyl-1-methyl-1,2,3,4-tetrahydroquinolin-4-yl)amino]butan-2-ol

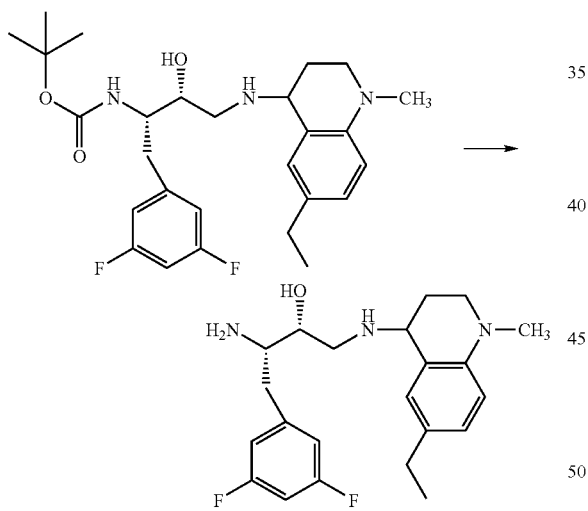

To a solution of tert-butyl (1S,2R)-1-(3,5-difluorobenzyl)-3-[(6-ethyl-1-methyl-1,2,3,4-tetrahydroquinolin-4-yl)amino]-2-hydroxypropylcarbamate (0.412 g) in MeOH (5 mL) was added 2N HCl in Et$_2$O (2.1 mL). The mixture was stirred at room temperature for fifteen minutes. The mixture was stripped of solvent under reduced pressure. The residue was partitioned between dichloromethane and aqueous sodium bicarbonate, and the organic was extracted three times, washed with brine, dried with sodium sulfate, filtered, and concentrated. A silica gel column was run for purification using 5% MeOH in dichloromethane with as the solvent solution. 0.255 g of the title product were recovered. (78% yield). MS (ESI+) for $C_{22}H_{29}F_2N_3O$ m/z 390.18 (M+H)$^+$.

A.18. N-{(1S,2R)-1-(3,5-difluorobenzyl)-3-[(6-ethyl-1-methyl-1,2,3,4-tetrahydroquinolin-4-yl)amino]-2-hydroxypropyl}acetamide

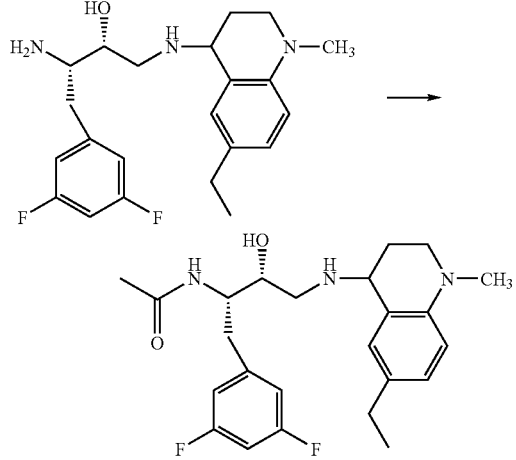

To a solution of (2R,3S)-3-amino-4-(3,5-difluorophenyl)-1-[(6-ethyl-1-methyl-1,2,3,4-tetrahydroquinolin-4-yl)amino]butan-2-ol (0.218 g) in dichloromethane (15 mL) was added 1-acetylimidazole (0.062 g). The mixture was stirred overnight at room temperature. The mixture was partitioned between dichloromethane and brine, and the organic was extracted three times, dried with sodium sulfate, filtered, and concentrated. A silica gel column was run for purification using 3% MeOH in dichloromethane with 0.5% NH$_4$OH as the solvent solution. HPLC still showed small amounts of starting material present, so the mixture was washed one time with 1N HCl, dried with magnesium sulfate, filtered, and concentrated. 0.115 g of the title product were recovered. (48% yield). MS (ESI+) for $C_{24}H_{31}F_2N_3O_2$ m/z 432.18 (M+H)$^+$.

A.19. N-((1S,2R)-1-(3,5-difluorobenzyl)-3-{[(4S)-6-ethyl-1-methyl-1,2,3,4-tetrahydroquinolin-4-yl]amino}-2-hydroxypropyl)acetamide and N-((1S,2R)-1-(3,5-difluorobenzyl)-3-{[(4R)-6-ethyl-1-methyl-1,2,3,4-tetrahydroquinolin-4-yl]amino}-2-hydroxypropyl)acetamide

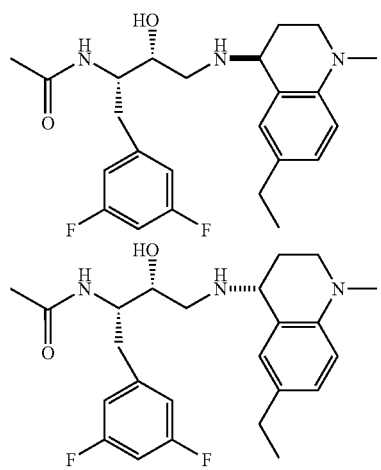

221

Silica gel chromatography of approximately 0.1 g of N-{(1S,2R)-1-(3,5-difluorobenzyl)-3-[(6-ethyl-1-methyl-1,2,3,4-tetrahydroquinolin-4-yl)amino]-2-hydroxypropyl}acetamide using methanol/dichloromethane (8/92) with 0.1% ammonium hydroxide gave 0.032 g of N-((1S,2R)-1-(3,5-difluorobenzyl)-3-{[(4S)-6-ethyl-1-methyl-1,2,3,4-tetrahydroquinolin-4-yl]amino}-2-hydroxypropyl)acetamide [$R_f$ (MeOH/CH$_2$Cl$_2$/NH$_4$OH)=0.40; MS (ESI+) for $C_{24}H_{31}F_2N_3O_2$ m/z 432.2 (M+H)$^+$]. Re-chromatography of mixed fractions gave 0.011 g of a 9:1 mixture of the 4R isomer [$R_f$ (MeOH/CH$_2$Cl$_2$/NH$_4$OH)=0.35; MS (ESI+) for $C_{24}H_{31}F_2N_3O_2$ m/z 432.2 (M+H)$^+$] and the 4S isomer.

B. N-{(1S,2R)-1-(3,5-difluorobenzyl)-2-hydroxy-3-[(6-neopentyl-1,2,3,4-tetrahydroquinolin-4-yl)amino]propyl}acetamide

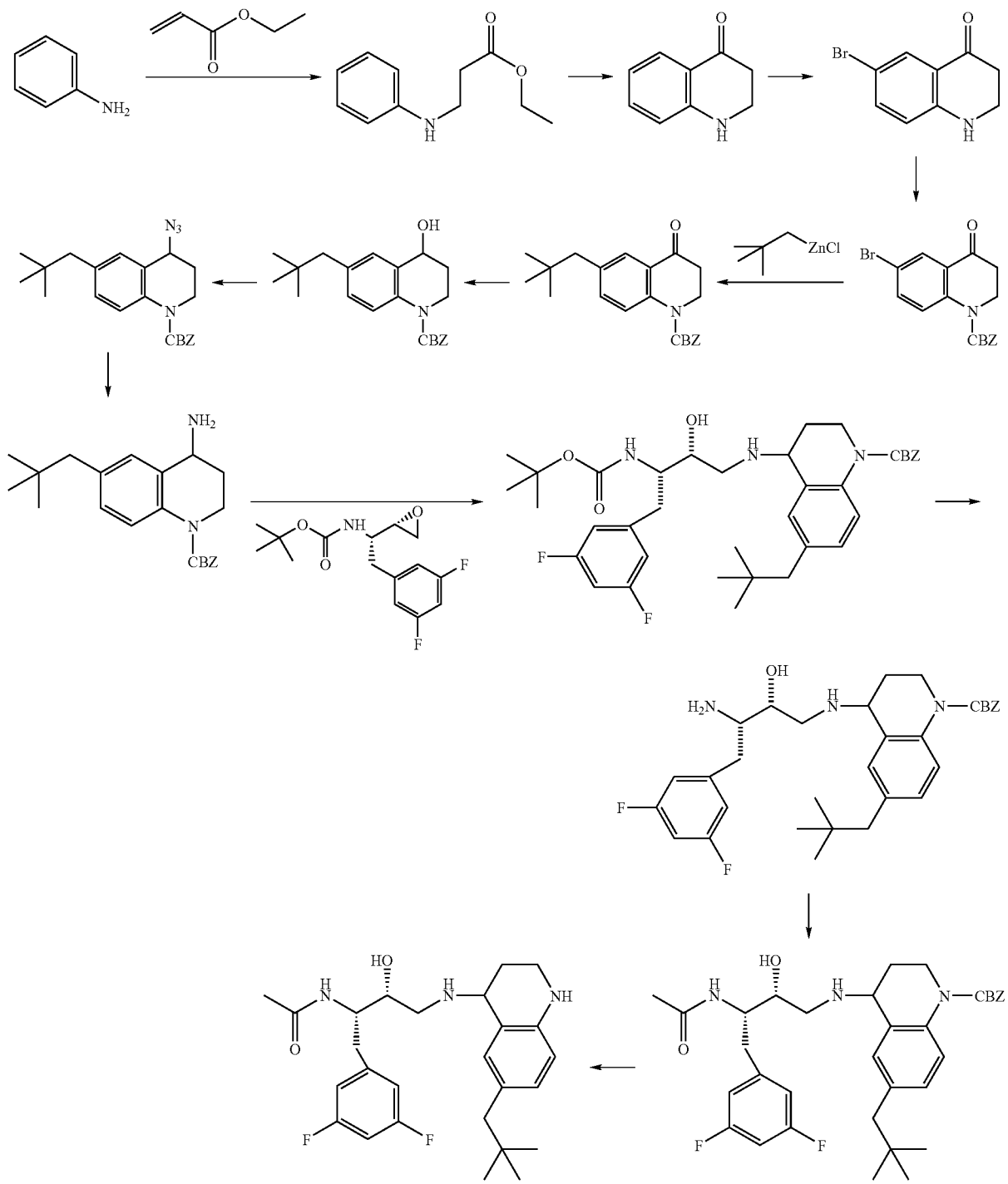

B.1. Ethyl N-phenyl-beta-alaninate

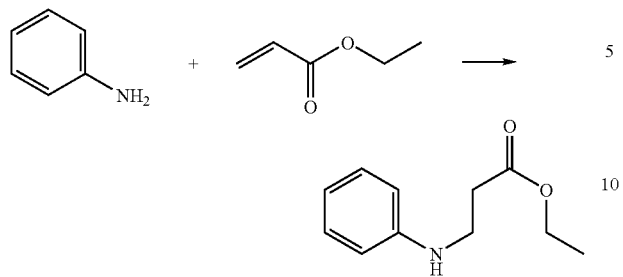

The above compound was prepared essentially according to the method of Example 109, step A.1. The crude product was purified by chromatography on silica gel using 15% ethyl acetate in heptane with 0.25% TFA solvent. The purified mixture comprised the mono and di-ester products (1:1) which were used in the next step. MS (ESI+) for $C_{11}H_{15}NO_2$ m/z 193.99 (M+H)$^+$.

B.2. 2,3-dihydroquinolin-4(1H)-one

The above compound was prepared essentially according to the method of Example 109, step A.2. The crude product was purified by column chromatography using a 20-30% ethyl acetate in heptane gradient. MS (ESI+) for $C_9H_9NO$ m/z 147.96 (M+H)$^+$.

B.3. 6-bromo-2,3-dihydroquinolin-4(1H)-one

To a solution of 2,3-dihydroquinolin-4(1H)-one (2.94 g) in dichloromethane (25 mL) was added N-bromosuccinimide (3.63 g). The mixture was stirred at room temperature for 1.5 h and was partitioned between aqueous sodium bicarbonate and dichloromethane. The organic layer was washed with brine, dried with sodium sulfate, filtered, and concentrated. The concentrate was chromatographed on silica gel using a 35% ethyl acetate in heptane solvent solution and gave 4.14 g of the title compound. MS (ESI−) for $C_9H_8BrNO$ m/z 225.77 (M−H)$^−$.

B.4. Benzyl 6-bromo-4-oxo-3,4-dihydroquinoline-1(2H)-carboxylate

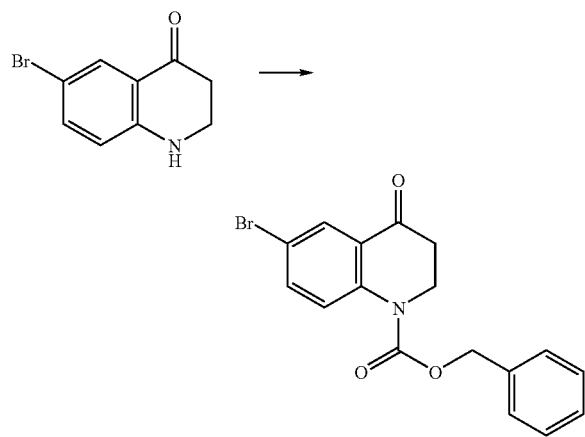

The above compound was prepared essentially according to the method of Example 109, step A.3. $^1$H NMR (CDCl$_3$) δ 2.78 (t, J=7 Hz, 2H), 4.22 (t, J=6 Hz, 2H), 5.28 (s, 2H), 7.40 (m, 5H), 7.58 (dd, J=2, 9 Hz, 1H), 7.75 (d, J=9 Hz, 1H), 8.10 (d, J=2 Hz, 1H).

B.5. Benzyl 6-neopentyl-4-oxo-3,4-dihydroquinoline-1(2H)-carboxylate

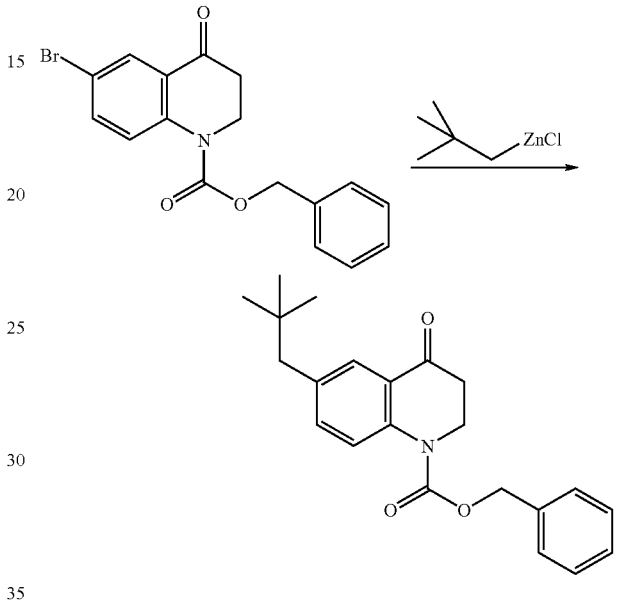

Benzyl 6-bromo-4-oxo-3,4-dihydroquinoline-1(2H)-carboxylate (3.10 g) and dichloro[1,1'-bis(diphenylphosphino)ferrocene]palladium(II)dichloromethane adduct (0.35 g) were combined in a round bottom flask. The mixture was put under high vacuum and purged with nitrogen. A 0.5 M solution of bromo(neopentyl)zinc (55 mL) prepared using the procedure of Negishi et al. *Tet Lett.* 1983, 24, 3823-3824, was added to the mixture and was stirred at room temperature for two days. The reaction had not gone to completion, so an additional 10 mL of bromo(neopentyl)zinc solution was added and the mixture was stirred for one additional day. The mixture was then partitioned between ethyl acetate and aqueous ammonium chloride, dried with magnesium sulfate, filtered, and concentrated. Silica gel chromatography using a 20% ethyl acetate in heptane solvent solution gave 2.17 g of the title compound. MS (ESI+) for $C_{22}H_{25}NO_3$ m/z 353.17 (M+H)$^+$.

B.6. Benzyl 4-hydroxy-6-neopentyl-3,4-dihydroquinoline-1(2H)-carboxylate

The above compound was prepared essentially according to the method of Example 17, step 2. The crude product was purified $^1$H NMR (CDCl$_3$) δ 0.90 (S, 9H), 1.80 (s, 1H), 2.06 (m, 2H), 2.45 (s, 2H), 3.68 (m, 1H), 4.12 (m, 1H), 4.75 (t, J=4 Hz, 1H), 5.24 (dd, J=12, 17 Hz, 2H), 7.02 (dd, J=2, 9 Hz, 1H), 7.12 (d, J=2 Hz, 1H), 7.35 (m, 5H), 7.76 (d, J=8 Hz, 1H).

B.7. Benzyl 4-amino-6-neopentyl-3,4-dihydroquinoline-1(2H)-carboxylate

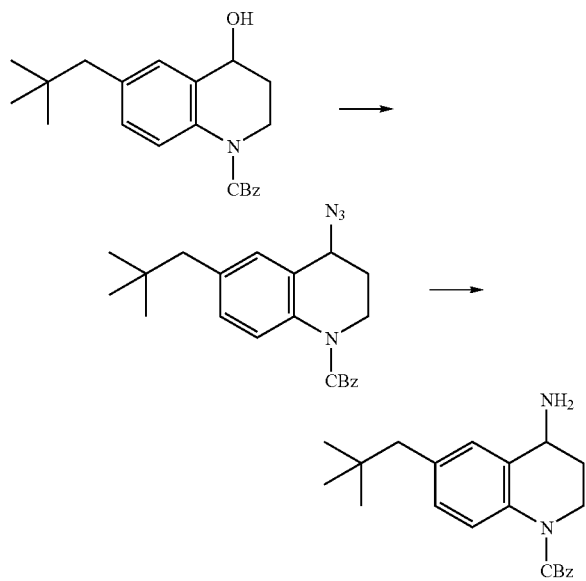

The above compound was prepared essentially according to the method of Example 17, step 2. First the azide was prepared and chromatographed on silica gel using a 15% ethyl acetate in heptane. $^1$H NMR (CDCl$_3$) δ 0.091 (s, 9H), 2.09 (m, 2H), 2.46 (s, 2H), 3.66 (m, 1H), 4.14 (m, 1H), 4.58 (t, J=4 Hz, 1H), 4.24 (dd, J=12, 15 Hz, 2H), 7.03 (d, J=2 Hz, 1H), 7.06 (dd, J=2, 9 Hz, 1H), 7.35 (m, 5H), 7.86 (d, J=8 Hz, 1H);

Second, the azide was reduced using PMe$_3$. The resulting amine was purified by silica gel chromatography using 2.5% methanol in dichloromethane with 0.5% ammonium hydroxide. MS (ESI+) for C$_{22}$H$_{28}$N$_2$O$_2$ m/z 353.19 (M+H)$^+$.

B.8. Benzyl 4-{[(2R,3S)-3-amino-4-(3,5-difluorophenyl)-2-hydroxybutyl]amino}-6-neopentyl-3,4-dihydroquinoline-1(2H)-carboxylate

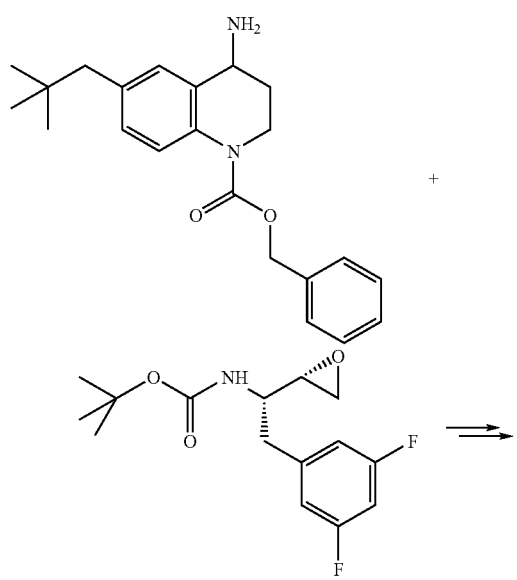

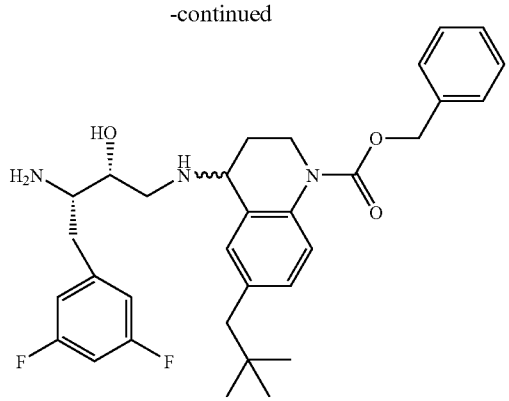

To a solution of benzyl 4-amino-6-neopentyl-3,4-dihydroquinoline-1(2H)-carboxylate (1.31 g) in isopropanol (25 mL) was added Example 134 (0.75 g) and the mixture was heated at 90° C. for 45 minutes. The temperature was reduced to 60° C. and the mixture was allowed to stir overnight. An additional 0.36 g of Example 134 were added to the mixture and it was heated to 80° C. for five hours. The mixture was cooled to room temperature and the solvent was removed under reduced pressure. The residue was partitioned between water and ethyl acetate and the organic layers were dried with magnesium sulfate, filtered, and concentrated. A silica gel column was run to attempt to separate the diasteriomers using a gradient of 2-4% MeOH in dichloromethane with 0.25% NH$_4$OH as the solvent system. The first fraction contained a 70:30 mixture of the two diasteriomers and the second fraction was a 50:50 mix of the diasteriomers. The Boc groups were removed by dissolving each fraction in a minimal amount of dichloromethane and adding 15 mL of 2N HCl in ether to each of the two mixtures. The mixtures were stirred for two hours and concentrated under reduced pressure. The mixtures were then partitioned between 1N sodium hydroxide and ethyl acetate, dried with magnesium sulfate, filtered, and concentrated to give 0.23 g of the 70:30 title compound mixture and 0.30 g of the 50:50 mixture. MS (ESI+) for C$_{32}$H$_{39}$F$_2$N$_3$O$_3$ m/z 552.32 (M+H)$^+$ for the 70:30 mixture and m/z 552.27 (M+H)$^+$ for the 50:50 mixture. Each of these mixtures was carried on separately to final product; the following procedures illustrate that for the 70:30 mixture only.

B.9. Benzyl 4-{[(2R,3S)-3-(acetylamino)-4-(3,5-difluorophenyl)-2-hydroxybutyl]amino}-6-neopentyl-3,4-dihydroquinoline-1(2H)-carboxylate

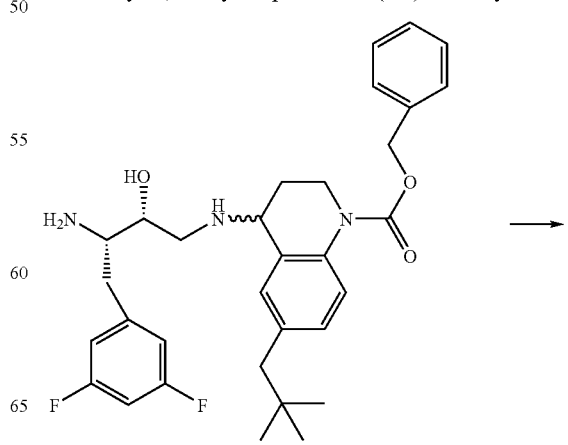

-continued

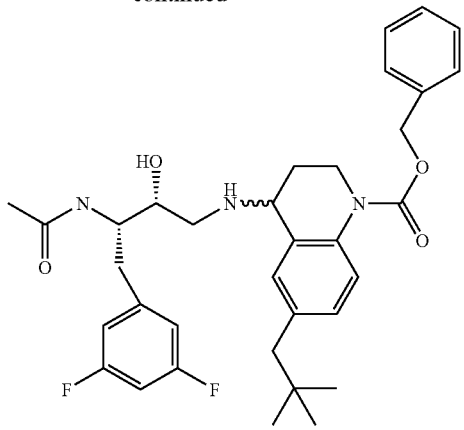

To a solution of benzyl 4-{[(2R,3S)-3-amino-4-(3,5-difluorophenyl)-2-hydroxybutyl]amino}-6-neopentyl-3,4-dihydroquinoline-1(2H)-carboxylate (0.226 g) in dichloromethane (5 mL) was added N,N-diacetyl-O-methylhydroxylamine (0.064 g). The mixture was stirred over the weekend at room temperature. The solvent was then removed under reduced pressure and the residue was partitioned between 1N HCl and ethyl acetate, dried with magnesium sulfate, filtered, and concentrated to give 0.243 g of the title compound. (99% yield). MS (ESI+) for $C_{34}H_{41}F_2N_3O_4$ m/z 594.31 $(M+H)^+$.

B.10. N-{(1S,2R)-1-(3,5-difluorobenzyl)-2-hydroxy-3-[(6-neopentyl-1,2,3,4-tetrahydroquinolin-4-yl)amino]propyl}acetamide

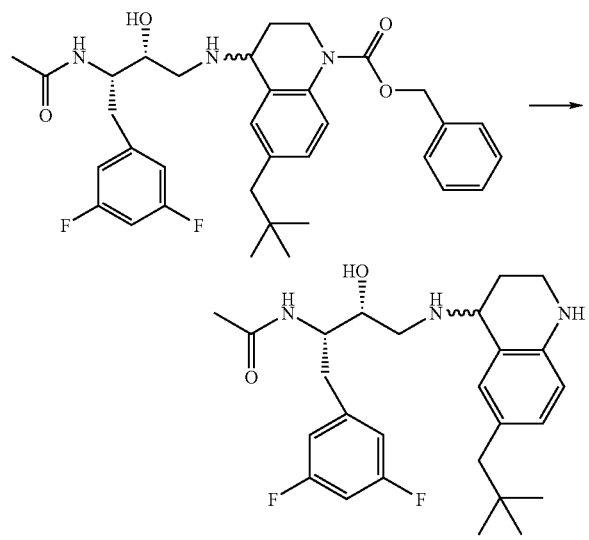

To a solution of benzyl 4-{[(2R,3S)-3-(acetylamino)-4-(3,5-difluorophenyl)-2-hydroxybutyl]amino}-6-neopentyl-3,4-dihydroquinoline-1(2H)-carboxylate (0.242 g) in EtOH (30 mL) was added 1N HCl (1.0 mL) and 10% palladium on carbon (0.030 g). The mixture was degassed with $N_2$ for five minutes. The mixture was placed on a hydrogenation apparatus under 47 psi of $H_2$ and was shaken for 4.5 hours. The palladium was filtered off using Celite and the solvent was concentrated under reduced pressure. The residue was then partitioned between water and ethyl acetate and the organic layers were washed with aqueous sodium bicarbonate, dried with magnesium sulfate, filtered, and concentrated. A silica gel column using 4% MeOH in dichloromethane with 0.25% $NH_4OH$ as the solvent solution gave 0.095 g of the title compound. MS (ESI+) for $C_{26}H_{35}F_2N_3O_2$ m/z 460.27 $(M+H)^+$.

The compounds named in Examples 109 (C-TT) can be made according to the methods analogous to those described above, as well as those known in the art.

| Example No. | Name |
|---|---|
| C. | N—((1S,2R)-1-(3,5-difluorobenzyl)-2-hydroxy-3-{[(4S)-6-neopentyl-1,2,3,4-tetrahydroquinolin-4-yl]amino}propyl)acetamide; |
| D. | N—((1S,2R)-1-(3,5-difluorobenzyl)-2-hydroxy-3{[(4S)-6-isobutyl-1,2,3,4-tetrahydroquinolin-4-yl]amino}propyl)acetamide; |
| E. | N—((1S,2R)-1-(3,5-difluorobenzyl)-2-hydroxy-3-{[(4S)-6-isopropyl-1,2,3,4-tetrahydroquinolin-4-yl]amino}propyl)acetamide; |
| F. | N—[(1S,2R)-3-{[(4S)-6-tert-butyl-1,2,3,4-tetrahydroquinolin-4-yl]amino}-1-(3,5-difluorobenzyl)-2-hydroxypropyl]acetamide; |
| G. | N—((1S,2R)-1-(3,5-difluorobenzyl)-3-{[(4S)-6-ethyl-1,2,3,4-tetrahydroquinolin-4-yl]amino}-2-hydroxypropyl)acetamide; |
| H. | N—((1S,2R)-1-(3,5-difluorobenzyl)-3-{[(4S)-7-fluoro-6-isopropyl-1,2,3,4-tetrahydroquinolin-4-yl]amino}-2-hydroxypropyl)acetamide; |
| I. | N—[(1S,2R)-3-{[(4S)-6-tert-butyl-7-fluoro-1,2,3,4-tetrahydroquinolin-4-yl]amino}-1-(3,5-difluorobenzyl)-2-hydroxypropyl]acetamide; |
| J. | N—((1S,2R)-1-(3,5-difluorobenzyl)-3-{[(4S)-7-fluoro-6-isobutyl-1,2,3,4-tetrahydroquinolin-4-yl]amino}-2-hydroxypropyl)acetamide; |
| K. | N—((1S,2R)-1-(3,5-difluorobenzyl)-3-{[(4S)-7-fluoro-6-neopentyl-1,2,3,4-tetrahydroquinolin-4-yl]amino}-2-hydroxypropyl)acetamide; |
| L. | N—((1S,2R)-1-(3,5-difluorobenzyl)-2-hydroxy-3-{[(4S)-1-methyl-6-neopentyl-1,2,3,4-tetrahydroquinolin-4-yl]amino}propyl)acetamide; |
| M. | N—((1S,2R)-1-(3,5-difluorobenzyl)-2-hydroxy-3-{[(4S)-6-isobutyl-1-methyl-1,2,3,4-tetrahydroquinolin-4-yl]amino}propyl)acetamide; |
| N. | N—((1S,2R)-1-(3,5-difluorobenzyl)-2-hydroxy-3-{[(4S)-6-isopropyl-1-methyl-1,2,3,4-tetrahydroquinolin-4-yl]amino}propyl)acetamide; |
| O. | N—[(1S,2R)-3-{[(4S)-6-tert-butyl-1-methyl-1,2,3,4-tetrahydroquinolin-4-yl]amino}-1-(3,5-difluorobenzyl)-2-hydroxypropyl]acetamide; |
| P. | N—[(1S,2R)-3-{[(4S)-6-tert-butyl-1-(2-hydroxyethyl)-1,2,3,4-tetrahydroquinolin-4-yl]amino}-1-(3,5-difluorobenzyl)-2-hydroxypropyl]acetamide; |
| Q. | N—((1S,2R)-1-(3,5-difluorobenzyl)-2-hydroxy-3-{[(4S)-1-(2-hydroxyethyl)-6-isopropyl-1,2,3,4-tetrahydroquinolin-4-yl]amino}propyl)acetamide; |
| R. | N—((1S,2R)-1-(3,5-difluorobenzyl)-2-hydroxy-3-{[(4S)-1-(2-hydroxyethyl)-6-isobutyl-1,2,3,4-tetrahydroquinolin-4-yl]amino}propyl)acetamide; |
| S. | N—((1S,2R)-1-(3,5-difluorobenzyl)-2-hydroxy-3-{[(4S)-1-(2-hydroxyethyl)-6-neopentyl-1,2,3,4-tetrahydroquinolin-4-yl]amino}propyl)acetamide; |
| T. | N—[(1S,2R)-3-{[(4S)-1-acetyl-6-neopentyl-1,2,3,4-tetrahydroquinolin-4-yl]amino}-1-(3,5-difluorobenzyl)-2-hydroxypropyl]acetamide; |
| U. | N—[(1S,2R)-3-{[(4S)-1-acetyl-6-isobutyl-1,2,3,4-tetrahydroquinolin-4-yl]amino}-1-(3,5-difluorobenzyl)-2-hydroxypropyl]acetamide; |
| V. | N—[(1S,2R)-3-{[(4S)-1-acetyl-6-isopropyl-1,2,3,4-tetrahydroquinolin-4-yl]amino}-1-(3,5-difluorobenzyl)-2-hydroxypropyl]acetamide; |

-continued

| Example No. | Name |
|---|---|
| W. | N—[(1S,2R)-3-{[(4S)-1-acetyl-6-tert-butyl-1,2,3,4-tetrahydroquinolin-4-yl]amino}-1-(3,5-difluorobenzyl)-2-hydroxypropyl]acetamide; |
| X. | N—[(1S,2R)-3-{[(4S)-6-tert-butyl-1-(cyanomethyl)-1,2,3,4-tetrahydroquinolin-4-yl]amino}-1-(3,5-difluorobenzyl)-2-hydroxypropyl]acetamide; |
| Y. | N—[(1S,2R)-3-{[(4S)-1-(cyanomethyl)-6-isopropyl-1,2,3,4-tetrahydroquinolin-4-yl]amino}-1-(3,5-difluorobenzyl)-2-hydroxypropyl]acetamide; |
| Z. | N—[(1S,2R)-3-{[(4S)-1-(cyanomethyl)-6-isobutyl-1,2,3,4-tetrahydroquinolin-4-yl]amino}-1-(3,5-difluorobenzyl)-2-hydroxypropyl]acetamide; |
| AA. | N—[(1S,2R)-3-{[(4S)-1-(cyanomethyl)-6-neopentyl-1,2,3,4-tetrahydroquinolin-4-yl]amino}-1-(3,5-difluorobenzyl)-2-hydroxypropyl]acetamide; |
| BB. | N—((1S,2R)-1-(3,5-difluorobenzyl)-2-hydroxy-3-{[(4S)-6-(1-hydroxy-2,2-dimethylpropyl)-1,2,3,4-tetrahydroquinolin-4-yl]amino}propyl)acetamide; |
| CC. | N—((1S,2R)-1-(3,5-difluorobenzyl)-2-hydroxy-3-{[(4S)-6-(1-hydroxy-2,2-dimethylpropyl)-1-methyl-1,2,3,4-tetrahydroquinolin-4-yl]amino}propyl)acetamide; |
| DD. | N—((1S,2R)-1-(3,5-difluorobenzyl)-3-{[(4S)-2,2-dimethyl-6-neopentyl-1,2,3,4-tetrahydroquinolin-4-yl]amino}-2-hydroxypropyl)acetamide; |
| EE. | N—((1S,2R)-1-(3,5-difluorobenzyl)-2-hydroxy-3-{[(4S)-1,2,2-trimethyl-6-neopentyl-1,2,3,4-tetrahydroquinolin-4-yl]amino}propyl)acetamide; |
| FF. | N—((1S,2R)-1-(3,5-difluorobenzyl)-3-{[(4S)-1,4-dimethyl-6-neopentyl-1,2,3,4-tetrahydroquinolin-4-yl]amino}-2-hydroxypropyl)acetamide; |
| GG. | N—((1S,2R)-1-(3,5-difluorobenzyl)-2-hydroxy-3-{[(4S)-4-methyl-6-neopentyl-1,2,3,4-tetrahydroquinolin-4-yl]amino}propyl)acetamide; |
| HH. | N—((1S,2R)-1-(3,5-difluorobenzyl)-2-hydroxy-3-{[(4S)-6-isobutyl-4-methyl-1,2,3,4-tetrahydroquinolin-4-yl]amino}propyl)acetamide; |
| II. | N—((1S,2R)-1-(3,5-difluorobenzyl)-2-hydroxy-3-{[(4S)-6-isobutyl-1,4-dimethyl-1,2,3,4-tetrahydroquinolin-4-yl]amino}propyl)acetamide; |
| JJ. | N—[(1S,2R)-3-[(6-tert-butoxy-1,2,3,4-tetrahydroquinolin-4-yl)amino]-1-(3,5-difluorobenzyl)-2-hydroxypropyl]acetamide; |
| KK. | N—[(1S,2R)-3-[(6-tert-butoxy-4-methyl-1,2,3,4-tetrahydroquinolin-4-yl)amino]-1-(3,5-difluorobenzyl)-2-hydroxypropyl]acetamide; |
| LL. | N—[(1S,2R)-3-[(6-tert-butoxy-4,8-dimethyl-1,2,3,4-tetrahydroquinolin-4-yl)amino]-1-(3,5-difluorobenzyl)-2-hydroxypropyl]acetamide; |
| MM. | N—{(1S,2R)-1-(3,5-difluorobenzyl)-2-hydroxy-3-[(4-methyl-6-neopentyl-1,2,3,4-tetrahydroquinolin-4-yl)amino]propyl}acetamide; |
| NN. | N—{(1S,2R)-1-(3,5-difluorobenzyl)-3-[(4,8-dimethyl-6-neopentyl-1,2,3,4-tetrahydroquinolin-4-yl)amino]-2-hydroxypropyl}acetamide; |
| OO. | N—{(1S,2R)-1-(3,5-difluorobenzyl)-2-hydroxy-3-[(8-methyl-6-neopentyl-1,2,3,4-tetrahydroquinolin-4-yl)amino]propyl}acetamide; |
| PP. | N—((1S,2R)-1-(3,5-difluorobenzyl)-2-hydroxy-3-{[6-(2-hydroxy-2-methylpropyl)-8-methyl-1,2,3,4-tetrahydroquinolin-4-yl]amino}propyl)acetamide; |
| QQ. | N—((1S,2R)-1-(3,5-difluorobenzyl)-2-hydroxy-3-{[6-(2-hydroxy-2-methylpropyl)-4-methyl-1,2,3,4-tetrahydroquinolin-4-yl]amino}propyl)acetamide; |
| RR. | N—((1S,2R)-1-(3,5-difluorobenzyl)-2-hydroxy-3-{[6-(2-hydroxy-2-methylpropyl)-1,2,3,4-tetrahydroquinolin-4-yl]amino}propyl)acetamide; |
| SS. | N—((1S,2R)-1-(3,5-difluorobenzyl)-2-hydroxy-3-{[6-(1-hydroxy-2,2-dimethylpropyl)-1,2,3,4-tetrahydroquinolin-4-yl]amino}propyl)acetamide; and |
| TT. | N—((1S,2R)-1-(3,5-difluorobenzyl)-2-hydroxy-3-{[6-(1-hydroxy-2,2-dimethylpropyl)-4-methyl-1,2,3,4-tetrahydroquinolin-4-yl]amino}propyl)acetamide. |

EXAMPLE 111

Reactions were monitored, and purity evaluated by TLC on silica gel GF, 250 μ slides obtained from Analtech, Inc., Newark, Del. Preparative low pressure (flash) chromatography was carried out on silica gel 60 (230-400 mesh ASTM) from EM Science, Gibbstown, N.J. Proton NMR spectra were collected on a Bruker Avance 400 spectrometer. Chemical shifts (δ) are in ppm, coupling constants (J) are in Hz. IR absorbances greater than 1200 cm$^{-1}$ are reported. All reagents were obtained from commercial sources and were used without further purification. Unless otherwise noted, all solvents used in reaction were run under an inert atmosphere of nitrogen in over-dried glassware. Preparative flash chromatography was performed on silica gel 60 (230-240 mesh) from EM Science. HPLC analysis were carried out on a HP1100 system (Agilent) with the following a 1.0 mL/min linear gradient of 0.05% aqueous TFA (A) and 0.05% TFA in acetonitrile (B): 0% B: 5 min: 60% B, 15 min: 90% B, 2 min: 0% B. All solvents for chromatography were HPLC grade. Where not commercially available, starting materials and intermediates, including new and known compounds, were prepared by synthetic methods known in the art. HATU, which stands for N-[(dimethylamino)-1-H-1,2,3-triazolo[4,5-b]pyrindin-1-ylmethylene]-N-methylmethanaminium hexafluorophosphate N-oxide, was bought from PE Biosystems. All hydrochloride salts were formed by addition of ethereal hydrochloric acid to an ethereal solution of amine, followed by concentration to dryness.

A. 5-bromo-2-hydroxybenzamide

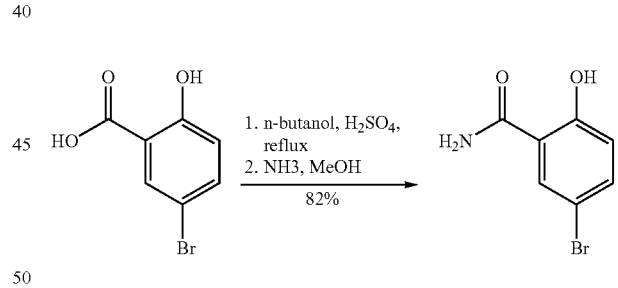

To a stirred solution of 5-Bromosalicyclic acid (30 g, 135.5 mmol) in n-butylalcohol (60 mL) was added H$_2$SO$_4$ (95.6%, 289 μL, 5.42 mmol) in a 100 ml round bottom flask connected by a Dean-Stark trap/reflux condenser that was filled with 12 ml of n-butylalcohol. After heated to reflux for 2 days, the reaction was cooled down to R.T. and concentrated to give a pale yellow oil. The mixture was added 50 mL MeOH, followed by NH$_3$ in MeOH (7 N, 116 mL). The reaction was stirred at R.T. for another 2 days, monitored by HPLC. After the reaction complete, it was concentrated to give a white solid. The crude solid was washed with small amount of EtOAc and hexane to afford 24 g of the product as a white crystalline solid (82% yield). $^1$H NMR (CDCl$_3$) δ 12.15 (s, 1H), 7.54 (m, 2H), 6.97 (d, J=12 Hz, 1H), 6.00 (broad, 2H).

B. 2-hydroxy-5-isobutylbenzamide

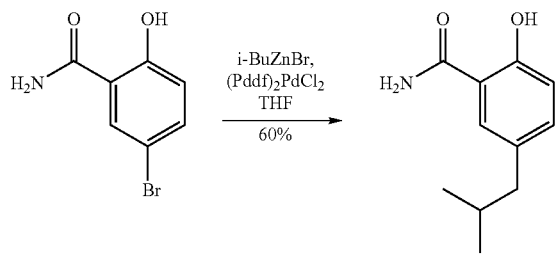

To a stirred solution of the bromobenzamide (8.64 g, 40 mmol) in THF (100 mL) under argon was added [1,1'-Bis (diphenylphosphino)ferrocene]dichloropaladium(II) (1.96 g, 2.4 mmol) followed by i-BuZnBr (0.5 M, 200 mL). The reaction mixture was stirred at R.T. for 4 days. The reaction was quenched with 1N HCl, and then concentrated. The resulting crude was diluted with ethyl acetate, and washed with water and brine, dried with sodium sulfate, filtered, and concentrated under reduced pressure. The crude product was purified by flash column chromatography (5~10% ethyl acetate: hexane) to afford 4.63 g of the isobutylbenzamide product as an off-white solid (60% yield). $^1$H NMR (CDCl$_3$) δ 12.02 (s, 1H), 7.24 (d, J=8 Hz, 1H), 7.12 (s, 1H), 6.93 (d, J=8 Hz, 1H), 2.44 (d, J=8 Hz, 2H), 1.83 (m, 1H), 0.93 (d, J=8 Hz, 6H)

C. 2-cyano-4-isobutylphenyl trifluoromethanesulfonate

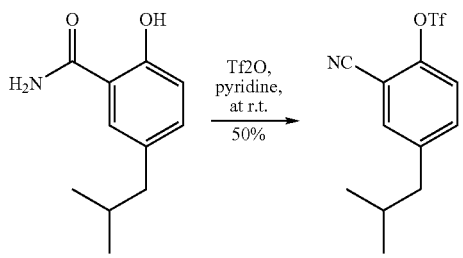

At 0° C., to a stirred solution of the hydroxy-isobutylbenzamide (3.72 g, 19.3 mmol) in pyridine (15 mL) under argon was added trifluoromethanesulfonic anhydride (10.2 ml, 57.8 mmol). The reaction mixture was eventually warmed up to room temperature and stirred overnight. The reaction was diluted with ethyl acetate, and washed with 1N HCl (×2), water (×1) and brine (×1), dried with sodium sulfate, filtered, and concentrated under reduced pressure. The crude product was purified by flash column chromatography (5% ethyl acetate: hexane) to afford 2.66 g of the desired product as a clear oil (50% yield). $^1$H NMR (CDCl$_3$) δ 7.56 (s, 1H), 7.50 (d, J=8 Hz, 1H), 7.43 (d, J=8 Hz, 1H), 2.57 (d, J=8 Hz, 2H), 1.92 (m, 1H), 0.97 (d, J=4 Hz, 6H).

D. 4-isobutyl-1,1'-biphenyl-2-carbonitrile

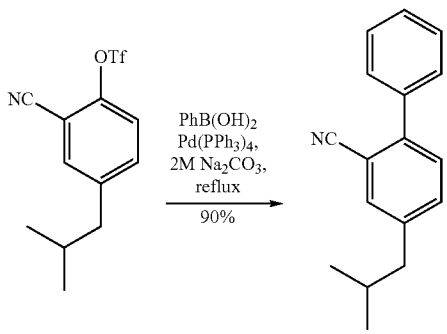

To a stirred solution of the cyano compound (610 mg, 1.88 mmol), aqueous sodium carbonate (2.0 M, 3.76 mmol) in DME (6 mL) was added tetrakis(triphenylphosphine) palladium(0) (109 mg, 0.094 mmol) followed by phenylboronic acid (280 mg, 2.26 mmol). The reaction mixture was heated to reflux overnight, and then cooled to R.T. The reaction was diluted with ethyl acetate, and was washed with water and brine, dried with sodium sulfate, filtered, and concentrated under reduced pressure. The crude product was purified by flash column chromatography (3% ethyl acetate: hexane) to afford 450 mg of the product as a white solid (90% yield). $^1$H NMR (CDCl$_3$) δ 7.60 (m, 3H), 7.54 (m, 2H), 7.48 (m, 3H), 2.60 (d, J=8 Hz, 2H), 1.96 (m, 1H), 1.00 (d, J=6 Hz, 6H).

E. (4-isobutyl-1,1'-biphenyl-2-yl)methylamine

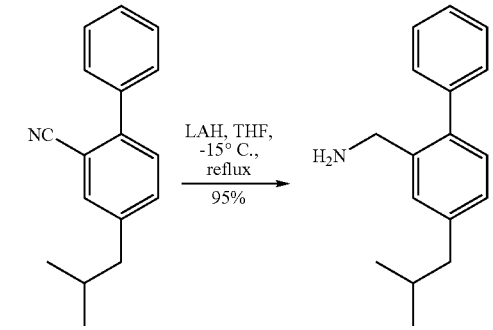

The above compound was prepared essentially according to the method of Example 10. $^1$H NMR (CDCl$_3$) δ 7.47 (m, 2H), 7.44 (m, 3H), 7.30 (s, 1H), 7.20 (d, J=8 Hz, 1H), 7.14 (m, 1H), 3.84 (s, 2H), 2.58 (d, J=8 Hz, 2H), 1.93 (m, 1H), 1.47 (s, 2H), 1.00 (d, J=4 Hz, 6H); ESI-MS [M+H$^+$]$^+$=240.22.

F. tert-butyl (1S,2R)-1-(3,5-difluorobenzyl)-2-hydroxy-3-{[(4-isobutyl-1,1'-biphenyl-2-yl)methyl]amino}propylcarbamate

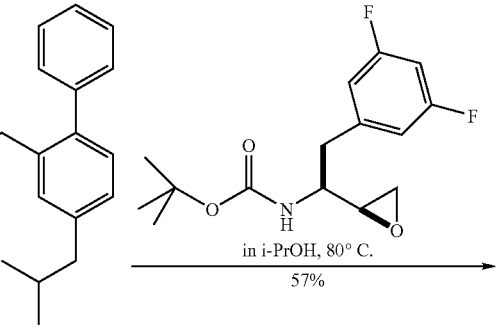

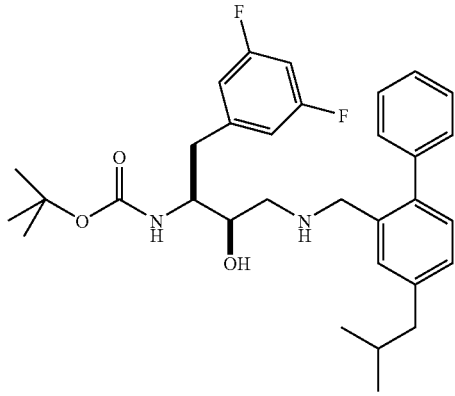

To a stirred solution of the biphenyl amine (400 mg, 1.67 mmol) in i-propanol (10 mL) was added Example 134 (name generated using ACD Namepro version 5.09) (336 mg, 1.12 mmol). The reaction mixture was heated at 80° C. overnight. The reaction mixture was concentrated, and purified by flash column chromatography (2-5% MeOH: CH$_2$Cl$_2$) to afford 510 mg of product as an off-white solid (57% yield). $^1$H NMR (CDCl$_3$) δ 7.45 (m, 2H), 7.38 (m, 3H), 7.25 (s, 1H), 7.21 (m, 1H), 7.16 (m, 1H), 6.76 (m, 2H), 6.70 (m, 1H), 4.55 (m, 1H), 3.76 (m, 3H), 3.34 (m, 1H), 2.90 (m, 1H), 2.78 (m, 2H), 2.64 (m, 2H), 2.55 (m, 3H), 1.93 (m, 1H), 1.40 (s, 9H), 1.00 (d, 6H); ESI-MS [M+H$^+$]$^+$=539.22.

G. N-((1S,2R)-1-(3,5-difluorobenzyl)-2-hydroxy-3-{[(4-isobutyl-1,1'-biphenyl-2-yl)methyl]amino}propyl) acetamide

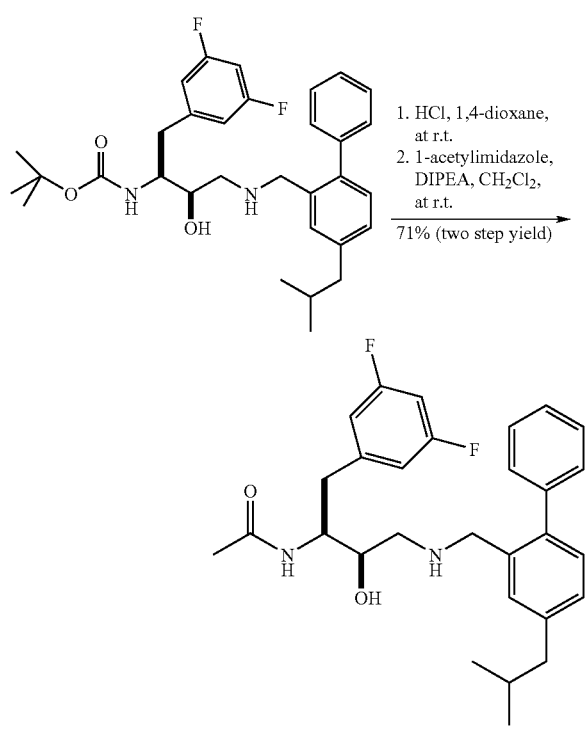

Step 1: To a stirred solution of the starting material (377 mg, 0.7 mmol) in MeOH (5 mL) was added HCl in 1,4-dioxane (4.0 M, 2 mL). After stirring at R.T. overnight, the reaction mixture was concentrated under reduced pressure to provide an off-white solid, which was used without further purification.

Step 2: To a stirred solution of amine from step 1 in CH$_2$Cl$_2$ (8 mL) was added DIPEA (304 μL, 1.75 mmol), and then 1-acetylimidazole (86 mg, 0.77 mmol). The reaction mixture was stirred at R.T. overnight, quenched by addition of 50% ammonium hydroxide, and diluted with CH$_2$Cl$_2$. The organic layer was washed with washed with 1N HCl (×2), saturated aqueous sodium bicarbonate (×2) and brine (×1), dried with sodium sulfate, filtered, and concentrated under reduced pressure. The crude product was purified by flash column chromatography (3-5% MeOH: CH$_2$Cl$_2$) to afford 240 mg of product as an off-white solid (71% yield, two steps). $^1$H NMR (CDCl$_3$) δ 9.63 (b, 1H), 8.48 (b, 1H), 7.63 (s, 1H), 7.46 (m, 3H), 7.28 (m, 4H), 6.74 (m, 2H), 6.67 (m, 1H), 4.24 (m, 1H), 4.17 (m, 1H), 4.05 (m, 2H), 2.80 (m, 4H), 2.57 (m, 3H), 1.97 (m, 4H), 0.97 (d, 6H); ESI-MS [M+H$^+$]$^+$=481.35.

H. 5-bromo-2-(1H-imidazol-1-yl)benzonitrile

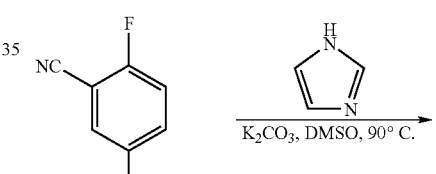

To a stirred solution 5-Bromo-2-fluorobenzonitrile (2.5 g, 12.2 mmol) in DMSO (50 mL) was added K$_2$CO$_3$ (3.337 g, 24.4 mmol), and then 1H-imidazole (996 mg, 14.64 mmol). The reaction mixture was heated to 90° C. overnight, and diluted with water. The reaction mixture was extracted with EtOAC (×2). The organic layer was washed with washed with water (×1) and brine (×1), dried with sodium sulfate, filtered, and concentrated under reduced pressure to afford 2.97 g of the imidazolylbenzonitrile as an off-white solid (98% yield). $^1$H NMR (CDCl$_3$) δ 7.97 (m, 2H), 7.90 (m, 1H), 7.41 (d, J=8 Hz, 1H), 7.37 (s, 1H), 7.32 (s, 1H).

I. 2-(1H-imidazol-1-yl)-5-isobutylbenzonitrile

The above compound was prepared essentially according to the method of Example 111, step B, but the reaction mixture was only stirred overnight. The resulting crude product was purified by flash column chromatography (50-100% ethyl acetate: hexane) to afford the product as a dark-brown oil. $^1$H NMR (CDCl$_3$) δ 7.89 (s, 1H), 7.60 (s, 1H), 7.53 (d, J=8 Hz, 1H), 7.40 (m, 2H), 7.28 (m, 1H), 2.60 (d, J=8 Hz, 2H), 1.93 (m, 1H), 0.97 (d, 6H); ESI-MS [M+H$^+$]$^+$=226.03.

J. tert-butyl (1S,2R)-1-(3,5-difluorobenzyl)-2-hydroxy-3-{[2-(1H-imidazol-1-yl)-5-isobutylbenzyl]amino}propylcarbamate

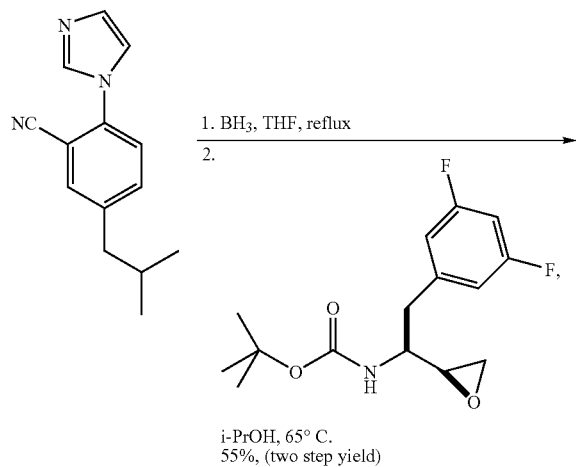

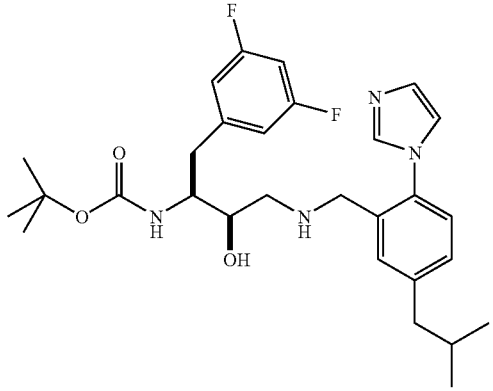

Step 1: At 0° C., to a stirred solution of BH$_3$ (1.5 M in THF, 4.9 mL) was added the imidazolyl product from (I) (722 mg, 3.2 mmol) in anhydrous THF (8 mL). The reaction was eventually warmed up to R.T., and then refluxed for overnight, and then refluxed for 1 hour. The reaction mixture was cooled down to R.T, and then quenched with 5N aqueous HCl. The reaction was poured into CH$_2$Cl$_2$ (10 mL), washed with saturated aqueous sodium bicarbonate (×2) and brine (×1), dried with sodium sulfate, filtered, and concentrated under reduced pressure without further purification.

Step 2: To a stirred solution of amine from step 1 in i-propanol (14 mL) was added (1S)-2-(3,5-difluorophenyl)-1-[(2S)-oxiran-2-yl]ethylcarbamate (509 mg, 1.7 mmol). The reaction mixture was heated at 65° C. overnight. The reaction mixture was concentrated, and purified by flash column chromatography (5-20% MeOH: CH$_2$Cl$_2$) to afford 537 mg of product as an off-white solid (55% yield, two steps). ESI-MS [M+H$^+$]$^+$=529.35.

K. N-((1S,2R)-1-(3,5-difluorobenzyl)-2-hydroxy-3-{[2-(1H-imidazol-1-yl)-5-isobutylbenzyl]amino}propyl)acetamide

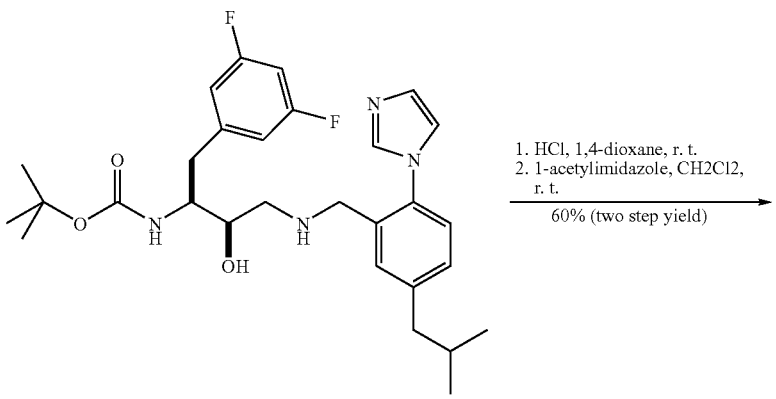

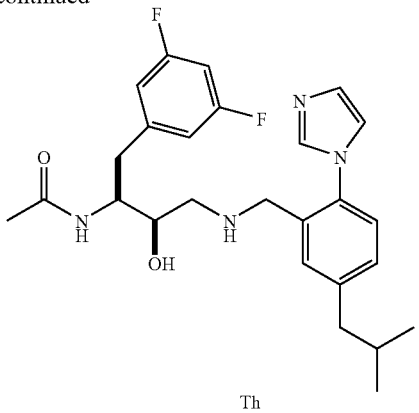

The above compound was prepared essentially according to the method of Example 111, step G. The crude acetamide was purified by flash column chromatography (5-20% MeOH:CH$_2$Cl$_2$) to afford the desired product as an off-white solid (60% yield, two steps). ESI-MS [M+H$^+$]$^+$=471.33.

L. N-((1S,2R)-1-(3,5-difluorobenzyl)-2-hydroxy-3-{[5-isobutyl-2-(1H-1,2,4-triazol-1-yl)benzyl]amino}propyl)acetamide

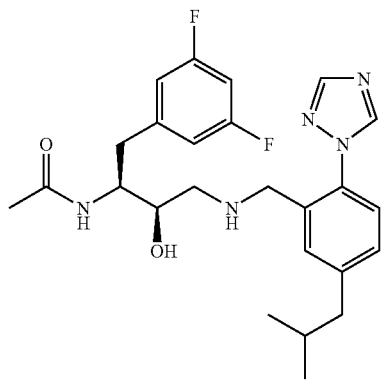

The above compound is synthesized using procedures essentially similar to Example 111, steps J and K. ESI-MS [M+H$^+$]$^+$=472.0

M. 2-Iodo-5-isobutylbenzamide

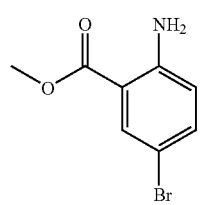

1. i-BuZnBr, Pd(dppf)Cl$_2$, THF, r. t.
2. NaNO$_2$, H$_2$SO$_4$, KI, H$_2$O, r. t.
3. LiOH, THF/MeOH/H$_2$O, r. t.
4. NH$_4$Cl, EDC, HOBt, DIPEA, r. t.
   20% (four step yield)

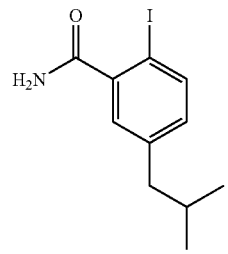

Step 1: To a stirred solution of methyl 2-amino-5-bromobenzoate (5.77 g, 25 mmol) in THF (20 mL) under argon was added [1,1'-Bis(diphenylphosphino)ferrocene]dichloropalladium(II) (2.04 g, 2.5 mmol) followed by i-BuZnBr (0.5 M, 200 mL). The reaction mixture was stirred at R.T. for overnight. The reaction was quenched with 1N HCl, and then concentrated. The resulting crude was diluted with ethyl acetate, and washed with water and brine, dried with sodium sulfate, filtered, and concentrated under reduced pressure without further purification.

Step 2: At R.T. amine from step 1 was treated with 5% H$_2$SO$_4$ (3.2 mL), and the reaction was heated to 60° C. for 5-10 minutes. The reaction mixture was cooled down to ice-cold, and then was added drop-wise NaNO$_2$ (1.87 g, 27 mmol) in H$_2$O (10 mL). After the addition was complete, the reaction was stirred at ice-cold temperature for 15-20 minutes, and then KI (4.94 g, 29.7 mmol>in H$_2$O (20 mL) was added. The reaction was stirred at R.T. overnight. The next day, the reaction was extracted with EtOAC (×3). The organic layer was washed with washed with brine (×1), dried (sodium sulfate), filtered, and concentrated. The crude product was purified by flash column chromatography (5-10% MeOH:CH$_2$Cl$_2$) to afford 2 g of iodinated product.

Step 3: To a stirred solution of iodinated product from step 2 (6.6 g, 20.9 mmol) in a mixed solvent of MeOH (30 mL), THF (30 mL), and water (30 mL) was added LiOH.H$_2$O (4.4 mg, 104.5 mmol) at room temperature. After stirred for 12 hour at room temperature, the reaction mixture was quenched with 1N HCl, diluted with CH$_2$Cl$_2$, washed with saturated aqueous sodium bicarbonate (×1), water (×2), and brine (×2), dried over sodium sulfate, and concentrated under reduced pressure. The crude product was used for the next step without further purification.

Step 4: Was performed essentially according to the method of Example 56. The resulting crude product was purified by flash column chromatography (10-50% EtOAC: CH₂Cl₂) to afford 900 mg of product as an off-white solid (20% yield, four steps). ¹H NMR (CDCl₃) δ 7.80 (d, J=8 Hz, 1H), 7.30 (s, 1H), 6.95 (d, J=8 Hz, H), 5.80 (b, 2H), 2.47 (d, J=6 Hz, 2H), 1.87 (m, 1H), 0.93 (2, H).

N. N-{(1S,2R)-1-(3,5-difluorobenzyl)-2-hydroxy-3-[(2-iodo-5-isobutylbenzyl)amino]propyl}acetamide

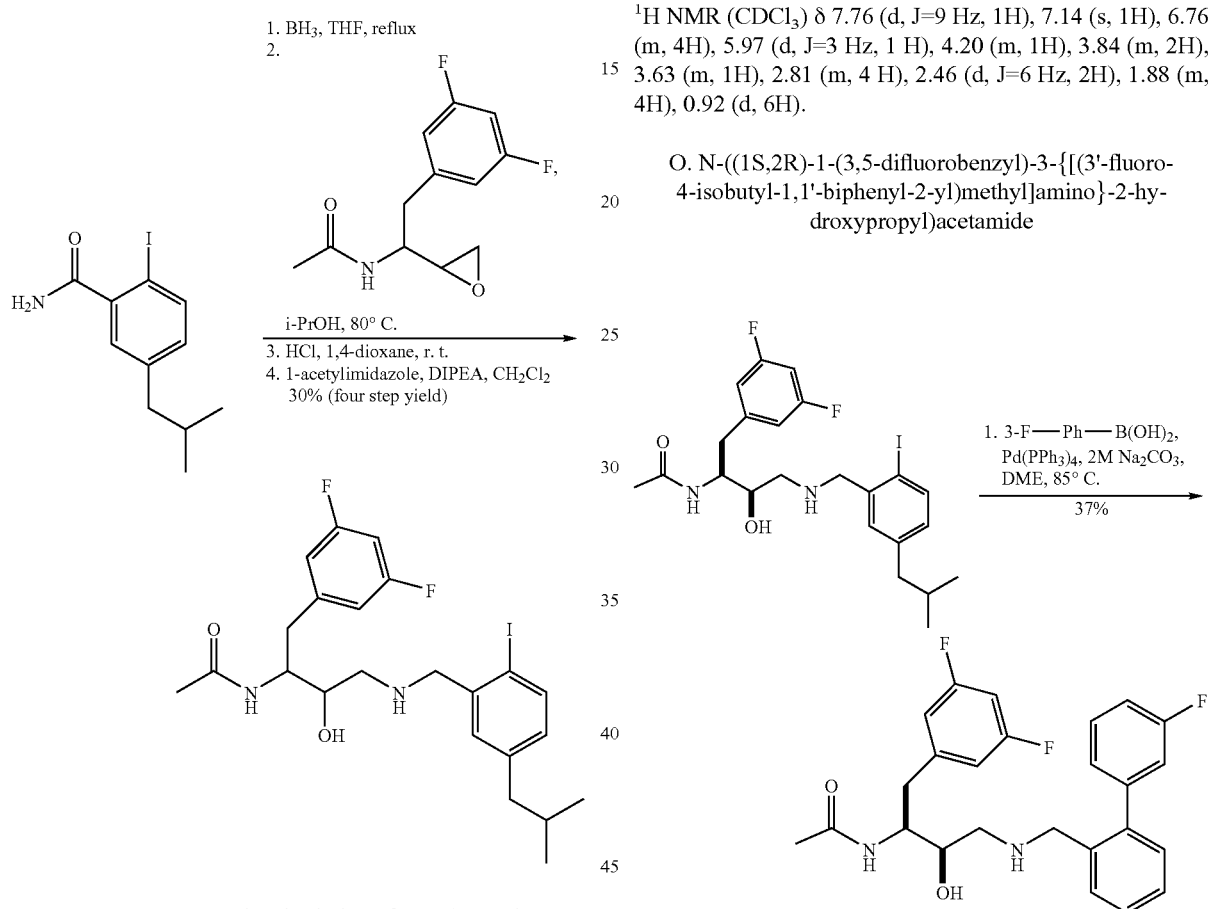

Step 1: At 0° C., to a stirred solution of BH₃ (1.5 M in THF, 9.3 mL) was added (1.838 g, 6.1 mmol) in anhydrous THF (16 mL). The reaction was eventually warmed up to R.T., and then refluxed for overnight, and then refluxed for 1 hour. The reaction mixture was cooled down to R.T, and then quenched with 5N aqueous HCl. The reaction was poured into CH₂Cl₂ (10 mL), washed with saturated aqueous sodium bicarbonate (×2) and brine (×1), dried with sodium sulfate, filtered, and concentrated under reduced pressure without further purification.

Step 2: Was performed essentially according to the method of Example 15, step 2. The reaction mixture was concentrated under reduced pressure without further purification.

Step 3: To a stirred solution of crude form step 2 in MeOH (10 mL) was added HCl in 1,4-dioxane (4.0 M, 5.6 mL). After stirred at R.T. overnight, the reaction mixture was concentrated under reduced pressure to provide an off-white solid. The crude was re-dissolve in CH₂Cl₂, washed with saturated aqueous sodium bicarbonate (×2) and brine (×1), dried with sodium sulfate, filtered, and concentrated under reduced pressure without further purification.

Step 4: To a stirred solution of amine from step 3 in CH₂Cl₂ (60 mL) was added DIPEA (3.88 mL, 22.3 mmol), and then 1-acetylimidazole (516 mg, 4.46 mmol). The reaction mixture was stirred at R.T. overnight, quenched by addition of 50% ammonium hydroxide, and diluted with CH₂Cl₂. The organic layer was washed with washed with 1N HCl (×2), saturated aqueous sodium bicarbonate (×2) and brine (×1), dried with sodium sulfate, filtered, and concentrated under reduced pressure. The crude product was purified by flash column chromatography (3-5% MeOH: CH₂Cl₂) to afford 1 mg of product as an off-white solid (30% yield, four steps). ¹H NMR (CDCl₃) δ 7.76 (d, J=9 Hz, 1H), 7.14 (s, 1H), 6.76 (m, 4H), 5.97 (d, J=3 Hz, 1 H), 4.20 (m, 1H), 3.84 (m, 2H), 3.63 (m, 1H), 2.81 (m, 4 H), 2.46 (d, J=6 Hz, 2H), 1.88 (m, 4H), 0.92 (d, 6H).

O. N-((1S,2R)-1-(3,5-difluorobenzyl)-3-{[(3'-fluoro-4-isobutyl-1,1'-biphenyl-2-yl)methyl]amino}-2-hydroxypropyl)acetamide To a stirred solution of the product of step (N) (97 mg, 0.183 mmol), aqueous sodium carbonate (2.0 M, 0.403 mmol) in DME (1 mL) was added tetrakis(triphenylphosphine) palladium(0) (21 mg, 0.0183 mmol) followed by 3-fluoro-phenylboronic acid (64 mg, 0.458 mmol). The reaction mixture was heated to reflux overnight, and then cooled to R.T. The reaction was diluted with CH₂Cl₂, and was washed with water and brine, dried with sodium sulfate, filtered, and concentrated under reduced pressure. The crude product was purified by flash column chromatography (3-10% MeOH: CH₂Cl₂) to afford 36 mg of the product as a white solid (37% yield). ESI-MS [M+H⁺]⁺=499.32.

Compounds shown in Examples P-Z are synthesized using methods that are analogous to those previously described.

| Example | | |
|---|---|---|
| P. | N—((1S,2R)-1-(3,5-difluorobenzyl)-2-hydroxy-3-{[(4-isobutyl-1,1'-biphenyl-2-yl)methyl]amino}propyl)acetamide | ESI-MS [M + H+]+ = 481.35 |
| Q. | N—{(1S,2R)-1-(3,5-difluorobenzyl)-2-hydroxy-3-[(5-isobutyl-2-pyridin-3-ylbenzyl)amino]propyl}acetamide | ESI-MS [M + H+]+ = 482.33 |
| R. | N—{(1S,2R)-1-(3,5-difluorobenzyl)-2-hydroxy-3-[(5-isobutyl-2-pyridin-4-ylbenzyl)amino]propyl}acetamide | ESI-MS [M + H+]+ = 482.33 |
| S. | N—((1S,2R)-1-(3,5-difluorobenzyl)-3-{[(4'-fluoro-4-isobutyl-1,1'-biphenyl-2-yl)methyl]amino}-2-hydroxypropyl)acetamide | ESI-MS [M + H+]+ = 499.31 |
| T. | N—((1S,2R)-1-(3,5-difluorobenzyl)-3-{[(2'-fluoro-4-isobutyl-1,1'-biphenyl-2-yl)methyl]amino}-2-hydroxypropyl)acetamide | ESI-MS [M + H+]+ = 499.32 |
| U. | N—((1S,2R)-1-(3,5-difluorobenzyl)-2-hydroxy-3-{[5-isobutyl-2-(6-methoxypyridin-3-yl)benzyl]amino}propyl)acetamide | ESI-MS [M + H+]+ = 512.33 |
| V. | N—((1S,2R)-1-(3,5-difluorobenzyl)-2-hydroxy-3-{[(3'-hydroxy-4-isobutyl-1,1'-biphenyl-2-yl)methyl]amino}propyl)acetamide | ESI-MS [M + H+]+ = 497.36 |
| W. | N—[(1S,2R)-3-{[(3'-acetyl-4-isobutyl-1,1'-biphenyl-2-yl)methyl]amino}-1-(3,5-difluorobenzyl)-2-hydroxypropyl]acetamide | ESI-MS [M + H+]+ = 523.33 |
| X. | N—((1S,2R)-1-(3,5-difluorobenzyl)-2-hydroxy-3-{[5-isobutyl-2-(5-methoxypyridin-3-yl)benzyl]amino}propyl)acetamide | ESI-MS [M + H+]+ = 512.30 |
| Y. | N—((1S,2R)-1-(3,5-difluorobenzyl)-3-{[2-(3-furyl)-5-isobutylbenzyl]amino}-2-hydroxypropyl)acetamide | ESI-MS [M + H+]+ = 471.32 |
| Z. | N—((1S,2R)-1-(3,5-difluorobenzyl)-3-{[2-(2-furyl)-5-isobutylbenzyl]amino}-2-hydroxypropyl)acetamide | ESI-MS [M + H+]+ = 471.32 |

EXAMPLE 112

See Albright, J. D., *J. Heterocycl. Chem.*, 2000, 37, 41-6 for a general reference on preparing pyridyl tetralin compounds.

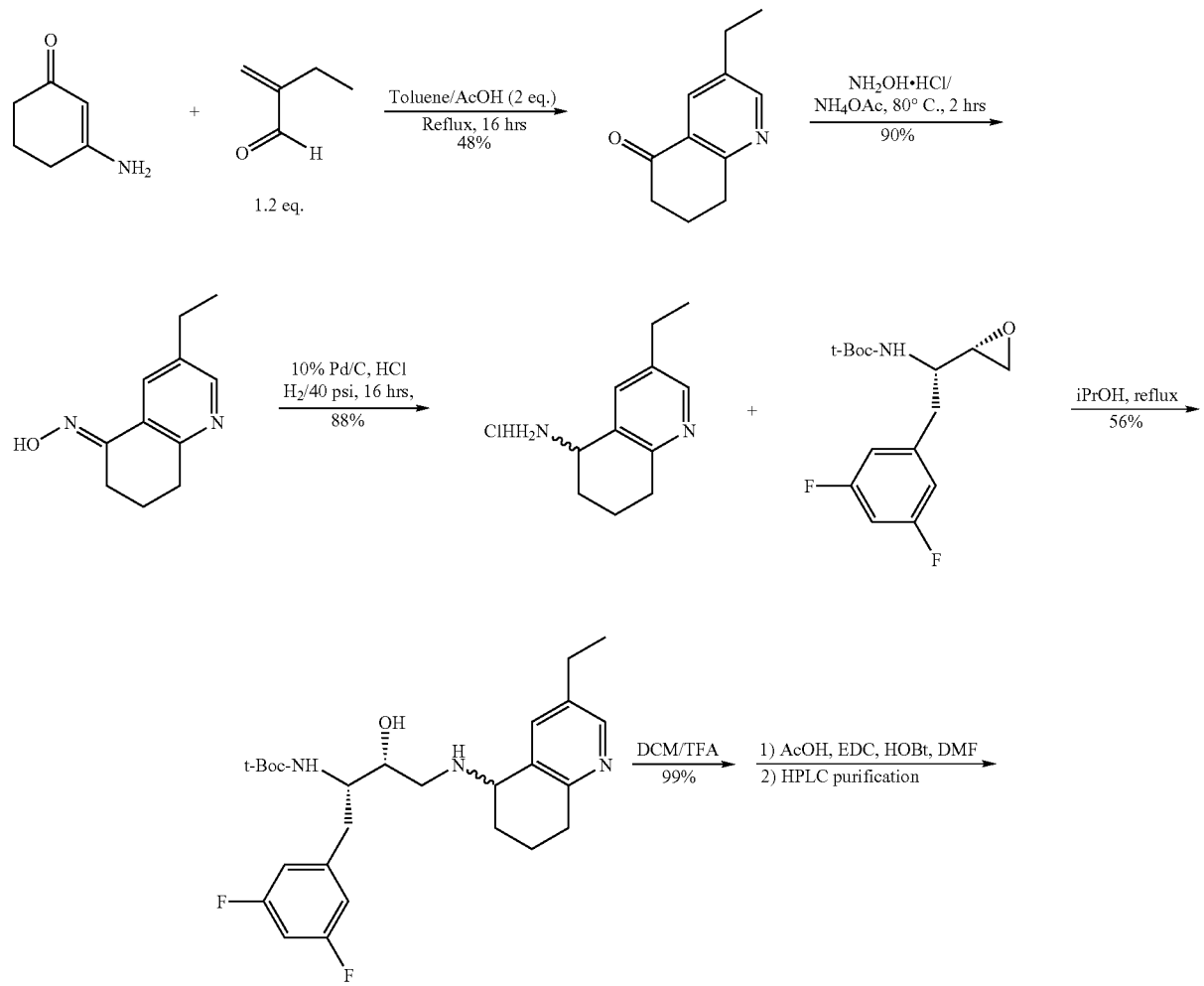

-continued

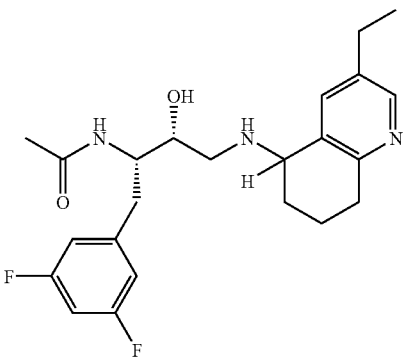

STEP 1

To 5.5 g of 3-amino-2-cyclohexan-1-one (49.5 mmole) and 5 g of 2-ethyl acrolein (59.4 mmole, 1.2 eq.) was added 6 ml of acetic acid and 25 ml of toluene. The reaction mixture was heated to reflux overnight. The reaction was monitored by TLC to show formation of a new spot with Rf=0.73 (50% MeOH/DCM+20% EtOH/Hexane.) Solvent was removed and the residue taken up in toluene, which was removed again. The residue was extracted with DCM (2×), washed with saturated NaHCO$_3$, dried over anhydrous sodium sulfate, and concentrated to give 9.38 g crude dark tan oil. This crude oil was extracted with hot hexanes (2× of 125 ml). The extracts were concentrated and dried in vacuo to give a light tan solid. (4.13 g, 23.6 mmole, 48%). MH+ (ESI)=176.1.

Step 2

The oxime was formed using procedures described elsewhere in the application. yield: 90%; MH+ (ESI)=191.1.

STEP 3

Reduction of the oxime was performed essentially according to procedures described elsewhere in the application. yield: 88%; MH+ (ESI)=177.1.

STEP 4

The amine hydrochloride salt was free based by partitioning between 1 N NaOH and EtOAc. The free base solution was then concentrated and used in the epoxide opening reaction as previously described: yield: 56%; MH+ (ESI)=476.2.

STEP 5

Boc deprotection and acetylation was performed as previously described. Reverse phase HPLC was effective in the resolution of the two diasteromers:

N- (1S,2R)-[1-(3,5-Difluorobenzyl)-3-((5S)-3-ethyl-5,6,7,8-tetrahydroquinolin-5-ylamino)-2-hydroxypropyl]-acetamide: MH+ (ESI)=418.2.

N-(1S,2R)-[1-(3,5-Difluorobenzyl)-3-((5R)-3-ethyl-5,6,7,8-tetrahydroquinolin-5-ylamino)-2-hydroxypropyl]-acetamide: MH+ (ESI)=418.2.

EXAMPLE 113

A. Synthesis of Chiral Amine 2b

The compound (1), which is readily available, was protected and then underwent palladium-mediated coupling with neo-pentylzinc chloride (generated in situ) to give neo-pentyl substituted tetraline 2a. Subsequent deprotection afforded intermediate amine 2b as its hydrochloride salt, which was utilized in the construction of additional targets (infra).

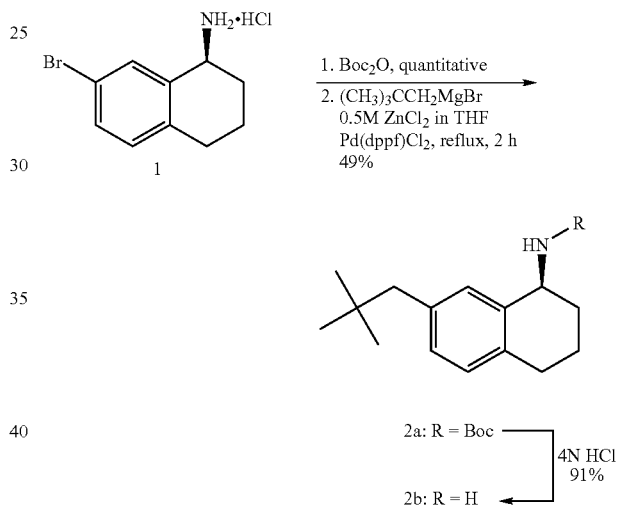

B. Synthesis of Tetralone 4

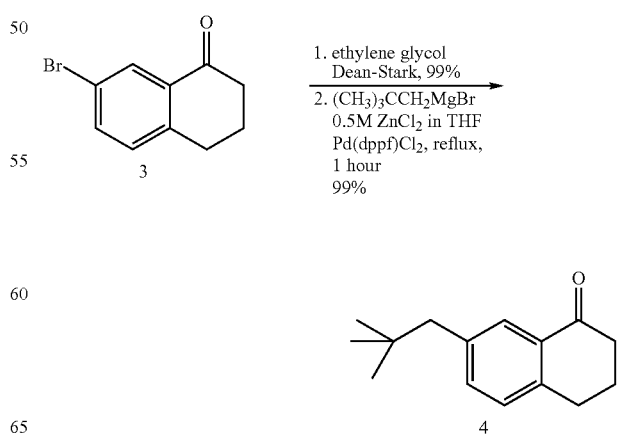

7-Bromotetralone (3) was protected as its dioxolane and then underwent palladium-mediated coupling with neo-pentylzinc chloride (generated in situ) to afford, after acidic work-up, neo-pentyl substituted tetralone 4.

C. Synthesis of Tetralin Compound 7

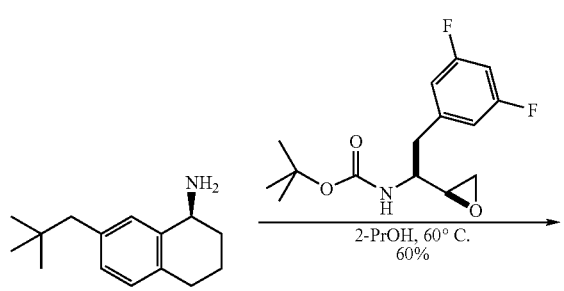

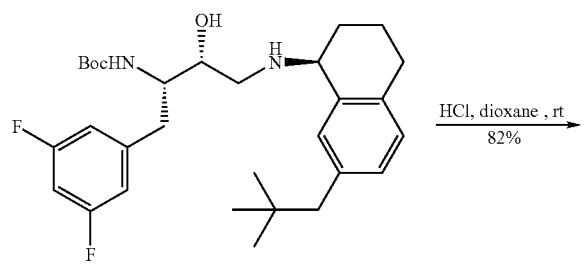

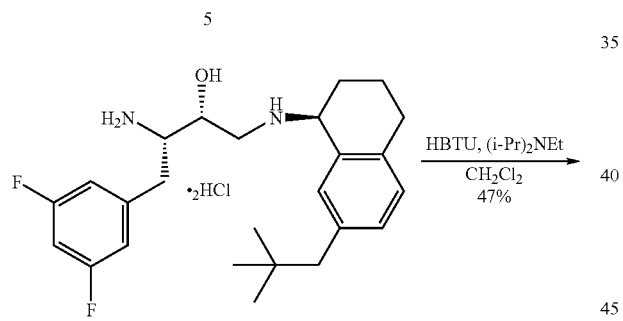

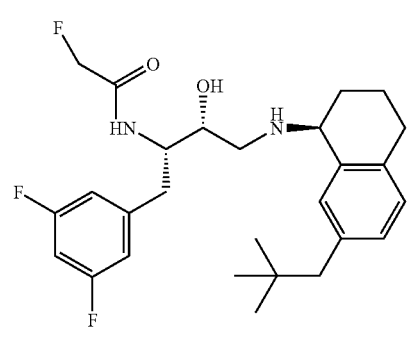

Coupling the enantiomerically pure tetralin amine of amine 2b with (1S)-2-(3,5-difluorophenyl)-1-[(2S)-oxiran-2-yl]ethylcarbamate followed by Boc-deprotection and HBTU-mediated acylation afforded the final compound (7), as predominantly one diastereoisomer.

D. Synthesis of Thiazoles 18 and 20

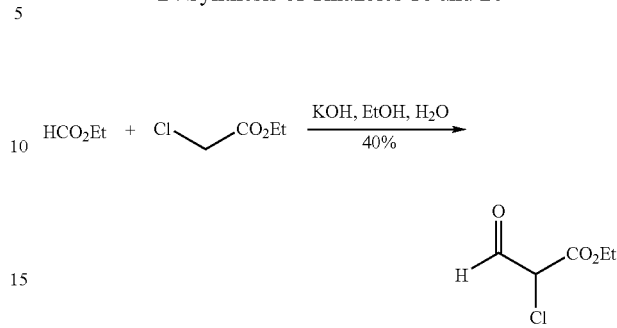

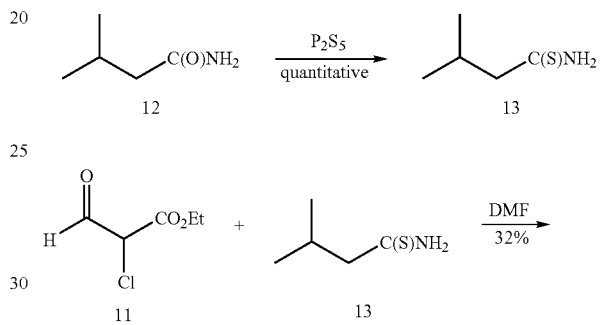

Claisen condensation of ethyl formate and ethyl chloroacetate gave ester 11. Treatment of isovaleramide (12) with phosphorus pentasulfide afforded 3-methyl-thiobutyramide (13). Cyclization of 11 and 13 afforded 5-carboethoxy-2-isobutylthiazole (14).

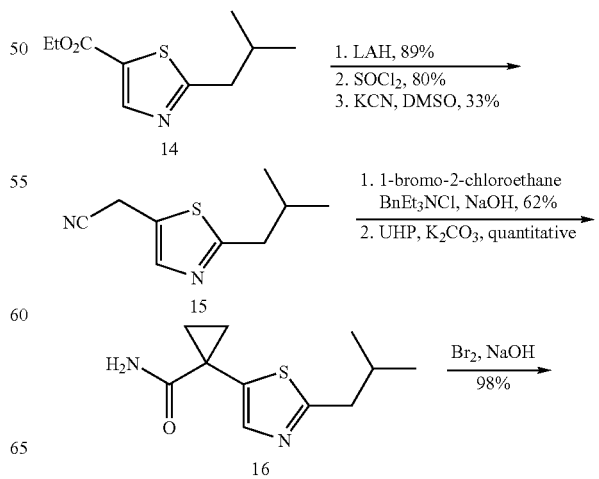

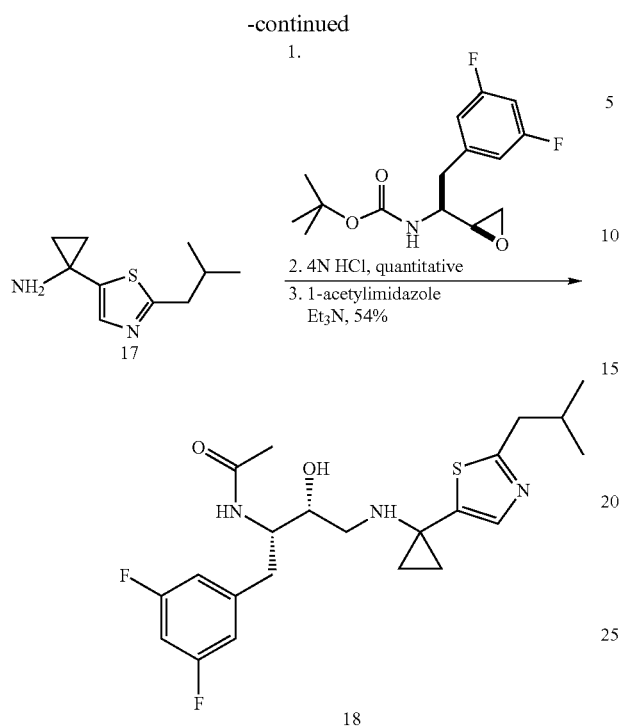

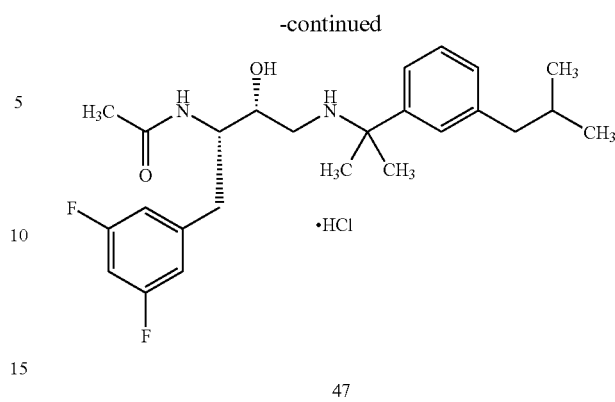

Reduction of ester 14 followed by treatment of the resulting alcohol with thionyl chloride followed by nucleophilic substitution with potassium cyanide gave benzyl nitrile 15. Cyclopropanation of 15 followed by hydrolysis afforded amide 16. Hoffman rearrangement of 16 afforded amine 17. N-Alkylation of 17 followed by de-protection and N-acetylation provided (18).

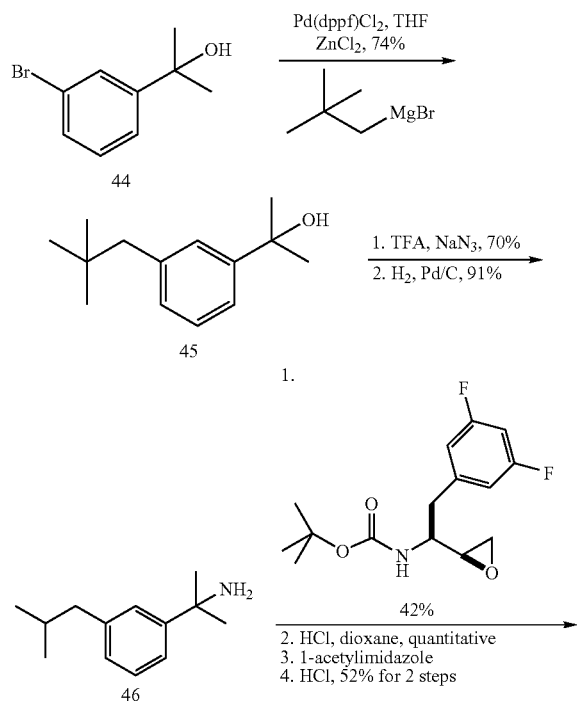

Palladium coupling of bromide 44 with neo-pentyl zinc generated in situ gave alcohol 45). Conversion of alcohol 45 to amine 46 was carried out in two steps. Epoxide opening, deprotection, and acetylation resulted in (47).

E. Synthesis of Chroman 32

The synthesis of aminochroman (29) is illustrated in scheme II. In scheme II, phenol H140 underwent Michael addition with acrylonitrile to give nitrile H141. Subsequent acid hydrolysis gave carboxylic acid H142, which was then converted to the acid chloride and cyclized intramolecularly to give chromonone H143. Alpha bromination of ketone H143 gave bromide H144, which was reduced with sodium borohydride to give bromo alcohol H145. Using Ritters reaction conditions, H145 was transformed to racemic amino alcohol 29. More specific experimental procedures follow the scheme.

Scheme II

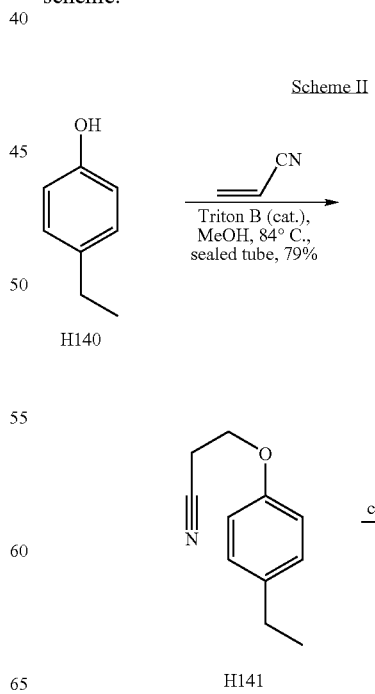

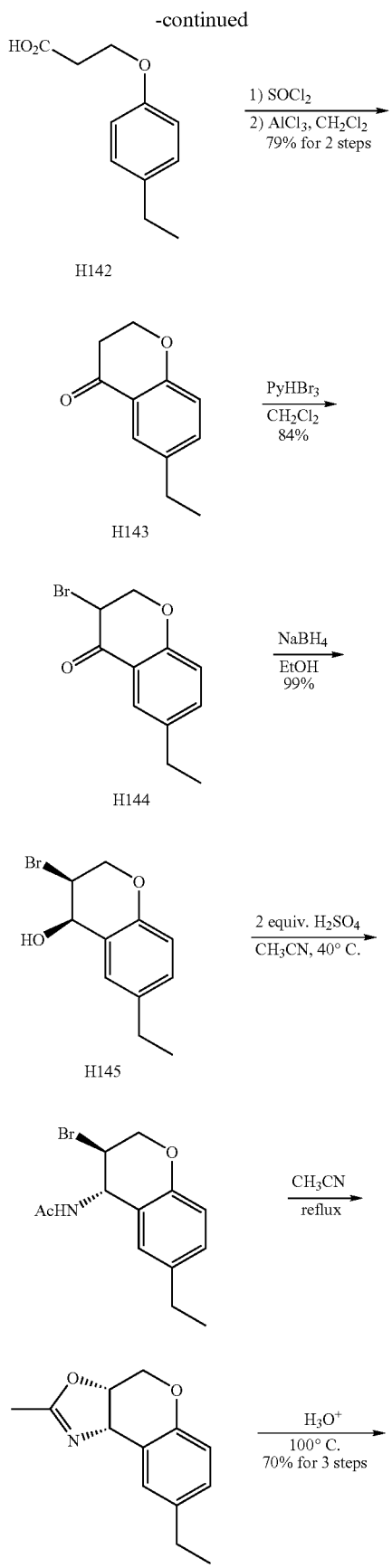

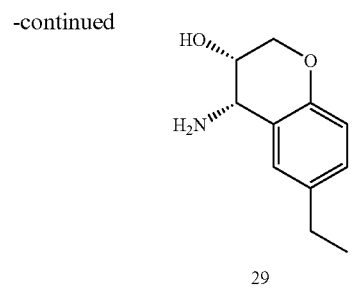

Step 1: A mixture of 4-etylphenol (H140, 26,69 g, 0.218. mol), acrylonitrile (50 mL, 0.754 mol, 3.5 equiv), and triton B (40 wt % in methanol, 5 mL, 0.011 mol, 0.05 equiv) was stirred at 84° C. in a sealed tube overnight. The reaction mixture was diluted with ether (300 mL) and the brown precipitate was removed by suction filtration. The ether solution was washed with 2 M sodium hydroxide aqueous solution (2×100 mL), 1 M hydrochloric acid (100 mL) and saturated sodium chloride, dried (magnesium sulfate), and concentrated under reduced pressure. Purification by flash column chromatography (silica, gradient 10:1, and 6:1 hexanes/ethyl acetate) provided nitrile H141 (30.17 g, 79%) as a white solid: $^1$H NMR (300 MHz, CDCl$_3$) δ 7.17-7.08 (m, 2H), 6.87-6.79 (m, 2H), 4.18 (t, J=6.4 Hz, 2H), 2.80 (t, J=6.4 Hz, 2H), 2.60 (q, J=7.6 Hz, 2H), 1.20 (t, J=7.6 Hz, 3H); ESI MS m/z 176 [C$_{11}$H$_{13}$NO+H]$^+$.

Step 2: Nitrile H141 (30.17 g, 0.172 mol) was stirred with concentrated hydrochloric acid solution (100 mL, 1.20 mol, 7 equiv) at reflux overnight. White precipitate formed as the reaction proceeded. The reaction mixture was cooled to room temperature and the solid was collected by suction filtration. The filter cake was washed several times with cold water and dried in a vacuum oven at 50° C. for 14 h. Carboxylic acid H142 was obtained as a white solid (31.79 g, 95%): $^1$H NMR (300 MHz, CDCl$_3$) δ 7.13-7.08 (m, 2H), 6.88-6.80 (m, 2H), 4.20 (t, J=6.3 Hz, 2H), 2.85 (t, J=6.3 Hz, 2H), 2.58 (q, J=7.6 Hz, 2H), 1.18 (t, J=7.6 Hz, 3H); ESI MS m/z 193 [C$_{11}$H$_{14}$O$_3$−H].

Step 3: The carboxylic acid H142 (0.800 g, 4.12 mmol) was stirred with thionyl chloride (6 mL, 82.4 mmol, 20 equiv) at reflux for 2 h. Excess thionyl chloride was removed under reduced pressure. The acid chloride thus obtained was used without further purification in the next reaction.

Aluminum chloride (1.10 g, 8.24 mmol, 2 equiv) was added in one portion to a solution of acid chloride as above in dry methylene chloride (50 mL) and the resulting brown mixture was stirred at reflux for 14 h and cooled to room temperature. The mixture was poured onto crushed ice in a beaker, followed by the addition of 6 M hydrochloric acid (20 mL) and extraction with methylene chloride (3×40 mL). The combined organics were washed with saturated sodium chloride, dried (magnesium sulfate), and concentrated under reduced pressure. Purification by flash column chromatography (silica, gradient 10:1, and 6:1 hexanes/ethyl acetate) gave chromonone H143 (574 mg, 79%) as a colorless oil: $^1$H NMR (300 MHz, CDCl$_3$) δ 7.72 (d, J=2.2 Hz, 1H), 7.32 (dd, J=8.5, 2.2 Hz, 1H), 6.90 (d, J=8.5 Hz, 1H), 4.52 (t, J=6.5 Hz, 2H), 2.80 (t, J=6.5 Hz, 2H), 2.60 (q, J=7.6 Hz, 2H), 1.20 (t, J=7.6 Hz, 3H); ESI MS m/z 177 [C$_{11}$H$_{12}$O$_2$+H]$^+$.

Step 4: Pyridinium hydrobromide perbromide (743 mg, 2.32 mmol) was added to a solution of chromonone H143 (372 mg, 2.11 mmol) in dry methylene chloride (15 mL) and the reaction mixture was stirred at room temperature for 2 h.

Water (15 mL) was added to the mixture and the layers were separated. The aqueous layer was further extracted with methylene chloride (2×15 mL). The combined organics were dried (magnesium sulfate) and concentrated under reduced pressure. Purification by flash column chromatography (silica, gradient 20:1, and 10:1 hexanes/ethyl acetate) provided bromo ketone H144 (450 mg, 84%) as a slightly yellow oil: $^1$H NMR (300 MHz, CDCl$_3$) δ 7.77 (d, J=2.2 Hz, 1H), 7.39 (dd, J=8.5, 2.2 Hz, 1H), 6.97 (d, J=8.5 Hz, 1H), 4.68-4.52 (m, 3H), 2.62 (q, J=7.6 Hz, 2H), 1.22 (t, J=7.6 Hz, 3H); ESI MS m/z 255 [C$_{11}$C$_{11}$BrO$_2$+H]$^+$.

Step 5: Sodium borohydride (99 mg, 2.61 mmol, equiv) was added to a solution of bromo ketone H144 (444 mg, 1.74 mmol) in absolute ethanol (15 mL) and the reaction mixture was stirred at room temperature for 2 h. the reaction mixture was quenched with the addition of 1 M hydrochloric acid (4 mL) and most of ethanol was removed by rotary evaporation. The residue was partitioned between water and methylene chloride. The aqueous layer was further extracted with methylene chloride. The combined organics were dried (sodium sulfate) and concentrated under reduced pressure. Bromo alcohol H145 was obtained as a white solide (443 mg, 99%) and used in the next step without further purification: $^1$H NMR (300 MHz, CD$_3$OD) δ 7.14 (d, J=1.5 Hz, 1H), 7.03 (dd, J=8.3, 1.5 Hz, 1H), 6.69 (d, J=8.3 Hz, 1H), 4.78 (d, J=3.2 Hz, 1H), 4.58-4.49 (m, 1H), 4.35-4.26 (m,2H), 2.56 (q, J=7.6 Hz, 2H), 1.16 (t, J=7.6 Hz, 2H), 1.16 (t, J=7.6 Hz, 3H).

Step 6: The bromo alcohol from step 5H145 (443 mg, 1.72 mmol) was dissolved in anhydrous acetonitrile (10 mL) and concentrated sulfuric acid (0.19 mL, 3.47 mmol) was added via syringe. The reaction mixture was stirred at 40° C. for 5 h and then reflux for 12 h. Water (10 mL) was added and most of the acetonitrile was removed under reduced pressure. To the residue was added 6 M hydrochloric acid (10 mL) and the resulting mixture was stirred at reflux for 14 h. The reaction mixture was cooled to room temperature, and placed in an ice bath. To this was added 6 M sodium hydroxide until pH 12, and the mixture was extracted with methylene chloride (3×50 mL). The combined organics were washed with saturated sodium chloride, dried (sodium sulfate) and concentrated. Purification by flash column chromatography (silica, gradient 20:1, 10:1 and 1:1 methylene chloride/methanol) provided amino alcohol (29, 233 mg, 70%) as a white solid: $^1$H NMR (300 MHz, CDCl$_3$) δ 7.12 (d, J=1.5 Hz, 1H), 7.01 (dd, J=8.3, 1.5 Hz, 1H) 6.78 (d, J=8.3 Hz, 1H), 4.09 (d, J=11.5 Hz, 1H), 4.00-3.91 (m, 2H), 3.88-3.75 (m, 1H), 2.58 (q, J=7.6 Hz, 2H), 1.60 (br s, 3H) 1.20 (t, J=7.6 Hz, 3H); ESI MS m/z 194 [C$_{11}$H$_{15}$NO$_2$+H]$^+$; HPLC (method E) 96.7% (AUC), $^t_R$=9.4 min.

Scheme II-a

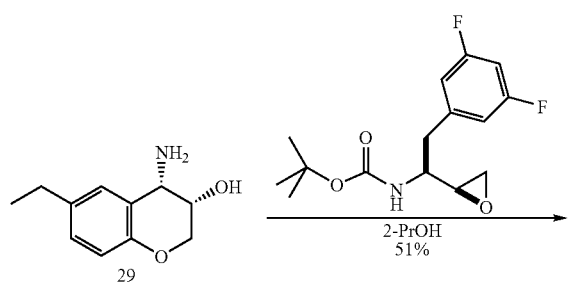

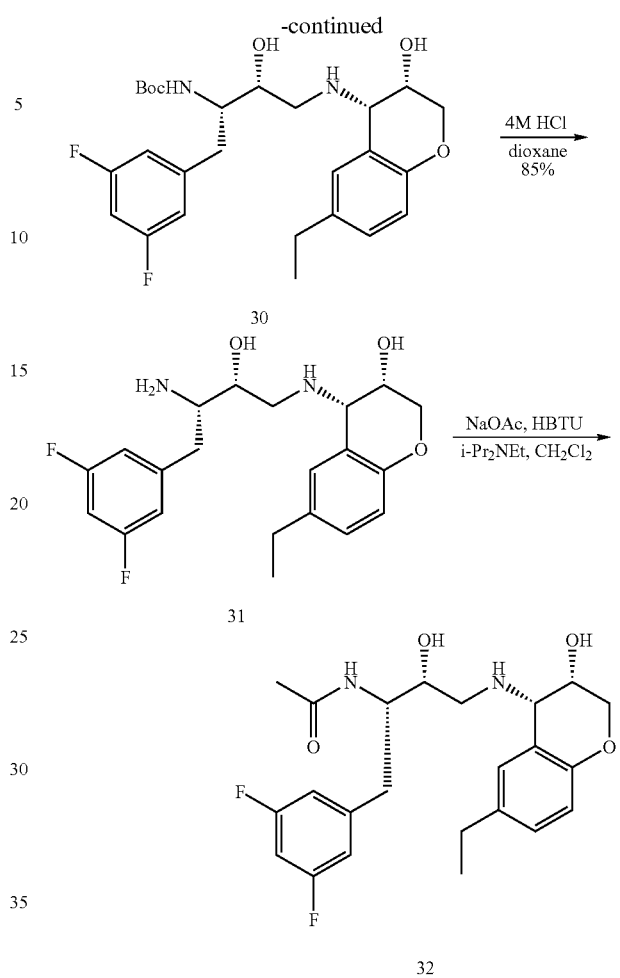

Subsequent coupling of racemic aminochroman 29 with Example 134, followed by Boc deprotection and HBTU-mediated acylation afforded (32), as a mixture of diastereoisomers (Scheme II-a). One possible procedure for preparing compound 32 is described below.

Synthesis of Compound (32)

Step 1: To a solution of 29 (1.00 g, 5.18 mmol) in 2-propanol (60 mL) was added Example 134 (1.40 g, 4.71 mmol) and the reaction mixture was heated to 50° C. for 17 h and then to 80° C. for 1 h. The reaction mixture was cooled to room temperature, and the solvent removed under reduced pressure. The residue was partitioned between methylene chloride (20 mL) and water (20 mL). The aqueous phase was extracted with methylene chloride (10 mL), the combined organic phase washed successively with 0.5 N hydrochloric acid (10 mL), saturated sodium bicarbonate (10 mL) and sodium chloride (10 mL), dried (sodium sulfate), filtered and concentrated under reduced pressure. The crude product was purified by flash chromatography (silica, 95:5 methylene chloride/methanol) to afford amino alcohol 30 (1.30 g, 51%) as a white solid: $^1$H NMR (300 MHz, CDCl$_3$) δ 7.42-7.38 (m, 1H), 7.20-6.96 (m, 1H), 6.78-6.62 (m, 5H), 4.64-4.58 (m, 1H), 4.56-4.20 (m, 1H), 4.18-4.08 (m, 2H), 3.90-3.48 (m, 4H), 3.16-2.70 (m, 5H), 2.64-2.50 (m, 2H), 1.50-1.30 (s, 9H), 1.23-1.18 (m, 3H); ESI MS m/z 493 [C$_{26}$H$_{34}$F$_2$N$_2$O$_5$+H].

Step 2: To a solution of amino alcohol 30 (0.47 g, 0.95 mmol) in dioxane (20 mL) at room temperature was added hydrogen chloride (4.77 mL, 4 M solution in dioxane, 19.09 mmol) and the reaction mixture stirred for 17 h. The reaction mixture was concentrated under reduced pressure and the residue triturated with diethyl ether to afford amine 31 (0.38 g, 85%) as a white solid: $^1$H NMR (300 MHz, CD$_3$OD) δ 7.40 (s, 1H), 7.19-7.17 (m, 1H), 7.05-6.83 (m, 5H), 4.71-4.69 (m, 1H), 4.44-4.40 (m, 2H), 4.19-4.08 (m, 3H), 3.78 (br s, 1H), 3.78-3.52 (m, 1H), 3.49-3.47 (m, 1H), 3.34-3.30 (m, 1H), 3.12-3.01 (m 2H), 2.98-2.63 (m, 4H), 1.30-1.17 (m, 3H); ESI MS m/z 393 [C$_{21}$H$_{26}$F$_2$N$_2$O$_3$+H].

Step 3: To a suspension of sodium acetate (0.67 g, 0.82 mmol), diisopropylethylamine (0.71 mL, 4.09 mmol) and HBTU (0.31 g, 0.82 mmol) in methylene chloride (5 mL) was added an additional solution of amine 31 (0.38 g, 0.82 mmol), diisopropylethylamine (0.71 mL, 4.09 mmol) in methylene chloride (5 mL) and the combined mixture was stirred at room temperature for 24 h. Water (30 mL) was added and the aqueous phase was extracted with additional methylene chloride (5 mL). The combined organic phase was washed successively with 0.5 N hydrochloric acid (10 mL) and saturated sodium chloride (10 mL), dried (sodium sulfate), filtered and concentrated under reduced pressure. Purification by preparative HPLC (Method G) afforded ALB 15297 (32, 55 mg, 4%) as a white foam: IR (ATR) 3254, 2966, 1657, 1627, 1596 cm$^{-1}$; $^1$H NMR (300 MHz, CD$_3$OD) δ 7.34-7.28 (m, 1H), 7.17-7.14 (m, 1H), 6.88-6.75 (m, 5H), 4.56-4.54 (m, 1H), 4.39-4.34 (m, 1H), 4.16-4.04 (m, 3H), 3.90-3.85 (m, 1H), 3.77-3.62 (m, 1H), 3.54-3.10 (m, 5H), 2.71-2.57 (m, 3H), 1.85-1.82 (m, 3H), 1.28-1.16 (m, 3H); ESI MS m/z 435 [C$_{23}$H$_{28}$F$_2$N$_2$O$_4$+H]; HPLC (Method F) 94.1 (AUC), t$_R$=11.1, 11.5 min (3:2 mixture of diastereeoisomers).

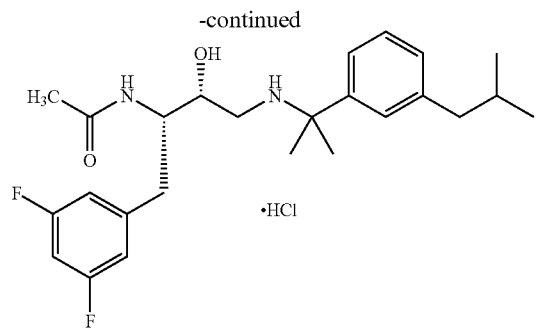

158

F. Synthesis of Acetate 158

Addition of methyl Grignard to ester 155 followed by coupling with 2-methylpropyl boronic acid gave alcohol 156. Conversion of the alcohol to the azide and reduction provided amine 157. Epoxide opening, removal of the protecting group, acetalization, and formation of the hydrochloric acid salt gave (158).

General HPLC Methods

Method A: Phenomenex Luna C18(2) Column, 150×4.6 mm, 5μ
A: 0.05% TFA in 95:5H$_2$O/CH$_3$CN; B: 0.05% TFA in 5:95H$_2$O/CH$_3$CN
Gradient: 10-90% B over 15 min; flow 1.0 mL/min
Detection: 254 nm Method B: Phenomenex Luna C18(2) Column, 150×4.6 mm, 5μ
A: 0.05% TFA in 95:5H$_2$O/CH$_3$CN; B: 0.05% TFA in 5:95H$_2$O/CH$_3$CN
Gradient: 30-100% B over 15 min; flow 1.0 mL/min
Detection: 254 nm Method C: Phenomenex Synergi Max-RP Column, 150×4.6 mm, 4μ
A: H$_2$O; B: CH$_3$CN
Gradient: 30-100% B over 15 min; flow 1.0 mL/min
Detection: 220 nm Method D: Phenomenex Luna C18(2) Column, 150×4.6 mm, 4μ
A: 95:5H$_2$O/CH$_3$CN; B: 5:95H$_2$O/CH$_3$CN
Gradient: 40-100% B over 15 min; flow 1.0 mL/min
Detection: 254 nm Method E: Phenomenex Luna C18(2) Column, 150×4.6 mm, 4μ
A: 95:5H$_2$O/CH$_3$CN; B: 5:95H$_2$O/CH$_3$CN
Gradient: 1-99% B over 15 min; flow 1.0 mL/min
Detection: 254 nm Method F: Phenomenex Luna C18(2) Column, 150×4.6 mm, 5μ
A: 0.05% TFA in 95:5H$_2$O/CH$_3$CN; B: 0.05% TFA in 5:95H$_2$O/CH$_3$CN
Gradient: 10-90% B over 15 min; flow 1.0 mL/min
Detection: 225 nm

EXAMPLE 114

A. Synthesis of Neo-Pentylmagnesium Bromide

A 3-necked, round-bottom flask fitted with an addition funnel, water condenser and magnetic stir bar was charged

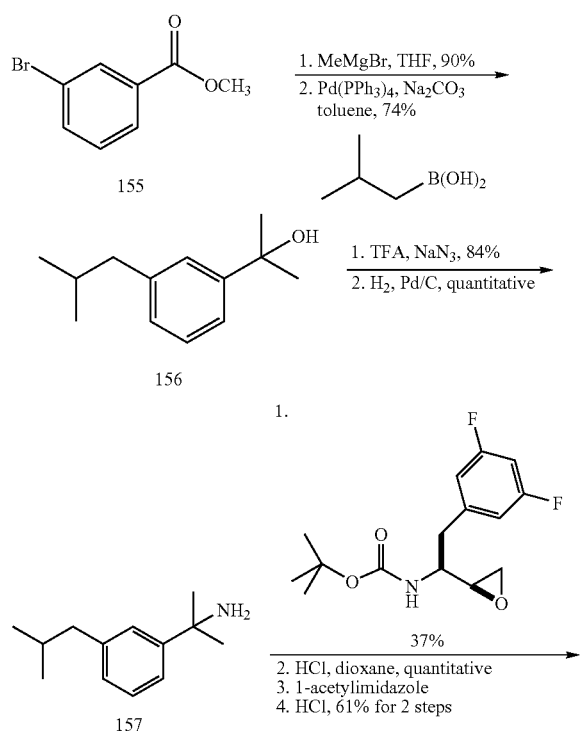

with magnesium turnings (10.0 g, 413.8 mmol), iodine (100 mg), and glass shards and then heated vigorously under vacuum with stirring for 20 min. The reaction flask was cooled to room temperature and then charged with argon and the magnesium turnings stirred for an additional 0.5 h. The flask was then charged with diethyl ether (65 mL) and the addition funnel charged with a solution of neo-pentyl bromide (20.0 g, 132.4 mmol) in diethyl ether (100 mL). Neat neo-pentyl bromide (2.5 g, 16.55 mmol) was added directly to the reaction mixture and the solution was gently warmed with a heat gun to initiate the reaction. Once the reaction was initiated, the contents of the addition funnel were added dropwise over the course of 1 h to maintain a gentle reflux. Another aliquot of neat neo-pentyl bromide (2.5 g, 16.55 mmol) was then added to the reaction mixture in one portion followed by dropwise addition of 1,2-dibromoethane (14.3 mL, 165.5 mmol) over the course of 1 h. Ethane gas generated was swept from the reaction flask by a steady stream of nitrogen. The reaction mixture was then heated at reflux for 24 h and cooled to room temperature to yield a black solution. The suspended solid was allowed to settle and the solution above the solid residue was neo-pentylmagnesium bromide (ca. 1.0 M in ether, 165.5 mmol), which was used in subsequent coupling reactions.

B. Synthesis of Amine 2b

Step 1: Di-tert-butyl dicarbonate (5.45 g, 25.0 mmol) was added in one portion at room temperature to a solution of compound (1) (5.05 g, 19.23 mmol) and N,N-diisopropylethylamine (10.0 mL, 57.7 mmol) in acetonitrile (32 mL) and the reaction mixture was stirred at room temperature for 36 h. The solvent was removed under reduced pressure and the residue partitioned between ethyl acetate and saturated sodium bicarbonate. The phases were separated and the organic phase was washed with water, saturated sodium chloride, dried (sodium sulfate), filtered, and concentrated under reduced pressure to yield the desired protected amine (7.38 g, quantitative) as a waxy solid, which was used in the next step without further purification: $^1$H NMR (300 MHz, CDCl$_3$) δ 7.47 (s, 1H), 7.28-7.24 (m, 1H), 6.94 (d, J=8.2 Hz, 1H), 4.77 (m, 2H), 2.72-2.66 (m, 2H), 2.04-2.00 (m, 1H), 1.83-1.72 (m, 3H), 1.44 (s, 9H).

Step 2: A solution of the neo-pentylmagnesium bromide prepared above (115.4 mL) was added dropwise at room temperature to a solution of zinc chloride (115.4 mL, 0.5 M in tetrahydrofuran, 57.7 mmol) over 40 min. Following Grignard addition, the reaction mixture was stirred for 0.5 h to yield a white heterogenous suspension. [1,1'-Bis(diphenylphosphino)ferrocene]dichloropalladium(II) complex with dichloromethane (1:1) (1.60 g, 1.92 mmol) was added in one portion followed by dropwise addition over 20 min of a solution of the protected amine prepared in step 1 (7.38 g, 19.23 mmol) in tetrahydrofuran (20 mL) to yield a yellow reaction mixture. The reaction mixture was stirred at room temperature for 0.5 h then heated at reflux for 2 h to yield a brown solution. The reaction mixture was cooled to room temperature and carefully quenched with 10% hydrochloric acid (100 mL) and the reaction mixture was stirred at room temperature overnight. The reaction mixture was diluted with diethyl ether and the phases separated. The organic phase was then washed with water, saturated sodium chloride, dried (sodium sulfate), filtered, and concentrated under reduced pressure to yield a brown semisolid. Purification by flash column chromatography (silica, 19:1 hexanes/ethyl acetate) afforded protected amine 2a (3.0 g, 49%) as a yellow oil: $^1$H NMR (300 MHz, CDCl$_3$) δ 7.08 (s, 1H), 6.98-6.90 (m, 2H), 4.82-4.75 (m, 2H), 2.76-2.69 (m, 2H), 2.43 (s, 2H), 2.04-1.97 (m, 1H), 1.84-1.80 (m, 3H), 1.47 (s, 9H), 0.88 (m, 9H); ESI MS m/z 318 [C$_{20}$H$_{31}$NO$_2$+H]$^+$.

Step 3: To a solution of amine 2a (3.00 g, 9.45 mmol) in 1,4-dioxane (25 mL) was added at room temperature a solution of hydrochloric acid (23.5 mL, 4 N in 1,4-dioxane, 94.5 mmol) and the reaction mixture stirred at room temperature overnight to yield a white precipitate. Vacuum filtration yielded amine 2b (2.15 g, 91%) as a white solid: $^1$H NMR (300 MHz, CDCl$_3$+CD$_3$OD) δ 7.21 (s, 1H), 7.08-7.02 (m, 2H), 4.43 (m, 1H), 3.01-2.76 (m, 5H), 2.48 (s, 2H), 2.19-2.12 (m, 2H), 1.96-1.87 (m, 2H), 0.90 (m, 9H); ESI MS m/z 201 [C$_{15}$H$_{20}$]$^+$.

C. Synthesis of Tetralone 4

Step 1: A solution of tetralone 3 (5.0 g, 22.21 mmol) in benzene (100 mL) containing ethylene glycol (5.0 mL, 88.8 mmol) and p-toluenesulfonic acid monohydrate (420 mg, 2.22 mmol) was heated at reflux in a Dean-Stark apparatus for 24 h. The reaction mixture was cooled to room temperature, concentrated under reduced pressure, and the resulting residue partitioned between ethyl acetate and water. The phases were separated and the organic phase was washed with saturated sodium chloride, dried (sodium sulfate), filtered, and concentrated under reduced pressure to yield the desired dioxolane (5.97 g, 99%) as a golden oil: $^1$H NMR (300 MHz, CDCl$_3$) δ 7.57 (d, J=2.0 Hz, 1H), 7.32 (dd, J=8.2, 2.0 Hz, 1H), 6.96 (d, J=8.2 Hz, 1H), 4.23-4.07 (m, 4H), 2.73-2.72 (m, 2H), 2.04-1.94 (m, 4H).

Step 2: A solution of the neo-pentylmagnesium bromide prepared above (60 mL) was added dropwise at room temperature over 20 min to a solution of zinc chloride (60 mL, 0.5 M in tetrahydrofuran, 30.0 mmol). Following Grignard addition, the reaction mixture was stirred for 0.5 h to yield a white heterogenous suspension. [1,1'-Bis(diphenylphosphino)ferrocene]dichloropalladium(II) complex with dichloromethane (1:1) (816 mg, 1.0 mmol) was added in one portion followed by dropwise addition of a solution of the dioxolane prepared in step 1 (2.69 g, 10.0 mmol) in tetrahydrofuran (10 mL) to yield a yellow reaction mixture, which was then heated at reflux for 1 h to yield a brown solution. The reaction mixture was cooled to room temperature and carefully quenched with 10% hydrochloric acid (100 mL) and the reaction mixture was stirred at room temperature overnight. The reaction mixture was diluted with diethyl ether and the phases separated. The organic phase was then washed with water, saturated sodium chloride, dried (sodium sulfate), filtered, and concentrated under reduced pressure to yield a black oil. Purification by flash column chromatography (silica, 19:1 hexanes/ethyl acetate) afforded compound (4) (2.17 g, 99%) as a yellow oil: IR (ATR) 3359, 2957, 1762, 1686, 1521, 1236, 1126, 1076, 1053, 1028 cm$^{-1}$; $^1$H NMR (3.00 MHz, CDCl$_3$) δ 7.79 (s, 1H), 7.26-7.22 (m, 1H), 7.15 (m, 1H), 2.96-2.92 (m, 2H), 2.67-2.62 (m, 2H), 2.50 (s, 2H), 2.17-2.08 (m, 2H), 0.89 (s, 9H); ESI MS m/z 217 [C$_{15}$H$_{20}$O+H]$^+$; HPLC: (Method D) >99% (AUC), t$_R$=13.30 min.

D. Synthesis of Compound (7)

Step 1: To a solution of 2b (0.22 g, 1.03 mmol) in 2-propanol (10 mL) was added Example 134 (0.31 g, 1.03 mmol) and the reaction mixture was heated to 50° C. for 17 h. The reaction mixture was cooled to room temperature, and the solvent removed under reduced pressure. The resulting residue was partitioned between methylene chloride (20 mL) and water (20 mL). The aqueous phase was extracted with methylene chloride (10 mL), the combined organic phase washed successively with 0.5 N hydrochloric acid (10 mL), saturated sodium bicarbonate (10 mL) and sodium chloride (10 mL), dried (sodium sulfate), filtered and concentrated under reduced pressure. The crude product was purified by flash chromatography (silica, 95:5 methylene chloride/methanol) to afford amino alcohol 5 (0.32 g, 60%) which was carried on without further characterization: ESI MS m/z 517 [$C_{30}H_{42}F_2N_2O_3$+H].

Step 2: To a solution of amino alcohol 5 (0.32 g, 0.61 mmol) in dioxane (5 mL) at room temperature was added hydrogen chloride (1.50 mL, 4 M solution in dioxane, 6.18 mmol) and the reaction mixture stirred for 17 h. The reaction mixture was concentrated under reduced pressure and the resulting residue triturated with diethyl ether to afford amine 6 (0.25 g, 85%) as a white solid, which was carried on without further purification or characterization: ESI MS m/z 417 [$C_{25}H_{36}Cl_2F_2N_2O$+H].

Step 3: To a suspension of sodium fluoroacetate (0.04 g, 0.82 mmol), N,N-diisopropylethylamine (0.23 mL, 1.41 mmol) and HBTU (0.17 g, 0.47 mmol) in methylene chloride (2 mL) was added a solution of amine 6 (0.23 g, 0.47 mmol) and N,N-diisopropylethylamine (0.15 mL, 0.94 mmol) in methylene chloride (2 mL) and the combined mixture was stirred at room temperature for 24 h. Water (20 mL) was added and the aqueous phase was extracted with additional methylene chloride (5 mL). The combined organic phase was washed successively with 0.5 N hydrochloric acid (10 mL) and saturated sodium chloride (10 mL), dried (sodium sulfate), filtered and concentrated under reduced pressure. Purification by preparative HPLC (Method B) afforded compound (7) (106 mg, 47%) as a white solid: IR (ATR) 3324, 2957, 1659, 1594 cm$^{-1}$; $^1$H NMR (300 MHz, CDCl$_3$) δ 7.29 (s, 1H), 7.12-6.95 (m, 2H), 6.82-6.55 (m, 4H), 4.93-4.83 (m, 1H), 4.81-4.67 (m, 1H), 4.27-4.18 (m, 1H), 3.75-3.74 (m, 1H), 3.57-3.52 (m, 1H), 3.10-3.04 (m, 1H), 2.94-2.67 (m, 5H), 2.48 (s, 2H), 1.98-1.75 (m, 4H), 1.60-1.40 (br s, 2H), 0.93 (s, 9H); ESI MS m/z 476 [$C_{27}H_{35}F_3N_2O_2$+H]; HPLC (Method C) >99% (AUC), $t_R$=8.60 min.

E. Synthesis of 5-Carboethoxy-2-iso-butylthiazole (14)

Step 1: A solution of ethyl formate (38 mL, 470 mmol) and ethyl chloroacetate (44 mL, 416 mmol) in diethyl ether (200 mL) was added to an ice-cold solution of potassium ethoxide (33.5 g, 400 mmol) in 1:2 ethyl alcohol/diethyl ether (300 mL). The resulting suspension was stirred overnight at room temperature. The solid was filtered, washed with diethyl ether and dissolved in water (200 mL). The solution was cooled in an ice bath and acidified to pH 4 with concentrated hydrochloric acid. The solution was extracted with diethyl ether and the organic layer washed with saturated sodium chloride, dried (sodium sulfate), filtered, and concentrated under reduced pressure to give formylchloroacetate (11, 24.2 g, 40%) as a yellow oil: $^1$H NMR (300 MHz, CDCl$_3$) δ 4.99-4.19 (m, 2H), 4.08 (s, 1H), 3.64-3.57 (m, 1H), 1.35-1.18 (m, 3H).

Step 2: Phosphorus pentasulfide (3.8 g, 10.9 mmol) was added in portions to a solution of isovaleramide (12, 10 g, 99 mmol) in diethyl ether (400 mL). The reaction mixture was stirred at room temperature for 2 h and then filtered. The filtrate was concentrated under reduced pressure to give isovalerothioamide (13, 11.60 g, quantitative) as a yellow oil: $^1$H NMR (300 MHz, DMSO-d$_6$) δ 9.34 (s, 1H), 9.12 (s, 1H), 2.33 (d, J=7.3 Hz, 2H), 2.17-2.12 (m, 1H), 0.86 (d, J=8.4 Hz, 6H).

Step 3: A solution of 13 (11.60 g, 98.97 mmol) and 11 (9.98 g, 66.31 mmol) in N,N-dimethylformamide (40 mL) was heated at 95° C. overnight. The reaction mixture was cooled to 0° C. and cold water (100 mL) added. The reaction mixture was adjusted to pH 8 by slow addition of solid sodium bicarbonate and extracted with diethyl ether. The organic layer was washed with water, saturated sodium chloride, dried (sodium sulfate), filtered, and concentrated under reduced pressure. Purification by flash column chromatography (silica, 90:10 hexanes/ethyl acetate) gave 5-carboethoxy-2-iso-butylthiazole (14, 4.53 g, 32%) as a yellow oil: $^1$H NMR (300 MHz, CDCl$_3$) δ 4.36 (q, J=7.2 Hz, 2H), 2.90 (d, J=7.2 Hz, 2H), 2.15 (m, 1H), 1.38 (t, J=7.2 Hz, 3H), 1.06 (d, J=6.7 Hz, 6H).

F. Synthesis of Compound (18)

Step 1: To an ice-cold solution of lithium aluminum hydride (18.7 mL, 1.0 M in tetrahydrofuran, 18.7 mmol) was added a solution of 14 (2.0 g, 9.37 mmol) in tetrahydrofuran (3 mL). The reaction mixture was stirred at 0° C. for 0.5 h and then overnight at room temperature. The reaction mixture was quenched by sequential addition of water (1 mL), 15% sodium hydroxide (1 mL) and water (1 mL). The resulting mixture was dried (sodium sulfate), filtered, and concentrated under reduced pressure to give the desired alcohol (1.43 g, 89%) as a light yellow oil: $^1$H NMR (300 MHz, CDCl$_3$) δ 7.48 (s, 1H), 4.81 (s, 2H), 2.83 (d, J=7.2 Hz, 2H), 2.71 (s, 1H), 2.10 (m, 1H), 0.98 (d, J=6.7 Hz, 6 Hz).

Step 2: To an ice-cold solution of the alcohol prepared in step 1 (1.3 g, 7.6 mmol) in methylene chloride (5 mL) was added thionyl chloride (5.53 mL, 76 mmol). The reaction mixture was stirred at room temperature for 1 h and evaporated under reduced pressure. The residue was neutralized by saturated sodium bicarbonate and then partitioned between water and methylene chloride. The organic layer was washed with saturated sodium chloride, triethylamine was added, and the resulting solution was dried (sodium sulfate), filtered, and concentrated under reduced pressure to give the desired chloride (1.15 g, 80%) as a yellow oil: $^1$H NMR (300 MHz, CDCl$_3$) δ 7.59 (s, 1H), 4.78 (s, 2H), 2.85 (d, J=7.2 Hz, 2H), 2.10 (m, 1H), 0.99 (d, J=6.7 Hz, 6H).

Step 3: To a solution of the chloride prepared in step 2 (1.15 g, 6.1 mmol) in dimethyl sulfoxide (5 mL) was added potassium cyanide (475 mg, 7.3 mmol). The reaction mixture was stirred at room temperature overnight and then partitioned between water and ethyl acetate. The organic layer was washed with saturated sodium chloride, dried (sodium sulfate), filtered, and concentrated under reduced pressure to give a black oil. Purification by flash column chromatography (silica, 66:34 hexanes/ethyl acetate) gave nitrile 15 (363 mg, 33%) as a yellow oil: $^1$H NMR (300 MHz, CDCl$_3$) δ 7.57 (s, 1H), 3.89 (s, 2H), 2.85 (d, J=7.2 Hz, 2H), 2.10 (m, 1H), 0.99 (d, J=6.6 Hz, 6H).

Step 4: To a mixture of 15 (367 mg, 2.04 mmol), 1-bromo-2-chloroethane (2.5 mL, 30.5 mmol), and benzyltriethylammonium chloride (14 mg, 0.06 mmol) at 50° C. was added a solution of 50% sodium hydroxide (3.6 mL). The reaction mixture was stirred at 50° C. for 1 h, cooled to room temperature and then partitioned between water and methylene chloride. The organic layer was washed with saturated sodium chloride, dried (sodium sulfate), filtered, and concentrated under reduced pressure to give a black oil. Purification by flash column chromatography (silica, 66:34 hexanes/ethyl acetate) gave the desired cyclopropylbenzylnitrile (260 mg, 62%) as a light yellow oil: $^1$H NMR (300 MHz, CDCl$_3$) δ 7.54 (s, 1H), 2.81 (d, J=7.2 Hz, 2H), 2.05 (m, 1H), 1.77 (m, 2H), 1.43 (m, 2H), 0.98 (d, J=6.6 Hz, 6H).

Step 5: To a solution of the nitrile prepared in step 4 (250 mg, 1.21 mmol) in 1:1 acetone/water (2 mL) was added potassium carbonate (17 mg, 0.12 mmol) and urea hydrogen peroxide (456 mg, 4.85 mmol). The reaction mixture was stirred at room temperature overnight. Acetone was evaporated under reduced pressure and the residue diluted with water. Desired amide 16 (270 mg, quantitative) was collected by filtration. This compound was used in the next step without further characterization.

Step 6: To an ice-cold solution of sodium hydroxide (228 mg, 5.7 mmol) in water (2.5 mL) was added bromine (94 µL, 1.84 mmol) dropwise. After stirring for 5 min at 0° C., amide 16 (336 mg, 1.5 mmol) was added in one portion. The reaction mixture was stirred at room temperature for 20 min and then heated at 75° C. for 5 h. The reaction mixture was diluted with water and extracted with methylene chloride. The organic layer was washed with saturated sodium chloride, dried (sodium sulfate), filtered, and concentrated under reduced pressure to give a yellow solid. Purification by flash column chromatography (silica, 95:5 methylene chloride/methanol) gave amine 17 (288 mg, 98%) as a light yellow solid: $^1$H NMR (300 MHz, CDCl$_3$) δ 7.35 (s, 1H), 2.79 (d, J=7.2 Hz, 2H), 2.08 (m, 1H), 1.13 (m, 1H), 1.06-0.97 (m, 8H).

Step 7: A solution of amine 17 (150 mg, 0.76 mmol) and Example 134 (206 mg, 0.68 mmol) in 2-propanol (5 mL) was heated at 70° C. overnight. The reaction mixture was cooled to room temperature and then partitioned between water and methylene chloride. The organic layer was washed with saturated sodium chloride, dried (sodium sulfate), filtered, and concentrated under reduced pressure. Purification by flash column chromatography (silica, 95:5 methylene chloride/methanol) gave the N-alkylated amine (108 mg, 32%) as a yellow solid: ESI MS m/z 496 [C$_{25}$H$_{35}$F$_2$N$_3$O$_3$S+H]$^+$.

Step 8: Hydrogen chloride (2.0 mL, 4 N in 1,4-dioxane, 8 mmol) was added at room temperature to a solution of the amine prepared in step 7 (108 mg, 0.22 mmol) in 1,4-dioxane (1 mL). The reaction mixture was stirred at room temperature for 3 h and then concentrated under reduced pressure to give 19 (103 mg, quantitative) as a yellow solid: ESI MS m/z 396 [C$_{20}$H$_{27}$F$_2$N$_3$OS+H]$^+$.

Step 9: To an ice-cold solution of 19 (103 mg, 0.22 mmol) and triethylamine (129 µL, 0.92 mmol) in methylene chloride (2 mL) was added 1-acetylimidazole (24 mg, 0.22 mmol). The reaction mixture was stirred at room temperature overnight and then partitioned between methylene chloride and water. The organic layer was washed with saturated sodium chloride, dried (sodium sulfate), filtered, and concentrated under reduced pressure. Purification by flash column chromatography (silica, 95:5 methylene chloride/methanol) gave compound (18) (51 mg, 54%) as an off-white solid: IR (ATR) 3330, 2960, 1647, 1595, 1529, 1458, 1112, 980 cm$^{-1}$; $^1$H NMR (300 MHz, CDCl$_3$) δ 7.34 (s, 1H), 6.74-6.63 (m, 3H), 5.52 (d, J=9.1 Hz, 1H), 4.08-4.10 (m, 1H), 3.43-3.41 (m, 1H), 2.98-2.96 (m, 1H), 2.98-2.70 (m, 5H), 2.10-2.00 (m, 1H), 1.89 (s, 3H), 1.06-0.96 (m, 10H); ESI MS m/z 438 [C$_{22}$H$_{29}$F$_2$N$_3$O$_2$S+H]$^+$; HPLC (Method E) 98.1% (AUC), t$_R$=11.45 min. Anal. Calcd for C$_{22}$H$_{29}$F$_2$N$_3$O$_2$S: C, 60.39; H, 6.68; N, 9.60. Found: C, 60.10; H, 6.73; N, 9.57.

G. Synthesis of Compound (47)

Step 1: To a stirred solution of neo-pentyl zinc bromide (20.93 mL, 0.5 M in diethyl ether, 10.47 mmol), prepared as describe previously, was added zinc chloride (20.93 mL, 0.5 M in diethyl ether, 10.47 mmol). The reaction mixture was stirred for 1 h then Pd(dppf)Cl$_2$ (285 mg, 0.349 mmol) was added. The reaction mixture was stirred for 5 min then bromide 44 (750 mg, 3.49 mmol) was added and the reaction mixture was stirred overnight. The reaction mixture was partitioned between ethyl acetate and saturated ammonium chloride. The organic layer was dried (sodium sulfate), filtered, and concentrated under reduced pressure. Purification by flash column chromatography (silica, 5:1 hexanes/ethyl acetate) gave alcohol 45 (590 mg, 74%) as a yellow oil: $^1$H NMR (300 MHz, CDCl$_3$) δ 7.31 (d, J=7.2 Hz, 1H), 7.25 (obs m, 2H), 6.98 (d, J=7.2 Hz, 1H), 2.51 (s, 2H), 1.58 (s, 6H), 0.90 (s, 9H).

Step 2: To an ice-cold solution of alcohol 45 (590 mg, 2.60 mmol) and sodium azide (338 mg, 5.20 mmol) in methylene chloride (12 mL) was added trifluoroacetic acid (2.37 g, 20.80 mmol) in methylene chloride (5 mL) over 1 h. The reaction mixture was treated with water (3 mL) followed by 1:1 water/concentrated ammonium hydroxide (6 mL) and then diluted with ethyl acetate. The organic layer was dried (sodium sulfate), filtered, and concentrated under reduced pressure. Purification by flash column chromatography (silica, 9:1 hexanes/ethyl acetate) gave an azide (420 mg, 70%) as a yellow oil: $^1$H NMR (300 MHz, CDCl$_3$) ☐ 7.27 (obs m, 2H), 7.21-6.98 (m, 2H), 2.53 (s, 2H), 1.63 (s, 6H), 0.91 (s, 9H).

Step 3: A mixture of azide from step 2 (420 mg, 1.82 mmol) and 10% Pd/C was shaken under an atmosphere of hydrogen for 5 h at 45 psi. The reaction mixture was filtered through diatomaceous earth and concentrated under reduced pressure to give amine 46 (340 mg, 91%) as a yellow oil. This amine was used without any further purification or characterization.

Step 4: A mixture of amine 46 (340 mg, 1.66 mmol) and Example 134 (496 mg, 1.66 mmol) was heated to 60° C. overnight. The reaction mixture was cooled to room temperature and concentrated under reduced pressure. Purification by flash column chromatography (silica, 97:3:1 methylene chloride/methanol/concentrated ammonium hydroxide) gave an amine (350 mg, 42%) as a white foam: $^1$H NMR (300 MHz, CDCl$_3$) δ 7.24-7.11 (m, 4H), 6.85-6.79 (m, 3H), 4.52 (m, 1H), 3.74 (m, 1H), 3.36 (m, 1H), 2.84 (m, 1H), 2.48 (m, 3H), 1.82 (m, 1H), 1.53 (s, 5H), 1.36 (s, 9H), 0.91 (d, J=7.2 Hz, 9H).

Step 5: To a stirred solution of the amine from step 4 (350 mg, 0.694 mmol) in dioxane (3 mL) was added hydrochloric acid (0.69 mL, 4 N in dioxane, 2.78 mmol). The reaction mixture was stirred for 72 h and then concentrated under reduced pressure to give the hydrochloride salt (370 mg, quantitative), which was used without any further purification or characterization.

Step 6: To a stirred mixture of the salt from step 5 (150 mg, 0.32 mmol) and triethylamine (144 mg, 1.43 mmol) in methylene chloride (5 mL) was added 1-acetylimidazole (35 mg, 0.32 mmol). The reaction mixture was stirred overnight and then partitioned between methylene chloride and water. The organic layer was dried (sodium sulfate), filtered, and concentrated under reduced pressure. Purification by flash column chromatography (silica, 9.5:1:1 methylene chloride/methanol/concentrated ammonium hydroxide) gave a white solid. The solid was dissolved in methanol (1 mL) and hydrochloric acid (1 mL, 1 N in diethyl ether, 1 mmol) was added. The resulting solution was concentrated under reduced pressure to provide ALB 16810 (47, 80 mg, 52%) as a white solid: IR (ATR) 3253, 2953, 1725, 1622 cm$^{-1}$; $^1$H NMR (300 MHz, DMSO-d$_6$) δ 9.35 (br s, 1H), 9.01 (br s, 1H), 7.92 (d, J=7.4 Hz, 1H), 7.39-7.29 (m, 3H), 7.17 (d, J=7.4 Hz, 1H), 7.01-6.97 (m, 1H), 6.91-6.84 (m, 2H), 5.82 (d, J=5.9 Hz, 1H), 3.82-3.67 (m, 2H), 2.98 (m, 1H), 2.65 (m, 1H), 2.49 (d, J=7.2 Hz, 2H), 2.48 (m, 2H), 1.87 (m, 1H), 1.74 (s, 6H), 1.61 (s, 3H), 0.86 (s, 9H); ESI MS m/z 447 [C$_{26}$H$_{36}$F$_2$N$_2$O$_2$+H]$^+$; HPLC (Method B) >99% (AUC), t$_R$=8.92 min.

H. Synthesis of Compound (158)

Step 1: To an ice-cold, stirred solution of ester 155 (4.64 g, 21.57 mmol) in tetrahydrofuran (100 mL) was added methylmagnesium bromide (25.16 mL, 3.0 M solution in diethyl ether, 75.48 mmol). The reaction mixture was warmed to room temperature and stirred overnight. The reaction mixture was quenched by the addition of saturated ammonium chloride and diluted with diethyl ether. The organic layer was dried (sodium sulfate), filtered, and concentrated under reduced pressure. Purification by flash column chromatography (silica, 6:1 hexanes/ethyl acetate) gave an alcohol (3.72 g, 90%) as a clear oil: $^1$H NMR (300 MHz, CDCl$_3$) δ 7.67 (s, 1H), 7.38 (d, J=8.7 Hz, 2H), 7.21 (m, 1H), 1.57 (s, 6H).

Step 2: A mixture of the alcohol from step 1 (1.68 g, 7.82 mmol), 2-methylpropylboronic acid (1.19 g, 11.73 mmol), and sodium carbonate (13.69 mL, 2 M aq, 27.38 mmol) was degassed with nitrogen for 20 min. Tetrakis(triphenylphosphine)palladium(0) (450 mg, 0.391 mmol) was added and the reaction mixture was heated at reflux overnight. The reaction mixture was cooled to room temperature, filtered through diatomaceous earth, and concentrated under reduced pressure. Purification by flash column chromatography (silica, 4:1 hexanes/ethyl acetate) gave alcohol 156 (1.11 g, 74%) as a clear oil: $^1$H NMR (300 MHz, CDCl$_3$) δ 7.28-7.24 (m, 3H), 7.11 (d, J=7.2 Hz, 1H), 2.48 (d, J=6.1 Hz, 2H), 1.84 (m, 1H), 1.58 (s, 6H), 0.92 (d, J=7.1 Hz, 3H).

Step 3: To an ice-cold, stirred solution of alcohol 156 (360 mg, 1.87 mol) and sodium azide (244 mg, 3.75 mmol) in methylene chloride (10 mL) was added trifluoroacetic acid (1.71 g, 14.96 mmol) in methylene chloride (3 mL) dropwise over 1 h. The reaction mixture was treated with water (2 mL) and 1:1 concentrated ammonium hydroxide/water (4 mL) after 1 h. The reaction mixture was diluted with diethyl ether, the organic layer was dried (sodium sulfate), filtered, and concentrated under reduced pressure. Purification by flash column chromatography (silica, hexanes) gave an azide (340 mg, 84%) as a clear oil: $^1$H NMR (300 MHz, CDCl$_3$) δ 7.28-7.24 (m, 4H), 2.50 (d, J=6.1 Hz, 2H), 1.84 (m, 1H), 1.63 (s, 6H), 0.92 (d, J=7.1 Hz, 3H).

Step 4: A mixture of the azide from step 3 (340 mg, 1.57 mmol) and 10% Pd/C was shaken under an atmosphere of hydrogen for 2 h at 50 psi. The reaction mixture was filtered through diatomaceous earth and concentrated under reduced pressure to give amine 157 (300 mg, quantitative) as a yellow oil: $^1$H NMR (300 MHz, CDCl$_3$) δ 7.28-7.24 (m, 4H), 2.49 (d, J=6.1 Hz, 2H), 1.84 (m, 1H), 1.58 (s, 6H), 0.92 (d, J=7.1 Hz, 3H).

Step 5: A mixture of amine 157 (150 mg, 0.79 mmol) and Example 134 (215 mg, 0.79 mmol) in 2-propanol (5 mL) was heated at reflux overnight. The reaction mixture was cooled to room temperature and concentrated under reduced pressure. The crude residue was partitioned between methylene chloride and 1 N hydrochloric acid. The organic layer was dried (sodium sulfate), filtered, and concentrated under reduced pressure. Purification by flash column chromatography (8:1 methylene chloride/methanol) gave an alcohol (144 mg, 37%) as a white foam: $^1$H NMR (300 MHz, CDCl$_3$) δ 7.27-7.11 (m, 4H), 6.89-6.77 (m, 3H), 4.55 (m, 1H), 3.78 (m, 1H), 3.36 (m, 1H), 2.84 (m, 1H), 2.48 (m, 3H), 1.82 (m, 1H), 1.53 (s, 5H), 1.36 (s, 9H), 0.91 (d, J=7.2 Hz, 3H).

Step 6: A mixture of the alcohol from step 5 (144 mg, 0.29 mmol) and hydrochloric acid (2.20 mL, 4 N solution in dioxane, 8.81 mmol) in dioxane (1 mL) was stirred overnight. The reaction mixture was concentrated under reduced pressure to give a dihydrochloride salt (136 mg, quantitative) as a white foam: $^1$H NMR (300 MHz, DMSO-d$_6$) δ 9.91 (br s, 1H), 9.36 (br s, 1H), 8.11 (br s, 4H), 7.54-6.98 (m, 7H), 6.28 (m, 1H), 4.12 (br s, 1H), 3.10-2.74 (m, 4H), 2.47 (d, J=6.8 Hz, 2H), 1.91 (m, 1H), 1.72 (s, 6H), 0.87 (d, J=7.1 Hz, 6H).

Step 7: To a stirred mixture of the salt from step 6 (136 mg, 0.29 mmol) and triethylamine (135 mg, 1.33 mmol) in methylene chloride (5 mL) was added 1-acetylimidazole (33 mg, 0.29 mmol). The reaction mixture was stirred overnight and then partitioned between methylene chloride and water. The organic layer was dried (sodium sulfate), filtered, and concentrated under reduced pressure. Purification by flash column chromatography (silica, 9.5:1:1 methylene chloride/methanol/concentrated ammonium hydroxide) gave a white solid. The solid was dissolved in methanol (1 mL) and hydrochloric acid (1 mL, 1 N in diethyl ether, 1 mmol) was added. The resulting solution was concentrated under reduced pressure to provide compound (158) (85 mg, 61%) as a white solid: $^1$H NMR (300 MHz, DMSO-d$_6$) δ 9.45 (br s, 1H), 9.03 (br s, 1H), 7.95 (d, J=7.4 Hz, 1H), 7.41-7.35 (m, 3H), 7.19 (d, J=7.4 Hz, 1H), 7.01-6.97 (m, 1H), 6.91-6.84 (m, 2H), 5.82 (d, J=5.9 Hz, 1H), 3.82-3.67 (m, 2H), 2.98 (m, 1H), 2.65 (m, 1H), 2.49 (d, J=7.2 Hz, 2H), 2.48 (m, 2H), 1.87 (m, 1H), 1.74 (s, 6H), 1.61 (s, 3H), 0.86 (d, J=6.5 Hz, 3H); ESI MS m/z 433 [C$_{25}$H$_{344}$F$_2$N$_2$O$_2$+H]$^+$; HPLC (Method A)>99% (AUC), t$_R$=10.45 min.

EXAMPLE 115

The invention further comprises indole and fluorene compounds, such as the compounds contained in Tables YY and ZZ.

TABLE 115.YY (Fluorenes)

| Example No. | Compound | MS DATA |
|---|---|---|
| YY1 | N—{(1S,2R)-1-(3,5-difluorobenzyl)-3-[(2-ethyl-7-fluoro-9H-fluoren-9-yl)amino]-2-hydroxypropyl}acetamide | C$_{27}$H$_{27}$F$_3$N$_2$O$_2$ + H$^+$ requires 547, found 547 |
| YY2 | N—{(1S,2R)-1-(3,5-difluorobenzyl)-2-hydroxy-3-[(2-isobutyl-9H-fluoren-9-yl)amino]propyl}acetamide | C$_{29}$H$_{32}$F$_2$N$_2$O$_2$ + H$^+$ requires 479, found 479 |
| YY3 | N—[(1S,2R)-3-[(2-bromo-9-methyl-9H-fluoren-9-yl)amino]-1-(3,5-difluorobenzyl)-2-hydroxypropyl]acetamide | C$_{26}$H$_{25}$BrF$_2$N$_2$O$_2$ + H$^+$ requires 557, found 557 |
| YY4 | N—((1S,2R)-1-(3,5-difluorobenzyl)-3-{[2-(1-ethylpropyl)-9H-fluoren-9-yl]amino}-2-hydroxypropyl)acetamide | C$_{30}$H$_{34}$F$_2$N$_2$O$_2$ + H$^+$ requires 491, found 491 |

TABLE 115.YY-continued (Fluorenes)

| Example No. | Compound | MS DATA |
|---|---|---|
| YY5 | N—[(1S,2R)-3-[(2-cyclopentyl-9H-fluoren-9-yl)amino]-1-(3,5-difluorobenzyl)-2-hydroxypropyl]acetamide | $C_{30}H_{32}F_2N_2O_2 + H^+$ requires 493, found 493 |
| YY6 | N—{(1S,2R)-1-(3,5-difluorobenzyl)-3-[2-ethyl-9-methyl-9H-fluoren-9-yl)amino]-2-hydroxypropyl}acetamide | $C_{28}H_{30}F_2N_2O_2 + H^+$ requires 465, found 465 |
| YY7 | N—[(1S,2R)-3-[(2-cyclohexyl-9H-fluoren-9-yl)amino]-1-(3,5-difluorobenzyl)-2-hydroxypropyl]acetamide | $C_{31}H_{34}F_2N_2O_2 + H^+$ requires 505, found 505 |
| YY8 | N—((1S,2R)-1-(3,5-difluorobenzyl)-3-{[2-(dimethylamino)-9H-fluoren-9-yl]amino}-2-hydroxypropyl)acetamide | $C_{27}H_{29}F_2N_3O_2 + H^+$ requires 466, found 466 |
| YY9 | N—{(1S,2R)-1-(3,5-difluorobenzyl)-3-[(2-ethyl-6-fluoro-9H-fluoren-9-yl)amino]-2-hydroxypropyl}acetamide | $C_{27}H_{27}F_3N_2O_2 + H^+$ requires 467, found 467 |
| YY10 | N—((1S,2R)-1-(3,5-difluorobenzyl)-2-hydroxy-3-{[2-(methoxymethyl)-9H-fluoren-9-yl]amino}propyl)acetamide. | $C_{27}H_{28}F_2N_2O_3 + H^+$ requires 469, found 469 |
| YY11 | N—((1S,2R)-1-(3,5-difluorobenzyl)-3-{[2-ethyl-5-(trifluoromethyl)-9H-fluoren-9-yl]amino}-2-hydroxypropyl)acetamide | $C_{28}H_{27}F_5N_2O_2 + H^+$ requires 519, found 519 |
| YY12 | N—((1S,2R)-1-(3,5-difluorobenzyl)-2-hydroxy-3-{[2-(3-methylbutyl)-9H-fluoren-9-yl]amino}propyl)acetamide | $C_{30}H_{34}F_2N_2O_2 + H^+$ requires 493, found 493 |
| YY13 | N—{(1S,2R)-1-(3,5-difluorobenzyl)-2-hydroxy-3-[(2-isopropyl-9H-fluoren-9-yl)amino]propyl}acetamide | $C_{28}H_{30}F_2N_2O_2 + H^+$ requires 465, found 465, |
| YY14 | N—{(1S,2R)-1-(3,5-difluorobenzyl)-2-hydroxy-3-[(2-neopentyl-9H-fluoren-9-yl)amino]propyl}acetamide. | $C_{30}H_{34}F_2N_2O_2 + H^+$ requires 493, found 493 |
| YY15 | N—{(1S,2R)-1-(3,5-difluorobenzyl)-2-hydroxy-3-[(2-isopropenyl-9H-fluoren-9-yl)amino]propyl}acetamide | $C_{28}H_{28}F_2N_2O_2 + H^+$ requires 463, found 463 |
| YY16 | N—((1S,2R)-1-(3,5-difluorobenzyl)-2-hydroxy-3-{[2-(isopropylamino)-9H-fluoren-9-yl]amino}propyl)acetamide | $C_{28}H_{31}F_2N_3O_2 + H^+$ requires 480, found 480 |
| YY17 | N—[(1S,2R)-3-[(2-chloro-7-ethyl-9H-fluoren-9-yl)amino]-1-(3,5-difluorobenzyl)-2-hydroxypropyl]acetamide | $C_{27}H_{27}ClF_2N_2O_2 + H^+$ requires 543, found 543 |
| YY18 | N—[(1S,2R)-3-{[2-(tert-butylamino)-9H-fluoren-9-yl]amino}-1-(3,5-difluorobenzyl)-2-hydroxypropyl]acetamide | $C_{29}H_{33}F_2N_3O_2 + H^+$ requires 494, found 494. |
| YY19 | N—[(1S,2R)-3-{[2-(tert-butylamino)-9H-fluoren-9-yl]amino}-1-(3,5-difluorobenzyl)-2-hydroxypropyl]acetamide | $C_{29}H_{33}F_2N_3O_2 + H^+$ requires 494, found 494 |
| YY20 | N—[(1S,2R)-3-{[2-(tert-butylamino)-9H-fluoren-9-yl]amino}-1-(3,5-difluorobenzyl)-2-hydroxypropyl]acetamide | $C_{29}H_{33}F_2N_3O_2 + H^+$ requires 494, found 494 |
| YY21 | N—{(1S,2R)-1-(3,5-difluorobenzyl)-2-hydroxy-3-[(2-morpholin-4-yl-9H-fluoren-9-yl)amino]propyl}acetamide | $C_{29}H_{31}F_2N_3O_3 + H^+$ requires 508, found 508 |
| YY22 | N—((1S,2R)-1-(3,5-difluorobenzyl)-2-hydroxy-3-{[2-(neopentylamino)-9H-fluoren-9-yl]amino}propyl)acetamide | $C_{30}H_{35}F_2N_3O_2 + H^+$ requires 508, found 508 |

TABLE 115.ZZ (Indoles)

| Ex. No. | Compound | MS Data |
|---|---|---|
| ZZ1 | N—[(1S,2R)-3-{[(5-bromo-2,3-dihydro-1H-indol-7-yl)methyl]amino}-1-(3,5-difluorobenzyl)-2-hydroxypropyl]acetamide | $C_{21}H_{24}BrF_2N_3O_2 + H^+$ requires 468, found 468 |
| ZZ2 | N—{(1S,2R)-3-{[(5-bromo-1-ethyl-2,3-dihydro-1H-indol-7-yl)methyl]amino}-1-(3,5-difluorobenzyl)-2-hydroxypropyl]acetamide | $C_{23}H_{28}BrF_2N_3O_2 + H^+$ requires 498, found 498 |
| ZZ3 | N—[(1S,2R)-3-{[(1,5-diethyl-2,3-dihydro-1H-indol-7-yl)methyl]amino}-1-(3,5-difluorobenzyl)-2-hydroxypropyl]acetamide | $C_{25}H_{33}F_2N_3O_2 + H^+$ requires 446, found 446 |
| ZZ4 | N—[(1S,2R)-3-{[(1-benzyl-5-isobutyl-2,3-dihydro-1H-indol-7-yl)methyl]amino}-1-(3,5-difluorobenzyl)-2-hydroxypropyl]acetamide | $C_{32}H_{39}F_2N_3O_2 + H^+$ requires 536, found 536 |
| ZZ5 | N—((1S,2R)-1-(3,5-difluorobenzyl)-2-hydroxy-3-{[(5-isobutyl-2,3-dihydro-1H-indol-7-yl)methyl]amino}propyl)acetamide | $C_{25}H_{33}F_2N_3O_2 + H^+$ requires 446, found 446 |
| ZZ6 | N—((1S,2R)-1-(3,5-difluorobenzyl)-2-hydroxy-3-{[(5-isobutyl-1-propyl-2,3-dihydro-1H-indol-7-yl)methyl]amino}propyl)acetamide | $C_{28}H_{39}F_2N_3O_2 + H^+$ requires 488, found 488 |
| ZZ7 | N—[(1S,2R)-3-{[(1-butyl-5-isobutyl-2,3-dihydro-1H-indol-7-yl)methyl]amino}-1-(3,5-difluorobenzyl)-2-hydroxypropyl]acetamide | $C_{29}H_{41}F_2N_3O_2 + H^+$ requires 502, found 502 |
| ZZ8 | N—((1S,2R)-1-(3,5-difluorobenzyl)-2-hydroxy-3-{[(5-isobutyl-1-isopropyl-2,3-dihydro-1H-indol-7-yl)methyl]amino}propyl)acetamide | $C_{28}H_{39}F_2N_3O_2 + H^+$ requires 488, found 488 |
| ZZ9 | N—[(1S,2R)-3-{[(1-allyl-5-isobutyl-2,3-dihydro-1H-indol-7-yl)methyl]amino}-1-(3,5-difluorobenzyl)-2-hydroxypropyl]acetamide | $C_{28}H_{37}F_2N_3O_2 + H^+$ requires 486, found 486 |
| ZZ10 | N—[(1S,2R)-3-{[(1-benzyl-5-isobutyl-1H-indol-7-yl)methyl]amino}-1-(3,5-difluorobenzyl)-2-hydroxypropyl]acetamide | $C_{32}H_{37}F_2N_3O_2 + H^+$ requires 534, found 534 |
| ZZ11 | N—((1S,2R)-1-(3,5-difluorobenzyl)-2-hydroxy-3-{[(5-isobutyl-1H-indol-7-yl)methyl]amino}propyl)acetamide | $C_{25}H_{31}F_2N_3O_2 + H^+$ requires 444, found 444 |
| ZZ12 | N—((1S,2R)-1-(3,5-difluorobenzyl)-2-hydroxy-3-{[(5-isobutyl-1-propyl-1H-indol-7-yl)methyl]amino}propyl)acetamide | $C_{28}H_{37}F_2N_3O_2 + H^+$ requires 486, found 486 |
| ZZ13 | N—[(1S,2R)-3-{[(1-butyl-5-isobutyl-1H-indol-7-yl)methyl]amino}-1-(3,5-difluorobenzyl)-2-hydroxypropyl]acetamide | $C_{29}H_{39}F_2N_3O_2 + H^+$ requires 500, found 500 |

EXAMPLES 116-118

The general Scheme below can be used to synthesize the compounds disclosed and described in Examples 116-118 and is not limiting to the scope of the invention.

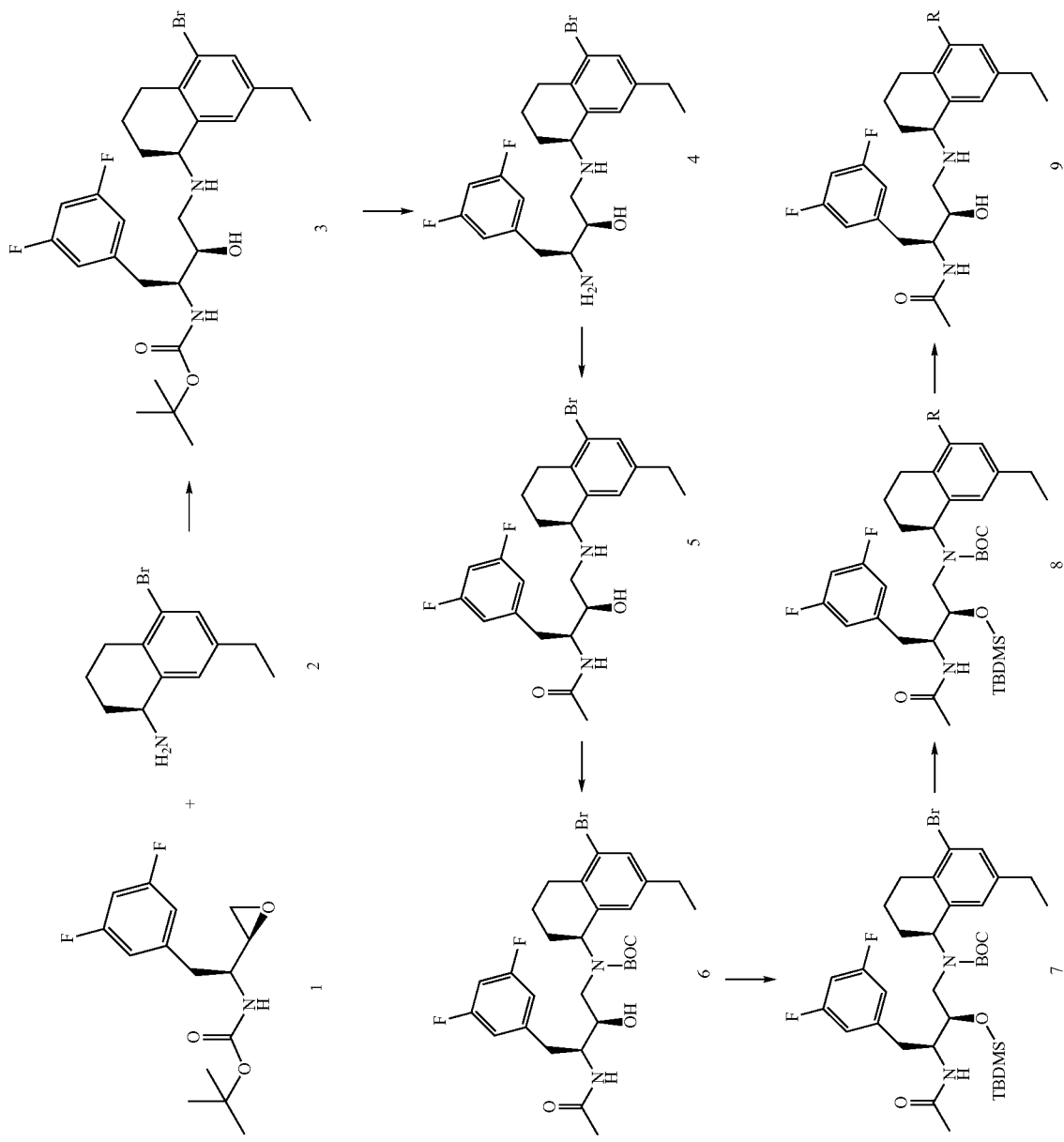

EXAMPLE 116

Synthesis of N-[(1S, 2R)-3-((1S)-5-Butyl-7-ethyl-1,2,3,4-tetrahydro-naphthalen-1-ylamino)-1-(3,5-difluorobenzyl)-2-hydroxy-propyl]-acetamide

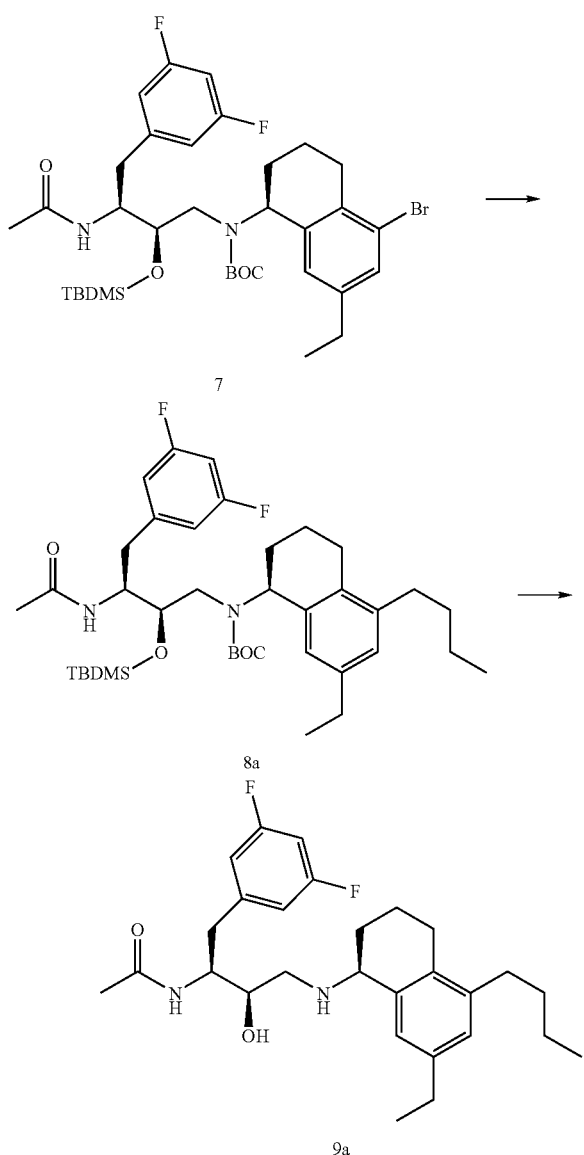

A. Preparation of [(1S, 2R)-3-((1S)-5-Bromo-7-ethyl-1,2,3,4-tetrahydro-naphthalen-1-ylamino)-1-(3,5-difluoro-benzyl)-2-hydroxypropyl]-carbamic acid tert-butyl ester 3

A solution of N—BOC-epoxide 1 (869 mg, 2.91 mmol) and the bromo-substituted 1-amino-tetrahydronapthalene 2 (783 mg, 2.91 mmol) in 10 mL isopropanol, is heated to 80° C. for 6 hours. After completion of the reaction, the mixture is cooled and product 3 crystallizes from the crude solution, and collected by filtration. The crystals are washed with cold ethanol. After vacuum is applied to remove traces of volatiles, the reaction yields about 995 mg of 3 ([M+H]$^+$=552.8).

B. Preparation of (3S, 2R)-3-Amino-1-((1S)-5-bromo-7-ethyl-1,2,3,4-tetrahydro-naphthalen-1-ylamino)-4-(3,5-difluoro-phenyl)-butan-2-ol 4

Compound 3 (995 mg) is dissolved in 10 mL of anhydrous CH$_2$Cl$_2$ followed by the addition of 10 mL of trifluoroacetic acid (anhydrous). The solution stands for 90 min. then the volatiles are removed with a stream of nitrogen. The compound is desalted by extraction between ethyl acetate, 10 mL, and saturated aqueous sodium bicarbonate, 20 mL. The ethyl acetate phase is washed a second time with saturated sodium bicarbonate. The organic phase is then dried with MgSO$_4$ (anhydrous), filtered, and evaporated of volatiles yielding 865 mg of 4 ([M+H]$^+$=452.8).

C. Preparation of N-[(1S, 2R)-3-((1S)-5-Bromo-7-ethyl-1,2,3,4-tetrahydro-naphthalen-1-ylamino)-1-(3,5-difluorobenzyl)-2-hydroxypropyl]-acetamide 5

To a solution of diamine 4 (350 mg, 0.77 mmol) in 5 mL anhydrous CH$_2$Cl$_2$, is added HOBt (125 mg, 0.93 mmol), N-methyl-morpholine (0.17 mL, 1.55 mmol), and glacial acetic acid (46.4 mg, 0.773).

This solution is cooled to 0° C. via ice bath and then solid EDC-HCl (1-[3-(Dimethylamino)propyl]-3-ethylcarbodiimide hydrochloride, 163 mg, 0.85 mmol) and a stir bar was added. The reaction is stirred at 0° C. for 12 hours. After the warming to room temperature, the solvent is removed with a stream of N$_2$, and the residue washed between ethyl acetate and aqueous saturated sodium bicarbonate. The ethyl acetate phase is dried with MgSO$_4$ (anhydrous), filtered then removed of solvent by rotory evaporation and high vacuum to yield 295 mg of compound 5 ([M+H]$^+$=494.8).

D. Preparation of [(3S, 2R)-3-Acetylamino-4-(3,5-difluorophenyl)-2-hydroxybutyl]-((1S)-5-bromo-7-ethyl-1,2,3,4-tetrahydronaphthalen-1-yl)-carbamic acid tert-butyl ester 6

To a solution of amine 5 (295 mg, 0.6 mmol) in 5 mL anhydrous THF is added N,N'-diisopropylethylamine (0.35 mL, 1.2 mmol) and di-t-butyl dicarbonate (145 mg, 0.66 mmol). The solution is stirred overnight followed by solvent removal with stream of nitrogen. The product is isolated by first washing the residue between ethyl acetate (10 mL) and 1N sodium bisulfate (20 mL). The ethyl acetate layer was then washed against aqueous saturated sodium bicarbonate (20 mL). The ethyl acetate layer was dried with MgSO$_4$ (anhydrous), filtered then removed of solvent by rotory evaporation and high vacuum to yield 354.4 mg of 6 ([M+H]$^+$=594.5).

E. Preparation of [(1s, 2R)-3-Acetylamino-2-(tert-butyl-dimethyl-silanyloxy)-4-(3,5-difluorophenyl)-butyl]-((1S)-5-bromo-7-ethyl-1,2,3,4-tetrahydro-naphthalen-1-yl)-carbamic acid tert-butyl ester 7

To a solution of t-butyldimethylsilyl chloride (105 mg, 0.66 mmol) and imidazole (102 mg, 1.5 mmol) in anhydrous dimethylformamide (3 mL) is added 6 (354 mg, 0.6 mmol) and the solution allowed to stir at room temperature for 16 hrs. The DMF is removed via rotory evaporation. The resulting residue is dissolved in ethyl acetate and washed against 1N soduim bisulfate and then saturated aqueous sodium bicarbonate. The ethyl acetate phase is dried with solid MgSO$_4$, filtered, and evaporated of volatiles via rotory evaporation and high vacuum. The product 7 gave M+H=731.2, and was used in palladium-catalysed couplings without further purification.

F. Preparation of [(1S, 2R)-3-Acetylamino-2-(tert-butyldimethylsilanyloxy)-4-(3,5-difluorophenyl)-butyl]-((1S)-5-butyl-7-ethyl-1,2,3,4-tetrahydro-naphthalen-1-yl)-carbamic acid tert-butyl ester 8a The following process is performed in a nitrogen-filled glove box. To a solution of 7 (73 mg, 0.1 mmol) in 0.1 mL of anhydrous THF is added a solution of Pd(OAc)$_2$ (2.25 mg, 0.01 mmol) and 2-(di-t-butylphosphino)biphenyl (5.9 mg, 0.01 mmol) in 0.1 mL of anhydrous THF. The reaction is started by addition of butylzinc bromide (0.5M in THF, 0.5 mL, 0.25 mmol). The reaction is stirred for 16 hrs, after which the solvent is removed with a stream of nitrogen, and the residue is redissolved in methanol (1 mL) for purification by reversed phase HPLC. The butylated product 8a ([M+H]$^+$ =709.1) is obtained as an oil after evaporation of solvent (rotory evaporation and high vacuum).

G. Preparation of N-[(1S, 2R)-3-((1S)-5-Butyl-7-ethyl-1,2,3,4-tetrahydro-naphthalen-1-ylamino)-1-(3,5-difluorobenzyl)-2-hydroxypropyl]-acetamide 9a To a solution of 8a in 1 mL of CH$_2$Cl$_2$ is added 1 mL of anhydrous trifluoroacetic acid. After 1 hr, the volatiles are removed with a stream of N$_2$ followed by high vacuum to yield 9a ([M+H]$^+$=472.8).

EXAMPLE 117

General Procedure for the Preparation of Compounds 9

Compounds 8 were prepared from compounds 7 according to the procedure for preparing 8a (G above), except that the butylzinc bromide used in the preparation of 8a was replaced with other zinc reagents as noted in Table 117.A. The protecting groups were removed from the intermediate compounds 8 as described for the preparation of 9a from 8a.

TABLE 117.A

| Compound | Reagent | m/z (M + H)$^+$ |
|---|---|---|
| N—[(1S,2R)-3-((1S)-5,7-Diethyl-1,2,3,4-tetrahydronaphthalen-1-ylamino)-1-(3,5-difluorobenzyl)-2-hydroxypropyl]-acetamide | Et$_2$Zn (Diethylzinc) | 444.8 |
| N—[1-((1S,2R)-3,5-Difluorobenzyl)-3-((1S)-7-ethyl-5-propyl-1,2,3,4-tetrahydro-naphthalen-1-ylamino)-2-hydroxypropyl]-acetamide | PrZnBr (Propylzinc bromide) | 458.8 |
| N—[(1S,2R)-1-(3,5-Difluorobenzyl)-3-((1S)-7-ethyl-5-isobutyl-1,2,3,4-tetrahydronaphthalen-1-ylamino)-2-hydroxypropyl]-acetamide | i-BuZnBr (Isobutylzinc Bromide) | 472.8 |

EXAMPLE 118

General scheme 118 represents a synthetic route that can be used to synthesize Compound 15.

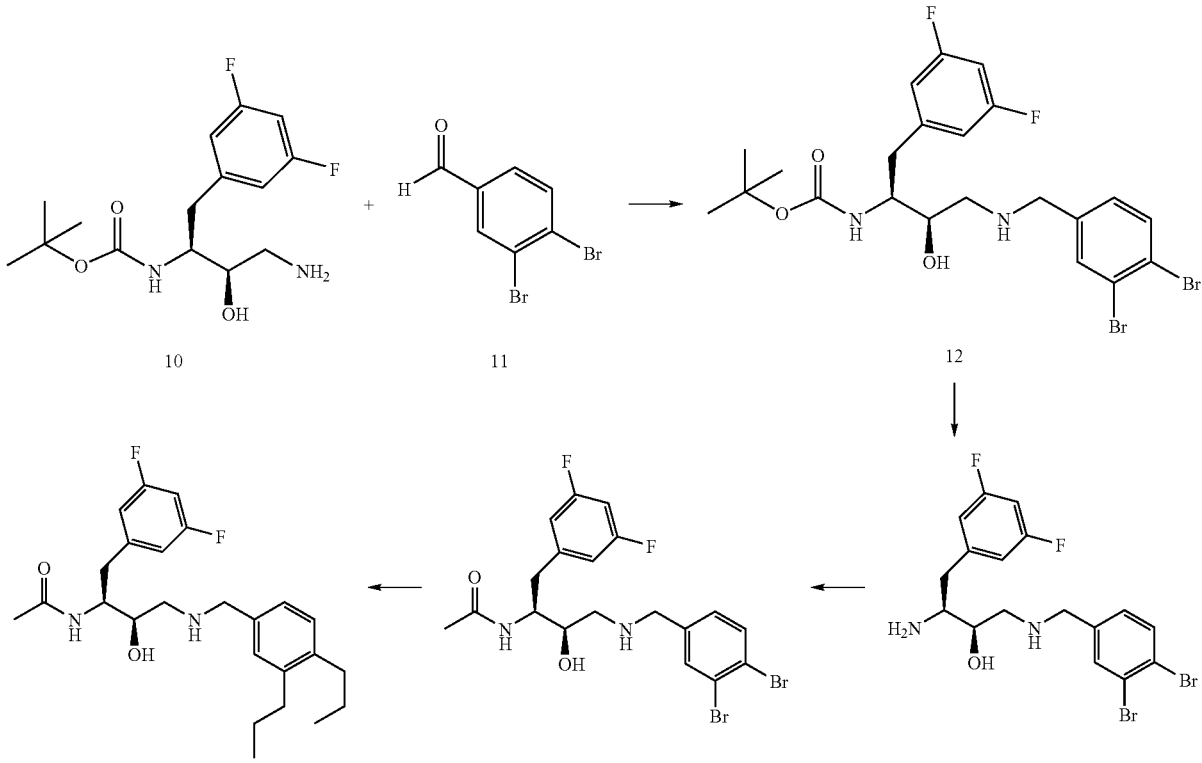

Scheme 118

A. Preparation of [(1S,2R)-3-(3,4-Dibromobenzylamino)-1-(3,5-difluorobenzyl)-2-hydroxypropyl] carbamic acid tert-butyl ester 12

Commercially available 3,4-dibromobenzaldehyde (250 mg, 0.95 mmol) and N-BOC-diamine 10 (250 mg, 0.79 mmol), are dissolved together in 10 mL of 10% acetic acid in THF. After the solution was allowed to stand at room temperature for 30 min., 1.7 g (~3.8 mmol) of MP-cyanoborohydride (a macroporous triethylammonium methylpolystyrene cyanoborohydride, Argonaut Corporation) is added. The suspension is agitated for 3 h. using an orbit shaker (J-Kem), after which the suspension is filtered, and the solvent is removed by rotory evaporation. The residue is dissolved in methanol and divided into 10 aliquots for fractionation by reversed phase HPLC. Fractions containing pure compound 12 are combined and stripped of volatiles by rotory evaporation and/or vacuum application. Mass spectrometry of the final product 12 gave [M+H]+=564.7.

B. Preparation of (3S,2R)-3-Amino-1-(3,4-dibromobenzylamino)-4-(3,5-difluorophenyl)-butan-2-ol 13

Compound 13 was be prepared from compound 12 using the procedure described above for the preparation of 4 from 3. Mass spectral analysis gave m/z=464.8.

C. Preparation of N-[(1S,2R)-3-(3,4-Dibromobenzylamino)-1-(3,5-difluorobenzyl)-2-hydroxy-propyl]-acetamide 14

Compound 14 was prepared from compound 13 using the procedure described above for the preparation of 5 from 4. Mass spectral analysis gave m/z=506.8

D. Preparation of N-[(1S,2R)-1-(3,5-Difluorobenzyl)-3-(3,4-dipropylbenzylamino)-2-hydroxypropyl]-acetamide 15

Preparation of 15 from 14 was performed using the procedure described above for the preparation of 8a from 7 except that propylzinc bromide is used instead of the butylzinc bromide. Mass spectral analysis of the product 13 gave [M+H]+= 432.9).

EXAMPLE 119

The compounds of the invention that comprise cyclohexyl moieties can be synthesized according the following general Scheme 119.

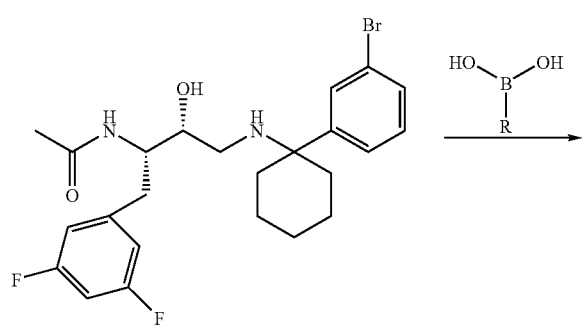

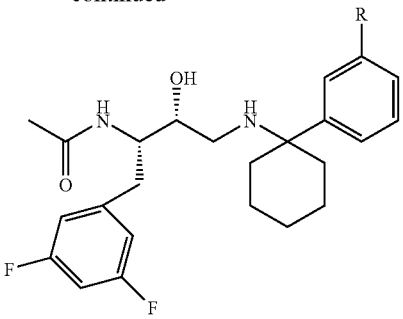

A. N-(1S, 2R)-(1-(3,5-Difluoro-benzyl)-2-hydroxy-3-{1-[3-(4-methyl-thiophen-2-yl)-phenyl]-cyclohexylamino}-propyl)-acetamide

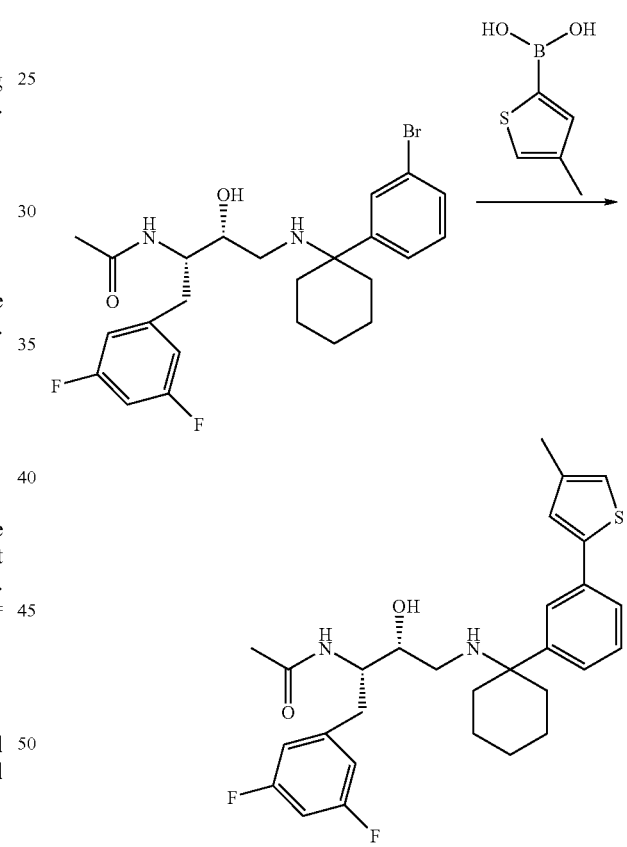

Palladium acetate (Pd(OAc)₂) (0.82 mgs, 10 mol. Wt. %) and Biphenyl-2-yl-di-tert-butyl-phosphane (2.16 mgs, 20 mol. Wt. %) was added to the reaction vessel (Vessel 1). N-(1S, 2R)-[3-[1-(3-Bromo-phenyl)-cyclohexylamino]-1(3, 5-difluoro-benzyl)-2-hydroxy-propyl]-acetamide (0.09075 mM) was placed in a separate reaction vessel (Vessel 2) and dissolved in 200 mL DME. 4-Methylthiophene-2-boronic acid and Potassium Fluoride (KF) (3 eq., 6.33 mgs) were added to a separate reaction vessel and dissolved in 200 μL DME (Vessel 3). Solvents in Vessels 2 and 3 were added to Vessel 1 under nitrogen. Vessel 1 was stirred over night at room temperature. Reaction was then concentrated down by vacuum. Crude material purified by Prep-HPLC. Product fractions collected and concentrated down by vacuum. MS (ESI+) for $C_{29}H_{34}F_2N_2O_2S$ m/z 513.0 $(M+H)^+$

B. Additional Compounds

All compounds in Table 119.A are synthesized according to the same procedure as that used for synthesizing N-(1S, 2R)-(1-(3,5-Difluoro-benzyl)-2-hydroxy-3-{1-[3-(4-methyl-thiophen-2-yl)-phenyl]-cyclohexylamino}-propyl)-acetamide; however in place of 4-methylthiophene-2-boronic acid, the reagents listed next to the final products can be used.

TABLE 119.A

| Example No. | Final Compound | Reagent | m/z (M+H)+ |
|---|---|---|---|
| 119 C | N-(1S, 2R)-[3-{1-[3-(5-Acetyl-thiophen-2-yl)-phenyl]-cyclohexylamino}-1-(3,5-difluoro-benzyl)-2-hydroxy-propyl]-acetamide | 5-Acetyl-2-thiophene-2-boronic acid | 540.8 |
| 119 D | N-(1S, 2R)-{1-(3,5-Difluoro-benzyl)-2-hydroxy-3-[1-(3-thiophen-3-yl-phenyl)-cyclohexylamino]-propyl}-acetamide | Thiophene-3-boronic acid | 498.8 |
| 119 E | N-(1S, 2R)-[3[1-(3'-Acetylamino-biphenyl-3-yl)-cyclohexylamino}-1-(3,5-difluoro-benzyl)-2-hydroxy-propyl]-acetamide | 3-Acetamidobenzene boronic acid | 549.9 |
| 119 F | N-(1S, 2R)-(1-(3,5-Difluoro-benzyl)-3-{1-[3-(5-formyl-thiophen-2-yl)-phenyl]-cyclohexyl-amino}-2-hydroxy-propyl)-acetamide | 5-Formyl-2-thiophene boronic acid | 526.8 |
| 119 G | N-(1S, 2R)-{1-(3,5-Difluoro-benzyl)-3-{1-(3-furan-3-yl-phenyl)-cyclohexylamino]-2-hydroxy-propyl}-acetamide | 3-Furan-boronic acid | 482.9 |

TABLE 119.A-continued

| Example No. | Final Compound | Reagent | m/z (M+H)+ |
|---|---|---|---|
| 119 H | N-(1S, 2R)-(1-(3,5-Difluoro-benzyl)-3-{1-[3-(3-formyl-furan-2-yl)-phenyl]-cyclohexyl-amino}-2-hydroxy-propyl)-acetamide | 3-Formylfuran-2-boronic acid | 510.8 |

EXAMPLE 120

A. Step 1. 5-Bromo-2-iodobenzamide

To 5-bromo-2-iodobenzoic acid (20 g, 61.2 mmol) in 1:1 mixture of dichloromethane and dimethylformamide (200 mL) was added HATU (25 g, 65.8 mmol), and the solution stirred 2 min. Excess ammonium chloride (20 g) was added, and the heterogeneous mixture was stirred 1 h. Ammonium hydroxide (20 mL) was added causing a white precipitate. The precipitate was filtered and washed with ethyl acetate. The solution was diluted with ethyl acetate, washed with water, 1 N hydrochloric acid, saturated sodium bicarbonate, and saturated sodium chloride, dried (magnesium sulfate), filtered, and concentrated under reduced pressure resulting in the formation of a white precipitate. The solid was filtered to provide the title compound (14.4 g). ESI MS m/z 327.0 $[M+H]^+$.

Step 2. (4-Bromo-1,1'-biphenyl-2-yl)methylamine

To a stirred solution of 5-bromo-2-iodobenzamide (14.1 g, 43.3 mmol), phenyl boronic acid (5.3 g, 43.3 mmol), and potassium carbonate (24.4 g, 176.8 mmol) in dimethylformamide (sparged with nitrogen, 100 mL), was added palladium (0) tetrakis(triphenylphosphine) (2.6 g, 2.2 mmol). The reaction was refluxed overnight under $N_2$. The brown solution was cooled and filtered through Celite. The solution was diluted in ethyl acetate and water, and then partitioned. The organic layer was washed with water, 1 N hydrochloric acid, saturated sodium bicarbonate, and saturated sodium chloride, dried (magnesium sulfate), filtered, and concentrated under reduced pressure to a tar. Flash chromatography (silica, 50% ethyl acetate/hexane) gave a tan solid (2.4 g). The biphenyl amide was dissolved in tetrahydrofuran (20 mL), and $BH_3$-THF (1N, 20 mL, 20 mmol) was added slowly. The reaction was refluxed overnight under $N_2$. The reaction was cooled to 0° C. and quenched with ethyl acetate resulting in gas evolution. After gas evolution ceased, the organics were washed with water, saturated sodium bicarbonate, saturated sodium chloride, dried (sodium sulfate), filtered, and concentrated to give the title compound as a gray semi-solid (2.4 g). ESI MS m/z 262.0/264.0 $[M+H]^+$.

Step 3. N-[(1S,2R)-3-{[(4-Bromo-1,1'-biphenyl-2-yl)methyl]amino}-1-(3,5-difluorobenzyl)-2-hydroxypropyl]acetamide

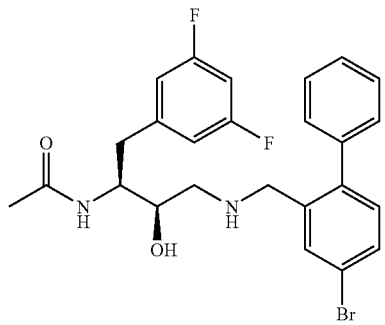

To solution of (4-bromo-1,1'-biphenyl-2-yl)methylamine (2.4 g, 9.2 mmol) in isopropanol (50 mL) was added Example 134 (1.8 g, 6.1 mmol), and the reaction was refluxed 2 h. The solution was concentrated, and the residue was redissolved in ethyl acetate, washed with 1 N hydrochloric acid and saturated sodium chloride, dried (sodium sulfate), filtered, and concentrated under reduced pressure. The residue (3.3 g) was redissolved in methanol, and 4 N hydrochloric acid in dioxane (5 mL) was added. The reaction stirred 30 min, then concentrated to a tan foam (3.1 g). The salt was dissolved in dichloromethane (25 mL) and diisopropylethylamine (4 mL, 23 mmol), then acetylimidazole (636 mg, 5.8 mmol) was added. The reaction stirred overnight at room temperature. The organics were washed with water, 1N hydrochloric acid, saturated sodium bicarbonate, and saturated sodium chloride, dried (sodium sulfate), filtered, and concentrated under reduced pressure. Purification by flash chromatography (silica, 10% methanol/dichloromethane) provided the title compound (550 mg). ESI MS m/z 504.3 [M+H]$^+$. A small amount of the product was dissolved in ether, precipitated with excess 1N HCl in ether, and concentrated to provide the mono-HCl salt.

B. Step 1. N-[(1S,2R)-3-{[(4-Acetyl-1,1'-biphenyl-2-yl)methyl]amino}-1-(3,5-difluorobenzyl)-2-hydroxypropyl]acetamide hydrochloride

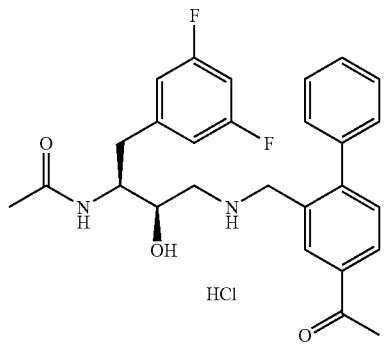

To N-[(1S,2R)-3-{[(4-bromo-1,1'-biphenyl-2-yl)methyl]amino}-1-(3,5-difluorobenzyl)-2-hydroxypropyl]acetamide (120 mg, 0.24 mmol) in toluene (1 mL) was added tributyl (1-ethoxyvinyl)tin (100 μL, 0.28 mmol) and bis-triphenylphoshine palladium(II) dichloride (10 mg, 0.012 mmol), and the reaction was heated at 100° C. 3 h under N$_2$. The solution was cooled to room temperature, 1N hydrochloric acid (1 mL) was added, and the mixture was stirred 20 min. The mixture was partitioned, and the organics were washed with saturated potassium fluoride (aq). The reaction mixture was dried (sodium sulfate), filtered, and concentrated under reduced pressure. Purification by flash column chromatography (silica gel, 8% methanol/methylene chloride) provided an oil. The residue was dissolved in ether, precipitated with excess 1N HCl in ether, and concentrated to provide the title compound (11 mg). ESI MS m/z 467.28 [M+H]$^+$.

C. N-[(1S,2R)-3-{[(4-sec-Butyl-1,1'-biphenyl-2-yl)methyl]amino}-1-(3,5-difluorobenzyl)-2-hydroxypropyl]acetamide

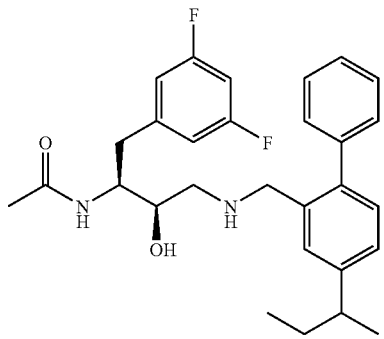

To N-[(1S,2R)-3-{[(4-bromo-1,1'-biphenyl-2-yl)methyl]amino}-1-(3,5-difluorobenzyl)-2-hydroxypropyl]acetamide (150 mg, 0.3 mmol) in THF (2 mL) was added 2M potassium phosphate (0.65 mmol), tri-sec butylborane (1M in THF, 330 μL, 0.33 mmol), and bis-triphenylphoshine palladium(II) dichloride (3 mg, 0.003 mmol), and the reaction was heated at reflux for 2 days. Tri-sec butylborane (1M in THF, 1.2 mL, 1.2 mmol) was added, then bis-triphenylphoshine palladium(II) dichloride (10 mg, 0.012 mmol), and the reaction was refluxed 16 h. The solution is diluted in ethyl acetate and washed with water, 1N hydrochloric acid, saturated sodium bicarbonate, and saturated sodium chloride. The organic layer was dried over sodium sulfate, filtered and concentrated under reduced pressure. Flash chromatography (7% methanol/dichloromethane) gave the title compound. MS (ESI) [M+H$^+$]=481.34.

D. Step 1. 4-Neopentyl-1,1'-biphenyl-2-carboxamide

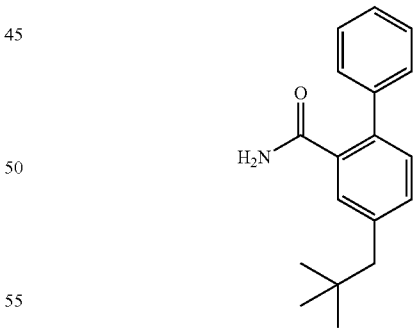

To methyl 5-bromo-2-iodobenzoate (4.41 g, 13 mmol), phenylboronic acid (1.6 g, 13 mmol), potassium carbonate (3.6 g, 26 mmol), and cesium carbonate (4.2 g, 13 mmol) in DMF (50 mL, sparged with nitrogen) was added palladium(0) tetrakis(triphenylphosphine) (751 mg, 0.65 mmol). The reaction was refluxed 16 h, cooled and washed with water, 1N hydrochloric acid, saturated sodium bicarbonate, and saturated sodium chloride. The organic layer was dried over sodium sulfate, filtered and concentrated under reduced pressure. The residue was purified by flash chromatography (5% ethyl acetate/hexane) to yield methyl 4-bromo-1,1'-biphenyl- 2-carboxylate (1.3 g). To methyl 4-bromo-1,1'-biphenyl-2-carboxylate (500 mg, 1.72 mmol) and Pd(dppf)Cl$_2$—CH$_2$Cl$_2$ (70 mg, 0.086 mmol) in THF (5 mL) was added 1M neopentyl magnesium chloride (5 mL, 5 mmol) slowly at room temperature. The reaction was stirred overnight and then quenched with water. The reaction was diluted in ethyl acetate, and the resulting brown solid was filtered away. The organic layer was washed with water, 1N hydrochloric acid, saturated sodium bicarbonate, and saturated sodium chloride. The organic layer was dried over sodium sulfate, filtered and concentrated under reduced pressure. The residue was purified by flash chromatography (1% ethyl acetate/hexane) to yield a yellow solid (200 mg).

The solid was redissolved in 2:1:1 THF/methanol/water (8 mL) and lithium hydroxide monohydrate (60 mg, 1.4 mmol) was added. The reaction stirred 6 days, and the solution was concentrated to dryness. (An addition 1.7 g 4-bromo-1,1'-biphenyl-2-carboxylate was used to prepare a combined total of 1.8 g residue from hydrolysis). The pooled lots were redissolved in DMF (10 mL), and diisopropylethylamine (3.7 mL, 21 mmol), HATU (4 g, 10.2 mmol), and ammonium chloride (5 g) were added. The reaction was stirred 1 h. Ammonium hydroxide was added causing a white precipitate. The liquid was diluted in ethyl acetate and was washed with water, 1N hydrochloric acid, saturated sodium bicarbonate, and saturated sodium chloride. The organic layer was dried over sodium sulfate, filtered and concentrated under reduced pressure to a black oil. The residue was purified by flash chromatography (60% ethyl acetate/hexane) to yield the title compound as a tan solid (210 mg). ESI MS m/z 268 [M+H]$^+$.

Step 2.
(4-Neopentyl-1,1'-biphenyl-2-yl)methylamine

To borane-THF (1M, 1.7 mL, 1.7 mmol) was added 4-neopentyl-1,1'-biphenyl-2-carboxamide (200 mg, 0.75 mmol), and the reaction stirred at reflux 16 h. The solution was cooled and quenched with 1N HCl. The solution was basified with saturated sodium bicarbonate, and the product was extracted into ethyl acetate. The organics were washed with saturated sodium chloride, dried (sodium sulfate), filtered, and concentrated in vacuo to give the title compound as an oil (200 mg). ESI MS m/z 254.22 [M+H]$^+$.

Step 3. N-((1S,2R)-1-(3,5-Difluorobenzyl)-2-hydroxy-3-{[(4-neopentyl-1,1'-biphenyl-2-yl)methyl]amino}propyl)acetamide hydrochloride

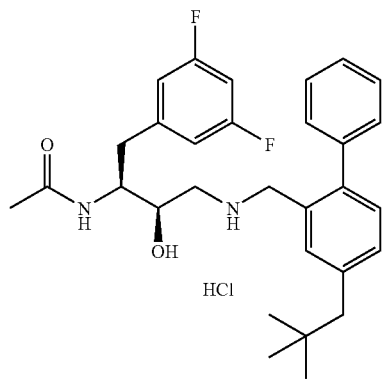

To solution of (4-Neopentyl-1,1'-biphenyl-2-yl)methylamine (200 mg, 0.8 mmol) in isopropanol (5 mL) was added Example 134 (120 mg, 0.4 mmol), and the reaction was refluxed 2 h. The solution was concentrated, and the residue was dissolved in ethyl acetate, washed with 1 N hydrochloric acid and saturated sodium chloride, dried (sodium sulfate), filtered, and concentrated under reduced pressure. The residue was dissolved in methanol, and 4 N hydrochloric acid in dioxane (5 mL) was added. The reaction stirred 30 min, then concentrated to a white foam (100 mg). The salt was dissolved in dichloromethane (2 mL) and diisopropylethylamine (100 µL, 0.5 mmol), then acetylimidazole (30 mg, 0.3 mmol) was added. The reaction stirred 1 h at room temperature. The organics were washed with water, 1N hydrochloric acid, saturated sodium bicarbonate, and saturated sodium chloride, dried (sodium sulfate), filtered, and concentrated under reduced pressure. Purification by flash chromatography (silica, 8% methanol/dichloromethane) provided the title compound (60 mg) in crude form. The material was purified by preparative RP-HPLC to give the desired compound. The product was dissolved in ether, precipitated with excess 1N HCl in ether, and concentrated to provide the mono-HCl salt (6 mg). ESI MS m/z 495 [M+H]$^+$.

E. Step 1. 2-Fluoro-5-isobutyl-benzonitrile

To 5-bromo-2-fluorobenzonitrile (2.3 g, 11.7 mmol) in THF (5 mL) was added 0.5 M isobutylzinc bromide (70 mL, 35 mmol), then Pd(dppf)Cl$_2$ (955 mg, 1.17 mmol), and the reaction was stirred 16 h at room temperature under N$_2$. The reaction was quenched with excess aqueous hydrochloric acid (1N). Ethyl acetate was added, and the solution was partitioned. The organic layer was washed with saturated sodium chloride. Flash chromatography (silica, 4% ethyl acetate/hexane) yielded a colorless oil (1.3 g).

Step 2

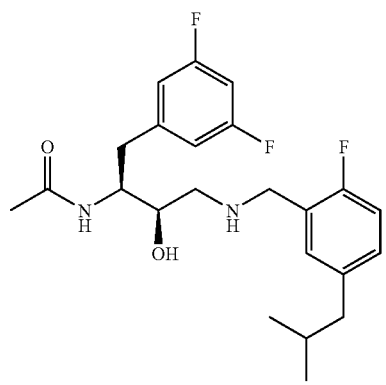

To (product from step 1) (230 mg, 1.3 mmol) in THF (2 mL) was added borane-THF (1M, 3 mL, 3 mmol) slowly at 0° C. The reaction was stirred 16 h at room temperature. The solution was cooled and quenched with 1N HCl. The solution was basified with saturated sodium bicarbonate, and the product was extracted into ethyl acetate. The organics were washed with saturated sodium chloride, dried (sodium sulfate), filtered, and concentrated in vacuo to give an oil. The residue was dissolved in isopropanol (2 mL), Example 134 (120 mg, 0.4 mmol) was added, and the reaction was refluxed 3 h. 4 N hydrochloric acid in dioxane (5 mL) was added, and the reaction stirred 1.5 h, then concentrated to a white foam. The residue was dissolved in dichloromethane (5 mL) and diisopropylethylamine (678 µL, 3.9 mmol), then acetylimidazole (66 mg, 0.6 mmol) was added. The reaction stirred 30 min at room temperature. Additional acetylimidazole (30 mg, 0.3 mmol) was added. The organics were washed with water, saturated sodium bicarbonate, and saturated sodium chloride, dried (sodium sulfate), filtered, and concentrated under reduced pressure. Purification by flash chromatography (silica, 8% methanol/dichloromethane) provided the title compound as a white solid (89 mg). ESI MS m/z 423 [M+H]+.

F. N-[(1S,2R)-1-(3,5-Difluorobenzyl)-2-hydroxy-3-({2-[(2-hydroxyethyl)amino]-5-isobutylbenzyl}amino)propyl]acetamide

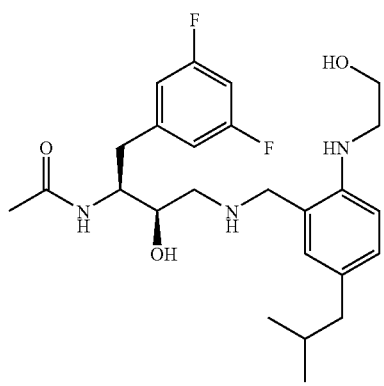

2-Fluoro-5-isobutyl-benzonitrile (533 g, 3 mmol) in ethanolamine (5 mL) was heated at 100° C. 2 h in a sealed tube. The reaction was diluted in ethyl acetate, and the organic layer was washed with water and saturated sodium chloride. The solution was dried (sodium sulfate), filtered, and concentrated to an oil. The residue was redissolved in THF (3 mL), and this solution was added to borane-THF (9 mL) at 0° C. The reaction was stirred at room temperature 16 h. The solution was poured onto ice, and ethyl acetate was added. The organic was partitioned, washed with saturated sodium chloride, dried (sodium sulfate), filtered, and concentrated to an oil (220 mg). The residue was dissolved in isopropanol (5 mL), 2-Fluoro-5-isobutyl-benzonitrile (160 mg, 0.5 mmol) was added, and the reaction was refluxed 2 h. The reaction was cooled and concentrated. Flash chromatography (silica, 8% methanol/dichloromethane) yielded an oil (108 mg). The residue was treated with 4 N hydrochloric acid in dioxane (5 mL), and the reaction stirred 1 h, then concentrated to a white solid. The residue was dissolved in dichloromethane (5 mL) and diisopropylethylamine (108 µL, 0.6 mmol), then acetylimidazole (44 mg, 0.4 mmol) was added. The reaction stirred 30 min at room temperature. The organics were washed with water, saturated sodium bicarbonate, and saturated sodium chloride, dried (sodium sulfate), filtered, and concentrated under reduced pressure. Purification by flash chromatography (silica, 8% methanol/dichloromethane) provided the title compound as an oil (18 mg). ESI MS m/z 464.34 [M+H]+.

EXAMPLE 122

Synthesis of N-(1S, 2R)-{1-(3,5-Difluoro-benzyl)-3-[3-(2,2-dimethyl-propyl)-benzylamino]-2-hydroxy-propyl}-acetamide

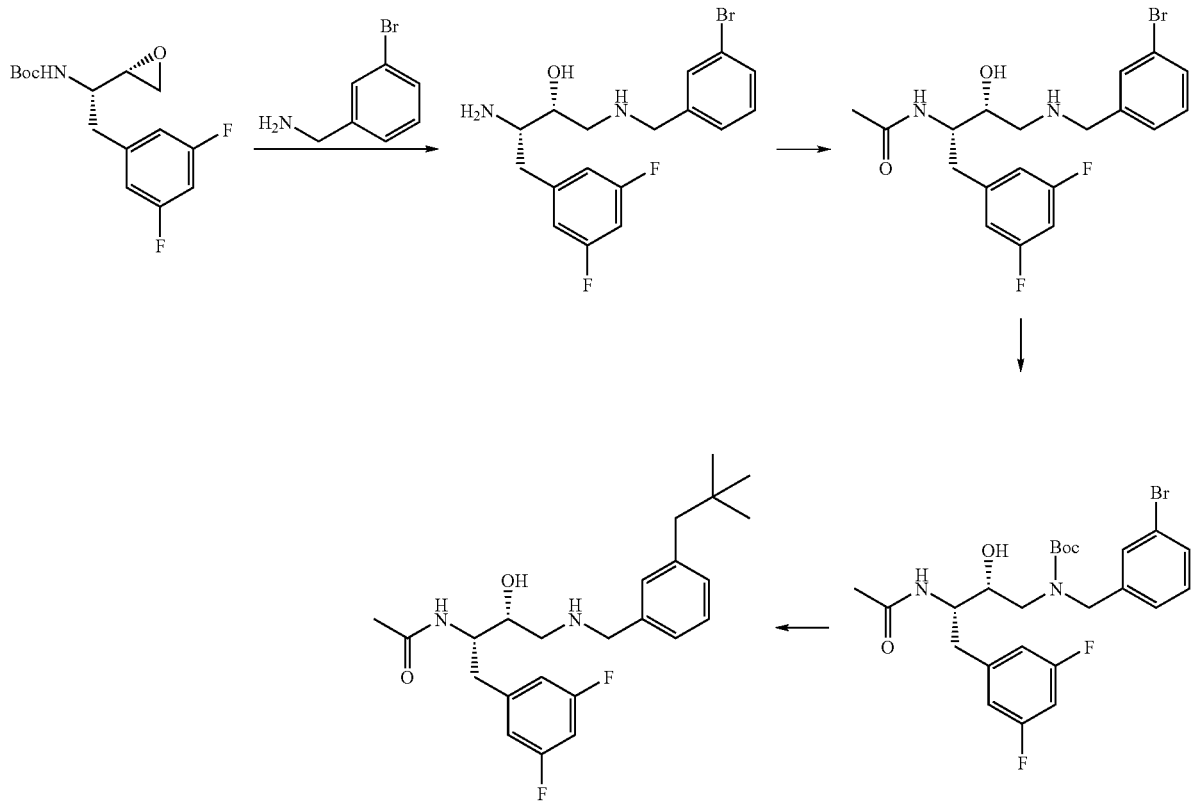

A. 3-Bromo-benzylamine

3-Bromo-benzylamine HCl salt (0.75 g) was dissolved in 10 mL 15% IPA in $CH_2Cl_2$. 7 drops of 10N Sodium Hydroxide (NaOH) was added and stirred for 3 minutes. To the reaction mixture, 5 mL of $dH_2O$ was added and stirred for 5 minutes. The IPA/$CH_2Cl_2$ layer was extracted. The aqueous layer was rinsed with 10 mL 15% IPA in $CH_2Cl_2$. All organic layers were added together and concentrated under vacuum. MS (ESI+) for $C_7H_8BrN$ m/z 186.3 $(M+H)^+$

B. (1S,2R)-3-Amino-1-(3-bromobenzylamino)-4-(3,5-difluorophenyl)butan-2-ol

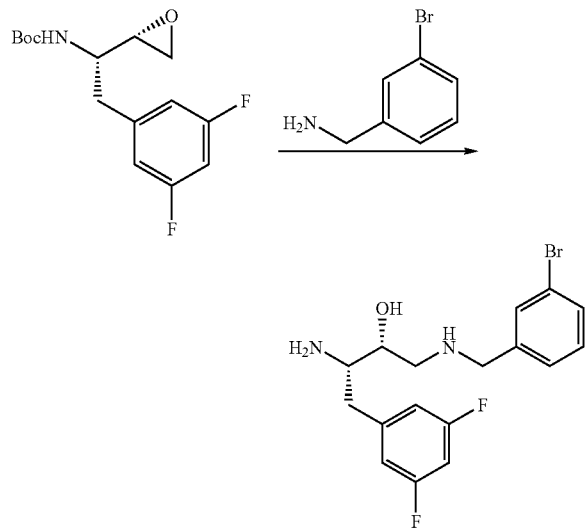

(1S, 2R)-[2-(3,5-Difluoro-phenyl)-1-oxiranyl-ethyl]-carbamic acid tert-butyl ester (0.32 g, 1.075 mM) was added to a sealed tube along with 3-Bromo-benzylamine (0.2 g, 1.075 mM). 2 mL of IPA was added to the sealed tube. The reaction mixture was stirred and heated at 80° C. for 2 hours. Once the reaction was complete, the reaction mixture was concentrated down by vacuum. The product was then dissolved in 750 μL of 4N HCl in dioxane. Reaction stood for 1 hour. The reaction was then concentrated down by vacuum. MS (ESI+) for $C_{17}H_{19}BrF_2N_2O$ m/z 387.1 $(M+H)^+$

C. N-(1S,2R)-[3-(3-bromobenzylamino)-1-(3,5-difluorobenzyl)-2-hydroxypropyl]acetamide (1S, 2R)-3-Amino-1-(3-bromo-benzylamino)-4-(3,5-difluoro-phenyl)-butan-2-ol (0.348 g, 0.9040 mM) was dissolved in 9 mL of $CH_2Cl_2$. N-Methylmorpholine (NMM) (0.4114 g, 4.0679 mM) was added to the reaction mixture. The reaction mixture was cooled to 0° C. and stirred for 15 minutes. Acetic acid (0.057 g, 0.9944 mM) was added slowly to reaction mixture and stirred for 5 minutes. HOBt (0.134 g, 0.9944 mM) was then added, then EDC (0.190 g, 0.9944 mM). The reaction mixture stirred at room temperature for two days. Once reaction complete, solvent was taken off by vacuum. The crude material was purified on a Silica column using 10% Methanol in $CH_2Cl_2$. MS (ESI+) for $C_{19}H_{21}BrF_2N_2O_2$ m/z 427.2 $(M+H)^+$

D. (1S,2R)-[3-Acetylamino-4-(3,5-difluorophenyl)-2-hydroxybutyl]-(3-bromobenzyl)-carbamic acid tert-butyl ester N-(1s, 2r)-[3-(3-bromo-benzylamino)-1-(3,5-difluoro-benzyl)-2-hydroxy-propyl]-acetamide (0.10 g, 0.234 mm) was dissolved in $ch_2cl_2$ (2.3 ml, 0.1 m). Reaction cooled to 0° C. Di-tert-butyl dicarbonate ($boc_2o$) (0.051 g, 0.234 mm) added slowly to reaction. Allowed reaction to stir at room temperature over night. The reaction was concentrated down by vacuum. Ms (esi+) for $c_{24}h_{29}brf_2n_2o_4$ m/z 529.1 $(m+h)^+$

E. N-(1s,2r)-{1-(3,5-difluoro-benzyl)-3-[3-(2,2-dimethyl-propyl)-benzylamino]-2-hydroxy-propyl}-acetamide

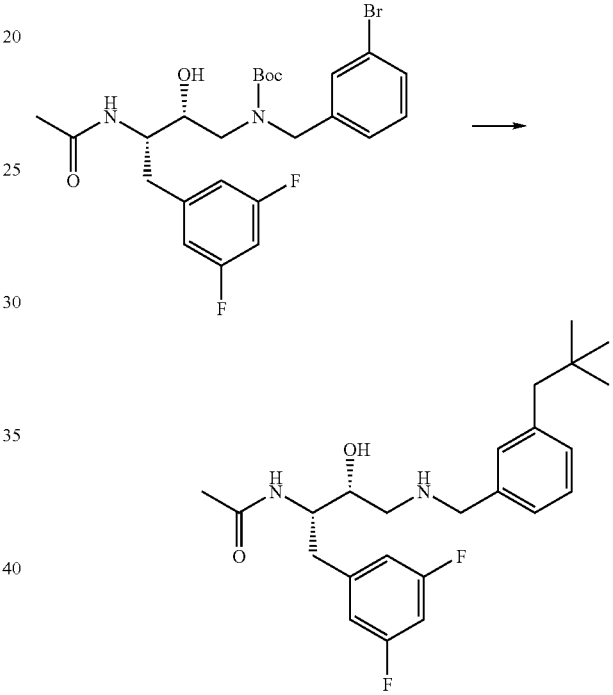

1-Iodo-2,2-dimethyl-propane (1.5 eq., 0.0579 g, 0.2926 mM) and Zinc metal (1.6 eq., 0.0204 g, 0.3122 mM) was added to an oven dried sealed tube (with rubber septa for the top). 2 mL THF was added to the sealed tube. The reaction stirred for 30 minutes under nitrogen. 1-Methyl-2-pyrrolidinone (dried with Molecular Sieves) (0.43 mL) was added to the reaction mixture. Bis(Tri-t-butylphosphine) Palladium [0] (0.15 eq., 0.0149 g, 0.02926 mM) and N-(1S, 2R)-[3-Acetylamino-4-(3,5-difluoro-phenyl)-2-hydroxy-butyl]-(3-bromo-benzyl)-carbamic acid tert-butyl ester (0.1029 g, 0.1951 mM) was added to the reaction mixture. The screw cap was added to the sealed tube. The reaction was heated to 100° C. over night. The reaction mixture was then cooled to room temperature and transferred to separatory funnel. The reaction mixture was diluted with 10 mL Ethyl Acetate. Organic layer washed once with 7 mL $dH_2O$ and once with 7 mL Brine. Organic layer dried with Magnesium Sulfate, filtered, and concentrated under vacuum. Product was then dissolved in 500 μL 4N HCl and stood for 1 hour. Reaction concentrated down by vacuum and purified by Prep-HPLC. MS (ESI+) for $C_{24}H_{32}F_2N_2O_2$ m/z 419.2 $(M+H)^+$

EXAMPLE 123

General Synthesis for N-(1S, 2R)-[1-(3,5-Difluoro-benzyl)-2-hydroxy-3-(1S)-(1,2,3,4-tetrahydro-naphthalen-1-ylamino)-propyl]-acetamide

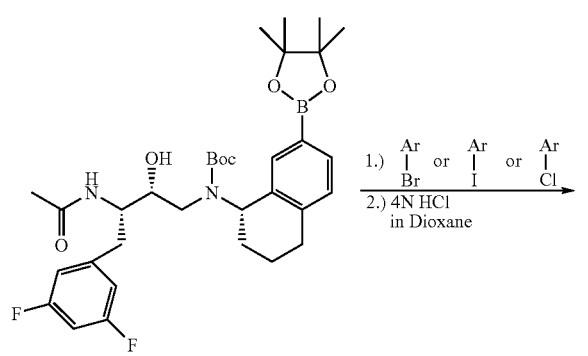

EXAMPLE 124

General Synthesis for N-(1S, 2R)-[1-(3,5-Difluoro-benzyl)-3-((1S)-7-furan-3-yl-1,2,3,4-tetrahydro-naphthalen-1-ylamino)-2-hydroxy-propyl]-acetamide

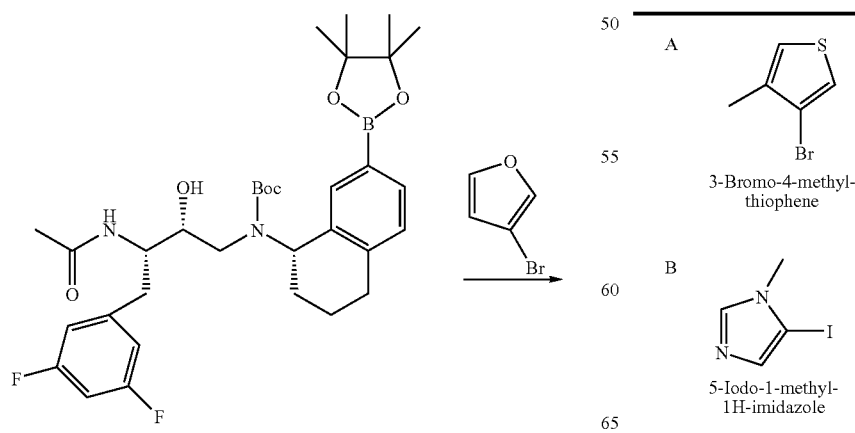

-continued

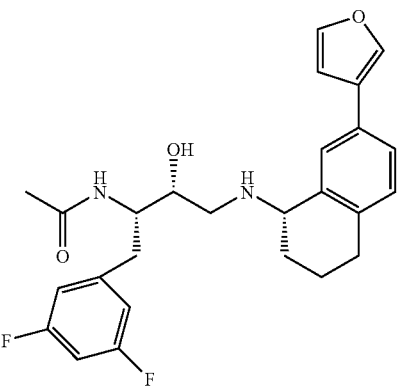

3-Bromofuran (4.85 mgs, 0.033 mM) and Tetrakis(triphenyl-phosphine)palladium [0] (3.81 mgs, 10 mol. wt %) was dissolve in 300 μL 1,2-Dimethoxyethane (glyme) (DME). 99 μL 2M $Na_2CO_3$ in $dH_2O$ was added to the reaction mixture. N-(1S, 2R)-[3-Acetylamino-4-(3,5-difluoro-phenyl)-2-hydroxy-butyl]-[7-(4,4,5,5-tetramethyl-[1,3,2]dioxaborolan-2-yl)-(1S)-1,2,3,4-tetrahydro-naphthalen-1-yl]-carbamic acid tert-butyl ester (20.28 mgs, 0.033 mM) was added to the reaction mixture and stirred at 90° C. over night. The reaction mixture was concentrated down under vacuum then dissolves in 1.5 mL methanol. The reaction mixture was purified by Prep-HPLC. The isolate product was concentrated down by vacuum. The product was dissolved in 500 μL 4N HCl in Dioxane and stood at room temperature for 30 minutes. The reaction mixture was then concentrated down by vacuum. MS (ESI+) for $C_{26}H_{28}F_2N_2O_3$ m/z 455.2 $(M+H)^+$ All final compounds in Table 124.A can be synthesized using the same procedure as that for N-(1S, 2R)-[1-(3,5-Difluoro-benzyl)-3-((1S)-7-furan-3-yl-1,2,3,4-tetrahydro-naphthalen-1-ylamino)-2-hydroxy-propyl]-acetamide; however in place of 3-bromofuran, the reagents listed next to the final products were used.

TABLE 124.A

| Example No. | Reagent | Final Compound | m/z $(M+H)^+$ |
|---|---|---|---|
| A | 3-Bromo-4-methyl-thiophene | N-(1S, 2R)-{1-(3,5-Difluoro-benzyl)-2-hydroxy-3-(1S)-[7-(4-methyl-thiopen-3-yl)-1,2,3,4-tetrahydro-naphthalen-1-ylamino]-propyl}-acetamide | 485.1 |
| B | 5-Iodo-1-methyl-1H-imidazole | N-(1S, 2R)-{1-(3,5-Difluoro-benzyl)-2-hydroxy-3-(1S)-[7-(3-methyl-3H-imidazol-4-yl)-1,2,3,4-tetrahydro-naphthalen-1-ylamino]-propyl}-acetamide | 469.2 |

TABLE 124.A-continued

| Example No. | Reagent | Final Compound | m/z (M+H)+ |
|---|---|---|---|
| C | 2-Bromo-pyrimidine | N-(1S, 2R)-{1-(3,5-Difluoro-benzyl)-2-hydroxy-3-(1S)-(7-pyrimidin-2-yl-1,2,3,4-tetrahydro-naphthalen-1-ylamino)-propyl]-acetamide | 467.2 |
| D | 2-Chloro-4-trifluoromethyl-pyrimidine | N-(1S, 2R)-{1-(3,5-Difluoro-benzyl)-2-hydroxy-3-(1S)-[7-(4-trifluoromethyl-pyrimidin-2-yl)-1,2,3,4-tetrahydro-naphthalen-1-ylamino]-propyl}-acetamide | 535.2 |
| E | 4-Chloro-2-methylsulfanyl-pyrimidine | N-(1S, 2R)-{1-(3,5-Difluoro-benzyl)-2-hydroxy-3-(1S)-[7-(2-methylsulfanyl-pyrimidin-4-yl)-1,2,3,4-tetrahydro-naphthalen-1-ylamino]-propyl}-acetamide | 513.2 |
| F | 5-Bromo-pyrimidine | N-(1S, 2R)-{1-(3,5-Difluoro-benzyl)-2-hydroxy-3-(1S)-(7-pyrimidin-5-yl-1,2,3,4-tetrahydro-naphthalen-1-ylamino)-propyl]-acetamide | 467.2 |
| G | 2-Iodo-pyridine | N-(1S, 2R)-{1-(3,5-Difluoro-benzyl)-2-hydroxy-3-(1S)-(7-pyridin-2-yl-1,2,3,4-tetrahydro-naphthalen-1-ylamino)-propyl]-acetamide | 466.6 |
| H | 2-Bromo-5-methyl-pyridine | N-(1S, 2R)-{1-(3,5-Difluoro-benzyl)-2-hydroxy-3-(1S)-[7-(5-methyl-pyridin-2-yl)-1,2,3,4-tetrahydro-naphthalen-1-ylamino]-propyl}-acetamide | 480.2 |
| I | 3-Iodo-pyridine | N-(1S, 2R)-{1-(3,5-Difluoro-benzyl)-2-hydroxy-3-(1S)-(7-pyridin-3-yl-1,2,3,4-tetrahydro-naphthalen-1-ylamino)-propyl}-acetamide | 466.2 |
| J | 2-Bromo-3-methyl-pyridine | N-(1S, 2R)-{1-(3,5-Difluoro-benzyl)-2-hydroxy-3-(1S)-[7-(3-methyl-pyridin-2-yl)-1,2,3,4-tetrahydro-naphthalen-1-ylamino]-propyl}-acetamide | 480.3 |
| K | 3-Chloro-6-methyl-pyridazine | N-(1S, 2R)-{1-(3,5-Difluoro-benzyl)-2-hydroxy-3-(1S)-[7-(6-methyl-pyridazin-3-yl)-1,2,3,4-tetrahydro-naphthalen-1-ylamino]-propyl}-acetamide | 481.2 |
| L | 4-Iodo-pyridine | N-(1S, 2R)-{1-(3,5-Difluoro-benzyl)-2-hydroxy-3-(1S)-[7-pyridin-4-yl-1,2,3,4-tetrahydro-naphthalen-1-ylamino]-propyl}-acetamide | 466.2 |
| M | 5-Bromo-2-methyl-pyridine | N-(1S, 2R)-{1-(3,5-Difluoro-benzyl)-2-hydroxy-3-(1S)-[7-(6-methyl-pyridin-3-yl)-1,2,3,4-tetrahydro-naphthalen-1-ylamino]-propyl}-acetamide | 480.2 |
| N | 3-Chloro-6-methoxy-pyridazine | N-(1S, 2R)-{1-(3,5-Difluoro-benzyl)-2-hydroxy-3-(1S)-[7-(6-methoxy-pyridazin-3-yl)-1,2,3,4-tetrahydro-naphthalen-1-ylamino]-propyl}-acetamide | 497.2 |
| O | 3-Bromo-4-methyl-pyridine | N-(1S, 2R)-{1-(3,5-Difluoro-benzyl)-2-hydroxy-3-(1S)-[7-(4-methyl-pyridin-3-yl)-1,2,3,4-tetrahydro-naphthalen-1-ylamino]propyl}-acetamide | 480.2 |
| P | 2-Chloro-pyrazine | N-(1S, 2R)-{1-(3,5-Difluoro-benzyl)-2-hydroxy-3-(1S)-(7-pyrazin-2-yl-1,2,3,4-tetrahydro-naphthalen-1-ylamino)-propyl]-acetamide | 467.2 |

TABLE 124.A-continued

| Example No. | Reagent | Final Compound | m/z (M+H)+ |
|---|---|---|---|
| Q | 3-Chloro-2,5-dimethyl-pyrazine | N-(1S, 2R)-{1-(3,5-Difluoro-benzyl)-2-hydroxy-3-(1S)-[7-(3,6-dimethyl-pyrazin-2-yl)-1,2,3,4-tetrahydro-naphthalen-1-ylamino]-2-hydroxy-propyl}-acetamide | 495.3 |
| R | 2-Bromo-5-methyl-thiophene | N-(1S, 2R)-{1-(3,5-Difluoro-benzyl)-2-hydroxy-3-(1S)-[7-(5-methyl-thiopen-2-yl)-1,2,3,4-tetrahydro-naphthalen-1-ylamino]-propyl}-acetamide | 485.2 |
| S | 2-Bromo-furan | N-(1S, 2R)-{1-(3,5-Difluoro-benzyl)-2-hydroxy-3-(1S)--(7-furan-2-yl-1,2,3,4-tetrahydro-naphthalen-1-ylamino)-2-hydroxy-propyl]-acetamide | 455.2 |
| T | 2-Bromo-thiazole | N-(1S, 2R)-{1-(3,5-Difluoro-benzyl)-2-hydroxy-3-(1S)-(7-thiazol-2-yl-1,2,3,4-tetrahydro-naphthalen-1-ylamino)-propyl]-acetamide | 472.2 |
| U | 3-Bromo-thiophene | N-(1S, 2R)-{1-(3,5-Difluoro-benzyl)-2-hydroxy-3-(1S)-(7-thiophen-3-yl-1,2,3,4-tetrahydro-naphthalen-1-ylamino)-propyl]-acetamide | 471.2 |
| V | (2-Bromo-vinyl)-benzene | N-(1S, 2R)-{1-(3,5-Difluoro-benzyl)-2-hydroxy-3-(1S)-(7-styryl-1,2,3,4-tetrahydro-naphthalen-1-ylamino)-propyl]-acetamide | 491.2 |
| W | 4-Iodo-3,5-dimethyl isoxazole | N-(1S, 2R)-{1-(3,5-Difluoro-benzyl)-2-hydroxy-3-(1S)-[7-(3,5-dimethyl-isoxazol-4-yl)-1,2,3,4-tetrahydro-naphthalen-1-ylamino]-2-hydroxy-propyl}-acetamide | 484.1 |
| X | 2-Iodo-1-methyl-1H-imidazole | N-(1S, 2R)-{1-(3,5-Difluoro-benzyl)-2-hydroxy-3-(1S)--[7-(1-methyl-1H-imidazol-2-yl)-1,2,3,4-tetrahydro-naphthalen-1-ylamino]propyl}-acetamide | 469.2 |
| Y | 2-Bromo-thiophene | N-(1S, 2R)-{1-(3,5-Difluoro-benzyl)-2-hydroxy-3-(1S)-(7-thiophen-2-yl-1,2,3,4-tetrahydro-naphthalen-1-ylamino)-propyl]-acetamide | 471.2 |
| Z | 2-Bromo-3-methyl-thiophene | N-(1S, 2R)-{1-(3,5-Difluoro-benzyl)-2-hydroxy-3-(1S)-[7-(3-methyl-thiophen-2-yl)-1,2,3,4-tetrahydro-naphthalen-1-ylamino]-propyl}-acetamide | 485.2 |
| AA | 2-Chloro-5-ethyl-pyrimidine | N-(1S, 2R)-{1-(3,5-Difluoro-benzyl)-2-hydroxy-3-(1S)-[7-(5-ethyl-pyrimidin-2-yl)-1,2,3,4-tetrahydro-naphthalen-1-ylamino]-2-hydroxy-propyl}-acetamide | 495.2 |
| BB | 2-Bromo-4-methyl-pyridine | N-(1S, 2R)-{1-(3,5-Difluoro-benzyl)-2-hydroxy-3-(1S)-[7-(4-methyl-pyridin-2-yl)-1,2,3,4-tetrahydro-naphthalen-1-ylamino]-propyl}-acetamide | 480.2 |
| CC | 2-Bromo-propene | N-(1S, 2R)-{1-(3,5-Difluoro-benzyl)-2-hydroxy-3-(1S)-(7-isopropenyl-1,2,3,4-tetrahydro-naphthalen-1-ylamino)-propyl]acetamide | 429.1 |

EXAMPLE 125

Synthesis of N-(1S, 2R)-[1-(3,5-Difluoro-benzyl)-2-hydroxy-3-(3-isopropenyl-benzylamino)-propyl]-acetamide and N-(1S,2R)-[1-(3,5-Difluoro-benzyl)-2-hydroxy-3-(3-isopropyl-benzylamino)-propyl]-acetamide

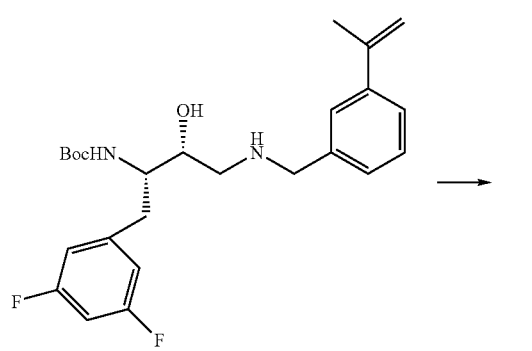

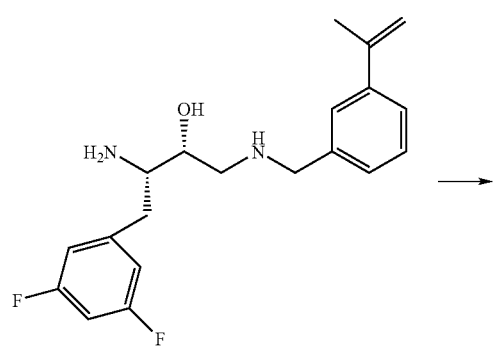

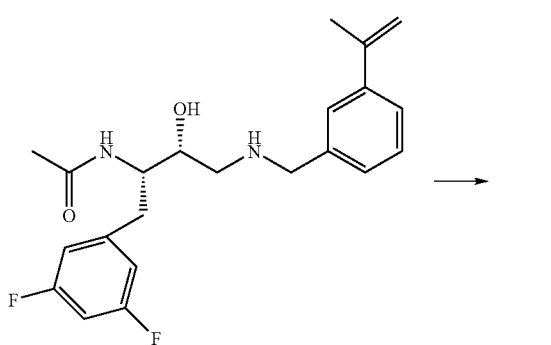

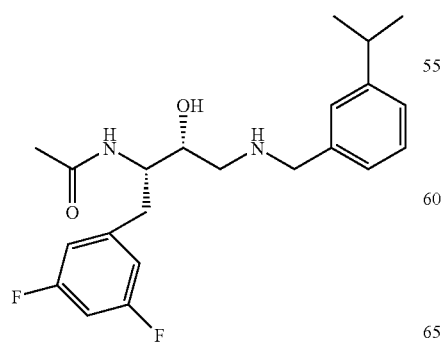

A. (1S,2R)-3-Amino-4-(3,5-difluoro-phenyl)-1-(3-isopropenyl-benzylamino)-butan-2-ol (1S,2R)-[1-(3,5-Difluoro-benzyl)-2-hydroxy-3-(3-isopropenyl-benzylamino)-propyl]-carbamic acid tert-butyl ester was dissolved in 6 mL $CH_2Cl_2$ with 600 µL TFA. The reaction mixture stirred for 4 hours at room temperature. 15 mL of 15% IPA in Chloroform was added to reaction mixture was washed with 10 mL Saturated Sodium Bicarbonate (Sat. $NaHCO_3$) in $dH_2O$. The Sat. $NaHCO_3$ in $dH_2O$ layer was rinsed with 15% IPA in Chloroform. All organic layers were combined and dried with Magnesium Carbonate, filtered and concentrated under vacuum. MS (ESI+) for $C_{20}H_{24}F_2N_2O$ m/z 347.4 $(M+H)^+$

B. N-(1S,2R)-[1-(3,5-Difluoro-benzyl)-2-hydroxy-3-(3-isopropenyl-benzylamino)-propyl]-acetamide The above compound was prepared essentially according to the method of Example 56. The crude material was purified on Silica gel using 5% Methanol in $CH_2Cl_2$. MS (ESI+) for $C_{22}H_{26}F_2N_2O_2$ m/z 389.5 $(M+H)^+$

C. N-(1S,2R)-[1-(3,5-Difluoro-benzyl)-2-hydroxy-3-(3-isopropyl-benzylamino)-propyl]-acetamide The product from step B (0.036 g) was dissolved in 2 mL Methanol. 5% Pd/C (0.004 g) was added to the vial. The reaction was hydrogenated at 50 psi for 4 hours. The reaction mixture was filtered and the filtrate was concentrated. MS (ESI+) for $C_{22}H_{28}F_2N_2O_2$ m/z 391.4 $(M+H)^+$

EXAMPLE 126

N-(1S,2R)-(1-(3,5-Difluoro-benzyl)-2-hydroxy-3-{1-[3-(4-methyl-thiophen-2-yl)-phenyl]-cyclopropylamino}-propyl)-acetamide

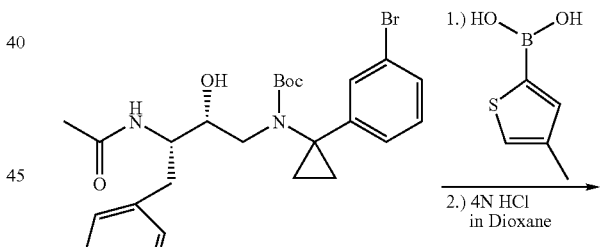

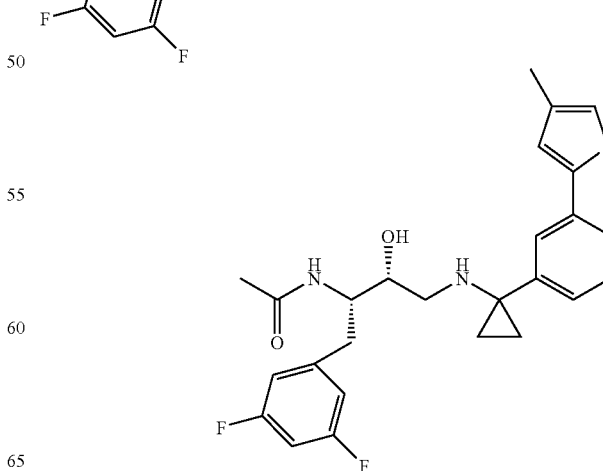

Palladium acetate (Pd(OAc)$_2$) (0.82 mgs, 10 mol. wt. %) and Biphenyl-2-yl-di-tert-butyl-phosphane (2.16 mgs, 20 mol. wt. %) was added to the reaction vessel (Vessel 1). N-(1S, 2R)-[3-Acetylamino-4-(3,5-difluoro-phenyl)-2-hydroxy-butyl]-[1-(3-bromo-phenyl)-cyclopropyl]-carbamic acid tert-butyl ester (13.88 mgs, 0.09075 mM) was placed in a separate reaction vessel (Vessel 2) and dissolved in 200 mL DME. 4-Methylthiophene-2-boronic acid and Potassium Fluoride (KF) (3 eq., 6.33 mgs) were added to a separate reaction vessel and dissolved in 200 µL DME (Vessel 3). Solvents in Vessels 2 and 3 were added to Vessel 1 under nitrogen. Vessel 1 was stirred over night at room temperature.

Reaction was then concentrated down by vacuum. Crude material purified by Prep-HPLC. Product fractions collected and concentrated down by vacuum. Product then dissolved in 500 µL 4N HCl in dioxane. Allowed to stand for 30 minutes at room temperature. Reaction mixture then concentrated down by vacuum. MS (ESI+) for $C_{26}H_{28}F_2N_2O_2S$ m/z 471.2 (M+H)$^+$ All compounds in Table 126.A were synthesized using the same general procedure as used in the synthesis of Example 126. The table illustrates the boronic acid derivative that was used, the mass of the product, and the name of the product.

TABLE 126.A

[Structure of the core compound with substituent Z]

| Example No. | Z | m/z (M+H)$^+$ | Product |
|---|---|---|---|
| 127 | 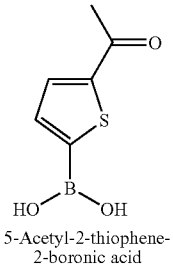<br>5-Acetyl-2-thiophene-2-boronic acid | 499.2 | N-(1S, 2R)-[3-{1-[3-(5-Acetyl-thiophen-2-yl)-phenyl]-cyclopropylamino}-1-(3,5-difluoro-benzyl)-2-hydroxy-propyl]-acetamide |
| 128 | 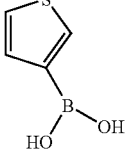<br>Thiophene-3-boronic acid | 457.2 | N-(1S, 2R)-{1-(3,5-Difluoro-benzyl)-2-hydroxy-3-[1-(3-thiophen-3-yl-phenyl)-cyclopropylamino]-propyl}-acetamide |
| 129 | 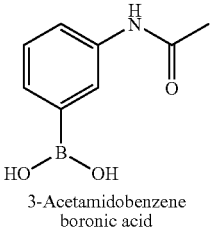<br>3-Acetamidobenzene boronic acid | 508.1 | N-(1S, 2R)-[3-[1-(3'-Acetylamino-biphenyl-3-yl)-cyclopropylamino]-1-(3,5-difluoro-benzyl)-2-hydroxy-propyl]acetamide |

TABLE 126.A-continued

| Example No. | Z | m/z (M+H)+ | Product |
|---|---|---|---|
| 130 | 2-Methoxy-5-pyridine bornonic acid | 482.3 | N-(1S, 2R)-(1-(3,5-Difluoro-benzyl)-2-hydroxy-3-{1-[3-(6-methoxy-pyridin-3-yl)-phenyl]-cyclopropylamino}-propyl)-acetamide |
| 131 | 3-Furan-boronic acid | 441.2 | N-(1S, 2R)-{1-(3,5-Difluoro-benzyl)-3-[1-(3-furan-3-yl-phenyl)-cyclopropylamino]-2-hydroxy-propyl}-acetamide |
| 132 | 3,5-Dimethyl isoxazole-4-boronic acid | 470.2 | N-(1S, 2R)-(1-(3,5-Difluoro-benzyl)-3-{1-[3-(3,5-dimethyl-isoxazol-4-yl)-phenyl]-cyclopropylamino}-2-hydroxy-propyl)-acetamide |

EXAMPLE 133

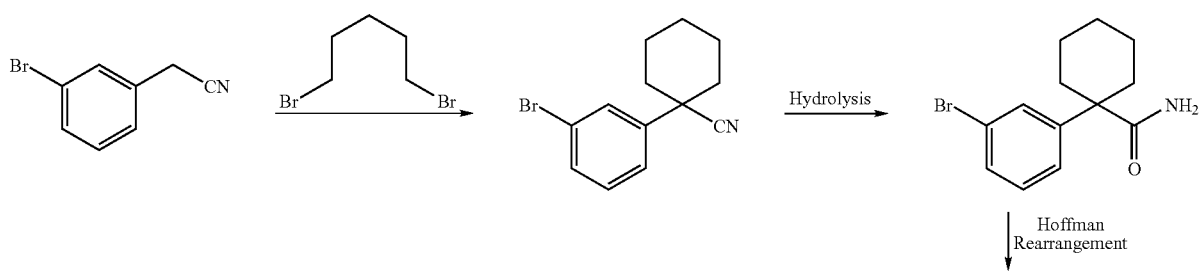

-continued

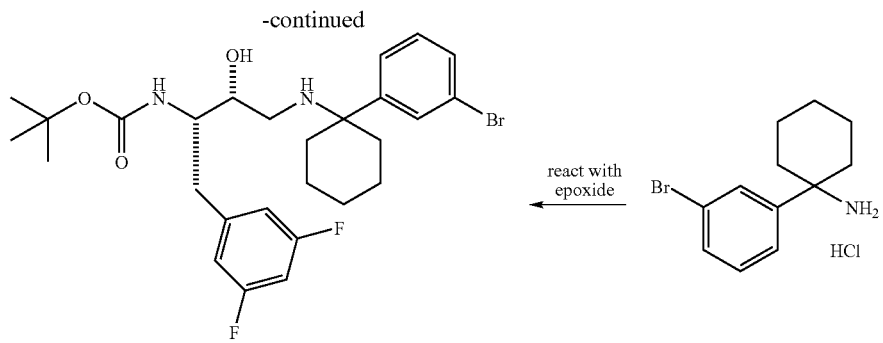

react with epoxide

3-Bromobenzylnitrile was obtained from Kimera. Powder KOH was obtained from Oxechem. Other reagents were from Aldrich.

Step 1: 1-(3-bromophenyl)cyclohexanecarbonitrile

To a 5 L 3-neck round bottom flask equipped with $N_2$ inlet, temperature probe, addition funnel, and mechanical stirrer was added 3-bromobenzylnitrile (297 g, 1.51 mol, 1.0 eq) and THF (2.75 L). The clear solution was cooled to 0-5° C. via ice bath. KOtBu (374 g, 3.33 mol, 2.2 eq) was weighed out inside the glove box into a 200 mL round bottom flask and added to the cold clear solution in shots. The first shot (71.1 g) was added over 30 seconds and an immediate exotherm of 9° C. was observed along with color change from clear to orange/brown solution. After waiting for 15 min for the solution to cool back down to 5.1° C., the second shot (96.0 g) was added and an exotherm of 6.5° C. was observed. After another 15 min, the third shot (100.4 g) was added and an exotherm of 5° C. was observed. After another 15 min, the fourth and final shot (106.5 g) was added and an exotherm of 3.8° C. was observed. The orange/brown solution was stirred in ice bath for 30 min upon which the solution thickened. Carefully add 1,5-dibromopentane (365.5 g, 1.56 mol, 1.05 eq) to orange/brown mixture at such a rate to maintaining reaction temperature <15° C. The reaction will change from solution to brown slurry and the exotherm will continue to climb during addition. The addition took ca 2 hours. The addition funnel was rinsed with THF (250 mL) and added to the brown slurry. The ice bath was then removed and the slurry self-warmed to RT while maintaining medium agitation. Sample of the slurry was pulled after 1 hour of stirring. GC indicated completion with only excess 1,5-dibromopentane and product. The light brown slurry was then filtered over a pad of celite to remove salts. The cake was rinsed with THF (ca 2 L) until clear. Ice (ca 1 L in volume) was then added to the burgundy filtrate and stirred at RT overnight. The mixture was then concentrated to remove THF and the resultant biphasic brown mixture was extracted with EtOAc and saturated NaCl solution. The orange organic layers were dried with anhydrous $Na_2SO_4$, filtered and rinsed with EtOAc. The orange filtrate was then concentrated to dryness to give red oil. EtOAc (100 mL) was added to redissolve oil. While stirring at medium speed, heptane (2 L) was added over 1-2 min upon which burgundy oil sticks to bottom and sides of flask. The yellow solution was then carefully decanted away from the sticky oil and concentrated to dryness to give light orange oil (379.7 g, 95% yield). GC of light orange oil indicated excess 1,5-dibromopentane (2.8 area %), product (95.3 area %), and 7 other peaks having less than 0.5 area % (total=1.9 area %).

GC Conditions: 15 m DB5 0.25×0.25 micron; Init. Temp.=75° C., Init. Time=5 min, Rate=15° C./min, Final Temp.=275° C., Final Time=2 min, Inj. Temp.=275° C., Det. Temp.=250° C.; 1,5-dibromopentane RT=6.35 min, Prod. RT=13.47 min.

$^1$H NMR (400 MHz, CDCl$_3$) δ 7.62 (s, 1H), 7.45 (d, 2H), 7.26 (t, 1H), 2.14 (d, 2H), 1.74-1.88 (m, 6H), 1.26-1.29 (m, 2H). $^{13}$C NMR (100.6 MHz, CDCl$_3$) δ 143.63, 130.98, 130.40, 128.73, 124.41, 122.94, 122.07, 44.14, 37.23, 24.82, 23.46.

Step 2: 1-(3-bromophenyl)cyclohexanecarboxamide

With overhead stirrer, a mixture of crude product from step 1, above, (380 g, 1207 mmol), powdered KOH (720 g) and t-BuOH (2.5 L) was heated at reflux overnight. See Hall, J. H.; Gisler, M. A simple method for converting nitriles to amides. Hydrolysis with potassium hydroxide in tert-butyl alcohol. *J. Org. Chem.* 1976, 41, 3769-3770. If deemed complete by GC analysis, it was cooled with ice-water (cool slowly to avoid shock to the glass), quenched with ice-water (1500 mL). The quenched mixture was then extracted with MTBE (3.5 L+1.5 L). MTBE layers were concentrated to a yellow solid, 390 g.

GC Conditions: 15 m DB5 0.25×0.25 micron; Init. Temp.=75° C., Init. Time=5 min, Rate=15° C./min, Final Temp.=275° C., Final Time=2 min, Inj. Temp.=275° C., Det. Temp.=250° C.; Product RT=15.3 min.

Step 3: 1-(3-bromophenyl)cyclohexanamine hydrochloride

The product from step 2, above (189 g, 603 mmol) was suspended in warmed t-BuOH (1140 mL) at ~35° C., 3N NaOH (570 mL, 2.8 equiv) was added. The reaction cooled to 30° C. NaOCl (380 mL, 13.6 wt %, 1.4 equiv.) was added in one portion. The reaction mixture was cooled to 26° C., and then started to warm up. Ice was directly added to the mixture to controlled the temperature <35° C. A total of 300 g of ice was used. The heat generation stopped after 15 min. All solids dissolved at that point. Assayed organic layer at 30 min, GC indicated completion. The mixture was extracted with 1100 mL of MTBE. The organic layer was combined with the organic layer of a parallel run of the same scale, and filtered to remove some white ppt (likely urea side product). The aqueous layers were extracted with 300 mL of MTBE. The combined MTBE layers (ca. 5 L) was treated with 150 mL of conc. HCl (1.8 mol), stirred for 4 h, cooled to 0° C. and filtered. The white solid was dried at 50° C. to give 1st crop 180 g (52%) of material. The filtrate was treated with NaOH and NaHSO₃ to pH>12. The organic layer was concentrated to an oil. This oil was dissolved in 1 L of MTBE and treated with 75 mL of conc. HCl, cooled, filtered and dried to give 140 g (40%) of the desired product. Anal. Calcd for C₁₂H₁₆BrN.HCl: C, 49.59; H, 5.90; N, 4.82; Br, 27.49; Cl, 12.20; Found: C, 50.34; H, 6.23; N, 4.70; HRMS calcd for C₁₂H₁₆BrN⁺ 253.0467, found 253.0470.

GC Conditions: 15 m DB5 0.25×0.25 micron; Init. Temp.=75° C., Init. Time=5 min, Rate=15° C./min, Final Temp.=275° C., Final Time=2 min, Inj. Temp.=275° C., Det. Temp.=250° C.; Product RT=12.9 min.

Step 4: tert-butyl-(1S,2R)-3-{[1-(3-bromophenyl)cyclohexyl]amino}-1-(3,5-difluorobenzyl)-2-hydroxypropylcarbamate The product from step 3, above (90 g, 310 mmol, 1.5 eq) was converted into a free base in 1000 mL of MTBE/400 mL of 2N NaOH. MTBE layer was separated, washed with brine. Aqueous layers were back extracted with 400 mL of MTBE. Combined MTBE layer was concentrated (thereotical 78.3 g) to afford the free base.

61.7 g the epoxide (206 mmol, 1 eq., FW 299.3) and the above free base were suspended in 320 ml t-BuOH (warm). A mantle and thermo/probe was used to heat the stirring mixture to 80° C. at 5° C./hour ramp overnight. The mixture was concentrated on rotovap with 20° C. condenser. The resulting oil was dissolved in MTBE (1L), washed with 1N HCl (200 ml, then 100 mL×5) (contain the product from step 3, the first wash was quickly separated to avoid crash out). Aqueous layer was sequentially back-extracted with MTBE (200 mL). The MTBE layer was stirred with 1N NaOH (500 mL) for 30 min, then separated. MTBE layer was washed with brine and then concentrated to dryness. Recrystallized in MTBE/Heptane (150/900 mL). Filtered at 0° C. and washed with heptane (150 mL×2), dried at 45° C., 95.3 g (83.5%).

The HCl washes (suspension) were basified with 50% NaOH (ca. 50 g), extracted with MTBE (400 mL+200 mL). The MTBE layer was treated with conc. HCl (15 mL). The resulting suspension was cooled and filtered to give the unreacted starting amine, the product from step 3, above, 31.3 g (52%).

HPLC conditions: Luna C18(2), 3 micron, min, 80:20 0.1% TFA in MeOH/0.1% TFA in water; 10 min, Product, RT=2.0 min.

EXAMPLE 134 tert-butyl (1S)-2-(3,5-difluorophenyl)-1-[(2S)-oxiran-2-yl]ethylcarbamate

Step 1: (2S)-2-[(tert-butoxycarbonyl)amino]-3-(3,5-difluorophenyl)propanoic acid methyl ester

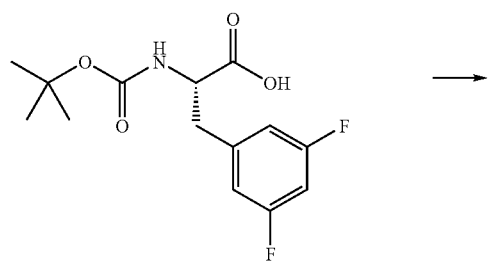

-continued

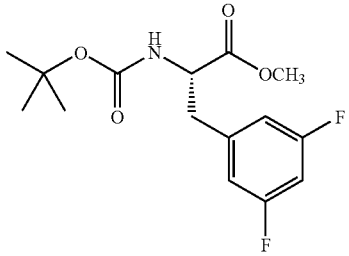

To a 1-L 3-neck round bottom flask equipped with a magnetic stirrer, nitrogen inlet and thermocouple is added (2S)-2-[(tert-butoxycarbonyl)amino]-3-(3,5-difluorophenyl)propanoic acid (I, 40 g, 0.133 moles, 1 equivalent) followed by THF (240 mL). Lithium hydroxide monohydrate (5.6 g, 0.133 moles, 1 equivalent) is added in a single portion and is allowed to stir for 30 min at which time, the contents are cooled to 0°. Once cooled, dimethyl sulfate (12.6 mL, 0.133 moles, 1 equivalent) is added dropwise via syringe and then stirred for 30 min. The mixture is then heated to about 50° and monitored (by HPLC) until 90% conversion had been achieved. At that time, the mixture is cooled to below 20° (solids form). The mixture is then poured into sodium bicarbonate (200 mL), stirred for 15 min then extracted with methyl t-butyl ether (200 mL). The phases are separated and the aqueous layer is extracted with methyl t-butyl ether (2×200 mL). The combined organic phases are washed with water (400 mL) dried over sodium sulfate, filtered and concentrated under reduced pressure to give a solid. This material is then recrystallized from hexanes to give the title compound, NMR (DMSO-d₆) δ 7.51, 7.15-7.25, 4.43, 3.81, 3.00-3.26 and 1.49; CMR (DMSO-d₆) δ 172.43, 163.74, 161.20, 155.67, 142.58, 112.70, 120.23, 78.69, 54.71, 52.24, 39.25 and 28.37.

Step 2: tert-butyl (1S)-3-chloro-1-(3,5-difluorobenzyl)-2-oxopropylcarbamate (III)

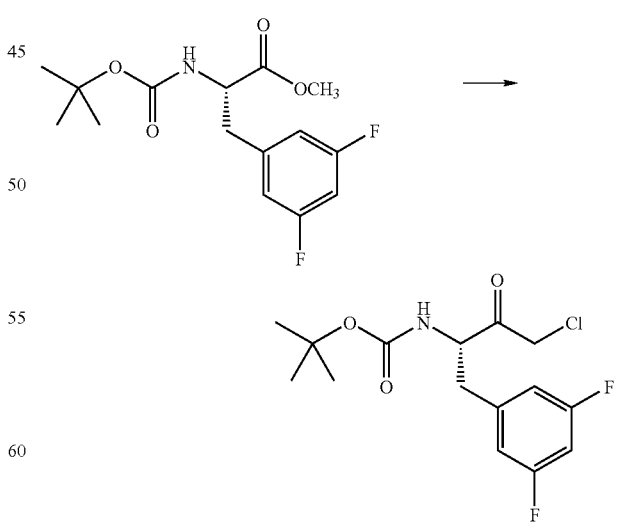

To a 1-L 3-neck round bottom flask equipped with a magnetic stirrer, nitrogen inlet, thermocouple and additional funnel is added (2S)-2-[(tert-butoxycarbonyl)amino]-3-(3,5-difluorophenyl)propanoic acid methyl ester (II, Step 1, 10.0 g, 0.0317 moles, 1 equivalent) followed by THF (175 mL) then cooled to −78°. Once the mixture is cooled, iodochloromethane (9.25 mL, 0.127 moles, 4 equivalents) is added in one portion via syringe. The addition funnel is charged with LDA (79 mL, 0.158 moles, 5 equivalents, 2.0 M in heptane/THF) and is subsequently added dropwise to the mixture keeping the internal temperature below −70°. Once the addition is complete, the contents are stirred for 15 min at which time acetic acid (47.2 mL, 0.824 moles, 26 equivalents) is added dropwise via the addition funnel keeping the internal temperature below −65°. Once this addition is complete, the mixture is stirred for 15 min then warmed to 0° and poured into water (500 mL), saline (500 mL) and methyl t-butyl ether (500 mL) then transferred to a separatory funnel. The phases are separated and the aqueous phase is extracted with methyl t-butyl ether (2×250 mL). The combined organic phases are washed with saturated sodium bicarbonate (500 mL), sodium sulfite (500 mL) and water (500 mL). The organic phase is then dried over sodium sulfate, filtered and concentrated under reduced pressure to give a solid. The solid is recrystallized from heptane/i-propyl alcohol (10/1) to give the title compound, NMR (DMSO-d$_6$) δ 7.47, 7.06-7.14, 4.78, 4.49, 3.20, 2.82 and 1.40; CMR (DMSO-d6) δ 200.87, 163.74, 161.20, 142.74, 112.80, 102.13, 79.04, 58.97, 47.72, 34.95 and 28.30.

Step 3: tert-butyl (1S,2S)-3-chloro-1-(3,5-difluorobenzyl)-2-hydroxypropylcarbamate (IV)

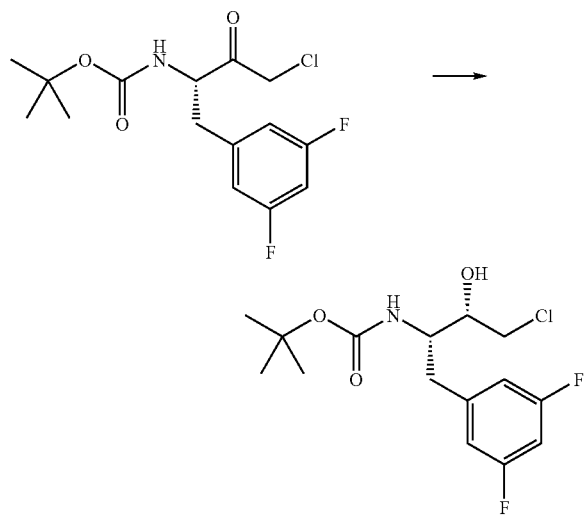

To a 250 mL 3-neck round bottom flask equipped with magnetic stir bar, nitrogen inlet and thermocouple, is added tert-butyl (1S)-3-chloro-1-(3,5-difluorobenzyl)-2-oxopropylcarbamate (III, Step 2, 4.4 g, 0.0132 moles, 1 equivalent) followed by THF (20 mL) and ethanol (30 mL) then cooled to −78°. Once the mixture is cooled, sodium borohydride (2.0 g, 0.0527 moles, 4 equivalents) is added as a solid portion wise over 30 min keeping the internal temperature below −70°. Once this addition is complete, the contents are stirred for 2 hr at −78° then warmed to 0° and stirred an additional 1 hr. The mixture is quenched by the addition of saturated potassium bisulfate (15 mL) and water (15 mL). This slurry is stirred for 30 min at 20-25° then concentrated under reduced pressure to half its volume. The mixture is then cooled to 0° and stirred for 30 min. After this time, the resultant solids are collected by filtration and washed with water (2×50 mL) then dried under reduced pressure at 50° to give crude product. A syn/anti ratio of 4-9:1 has been observed. The desired product is recrystallized from hexanes/ethanol (25/1) to give the title compound, NMR (DMSO-d$_6$) δ 6.89-7.16, 5.61, 3.64-3.83, 3.19, 2.69 and 1.41; CMR (DMSO-d$_6$) δ 163.67, 161.24, 155.44, 112.70, 101.55, 78.04, 72.99, 54.29, 48.24, 35.97 and 28.37.

Step 4: tert-Butyl (1S)-2-(3,5-difluorophenyl)-1-[(2S)-oxiran-2-yl]ethylcarbamate

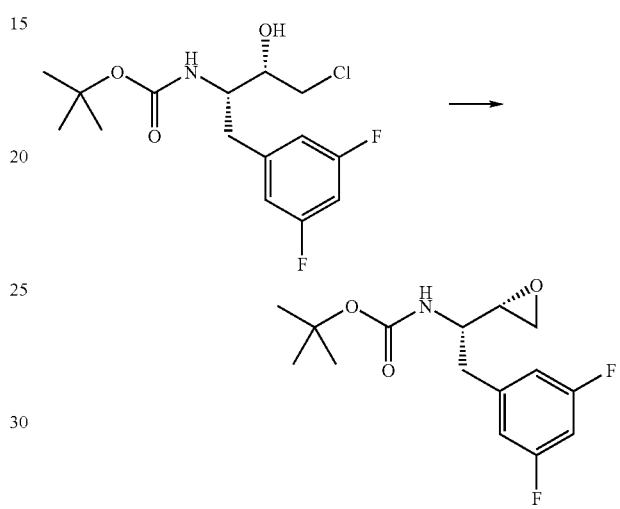

To a 250 mL 3-neck round bottom flask equipped with magnetic stir bar, nitrogen inlet and thermocouple, is added tert-butyl (1S,2S)-3-chloro-1-(3,5-difluorobenzyl)-2-hydroxypropylcarbamate (IV, Step 3, 3.5 g, 0.010 moles, 1 equivalent) followed by absolute ethanol (60 mL) and cooled to 0°. To this mixture is added potassium hydroxide (0.73 g, 0.013 moles, 1.25 equivalents) dissolved in absolute ethanol (10 mL) over 1 hr and the resulting suspension is warmed to 15-20° and stirred for 1 hr. At this time, water (100 mL) is added and the reaction contents are cooled to −5° and stirred for 30 min. The solids are collected by filtration and washed with cold water (2×25 mL) then dried under reduced pressure at 45° to give the title compound; NMR (DMSO-d$_6$) δ 7.03, 3.61, 2.68-2.98 and 1.33; CMR (DMSO-d$_6$) δ 163.72, 161.29, 155.55, 143.35, 112.65, 101.80, 78.17, 53.42, 52.71, 44.90, 36.98 and 28.36.

EXAMPLE 135

The following compounds are prepared essentially according to the procedures set forth in the above examples and schemes.

| Ex. No. | Compound Name |
|---|---|
| A1. | N—[(1S,2R)-3-{[(1R)-5-(3-aminophenyl)-7-ethyl-1,2,3,4-tetrahydronaphthalen-1-yl]amino}-1-(3,5-difluorobenzyl)-2-hydroxypropyl]acetamide; |
| A2. | N—((1S,2R)-1-(3,5-difluorobenzyl)-3-{[(1R)-7-ethyl-5-(1,3-thiazol-2-yl)-1,2,3,4-tetrahydronaphthalen-1-yl]amino}-2-hydroxypropyl)acetamide; |

| Ex. No. | Compound Name |
|---|---|
| A3. | N—((1S,2R)-1-(3,5-difluorobenzyl)-3-{[(1R)-7-ethyl-5-pyridin-2-yl-1,2,3,4-tetrahydronaphthalen-1-yl]amino}-2-hydroxypropyl)acetamide; |
| A4. | N—((1S,2R)-1-(3,5-difluorobenzyl)-3-{[(1R)-7-ethyl-5-(3-methylpyridin-2-yl)-1,2,3,4-tetrahydronaphthalen-1-yl]amino}-2-hydroxypropyl)acetamide; |
| A5. | N—((1S,2R)-1-(3,5-difluorobenzyl)-3-{[(1R)-7-ethyl-5-(4-methylpyridin-2-yl)-1,2,3,4-tetrahydronaphthalen-1-yl]amino}-2-hydroxypropyl)acetamide; |
| A6. | N—[(1S,2R)-3-{[1-acetyl-4-(3-isopropylphenyl)piperidin-4-yl]amino}-1-(3,5-difluorobenzyl)-2-hydroxypropyl]acetamide; |
| A7. | N—((1S,2R)-1-(3,5-difluorobenzyl)-2-hydroxy-3-{[4-(3-isopropylphenyl)-1-(methylsulfonyl)piperidin-4-yl]amino}propyl)acetamide; |
| A8. | N—((1R,2S)-1-[4-(benzyloxy)-3-fluorobenzyl]-3-{[(1S)-7-(2,2-dimethylpropyl)-1,2,3,4-tetrahydronaphthalen-1-yl]amino}-2-hydroxypropyl)acetamide; |
| A9. | N—[(1R,2S)-3-{[4-(3-tert-butylphenyl)tetrahydro-2H-pyran-4-yl]amino}-1-(3,5-difluorobenzyl)-2-hydroxypropyl]acetamide; |
| A10. | N—[(1R,2S)-1-(3,5-difluorobenzyl)-2-hydroxy-3-({1-[3-(trifluoromethyl)phenyl]cyclohexyl}amino)propyl]acetamide; |
| A11. | N—((1S,2R)-1-(3,5-difluorobenzyl)-3-{[(4R)-6-(2,2-dimethylpropyl)-3,4-dihydro-2H-chromen-4-yl]amino}-2-hydroxypropyl)-2-fluoroacetamide; |
| A12. | N—((1R,2S)-1-(3,5-difluorobenzyl)-2-hydroxy-3-{[4-(3-isopropoxyphenyl)tetrahydro-2H-pyran-4-yl]amino}propyl)-N'-phenylurea; |
| A13. | phenyl{(1R,2S)-1-(3,5-difluorobenzyl)-2-hydroxy-3-[(6-isopropoxy-1,1-dimethyl-3,4-dihydro-1H-isochromen-4-yl)amino]propyl}carbamate; |
| A14. | N—((1R,2S)-1-(3,5-difluorobenzyl)-2-hydroxy-3-{[1-(2-isobutyl-1,3-thiazol-5-yl)-1-methylethyl]amino}propyl)acetamide; |
| A15. | N—[(1S,2R)-3-({1-[3-(2-adamantyl)phenyl]cyclohexyl}amino)-1-(3,5-difluorobenzyl)-2-hydroxypropyl]acetamide; |
| A16. | N—[(1S,2R)-3-{[1-(3-cyclopentylphenyl)cyclopropyl]amino}-1-(3,5-difluorobenzyl)-2-hydroxypropyl]acetamide; |
| A17. | N—[(1S,2R)-3-{[1-(3-bicyclo[2.2.1]hept-2-ylphenyl)cyclopropyl]amino}-1-(3,5-difluorobenzyl)-2-hydroxypropyl]acetamide; |
| A18. | Ethyl 3-[3-(1-{[(2R,3S)-3-(acetylamino)-4-(3,5-difluorophenyl)-2-hydroxybutyl]amino}cyclohexyl)phenyl]propanoate; |
| A19. | N—[(1S,2R)-3-{[1-(3-sec-butylphenyl)cyclopropyl]amino}-1-(3,5-difluorobenzyl)-2-hydroxypropyl]acetamide; |
| A20. | N—((1S,2R)-1-(3,5-difluorobenzyl)-3-{[1-(3',5'-difluorobiphenyl-3-yl)cyclopropyl]amino}-2-hydroxypropyl)acetamide; |
| A21. | N—((1S,2R)-1-(3,5-difluorobenzyl)-3-{[5-(2,2-dimethylpropyl)-2-(2-propyl-1H-imidazol-1-yl)benzyl]amino}-2-hydroxypropyl)acetamide; |
| A22. | N—[(1S,2R)-3-{[1-(3-sec-butylphenyl)cyclohexyl]amino}-1-(3,5-difluorobenzyl)-2-hydroxypropyl]acetamide; |
| A23. | N—((1S,2R)-1-(3,5-difluorobenzyl)-2-hydroxy-3-({1-[3-(3-methylbutyl)phenyl]cyclohexyl}amino)propyl]acetamide; |
| A24. | N—((1S,2R)-1-(3,5-difluorobenzyl)-3-({1-[3-(1-ethylpropyl)phenyl]cyclohexyl}amino)-2-hydroxypropyl]acetamide; |
| A25. | N—[(1S,2R)-3-{[1-(3-cyclopentylphenyl)cyclohexyl]amino}-1-(3,5-difluorobenzyl)-2-hydroxypropyl]acetamide; |
| A26. | N—((1S,2R)-1-(3,5-difluorobenzyl)-2-hydroxy-3-{[1-(3-pent-4-en-1-ylphenyl)cyclohexyl]amino}propyl)acetamide; |
| B1. | N—((1S,2R)-1-(3,5-difluorobenzyl)-2-hydroxy-3-{[1-(3-pyridin-2-ylphenyl)cyclohexyl]amino}propyl)acetamide; |
| B2. | N—[(1S,2R)-1-(3,5-difluorobenzyl)-2-hydroxy-3-({1-[3-(3-methylpyridin-2-yl)phenyl]cyclohexyl}amino)propyl]acetamide; |
| B3. | N—[(1S,2R)-1-(3,5-difluorobenzyl)-2-hydroxy-3-({1-[3-(1,3-thiazol-2-yl)phenyl]cyclohexyl}amino)propyl]acetamide; |
| B4. | N—[(1S,2R)-1-(3,5-difluorobenzyl)-2-hydroxy-3-({1-[3-(3-methyl-2-thienyl)phenyl]cyclohexyl}amino)propyl]acetamide; |
| B5. | N—[(1S,2R)-1-(3,5-difluorobenzyl)-3-({1-[3-(2-fluorobenzyl)phenyl]cyclohexyl}amino)-2-hydroxypropyl]acetamide; |
| B6. | N—[(1S,2R)-1-(3,5-difluorobenzyl)-3-({1-[3-(4-fluorobenzyl)phenyl]cyclohexyl}amino)-2-hydroxypropyl]acetamide; |
| B7. | N—[(1R,2S)-3-{[(1S)-7-(2,2-dimethylpropyl)-1,2,3,4-tetrahydronaphthalen-1-yl]amino}-1-(3-fluoro-4-hydroxybenzyl)-2-hydroxypropyl]acetamide; and |
| B8. | N—((1S,2S)-1-(3,5-difluorobenzyl)-2-hydroxy-3-{[3-(3-isopropylphenyl)tetrahydro-2H-pyran-3-yl]amino}propyl)acetamide. |

EXAMPLE 136

The following compounds are prepared essentially according to the procedures set forth in the above examples and schemes.

| Ex. No. | Compound |
|---|---|
| A1. | (1S,2R)—N-[3-[1-(3-tert-Butyl-phenyl)-4-oxo-cyclohexylamino]-1-(3,5-difluoro-benzyl)-2-hydroxy-propyl]-acetamide; |
| A2. | (1S,2R)—N-[3-[5-(3-tert-Butyl-phenyl)-2-oxo-[1,3]oxazinan-5-ylamino]-1-(3,5-difluoro-benzyl)-2-hydroxy-propyl]-acetamide; |
| A3. | (1S,2R)—N-[3-[5-(3-tert-Butyl-phenyl)-2-oxo-hexahydro-pyrimidin-5-ylamino]-1-(3,5-difluoro-benzyl)-2-hydroxy-propyl]-acetamide; |
| A4. | (1S,2R)—N-[3-[1-(3-Bromo-5-tert-butyl-phenyl)-cyclohexylamino]-1-(3,5-difluoro-benzyl)-2-hydroxy-propyl]-acetamide; |
| A5. | (1S,2R)—N-[3-[1-(3-tert-Butyl-5-ethyl-phenyl)-cyclohexylamino]-1-(3,5-difluoro-benzyl)-2-hydroxy-propyl]-acetamide; |
| A6. | (1S,2R)—N-[3-[4-(3-tert-Butyl-5-ethyl-phenyl)-tetrahydropyran-4-ylamino]-1-(3,5-difluoro-benzyl)-2-hydroxypropyl]-acetamide; |
| A7. | (1S,2R)—N-[3-[4-(3-Bromo-5-tert-butyl-phenyl)-tetrahydropyran-4-ylamino]-1-(3,5-difluoro-benzyl)-2-hydroxypropyl]-acetamide; |
| A8. | (1S,2R)—N-[3-[1-(3-tert-Butyl-5-ethylphenyl)cyclopropylamino]-1-(3,5-difluorobenzyl)-2-hydroxypropyl]-acetamide; |
| A9. | (1S,2R)—N-[3-{1-[3-Bromo-5-(2,2-dimethyl-propyl)-phenyl]-cyclopropylamino}-1-(3,5-difluoro-benzyl)-2-hydroxy-propyl]-acetamide; |
| A10. | (1S,2R)—N-(1-(3,5-Difluorobenzyl)-3-{1-[5-(2,2-dimethylpropyl)-2-imidazol-1-yl-phenyl]-cyclopropylamino}-2-hydroxy-propyl)-acetamide; |
| A11. | (1S,2R)—N-{1-(3,5-Difluoro-benzyl)-3-[5-(2,2-dimethylpropyl)-2-(5-ethyl-imidazol-1-yl)-benzylamino]-2-hydroxypropyl}-acetamide; |
| A12. | (1S,2R)—N-[3-[3-Chloro-5-(2,2-dimethyl-propyl)-2-imidazol-1-yl-benzylamino]-1-(3,5-difluoro-benzyl)-2-hydroxy-propyl]-acetamide; |
| A13. | (1S,2R)—N-{1-(3,5-Difluoro-benzyl)-3-[5-(2,2-dimethyl-propyl)-2-tetrazol-1-yl-benzylamino]-2-hydroxy-propyl}-acetamide; |

-continued

| Ex. No. | Compound |
|---|---|
| A14. | (1S,2R)—N-{1-(3,5-Difluoro-benzyl)-3-[5-(2,2-dimethyl-propyl)-2-oxazol-5-yl-benzylamino]-2-hydroxy-propyl}-acetamide; |
| A15. | (1S,2R)—N-{1-(3,5-Difluoro-benzyl)-3-[5-(2,2-dimethyl-propyl)-2-oxazol-2-yl-benzylamino]-2-hydroxy-propyl}-acetamide; |
| A16. | (1S,2R)—N-{1-(3,5-Difluoro-benzyl)-3-[6-(2,2-dimethyl-propyl)-1-methyl-1,2,3,4-tetrahydro-quinolin-4-ylamino]-2-hydroxy-propyl}-acetamide; |
| A17. | (1S,2R)—N-{1-(3,5-Difluoro-benzyl)-3-[6-(2,2-dimethyl-propyl)-thiochroman-4-ylamino]-2-hydroxy-propyl}-acetamide; |
| A18. | (1S,2R)—N-{1-(3,5-Difluoro-benzyl)-3-[6-(2,2-dimethyl-propyl)-8-ethyl-chroman-4-ylamino]-2-hydroxy-propyl}-acetamide; |
| A19. | (1S,2R)—N-[3-[8-Bromo-6-(2,2-dimethylpropyl)-chroman-4-ylamino]-1-(3,5-difluoro-benzyl)-2-hydroxypropyl]-acetamide; |
| A20. | (1S,2R)—N-{1-(3,5-Difluoro-benzyl)-3-[6-(2,2-dimethyl-propyl)-2-oxo-chroman-4-ylamino]-2-hydroxy-propyl}-acetamide; |
| A21. | (1S,2R)—N-{1-(3,5-Difluoro-benzyl)-3-[7-(2,2-dimethyl-propyl)-4-oxo-1,2,3,4-tetrahydro-naphthalen-1-ylamino]-2-hydroxy-propyl}-acetamide; |
| A22. | (1S,2R)—N-{1-(3,5-Difluoro-benzyl)-3-[6-(2,2-dimethyl-propyl)-1-oxo-1λ⁴-thiochroman-4-ylamino]-2-hydroxypropyl}-acetamide; |
| A23. | (1S,2R)—N-{1-(3,5-Difluoro-benzyl)-3-[6-(2,2-dimethyl-propyl)-1,1-dioxo-1λ⁶-thiochroman-4-ylamino]-2-hydroxy-propyl}-acetamide; |
| A24. | N—((1S,2R)-1-(3,5-difluorobenzyl)-3-{[7-(2,2-dimethylpropyl)-5-ethyl-1,2,3,4-tetrahydronaphthalen-1-yl]amino}-2-hydroxypropyl)acetamide; |
| A25. | N—((1S,2R)-1-(3,5-difluorobenzyl)-3-{[(4R)-6-(2,2-dimethylpropyl)-3,4-dihydro-2H-chromen-4-yl]amino}-2-hydroxypropyl)acetamide; |
| A26. | N—((1S,2R)-1-(3,5-difluorobenzyl)-3-{[(1S)-7-(2,2-dimethylpropyl)-1,2,3,4-tetrahydronaphthalen-1-yl]amino}-2-hydroxypropyl)acetamide; |
| B1. | N—[(1S,2R)-3-{[1-(3-tert-butylphenyl)cyclohexyl]amino}-1-(3,5-difluorobenzyl)-2-hydroxypropyl]acetamide; |
| B2. | N—[(1S,2R)-3-{[4-(3-tert-butylphenyl)tetrahydro-2H-pyran-4-yl]amino}-1-(3,5-difluorobenzyl)-2-hydroxypropyl]acetamide; |
| B3. | N—((1S,2R)-1-(3,5-difluorobenzyl)-3-{[6-(2,2-dimethylpropyl)-1,2,3,4-tetrahydroquinolin-4-yl]amino}-2-hydroxypropyl)acetamide; |
| B4. | N—((1S,2R)-1-(3,5-difluorobenzyl)-2-hydroxy-3-{[1-(3-isopropylphenyl)-4-oxocyclohexyl]amino}propyl)acetamide; |
| B5. | N—[(1S,2R)-3-{[(4S)-6-(2,2-dimethylpropyl)-3,4-dihydro-2H-chromen-4-yl]amino}-1-(3-fluorobenzyl)-2-hydroxypropyl]acetamide; |
| B6. | N—((1S,2R)-1-(3,5-difluorobenzyl)-3-{[5-(2,2-dimethylpropyl)-2-(1H-imidazol-1-yl)benzyl]amino}-2-hydroxypropyl)acetamide; |
| B7. | N—((1S,2R)-1-(3,5-difluorobenzyl)-3-{[7-(2,2-dimethylpropyl)-1-methyl-1,2,3,4-tetrahydronaphthalen-1-yl]amino}-2-hydroxypropyl)acetamide; |
| B8. | N—((1S,2R)-1-(3,5-difluorobenzyl)-3-{[6-(2,2-dimethylpropyl)-4-methyl-3,4-dihydro-2H-chromen-4-yl]amino}-2-hydroxypropyl)acetamide; |
| B9. | N—((1S,2R)-1-(3-fluoro-4-hydroxybenzyl)-2-hydroxy-3-{[1-(3-isopropylphenyl)cyclohexyl]amino}propyl)acetamide; |
| B10. | N—((1S,2R)-1-(3,5-difluorobenzyl)-2-hydroxy-3-{[1-(3-isopropylphenyl)cyclohexyl]amino}propyl)-2-fluoroacetamide; |
| B11. | N—((1S,2R)-1-[3-(allyloxy)-5-fluorobenzyl]-2-hydroxy-3-{[1-(3-isopropylphenyl)cyclohexyl]amino}propyl)acetamide; |
| B12. | N—[(1S,2R)-1-(3,5-difluorobenzyl)-3-({1-[3-(2,2-dimethylpropyl)phenyl]-1-methylethyl}amino)-2-hydroxypropyl]-2-fluoroacetamide; |
| B13. | N—((1S,2R)-1-(3,5-difluorobenzyl)-3-{[(1S)-7-(2,2-dimethylpropyl)-1,2,3,4-tetrahydronaphthalen-1-yl]amino}-2-hydroxypropyl)-2-fluoroacetamide; |
| B14. | N—[(1S,2R)-1-(3,5-difluorobenzyl)-2-hydroxy-3-({1-[3-(3-thienyl)phenyl]cyclohexyl}amino)propyl]acetamide; |
| B15 | N—[(1S,2R)-1-(3,5-difluorobenzyl)-3-({1-[4-(2,2-dimethylpropyl)pyridin-2-yl]cyclopropyl}amino)-2-hydroxypropyl]acetamide |
| B16 | N—((1R,2S)-1-(3,5-difluorobenzyl)-2-hydroxy-3-{[(1S)-7-propyl-1,2,3,4-tetrahydronaphthalen-1-yl]amino}propyl)acetamide |
| B17 | N—((1S,2R)-1-(3,5-difluorobenzyl)-2-hydroxy-3-{[1-(3-isobutylphenyl)cyclohexyl]amino}propyl)acetamide |
| B18 | N—((1S,2R)-2-hydroxy-1-(4-hydroxybenzyl)-3-{[1-(3-isopropylphenyl)cyclohexyl]amino}propyl)acetamide |
| B19 | N—((1R,2S)-1-(3,5-difluorobenzyl)-3-{[(1S)-7-ethyl-1,2,3,4-tetrahydronaphthalen-1-yl]amino}-2-hydroxypropyl)-2-ethoxyacetamide |
| B20 | N—((1S,2R)-1-(3,5-difluorobenzyl)-3-{[(1R)-7-ethyl-1,2,3,4-tetrahydronaphthalen-1-yl]amino}-2-hydroxypropyl)-2,2-difluoroacetamide |

EXAMPLE 137

The following compounds are prepared essentially according to the procedures set forth in the above examples and schemes.

| Ex. No. | Compound |
|---|---|
| A1. | N-{1-(3,5-Difluoro-benzyl)-2-hydroxy-3-[1-(3-isopropyl-phenyl)-cyclobutylamino]-propyl}-acetamide; |
| A2. | N-{1-(3,5-Difluoro-benzyl)-2-hydroxy-3-[1-(3-isopropyl phenyl)-cyclopentylamino]-propyl}-acetamide; |
| A3. | N-{1-(3,5-Difluoro-benzyl)-2-hydroxy-3-[3-(3-isopropyl-phenyl)-bicyclo[3.1.0]hex-3-ylamino]-propyl}-acetamide; |
| A4. | N-{1-(3,5-Difluoro-benzyl)-2-hydroxy-3-[3-(3-isopropyl-phenyl)-6-aza-bicyclo[3.1.0]hex-3-ylamino]-propyl}-acetamide; |
| A5. | N-{1-(3,5-Difluoro-benzyl)-2-hydroxy-3-[3-(3-isopropyl-phenyl)-6-methyl-6-aza-bicyclo[3.1.0]hex-3-ylamino]-propyl}-acetamide; |
| A6. | N-[3-[6-Acetyl-3-(3-isopropyl-phenyl)-6-aza-bicyclo[3.1.0]hex-3-ylamino]-1-(3,5-difluoro-benzyl)-2-hydroxy-propyl]-acetamide; |
| A7. | N-{1-(3,5-Difluoro-benzyl)-2-hydroxy-3-[3-(3-isopropyl-phenyl)-6-methanesulfonyl-6-aza-bicyclo[3.1.0]hex-3-ylamino]-propyl}-acetamide; |
| A8. | N-{1-(3,5-Difluoro-benzyl)-2-hydroxy-3-[1-(3-isopropyl-phenyl)-2,2,4,4-tetramethyl-3-oxo-cyclobutylamino]-propyl}-acetamide; |
| A9. | N-{1-(3,5-Difluoro-benzyl)-2-hydroxy-3-[3-hydroxy-1-(3-isopropyl-phenyl)-2,2,4,4-tetramethyl-cyclobutylamino]-propyl}-acetamide; |
| A10. | N-{1-(3,5-Difluoro-benzyl)-2-hydroxy-3-[5-(3-isopropyl-phenyl)-octahydro-cyclopenta[c]pyrrol-5-ylamino]-propyl}-acetamide; |
| A11. | N-{1-(3,5-Difluoro-benzyl)-2-hydroxy-3-[5-(3-isopropyl-phenyl)-2-methyl-octahydro-cyclopenta[c]pyrrol-5-ylamino]-propyl}-acetamide; |
| A12. | N-[3-[2-Acetyl-5-(3-isopropyl-phenyl)-octahydro-cyclopenta[c]pyrrol-5-ylamino]-1-(3,5-difluoro-benzyl)-2-hydroxy-propyl]-acetamide; |
| A13. | N-{1-(3,5-Difluoro-benzyl)-2-hydroxy-3-[5-(3-isopropyl-phenyl)-2-methanesulfonyl-octahydro-cyclopenta[c]pyrrol-5-ylamino]-propyl}-acetamide; |
| A14. | N-{1-(3,5-Difluoro-benzyl)-2-hydroxy-3-[2-(3-isopropyl-phenyl)-5-oxo-octahydro-pentalen-2-ylamino]-propyl}-acetamide; |

| Ex. No. | Compound |
|---|---|
| A15. | N-{1-(3,5-Difluoro-benzyl)-2-hydroxy-3-[5-hydroxy-2-(3-isopropyl-phenyl)-octahydro-pentalen-2-ylamino]-propyl}-acetamide; |
| A16. | N-{1-(3,5-Difluoro-benzyl)-2-hydroxy-3-[2-(3-isopropyl-phenyl)-3a,6a-dimethyl-5-oxo-octahydro-pentalen-2-ylamino]-propyl}-acetamide; |
| A17. | N-{1-(3,5-Difluoro-benzyl)-2-hydroxy-3-[5-hydroxy-2-(3-isopropyl-phenyl)-3a,6a-dimethyl-octahydro-pentalen-2-ylamino]-propyl}-acetamide; |
| A18. | N-{1-(3,5-Difluoro-benzyl)-2-hydroxy-3-[2-(3-isopropyl-phenyl)-5-oxo-cyclohexylamino]-propyl}-acetamide; |
| A19. | N-{1-(3,5-Difluoro-benzyl)-2-hydroxy-3-[5-hydroxy-2-(3-isopropyl-phenyl)-5-methyl-cyclohexylamino]-propyl}-acetamide; |
| A20. | N-{1-(3,5-Difluoro-benzyl)-2-hydroxy-3-[2-(3-isopropyl-phenyl)-5-methanesulfonylamino-cyclohexylamino]-propyl}-acetamide; |
| A21. | N-[3-[5-Acetylamino-2-(3-isopropyl-phenyl)-cyclohexylamino]-1-(3,5-difluoro-benzyl)-2-hydroxy-propyl]-acetamide; |
| A22. | N-{1-(3,5-Difluoro-benzyl)-2-hydroxy-3-[2-(3-isopropyl-phenyl)-4-oxo-cyclohexylamino]-propyl}-acetamide; |
| A23. | N-{1-(3,5-Difluoro-benzyl)-2-hydroxy-3-[4-hydroxy-2-(3-isopropyl-phenyl)-4-methyl-cyclohexylamino]-propyl}-acetamide; |
| A24. | N-[3-[4-Acetylamino-2-(3-isopropyl-phenyl)-cyclohexylamino]-1-(3,5-difluoro-benzyl)-2-hydroxy-propyl]-acetamide; |
| A25. | N-{1-(3,5-Difluoro-benzyl)-2-hydroxy-3-[2-(3-isopropyl-phenyl)-4-methanesulfonylamino-cyclohexylamino]-propyl}-acetamide; |
| A26. | N-{1-(3,5-Difluoro-benzyl)-2-hydroxy-3-[2-(3-isopropyl-phenyl)-4-oxo-cyclopentylamino]-propyl}-acetamide; |
| B1. | N-{1-(3,5-Difluoro-benzyl)-2-hydroxy-3-[4-hydroxy-2-(3-isopropyl-phenyl)-4-methyl-cyclopentylamino]-propyl}-acetamide; |
| B2. | N-[3-[4-Acetylamino-2-(3-isopropyl-phenyl)-cyclopentylamino]-1-(3,5-difluoro-benzyl)-2-hydroxy-propyl]-acetamide; |
| B3. | N-{1-(3,5-Difluoro-benzyl)-2-hydroxy-3-[2-(3-isopropyl-phenyl)-4-methanesulfonylamino-cyclopentylamino]-propyl}-acetamide; |
| B4. | N-{1-(3,5-Difluoro-benzyl)-3-[4-(2,2-dimethyl-propyl)-pyridin-3-ylamino]-2-hydroxy-propyl}-acetamide; |
| B5. | N-(1-(3,5-Difluoro-benzyl)-3-{[4-(2,2-dimethyl-propyl)-pyridin-3-ylmethyl]-amino}-2-hydroxy-propyl)-acetamide; |
| B6. | N-[1-(3,5-Difluoro-benzyl)-2-hydroxy-3-(5-isobutyl-2-piperazin-1-yl-benzylamino)-propyl]-acetamide; |
| B7. | N-{1-(3,5-Difluoro-benzyl)-2-hydroxy-3-[5-isobutyl-2-(4-methyl-piperazin-1-yl)-benzylamino]-propyl}-acetamide; |
| B8. | N-[3-[2-(4-Acetyl-piperazin-1-yl)-5-isobutyl-benzylamino]-1-(3,5-difluoro-benzyl)-2-hydroxy-propyl]-acetamide; |
| B9. | N-{1-(3,5-Difluoro-benzyl)-2-hydroxy-3-[5-isobutyl-2-(4-methanesulfonyl-piperazin-1-yl)-benzylamino]-propyl}-acetamide; |
| B10. | N-{1-(3,5-Difluoro-benzyl)-3-[4-(2,2-dimethyl-propyl)-piperidin-3-ylamino]-2-hydroxy-propyl}-acetamide; |
| B11. | N-(1-(3,5-Difluoro-benzyl)-3-{[4-(2,2-dimethyl-propyl)-piperidin-3-ylmethyl]-amino}-2-hydroxy-propyl)-acetamide; |
| B12. | N-[3-[1-Acetyl-4-(2,2-dimethyl-propyl)-piperidin-3-ylamino]-1-(3,5-difluoro-benzyl)-2-hydroxy-propyl]-acetamide; |
| B13. | N-[3-{[1-Acetyl-4-(2,2-dimethyl-propyl)-piperidin-3-ylmethyl]-amino}-1-(3,5-difluoro-benzyl)-2-hydroxy-propyl]-acetamide; |
| B14. | N-{1-(3,5-Difluoro-benzyl)-3-[4-(2,2-dimethyl-propyl)-1-methanesulfonyl-piperidin-3-ylamino]-2-hydroxy-propyl}-acetamide; |
| B15. | N-(1-(3,5-Difluoro-benzyl)-3-{[4-(2,2-dimethyl-propyl)-1-methanesulfonyl-piperidin-3-ylmethyl]-amino}-2-hydroxy-propyl)-acetamide; |
| B16. | N-[1-(3,5-Difluoro-benzyl)-2-hydroxy-3-(6-isopropyl-2-oxo-1,2,3,4-tetrahydro-quinolin-4-ylamino)-propyl]-acetamide; |
| B17. | N-[1-(3,5-Difluoro-benzyl)-2-hydroxy-3-(5-isopropyl-2-oxo-2,3-dihydro-1H-indol-3-ylamino)-propyl]-acetamide; |
| B18. | N-[1-(3,5-Difluoro-benzyl)-2-hydroxy-3-(7-isopropyl-3-oxo-1,2,3,4-tetrahydro-naphthalen-1-ylamino)-propyl]-acetamide; |
| B19. | N-[1-(3,5-Difluoro-benzyl)-2-hydroxy-3-(3-hydroxy-7-isopropyl-3-methyl-1,2,3,4-tetrahydro-naphthalen-1-ylamino)-propyl]-acetamide; |
| B20. | N-[3-(3-Acetylamino-7-isopropyl-1,2,3,4-tetrahydro-naphthalen-1-ylamino)-1-(3,5-difluoro-benzyl)-2-hydroxy-propyl]-acetamide; |
| B21. | N-[1-(3,5-Difluoro-benzyl)-2-hydroxy-3-(7-isopropyl-3-methanesulfonylamino-1,2,3,4-tetrahydro-naphthalen-1-ylamino)-propyl]-acetamide; |
| B22. | N-[1-(3,5-Difluoro-benzyl)-2-hydroxy-3-(6-isopropyl-2-oxo-indan-1-ylamino)-propyl]-acetamide; |
| B23. | N-[1-(3,5-Difluoro-benzyl)-2-hydroxy-3-(2-hydroxy-6-isopropyl-2-methyl-indan-1-ylamino)-propyl]-acetamide; |
| B24. | N-[3-(2-Acetylamino-6-isopropyl-indan-1-ylamino)-1-(3,5-difluoro-benzyl)-2-hydroxy-propyl]-acetamide; |
| B25. | N-[1-(3,5-Difluoro-benzyl)-2-hydroxy-3-(6-isopropyl-2-methanesulfonylamino-indan-1-ylamino)-propyl]-acetamide; |
| B26. | N-[1-(3,5-Difluoro-benzyl)-2-hydroxy-3-(5-isobutyl-2-piperidin-4-yl-benzylamino)-propyl]-acetamide; |
| C1. | N-[3-[2-(1-Acetyl-piperidin-4-yl)-5-isobutyl-benzylamino]-1-(3,5-difluoro-benzyl)-2-hydroxy-propyl]-acetamide; |
| C2. | N-{1-(3,5-Difluoro-benzyl)-2-hydroxy-3-[5-isobutyl-2-(1-methanesulfonyl-piperidin-4-yl)-benzylamino]-propyl}-acetamide; |
| C3. | N-{1-(3,5-Difluoro-benzyl)-3-[5-(2,2-dimethyl-propyl)-2-piperidin-4-yl-benzylamino]-2-hydroxy-propyl}-acetamide; |
| C4. | N-[3-[2-(1-Acetyl-piperidin-4-yl)-5-(2,2-dimethyl-propyl)-benzylamino]-1-(3,5-difluoro-benzyl)-2-hydroxy-propyl]-acetamide |
| C5. | N-{1-(3,5-Difluoro-benzyl)-3-[5-(2,2-dimethyl-propyl)-2-(1-methanesulfonyl-piperidin-4-yl)-benzylamino]-2-hydroxy-propyl}-acetamide; |
| C6. | N-[1-(3,5-Difluoro-benzyl)-2-hydroxy-3-(6-isobutyl-2,2-dioxo-1,2,3,4-tetrahydro-2λ$^6$-benzo[c][1,2]thiazin-4-ylamino)-propyl]-acetamide; |
| C7. | N-{1-(3,5-Difluoro-benzyl)-3-[6-(2,2-dimethyl-propyl)-1-methyl-2,2-dioxo-1,2,3,4-tetrahydro-2λ$^6$-benzo[c][1,2]thiazin-4-ylamino]-2-hydroxy-propyl}-acetamide; |
| C8. | N-[3-[6-(2,2-Dimethyl-propyl)-2,2-dioxo-1,2,3,4-tetrahydro-2λ$^6$-benzo[c][1,2]thiazin-4-ylamino]-1-(3-fluoro-4-hydroxy-benzyl)-2-hydroxy-propyl}-acetamide; |
| C9. | N-{1-(3,5-Difluoro-benzyl)-3-[5-(2,2-dimethyl-propyl)-2-methanesulfonylamino-benzylamino]-2-hydroxy-propyl}-acetamide; |
| C10. | N-[3-[2-Benzenesulfonylamino-5-(2,2-dimethyl-propyl)-benzylamino]-1-(3,5-difluoro-benzyl)-2-hydroxy-propyl]-acetamide; |
| C11. | N-{1-(3,5-Difluoro-benzyl)-3-[5-(2,2-dimethyl-propyl)-2-phenylsulfamoyl-benzylamino]-2-hydroxy-propyl}-acetamide; |
| C12. | N-{1-(3,5-Difluoro-benzyl)-3-[5-(2,2-dimethyl-propyl)-2-methylsulfamoyl-benzylamino]-2-hydroxy-propyl}-acetamide; |
| C13. | N-{1-(3,5-Difluoro-benzyl)-3-[5-(2,2-dimethyl-propyl)-2-(2-oxo-piperidin-4-yl)-benzylamino]-2-hydroxy-propyl}-acetamide; |
| C14. | N-{1-(3,5-Difluoro-benzyl)-3-[5-(2,2-dimethyl-propyl)-2-(1-methyl-2-oxo-piperidin-4-yl)-benzylamino]-2-hydroxy-propyl}-acetamide; |
| C15. | N-[3-[6-(2,2-Dimethyl-propyl)-chroman-4-ylamino]-1-(3-fluoro-4-hydroxy-benzyl)-2-hydroxy-propyl]-acetamide; |
| C16. | N-[3-[7-(2,2-Dimethyl-propyl)-1,2,3,4-tetrahydro-naphthalen-1-ylamino]-1-(3-fluoro-4-hydroxy-benzyl)-2-hydroxy-propyl]-acetamide; |
| C17. | N-[3-[7-(2,2-Dimethyl-propyl)-1,2,3,4-tetrahydro-naphthalen-1-ylamino]-2-hydroxy-1-(5-hydroxy-pyridin-2-ylmethyl)-propyl]-acetamide; |
| C18. | N-[3-[6-(2,2-Dimethyl-propyl)-chroman-4-ylamino]-2-hydroxy-1-(5-hydroxy-pyridin-2-ylmethyl)-propyl]-acetamide; |

| Ex. No. | Compound |
|---|---|
| C19. | N-[3-[4-(3-tert-Butyl-phenyl)-tetrahydro-pyran-4-ylamino]-1-(3,5-difluoro-benzyl)-2-hydroxy-butyl]-acetamide; |
| C20. | N-[3-[4-(3-tert-Butyl-phenyl)-tetrahydro-pyran-4-ylamino]-1-(3,5-difluoro-benzyl)-2,4-dihydroxy-butyl]-acetamide; |
| C21. | N-[3-(5-tert-Butyl-2-imidazol-1-yl-benzylamino)-1-(3,5-difluoro-benzyl)-2-hydroxy-butyl]-acetamide; |
| C22. | N-[3-(5-tert-Butyl-2-imidazol-1-yl-benzylamino)-1-(3,5-difluoro-benzyl)-2,4-dihydroxy-butyl]-acetamide; |
| C23. | N—{(1S,2R)-1-(3,5-Difluoro-benzyl)-2-hydroxy-3-[4-(3-isopropyl-phenyl)-tetrahydro-thiopyran-4-ylamino]-propyl}-acetamide; |
| C24. | N—{(1S,2R)-1-(3,5-Difluoro-benzyl)-2-hydroxy-3-[4-(3-isopropyl-phenyl)-1,1-dioxo-tetrahydro-thiopyran-4-ylamino]-propyl}-acetamide; |
| C25. | N—{(1S,2R)-1-(3,5-Difluoro-benzyl)-2-hydroxy-3-[4-(3-isopropyl-phenyl)-1-oxo-tetrahydro-thiopyran-4-ylamino]-propyl}-acetamide; |
| C26. | N—{(1S,2R)-1-(3,5-Difluoro-benzyl)-2-hydroxy-3-[4-(3-isopropyl-phenyl)-1-methanesulfonyl-piperidin-4-ylamino]-propyl}-acetamide; |
| D1. | N—[(1S,2R)-3-[1-Acetyl-4-(3-isopropyl-phenyl)-piperidin-4-ylamino]-1-(3,5-difluoro-benzyl)-2-hydroxy-propyl]-acetamide; |
| D2. | N—{(1S,2R)-1-(3,5-Difluoro-benzyl)-2-hydroxy-3-[4-(3-isopropyl-phenyl)-piperidin-4-ylamino]-propyl}-acetamide; |
| D3. | N—{(1S,2R)-1-(3,5-Difluoro-benzyl)-2-hydroxy-3-[4-(3-isopropyl-phenyl)-1-trifluoroacetyl-piperidin-4-ylamino]-propyl}-acetamide; |
| D4. | N—{(1S,2R)-1-(3,5-Difluoro-benzyl)-2-hydroxy-3-[4-(3-isopropoxy-phenyl)-tetrahydro-pyran-4-ylamino]-propyl}-acetamide; |
| D5. | N—{(1S,2R)-1-(3,5-Difluoro-benzyl)-2-hydroxy-3-[4-(3-isopropyl-phenyl)-1,1-dimethyl-piperidin-4-ylamino]-propyl}-acetamide; |
| D6. | N—{(1S,2R)-1-(3,5-Difluoro-benzyl)-3-[1-formyl-4-(3-isopropyl-phenyl)-piperidin-4-ylamino]-2-hydroxy-propyl}-acetamide; |
| D7. | N—{(1S,2R)-1-(3,5-Difluoro-benzyl)-3-[1-ethyl-4-(3-isopropyl-phenyl)-piperidin-4-ylamino]-2-hydroxy-propyl}-acetamide; |
| D8. | N-[3-[4-(3-tert-Butyl-phenyl)-tetrahydro-pyran-4-ylamino]-1-(3,5-difluoro-benzyl)-2-hydroxy-propyl]-acetamide; |
| D9. | N—{(1S,2R)-1-(3,5-Difluoro-4-hydroxy-benzyl)-2-hydroxy-3-[1-(3-isopropyl-phenyl)-cyclohexylamino]-propyl}-acetamide; |
| D10. | N—{(1S,2R)-1-(3,5-Difluoro-benzyl)-2-hydroxy-3-[1-(2-isobutyl-thiazol-5-yl)-1-methyl-ethylamino]-propyl}-acetamide; |
| D11. | N—{(1S,2R)-1-(3,5-Difluoro-benzyl)-2-hydroxy-3-[3-(3-isopropoxy-phenyl)-tetrahydro-pyran-3-ylamino]-propyl}-acetamide; |
| D12. | N—{(1S,2R)-1-(3,5-Difluoro-benzyl)-2-hydroxy-3-[3-(3-isopropyl-phenyl)-tetrahydro-pyran-3-ylamino]-propyl}-acetamide; |
| D13. | N—{(1S,2R)-1-(3,5-Difluoro-benzyl)-2-hydroxy-3-[4-(3-isopropoxy-phenyl)-tetrahydro-pyran-4-ylamino]-propyl}-2-fluoro-acetamide; |
| D14. | N—{(1S,2R)-1-(3,5-Difluoro-benzyl)-3-[6-(2,2-dimethyl-propyl)-chroman-4-ylamino]-2-hydroxy-propyl}-2-fluoro-acetamide; |
| D15. | N—{(1S,2R)-1-(3,5-Difluoro-benzyl)-3-{1-[2-(2,2-dimethyl-propyl)-thiazol-5-yl]-1-methyl-ethylamino}-2-hydroxy-propyl)-acetamide; |
| D16. | N—{(1S,2R)-1-(3,5-Difluoro-benzyl)-3-{1-[3-(2,2-dimethyl-propyl)-phenyl]-1-methyl-ethylamino}-2-hydroxy-propyl)-2-fluoro-acetamide; |
| D17. | N—{(1S,2R)-1-(3,5-Difluoro-benzyl)-2-hydroxy-3-[4-(3-isopropyl-phenyl)-tetrahydro-pyran-4-ylamino]-propyl}-acetamide; |
| D18. | N—{(1S,2R)-1-(3,5-Difluoro-benzyl)-2-hydroxy-3-[4-(3-isopropyl-phenyl)-1-methyl-piperidin-4-ylamino]-propyl}-acetamide; |
| D19. | N—{(1S,2R)-1-(3,5-Difluoro-benzyl)-3-[1-ethanesulfonyl-4-(3-isopropyl-phenyl)-piperidin-4-ylamino]-2-hydroxy-propyl}-acetamide; |
| D20. | N—{(1S,2R)-1-(3,5-Difluoro-benzyl)-3-[1-propanesulfonyl-4-(3-isopropyl-phenyl)-piperidin-4-ylamino]-2-hydroxy-propyl}-acetamide; |
| D21. | N—{(1S,2R)-1-(3,5-Difluoro-benzyl)-3-[2-propanesulfonyl-4-(3-isopropyl-phenyl)-piperidin-4-ylamino]-2-hydroxy-propyl}-acetamide; |
| D22. | N—[(1S,2R)-3-[4-(3-tert-Butyl-phenyl)-1-ethanesulfonyl-piperidin-4-ylamino]-1-(3,5-difluoro-benzyl)-2-hydroxy-propyl]-acetamide; |
| D23. | N—[(1S,2R)-3-[4-(3-tert-Butyl-phenyl)-1-methanesulfonyl-piperidin-4-ylamino]-1-(3,5-difluoro-benzyl)-2-hydroxy-propyl]-acetamide; |
| D24. | 4-[(2R,3S)-3-Acetylamino-4-(3,5-difluoro-phenyl)-2-hydroxy-butylamino]-4-(3-tert-butyl-phenyl)-piperidine-1-carboxylic acid amide; |
| D25. | 4-[(2R,3S)-3-Acetylamino-4-(3,5-difluoro-phenyl)-2-hydroxy-butylamino]-4-(3-tert-butyl-phenyl)-piperidine-1-carboxylic acid methylamide; |
| D26. | 4-[(2R,3S)-3-Acetylamino-4-(3,5-difluoro-phenyl)-2-hydroxy-butylamino]-4-(3-tert-butyl-phenyl)-piperidine-1-carboxylic acid methyl ester; |
| E1. | N—[(1S,2R)-3-[(4S)-4-(3-tert-Butyl-phenyl)-1-methanesulfonyl-azepan-4-ylamino]-1-(3,5-difluoro-benzyl)-2-hydroxy-propyl]-acetamide; |
| E2. | N—[(1S,2R)-3-[(4R)-4-(3-tert-Butyl-phenyl)-1-methanesulfonyl-azepan-4-ylamino]-1-(3,5-difluoro-benzyl)-2-hydroxy-propyl]-acetamide; |
| E3. | N—[(1S,2R)-3-[(4R)-4-(3-tert-Butyl-phenyl)-azepan-4-ylamino]-1-(3,5-difluoro-benzyl)-2-hydroxy-propyl]-acetamide; and |
| E4. | N—[(1S,2R)-3-[(4S)-4-(3-tert-Butyl-phenyl)-azepan-4-ylamino]-1-(3,5-difluoro-benzyl)-2-hydroxy-propyl]-acetamide. |

EXAMPLE 138

The following compounds are prepared essentially according to the procedures set forth in the above examples and schemes.

| Ex. No. | Compound |
|---|---|
| A1. | N—[(1S,2R)-3-[(3-bromobenzyl)amino]-1-(3,5-difluorobenzyl)-2-hydroxypropyl]acetamide; |
| A2. | N—((1S,2R)-1-(3,5-difluorobenzyl)-2-hydroxy-3-{[(4R)-6-isopropyl-2,2-dioxido-3,4-dihydro-1H-isothiochromen-4-yl]amino}propyl)acetamide; |
| A3. | N—((1S,2R)-1-(3,5-difluorobenzyl)-2-hydroxy-3-{[(4S)-6-isopropyl-2,2-dioxido-3,4-dihydro-1H-isothiochromen-4-yl]amino}propyl)acetamide; |
| A4. | N—{(1S,2R)-1-(3,5-difluorobenzyl)-3-[(6-ethyl-2,2-dioxido-3,4-dihydro-1H-isothiochromen-4-yl)amino]-2-hydroxypropyl}acetamide; |
| A5. | N—{(1S,2R)-1-(3,5-difluorobenzyl)-3-[(6-ethyl-2,2-dioxido-3,4-dihydro-1H-isothiochromen-4-yl)amino]-2-hydroxypropyl}acetamide; |
| A6. | N—{(1S,2R)-3-{[1-(3-bromophenyl)cyclopropyl]amino}-1-(3,5-difluorobenzyl)-2-hydroxypropyl]acetamide hydrochloride; |
| A7. | methyl 3-{[(2R,3S)-3-(acetylamino)-4-(3,5-difluorophenyl)-2-hydroxybutyl]amino}-3-(3-bromophenyl)propanoate; |
| A8. | N—{(1S,2R)-1-(3,5-difluorobenzyl)-3-[(3-ethylbenzyl)amino]-2-hydroxypropyl}acetamide; |
| A9. | methyl 3-{[(2R,3S)-3-(acetylamino)-4-(3,5-difluorophenyl)-2-hydroxybutyl]amino}-3-(3-ethylphenyl)propanoate; |

| Ex. No. | Compound |
|---|---|
| A10. | 3-{[(2R,3S)-3-(acetylamino)-4-(3,5-difluorophenyl)-2-hydroxybutyl]amino}-3-(3-ethylphenyl)propanoic acid; |
| A11. | N—((1S,2R)-1-(3,5-difluorobenzyl)-3-{[1-(3-ethylphenyl)-3-hydroxypropyl]amino}-2-hydroxypropyl)acetamide; |
| A12. | N—{(1S,2R)-1-(3,5-difluorobenzyl)-2-hydroxy-3-[(1S)-1,2,3,4-tetrahydronaphthalen-1-ylamino]propyl}acetamide; |
| A13. | N—((1S,2R)-1-(3,5-difluorobenzyl)-3-[(2,2-dioxido-3,4-dihydro-1H-isothiochromen-4-yl)amino]-2-hydroxypropyl}acetamide; |
| A14. | N-[1-(3,5-Difluoro-benzyl)-3-(6-ethyl-2,2-dioxo-2λ$^6$-isothiochroman-4-ylamino)-2-hydroxy-propyl]-2-methylamino-acetamide; |
| A15. | N—{(1S,2R)-1-(3,5-difluorobenzyl)-2-hydroxy-3-[(3-iodobenzyl)amino]propyl}acetamide; |
| A16. | methyl 3-{[(2R,3S)-3-(acetylamino)-4-(3,5-difluorophenyl)-2-hydroxybutyl]amino}-3-(3-iodophenyl)propanoate; |
| A17. | methyl 3-{[(2R,3S)-3-(acetylamino)-4-(3,5-difluorophenyl)-2-hydroxybutyl]amino}-3-[3-(3-hydroxyprop-1-ynyl)phenyl]propanoate; |
| A18. | N—((1S,2R)-1-(3,5-difluorobenzyl)-2-hydroxy-3-{[3-hydroxy-1-(3-iodophenyl)propyl]amino}propyl)acetamide; |
| A19. | methyl 3-{[(2R,3S)-3-(acetylamino)-4-(3,5-difluorophenyl)-2-hydroxybutyl]amino}-3-[3-(3-hydroxypropyl)phenyl]propanoate; |
| A20. | N—{(1S,2R)-1-(3,5-difluorobenzyl)-2-hydroxy-3-[(7-methoxy-1,2,3,4-tetrahydronaphthalen-1-yl)amino]propyl}acetamide; |
| A21. | 2-Amino-N-[1-(3,5-difluoro-benzyl)-3-(6-ethyl-2,2-dioxo-2λ$^6$-isothiochroman-4-ylamino)-2-hydroxy-propyl]-acetamide; |
| A22. | N—((1S,2R)-1-(3,5-difluorobenzyl)-3-{[6-ethyl-2-(methylsulfonyl)-1,2,3,4-tetrahydroisoquinolin-4-yl]amino}-2-hydroxypropyl)acetamide; |
| A23. | N—((1S,2R)-1-(3,5-difluorobenzyl)-3-{[(1S)-7-ethyl-1,2,3,4-tetrahydronaphthalen-1-yl]amino}-2-hydroxypropyl)acetamide; |
| A24. | N—((1S,2R)-1-(3,5-difluorobenzyl)-3-{[(1R)-7-ethyl-1,2,3,4-tetrahydronaphthalen-1-yl]amino}-2-hydroxypropyl)acetamide; |
| A25. | N—[(1S,2R)-3-{[1-(3-bromophenyl)cyclopropyl]amino}-1-(3,5-difluorobenzyl)-2-hydroxypropyl]acetamide; |
| A26. | methyl 3-{[(2R,3S)-3-(acetylamino)-4-(3,5-difluorophenyl)-2-hydroxybutyl]amino}-3-[3-(5-formylthien-2-yl)phenyl]propanoate; |
| B1. | methyl 3-{[(2R,3S)-3-(acetylamino)-4-(3,5-difluorophenyl)-2-hydroxybutyl]amino}-3-(2'-acetyl-1,1'-biphenyl-3-yl)propanoate; |
| B2. | N-[1-(3,5-Difluoro-benzyl)-3-(6-ethyl-2,2-dioxo-2λ$^6$-isothiochroman-4-ylamino)-2-hydroxy-propyl]-3-methyl-butyramide; |
| B3. | N—[(1S,2R)-1-(3,5-difluorobenzyl)-2-hydroxy-3-({1-[3'-(hydroxymethyl)-1,1'-biphenyl-3-yl]cyclopropyl}amino)propyl]acetamide; |
| B4. | N—[(1S,2R)-1-(3,5-difluorobenzyl)-3-({1-[3-(5-formylthien-2-yl)phenyl]cyclopropyl}amino)-2-hydroxypropyl]acetamide; |
| B5. | N—[(1S,2R)-1-(3,5-difluorobenzyl)-3-(9H-fluoren-9-ylamino)-2-hydroxypropyl]acetamide; |
| B6. | methyl 3-{[(2R,3S)-3-(acetylamino)-4-(3,5-difluorophenyl)-2-hydroxybutyl]amino}-3-[3-(trifluoromethyl)phenyl]propanoate; |
| B7. | methyl 3-{[(2R,3S)-3-(acetylamino)-4-(3,5-difluorophenyl)-2-hydroxybutyl]amino}-3-(3-cyanophenyl)propanoate; |
| B8. | N-[1-(3,5-Difluoro-benzyl)-3-(6-ethyl-2,2-dioxo-2λ$^6$-isothiochroman-4-ylamino)-2-hydroxy-propyl]-3-hydroxy-2,2-dimethyl-propionamide; |
| B9. | N—((1S,2R)-1-(3,5-difluorobenzyl)-3-{[1-(3-ethylphenyl)cyclopropyl]amino}-2-hydroxypropyl)acetamide; |
| B10. | methyl 3-{[(2R,3S)-3-(acetylamino)-4-(3,5-difluorophenyl)-2-hydroxybutyl]amino}-3-(3-bromophenyl)propanoate; |
| B11. | N—((1S,2R)-1-(3,5-difluorobenzyl)-3-{[1-(3-ethynylphenyl)cyclopropyl]amino}-2-hydroxypropyl)acetamide; |
| B12. | N—[(1S,2R)-3-[(2-bromo-9H-fluoren-9-yl)amino]-1-(3,5-difluorobenzyl)-2-hydroxypropyl]acetamide; |
| B13. | N—{(1S,2R)-1-(3,5-difluorobenzyl)-3-[(2-ethyl-9H-fluoren-9-yl)amino]-2-hydroxypropyl}acetamide; |
| B14. | N—{(1S,2R)-1-(3,5-difluorobenzyl)-3-[(2,2-dioxido-3,4-dihydro-1,2-benzoxathiin-4-yl)amino]-2-hydroxypropyl}acetamide; |
| B15. | N—{(1S,2R)-1-(3,5-difluorobenzyl)-2-hydroxy-3-[(6-iodo-3,4-dihydro-2H-chromen-4-yl)amino]propyl}acetamide; |
| B16. | N—((1S,2R)-1-(3,5-difluorobenzyl)-2-hydroxy-3-{[(4S)-6-iodo-3,4-dihydro-2H-chromen-4-yl]amino}propyl)acetamide; |
| B17. | N—((1S,2R)-1-(3,5-difluorobenzyl)-2-hydroxy-3-{[(4R)-6-iodo-3,4-dihydro-2H-chromen-4-yl]amino}propyl)acetamide; |
| B18. | N-[1-(3,5-Difluoro-benzyl)-3-(6-ethyl-2,2-dioxo-2λ$^6$-isothiochroman-4-ylamino)-2-hydroxy-propyl]-3-hydroxy-propionamide; |
| B19. | N—{(1S,2R)-1-(3,5-difluorobenzyl)-3-[(6-ethyl-2,2-dioxido-3,4-dihydro-1,2-benzoxathiin-4-yl)amino]-2-hydroxypropyl}acetamide; |
| B20. | N—{(1S,2R)-1-(3,5-difluorobenzyl)-3-[(6-ethyl-2,2-dioxido-3,4-dihydro-1,2-benzoxathiin-4-yl)amino]-2-hydroxypropyl}acetamide; |
| B21. | N—((1S,2R)-1-(3,5-difluorobenzyl)-3-{[4-(3-ethylphenyl)tetrahydro-2H-pyran-4-yl]amino}-2-hydroxypropyl)acetamide; |
| B22. | N—{(1S,2R)-1-(3,5-difluorobenzyl)-3-{[1-(3-ethylphenyl)butyl]amino}-2-hydroxypropyl)acetamide; |
| B23. | N—((1S,2R)-1-(3,5-difluorobenzyl)-3-{[(4S)-6-ethyl-3,4-dihydro-2H-chromen-4-yl]amino}-2-hydroxypropyl)acetamide; |
| B24. | N—((1S,2R)-1-(3,5-difluorobenzyl)-3-{[(4R)-6-ethyl-3,4-dihydro-2H-chromen-4-yl]amino}-2-hydroxypropyl)acetamide; |
| B25. | N—{(1S,2R)-1-(3,5-difluorobenzyl)-3-[(7-ethyl-1,2,3,4-tetrahydronaphthalen-1-yl)amino]-2-hydroxypropyl}acetamide; |
| B26. | N-[1-(3,5-Difluoro-benzyl)-3-(6-ethyl-2,2-dioxo-2λ$^6$-isothiochroman-4-ylamino)-2-hydroxy-propyl]-3-hydroxy-butyramide; |
| C1. | N—((1S,2R)-1-(3,5-difluorobenzyl)-3-{[1-(3-ethylphenyl)cyclohexyl]amino}-2-hydroxypropyl)acetamide; |
| C2. | N—((1S,2R)-1-(3,5-difluorobenzyl)-3-{[1-(3-ethylphenyl)cyclopentyl]amino}-2-hydroxypropyl)acetamide; |
| C3. | N—{(1S,2R)-1-(3,5-difluorobenzyl)-3-[(6-ethyl-3,4-dihydro-1H-isothiochromen-4-yl)amino]-2-hydroxypropyl}acetamide; |
| C4. | N—{(1S,2R)-1-(3,5-difluorobenzyl)-3-[(2-ethyl-5-fluoro-9H-fluoren-9-yl)amino]-2-hydroxypropyl}acetamide; |
| C5. | methyl (3S)-3-{[(2R,3S)-3-(acetylamino)-4-(3,5-difluorophenyl)-2-hydroxybutyl]amino}-3-(3-ethylphenyl)butanoate; |
| C6. | N—((1S,2R)-1-(3,5-difluorobenzyl)-2-hydroxy-3-{[1-(3-isobutylisoxazol-5-yl)cyclopropyl]amino}propyl)acetamide; |
| C7. | N-[1-(3,5-Difluoro-benzyl)-3-(6-ethyl-2,2-dioxo-2λ$^6$-isothiochroman-4-ylamino)-2-hydroxy-propyl]-2-phenyl-acetamide; |
| C8. | N—{(1S,2R)-1-(3,5-difluorobenzyl)-3-[(2-ethyl-7-fluoro-9H-fluoren-9-yl)amino]-2-hydroxypropyl}acetamide; |
| C9. | methyl (3R)-3-{[(2R,3S)-3-(acetylamino)-4-(3,5-difluorophenyl)-2-hydroxybutyl]amino}-3-(3-ethylphenyl)butanoate; |
| C10. | N—{(1S,2R)-1-(3,5-difluorobenzyl)-3-[(2,5-dipropylbenzyl)amino]-2-hydroxypropyl}acetamide; |
| C11. | {[1-(3,5-Difluoro-benzyl)-3-(6-ethyl-2,2-dioxo-2λ$^6$-isothiochroman-4-ylamino)-2-hydroxy-propylcarbamoyl]-methyl}-methyl-carbamic acid tert-butyl ester; |
| C12. | N—{(1S,2R)-1-(3,5-difluorobenzyl)-2-hydroxy-3-[(2-isobutyl-9H-fluoren-9-yl)amino]propyl}acetamide; |
| C13. | N—((1S,2R)-1-(3,5-difluorobenzyl)-3-{[(1S)-6-ethyl-2,3-dihydro-1H-inden-1-yl]amino}-2-hydroxypropyl)acetamide; |
| C14. | N-[1-(3,5-Difluoro-benzyl)-3-(6-ethyl-2,2-dioxo-2λ$^6$-isothiochroman-4-ylamino)-2-hydroxy-propyl]-2-methyl-2-methylamino-propionamide; |
| C15. | N—((1S,2R)-1-(3,5-difluorobenzyl)-3-{[1-ethyl-1-(3-ethylphenyl)propyl]amino}-2-hydroxypropyl)acetamide; |

| Ex. No. | Compound |
|---|---|
| C16. | N—{(1S,2R)-1-(3,5-difluorobenzyl)-3-[(6-ethyl-2,2-dioxido-3,4-dihydro-1H-2,1-benzothiazin-4-yl)amino]-2-hydroxypropyl}acetamide; |
| C17. | N—{(1S,2R)-1-(3,5-difluorobenzyl)-3-[(6-ethyl-2,2-dioxido-3,4-dihydro-1H-2,1-benzothiazin-4-yl)amino]-2-hydroxypropyl}acetamide; |
| C18. | N—{(1S,2R)-1-(3,5-difluorobenzyl)-3-[(6-ethyl-3-methyl-2,2-dioxido-3,4-dihydro-1H-isothiochromen-4-yl)amino]-2-hydroxypropyl}acetamide; |
| C19. | N—{(1S,2R)-1-(3,5-difluorobenzyl)-3-[(6-ethyl-3-methyl-2,2-dioxido-3,4-dihydro-1H-isothiochromen-4-yl)amino]-2-hydroxypropyl}acetamide; |
| C20. | N—{(1S,2R)-1-(3,5-difluorobenzyl)-3-[(6-ethyl-1-methyl-1,2,3,4-tetrahydroquinolin-4-yl)amino]-2-hydroxypropyl}acetamide; |
| C21. | methyl 3-{[(2R,3S)-3-(acetylamino)-4-(3,5-difluorophenyl)-2-hydroxybutyl]amino}-3-(3-ethylphenyl)propanoate; |
| C22. | N-[1-(3,5-Difluoro-benzyl)-3-(6-ethyl-2,2-dioxo-2λ$^6$-isothiochroman-4-ylamino)-2-hydroxy-propyl]-2-(1H-imidazol-4-yl)-acetamide; |
| C23. | methyl 3-{[(2R,3S)-3-(acetylamino)-4-(3,5-difluorophenyl)-2-hydroxybutyl]amino}-3-(3-ethylphenyl)propanoate; |
| C24. | N—[(1S,2R)-3-[(2-bromo-9-methyl-9H-fluoren-9-yl)amino]-1-(3,5-difluorobenzyl)-2-hydroxypropyl]acetamide; |
| C25. | N—((1S,2R)-1-(3,5-difluorobenzyl)-3-{[2-(1-ethylpropyl)-9H-fluoren-9-yl]amino}-2-hydroxypropyl)acetamide; |
| C26. | N—[(1S,2R)-3-[(2-cyclopentyl-9H-fluoren-9-yl)amino]-1-(3,5-difluorobenzyl)-2-hydroxypropyl]acetamide; |
| D1. | N-[1-(3,5-Difluoro-benzyl)-3-(6-ethyl-2,2-dioxo-2λ$^6$-isothiochroman-4-ylamino)-2-hydroxy-propyl]-propionamide; |
| D2. | N—{(1S,2R)-1-(3,5-difluorobenzyl)-3-[(2-ethyl-9-methyl-9H-fluoren-9-yl)amino]-2-hydroxypropyl}acetamide; |
| D3. | N—[(1S,2R)-3-[(2-cyclohexyl-9H-fluoren-9-yl)amino]-1-(3,5-difluorobenzyl)-2-hydroxypropyl]acetamide; |
| D4. | N—((1S,2R)-1-(3,5-difluorobenzyl)-3-{[1-(4-ethylpyridin-2-yl)cyclopropyl]amino}-2-hydroxypropyl)acetamide; |
| D5. | N—((1S,2R)-1-(3,5-difluorobenzyl)-2-hydroxy-3-{[(4S)-6-(1H-pyrrol-3-yl)-3,4-dihydro-2H-chromen-4-yl]amino}propyl)acetamide; |
| D6. | N—((1S,2R)-1-(3,5-difluorobenzyl)-3-{[(5R)-3-ethyl-6,7,8,9-tetrahydro-5H-benzo[7]annulen-5-yl]amino}-2-hydroxypropyl)acetamide; |
| D7. | N—[(1S,2R)-3-{[1-(3-bromophenyl)-1-methylethyl]amino}-1-(3,5-difluorobenzyl)-2-hydroxypropyl]acetamide; |
| D8. | N—((1S,2R)-1-(3,5-difluorobenzyl)-3-{[2-(dimethylamino)-9H-fluoren-9-yl]amino}-2-hydroxypropyl)acetamide; |
| D9. | N—((1S,2R)-1-(3,5-difluorobenzyl)-2-hydroxy-3-{[(1S)-7-propyl-1,2,3,4-tetrahydronaphthalen-1-yl]amino}propyl)acetamide; |
| D10. | N—[(1S,2R)-1-(3,5-difluorobenzyl)-3-({(1S)-7-[(dimethylamino)methyl]-1,2,3,4-tetrahydronaphthalen-1-yl}amino)-2-hydroxypropyl]acetamide; |
| D11. | N—[(1S,2R)-3-{[(1S)-7-bromo-1,2,3,4-tetrahydronaphthalen-1-yl]amino}-1-(3,5-difluorobenzyl)-2-hydroxypropyl]acetamide; |
| D12. | N—((1S,2R)-1-(3,5-difluorobenzyl)-2-hydroxy-3-{[1-(3-propylphenyl)cyclopropyl]amino}propyl)acetamide; |
| D13. | N—((1S,2R)-1-(3,5-difluorobenzyl)-3-{[1-(3-ethylphenyl)cycloheptyl]amino}-2-hydroxypropyl)acetamide; |
| D14. | N—{(1S,2R)-1-(3,5-difluorobenzyl)-2-hydroxy-3-[(6-isopropyl-3,4-dihydro-2H-chromen-4-yl)amino]propyl}acetamide; |
| D15. | N—{(1S,2R)-1-(3,5-difluorobenzyl)-3-[(6-ethyl-2-hydroxy-2,3-dihydro-1H-inden-1-yl)amino]-2-hydroxypropyl}acetamide; |
| D16. | N—{(1S,2R)-1-(3,5-difluorobenzyl)-3-[(2-ethyl-6-fluoro-9H-fluoren-9-yl)amino]-2-hydroxypropyl}acetamide; |
| D17. | N—((1S,2R)-1-(3,5-difluorobenzyl)-2-hydroxy-3-{[2-(methoxymethyl)-9H-fluoren-9-yl]amino}propyl)acetamide; |
| D18. | N—((1S,2R)-1-(3,5-difluorobenzyl)-3-{[1-(3-ethylphenyl)-2-(5-methyl-1,3-oxazol-2-yl)ethyl]amino}-2-hydroxypropyl)acetamide hydrochloride; |
| D19. | N—[(1S,2R)-1-(3,5-difluorobenzyl)-3-(3,4-dihydro-2H-chromen-4-ylamino)-2-hydroxypropyl]acetamide; |
| D20. | N—((1S,2R)-1-(3,5-difluorobenzyl)-3-{[2-ethyl-5-(trifluoromethyl)-9H-fluoren-9-yl]amino}-2-hydroxypropyl)acetamide; |
| D21. | N—((1S,2R)-1-(3,5-difluorobenzyl)-2-hydroxy-3-{[2-(3-methylbutyl)-9H-fluoren-9-yl]amino}propyl)acetamide; |
| D22. | N—{(1S,2R)-1-(3,5-difluorobenzyl)-2-hydroxy-3-[(2-isopropyl-9H-fluoren-9-yl)amino]propyl}acetamide; |
| D23. | N—{(1S,2R)-1-(3,5-difluorobenzyl)-2-hydroxy-3-[(2-neopentyl-9H-fluoren-9-yl)amino]propyl}acetamide; |
| D24. | N—{(1S,2R)-1-(3,5-difluorobenzyl)-2-hydroxy-3-[(2-isopropenyl-9H-fluoren-9-yl)amino]propyl}acetamide; |
| D25. | N—((1S,2R)-1-(3,5-difluorobenzyl)-3-{[1-(3-ethylphenyl)-1-methylethyl]amino}-2-hydroxypropyl)acetamide hydrochloride; |
| D26. | N—((1S,2R)-1-(3,5-difluorobenzyl)-2-hydroxy-3-{[(4S)-6-isobutyl-3,4-dihydro-2H-chromen-4-yl]amino}propyl)acetamide; |
| E1. | N—[(1S,2R)-3-{[(4S)-6-cyano-3,4-dihydro-2H-chromen-4-yl]amino}-1-(3,5-difluorobenzyl)-2-hydroxypropyl]acetamide; |
| E2. | N—((1S,2R)-1-(3,5-difluorobenzyl)-2-hydroxy-3-{[(4S)-6-neopentyl-3,4-dihydro-2H-chromen-4-yl]amino}propyl)acetamide; |
| E3. | N—{(1S,2R)-1-(3,5-difluorobenzyl)-2-hydroxy-3-[(6-neopentyl-3,4-dihydro-2H-chromen-4-yl)amino]propyl}acetamide; |
| E4. | N—((1S,2R)-1-(3,5-difluorobenzyl)-2-hydroxy-3-{[2-(isopropylamino)-9H-fluoren-9-yl]amino}propyl)acetamide; |
| E5. | N—((1S,2R)-1-(3,5-difluorobenzyl)-2-hydroxy-3-{[1-(3-isobutylphenyl)cyclopropyl]amino}propyl)acetamide; and |
| E6. | N—((1S,2R)-1-(3,5-difluorobenzyl)-2-hydroxy-3-{[(4-isobutyl-1,1'-biphenyl-2-yl)methyl]amino}propyl)acetamide. |

Generally, the protection of amines is conducted, where appropriate, by methods known to those skilled in the art. Amino protecting groups are known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. When the amino protecting group is no longer needed, it is removed by methods known to those skilled in the art. By definition the amino protecting group must be readily removable. A variety of suitable methodologies are known to those skilled in the art; see also T. W. Green and P. G. M. Wuts in "Protective Groups in Organic Chemistry, John Wiley and Sons, 3$^{rd}$ edition, 1999. Suitable amino protecting groups include t-butoxycarbonyl, benzyloxycarbonyl, formyl, trityl, phthalimido, trichloro-acetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxy-carbonyl, cyclopentanyloxycarbonyl, 1-methylcyclo-pentanyloxycarbonyl, cyclohexanyloxycarbonyl, 1-methyl-cyclohexanyloxycabonyl, 2-methylcyclohexanyloxycarbonyl, 2-(4-toluylsulfonyl)ethoxycarbonyl, 2-(methylsulfonyl)-ethoxycarbonyl, 2-(triphenylphosphino)ethoxycarbonyl, fluorenylmethoxycarbonyl, 2-(trimethylsilyl)ethoxy-carbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl, 1-piperidyloxycarbonyl, 9-fluoroenylmethyl carbonate, —CH—CH=CH$_2$ and phenyl-C(=N—)—H.

It is preferred that the protecting group be t-butoxycarbonyl (BOC) and/or benzyloxycarbonyl (CBZ), it is more preferred that the protecting group be t-butoxycarbonyl. One skilled in the art will recognize suitable methods of introducing a t-butoxycarbonyl or benzyloxycarbonyl protecting group and may additionally consult T. W. Green and P. G. M. Wuts in "Protective Groups in Organic Chemistry, John Wiley and Sons, 3$^{rd}$ edition, 1999 for guidance.

The compounds of the invention may contain geometric or optical isomers as tautomers. Thus, the invention includes all tautomers and pure geometric isomers, such as the E and Z geometric isomers, as mixtures thereof. Further, the invention includes pure enantiomers, diastereomers and/or mixtures thereof, including racemic mixtures. The individual geometric isomers, enantiomers or diastereomers may be prepared or isolated by methods known to those in the art, including but not limited to chiral chromatography; preparing diastereomers, separating the diastereomers and then converting the diastereomers into enantiomers.

Compounds of the invention with designated stereochemistry can be included in mixtures, including racemic mixtures, with other enantiomers, diastereomers, geometric isomers or tautomers. In a preferred aspect, compounds of the invention are typically present in these mixtures in diastereomeric and/or enantiomeric excess of at least 50 percent. Preferably, compounds of the invention are present in these mixtures in diastereomeric and/or enantiomeric excess of at least 80 percent. More preferably, compounds of the invention with the desired stereochemistry are present in diastereomeric and/or enantiomeric excess of at least 90 percent. Even more preferably, compounds of the invention with the desired stereochemistry are present in diastereomeric and/or enantiomeric excess of at least 99 percent. Preferably the compounds of the invention have the "S" configuration at position 1. Also preferred are compounds that have the "R" configuration at position 2. Most preferred are compounds that have the "1S, 2R" configuration.

All compound names were generated using ACD Namepro version 5.09, Chemdraw v. 6.02, or were derived therefrom.

Several of the compounds of formula (I) are amines, and as such form salts when reacted with acids. Pharmaceutically acceptable salts are preferred over the corresponding amines since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanilic, sulfonic, sulfuric, tannic, tartaric, teoclic and toluenesulfonic. For other acceptable salts, see *Int. J. Pharm.*, 33, 201-217 (1986) and *J. Pharm. Sci.*, 66(1), 1, (1977).

The invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the onset of the disease.

Dosage Forms and Amounts

The compounds of the invention can be administered orally, parenterally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

About 1 to 500 mg of a compound or mixture of compounds of the invention or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medi-pads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenteral dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

In addition, the compounds of formula (I) can also be used with inhibitors of P-glycoprotein (P-gp). P-gp inhibitors and the use of such compounds are known to those skilled in the art. See for example, *Cancer Research,* 53, 4595-4602 (1993), *Clin. Cancer Res.*, 2, 7-12 (1996), *Cancer Research,* 56, 4171-4179 (1996), International Publications WO99/64001 and WO01/10387. The important thing is that the blood level of the P-gp inhibitor be such that it exerts its effect in inhibiting P-gp from decreasing brain blood levels of the compounds of formula (A). To that end the P-gp inhibitor and the compounds of formula (A) can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102, 918 and other steroids. It is to be understood that additional agents will be found that have the same function and therefore achieve the same outcome; such compounds are also considered to be useful.

The P-gp inhibitors can be administered orally, parenterally, (IV, IM, IM-depo, SO, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository or by implants, both of which are known to those skilled in the art.

There is nothing novel about the route of administration nor the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, fluorometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et al., 1999, Mol. Cell. Neurosci. 14:419-427; Vassar et al., 1999, Science 286:735-741; Yan et al., 1999, Nature 402:533-537; Sinha et al., 1999, Nature 40:537-540; and Lin et al., 2000, PNAS USA 97:1456-1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described by Kang et al., 1987, Nature 325:733-6, the 770 amino acid isotype described by Kitaguchi et. al., 1981, Nature 331:530-532, and variants such as the Swedish Mutation (KM670-1NL) (APP-SW), the London Mutation (V7176F), and others. See, for example, U.S. Pat. No. 5,766, 846 and also Hardy, 1992, Nature Genet. 1:233-234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et al., 1999, Neuro. Lett. 249:21-4, and in U.S. Pat. No. 5,612,486. Useful antibodies to detect A beta include, for example, the monoclonal antibody 6E10 (Senetek, St. Louis, Mo.) that specifically recognizes an epitope on amino acids 1-16 of the A beta peptide; antibodies 162 and 164 (New York State Institute for Basic Research, Staten Island, N.Y.) that are specific for human A beta 1-40 and 1-42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beta-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos.: 5,877,399; 5,612,486; 5,387,742; 5,720,936; 5,850,003; 5,877,015, and 5,811,633, and in Ganes et al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

Definitions

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

Pharmaceutically acceptable refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, a polycyclic fused system, or a bi or polycyclic bridged system, such as adamantyl or bicyclo [2.2.1] heptyl. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono ($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di ($C_1$-$C_6$)alkylamino($C_1$-$C_6$)alkyl.

By "aryl" is meant an aromatic carbocyclic group having a single ring (e.g., phenyl) or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$) alkylamino ($C_1$-$C_6$)alkyl.

By "heteroaryl" is mean at least one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, tetrahydrocarbazole, tetrahydrobetacarboline. The heteroaryl groups herein are unsubstituted or, as specified, substituted in one or more substitutable positions with various groups. For example, such heteroaryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazalidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$) alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl, di($C_1$-$C_6$)alkylamino($C_1$-$C_6$)alkyl or =O.

All patents and publications referred to herein are hereby incorporated by reference for all purposes.

Structures were named using Name Pro IUPAC Naming Software, version 5.09, available from Advanced Chemical Development, Inc., 90 Adelaide Street West, Toronto, Ontario, M5H 3V9, Canada.

The present invention may be better understood with reference to the following examples. These examples are intended to be representative of specific embodiments of the invention, and are not intended as limiting the scope of the invention.

The following abbreviations may be used in the Examples:

EDC stands for 1-(3-dimethylaminopropyl)-3-ethylcarbodiimide or the hydrochloride salt;

DIEA stands for diisopropylethylamine;

PyBOP stands for benzotriazol-1-yloxy)tripyrrolidinophosphonium hexafluorophosphate;

HATU stands for O-(7-azabenzotriazol-1-yl)-1,1,3,3-tetramethyluronium hexafluorophosphate;

THF stands for tetrahydrofuran;

EtBz stands for ethylbenzene;

DCM stands for dichloromethane.

BIOLOGY EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et al, 1999, *Nature* 40:537-540) or recombinantly produced as the full-length enzyme (amino acids 1-501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaOAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well was transferred to a corresponding anti- MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, preferred compounds of the invention exhibit an $IC_{50}$ of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
                                                [SEQ ID NO: 1]
Biotin-SEVNL-DAEFRC[oregon green]KK

[SEQ ID NO: 2]
Biotin-SEVKM-DAEFRC[oregon green]KK

[SEQ ID NO: 3]
Biotin-GLNIKTEEISEISY-EVEFRC[oregon green]KK

[SEQ ID NO: 4]
Biotin-ADRGLTTRPGSGLTNIKTEEISEVNL-DAEFRC[oregon
green]KK

[SEQ ID NO: 5]
Biotin-FVNQHLCoxGSHLVEALY-LVCoxGERGFFYTPKAC[oregon
green]KK
```

The enzyme (0.1 nanomolar) and test compounds (0.001-100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, preferred compounds of the invention exhibit an $IC_{50}$ of less than 50 micromolar. More preferred compounds of the invention exhibit an $IC_{50}$ of less than 10 micromolar. Even more preferred compounds of the invention exhibit an $IC_{50}$ of less than 5 micromolar.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence:

```
                                                [SEQ ID NO: 6]
(biotin) CGGADRGLTTRPGSGLTNIKTEEISEVNLDAEF
```

The P26-P1 standard has the sequence:

```
                                                [SEQ ID NO: 7]
(biotin) CGGADRGLTTRPGSGLTNIKTEEISEVNL
```

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays Using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et al., 1992, Nature 360:672-674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et al., 1995, Nature 373:523-527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

The invention has been described with reference to various specific and preferred embodiments and techniques. However, it should be understood that many variations and modifications may be made while remaining within the spirit and scope of the invention.

What is claimed is:

1. A compound of the formula I:

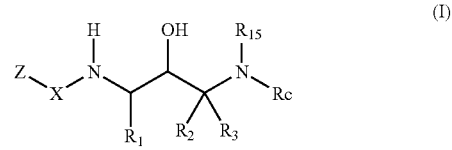

or pharmaceutically acceptable salts thereof, wherein

Z is hydrogen, or

Z is $(C_3\text{-}C_7$ cycloalkyl$)_{0\text{-}1}(C_1\text{-}C_6$ alkyl)-, $(C_3\text{-}C_7$ cycloalkyl$)_{0\text{-}1}(C_2\text{-}C_6$ alkenyl)-, $(C_3\text{-}C_7$ cycloalkyl$)_{0\text{-}1}(C_2\text{-}C_6$ alkynyl)- or $(C_3\text{-}C_7$ cycloalkyl)-, wherein each of said groups is optionally substituted with 1, 2, or 3 $R_Z$ groups, wherein 1 or 2 methylene groups within said $(C_3\text{-}C_7$ cycloalkyl$)_{0\text{-}1}(C_1\text{-}C_6$ alkyl)-, $(C_3\text{-}C_7$ cycloalkyl$)_{0\text{-}1}(C_2\text{-}C_6$ alkenyl)-, $(C_3\text{-}C_7$ cycloalkyl$)_{0\text{-}1}(C_2\text{-}C_6$ alkynyl)- or $(C_3\text{-}C_7$ cycloalkyl)- groups are optionally replaced with —(C=O)—;

$R_Z$ at each occurrence is independently halogen (in one aspect, F or Cl), —OH, —SH, —CN, —$CF_3$, —$OCF_3$, $C_1$-$C_6$ alkoxy, $C_3$-$C_7$ cycloalkyl, $C_3$-$C_7$ cycloalkoxy or —$NR_{100}R_{101}$;

$R_{100}$ and $R_{101}$ at each occurrence are independently H, $C_1$-$C_6$ alkyl, phenyl, CO($C_1$-$C_6$ alkyl) or $SO_2C_1$-$C_6$ alkyl;

X is —(C=O)—;

$R_1$ is $C_1$-$C_{10}$ alkyl substituted with aryl, or heteroaryl, wherein aryl group is optionally substituted with 1, 2 or 3 $R_{50}$ groups; and each heteroaryl is optionally substituted with 1 or 2 $R_{50}$ groups;

$R_{50}$ is selected from halogen, OH, SH, CN, —CO—($C_1$-$C_4$ alkyl), —$NR_7R_8$, —S(O)$_{0-2}$—($C_1$-$C_4$ alkyl), $C_1$-$C_6$ alkyl, $C_2$-$C_6$ alkenyl, $C_2$-$C_6$ alkynyl, $C_1$-$C_6$ alkoxy and $C_3$-$C_8$ cycloalkyl; wherein the alkyl, alkenyl, alkynyl, alkoxy and cycloalkyl groups are optionally substituted with 1 or 2 substituents independently selected from $C_1$-$C_4$ alkyl, halogen, OH, —$NR_5R_6$, CN, $C_1$-$C_4$ haloalkoxy, $NR_7R_8$, and $C_1$-$C_4$ alkoxy; wherein $R_5$ and $R_6$ are independently H or $C_1$-$C_6$ alkyl; or $R_5$ and $R_6$ and the nitrogen to which they are attached form a 5 or 6 membered heterocycloalkyl ring;

$R_7$ and $R_8$ are independently selected from H; —$C_1$-$C_4$ alkyl optionally substituted with 1, 2, or 3 groups independently selected from —OH, —$NH_2$, and halogen; —$C_3$-$C_6$ cycloalkyl; —($C_1$-$C_4$ alkyl)-O—($C_1$-$C_4$ alkyl); —$C_2$-$C_4$ alkenyl; and —$C_2$-$C_4$ alkynyl;

$R_2$ and $R_3$ are independently selected from H; F; —$C_1$-$C_6$ alkyl optionally substituted with —F, —OH, —C≡N, —$CF_3$, $C_1$-$C_3$ alkoxy, or —$NR_5R_6$; —$(CH_2)_{0-2}$—$R_{17}$; —$(CH_2)_{0-2}$—$R_{18}$; —$C_2$-$C_6$ alkenyl or $C_2$-$C_6$ alkynyl, wherein the alkenyl and alkynyl groups are optionally substituted with 1 or 2 groups that are independently —F, —OH, —C≡N, —$CF_3$ or $C_1$-$C_3$ alkoxy; —(C$H_2$)$_{0-2}$—$C_3$-$C_7$ cycloalkyl, which is optionally substituted with 1 or 2 groups that are independently —F, —OH, —C≡N, —$CF_3$, $C_1$-$C_3$ alkoxy and —$NR_5R_6$;

$R_{17}$ at each occurrence is an aryl group wherein said aryl group is optionally substituted with one or two groups that are independently —$C_1$-$C_3$ alkyl; —$C_1$-$C_4$ alkoxy; $CF_3$; —$C_2$-$C_6$ alkenyl or —$C_2$-$C_6$ alkynyl each of which is optionally substituted with one substituent selected from F, OH, $C_1$-$C_3$ alkoxy; halogen; OH; —C≡N; —$C_3$-$C_7$ cycloalkyl; —CO—($C_1$-$C_4$ alkyl); or —$SO_2$—($C_1$-$C_4$ alkyl);

$R_{18}$ is a heteroaryl group wherein said heteroaryl groups are optionally substituted with one or two groups that are independently —$C_1$-$C_6$ alkyl optionally substituted with one substituent selected from OH, C≡N, $CF_3$, $C_1$-$C_3$ alkoxy, and —$NR_5R_6$;

or $R_2$, $R_3$ and the carbon to which they are attached form a $C_3$-$C_7$ carbocycle, wherein 1, 2, or 3 carbon atoms are optionally replaced by groups that are independently selected from —O—, —S—, —$SO_2$—, —C(O)—, or —$NR_7$—;

$R_{15}$ is selected from hydrogen, and $C_1$-$C_6$ alkyl;

$R_c$ is selected from

—$(CH_2)_{0-3}$—($C_3$-$C_8$) cycloalkyl wherein the cycloalkyl is optionally substituted with 1, 2, or 3 groups independently selected from —$R_{205}$, and —$CO_2$—($C_1$-$C_4$ alkyl);

—$(CR_{245}R_{250})_{0-4}$-aryl;

—$(CR_{245}R_{250})_{1-4}$-heteroaryl;

—$(CR_{245}R_{250})_{1-4}$-heterocycloalkyl;

—$(CR_{245}R_{250})_{0-4}$-aryl-heteroaryl;

—$(CR_{245}R_{250})_{0-4}$-aryl-heterocycloalkyl;

—$(CR_{245}R_{250})_{0-4}$-aryl-aryl;

—$(CR_{245}R_{250})_{1-4}$-heteroaryl-aryl;

—$(CR_{245}R_{250})_{1-4}$-heteroaryl-heterocycloalkyl;

—$(CR_{245}R_{250})_{1-4}$-heteroaryl-heteroaryl;

—$CHR_{245}$—$CHR_{250}$-aryl;

—$(CR_{245}R_{250})_{1-4}$-heterocycloalkyl-heteroaryl;

—$(CR_{245}R_{250})_{1-4}$-heterocycloalkyl-heterocycloalkyl;

—$(CR_{245}R_{250})_{1-4}$-heterocycloalkyl-aryl;

a monocyclic or bicyclic ring of 5, 6, 7 8, 9, or 10 carbons fused to 1 or 2 aryl, heteroaryl, or heterocycloalkyl groups;

wherein 1, 2 or 3 carbons of the monocyclic or bicyclic ring are optionally replaced with —NH—, —N(CO)$_{0-1}R_{215}$—, —N(CO)$_{0-1}R_{220}$—, —O—, or —S(=O)$_{0-2}$—, and wherein the monocyclic or bicyclic ring is optionally substituted with 1, 2 or 3 groups that are independently —$R_{205}$, —$R_{245}$, —$R_{250}$ or =O;

and —$C_2$-$C_6$ alkenyl optionally substituted with 1, 2, or 3 $R_{205}$ groups;

wherein each aryl or heteroaryl group attached directly or indirectly to the —$(CR_{245}R_{250})_{0-4}$ group is optionally substituted with 1, 2, 3 or 4 $R_{200}$ groups;

wherein each heterocycloalkyl attached directly or indirectly to the —$(CR_{245}R_{250})_{0-4}$ group is optionally substituted with 1, 2, 3, or 4 $R_{210}$;

$R_{200}$ at each occurrence is independently selected from —$C_1$-$C_6$ alkyl optionally substituted with 1, 2, or 3 $R_{205}$ groups; —OH; —$NO_2$; -halogen; —C≡N; —$(CH_2)_{0-4}$—CO—$NR_{220}R_{225}$; —$(CH_2)_{0-4}$—CO—($C_1$-$C_8$ alkyl); —$(CH_2)_{0-4}$—CO—($C_2$-$C_8$ alkenyl); —$(CH_2)_{0-4}$—CO—($C_2$-$C_8$ alkynyl); —$(CH_2)_{0-4}$—CO—($C_3$-$C_7$ cycloalkyl); —$(CH_2)_{0-4}$—(CO)$_{0-1}$-aryl —$(CH_2)_{0-4}$—(CO)$_{0-1}$-heteroaryl; —$(CH_2)_{0-4}$—(CO)$_{0-1}$-heterocycloalkyl —$(CH_2)_{0-4}$—$CO_2R_{215}$; —$(CH_2)_{0-4}$—$SO_2$—$NR_{220}R_{225}$; —$(CH_2)_{0-4}$—S(O)$_{0-2}$—($C_1$-$C_8$ alkyl); —$(CH_2)_{0-4}$—S(O)$_{0-2}$—($C_3$-$C_7$ cycloalkyl); —$(CH_2)_{0-4}$—N(H or $R_{215}$)—$CO_2R_{215}$; —$(CH_2)_{0-4}$—N(H or $R_{215}$)—$SO_2$—$R_{220}$; —$(CH_2)_{0-4}$—N(H or $R_{215}$)—CO—N($R_{215}$)$_2$; —$(CH_2)_{0-4}$—N(—H or $R_{215}$)—CO—$R_{220}$; —(C$H_2$)$_{0-4}$—$NR_{220}R_{225}$; —$(CH_2)_{0-4}$—O—CO—($C_1$-$C_6$ alkyl); —$(CH_2)_{0-4}$—O—($R_{215}$); —$(CH_2)_{0-4}$—S—($R_{215}$); —$(CH_2)_{0-4}$—O—($C_1$-$C_6$ alkyl optionally substituted with 1, 2, 3, or 5 —F); —$C_2$-$C_6$ alkenyl optionally substituted with 1 or 2 $R_{205}$ groups; —$C_2$-$C_6$ alkynyl optionally substituted with 1 or 2 $R_{205}$ groups; adamantly, and —$(CH_2)_{0-4}$—$C_3$-$C_7$ cycloalkyl;

each aryl and heteroaryl group included within $R_{200}$ is optionally substituted with 1, 2, or 3 groups that are independently —$R_{205}$, —$R_{210}$ or —$C_1$-$C_6$ alkyl substituted with 1, 2, or 3 groups that are independently $R_{205}$ or $R_{210}$;

each heterocycloalkyl group included within $R_{200}$ is optionally substituted with 1, 2, or 3 groups that are independently $R_{210}$;

$R_{205}$ at each occurrence is independently selected from —$C_1$-$C_6$ alkyl, —$C_2$-$C_6$ alkenyl, —$C_2$-$C_6$ alkynyl, —$C_1$-$C_6$ haloalkoxy, —$(CH_2)_{0-3}$($C_3$-$C_7$ cycloalkyl), -halogen, —$(CH_2)_{0-6}$—OH, —O-phenyl, OH, SH, —$(CH_2)_{0-6}$—C≡N, —$(CH_2)_{0-6}$—C(=O)$NR_{235}R_{240}$, —$CF_3$, —$C_1$-$C_6$ alkoxy, $C_1$-$C_6$ alkoxycarbonyl, and —$NR_{235}R_{240}$;

$R_{210}$ at each occurrence is independently selected from —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; $C_1$-$C_6$ alkanoyl; —$SO_2$—($C_1$-$C_6$ alkyl); —$C_2$-$C_6$ alkynyl optionally substituted with 1, 2, or 3 $R_{205}$ groups; -halogen; —$C_1$-$C_6$ alkoxy; —$C_1$-$C_6$ haloalkoxy; —$NR_{220}R_{225}$; —OH; —C≡N; —$C_3$-$C_7$ cycloalkyl optionally substituted with 1, 2, or 3 $R_{205}$ groups; —CO—($C_1$-$C_4$ alkyl); —$SO_2$—$NR_{235}R_{240}$; —CO—$NR_{235}R_{240}$; —$SO_2$—($C_1$-$C_4$ alkyl); and =O;

$R_{215}$ at each occurrence is independently selected from —$C_1$-$C_6$ alkyl, —$(CH_2)_{0-2}$-(aryl), —$C_2$-$C_6$ alkenyl, —$C_2$-$C_6$ alkynyl, —$C_3$—$C_7$ cycloalkyl, —$(CH_2)_{0-2}$-(heteroaryl), and —$(CH_2)_{0-2}$-(heterocycloalkyl); wherein the aryl group included within $R_{215}$ is optionally substituted with 1, 2, or 3 groups that are independently —$R_{205}$ or —$R_{210}$; wherein the heterocycloalkyl and heteroaryl groups included within $R_{215}$ are optionally substituted with 1, 2, or 3 $R_{210}$;

$R_{220}$ and $R_{225}$ at each occurrence are independently H, —$C_1$-$C_6$ alkyl, —CHO, hydroxy $C_1$-$C_6$ alkyl, $C_1$-$C_6$ alkoxycarbonyl, -amino $C_1$-$C_6$ alkyl, —$SO_2$—$C_1$-$C_6$ alkyl, $C_1$-$C_6$ alkanoyl optionally substituted with up to three halogens, —$C(O)NH_2$, —$C(O)NH(C_1$-$C_6$ alkyl), —$C(O)N(C_1$-$C_6$ alkyl)($C_1$-$C_6$ alkyl), -halo $C_1$-$C_6$ alkyl, —$(CH_2)_{0-2}$—($C_3$-$C_7$ cycloalkyl), —$(C_1$-$C_6$ alkyl)-O—($C_1$-$C_3$ alkyl), —$C_2$-$C_6$ alkenyl, —$C_2$-$C_6$ alkynyl, -aryl, -heteroaryl, or -heterocycloalkyl; wherein the aryl, heteroaryl and heterocycloalkyl groups included within $R_{220}$ and $R_{225}$ is optionally substituted with 1, 2, or 3 $R_{270}$ groups, $R_{270}$ at each occurrence is independently —$R_{205}$, —$C_1$-$C_6$ alkyl optionally substituted with 1, 2, or 3 $R_{205}$ groups; —$C_2$-$C_6$ alkenyl optionally substituted with 1, 2, or 3 $R_{205}$ groups; —$C_2$-$C_6$ alkynyl optionally substituted with 1, 2, or 3 $R_{205}$ groups; -phenyl; -halogen; —$C_1$-$C_6$ alkoxy; —$C_1$-$C_6$ haloalkoxy; —$NR_{235}R_{240}$; —OH; —C≡N; —$C_3$-$C_7$ cycloalkyl optionally substituted with 1, 2, or 3 $R_{205}$ groups; —CO—($C_1$-$C_4$ alkyl); —$SO_2$—$NR_{235}R_{240}$; —CO—$NR_{235}R_{240}$; —$SO_2$—($C_1$-$C_4$ alkyl); and =O;

$R_{235}$ and $R_{240}$ at each occurrence are independently —H, —$C_1$-$C_6$ alkyl, $C_2$-$C_6$ alkanoyl, —$SO_2$—($C_1$-$C_6$ alkyl), or -phenyl;

$R_{245}$ and $R_{250}$ at each occurrence are independently selected from H, —$(CH_2)_{0-4}CO_2C_1$-$C_4$ alkyl, —$(CH_2)_{0-4}C(=O)C_1$-$C_4$ alkyl, —$C_1$-$C_4$ alkyl, —$C_1$-$C_4$ hydroxyalkyl, —$C_1$-$C_4$ alkoxy, —$C_1$-$C_4$ haloalkoxy, —$(CH_2)_{0-4}$—$C_3$-$C_7$ cycloalkyl, —$C_2$-$C_6$ alkenyl, —$C_2$-$C_6$ alkynyl, —$(CH_2)_{0-4}$ aryl, —$(CH_2)_{0-4}$ heteroaryl, and —$(CH_2)_{0-4}$ heterocycloalkyl, or $R_{245}$ and $R_{250}$ are taken together with the carbon to which they are attached to form a monocycle or bicycle of 3, 4, 5, 6, 7 or 8 carbon atoms, where 1, 2, or 3 carbon atoms are optionally replaced by 1, 2, or 3 groups that are independently —O—, —S—, —$SO_2$—, —C(O)—, —$NR_{220}$—, or —$NR_{220}R_{220}$— wherein both $R_{220}$ groups are alkyl; and wherein the ring is optionally substituted with 1, 2, 3, 4, 5, or 6 groups that are independently $C_1$-$C_4$ alkyl, $C_1$-$C_4$ alkoxy, hydroxyl, $NH_2$, $NH(C_1$-$C_6$ alkyl), $N(C_1$-$C_6$ alkyl) ($C_1$-$C_6$ alkyl), —NH—$C(O)C_1$-$C_5$ alkyl, —NH—$SO_2$—($C_1$-$C_6$ alkyl), or halogen;

wherein the aryl, heteroaryl or heterocycloalkyl groups included within $R_{245}$ and $R_{250}$ are optionally substituted with 1, 2, or 3 groups that are independently halogen, $C_{1-6}$ alkyl, CN or OH.

2. A compound according to claim 1, wherein Z is $(C_3$-$C_7$ cycloalkyl)$_{0-1}$($C_1$-$C_6$ alkyl)-, $(C_3$-$C_7$ cycloalkyl)$_{0-1}$($C_2$-$C_6$ alkenyl)-, $(C_3$-$C_7$ cycloalkyl)$_{0-1}$($C_2$-$C_6$ alkynyl)- or $(C_3$-$C_7$ cycloalkyl)-, wherein each of said groups is optionally substituted with 1, 2, or 3 $R_Z$ groups;

wherein, $R_Z$ at each occurrence is independently halogen, —OH, —CN, $C_1$-$C_6$ alkoxy, $C_3$-$C_7$ cycloalkyl, $C_3$-$C_7$ cycloalkoxy, —$NR_{100}R_{101}$;

where $R_{100}$ and $R_{101}$ are independently H, $C_1$-$C_6$ alkyl, phenyl, $CO(C_1$-$C_6$ alkyl) or $SO_2C_1$-$C_6$ alkyl.

3. A compound according to claim 2, wherein Z is H.

4. A compound according to claim 1, wherein $R_1$ is $C_1$-$C_{10}$ alkyl substituted with aryl, wherein the aryl group is optionally substituted with 1 or 2 $R_{50}$ groups;

wherein $R_{50}$ is selected from halogen, OH, —CO—($C_1$-$C_4$ alkyl), —$NR_7R_8$, $C_1$-$C_6$ alkyl, $C_1$-$C_6$ alkoxy and $C_3$-$C_8$ cycloalkyl;

wherein the alkyl, alkoxy and cycloalkyl groups are optionally substituted with 1 or 2 substituents independently selected from $C_1$-$C_4$ alkyl, halogen, OH, —$NR_5R_6$, $NR_7R_8$, and $C_1$-$C_4$ alkoxy;

wherein $R_5$ and $R_6$ at are independently H or $C_1$-$C_6$ alkyl; or wherein $R_5$ and $R_6$ and the nitrogen to which they are attached form a 5 or 6 membered heterocycloalkyl ring; and wherein $R_7$ and $R_8$ are independently selected from —H; —$C_1$-$C_4$ alkyl optionally substituted with 1, 2, or 3 groups independently selected from —OH, —$NH_2$, and halogen; —$C_3$-$C_6$ cycloalkyl; —($C_1$-$C_4$ alkyl)-O—($C_1$-$C_4$ alkyl).

5. A compound according to claim 4, wherein $R_1$ is —$CH_2$-phenyl where the phenyl ring is optionally substituted with 1 or 2 groups independently selected from halogen, $C_1$-$C_2$ alkyl, $C_1$-$C_2$ alkoxy and hydroxy.

6. A compound according to claim 5, wherein $R_1$ is benzyl, 3-fluorobenzyl or 3,5-difluorobenzyl.

7. A compound according to claim 1, wherein $R_{15}$ is H.

8. A compound according to claim 6, wherein $R_{15}$ is H.

9. A compound according to claim 1 of the formula II:

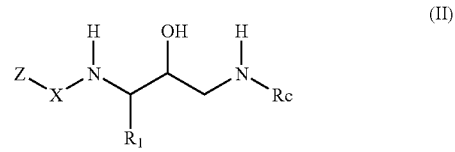

(II)

wherein Z is hydrogen, —$C_1$-$C_6$ alkyl, —$C_2$-$C_6$ alkenyl, —$C_2$-$C_6$ alkynyl or —$C_3$-$C_7$ cycloalkyl, where each of said groups is optionally substituted with 1 or 2 $R_Z$ groups, wherein 1 or 2 methylene groups within said —$C_1$-$C_6$ alkyl, —$C_2$-$C_6$ alkenyl, —$C_2$-$C_6$ alkynyl or —$C_3$-$C_7$ cycloalkyl groups are optionally replaced with —(C=O)—;

wherein $R_Z$ at each occurrence is independently halogen, —OH, —CN, —$CF_3$, $C_1$-$C_6$ alkoxy, $C_3$-$C_7$ cycloalkyl, $C_3$-$C_7$ cycloalkoxy or —$NR_{100}R_{101}$;

where R₁₀₀ and R₁₀₁ are independently H, C₁-C₆ alkyl, phenyl, CO(C₁-C₆ alkyl) or SO₂C₁-C₆ alkyl;
wherein X is —C(=O)—;
wherein R₁ is C₁-C₁₀ alkyl substituted with aryl, or heteroaryl wherein the aryl group is optionally substituted with 1 or 2 R₅₀ groups;
  where R₅₀ is halogen, OH, CN, —CO—(C₁-C₄ alkyl), —NR₇R₈, C₁-C₆ alkyl, C₂-C₆ alkenyl, C₂-C₆ alkynyl, C₁-C₆ alkoxy and C₃-C₈ cycloalkyl;
    where R₇ and R₈ are selected from H; —C₁-C₄ alkyl optionally substituted with 1, 2, or 3 groups selected from —OH, —NH₂ and halogen; —C₃-C₆ cycloalkyl; —(C₁-C₄ alkyl)-O—(C₁-C₄ alkyl); —C₂-C₄ alkenyl; and —C₂-C₄ alkynyl;
wherein R_c is selected from
—(CR₂₄₅R₂₅₀)₀₋₄-aryl;
—(CR₂₄₅R₂₅₀)₁₋₄-heteroaryl;
—(CR₂₄₅R₂₅₀)₁₋₄-heterocycloalkyl;
  where the aryl group attached to the —(CR₂₄₅R₂₅₀)₀₋₄— group is optionally substituted with 1, 2, 3 or 4 R₂₀₀ groups;
  where the heteroaryl group attached to the —(CR₂₄₅R₂₅₀)₁₋₄— group is optionally substituted with 1, 2, 3, or 4 R₂₀₀ groups;
  where the heterocycloalkyl group attached to the —(CR₂₄₅R₂₅₀)₁₋₄— group is optionally substituted with 1, 2, 3, or 4 R₂₁₀ groups.

10. A compound according to claim 9, wherein
Z is —C₁-C₆ alkyl;
R₁ is C₁-C₁₀ alkyl substituted with phenyl group, where the phenyl group attached to the alkyl is optionally substituted with 1 or 2 R₅₀ groups, where each R₅₀ is independently halogen, OH, CN, or C₁-C₆ alkyl; and
R_c is —(CR₂₄₅R₂₅₀)₀₋₄-aryl or —(CR₂₄₅R₂₅₀)₁₋₄-heteroaryl, where the aryl and heteroaryl groups are optionally substituted with 1 or 2 R₂₀₀ groups.

11. A compound according to claim 1 which is
N-[(1S,2R)-3-[(3-bromobenzyl)amino]-1-(3,5-difluorobenzyl)-2-hydroxypropyl]acetamide;
N-[(1S,2R)-3-{[1-(3-bromophenyl)cyclopropyl]amino}-1-(3,5-difluorobenzyl)-2-hydroxypropyl]acetamide hydrochloride;
methyl 3-{[(2R,3S)-3-(acetylamino)-4-(3,5-difluorophenyl)-2-hydroxybutyl]amino}-3-(3-bromophenyl)propanoate;
N-{(1S,2R)-1-(3,5-difluorobenzyl)-3-[(3-ethylbenzyl)amino]-2-hydroxypropyl}acetamide;
methyl 3-{[(2R,3S)-3-(acetylamino)-4-(3,5-difluorophenyl)-2-hydroxybutyl]amino}-3-(3-ethylphenyl)propanoate;
3-{[(2R,3S)-3-(acetylamino)-4-(3,5-difluorophenyl)-2-hydroxybutyl]amino}-3-(3-ethylphenyl)propanoic acid;
N-((1S,2R)-1-(3,5-difluorobenzyl)-3-{[1-(3-ethylphenyl)-3-hydroxypropyl]amino}-2-hydroxypropyl)acetamide;
N-{(1S,2R)-1-(3,5-difluorobenzyl)-2-hydroxy-3-[(1S)-1,2,3,4-tetrahydronaphthalen-1-ylamino]propyl}acetamide;
N-{(1S,2R)-1-(3,5-difluorobenzyl)-2-hydroxy-3-[(3-iodobenzyl)amino]propyl}acetamide;
methyl 3-{[(2R,3S)-3-(acetylamino)-4-(3,5-difluorophenyl)-2-hydroxybutyl]amino}-3-(3-iodophenyl)propanoate;
methyl 3-{[(2R,3S)-3-(acetylamino)-4-(3,5-difluorophenyl)-2-hydroxybutyl]amino}-3-[3-(3-hydroxyprop-1-ynyl)phenyl]propanoate;
N-((1S,2R)-1-(3,5-difluorobenzyl)-2-hydroxy-3-{[3-hydroxy-1-(3-iodophenyl)propyl]amino}propyl)acetamide;
methyl 3-{[(2R,3S)-3-(acetylamino)-4-(3,5-difluorophenyl)-2-hydroxybutyl]amino}-3-[3-(3-hydroxypropyl)phenyl]propanoate;
N-{(1S,2R)-1-(3,5-difluorobenzyl)-2-hydroxy-3-[(7-methoxy-1,2,3,4-tetrahydronaphthalen-1-yl)amino]propyl}acetamide;
N-((1S,2R)-1-(3,5-difluorobenzyl)-3-{[(1S)-7-ethyl-1,2,3,4-tetrahydronaphthalen-1-yl]amino}-2-hydroxypropyl)acetamide;
N-((1S,2R)-1-(3,5-difluorobenzyl)-3-{[(1R)-7-ethyl-1,2,3,4-tetrahydronaphthalen-1-yl]amino}-2-hydroxypropyl)acetamide;
N-[(1S,2R)-3-{[1-(3-bromophenyl)cyclopropyl]amino}-1-(3,5-difluorobenzyl)-2-hydroxypropyl]acetamide;
methyl 3-{[(2R,3S)-3-(acetylamino)-4-(3,5-difluorophenyl)-2-hydroxybutyl]amino}-3-[3-(5-formylthien-2-yl)phenyl]propanoate;
methyl 3-{[(2R,3S)-3-(acetylamino)-4-(3,5-difluorophenyl)-2-hydroxybutyl]amino}-3-(2'-acetyl-1,1'-biphenyl-3-yl)propanoate;
N-[(1S,2R)-1-(3,5-difluorobenzyl)-2-hydroxy-3-({1-[3'-(hydroxymethyl)-1,1'-biphenyl-3-yl]cyclopropyl}amino)propyl]acetamide
N-[(1S,2R)-1-(3,5-difluorobenzyl)-3-({1-[3-(5-formylthien-2-yl)phenyl]cyclopropyl}amino)-2-hydroxypropyl]acetamide;
N-[(1S,2R)-1-(3,5-difluorobenzyl)-3-(9H-fluoren-9-ylamino)-2-hydroxypropyl]acetamide;
methyl 3-{[(2R,3S)-3-(acetylamino)-4-(3,5-difluorophenyl)-2-hydroxybutyl]amino}-3-[3-(trifluoromethyl)phenyl]propanoate;
methyl 3-{[(2R,3S)-3-(acetylamino)-4-(3,5-difluorophenyl)-2-hydroxybutyl]amino}-3-(3-cyanophenyl)propanoate;
N-((1S,2R)-1-(3,5-difluorobenzyl)-3-{[1-(3-ethylphenyl)cyclopropyl]amino}-2-hydroxypropyl)acetamide;
methyl 3-{[(2R,3S)-3-(acetylamino)-4-(3,5-difluorophenyl)-2-hydroxybutyl]amino}-3-(3-bromophenyl)propanoate;
N-((1S,2R)-1-(3,5-difluorobenzyl)-3-{[1-(3-ethynylphenyl)cyclopropyl]amino}-2-hydroxypropyl)acetamide;
N-[(1S,2R)-3-[(2-bromo-9H-fluoren-9-yl)amino]-1-(3,5-difluorobenzyl)-2-hydroxypropyl]acetamide;
N-{(1S,2R)-1-(3,5-difluorobenzyl)-3-[(2-ethyl-9H-fluoren-9-yl)amino]-2-hydroxypropyl}acetamide;
N-((1S,2R)-1-(3,5-difluorobenzyl)-3-{[1-(3-ethylphenyl)butyl]amino}-2-hydroxypropyl)acetamide;
N-{(1S,2R)-1-(3,5-difluorobenzyl)-3-[(7-ethyl-1,2,3,4-tetrahydronaphthalen-1-yl)amino]-2-hydroxypropyl}acetamide;
N-((1S,2R)-1-(3,5-difluorobenzyl)-3-{[1-(3-ethylphenyl)cyclohexyl]amino}-2-hydroxypropyl)acetamide;
N-((1S,2R)-1-(3,5-difluorobenzyl)-3-{[1-(3-ethylphenyl)cyclopentyl]amino}-2-hydroxypropyl)acetamide;
N-{(1S,2R)-1-(3,5-difluorobenzyl)-3-[(2-ethyl-5-fluoro-9H-fluoren-9-yl)amino]-2-hydroxypropyl}acetamide;
methyl(3S)-3-{[(2R,3S)-3-(acetylamino)-4-(3,5-difluorophenyl)-2-hydroxybutyl]amino}-3-(3-ethylphenyl)butanoate;
N-((1S,2R)-1-(3,5-difluorobenzyl)-2-hydroxy-3-([1-{3-isobutylisoxazol-5-yl}cyclopropyl]amino}propyl)acetamide;
N-{(1S,2R)-1-(3,5-difluorobenzyl)-3-[(2-ethyl-7-fluoro-9H-fluoren-9-yl)amino]-2-hydroxypropyl}acetamide;

methyl(3R)-3-{[(2R,3S)-3-(acetylamino)-4-(3,5-difluo-rophenyl)-2-hydroxybutyl]amino}-3-(3-ethylphenyl) butanoate;

N-{(1S,2R)-1-(3,5-difluorobenzyl)-3-[(2,5-dipropylben-zyl)amino]-2-hydroxypropyl}acetamide;

N-{(1S,2R)-1-(3,5-difluorobenzyl)-2-hydroxy-3-[(2-isobutyl-9H-fluoren-9-yl)amino]propyl}acetamide;

N-((1S,2R)-1-(3,5-difluorobenzyl)-3-{[(1S)-6-ethyl-2,3-dihydro-1H-inden-1-yl]amino}-2-hydroxypropyl)ac-etamide;

N-((1S,2R)-1-(3,5-difluorobenzyl)-3-{[1-ethyl-1-(3-eth-ylphenyl)propyl]amino}-2-hydroxypropyl)acetamide;

methyl 3-{[(2R,3S)-3-(acetylamino)-4-(3,5-difluorophe-nyl)-2-hydroxybutyl]amino}-3-(3-ethylphenyl)pro-panoate;

methyl 3-{[(2R,3S)-3-(acetylamino)-4-(3,5-difluorophe-nyl)-2-hydroxybutyl]amino}-3-(3-ethylphenyl)pro-panoate;

N-[(1S,2R)-3-[(2-bromo-9-methyl-9H-fluoren-9-yl) amino]-1-(3,5-difluorobenzyl)-2-hydroxypropyl]aceta-mide;

N-((1S,2R)-1-(3,5-difluorobenzyl)-3-{[2-(1-ethylpro-pyl)-9H-fluoren-9-yl]amino}-2-hydroxypropyl)aceta-mide;

N-[(1S,2R)-3-[(2-cyclopentyl-9H-fluoren-9-yl)amino]-1-(3,5-difluorobenzyl)-2-hydroxypropyl]acetamide;

N-{(1S,2R)-1-(3,5-difluorobenzyl)-3-[(2-ethyl-9-methyl-9H-fluoren-9-yl)amino]-2-hydroxypropyl}acetamide;

N-[(1S,2R)-3-[(2-cyclohexyl-9H-fluoren-9-yl)amino]-1-(3,5-difluorobenzyl)-2-hydroxypropyl]acetamide;

N-((1S,2R)-1-(3,5-difluorobenzyl)-3-{[1-(4-ethylpyri-din-2-yl)cyclopropyl]amino}-2-hydroxypropyl)aceta-mide;

N-((1S,2R)-1-(3,5-difluorobenzyl)-3-{[(5R)-3-ethyl-6,7,8,9-tetrahydro-5H-benzo[7]annulen-5-yl]amino}-2-hydroxypropyl)acetamide;

N-[(1S,2R)-3-{[1-(3-bromophenyl)-1-methylethyl] amino}-1-(3,5-difluorobenzyl)-2-hydroxypropyl]ac-etamide;

N-((1S,2R)-1-(3,5-difluorobenzyl)-3-{[2-(dimethy-lamino)-9H-fluoren-9-yl]amino}-2-hydroxypropyl)ac-etamide;

N-((1S,2R)-1-(3,5-difluorobenzyl)-2-hydroxy-3-{[(1S)-7-propyl-1,2,3,4-tetrahydronaphthalen-1-yl] amino}propyl)acetamide;

N-[(1S,2R)-1-(3,5-difluorobenzyl)-3-({(1S)-7-[(dimethy-lamino)methyl]-1,2,3,4-tetrahydronaphthalen-1-yl}amino)-2-hydroxypropyl]acetamide;

N-[(1S,2R)-3-{[(1S)-7-bromo-1,2,3,4-tetrahydronaph-thalen-1-yl]amino}-1-(3,5-difluorobenzyl)-2-hydrox-ypropyl]acetamide;

N-((1S,2R)-1-(3,5-difluorobenzyl)-2-hydroxy-3-{[1-(3-propylphenyl)cyclopropyl]amino}propyl)acetamide;

N-((1S,2R)-1-(3,5-difluorobenzyl)-3-{[1-(3-ethylphenyl) cycloheptyl]amino}-2-hydroxypropyl)acetamide;

N-{(1S,2R)-1-(3,5-difluorobenzyl)-3-[(6-ethyl-2-hy-droxy-2,3-dihydro-1H-inden-1-yl)amino]-2-hydroxypropyl}acetamide;

N-{(1S,2R)-1-(3,5-difluorobenzyl)-3-[(2-ethyl-6-fluoro-9H-fluoren-9-yl)amino]-2-hydroxypropyl}acetamide;

N-((1S,2R)-1-(3,5-difluorobenzyl)-2-hydroxy-3-{[2-(methoxymethyl)-9H-fluoren-9-yl]amino}propyl)ac-etamide;

N-((1S,2R)-1-(3,5-difluorobenzyl)-3-{[1-(3-ethylphe-nyl)-2-(5-methyl-1,3-oxazol-2-yl)ethyl]amino}-2-hy-droxypropyl)acetamide hydrochloride;

N-((1S,2R)-1-(3,5-difluorobenzyl)-3-{[2-ethyl-5-(trifluo-romethyl)-9H-fluoren-9-yl]amino}-2-hydroxypropyl) acetamide;

N-((1S,2R)-1-(3,5-difluorobenzyl)-2-hydroxy-3-{[2-(3-methylbutyl)-9H-fluoren-9-yl]amino}propyl)aceta-mide;

N-{(1S,2R)-1-(3,5-difluorobenzyl)-2-hydroxy-3-[(2-iso-propyl-9H-fluoren-9-yl)amino]propyl}acetamide;

N-{(1S,2R)-1(3,5-difluorobenzyl)-2-hydroxy-3-[(2-neo-pentyl-9H-fluoren-9-yl)amino]propyl}acetamide;

N-{(1S,2R)-1-(3,5-difluorobenzyl)-2-hydroxy-3-[(2-iso-propenyl-9H-fluoren-9-yl)amino]propyl}acetamide;

N-((1S,2R)-1-(3,5-difluorobenzyl)-3-{[1-(3-ethylphe-nyl)-1-methylethyl]amino}-2-hydroxypropyl)aceta-mide hydrochloride;

N-((1S,2R)-1-(3,5-difluorobenzyl)-2-hydroxy-3-{[2-(iso-propylamino)-9H-fluoren-9-yl]amino}propyl)aceta-mide;

N-((1S,2R)-1-(3,5-difluorobenzyl)-2-hydroxy-3-{[1-(3-isobutylphenyl)cyclopropyl]amino}propyl)acetamide;

N-((1S,2R)-1-(3,5-difluorobenzyl)-2-hydroxy-3-{[(4-isobutyl-1,1'-biphenyl-2-yl)methyl]amino}propyl)ac-etamide;

N-((1S,2R)-1-(3,5-difluorobenzyl)-3-{[7-(2,2-dimethyl-propyl)-5-ethyl-1,2,3,4-tetrahydronaphthalen-1-yl] amino}-2-hydroxypropyl)acetamide;

N-((1S,2R)-1-(3,5-difluorobenzyl)-3-{[(1S)-7-(2,2-dim-ethylpropyl)-1,2,3,4-tetrahydronaphthalen-1-yl] amino}-2-hydroxypropyl)acetamide;

N-[(1S,2R)-3-{[1-(3-tert-butylphenyl)cyclohexyl] amino}-1-(3,5-difluorobenzyl)-2-hydroxypropyl]ac-etamide;

N-((1S,2R)-1-(3,5-difluorobenzyl)-2-hydroxy-3-{[1-(3-isopropylphenyl)-4-oxocyclohexyl]amino}propyl)ac-etamide;

N-((1S,2R)-1-(3,5-difluorobenzyl)-3-{[5-(2,2-dimethyl-propyl)-2-(1H-imidazol-1-yl)benzyl]amino}-2-hy-droxypropyl)acetamide;

N-((1S,2R)-1-(3,5-difluorobenzyl)-3-{[7-(2,2-dimethyl-propyl)-1-methyl-1,2,3,4-tetrahydronaphthalen-1-yl] amino}-2-hydroxypropyl)acetamide;

N-((1S,2R)-1-(3-fluoro-4-hydroxybenzyl)-2-hydroxy-3-{[1-(3-isopropylphenyl)cyclohexyl]amino}propyl)ac-etamide;

N-((1S,2R)-1-(3,5-difluorobenzyl)-2-hydroxy-3-{[1-(3-isopropylphenyl)cyclohexyl]amino}propyl)-2-fluoro-acetamide;

N-((1S,2R)-1-[3-(allyloxy)-5-fluorobenzyl]-2-hydroxy-3-{[1-(3-isopropylphenyl)cyclohexyl]amino}propyl) acetamide;

N-[(1S,2R)-1-(3,5-difluorobenzyl)-3-({1-[3-(2,2-dimeth-ylpropyl)phenyl]-1-methylethyl}amino)-2-hydrox-ypropyl]-2-fluoroacetamide;

N-((1S,2R)-1-(3,5-difluorobenzyl)-3-{[(1S)-7-(2,2-dim-ethylpropyl)-1,2,3,4-tetrahydronaphthalen-1-yl] amino}-2-hydroxypropyl)-2-fluoroacetamide;

N-[(1S,2R)-1-(3,5-difluorobenzyl)-2-hydroxy-3-({1-[3-(3-thienyl)phenyl]cyclohexyl}amino)propyl]aceta-mide;

N-[(1S,2R)-1-(3,5-difluorobenzyl)-3-({1-[4-(2,2-dimeth-ylpropyl)pyridin-2-yl]cyclopropyl}amino)-2-hydrox-ypropyl]acetamide;

N-((1R,2S)-1-(3,5-difluorobenzyl)-2-hydroxy-3-{[(1S)-7-propyl-1,2,3,4-tetrahydronaphthalen-1-yl] amino}propyl)acetamide;

N-((1S,2R)-1-(3,5-difluorobenzyl)-2-hydroxy-3-{[1-(3-isobutylphenyl)cyclohexyl]amino}propyl)acetamide;

N-((1S,2R)-2-hydroxy-1-(4-hydroxybenzyl)-3-{[1-(3-isopropylphenyl)cyclohexyl]amino}propyl)acetamide;

N-((1R,2S)-1-(3,5-difluorobenzyl)-3-{[(1S)-7-ethyl-1,2,3,4-tetrahydronaphthalen-1-yl]amino}-2-hydroxypropyl)-2-ethoxyacetamide; or N-((1S,2R)-1-(3,5-difluorobenzyl)-3-{[(1R)-7-ethyl-1,2,3,4-tetrahydronaphthalen-1-yl]amino}-2-hydroxypropyl)-2,2-difluoroacetamide;

or a pharmaceutically acceptable salt thereof.

12. A method for preparing a compound or salt of claim 1, wherein Z, X, $R_1$, $R_2$, $R_3$, $R_{15}$ and $R_c$ are as defined in claim 1, said method comprising a) reacting an epoxide of the formula

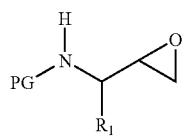

where PG is a nitrogen protecting group that is Cbz, Boc, or benzyl, with a compound of formula $H(R_{15})N$-Rc, to form a compound of the formula:

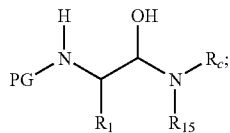

b) deprotecting the amine to form a compound of the formula:

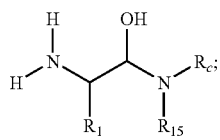

c) coupling the deprotected amine with a compound of formula Z-X-LG, where LG is a leaving group, to form a compound of the formula:

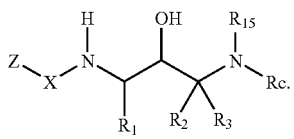

13. A method of treating a subject who has Alzheimer's disease (AD); treating subjects with mild cognitive impairment (MCI); treating Down's syndrome; treating subjects who have Hereditary Cerebral Hemorrhage with Amyloidosis of the Dutch-Type; treating cerebral amyloid angiopathy and preventing its potential consequences; treating other degenerative dementias; treating dementia associated with Parkinson's disease, progressive supranuclear palsy, or cortical basal degeneration; treating diffuse Lewy body type AD; and treating frontotemporal dementias with parkinsonism (FTDP), said method comprising administering a pharmaceutically acceptable amount of a compound according to claim 1 to a patient in need of such treatment.

14. A pharmaceutical composition comprising a compound or a salt according to claim 1 and at least one pharmaceutically acceptable carrier, solvent, adjuvant or diluent.

* * * * *